United States Patent
Yu et al.

(10) Patent No.: US 11,946,049 B2
(45) Date of Patent: Apr. 2, 2024

(54) TRNA/PRE-MIRNA COMPOSITIONS AND USE IN TREATING CANCER

(71) Applicant: The Regents of the University of California, Oakland, CA (US)

(72) Inventors: Aiming Yu, Granite Bay, CA (US); Pui Yan Ho, Davis, CA (US); Meijuan Tu, Davis, CA (US); Joseph L. Jilek, Davis, CA (US); Qianyu Zhang, Davis, CA (US); Hannah E. Petrek, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 142 days.

(21) Appl. No.: 17/056,203

(22) PCT Filed: May 21, 2019

(86) PCT No.: PCT/US2019/033232
§ 371 (c)(1),
(2) Date: Nov. 17, 2020

(87) PCT Pub. No.: WO2019/226603
PCT Pub. Date: Nov. 28, 2019

(65) Prior Publication Data
US 2021/0246446 A1    Aug. 12, 2021

Related U.S. Application Data

(60) Provisional application No. 62/674,939, filed on May 22, 2018.

(51) Int. Cl.
| | | |
|---|---|---|
| C07H 21/02 | (2006.01) | |
| A61K 45/06 | (2006.01) | |
| A61K 47/69 | (2017.01) | |
| C07H 21/04 | (2006.01) | |
| C12N 15/113 | (2010.01) | |

(52) U.S. Cl.
CPC ............ *C12N 15/113* (2013.01); *A61K 45/06* (2013.01); *A61K 47/6911* (2017.08); *C12N 2310/141* (2013.01); *C12N 2310/531* (2013.01)

(58) Field of Classification Search
CPC ....................... C12N 15/113; C12N 2310/141
See application file for complete search history.

(56) References Cited

U.S. PATENT DOCUMENTS

| | | |
|---|---|---|
| 9,228,207 B2 | 1/2016 | Liu et al. |
| 2016/0046961 A1 | 2/2016 | Charpentier et al. |

FOREIGN PATENT DOCUMENTS

| | | |
|---|---|---|
| WO | 2015183667 | 3/2015 |
| WO | WO 2016153880 | 9/2016 |
| WO | WO 2019204733 | 10/2019 |

OTHER PUBLICATIONS

Lin et al. (J. Gene Ther., 2016, 2(1), 1-14).*
Scherer et al. (Nucleic Acids Research, 2007, 35, 8, 2620-2628).*
Rohde et al. (Nucleic Acids Research, 25, 3, 2015, 141-151).*
Boudreau et al. (Molecular Therapy, 17, 1, 2009, 169-175).*
Li et al. (2018) "Bioengineered NRF2-siRNA Is Effective to Interfere with NRF2 Pathways and Improve Chemosensitivity of Human Cancer Cells" Drug Metabolism and Disposition, 46(1):2-10.
Wang et al. (2015) "Bioengineering Novel Chimeric microRNA-34a for Prodrug Cancer Therapy: High-Yield Expression and Purification, and Structural and Functional Characterization," The Journal of Pharmacology and Experimental Therapeutics, 354(2):131-141.
Yan Ho et al. (2018) "Bioengineered Noncoding RNAs Selectively Change Cellular miRNome Profiles for Cancer Therapy" J. Pharmacol. Exp. Ther., 365:494-506.
Chen et al. (2015) "A general approach to high-yield biosynthesis of chimeric RNAs bearing various types of functional small RNAs for broad applications" Nucleic Acids Research, 43(7):3857-3869.
Petrek et al. (2019) "Bioengineering of single ncRNA molecule for multi-targeting against NSCLC" The Faseb Journal, 33(S1):674.12.
Petrek et al. (2019) "Bioengineering of a single long noncoding RNA molecule that carries multiple small RNAs" Applied Microbiology and Biotechnology, 103(15):6107-6117.
Yan Ho et al. (2016) "Bioengineering of noncoding RNAs for research agents and therapeutics: Bioengineering of ncRNAs" Wiley Interdisciplinary Reviews: Rna, 7(2):186-197.

* cited by examiner

*Primary Examiner* — Amy H Bowman
(74) *Attorney, Agent, or Firm* — Brian E. Davy; Bozicevic, Field & Francis LLP

(57) ABSTRACT

Provided are hybrid tRNA/pre-miRNA molecules, e.g., comprising a single tRNA and one, two or more pre-miRNA molecules, useful for the production and therapeutic delivery of an inserted RNA sequence, e.g., one or more miRNAs. Also provided are liposomes and nanoparticles that include the hybrid tRNA/pre-miRNA molecules. Methods of treating cancer by administration of the hybrid tRNA/pre-miRNA molecules are also provided.

16 Claims, 87 Drawing Sheets

Specification includes a Sequence Listing.

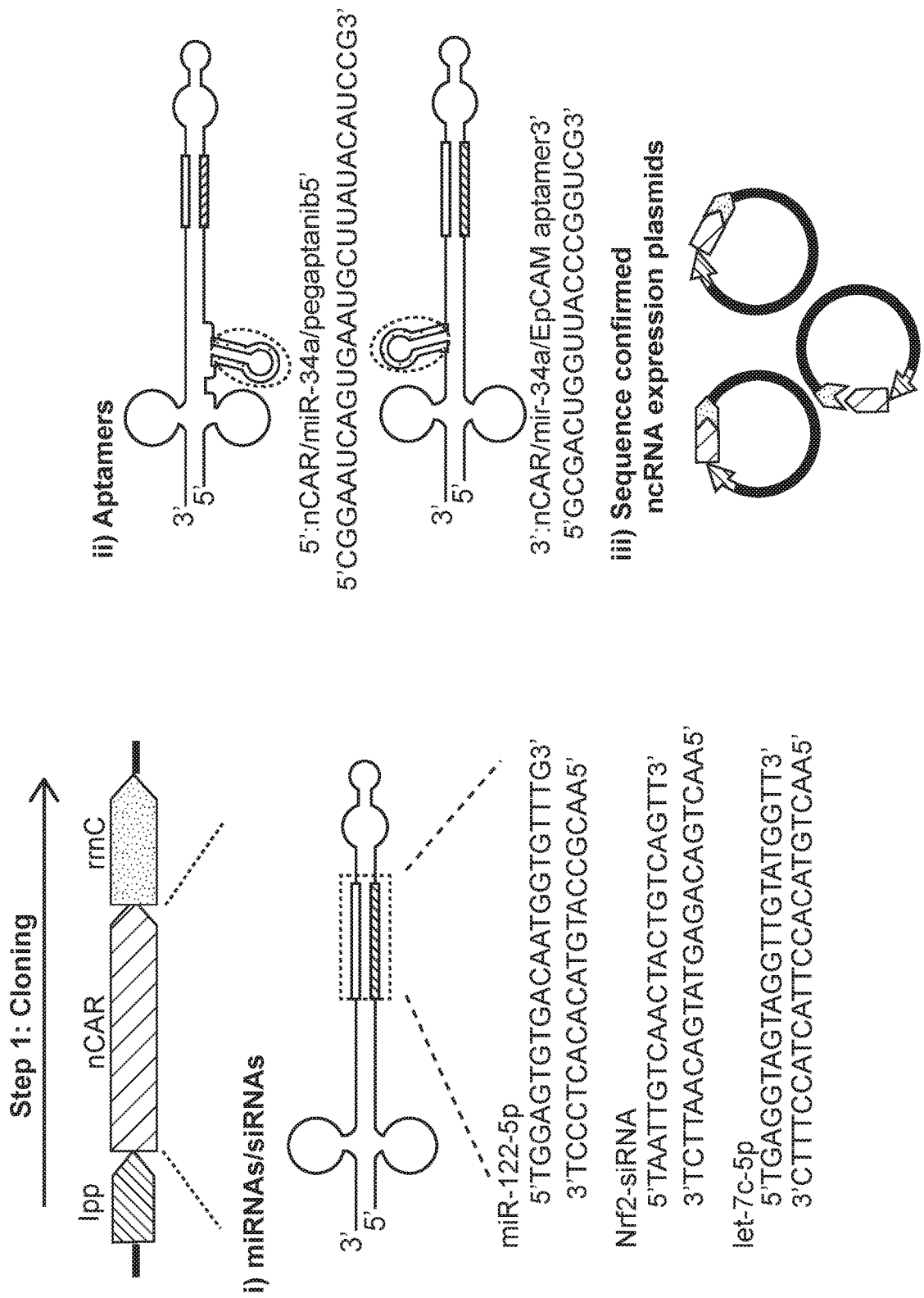

| Cell line | Control | | nCAR/miR-34a-5p | | nCAR/miR-124-3p | |
|---|---|---|---|---|---|---|
| | EC50 (nM) | Hill slope | EC50 (nM) | Hill slope | EC50 (nM) | Hill slope |
| A549 | 26.5 ± 1.06 | 1.46 ± 0.14 | 14.8 ± 1.04*** | 2.24 ± 0.19** | 12.6 ± 1.03*** | 2.09 ± 0.13* |
| H23 | 15.7 ± 1.03 | 3.27 ± 0.26 | 9.93 ± 1.05*** | 3.02 ± 0.43 | 9.96 ± 1.03*** | 3.55 ± 0.39 |
| H1299 | 32.5 ± 1.05 | 2.12 ± 0.21 | 18.6 ± 1.06*** | 1.87 ± 0.19 | 14.4 ± 1.04*** | 1.93 ± 0.14 |
| H1650 | 10.8 ± 1.02 | 7.42 ± 1.43 | 5.54 ± 1.01** | 4.79 ± 0.30 | 4.54 ± 1.06*** | 2.63 ± 0.33** |
| H1975 | 10.2 ± 1.06 | 2.25 ± 0.29 | 7.80 ± 1.04 | 2.67 ± 0.23 | 5.22 ± 1.02** | 2.00 ± 0.07 |

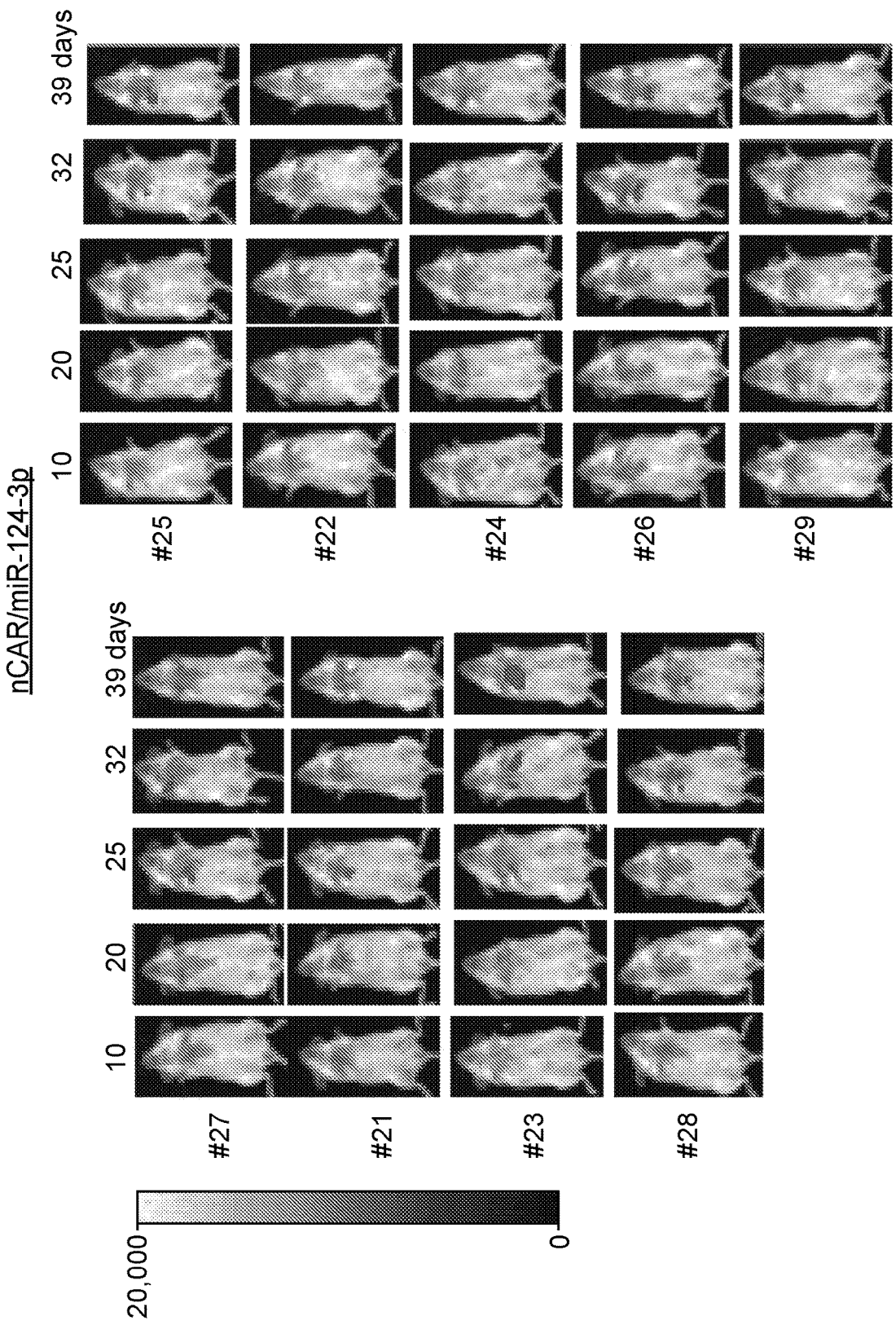

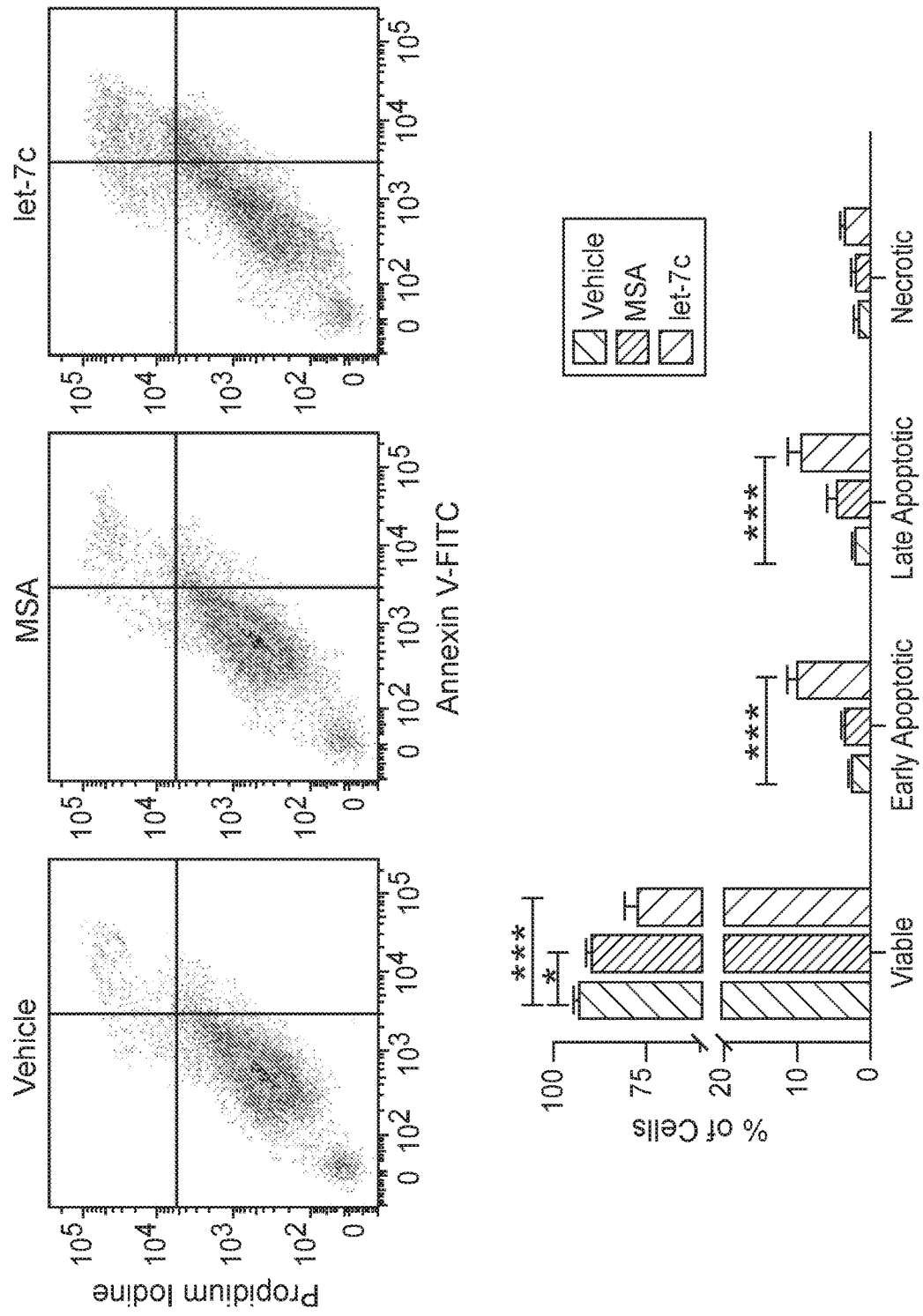

Primary Tumorspheres

Secondary Tumorspheres

Size:
102.4±5.9 nm

PDI: 0.245±0.012

Zeta Potential:
45.1±1.2 mV

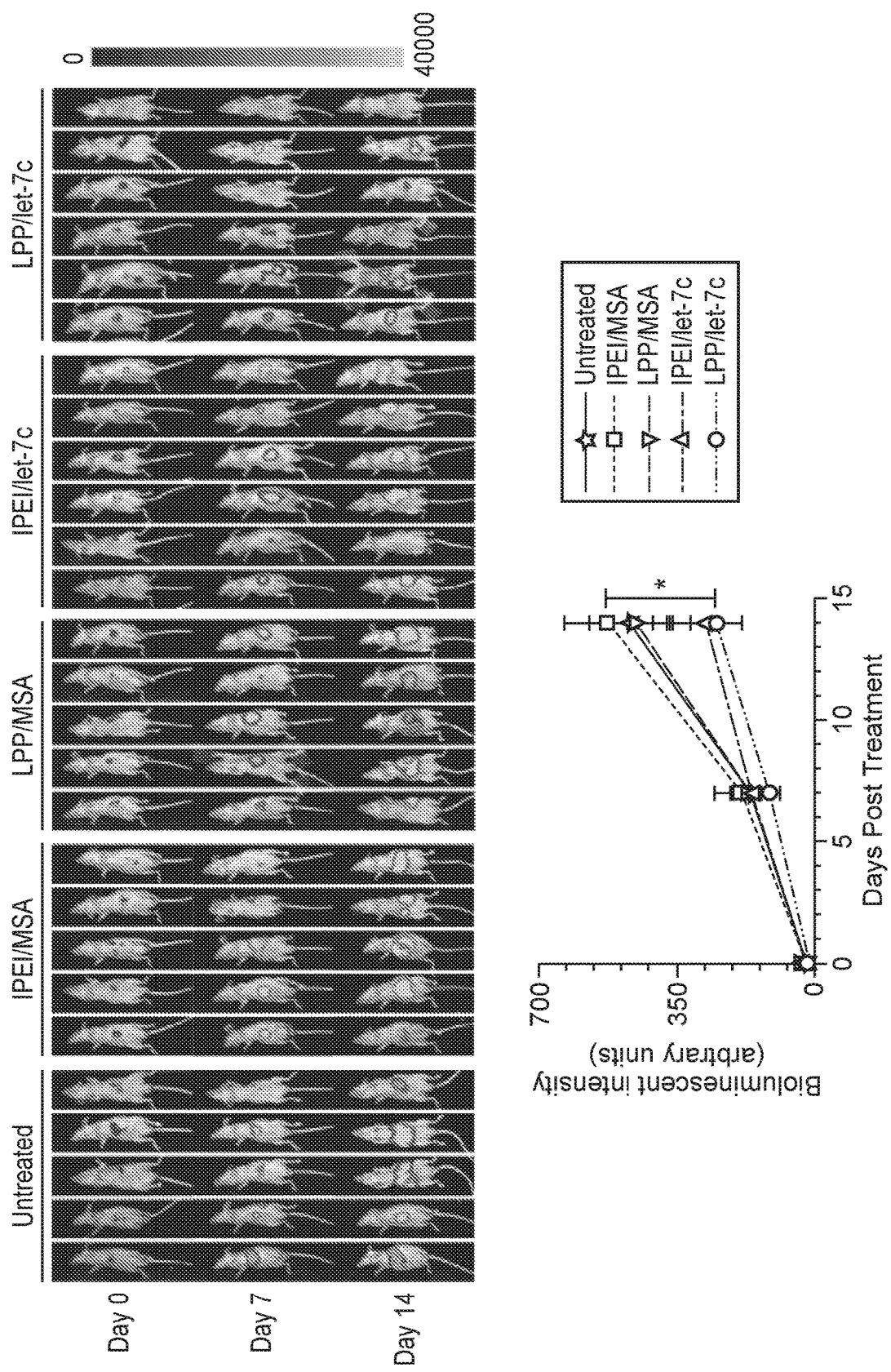

LPP/MSA

LPP/let-7c

Human PBMCs

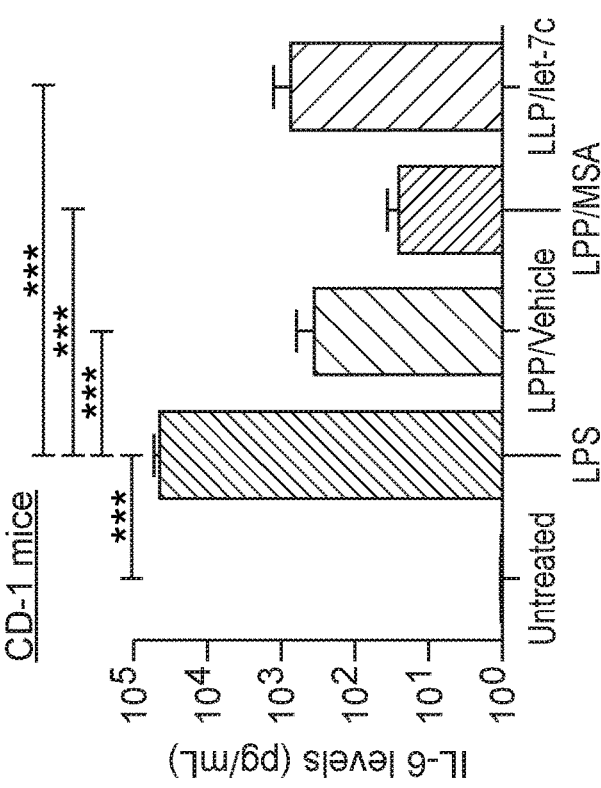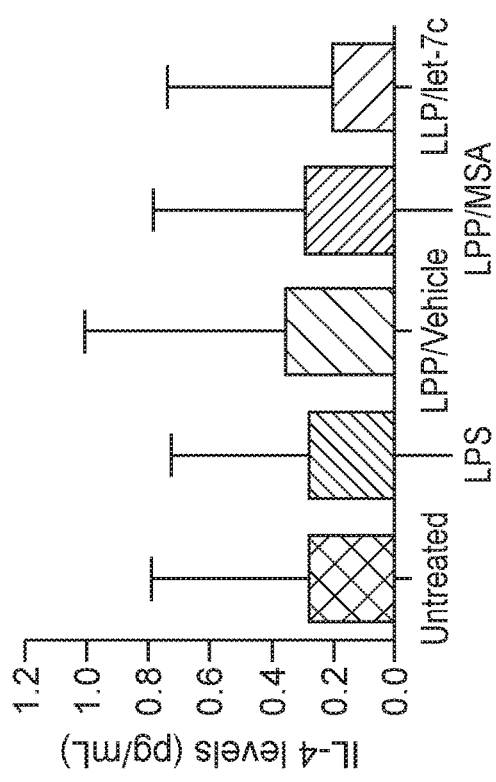
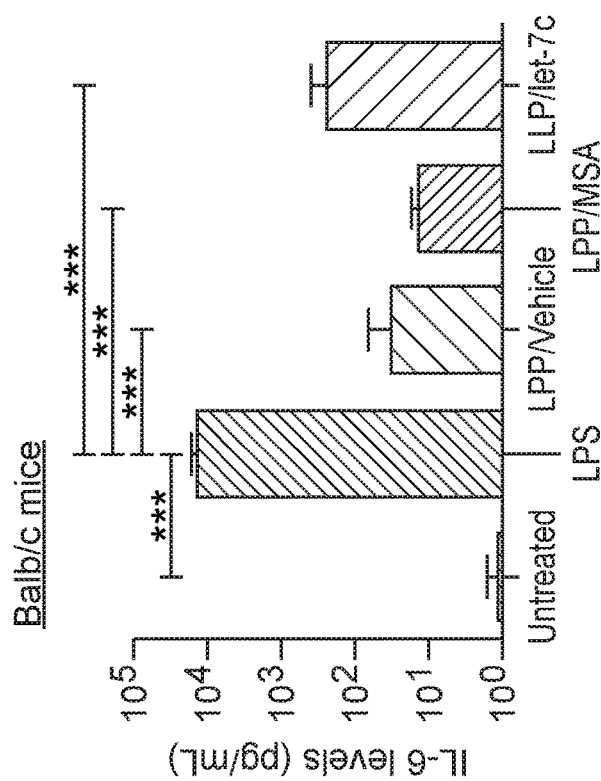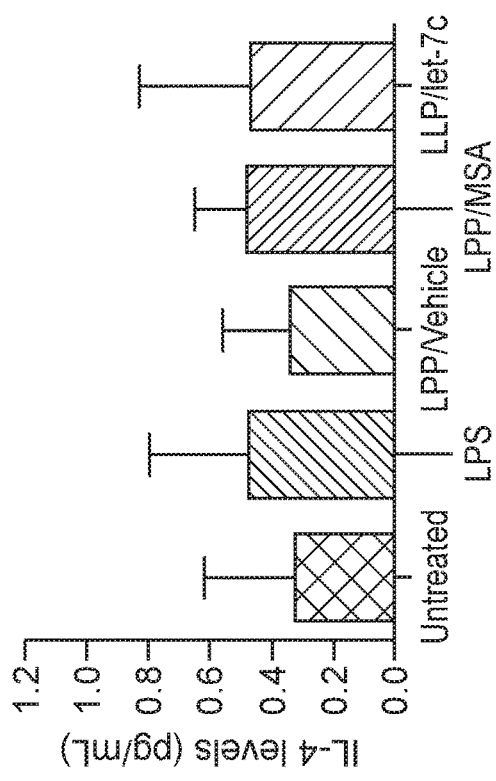
FIG. 26B
FIG. 26C

FIG. 32E

| Cell line | Drug | EC50 (nM) | Top (%) | Bottom (%) | Hill slope | Goodness of fit ($R^2$) |
|---|---|---|---|---|---|---|
| AsPC-1 | MSA | 40.4±1.8 | 104±2.2 | 37.0±1.4 | -1.51±0.06 | 0.99 |
| | MSA/mir-1291 | 14.6±5.5** | 86.7±2.3** | 24.3±1.8** | -1.18±0.41 | 0.97 |
| PANC-1 | MSA | 155±33 | 95.8±0.9 | 49.4±1.4 | -0.94±0.17 | 0.98 |
| | MSA/mir-1291 | 52.3±20.3* | 86.7±2.0** | 40.0±3.0* | -0.94±0.56 | 0.94 |

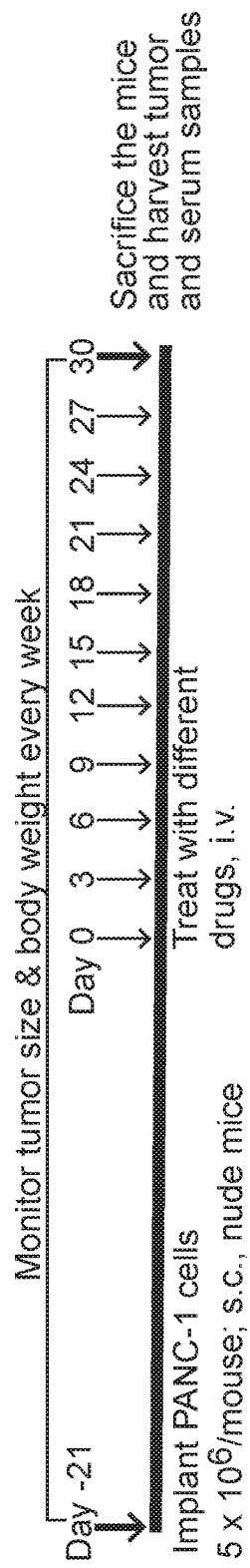
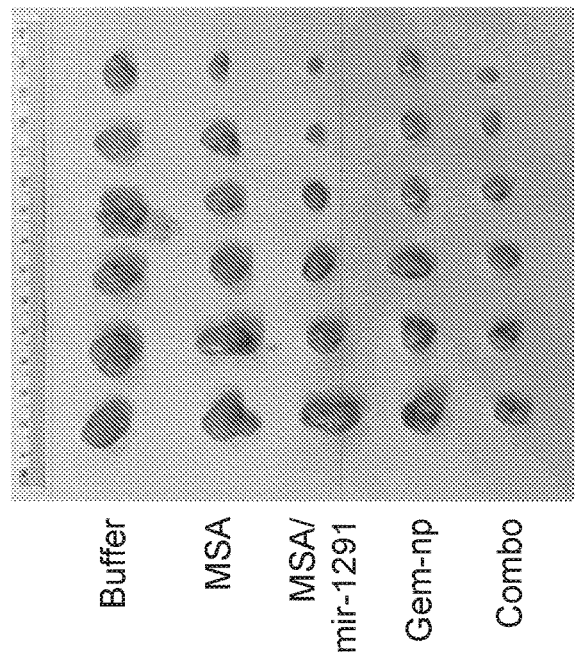
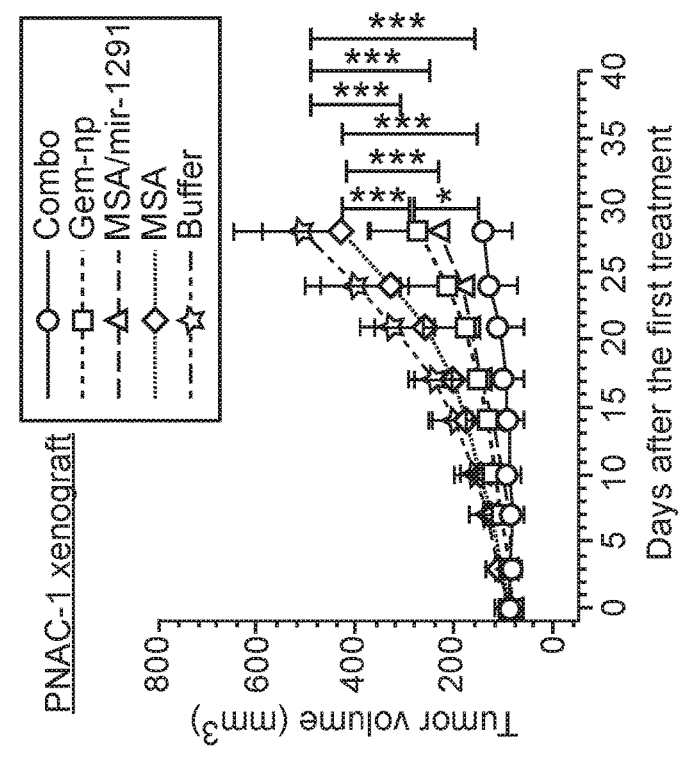
FIG. 33A
FIG. 33C
FIG. 33B

PANC-1 xenograft

PDX: PA-0387

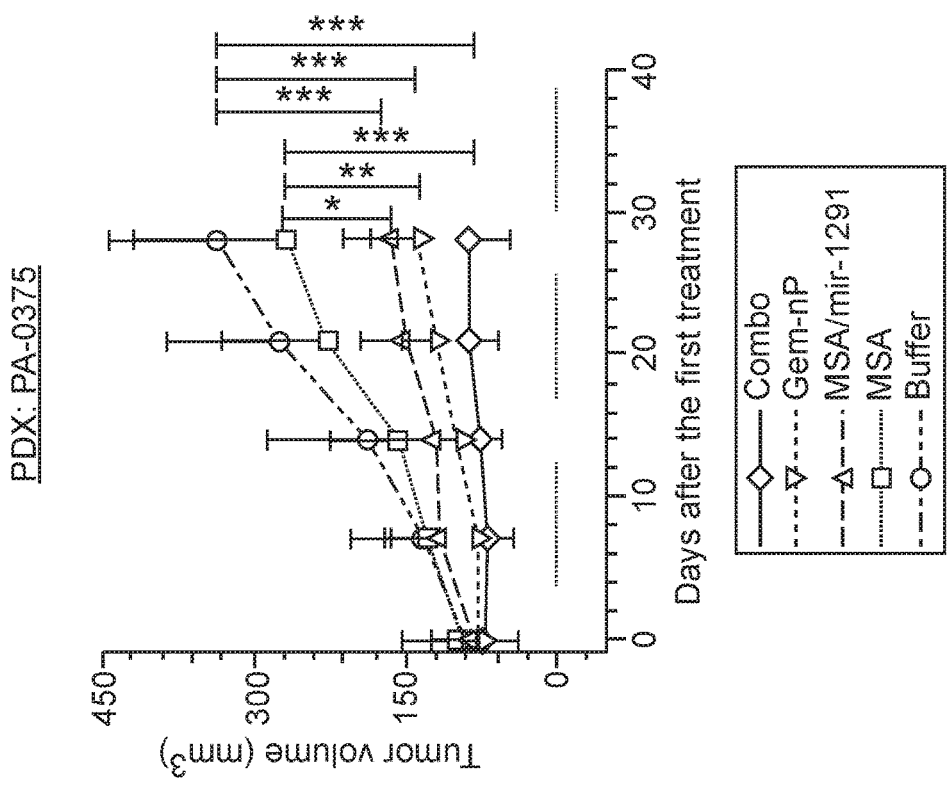
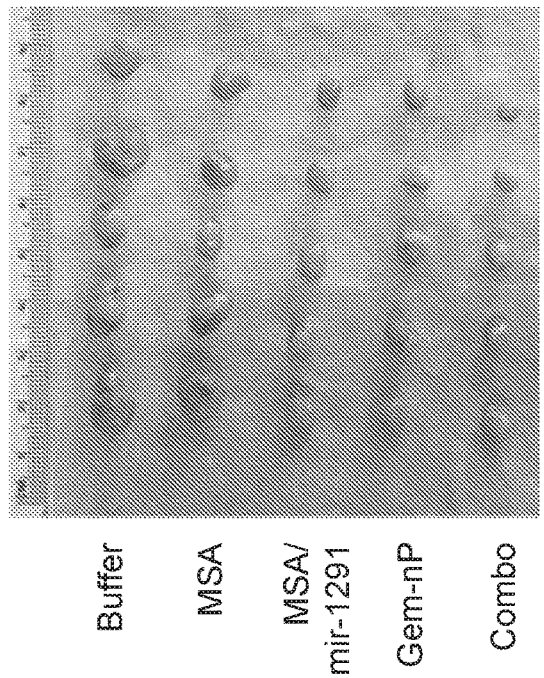
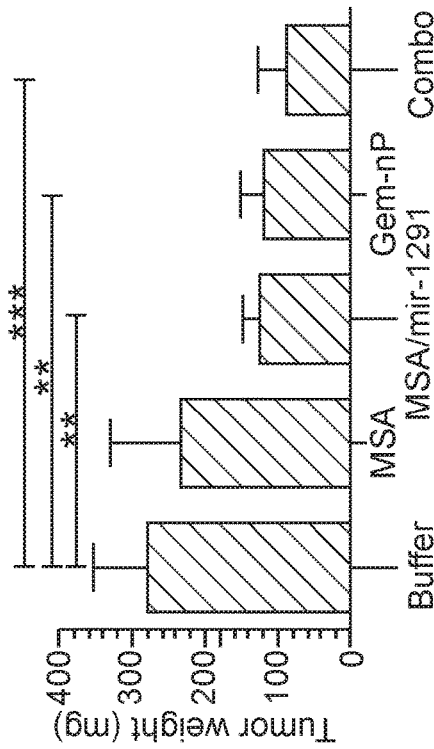
FIG. 37A
FIG. 37B
FIG. 37C

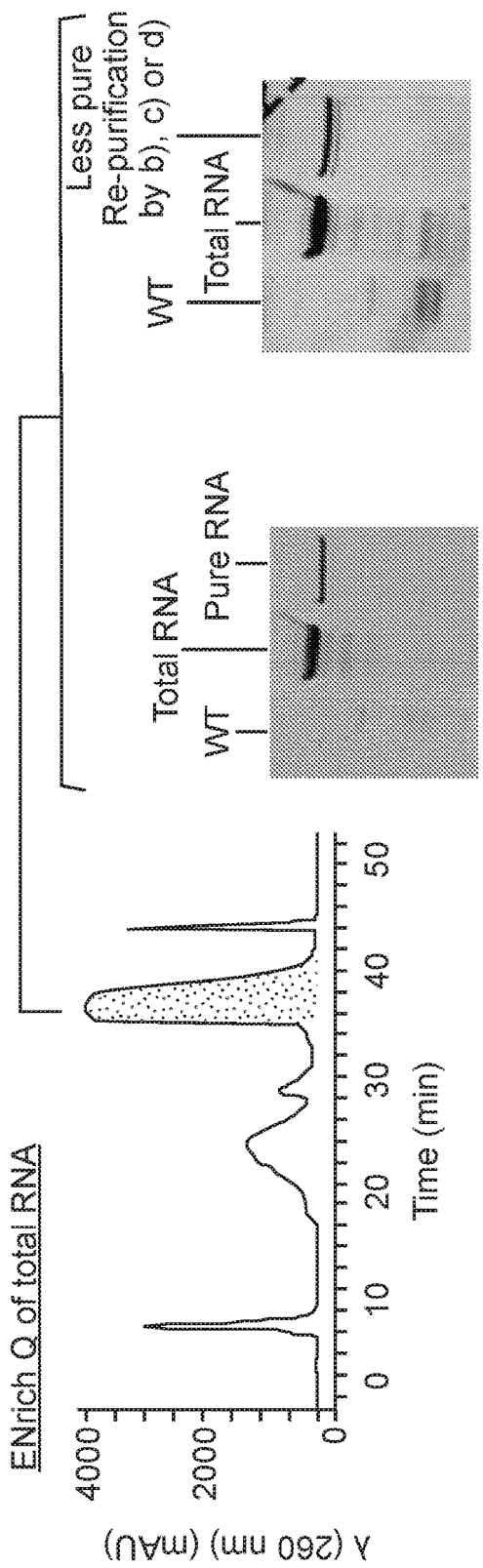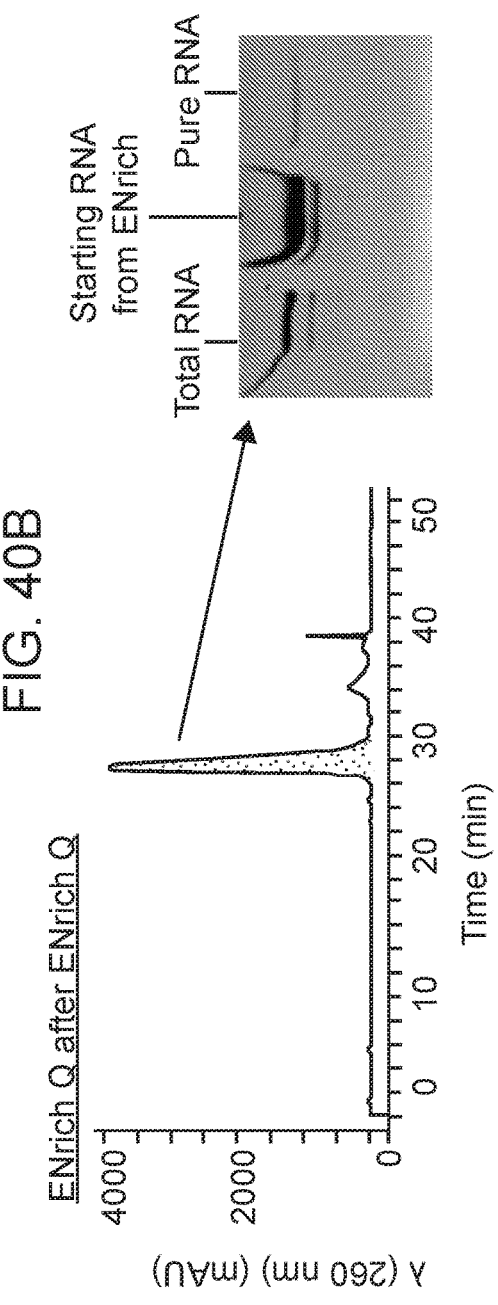
FIG. 40A
FIG. 40B

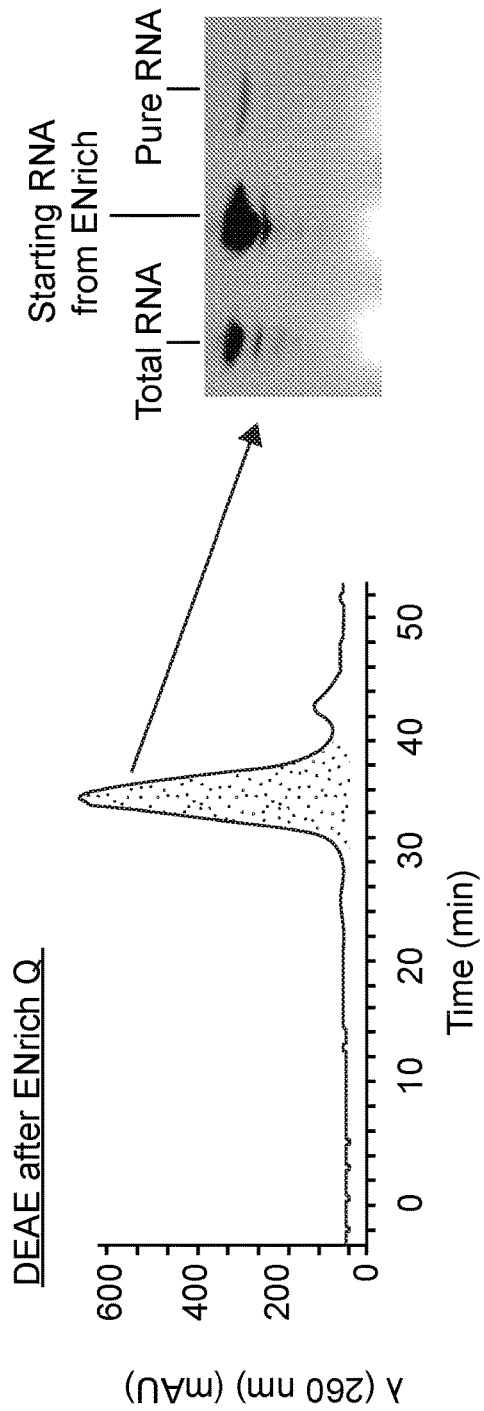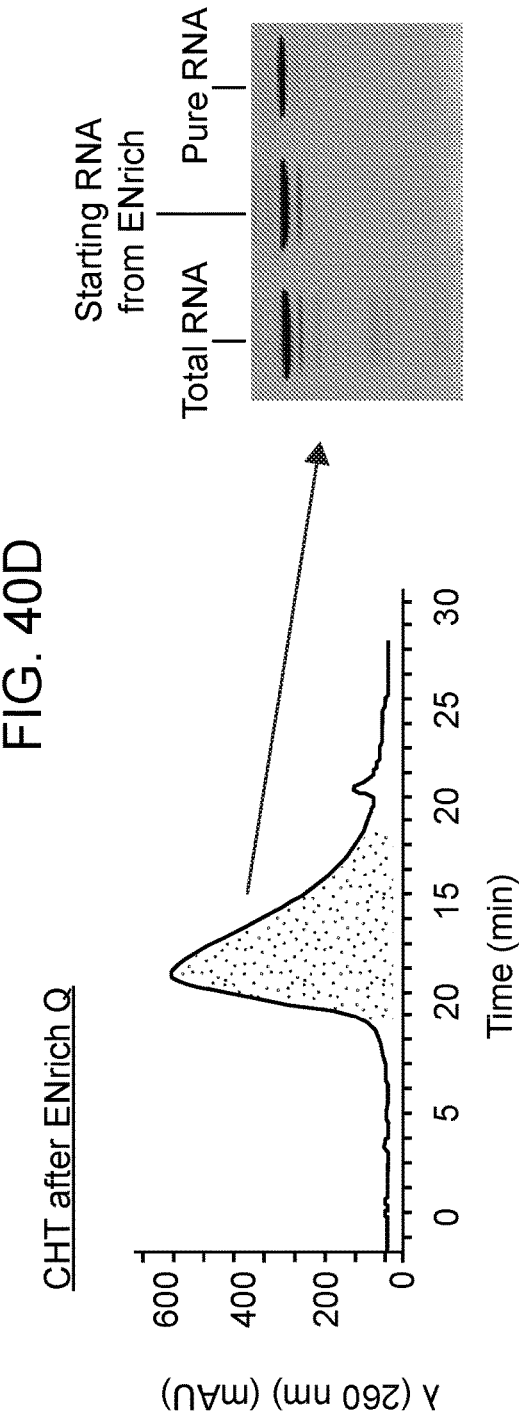

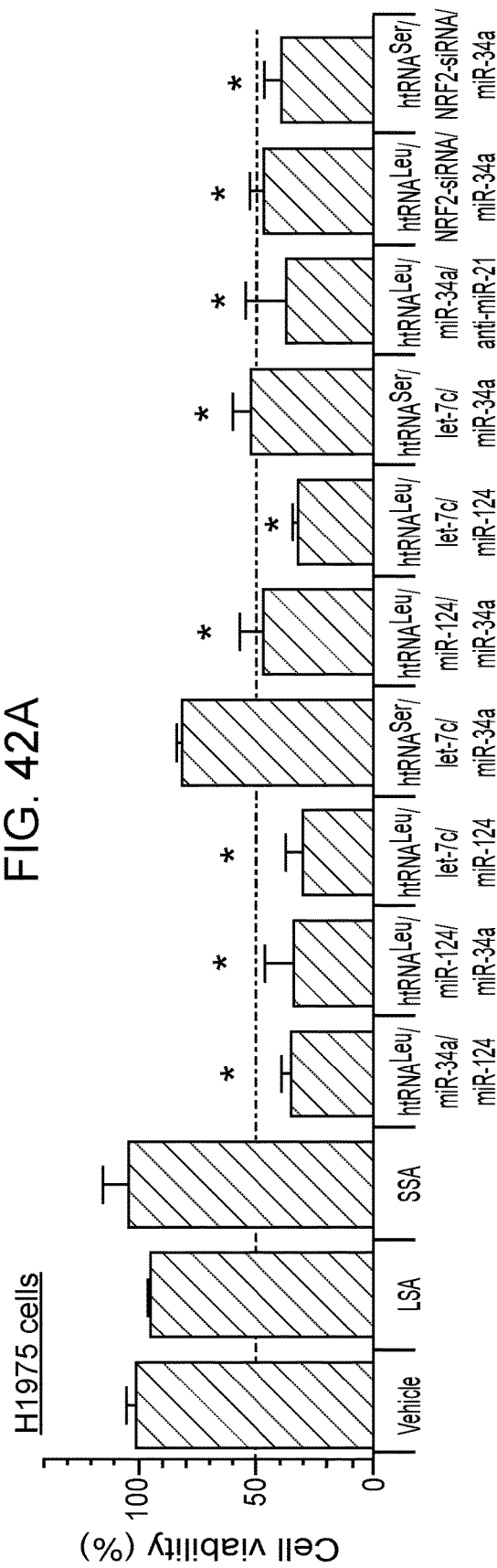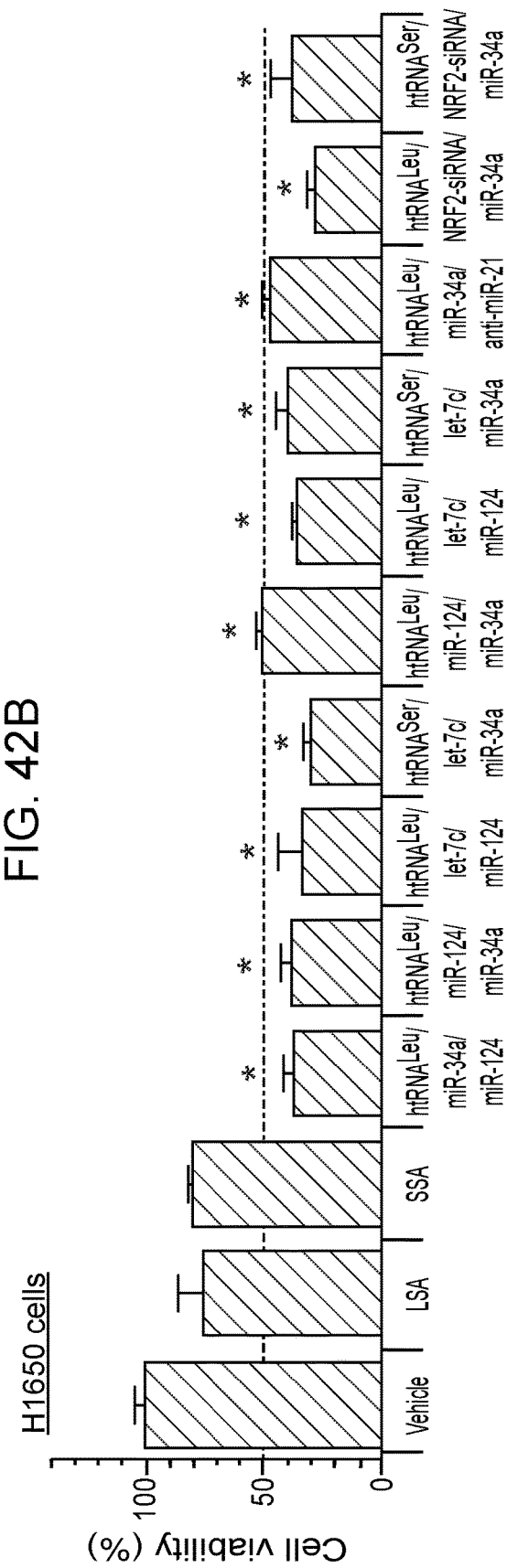

TRNA/PRE-MIRNA COMPOSITIONS AND USE IN TREATING CANCER

CROSS-REFERENCE TO RELATED APPLICATIONS

This application claims the benefit of U.S. Provisional Patent Application No. 62/674,939, filed May 22, 2018, which application is incorporated herein by reference in its entirety.

STATEMENT OF GOVERNMENTAL SUPPORT

This invention was made with government support under Grant Nos. R01GM113888, R35GM140835 and U01CA175315, awarded by the National Institutes of Health. The government has certain rights in the invention.

INCORPORATION BY REFERENCE OF SEQUENCE LISTING

A Sequence Listing is provided herewith as a text file, "UCDV-355 Seq List ST25.txt," created on Jan. 27, 2023 and having a size of 194,123 bytes. The contents of the text file are incorporated by reference herein in their entirety.

BACKGROUND

Noncoding RNAs such as miRNAs play important roles in the regulation of target gene expression underlying various cellular processes, and dysregulation of ncRNAs is highly associated with human diseases including cancer (Cech and Steitz, 2014; Rupaimoole and Slack, 2017; Thyagarajan et al., 2018). While the actions of ncRNAs have been extensively studied, our knowledge might not fully encompass these molecules on a true biological level. NcRNAs currently used for biomedical research are produced primarily by chemical synthesis and decorated extensively with a wide array of artificial modifications (Corey, 2007; Bramsen and Kjems, 2012; Khvorova and Watts, 2017). Such chemically-engineered/synthesized ncRNA agents from different manufacturers and laboratories vary broadly in the types, sites and degrees of artificial modifications, and thus likely have distinct higher-order structures, physicochemical properties, biological/pharmacological activities and safety profiles. Therefore, chemo-engineered ncRNA molecules may not represent the properties of natural ncRNAs produced within live cells (Ho and Yu, 2016; Pereira et al., 2017). Recognized as foreign invaders by specific factors such as toll-like receptors (Hornung et al., 2005; Robbins et al., 2009), synthetic ncRNAs have been well documented to cause off-target effects and induce immunogenicity, which also vary broadly with different chemical modifications. The recent termination of Phase I clinical study on synthetic miR-34a mimic (MRX34) (Beg et al., 2017), owing to high incidence of adverse immune responses, again testifies the body's capability to distinguish chemo-engineered RNAi agents as foreign. Therefore, biological approaches such as in vitro transcription (Beckert and Masquida, 2011) and especially, bioengineering in live cells (Ponchon and Dardel, 2007; Ponchon et al., 2009; Huang et al., 2013; Li et al., 2014; Chen et al., 2015; Li et al., 2015; Wang et al., 2015; Pereira et al., 2016; Fang et al., 2017; Li et al., 2018), are highly warranted to produce natural RNA molecules that should better represent cellular ncRNA properties for basic research and experimental therapy (Ho and Yu, 2016; Pereira et al., 2017).

Efforts have been made to produce biological ncRNAs via fermentation, whereas at a low yield or success rate. The use of p19 RNA-binding protein (Huang et al., 2013) offers a way to produce fully-processed siRNAs in *E. coli*; however, the low yield (e.g., 10-80 µg per liter bacterial culture) makes this method impractical for the production of milligram quantities of RNAi agents. Utilization of tRNA scaffold (Ponchon and Dardel, 2007; Ponchon et al., 2009) may facilitate large-scale (e.g., up to 20 mg per liter fermentation) production of ncRNAs; nevertheless, adoption of this method revealed that less than 20% of target ncRNAs could actually be expressed at isolatable levels (e.g., >3% of total RNAs) (Chen et al., 2015). Our recent efforts to produce recombinant pre-miRNA (mir) have demonstrated ample expression (10-20% of total RNAs) of a hybrid ncRNA molecule in *E. coli*, namely pre-miR-34a and tRNAMet fused Sephadex aptamer (MSA) (MSA/mir-34a) (Chen et al., 2015). Although MSA/mir-34a can be used as a versatile scaffold, the success rate for producing isolatable target ncRNAs is still less than 30%, and the dependence on Sephadex aptamer is unknown.

Here, we first report the development of a more stable and reliable ncRNA carrier (nCAR) for rapid production of milligrams of target ncRNA agents at an enormously higher expression level (40-80% of total RNAs) and success rate (~80%; 33 out of 42 target ncRNAs). We further established a readily adaptable pipeline for both small- and large-scale production of bioengineered ncRNAs, which we applied to generate a collection of ready-to-use biologic ncRNA molecules. Using two nCAR/miRNAs as examples, we further demonstrate that bioengineered miRNA agents, with intrinsic RNA properties for specific processing to target miRNAs, were able to selectively rewrite miRNome profiles and alter transcriptome of human cells, leading to antiproliferative properties against human lung carcinoma cells in vitro and antitumor activities in xenograft mouse models in vivo.

SUMMARY

In one aspect, provided is a polynucleotide comprising a tRNA operably linked to two or more pre-microRNA (pre-miRNA) molecules, e.g., a first pre-miRNA and a second pre-miRNA, wherein each of the two or more pre-miRNA are operably linked to an inserted RNA molecule. In some embodiments, the inserted RNA molecules are heterologous to the first and/or the second pre-miRNA. In some embodiments, all or part of the stem-loop anticodon of the tRNA is replaced with the first or the second pre-miRNA. In some embodiments, the inserted RNA molecule is inserted at, abutted with or operably linked to: a) the 5' end of the first and/or the second pre-miRNA; b) the 3' end of the first and/or the second pre-miRNA; c) the 5' of a dicer or RNase cleavage site of the first and/or the second pre-miRNA; or d) the 3' of a dicer or RNase cleavage site of the first and/or the second pre-miRNA. In some embodiments, the polynucleotide is from about 275 nucleotides, e.g., from about 280 nucleotides, e.g., from about 290 nucleotides and up to about 400 nucleotides in length. In some embodiments, the tRNA is a tRNA derived from coding for an amino acid selected from the group consisting of serine, leucine, glycine, glutamate, aspartate, glutamine, arginine, cysteine, lysine, methionine, asparagine, alanine, histidine, isoleucine, phenylalanine, proline, tryptophan, tyrosine, threonine, and valine. In some embodiments, the RNA coding for the tRNA comprises a 5' tRNA sequence and a 3' tRNA sequence having at least about 90%, 91%, 92%, 93%, 94%, 95%, 96%, 97%, 98%, 99% or 100% sequence identity to SEQ ID NOs: 300-355, e.g., 300/301, 302/303, 304/305, 306/307, 308/309, 310/311, 312/313, 314/315, 316/317, 318/319, 320/321, 322/323, 324/325, 326/32, 328/329, 330/331, 332/333, 334/335, 336/337, 338/339, 340/341, 342/343, 344/345, 346/347, 348/349, 350/351, 352/353, 354/355, as provided in Table 8. In some embodiments, the tRNA is a mammalian tRNA, e.g., a human tRNA. In some embodiments, the two or more pre-microRNA are derived from human pre-miRNA molecules. In some embodiments, two or more pre-miRNA are selected from the group consisting of pre-miR-34a, pre-miR-124, pre-miR-1291, pre-miR-200b, pre-miR-200a, pre-miR-141, pre-miR-429, pre-miR-133a, pre-let-7c, pre-miR-125a, pre-miR-328, pre-miR-126, pre-miR-298, pre-miR-148, pre-miR-144, pre-miR-1, pre-miR-133, pre-miR-888, pre-miR-6775, pre-miR-374, pre-miR-92, pre-miR-1180, pre-miR-218, pre-miR-7, pre-miR-378, pre-miR-17, pre-miR-18a, pre-miR-22, pre-miR-122, pre-miR-30b, pre-miR-449, pre-miR-506, pre-miR-98, pre-miR-4458, pre-miR-206, pre-miR-519, pre-miR-93, pre-miR-106, pre-miR-373, and pre-miR-520. In some embodiments, the two or more pre-miRNA are derived from the same pre-miRNA molecules. In some embodiments, the two or more pre-miRNA are derived from human pre-miR-34a molecules. In some embodiments, the two or more pre-miRNA are derived from different pre-miRNA molecules. In some embodiments, the inserted RNA is selected from the group consisting of a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), a guide RNA (gRNA), an antisense RNA (asRNA), a small activating RNA (saRNA), a catalytic RNA, a riboswitch, an RNA aptamer. In some embodiments, the inserted RNA has at least about 18 nucleotides and up to about 200 nucleotides, e.g., has at least about 18 nucleotides and up to about 50 nucleotides, e.g., has at least about 20 nucleotides and up to about 25 nucleotides, e.g., has 20, 21, 22, 23, 24, 25 nucleotides. In some embodiments, the inserted RNA is a mature miRNA. In some embodiments, the inserted RNA is a mature miRNA selected from the group consisting of let-7c, miR-298, miR-216, miR-34a, miR-124, miR-328, miR-144, miR-126, miR-16, miR-18, miR-125a, miR-195, miR-199a, miR-200, miR-224, miR-1291, miR-429, miR-148, miR-144, miR-1, miR-133, miR-888, miR-6775, miR-374, miR-92, miR-1180, miR-218, miR-7, miR-378, miR-17, miR-18a, miR-22, miR-122, miR-30b, miR-449, miR-506, miR-98, miR-4458, miR-206, miR-519, miR-93, miR-106, miR-373, and miR-520. In some embodiments, the inserted RNA in the two or more pre-miRNA are the same or different. In some embodiments, the inserted RNA are selected from the group consisting of let-7c, miR-1291, miR-200, miR-92, miR-34a and miR-124. In some embodiments, the inserted RNA are mature miRNA selected from the group consisting of miR-1291, miR-34, miR-124, miR-200, and miR-216. In some embodiments, the inserted RNA are mature miRNA selected from the group consisting of let-7c, miR-298, miR-216, miR-124, miR-328, miR-144, miR-126, miR-16, miR-18, miR-125a, miR-195, miR-199a, miR-200, and miR-224. In some embodiments, the tRNA, the first pre-miRNA and/or the second pre-miRNA are operably linked to one or more aptamers, small activating RNAs (saRNAs), or catalytic RNAs. In some embodiments, the aptamer, saRNA or catalytic RNA is inserted at, abutted with or operably linked to: a) the 5' end of the first and/or the second pre-miRNA; b) the 3' end of the first and/or the second pre-miRNA; c) 5' of a dicer or RNase cleavage site of the first and/or the second pre-miRNA; or d) 3' of a dicer or RNase cleavage site of the first and/or the second pre-miRNA. In some embodiments, the aptamer binds to a target antigen selected from the group consisting of sephedex, EpCAM, VEGF, fms related tyrosine kinase 1 (FLT1), theophylline, malachite green, HCC-22-5, keratin 23 (KRT23), alpha 2-HS glycoprotein (AHSG), ferritin light chain (FTL), MAGE-A1, MAGE-A3/4, NY-ESO-1, 14-3-3ζ, c-Myc, MDM2, NPM1, p16, p53, cyclin B1, KIF20A, MUC1, CA 19-9, DU-PAN-2, TAG-72, cadherin 3 (CDH3)/P-cadherin, Receptor-binding cancer antigen expressed on SiSo cells (RCAS1), and SC6. In some embodiments, the aptamer comprises a nucleic acid sequence comprising at least about 90%, 91%, 92%, 93%, 94%, 95%, 96%, 97%, 98%, 99% or 100% sequence identity to one of SEQ ID NOs: 356-359. In some embodiments, the pre-miRNA is naturally or artificially derived. In some embodiments, the polynucleotide comprises at least about 90%, 91%, 92%, 93%, 94%, 95%, 96%, 97%, 98%, 99% or 100% sequence identity to any one of SEQ ID NOs: 183-210, 265-288 and 296-298. In some embodiments, the polynucleotide is substantially non-immunogenic to a mammal.

In a further aspect, provided are polynucleotides comprising a tRNA operably linked to a pre-miRNA, wherein the polynucleotide comprises at least about 90%, 91%, 92%, 93%, 94%, 95%, 96%, 97%, 98%, 99% or 100% sequence identity to any one of SEQ ID NOs: 85-182 and 211-264. In another aspect, provided are polynucleotides comprising a human tRNA operably linked to a pre-miRNA comprising an inserted RNA molecule, e.g., that is heterologous to the pre-miRNA, wherein the polynucleotide comprises at least about 90%, 91%, 92%, 93%, 94%, 95%, 96%, 97%, 98%, 99% or 100% sequence identity to any one of SEQ ID NOs: 289-295. In some embodiments, all or part of the stem-loop anticodon of the tRNA is replaced with the pre-miRNA. In some embodiments, the polynucleotide is from about 150 nucleotides, e.g., from about 160 nucleotides, e.g., from about 170 nucleotides, e.g., from about 180 nucleotides, and up to about 230 nucleotides in length. In some embodiments, the tRNA is a tRNA derived from coding for an amino acid selected from the group consisting of serine, leucine, glycine, glutamate, aspartate, glutamine, arginine, cysteine, lysine, methionine, asparagine, alanine, histidine, isoleucine, phenylalanine, proline, tryptophan, tyrosine, threonine, and valine. In some embodiments, the RNA coding for the tRNA comprises a 5' tRNA sequence and a 3' tRNA sequence having at least about 90%, 91%, 92%, 93%, 94%, 95%, 96%, 97%, 98%, 99% or 100% sequence identity to SEQ ID NOs: 300-355, e.g., 300/301, 302/303, 304/305, 306/307, 308/309, 310/311, 312/313, 314/315, 316/317, 318/319, 320/321, 322/323, 324/325, 326/32, 328/329, 330/331, 332/333, 334/335, 336/337, 338/339, 340/341, 342/343, 344/345, 346/347, 348/349, 350/351, 352/353, 354/355, as provided in Table 8. In some embodiments, the tRNA is a mammalian tRNA, e.g., a human tRNA. In some embodiments, the inserted RNA is selected from the group consisting of a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), a guide RNA (gRNA), an antisense RNA (asRNA), a small activating RNA (saRNA), a catalytic RNA, a riboswitch, and an RNA aptamer. In some embodiments, the inserted RNA has at least about 18 nucleotides and up to about 200 nucleotides, e.g., has at least about 18 nucleotides and up to about 50 nucleotides, e.g., has at least about 20 nucleotides and up to about 25 nucleotides, e.g., has 20, 21, 22, 23, 24, 25 nucleotides. In some embodiments, the inserted RNA is a mature miRNA. In some embodiments, the inserted RNA is a mature miRNA selected from the group consisting of let-7c, miR-298, miR-216, miR-34a, miR-124, miR-328, miR-144, miR-126, miR-16, miR-18, miR-125a, miR-195, miR-199a, miR-200, miR-224, miR-1291, miR-429, miR-148, miR-144, miR-1, miR-133, miR-888, miR-6775, miR-374, miR-92, miR-1180, miR-218, miR-7, miR-378, miR-17, miR-18a, miR-22, miR-122, miR-30b, miR-449, miR-506, miR-98, miR-4458, miR-206, miR-519, miR-93, miR-106, miR-373, and miR-520. In some embodiments, the tRNA, the first pre-miRNA and/or the second pre-miRNA are operably linked to one or more aptamers, small activating RNAs (saRNAs), or catalytic RNAs. In some embodiments, the aptamer, saRNA or catalytic RNA is inserted at, abutted with or operably linked to: a) the 5' end of the first and/or the second pre-miRNA; b) the 3' end of the first and/or the second pre-miRNA; c) 5' of a dicer or RNase cleavage site of the first and/or the second pre-miRNA; or d) 3' of a dicer or RNase cleavage site of the first and/or the second pre-miRNA. In some embodiments, the aptamer binds to a target antigen selected from the group consisting of sephedex, EpCAM, VEGF, fms related tyrosine kinase 1 (FLT1), theophylline, malachite green, HCC-22-5, keratin 23 (KRT23), alpha 2-HS glycoprotein (AHSG), ferritin light chain (FTL), MAGE-A1, MAGE-A3/4, NY-ESO-1, 14-3-3ζ, c-Myc, MDM2, NPM1, p16, p53, cyclin B1, KIF20A, MUC1, CA 19-9, DU-PAN-2, TAG-72, cadherin 3 (CDH3)/P-cadherin, Receptor-binding cancer antigen expressed on SiSo cells (RCAS1), and SC6. In some embodiments, the aptamer comprises a nucleic acid sequence comprising at least about 90%, 91%, 92%, 93%, 94%, 95%, 96%, 97%, 98%, 99% or 100% sequence identity to one of SEQ ID NOs: 356-359. In some embodiments, the polynucleotide comprises at least about 90%, 91%, 92%, 93%, 94%, 95%, 96%, 97%, 98%, 99% or 100% sequence identity to SEQ ID NOs:85-298. In some embodiments, the pre-miRNA is naturally or artificially derived. In some embodiments, the polynucleotide is substantially non-immunogenic to a mammal.

In a further aspect, provided is an expression cassette comprising a polynucleotide encoding a tRNA/pre-miRNA hybrid molecule, as described above and herein. In a further aspect, provided is a viral vector comprising a polynucleotide encoding a tRNA/pre-miRNA hybrid molecule, or an expression cassette comprising such a polynucleotide, as described above and herein. In some embodiments, the viral vector is an adenovirus, adeno-associated virus, or lentivirus.

In a further aspect, provided is a liposome or a nanoparticle comprising a polynucleotide encoding a tRNA/pre-miRNA hybrid molecule, or an expression cassette comprising such a polynucleotide, as described above and herein. In some embodiments, the liposome comprises an inner core comprising a polynucleotide encoding a tRNA/pre-miRNA hybrid molecule, as described above and herein, complexed with a polyethylenimine (PEI) and an outer lipid bilayer. In some embodiments, the inner core comprises a liposomal-branched polyethylenimine (PEI) polyplex (LPP), e.g., having a molecular weight of about 10,000 daltons. In some embodiments, the outer lipid bilayer of the liposome comprises a mixture of 1,2-di-O-octadecenyl-3-trimethylammonium propane (DOTMA), cholesterol and 1,2-Dimyristoyl-sn-glycerol, methoxypolyethylene glycol (DMG-PEG2000).

In a further aspect, provided is a host cell transfected or transformed with a polynucleotide encoding a tRNA/pre-miRNA hybrid molecule, or an expression cassette, viral vector or liposome/nanoparticle comprising such a polynucleotide, as described above and herein. In some embodiments, the host cell is a prokaryotic cell or a eukaryotic cell. In some embodiments, the host cell is selected from a bacterial cell, a mammalian cell, an insect cell or a plant cell.

In another aspect, provided are method of preventing, mitigating, reducing, reversing and/or inhibiting the growth, proliferation, and/or progression of cancer in a subject in need thereof, comprising administering to the subject a polynucleotide encoding a tRNA/pre-miRNA hybrid molecule, or an expression cassette, viral vector or liposome/nanoparticle comprising such a polynucleotide, as described above and herein In some embodiments, the cancer is selected from the group consisting of breast cancer, lymphoma, colorectal cancer, hepatocellular carcinoma, pancreatic cancer, prostate cancer, and lung cancer. In some embodiments, the polynucleotide comprises one or more mature miRNAs selected from the group consisting of let-7c, miR-298, miR-216, miR-34a, miR-124, miR-328, miR-144, miR-126, miR-16, miR-18, miR-125a, miR-195, miR-199a, miR-200, miR-224, miR-1291, miR-429, miR-148, miR-144, miR-1, miR-133, miR-888, miR-6775, miR-374, miR-92, miR-1180, miR-218, miR-7, miR-378, miR-17, miR-18a, miR-22, miR-122, miR-30b, miR-449, miR-506, miR-98, miR-4458, miR-206, miR-519, miR-93, miR-106, miR-373, and miR-520. In some embodiments, the cancer is lung cancer and the polynucleotide comprises one or more mature miRNAs selected from the group consisting of miR-34a and miR-124. In some embodiments, the cancer is pancreatic cancer and the polynucleotide comprises one or more mature miRNAs selected from the group consisting of miR-1291, miR-34, miR-124, miR-200, and miR-216. In some embodiments, the cancer is hepatocellular carcinoma and the polynucleotide comprises one or more mature miRNAs selected from the group consisting of let-7c, miR-298, miR-216, miR-124, miR-328, miR-144, miR-126, miR-16, miR-18, miR-125a, miR-195, miR-199a, miR-200, and miR-224. In some embodiments, the methods comprise administering to the subject one or more tRNA/pre-miRNA hybrid molecules comprising at least about 90%, 91%, 92%, 93%, 94%, 95%, 96%, 97%, 98%, 99% or 100% sequence identity to SEQ ID NOs:85-298. In some embodiments, the polynucleotide, liposome or nanoparticle is administered via a route selected from intravenously, intraarterially, intraperitoneally, intraperitoneally, intrapulmonarily, intrahepatically, subcutaneously or intratumorally. In some embodiments, a therapeutic regimen of the polynucleotide, liposome or nanoparticle is administered is administered multiple times, e.g., daily, weekly, bi-weekly, monthly, e.g., until a predetermined or desired endpoint is reached. In some embodiments, the subject is exhibiting symptoms of cancer, e.g., has one or more tumors. In some embodiments, the subject is in remission and is at risk of redeveloping tumors. In some embodiments, the methods comprise co-administration of one or more chemotherapeutic or anticancer agents, e.g., gemcitibine. In some embodiments, the subject is tested for the overexpression or underexpression of one or more miRNAs prior to administration.

In another aspect, provided are kits comprising a polynucleotide, expression cassette, liposome, polymer, nanoparticle, viral vector and/or host cell, as described above and herein.

Definitions

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Green and Sambrook et al. Molecular Cloning: A Laboratory Manual, 4th ed., Cold Spring Harbor Laboratory Press, Cold Spring Harbor, N.Y. (2012) and Ausubel, ed., Current Protocols in Molecular Biology, John Wiley Interscience, (1990-2018)), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

The term "polynucleotide" refers to polymers composed of deoxyribonucleotides, ribonucleotides or any combination thereof.

As used herein, the term "nucleotide" refers to a chemical moiety having a sugar (modified, unmodified, or an analog thereof), a nucleotide base (modified, unmodified, or an analog thereof), and a phosphate group (modified, unmodified, or an analog thereof). Nucleotides include deoxyribonucleotides, ribonucleotides, and modified nucleotide analogs including, for example, locked nucleic acids ("LNAs"), peptide nucleic acids ("PNAs"), L-nucleotides, ethylene-bridged nucleic acids ("EN As"), arabinoside, and nucleotide analogs (including abasic nucleotides). Similarly, "nucleic acid," "nucleotide sequence," or "nucleic acid sequence" refer to a nucleotide, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. RNA may be used in the methods described herein and/or may be converted to cDNA by reverse-transcription and/or RNA for use in the methods described herein.

As used herein interchangeably, a "microRNA," "miR," or "miRNA" refer to the unprocessed or processed RNA transcript from a miRNA gene. The unprocessed miRNA gene transcript is also called a "miRNA precursor," and typically comprises an RNA transcript of about 70-100 nucleotides in length. The miRNA precursor can be processed by digestion with an RNAse (for example, Dicer, Argonaut, or RNAse III) into an active 19-25 nucleotide RNA molecule. This active 19-25 nucleotide RNA molecule is also called the "processed" miRNA gene transcript or "mature" miRNA.

The terms "pre-microRNA" or "pre-miR" or pre-miRNA" interchangeably refer to an RNA hairpin comprising within its polynucleotide sequence at least one mature micro RNA sequence and at least one dicer cleavable site.

The terms "identical" or percent "identity," in the context of two or more nucleic acids or polypeptide sequences, refer to two or more sequences or subsequences that are the same or have a specified percentage of amino acid residues or nucleotides that are the same (i.e., share at least about 80% identity, for example, at least about 85%, 90%, 91%, 92%, 93%, 94%, 95%, 96%, 97%, 98%, 99% identity over a specified region to a reference sequence, e.g., the tRNA, pre-microRNA and tRNA/microRNA hybrid polynucleotide molecules described herein, e.g, SEQ ID NOs: 1-369 when compared and aligned for maximum correspondence over a comparison window, or designated region as measured using a sequence comparison algorithms (e.g., BLAST, ALIGN, FASTA or any other known alignment algorithm) or by manual alignment and visual inspection. Such sequences are then said to be "substantially identical." This definition also refers to the compliment of a test sequence. Preferably, the identity exists over a region that is at least about 10, 15, 20, 25, 35, 40, 45, 50, 60, 70, 80, 90, 100, 110, 120 nucleotides in length, or over the full-length of a reference sequence.

As used herein, the term "short interfering nucleic acid" or "siRNA" refers to any nucleic acid molecule capable of down regulating (i.e., inhibiting) gene expression in a mammalian cells (preferably a human cell). siRNA includes without limitation nucleic acid molecules that are capable of mediating sequence specific RNAi, for example short interfering RNA (siRNA), double-stranded RNA (dsRNA), micro-RNA (miRNA), and short hairpin RNA (shRNA). Likewise, the term "sense region" refers to a nucleotide sequence of a siRNA molecule complementary (partially or fully) to an antisense region of the siRNA molecule. Optionally, the sense strand of a siRNA molecule may also include additional nucleotides not complementary to the antisense region of the siRNA molecule. Conversely, as used herein, the term "antisense region" refers to a nucleotide sequence of a siRNA molecule complementary (partially or fully) to a target nucleic acid sequence. Optionally, the antisense strand of a siRNA molecule may include additional nucleotides not complementary to the sense region of the siRNA molecule.

The terms "piRNA" and "Piwi-interacting RNA" are interchangeable and refer to a class of small RNAs involved in gene silencing. PiRNA molecules typically are between 26 and 31 nucleotides in length.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against the ncRNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription of any one or more of transcription of a microRNA, siRNA, piRNA, snRNA, ncRNA, antisense nucleic acid, or mRNA from a DNA or RNA template and can further include translation of a protein from an mRNA template. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequence. Homologous regions may vary in length, but will typically be between 4 and 40 nucleotides (e.g., from about 4 to about 40, from about 5 to about 40, from about 5 to about 35, from about 5 to about 30, from about 5 to about 20, from about 6 to about 30, from about 6 to about 25, from about 6 to about 15, from about 7 to about 18, from about 8 to about 20, from about 8 to about 15, etc.).

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

A "target site" or "target sequence" is the nucleic acid sequence recognized (i.e., sufficiently complementary for hybridization) by an antisense oligonucleotide or inhibitory RNA molecule.

As used herein, the term "subject" refers to a mammal, such as a human, but can also be another animal such as a non-human primate, a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a subject who is, or is suspected to be, afflicted with a disease.

As used herein, the terms "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions described herein can also be administered in combination with one or more additional therapeutic compounds.

The terms "cancer-associated antigen" or "tumor-associated antigen" or "tumor-specific marker" or "tumor marker" interchangeably refers to a molecule (typically protein, carbohydrate or lipid) that is preferentially expressed on the surface of a cancer cell in comparison to a normal cell, and which is useful for the preferential targeting of a pharmacological agent to the cancer cell. Oftentimes, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Illustrative aptamer targets include without limitation, EpCAM, VEGF, FLT1, theophylline, and malachite green. Illustrative tumor associated antigens on hepatocellular carcinoma cells, and which can be aptamer targets, include without limitation, e.g., HCC-22-5 tumor-associated antigen (Zhou, et al., Clin Chim Acta. 2006 April; 366(1-2):274-80) and KRT23, AHSG and FTL antigens (Wang, et al., Cancer Lett. 2009 Aug. 28; 281(2):144-50). Illustrative tumor associated antigens on lung cancer, e.g., non-small cell lung cancer cells, and which can be aptamer targets, include without limitation, e.g., MAGE-A1, MAGE-A3/4 and NY-ESO-1 (Grah, et al, Tumori. (2014) 100(1):60-8); 14-3-3ζ, c-Myc, MDM2, NPM1, p16, p53 and cyclin B1 (Dai, et al., Lung Cancer. (2016) 99:172-9). Illustrative tumor associated antigens on pancreatic cancer cells, and which can be aptamer targets, include without limitation, e.g., KIF20A (Imai, et al., *Br J Cancer*. (2011) 104(2):300-7); CA 19-9, DU-PAN-2, and TAG-72 (Toshkov, et al., *Int J Pancreatol*. (1994) 15(2):97-103); cadherin 3 (CDH3)/P-cadherin (Imai, et al., *Clin Cancer Res*. (2008) 14(20):6487-95); Receptor-binding cancer antigen expressed on SiSo cells (RCAS1) (Akashi, et al., *Pancreas* (2003) 26(1):49-55); and SC6 (Liu, et al., *World J Gastroenterol*. (2005) 11(48):7671-5). Aptamers that specifically bind tumor associated antigens can be included in the hybrid tRNA-pre-miRNA molecules described herein.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced, e.g., in comparison to the tumor burden prior to administration of a hybrid tRNA/pre-miRNA molecule, as described herein, optionally in combination with a chemotherapeutic or anticancer agent. In some embodiments, the growth, progression or spread of a tumor or cancer is inhibited, reduced or decreased by at least about 1-fold, 2-fold, 3-fold, 4-fold, or more in comparison to the tumor burden prior to administration of the hybrid tRNA/pre-miRNA molecule, optionally in combination with a chemotherapeutic or anticancer agent.

BRIEF DESCRIPTION OF THE DRAWINGS

FIG. 1A. tRNA standalone showed no expression in HST08 *E. coli*, whereas the fusion of a Sephadex aptamer (highlighted in orange) led to an overexpression of resulting MSA (FIG. 1B). FIG. 1C. Hybrid MSA/mir-34a was overexpressed in *E. coli* and pre-miR-34a itself showed relatively lower-level expression. FIG. 1D. The pre-miR-34a was refined toward a more stable structure (base changes dictated by red arrows), and the Sephadex aptamer was removed. Among these constructs, the tRNA/pre-miR-34a-G138U/139ΔG showed the highest level of heterogeneous expression (~50% of total RNAs) and therefore, was chosen as a carrier for ncRNA bioengineering. FIG. 1E provides a higher resolution image of pre-miR-34a shown in FIG. 1D.

FIGS. 3A-3C illustrate three-step strategy to bioengineer ncRNA agents using nCAR. FIG. 3A. In step 1, the ncRNAs of interest are cloned into the target vector (see FIG. 4), where the miR-34a duplex (red/green) is replaced by an inserted RNA referred to as target small RNA (sRNAs; e.g., miRNA (miR-122-5p (SEQ ID NO:582 and SEQ ID NO:583) and let-7c-5p (SEQ ID NO:586 and SEQ ID NO:587)), siRNA (Nfr2-siRNA (SEQ ID NO:584 and SEQ ID NO:585)) or antisense RNA, RNA aptamers (nCAR/miR-34a/pegaptnib (SEQ ID NO:358) and nCAR/mir-34a/EpCAM (SEQ ID NO:359)), etc.) of interest. FIG. 3B. In step 2, the verified plasmid is transformed into *E. coli*, and total RNAs are isolated post-fermentation for urea-PAGE analysis of target bioengineered or biologic ncRNA agent (BERA) expression. Among 42 target ncRNAs, 33 showed remarkable high-level expression (40-80% of total RNAs). Total RNAs from untransformed wild-type bacteria (WT) are used for comparison. FIG. 3C. Lastly in step 3, ncRNAs are isolated either on small scale using spin columns or large scale using fast protein liquid chromatography (FPLC) methods to offer micrograms or milligrams of BERAs, respectively. B, blank nontransformed *E. coli*; T, total RNA; FT, flow-through; W1-2, washes; E, eluate. Fractions 1-11 were collected at various times during FPLC isolation. RNA purity was verified by high performance liquid chromatography (HPLC) analysis (FIG. 5), and both methods could offer >98% pure, ready-to-use BERAs.

FIG. 6A. Small RNA sequencing analyses showed that (i) nCAR/miR-34a-5p and nCAR/miR-124-3p were selectively processed to target miR-34a-5p and miR-124-3p isoforms (length, starting site/position), respectively, in human cells (fold of change (FC), nCAR/miR versus control tRNA (con) treatment); and (ii) the level of miR-34a-5p (reads or rds) produced from BERA was largely affected by Dicer status, whereas miR-124-3p production was Dicer independent. Individual read counts represent enriched miRNAs with FC>1.2 or <0.8 with differential significance by EdgeR analysis. FIG. 6B. miR-34a-5p became the most abundant miRNA in both wild type and Dicer-KO cells after transfection with nCAR-miR-34a-5p, which was in sharp contrast to a nominal portion in control cells. Similarly, miR-124-3p became the seventh-most and most abundant miRNA in wild type and Dicer-KO cells, respectively, after transfection with nCAR-miR-124-3p.

FIG. 7A. Stem-loop RT qPCR quantification confirmed the degree of change in miR-34a-5p and miR-124-3p levels in wild type and Dicer-KO cells after treated with BERAs. Values are mean±SD (N=3 per group). *P<0.001; unpaired t-test. FIG. 7B. RT-qPCR validation of some downregulated transcripts in 293T cells identified by RNA sequencing study. AMER1, NECTIN1, and GAS1 are targets reported previously for miR-34a-5p; and SNAI2, IQGAP1, VAMP3, TMEM109, and NRAS are known targets for miR-124-3p. Values are mean±SD (N=9 per group). *P<0.001; two-way ANOVA with Bonferroni post-tests. FIG. 7C. Ct values of 18S housekeeping gene were not altered by nCAR/miRNA treatments.

FIG. 8A. Volcano plots of significantly-altered mRNAs (P<0.01) in 293T cells transfected with nCAR/miR-34a-5p or miR-124-3p, as compared to control. Many transcripts were downregulated in 293T cells by nCAR/miR. In Dicer-KO cells, nCAR/miR-34a-5p showed minimal impact on the transcriptome (only 6 genes were significantly downregulated), while effects of nCAR/miR-124-3p retained. Several reported targets of miR-34a-5p (blue) and miR-124-3p (red) are designated with arrows. FIG. 8B. Heatmap of the top 30 most downregulated genes in wild type and Dicer-KO 293T cells treated with nCAR/miRNA, as compared to the control tRNA treatment. FIG. 8C. Specificity of BERA in the regulation of miRNA target genes is supported by miRNA enrichment analyses, which readily identified miR-34/449 underlying nCAR/miR-34a-5p-downregulated mRNAs in 293T cells, whereas not in Dicer-KO cells. By contrast, miR-124/506 was enriched for nCAR/miR-124-3p-downregulated mRNAs in both wild type and Dicer-KO 293T cells, which supports not only the specificity of BERA/miR-124-3p in the modulation of target gene expression but also its independence on Dicer. FIG. 8D. Gene regulatory networks of major biological pathways affected by miR-34a-5p and miR-124-3p, respectively, as identified by Ingenuity Pathway Analysis (IPA).

FIG. 9A. High levels of miR-34a-5p produced from nCAR/miR-34a-5p led to a consistent reduction of protein levels of miR-34a targets (e.g., CDK6 and SIRT1) in 293T cells, whereas the effects might disappear (CDK6) or retain (SIRT1) in Dicer-KO cells due a much lower level of miR-34a-5p. FIG. 9B. The production of miR-124-3p at distinct lengths and positions in wild-type and Dicer-KO cells could cause different effects on the protein expression of some known miR-124 targets (e.g., STAT3 and MRP4). Western blots were conducted with selected antibodies, and β-actin was used as a loading control.

FIG. 10A. Dose-response curves of nCAR/miR-34a-5p and nCAR-miR-124-3p in inhibiting human lung carcinoma A549, H23, H1299, H1650, and H1975 cell proliferation. Each nCAR/miR is significantly more effective than control RNA (P<0.001, two-way ANOVA with Bonferroni post-tests), except miR-34a-5p against H1975 cells. Values are mean±SD (N=3 per group). FIG. 10B. Estimated EC50 and Hill Slope values. Data were fit to the normalized dose response relationship with variable slope. Values are mean±SD (N=3 per group). *P<0.05, P<0.01, and *P<0.001, compared to corresponding control (1-way ANOVA). FIG. 10C. Antiproliferative effects were associated with downregulation of miRNA target gene expression (cMET and CDK6 for miR-34a; STAT3, pSTAT3 and ABCC4/MRP4 for miR-124), as demonstrated by Western blots. *P<0.05, Student's t-test.

FIG. 11A. Mouse body weights showed a steady increase during the treatments and did not differ between treatment groups (P>0.05; two-way ANOVA), suggesting that BERA therapeutics were well tolerated in mice. FIG. 11B. Weights of the xenograft lungs were significantly lower for nCAR/miR-34a-5p treatment, as compared to the control (*P<0.05; one-way ANOVA with Dunnett's Multiple Comparison Test), suggesting the control of metastatic lung xenograft tumor progression. Values are mean±SD (N=9 per group).

FIG. 12A. Effects of nCAR/miR-34a-5p, nCAR/miR-124-3p and control RNA treatment on the progression of lung tumor progression in metastatic xenograft tumor mouse models (N=9 per group), which were monitored through live animal bioluminescent imaging after the administration of D-luciferin. Bioluminescent images were taken on days 10, 20, 25, 32, 39 post inoculation of A549 cells and normalized to the same exposure time. FIG. 12B. Local lung xenograft tumors were assessed via GFP imaging of ex vivo lung tissues at the end of the study. FIG. 12C. Representative H&E-stained slides of lung tumors (100×). The tumor areas were thus quantified as percentages of corresponding lung areas, which were significantly (P<0.05) lower for nCAR/miR-34a-5p treatment than the control.

FIG. 14A. Antiproliferative activities of a collection of bioengineered ncRNA agents (5 nM) against luciferase/GFP-expressing Sk-Hep-1 and Huh7 cells were examined by luminometric ATP assay. Values were normalized to transfection reagent/vehicle control (0% Inhibition). FIG. 14B. Dose-response curves of the top ranked ncRNA agents were further determined and their pharmacodynamic parameters were estimated, which indicate that let-7c is the most potent inhibitor of HCC cell viability in this collection of ncRNA agents. FIG. 14C. Values are mean±SD (N=3 per group). *P<0.05, compared to MSA control.

FIGS. 23A-F illustrate that LPP/let-7c nanotherapeutics largely reduces tumor growth in orthotopic HCC Huh7 xenograft mouse models. (A) Timeline of establishment of HCC xenograft mouse models and drug treatment. (B) Suppression of orthotopic HCC progression by LPP/let-7c was demonstrated by live animal imaging of luciferase bioluminescent signals. In vivo-jetPEI (IPEI)-formulated let-7c and MSA were used for comparison. (C) Ex vivo GFP fluorescence images of HCC-bearing livers further demonstrated the effectiveness of let-7c, which was associated with high levels of tumoral let-7c (D). (E) Serum AFP levels were significantly reduced in let-7c treated mice. (F) Representative H&E staining of tumor-bearing liver tissues and quantitative measurement of the percentage of tumor areas in corresponding liver slices. Areas circled in blue lines are necrotic areas, and the red lines are applied to distinguish tumors from healthy liver (L) tissues. Values are mean±SD (N=4-6 in each group). *P<0.05 and ***P<0.001 (1- or 2-way ANOVA with Bonferroni's post-hoc test).

FIGS. 26A-C illustrate that LPP/let-7c has no or limited impact on cytokine release in human PBMCs (A) and two strains of immunocompetent mice (B and C). LPS was used as positive control to induce cytokine release storm while untreated and LPP vehicle-treated mice or cells were considered as negative controls. Values are mean±SD. For Balb/c and CD-1 mice, 3 females and 3 males were included in each group (N=6). Bloods were harvested 1 h post treatment and serum samples were prepared for cytokine measurement. For human PBMCs, each treatment was conducted in triplicate (N=3), and cell culture medium was collected 24 h post treatment. n.d., non-detectable. P<0.01 and *P<0.001 (2-way ANOVA with Bonferroni's post-hoc test).

FIG. 27A, Computational analysis identified four putative MRE sites for miR-1291 (SEQ ID NO:590) within the 3'UTR of ARID3B mRNA (SEQ ID NO:589 and SEQ ID NOS:591-593). Underlined is the seed sequence of miR-1291. FIG. 27B, Dual luciferase reporter assay indicated that ARID3B 3'UTR luciferase activities were increased about 50% in AsPC-1 cells treated with MSA/mir-1291, as compared to controls. FIG. 27C, qPCR analyses revealed that MSA/mir-1291 was selectively processed to mature miR-1291 in PANC-1 and AsPC-1 cells, and subsequently upregulated ARID3B mRNA levels (FIG. 27D). FIG. 27E, Immunoblot analyses showed that ARID3B protein levels were elevated in PANC-1 and AsPC-1 cells after transfection with bioengineered miR-1291. Both the full-length ARID3B (ARID3B-Fl, ~61 kD) and the short-form ARID3B (ARID3B-sh, ~28 kD) were upregulated in PANC-1 (72 h post-transfection) and AsPC-1 (48 and 72 h) cells, as compared to vehicle and MSA controls. β-actin was used as a loading control. Values are mean±SD (N=3). *P<0.05, P<0.01, *P<0.001, compared to corresponding control (1- or 2-way ANOVA).

FIGS. 32A-E illustrate that bioengineered miR-1291 prodrug sensitizes human pancreatic cancer cells to Gem-nP. Compared to the MSA control, a low dose of MSA/miR-1291 had minimal effects on AsPC-1 (A) and PANC-1 (C) cell proliferation, whereas it significantly (*P<0.001; 2-way ANOVA with Bonferroni posttests) improved the sensitivity of AsPC-1 (B) and PANC-1 (D) cells to Gem-nP, which was also indicated by the estimated pharmacodynamics parameters (E). AsPC-1 and PANC-1 cells were treated with MSA/mir-1291 or MSA control alone (A, C) or in combination with various concentrations of Gem-nP (B, D; shown are total concentrations of Gem-nP at a fixed ratio of 8:1) for 48 h, and cell viability was determined by Cell Titer-Glo assay. Values are mean±SD (N=3). *P<0.05; **P<0.01, compared to corresponding MSA control treatment (1-way ANOVA).

FIGS. 33A-F illustrate that combination therapy with miR-1291 prodrug and Gem-nP is the most effective in suppressing PANC-1 xenograft tumor growth in mice and all therapies are well tolerated. A, Timeline of the establishment of PANC-1 xenograft mouse model and drug treatment. B, PANC-1 xenograft tumor growth was reduced to the greatest degree by combination treatment with miR-1291 prodrug and Gem-nP. *P<0.05, ***P<0.001 (2-way ANOVA with Bonferroni posttests). C, Visual comparison of dissected tumors from mice with different treatments. D, Weights of the dissected xenograft tumors. *P<0.05 (1-way ANOVA). E, Body weights were not altered by drug treatment. F, Blood biochemistry profiles including alanine transaminase (ALT), aspartate transaminase (AST), creatinine, blood urea nitrogen (BUN), and total bilirubin showed no significant difference by different treatments. Values are mean±SD (N=6 per group, except N=3 for blood chemistry profiles). The ranges of individual markers (derived from BALB/c mice; Comparative Pathology Laboratory at UC-Davis) were marked as references.

FIGS. 37A-F illustrate combination therapy with miR-1291 prodrug and Gem-nP is proven the most effective in controlling tumor growth in two other PDX mouse models established with patients' PDAC tissues (PA-0375: A, B, and C; PA-0327: D, E, and F). A and D, PDX tumor growth was significantly suppressed by miR-1291 monotherapy or combination therapy, as compared to MSA or buffer control. *P<0.05, P<0.01, and *P<0.001 (2-way ANOVA with Bonferroni post-tests). B and E, Comparison of dissected tumor from mice with different treatments. C and F, Weights of the dissected xenograft tumors. *P<0.05, P<0.01, *P<0.001 (1-way ANOVA). Values are mean±SD (N=5 per group). Because PA-0327 was more aggressive, dose of miR-1291 prodrug was increased to 20 μg/mouse for both monotherapy and combination therapy in this PDX model which, surprisingly, produced optimal outcomes.

FIG. 40. FPLC purification of CO-BERAs. a) CO-BERAs were separated from total bacterial RNA on an anion-exchange Enrich Q column. A few CO-BERAs requiring re-purification were proceeded to further FPLC separation by using either b) Enrich Q again, c) DEAE, or d) CHT Type I. Shown are representative FPLC traces.

DETAILED DESCRIPTION

1. Introduction

Figure 1A:
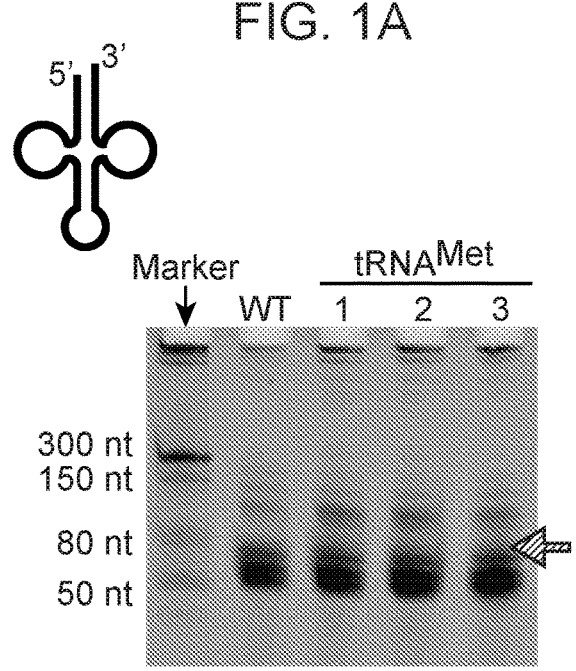
FIGS. 1A-1E illustrate identification of a new ncRNA carrier (nCAR) towards higher-level expression of recombinant RNAs.

Noncoding RNAs (ncRNAs) produced in live cells may better reflect intracellular ncRNAs for research and therapy. Attempts were made to produce biological ncRNAs, but at low yield or success rate. Here we first report a new ncRNA bioengineering technology, using more stable ncRNA carrier (nCAR) containing a pre-miR-34a derivative identified by rational design and experimental validation. This approach offered a remarkable higher-level expression (40-80% of total RNAs) of recombinant ncRNAs in bacteria, and gave an 80% success rate (33 out of 42 ncRNAs). New FPLC and spin-column based methods were also developed for largeand small-scale purification of milligrams and micrograms of recombinant ncRNAs from half liter and milliliters of bacterial culture, respectively. We then used two bioengineered nCAR/miRNAs to demonstrate the selective release of target miRNAs into human cells, which were revealed to be Dicer dependent (miR-34a-5p) or independent (miR-124a-3p), and subsequent changes of miRNome and transcriptome profiles. MiRNA enrichment analyses of altered transcriptome confirmed the specificity of nCAR/miRNAs in target gene regulation. Furthermore, nCAR assembled miR-34a-5p and miR-124-3p were active in suppressing human lung carcinoma cell proliferation through modulation of target gene expression (e.g., cMET and CDK6 for miR-34a-5p; STAT3 and ABCC4 for miR-124-3p). In addition, bioengineered miRNA molecules were effective in controlling metastatic lung xenograft progression, as demonstrated by live animal and ex vivo lung tissue bioluminescent imaging as well as histopathological examination. This novel ncRNA bioengineering platform can be easily adapted to produce various ncRNA molecules, and biologic ncRNAs hold the promise as new cancer therapeutics.

2. Hybrid tRNA/pre-miRNA Molecules

Generally, the polynucleotides comprise a tRNA operably linked to one or more pre-microRNAs, e.g., a first pre-miRNA and a second pre-miRNA. In some embodiments, the anticodon of the tRNA is replaced with a pre-microRNA molecule. For example, in some embodiments, the 3'-terminus and the 5'-terminus of the first and/or the second pre-microRNA are ligated or fused to the 3'-terminus and the 5'-terminus of the tRNA that are created when the anticodon is removed. The tRNA molecule and the first and/or the second pre-microRNA molecule can be, but need not be directly ligated or fused to one another to be operably linked. In some embodiments, the first and/or the second pre-microRNA can contain one or more dicer cleavable sites to allow for the high level expression and efficient cleavage of an inserted RNA molecule desired to be expressed from the hybrid tRNA/pre-microRNA polynucleotide.

Structurally, in some embodiments, the hybrid tRNA/dual pre-microRNA molecules comprise in the 5'- to 3'-direction (i) a 5' portion of the tRNA; (ii) a 5' portion of the first pre-miRNA comprising a first inserted RNA (e.g., mature miRNA); (iii) a 5' portion of the second pre-miRNA comprising a second inserted RNA (e.g., mature miRNA); (iv) a hairpin (e.g., which can be part of the second pre-miRNA); (v) a 3' portion of the second pre-miRNA comprising a substantially complementary sequence to the second inserted RNA (e.g., a guide miRNA); (vi) a 3' portion of the first pre-miRNA comprising a substantially complementary sequence to the second inserted RNA (e.g., mature miRNA); and (vii) a 3' portion of the tRNA.

In some embodiments, the hybrid tRNA/dual pre-microRNA molecule comprises at least 90%, 91%, 92%, 93%, 94%, 95%, 96%, 97%, 98%, 99% or 100% sequence identity to SEQ ID NO:296, e.g., in the 5'- to 3'-direction: 5'-1st or 5' tRNA portion—GGCCAGCUGUGAGUGUUUCUU[$N^1_{18-200}$]UGUGAGCGGCCAGCUGUGAGUGUUUCUU[$N^3_{18-200}$]UGUGAGCAAUAGUAAGGAAG[$N^4_{18-200}$] AGAAGUGCUGCACGUUGUUGGCCC GUAAGGAAG[$N^2_{18-200}$]AGAAGUGCUGCACGUUGUUGGCCC—2nd or 3' tRNA portion—3' (SEQ ID NO:296), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths); N3 and N4 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

In some embodiments, the hybrid tRNA/dual pre-microRNA molecule comprises at least 90%, 91%, 92%, 93%, 94%, 95%, 96%, 97%, 98%, 99% or 100% sequence identity to SEQ ID NO:297, e.g., in the 5'- to 3'-direction: 5'-1st or 5' tRNA portion—optional aptamer, small activating RNA (saRNA) or catalytic RNA—GGCCAGCUGUGAGUGUUUCUU[$N^1_{18-200}$]UGUGAGCGGCCAGCUGUGAGUGUUUCUU [$N^3_{18-200}$]UGUGAGCAAUAGUAAGGAAG[$N^4_{18-200}$] AGAAGUGCUGCACGUUGUUGGCCC GUAAGGAAG [$N^2_{18-200}$]AGAAGUGCUGCACGUUGUUGGCCC—optional aptamer, small activating RNA (saRNA) or catalytic RNA, small activating RNA (saRNA) or catalytic RNA—2nd or 3' tRNA portion—3' (SEQ ID NO:297), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths); N3 and N4 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

In some embodiments, the hybrid tRNA/dual pre-microRNA molecule comprises at least 90%, 91%, 92%, 93%, 94%, 95%, 96%, 97%, 98%, 99% or 100% sequence identity to SEQ ID NO:298, e.g., in the 5'- to 3'-direction: 5'-1st or 5' tRNA portion—GGCCAGCUGUGAGUGUUUCUU [$N^1_{18-200}$]UGUGAGC—optional aptamer, small activating RNA (saRNA) or catalytic RNA—GGCCAGCUGUGAGUGUUUCUU[$N^3_{18-200}$]UGUGAGCAAUAGUAAGGAAG[$N^4_{18-200}$]AGA AGUGCUGCACGUUGUUGGCCC—optional aptamer, small activating RNA (saRNA) or catalytic RNA—GUAAGGAAG[$N^2_{18-200}$] AGAAGUGCUGCACGUUGUUGGCCC—2nd or 3' tRNA portion—3' (SEQ ID NO:298), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths); N3 and N4 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

With respect to the hybrid tRNA/dual pre-microRNA molecules, in some embodiments, the tRNA is a human tRNA encoding an anticodon for any naturally occurring amino acid residue. In some embodiments, the RNA coding for the tRNA comprises a 5' tRNA sequence and a 3' tRNA sequence having at least about 90%, 91%, 92%, 93%, 94%, 95%, 96%, 97%, 98%, 99% or 100% sequence identity to SEQ ID NOs: 300-355, e.g., 300/301, 302/303, 304/305, 306/307, 308/309, 310/311, 312/313, 314/315, 316/317, 318/319, 320/321, 322/323, 324/325, 326/32, 328/329, 330/331, 332/333, 334/335, 336/337, 338/339, 340/341, 342/343, 344/345, 346/347, 348/349, 350/351, 352/353, 354/355, as provided in Table 8. In some embodiments, the first and second pre-miRNA are derived from the same pre-miRNA (e.g., pre-miRNA 34a). In some embodiments, the first and second pre-miRNA are derived from different pre-miRNA. In some embodiments, the first and second inserted RNA are the same (e.g., the same mature miRNA). In some embodiments, the first and second inserted RNA are different (e.g., different mature miRNAs). The hybrid tRNA/dual pre-microRNA molecules can optionally comprise one or more aptamer sequences, e.g., inserted at the 5'-end and or at the 3'-end of one or more of elements (i), (ii), (iii), (iv), (v), (vi) and/or (vii). In some embodiments, the one or more optional aptamer, small activating RNA (saRNA) or catalytic RNAs are inserted at, abutted with or operably linked to: (a) the 5' end of the pre-miRNA; (b) the 3' end of the pre-miRNA; (c) 5' of a dicer or RNase cleavage site of the pre-miRNA; or (d) 3' of a dicer or RNase cleavage site of the pre-miRNA. In some embodiments, the polynucleotide encoding a tRNA/dual pre-miRNA hybrid molecule is from about 275 nucleotides, e.g., from about 280 nucleotides, e.g., from about 290 nucleotides and up to about 400 nucleotides in length.

In some embodiments, the hybrid tRNA/pre-microRNA molecule comprises at least 90%, 91%, 92%, 93%, 94%, 95%, 96%, 97%, 98%, 99% or 100% sequence identity to SEQ ID NO:289, e.g., in the 5'- to 3'-direction: 5'-1st or 5' tRNA portion—optional aptamer, small activating RNA (saRNA) or catalytic RNA—GGCCAGCUGUGAGU-GUUUCUU[$N^1_{18-200}$]UGUGAGCAAUAGUAAGGAAG [$N^2_{18-200}$]AGA AGUGCUGCACGUUGUUGGCCC—optional aptamer, small activating RNA (saRNA) or catalytic RNA—2nd or 3' tRNA portion—3' (SEQ ID NO:289), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

In some embodiments, the hybrid tRNA/pre-microRNA molecule comprises at least 90%, 91%, 92%, 93%, 94%, 95%, 96%, 97%, 98%, 99% or 100% sequence identity to SEQ ID NO:290, e.g., in the 5'- to 3'-direction: 5'-1st or 5' tRNA portion—optional aptamer, small activating RNA (saRNA) or catalytic RNA—GGUAGAAUUCCAG [$N^1_{18-200}$]UGUACUGUG[$N^2_{18-200}$]AAAGGACUGUC-UUCCUG—optional aptamer, small activating RNA (saRNA) or catalytic RNA—2nd or 3' tRNA portion—3' (SEQ ID NO:290), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

In some embodiments, the hybrid tRNA/pre-microRNA molecule comprises at least 90%, 91%, 92%, 93%, 94%, 95%, 96%, 97%, 98%, 99% or 100% sequence identity to SEQ ID NO:291, e.g., in the 5'- to 3'-direction: 5'-1st or 5' tRNA portion—optional aptamer, small activating RNA (saRNA) or catalytic RNA—CCAG-CUCGGGCAGCCGUGGC[$N^1_{18-200}$]UGGAGUCAGGU-CUC[$N^2_{18-200}$]UGACGGCGGA GCCCUGCACG—optional aptamer, small activating RNA (saRNA) or catalytic RNA—2nd or 3' tRNA portion—3' (SEQ ID NO:291), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

In some embodiments, the hybrid tRNA/pre-microRNA molecule comprises at least 90%, 91%, 92%, 93%, 94%, 95%, 96%, 97%, 98%, 99% or 100% sequence identity to SEQ ID NO:292, e.g., in the 5'- to 3'-direction: 5'-1st or 5' tRNA portion—optional aptamer, small activating RNA (saRNA) or catalytic RNA—ACAAUGCUUUGCUAG [$N^1_{18-200}$]CGCCUCUUCAAUGGA[$N^2_{18-200}$]UAGC-UAUGCAUUGA—optional aptamer, small activating RNA (saRNA) or catalytic RNA—2nd or 3' tRNA portion—3' (SEQ ID NO:292), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

In some embodiments, the hybrid tRNA/pre-microRNA molecule comprises at least 90%, 91%, 92%, 93%, 94%, 95%, 96%, 97%, 98%, 99% or 100% sequence identity to SEQ ID NO:293, e.g., in the 5'- to 3'-direction: 5'-1st or 5' tRNA portion—optional aptamer, small activating RNA (saRNA) or catalytic RNA—UGCCAGUCUCUAGGj [$N^1_{18-200}$]GGACAUCCAGGGUC[$N^2_{18-200}$]UGGCGU-CUGGCC—optional aptamer, small activating RNA (saRNA) or catalytic RNA—2nd or 3' tRNA portion—3' (SEQ ID NO:293), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

In some embodiments, the hybrid tRNA/pre-microRNA molecule comprises at least 90%, 91%, 92%, 93%, 94%, 95%, 96%, 97%, 98%, 99% or 100% sequence identity to SEQ ID NO:294, e.g., in the 5'- to 3'-direction: 5'-1st or 5' tRNA portion—optional aptamer, small activating RNA (saRNA) or catalytic RNA—GCAUCCGGGU[$N^1_{18-200}$] UAGAGUUACACCCUGGGAGUUAA[$N^2_{18-200}$]UUG-GAGC—optional aptamer, small activating RNA (saRNA) or catalytic RNA—2nd or 3' tRNA portion—3' (SEQ ID NO:294), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

In some embodiments, the hybrid tRNA/pre-microRNA molecule comprises at least 90%, 91%, 92%, 93%, 94%, 95%, 96%, 97%, 98%, 99% or 100% sequence identity to SEQ ID NO:295, e.g., in the 5'- to 3'-direction: 5'-1st or 5' tRNA portion—optional aptamer, small activating RNA (saRNA) or catalytic RNA—AGGCCUCUCUCUC [$N^1_{18-200}$]UUAAAUGUCCAUACAAU[$N^2_{18-200}$] AAGAAUGGGCUG—optional aptamer, small activating RNA (saRNA) or catalytic RNA—2nd or 3' tRNA portion—3' (SEQ ID NO:295), wherein N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths).

The hybrid tRNA/pre-microRNA molecules can optionally comprise one or more aptamer sequences, e.g., inserted at the 5'-end and or at the 3'-end of one or more of elements (i), (ii), (iii), (iv), (v), (vi) and/or (vii). In some embodiments, the one or more optional aptamer, small activating RNA (saRNA) or catalytic RNAs are inserted at, abutted with or operably linked to: (a) the 5' end of the pre-miRNA; (b) the 3' end of the pre-miRNA; (c) 5' of a dicer or RNase cleavage site of the pre-miRNA; or (d) 3' of a dicer or RNase cleavage site of the pre-miRNA. In some embodiments, the polynucleotide encoding a tRNA/pre-miRNA hybrid molecule is from about 150 nucleotides, e.g., from about 175 nucleotides, e.g., from about 180 nucleotides and up to about 200 nucleotides in length.

The hybrid tRNA/pre-microRNA molecules can be produced by standard recombinant methods, or can be synthetically prepared. In some embodiments, the polynucleotides can have one or more chemical modifications, including without limitation, e.g., internucleotide linkages, internucleoside linkages, dideoxyribonucleotides, 2'-sugar modification, 2'-amino groups, 2'-fluoro groups, 2'-methoxy groups, 2'-alkoxy groups, 2'-alkyl groups, 2'-deoxyribonucleotides, 2-O-methyl ribonucleotides, 2'-deoxy-2'-fluoro ribonucleotides, universal base nucleotides, acyclic nucleotides, 5-C-methyl nucleotides, biotin groups, terminal glyceryl incorporation, inverted deoxy abasic residue incorporation, sterically hindered molecules, 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T), monophosphate nucleotide modification (MNM) of 3'-azido-3'-deoxythymidine (AZT), MNM-2',3'-dideoxy-3'-thiacytidine (3TC), MNM-2',3'-didehydro-2',3'-dideoxythymidine (d4T), capping moieties, L-nucleotides locked nucleic acid (LNA) nucleotides, 2'-methoxyethoxy (MOE) nucleotides, 2'-methyl-thio-ethyl, 2'-deoxy-2'-fluoro nucleotides, 2'-deoxy-2'-chloro nucleotides, 2'-azido nucleotides, 2'-O-methyl, cholesterol groups, 2'-O-methyl groups, phosphorothioate groups, 2'-fluoro groups, 2'-O-methyoxyethyl groups, boranophosphate groups, 4'-thioribose groups, bile acid, lipids, and bridges connecting the 2'-oxygen and 4'-carbon.

In some embodiments, the hybrid tRNA/pre-microRNA molecules comprise analog ribonucleotide bases. As used herein, the term "analog" defines possible derivatives of the ribonucleotide originating from the activity of tRNA post-transcriptional modification enzymes of the cell in which they are produced. The analogs of the ribonucleotides A, C, G and U which may be found in a tRNA depend on the cell in which that tRNA is produced and on the position of the ribonucleotide in question in the tRNA. A large number of analogs are given in Sprinzl et al. (1998) "Compilation of tRNA sequences and sequences of tRNA genes". Nucleic Acids Res., 26, 148-153 and on the basis of "RNA modification database" data (medstat.med.utah.edu/RNAmods/). The analogs of A may be selected more particularly from the group constituted by 1-methyl-A, inosine and 2'-O-methyl-A. The analogs of C may be selected more particularly from the group constituted by 5-methyl-C and 2'-O-methyl-C. The analogs of G may be selected more particularly from the group constituted by 7-methyl-G and 2'-O-methyl-G. The analogs of U may be selected more particularly from the group constituted by pseudouridine, ribothymidine, 2'-O-methyl-ribothymidine, dihydrouridine, 4-thiouridine and 3-(3-amino-3-carboxypropyl)-uridine.

a. tRNA

The general characteristics of a tRNA are well-known to the person skilled in the art. In some embodiments, a tRNA is formed of a single ribonucleotide chain which is capable of folding to adopt a characteristic, so-called cloverleaf secondary structure. This characteristic secondary structure comprises:

(i) an acceptor stem composed of the first 7 ribonucleotides of the 5' end of the ribonucleotide chain and the 7 ribonucleotides that precede the last 4 nucleotides of the 3' end of the ribonucleotide chain, thus forming a double-stranded structure comprising 6 or 7 pairs of ribonucleotides, it being possible for the ribonucleotides constituted by the first ribonucleotide of the 5' end of the ribonucleotide chain and the ribonucleotide that precedes the last 4 ribonucleotides of the 3' end of the ribonucleotide chain not to be paired;

(ii) a D arm constituted by 4 pairs of ribonucleotides and a D loop constituted by 8 to 10 ribonucleotides, formed by the folding of a part of the ribonucleotide chain that follows the first 7 ribonucleotides of the 5' end of the ribonucleotide chain;

(iii) a stem of the anticodon constituted by 5 pairs of ribonucleotides, and a loop of the anticodon constituted by 7 ribonucleotides (stem-loop of the anticodon), formed by the folding of a part of the ribonucleotide chain that follows the D arm and the D loop;

(iv) a variable loop constituted by from 4 to 21 ribonucleotides and formed by a part of the ribonucleotide chain that follows the stem of the anticodon and the loop of the anticodon;

(v) a T arm constituted by 5 pairs of ribonucleotides, and a T loop constituted by 8 ribonucleotides, formed by the folding of a part of the ribonucleotide chain that follows the variable loop and precedes the ribonucleotides of the 3' end of the ribonucleotide chain which are involved in the constitution of the acceptor stem.

In some embodiments, the chimeric tRNA defined above does not comprise the substantially intact stem of the anticodon of the tRNA from which it is derived. For example, in the chimeric tRNA, between the ribonucleotide that precedes the stem-loop of the anticodon in the tRNA before modification and the ribonucleotide that follows the stem-loop of the anticodon in the tRNA before modification, the stem of the anticodon of the tRNA before modification is no longer present.

The hybrid tRNA/pre-microRNA polynucleotides can contain any tRNA known in the art, e.g., for encoding any amino acid. In some embodiments, the tRNA is a tRNA derived from or coding for an amino acid selected from the group consisting of serine, leucine, glycine, glutamate, aspartate, glutamine, arginine, cysteine, lysine, methionine, asparagine, alanine, histidine, isoleucine, phenylalanine, proline, tryptophan, tyrosine, threonine, and valine. The selection of an appropriate tRNA molecule may be, in part, driven by the host cells to be used for expression of the inserted RNA. For example, when seeking to produce high expression levels of a desired inserted RNA molecule, the tRNA selected can be from a tRNA encoding for codon preferred by the species of host cell rather than from a rare codon in that species of host cell. In some embodiments, the tRNA is derived from the host cell used for expression. In some embodiments, the tRNA is a bacterial tRNA. In some embodiments, the tRNA is a mammalian tRNA. In some embodiments, the tRNA is a human tRNA.

Generally, in the hybrid tRNA/pre-miRNA hybrid molecules describe herein, the tRNA is split into a 5'-portion and a 3'-portion. In some embodiments, the RNA coding for the tRNA comprises a 5' tRNA sequence and a 3' tRNA sequence having at least about 90%, 91%, 92%, 93%, 94%, 95%, 96%, 97%, 98%, 99% or 100% sequence identity to SEQ ID NOs: 300-355, e.g., 300/301, 302/303, 304/305, 306/307, 308/309, 310/311, 312/313, 314/315, 316/317, 318/319, 320/321, 322/323, 324/325, 326/32, 328/329, 330/331, 332/333, 334/335, 336/337, 338/339, 340/341, 342/343, 344/345, 346/347, 348/349, 350/351, 352/353, 354/355, as provided in Table 8.

b. pre-miRNA

The hybrid tRNA/pre-microRNA polynucleotides can contain any pre-microRNA molecule or molecules known in the art, and can be obtained from naturally occurring or artificially derived sources. In some embodiments, the one or more pre-microRNA molecules are from a mammalian pre-microRNA molecule. In some embodiments, the one or more pre-microRNA molecules are from human pre-microRNA molecules. In molecules having two or more pre-miRNA molecules the pre-miRNA can be the same or different. In some embodiments, the pre-microRNA component of the hybrid tRNA/pre-microRNA polynucleotides is from about 80 nucleotides to about 120 nucleotides in length, e.g., from about 80 nucleotides to about 100 nucleotides in length, e.g., about 80, 85, 90, 95, 100, 105, 110, 115 or 120 nucleotides in length.

In some embodiments the two or more pre-miRNA, e.g., the first and/or second pre-miRNA, are selected from the group consisting of pre-miR-34a, pre-miR-124, pre-miR-1291, pre-miR-200b, pre-miR-200a, pre-miR-141, pre-miR-429, pre-miR-133a, pre-let-7c, pre-miR-125a, pre-miR-328, pre-miR-126, pre-miR-298, pre-miR-148, pre-miR-144, pre-miR-1, pre-miR-133, pre-miR-888, pre-miR-6775, pre-miR-374, pre-miR-92, pre-miR-1180, pre-miR-218, pre-miR-7, pre-miR-378, pre-miR-17, pre-miR-18a, pre-miR-22, pre-miR-122, pre-miR-30b, pre-miR-449, pre-miR-506, pre-miR-98, pre-miR-4458, pre-miR-206, pre-miR-519, pre-miR-93, pre-miR-106, pre-miR-373, and pre-miR-520.

In some embodiments the two or more pre-miRNA, e.g., the first and/or second pre-miRNA, are selected from the group consisting of hsa-let-7c (MI0000064), hsa-mir-1-1 (MI0000651), hsa-mir-1-2 (MI0000437), hsa-mir-7-1 (MI0000263), hsa-mir-7-2 (MI0000264), hsa-mir-7-3 (MI0000265), hsa-mir-17 (MI0000071), hsa-mir-18a (MI0000072), hsa-mir-18b (MI0001518), hsa-mir-22 (MI0000078), hsa-mir-30b (MI0000441), hsa-mir-34a (MI0000268), hsa-mir-92a-1 (MI0000093), hsa-mir-92a-2 (MI0000094), hsa-mir-92b (MI0003560), hsa-mir-93 (MI0000095), hsa-mir-98 (MI0000100), hsa-mir-106a (MI0000113), hsa-mir-106b (MI0000734), hsa-mir-122 (MI0000442), hsa-mir-124-1 (MI0000443), hsa-mir-124-2 (MI0000444), hsa-mir-124-3 (MI0000445), hsa-mir-125a (MI0000469), hsa-mir-126 (MI0000471), hsa-mir-133a-1 (MI0000450), hsa-mir-133a-2 (MI0000451), hsa-mir-141 (MI0000457), hsa-mir-144 (MI0000460), hsa-mir-148a (MI0000253), hsa-mir-148b (MI0000811), hsa-mir-200a (MI0000737), hsa-mir-200b (MI0000342), hsa-mir-200c (MI0000650), hsa-mir-206 (MI0000490), hsa-mir-218-1 (MI0000294), hsa-mir-218-2 (MI0000295), hsa-mir-298 (MI0005523), hsa-mir-328 (MI0000804), hsa-mir-373 (MI0000781), hsa-mir-374a (MI0000782), hsa-mir-374b (MI0005566), hsa-mir-374c (MI0016684), hsa-mir-378a (MI0000786), hsa-mir-378b (MI0014154), hsa-mir-378c (MI0015825), hsa-mir-378d-1 (MI0016749), hsa-mir-378d-2 (MI0003840), hsa-mir-378e (MI0016750), hsa-mir-378f (MI0016756), hsa-mir-378g (MI0016761), hsa-mir-378h (MI0016808803), hsa-mir-378i (MI0016902), hsa-mir-378j (MI0021273), hsa-mir-449a (MI0001648), hsa-mir-449b (MI0003673), hsa-mir-449c (MI0003823), hsa-mir-506 (MI0003193), hsa-mir-519a-1 (MI0003178), hsa-mir-519a-2 (MI0003182), hsa-mir-519b (MI0003151), hsa-mir-519c (MI0003148), hsa-mir-519d (MI0003162), hsa-mir-519e (MI0003145), hsa-mir-520a (MI0003149), hsa-mir-520b (MI0003155), hsa-mir-520c (MI0003158), hsa-mir-520d (MI0003164), hsa-mir-520e (MI0003143), hsa-mir-520f (MI0003146), hsa-mir-520g (MI0003166), hsa-mir-520h (MI0003175), hsa-mir-888 (MI0005537), hsa-mir-1180 (MI0006273), hsa-mir-1291 (MI0006353), hsa-mir-4458 (MI0016804), and hsa-mir-6775 (MI0022620).

In some embodiments the two or more pre-miRNA, e.g., the first and/or second pre-miRNA, are selected from the group consisting of hsa-let-7c (MI0000064), hsa-mir-34a (MI0000268), hsa-mir-124-1 (MI0000443), hsa-mir-124-2 (MI0000444), hsa-mir-124-3 (MI0000445), hsa-mir-125a (MI0000469), hsa-mir-133a-1 (MI0000450), hsa-mir-133a-2 (MI0000451), hsa-mir-200a (MI0000737), hsa-mir-200b (MI0000342), hsa-mir-200c (MI0000650), and hsa-mir-1291 (MI0006353).

In some embodiments, the pre-microRNA is a human pre-microRNA selected from the group consisting of hsa-let-7a-1 (miRBase.org accession no.: MI0000060), hsa-let-7a-2 (MI0000061), hsa-let-7a-3 (MI0000062), hsa-let-7b (MI0000063), hsa-let-7c (MI0000064), hsa-let-7d (MI0000065), hsa-let-7e (MI0000066), hsa-let-7f-1 (MI0000067), hsa-let-7f-2 (MI0000068), hsa-let-7g (MI0000433), hsa-let-7i (MI0000434), hsa-mir-1-1 (MI0000651), hsa-mir-1-2 (MI0000437), hsa-mir-7-1 (MI0000263), hsa-mir-7-2 (MI0000264), hsa-mir-7-3 (MI0000265), hsa-mir-9-1 (MI0000466), hsa-mir-9-2 (MI0000467), hsa-mir-9-3 (MI0000468), hsa-mir-10a (MI0000266), hsa-mir-10b (MI0000267), hsa-mir-15a (MI0000069), hsa-mir-15b (MI0000438), hsa-mir-16-1 (MI0000070), hsa-mir-16-2 (MI0000115), hsa-mir-17 (MI0000071), hsa-mir-18a (MI0000072), hsa-mir-18b (MI0001518), hsa-mir-19a (MI0000073), hsa-mir-19b-1 (MI0000074), hsa-mir-19b-2 (MI0000075), hsa-mir-20a (MI0000076), hsa-mir-20b (MI0001519), hsa-mir-21 (MI0000077), hsa-mir-22 (MI0000078), hsa-mir-23a (MI0000079), hsa-mir-23b (MI0000439), hsa-mir-23c (MI0016010), hsa-mir-24-1 (MI0000080), hsa-mir-24-2 (MI0000081), hsa-mir-25 (MI0000082), hsa-mir-26a-1 (MI0000083), hsa-mir-26a-2 (MI0000750), hsa-mir-26b (MI0000084), hsa-mir-27a (MI0000085), hsa-mir-27b (MI0000440), hsa-mir-28 (MI0000086), hsa-mir-29a (MI0000087), hsa-mir-29b-1 (MI0000105), hsa-mir-29b-2 (MI0000107), hsa-mir-29c (MI0000735), hsa-mir-30a (MI0000088), hsa-mir-30b (MI0000441), hsa-mir-30c-1 (MI0000736), hsa-mir-30c-2 (MI0000254), hsa-mir-30d (MI0000255), hsa-mir-30e (MI0000749), hsa-mir-31 (MI0000089), hsa-mir-32 (MI0000090), hsa-mir-33a (MI0000091), hsa-mir-33b (MI0003646), hsa-mir-34a (MI0000268), hsa-mir-34b (MI0000742), hsa-mir-34c (MI0000743), hsa-mir-92a-1 (MI0000093), hsa-mir-92a-2 (MI0000094), hsa-mir-92b (MI0003560), hsa-mir-93 (MI0000095), hsa-mir-95 (MI0000097), hsa-mir-96 (MI0000098), hsa-mir-98 (MI0000100), hsa-mir-99a (MI0000101), hsa-mir-99b (MI0000746), hsa-mir-100 (MI0000102), hsa-mir-101-1 (MI0000103), hsa-mir-101-2 (MI0000739), hsa-mir-103a-1 (MI0000109), hsa-mir-103a-2 (MI0000108), hsa-mir-103b-1 (MI0007261), hsa-mir-103b-2 (MI0007262), hsa-mir-105-1 (MI0000111), hsa-mir-105-2 (MI0000112), hsa-mir-106a (MI0000113), hsa-mir-106b (MI0000734), hsa-mir-107 (MI0000114), hsa-mir-122 (MI0000442), hsa-mir-124-1 (MI0000443), hsa-mir-124-2 (MI0000444), hsa-mir-124-3 (MI0000445), hsa-mir-125a (MI0000469), hsa-mir-125b-1 (MI0000446), hsa-mir-125b-2 (MI0000470), hsa-mir-126 (MI0000471), hsa-mir-127 (MI0000472), hsa-mir-128-1 (MI0000447), hsa-mir-128-2 (MI0000727), hsa-mir-129-1 (MI0000252), hsa-mir-129-2 (MI0000473), hsa-mir-130a (MI0000448), hsa-mir-130b (MI0000748), hsa-mir-132 (MI0000449), hsa-mir-133a-1 (MI0000450), hsa-mir-133a-2 (MI0000451), hsa-mir-133b (MI0000822), hsa-mir-134 (MI0000474), hsa-mir-135a-1 (MI0000452), hsa-mir-135a-2 (MI0000453), hsa-mir-135b (MI0000810), hsa-mir-136 (MI0000475), hsa-mir-137 (MI0000454), hsa-mir-138-1 (MI0000476), hsamir-138-2 (MI0000455), hsa-mir-139 (MI0000261), hsa-mir-140 (MI0000456), hsa-mir-141 (MI0000457), hsa-mir-142 (MI0000458), hsa-mir-143 (MI0000459), hsa-mir-144 (MI0000460), hsa-mir-145 (MI0000461), hsa-mir-146a (MI0000477), hsa-mir-146b (MI0003129), hsa-mir-147a (MI0000262), hsa-mir-147b (MI0005544), hsa-mir-148a (MI0000253), hsa-mir-148b (MI0000811), hsa-mir-149 (MI0000478), hsa-mir-150 (MI0000479), hsa-mir-151a (MI0000809), hsa-mir-151b (MI0003772), hsa-mir-152 (MI0000462), hsa-mir-153-1 (MI0000463), hsa-mir-153-2 (MI0000464), hsa-mir-154 (MI0000480), hsa-mir-155 (MI0000681), hsa-mir-181a-1 (MI0000289), hsa-mir-181a-2 (MI0000269), hsa-mir-181b-1 (MI0000270), hsa-mir-181b-2 (MI0000683), hsa-mir-181c (MI0000271), hsa-mir-181d (MI0003139), hsa-mir-182 (MI0000272), hsa-mir-183 (MI0000273), hsa-mir-184 (MI0000481), hsa-mir-185 (MI0000482), hsa-mir-186 (MI0000483), hsa-mir-187 (MI0000274), hsa-mir-188 (MI0000484), hsa-mir-190a (MI0000486), hsa-mir-190b (MI0005545), hsa-mir-191 (MI0000465), hsa-mir-192 (MI0000234), hsa-mir-193a (MI0000487), hsa-mir-193b (MI0003137), hsa-mir-194-1 (MI0000488), hsa-mir-194-2 (MI0000732), hsa-mir-195 (MI0000489), hsa-mir-196a-1 (MI0000238), hsa-mir-196a-2 (MI0000279), hsa-mir-196b (MI0001150), hsa-mir-197 (MI0000239), hsa-mir-198 (MI0000240), hsa-mir-199a-1 (MI0000242), hsa-mir-199a-2 (MI0000281), hsa-mir-199b (MI0000282), hsa-mir-200a (MI0000737), hsa-mir-200b (MI0000342), hsa-mir-200c (MI0000650), hsa-mir-202 (MI0003130), hsa-mir-203a (MI0000283), hsa-mir-203b (MI0017343), hsa-mir-204 (MI0000284), hsa-mir-205 (MI0000285), hsa-mir-206 (MI0000490), hsa-mir-208a (MI0000251), hsa-mir-208b (MI0005570), hsa-mir-210 (MI0000286), hsa-mir-211 (MI0000287), hsa-mir-212 (MI0000288), hsa-mir-214 (MI0000290), hsa-mir-215 (MI0000291), hsa-mir-216a (MI0000292), hsa-mir-216b (MI0005569), hsa-mir-217 (MI0000293), hsa-mir-218-1 (MI0000294), hsa-mir-218-2 (MI0000295), hsa-mir-219a-1 (MI0000296), hsa-mir-219a-2 (MI0000740), hsa-mir-219b (MI0017299), hsa-mir-221 (MI0000298), hsa-mir-222 (MI0000299), hsa-mir-223 (MI0000300), hsa-mir-224 (MI0000301), hsa-mir-296 (MI0000747), hsa-mir-297 (MI0005775), hsa-mir-298 (MI0005523), hsa-mir-299 (MI0000744), hsa-mir-300 (MI0005525), hsa-mir-301a (MI0000745), hsa-mir-301b (MI0005568), hsa-mir-302a (MI0000738), hsa-mir-302b (MI0000772), hsa-mir-302c (MI0000773), hsa-mir-302d (MI0000774), hsa-mir-302e (MI0006417), hsa-mir-302f (MI0006418), hsa-mir-320a (MI0000542), hsa-mir-320b-1 (MI0003776), hsa-mir-320b-2 (MI0003839), hsa-mir-320c-1 (MI0003778), hsa-mir-320c-2 (MI0008191), hsa-mir-320d-1 (MI0008190), hsa-mir-320d-2 (MI0008192), hsa-mir-320e (MI0014234), hsa-mir-323a (MI0000807), hsa-mir-323b (MI001420), hsa-mir-324 (MI0000813), hsa-mir-325 (MI0000824), hsa-mir-326 (MI0000808), hsa-mir-328 (MI0000804), hsa-mir-329-1 (MI0001725), hsa-mir-329-2 (MI0001726), hsa-mir-330 (MI0000803), hsa-mir-331 (MI0000812), hsa-mir-335 (MI0000816), hsa-mir-337 (MI0000806), hsa-mir-338 (MI0000814), hsa-mir-339 (MI0000815), hsa-mir-340 (MI0000802), hsa-mir-342 (MI0000805), hsa-mir-345 (MI0000825), hsa-mir-346 (MI0000826), hsa-mir-361 (MI0000760), hsa-mir-362 (MI0000762), hsa-mir-363 (MI0000076), hsa-mir-365a (MI0000767), hsa-mir-365b (MI0000769), hsa-mir-367 (MI0000775), hsa-mir-369 (MI0000777), hsa-mir-370 (MI0000778), hsa-mir-371a (MI0000779), hsa-mir-371b (MI0017393), hsa-mir-372 (MI0000780), hsa-mir-373 (MI0000781), hsa-mir-374a (MI0000782), hsa-mir-374b (MI0005566), hsa-mir-374c (MI0016684), hsa-mir-375 (MI0000783), hsa-mir-376a-1 (MI0000784), hsa-mir-376a-2 (MI0003529), hsa-mir-376b (MI0002466), hsa-mir-376c (MI0000776), hsa-mir-377 (MI0000785), hsa-mir-378a (MI0000786), hsa-mir-378b (MI0014154), hsa-mir-378c (MI0015825), hsa-mir-378d-1 (MI0016749), hsa-mir-378d-2 (MI0003840), hsa-mir-378e (MI0016750), hsa-mir-378f (MI0016756), hsa-mir-378g (MI0016761), hsa-mir-378h (MI0016808803), hsa-mir-378i (MI0016902), hsa-mir-378j (MI0021273), hsa-mir-379 (MI0000787), hsa-mir-380 (MI0000788), hsa-mir-381 (MI0000789), hsa-mir-382 (MI0000790), hsa-mir-383 (MI0000791), hsa-mir-384 (MI0001145), hsa-mir-409 (MI0001735), hsa-mir-410 (MI0002465), hsa-mir-411 (MI0003675), hsa-mir-412 (MI0002464), hsa-mir-421 (MI0003685), hsa-mir-422a (MI0001444), hsa-mir-423 (MI0001445), hsa-mir-424 (MI0001446), hsa-mir-425 (MI0001448), hsa-mir-429 (MI0001641), hsa-mir-431 (MI0001721), hsa-mir-432 (MI0003133), hsa-mir-433 (MI0001723), hsa-mir-448 (MI0001637), hsa-mir-449a (MI0001648), hsa-mir-449b (MI0003673), hsa-mir-449c (MI0003823), hsa-mir-450a-1 (MI0001652), hsa-mir-450a-2 (MI0003187), hsa-mir-450b (MI0005531), hsa-mir-451a (MI0001729), hsa-mir-451b (MI0017360), hsa-mir-452 (MI0001733), hsa-mir-454 (MI0003820), hsa-mir-455 (MI0003513), hsa-mir-466 (MI0014157), hsa-mir-483 (MI0002467), hsa-mir-484 (MI0002468), hsa-mir-485 (MI0002469), hsa-mir-486 (MI0002470), hsa-mir-486-2 (MI0023622), hsa-mir-487a (MI0002471), hsa-mir-487b (MI0003530), hsa-mir-488 (MI0003123), hsa-mir-489 (MI0003124), hsa-mir-490 (MI0003125), hsa-mir-491 (MI0003126), hsa-mir-492 (MI0003131), hsa-mir-493 (MI0003132), hsa-mir-494 (MI0003134), hsa-mir-495 (MI0003135), hsa-mir-496 (MI0003136), hsa-mir-497 (MI0003138), hsa-mir-498 (MI0003142), hsa-mir-499a (MI0003183), hsa-mir-499b (MI0017396), hsa-mir-500a (MI0003184), hsa-mir-500b (MI0015903), hsa-mir-501 (MI0003185), hsa-mir-502 (MI0003186), hsa-mir-503 (MI0003188), hsa-mir-504 (MI0003189), hsa-mir-505 (MI0003190), hsa-mir-506 (MI0003193), hsa-mir-507 (MI0003194), hsa-mir-508 (MI0003195), hsa-mir-509-1 (MI0003196), hsa-mir-509-2 (MI0005530), hsa-mir-509-3 (MI0005717), hsa-mir-510 (MI0003197), hsa-mir-511 (MI0003127), hsa-mir-512-1 (MI0003140), hsa-mir-512-2 (MI0003141), hsa-mir-513a-1 (MI0003191), hsa-mir-513a-2 (MI0003192), hsa-mir-513b (MI0006648), hsa-mir-513c (MI0006649), hsa-mir-514a-1 (MI0003198), hsa-mir-514a-2 (MI0003199), hsa-mir-514a-3 (MI0003200), hsa-mir-514b (MI0014251), hsa-mir-515-1 (MI0003144), hsa-mir-515-2 (MI0003147), hsa-mir-516a-1 (MI0003180), hsa-mir-516a-2 (MI0003181), hsa-mir-516b-1 (MI0003172), hsa-mir-516b-2 (MI0003167), hsa-mir-517a (MI0003161), hsa-mir-517b (MI0003165), hsa-mir-517c (MI0003174), hsa-mir-518a-1 (MI0003170), hsa-mir-518a-2 (MI0003173), hsa-mir-518b (MI0003156), hsa-mir-518c (MI0003159), hsa-mir-518d (MI0003171), hsa-mir-518e (MI0003169), hsa-mir-518f (MI0003154), hsa-mir-519a-1 (MI0003178), hsa-mir-519a-2 (MI0003182), hsa-mir-519b (MI0003151), hsa-mir-519c (MI0003148), hsa-mir-519d (MI0003162), hsa-mir-519e (MI0003145), hsa-mir-520a (MI0003149), hsa-mir-520b (MI0003155), hsa-mir-520c (MI0003158), hsa-mir-520d (MI0003164), hsa-mir-520e (MI0003143), hsa-mir-520f (MI0003146), hsa-mir-520g (MI0003166), hsa-mir-520h (MI0003175), hsa-mir-521-1 (MI0003176), hsa-mir-521-2 (MI0003163), hsa-mir-522 (MI0003177), hsa-mir-523 (MI0003153), hsa-mir-524 (MI0003160), hsa-mir-525 (MI0003152), hsa-mir-526a-1 (MI0003157), hsa-mir-526a-2 (MI0003168), hsa-mir-526b (MI0003150), hsa-mir-527 (MI0003179), hsa-mir-532 (MI0003205), hsa-mir-539 (MI0003514), hsa-mir-541 (MI0005539), hsa-mir-542 (MI0003686), hsa-mir-543 (MI0005565), hsa-mir-544a (MI0003515), hsa-mir-544b (MI0014159), hsa-mir-545 (MI0003516), hsa-mir-548a-1 (MI0003593. hsa-mir-548a-2 (MI000359), hsa-mir-548a-3 (MI0003612), hsa-mir-548aa-1 (MI0016689), hsa-mir-548aa-2 (MI0016690), hsa-mir-548ab (MI0016752), hsa-mir-548ac (MI0016762), hsa-mir-548ad (MI0016770), hsa-mir-548ae-1 (MI0016779), hsa-mir-548ae-2 (MI0016780), hsa-mir-548ag-1 (MI0016793), hsa-mir-548ag-2 (MI0016794), hsa-mir-548ah (MI0016796), hsa-mir-548ai (MI0016813), hsa-mir-548aj-1 (MI0016814), hsa-mir-548aj-2 (MI0016815), hsa-mir-548ak (MI0016840), hsa-mir-548al (MI0016851), hsa-mir-548am (MI0016904), hsa-mir-548an (MI0016907), hsa-mir-548ao (MI0017871), hsa-mir-548ap (MI0017875), hsa-mir-548aq (MI0019130), hsa-mir-548ar (MI0019131), hsa-mir-548as (MI0019132), hsa-mir-548at (MI0019137), hsa-mir-548au (MI0019145), hsa-mir-548av (MI0019152), hsa-mir-548aw (MI0019283), hsa-mir-548ax (MI0019286), hsa-mir-548ay (MI0022210), hsa-mir-548az (MI0022212), hsa-mir-548b (MI0003596), hsa-mir-548ba (MI0025747), hsa-mir-548c (MI0003630), hsa-mir-548d-1 (MI0003668), hsa-mir-548d-2 (MI0003671), hsa-mir-548e (MI0006344), hsa-mir-548f-1 (MI0006374), hsa-mir-548f-2 (MI0006375), hsa-mir-548f-3 (MI0006376), hsa-mir-548f-4 (MI0006377), hsa-mir-548f-5 (MI0006378), hsa-mir-548g (MI0006395), hsa-mir-548h-1 (MI0006411), hsa-mir-548h-2 (MI0006412), hsa-mir-548h-3 (MI0006413), hsa-mir-548h-4 (MI0006414), hsa-mir-548h-5 (MI0016751), hsa-mir-548i-1 (MI0006421), hsa-mir-548i-2 (MI0006422), hsa-mir-548i-3 (MI0006423), hsa-mir-548i-4 (MI0006424), hsa-mir-548j (MI0006345), hsa-mir-548k (MI0006354), hsa-mir-548l (MI0006361), hsa-mir-548m (MI0006400), hsa-mir-548n (MI0006399), hsa-mir-548o (MI0006402), hsa-mir-548o-2 (MI0016746), hsa-mir-548p (MI0006420), hsa-mir-548q (MI0010637), hsa-mir-548s (MI0014141), hsa-mir-548t (MI0014164), hsa-mir-548u (MI0014168), hsa-mir-548v (MI0014174), hsa-mir-548w (MI0014222), hsa-mir-548x (MI0014244), hsa-mir-548x-2 (MI0016833), hsa-mir-548y (MI0016595), hsa-mir-548z (MI0016688), hsa-mir-549a (MI0003679), hsa-mir-550a-1 (MI0003600), hsa-mir-550a-2 (MI0003601), hsa-mir-550a-3 (MI0003762), hsa-mir-550b-1 (MI0016686), hsa-mir-550b-2 (MI0016687), hsa-mir-551a (MI0003556), hsa-mir-551b (MI0003575), hsa-mir-552 (MI0003557), hsa-mir-553 (MI0003558), hsa-mir-554 (MI0003559), hsa-mir-555 (MI0003561), hsa-mir-556 (MI0003562), hsa-mir-557 (MI0003563), hsa-mir-558 (MI0003564), hsa-mir-559 (MI0003565), hsa-mir-561 (MI0003567), hsa-mir-562 (MI0003568), hsa-mir-563 (MI0003569), hsa-mir-564 (MI0003570), hsa-mir-566 (MI0003572), hsa-mir-567 (MI0003573), hsa-mir-568 (MI0003574), hsa-mir-569 (MI0003576), hsa-mir-570 (MI0003577), hsa-mir-571 (MI0003578), hsa-mir-572 (MI0003579), hsa-mir-573 (MI0003580), hsa-mir-574 (MI0003581), hsa-mir-575 (MI0003582), hsa-mir-576 (MI0003583), hsa-mir-577 (MI0003584), hsa-mir-578 (MI0003585), hsa-mir-579 (MI0003586), hsa-mir-580 (MI0003587), hsa-mir-581 (MI0003588), hsa-mir-582 (MI0003589), hsa-mir-583 (MI0003590), hsa-mir-584 (MI0003591), hsa-mir-585 (MI000359), hsa-mir-586 (MI0003594), hsa-mir-587 (MI0003595), hsa-mir-588 (MI0003597), hsa-mir-589 (MI0003599), hsa-mir-590 (MI0003602), hsa-mir-591 (MI0003603), hsa-mir-592 (MI0003604), hsa-mir-593 (MI0003605), hsa-mir-595 (MI0003607), hsa-mir-596 (MI0003608), hsa-mir-597 (MI0003609), hsa-mir-598 (MI0003610162), hsa-mir-599 (MI0003611), hsa-mir-600 (MI0003613), hsa-mir-601 (MI0003614), hsa-mir-602 (MI0003615), hsa-mir-603 (MI0003616), hsa-mir-604 (MI0003617), hsa-mir-605 (MI0003618), hsa-mir-606 (MI0003619), hsa-mir-607 (MI0003620), hsa-mir-608 (MI0003621), hsa-mir-609 (MI0003622), hsa-mir-610 (MI0003623), hsa-mir-611 (MI0003624), hsa-mir-612 (MI0003625), hsa-mir-613 (MI0003626), hsa-mir-614 (MI0003627), hsa-mir-615 (MI0003628), hsa-mir-616 (MI0003629), hsa-mir-617 (MI0003631), hsa-mir-618 (MI0003632), hsa-mir-619 (MI0003633), hsa-mir-620 (MI0003634), hsa-mir-621 (MI0003635), hsa-mir-622 (MI0003636), hsa-mir-623 (MI0003637), hsa-mir-624 (MI0003638), hsa-mir-625 (MI0003639), hsa-mir-626 (MI0003640), hsa-mir-627 (MI0003641), hsa-mir-628 (MI0003642), hsa-mir-629 (MI0003643), hsa-mir-630 (MI000364), hsa-mir-631 (MI0003645), hsa-mir-632 (MI0003647), hsa-mir-633 (MI0003648), hsa-mir-634 (MI0003649), hsa-mir-635 (MI0003650), hsa-mir-636 (MI0003651), hsa-mir-637 (MI0003652), hsa-mir-638 (MI0003653), hsa-mir-639 (MI0003654), hsa-mir-640 (MI0003655), hsa-mir-641 (MI0003656), hsa-mir-642a (MI0003657), hsa-mir-642b (MI0016685), hsa-mir-643 (MI0003658), hsa-mir-644a (MI0003659), hsa-mir-645 (MI0003660), hsa-mir-646 (MI0003661), hsa-mir-647 (MI0003662), hsa-mir-648 (MI0003663), hsa-mir-649 (MI0003664), hsa-mir-650 (MI0003665), hsa-mir-651 (MI0003666), hsa-mir-652 (MI0003667), hsa-mir-653 (MI0003674), hsa-mir-654 (MI0003676), hsa-mir-655 (MI0003677), hsa-mir-656 (MI0003678), hsa-mir-657 (MI0003681), hsa-mir-658 (MI0003682), hsa-mir-659 (MI0003683), hsa-mir-660 (MI0003684), hsa-mir-661 (MI0003669), hsa-mir-662 (MI0003670), hsa-mir-663a (MI0003672), hsa-mir-663b (MI0006336), hsa-mir-664a (MI0006442), hsa-mir-664b (MI0019134), hsa-mir-665 (MI0005563), hsa-mir-668 (MI0003761), hsa-mir-670 (MI0003933), hsa-mir-671 (MI0003760), hsa-mir-675 (MI0005416), hsa-mir-676 (MI0016436), hsa-mir-708 (MI0005543), hsa-mir-711 (MI0012488), hsa-mir-718 (MI0012489), hsa-mir-744 (MI0005559), hsa-mir-758 (MI0003757), hsa-mir-759 (MI0004065), hsa-mir-760 (MI0005567), hsa-mir-761 (MI0003941), hsa-mir-762 (MI0003892), hsa-mir-764 (MI0003944), hsa-mir-765 (MI0005116), hsa-mir-766 (MI0003836), hsa-mir-767 (MI0003763), hsa-mir-769 (MI0003834), hsa-mir-770 (MI0005118), hsa-mir-802 (MI0003906), hsa-mir-873 (MI0005564), hsa-mir-874 (MI0005532), hsa-mir-875 (MI0005541), hsa-mir-876 (MI0005542), hsa-mir-877 (MI0005561), hsa-mir-885 (MI0005560), hsa-mir-887 (MI0005562), hsa-mir-888 (MI0005537), hsa-mir-889 (MI0005540), hsa-mir-890 (MI0005533), hsa-mir-891a (MI0005524), hsa-mir-891b (MI0005534), hsa-mir-892a (MI0005528), hsa-mir-892b (MI0005538), hsa-mir-892c (MI0022560), hsa-mir-920 (MI0005712), hsa-mir-921 (MI0005713), hsa-mir-922 (MI0005714), hsa-mir-924 (MI0005716), hsa-mir-933 (MI0005755), hsa-mir-934 (MI0005756), hsa-mir-935 (MI0005757), hsa-mir-936 (MI0005758), hsa-mir-937 (MI0005759), hsa-mir-938 (MI0005760), hsa-mir-939 (MI0005761), hsa-mir-940 (MI0005762), hsa-mir-941-1 (MI0005763), hsa-mir-941-2 (MI0005764), hsa-mir-941-3 (MI0005765), hsa-mir-941-4 (MI0005766), hsa-mir-942 (MI0005767), hsa-mir-943 (MI0005768), hsa-mir-944 (MI0005769), hsa-mir-1178 (MI0006271), hsa-mir-1179 (MI0006272), hsa-mir-1180 (MI0006273), hsa-mir-1181 (MI0006274), hsa-mir-1182 (MI0006275), hsa-mir-1183 (MI0006276), hsa-mir-1184-1 (MI0006277), hsa-mir- 1184-2 (MI0015971), hsa-mir-1184-3 (MI0015972), hsa-mir-1185-1 (MI0003844), hsa-mir-1185-2 (MI0003821), hsa-mir-1193 (MI0014205), hsa-mir-1197 (MI0006656), hsa-mir-1199 (MI0020340), hsa-mir-1200 (MI0006332), hsa-mir-1202 (MI0006334), hsa-mir-1203 (MI0006335), hsa-mir-1204 (MI0006337), hsa-mir-1205 (MI0006338), hsa-mir-1206 (MI0006339), hsa-mir-1207 (MI0006340), hsa-mir-1208 (MI0006341), hsa-mir-1224 (MI0003764), hsa-mir-1225 (MI0006311), hsa-mir-1226 (MI0006313), hsa-mir-1227 (MI0006316), hsa-mir-1228 (MI0006318), hsa-mir-1229 (MI0006319), hsa-mir-1231 (MI0006321), hsa-mir-1233-1 (MI0006323), hsa-mir-1233-2 (MI0015973), hsa-mir-1234 (MI0006324), hsa-mir-1236 (MI0006326), hsa-mir-1237 (MI0006327), hsa-mir-1238 (MI0006328), hsa-mir-1243 (MI0006373), hsa-mir-1244-1 (MI0006379), hsa-mir-1244-2 (MI0015974), hsa-mir-1244-3 (MI0015975), hsa-mir-1245a (MI0006380), hsa-mir-1245b (MI0017431), hsa-mir-1246 (MI0006381), hsa-mir-1247 (MI0006382), hsa-mir-1248 (MI0006383), hsa-mir-1249 (MI0006384), hsa-mir-1250 (MI0006385), hsa-mir-1251 (MI0006386), hsa-mir-1252 (MI0006434), hsa-mir-1253 (MI0006387), hsa-mir-1254-1 (MI000638), hsa-mir-1254-2 (MI0016747), hsa-mir-1255a (MI0006389), hsa-mir-1255b-1 (MI0006435), hsa-mir-1255b-2 (MI0006436), hsa-mir-1256 (MI0006390), hsa-mir-1257 (MI0006391), hsa-mir-1258 (MI0006392), hsa-mir-1260a (MI0006394), hsa-mir-1260b (MI0014197), hsa-mir-1261 (MI0006396), hsa-mir-1262 (MI0006397), hsa-mir-1263 (MI0006398), hsa-mir-1264 (MI0003758), hsa-mir-1265 (MI0006401), hsa-mir-1266 (MI0006403), hsa-mir-1267 (MI0006404), hsa-mir-1268a (MI0006405), hsa-mir-1268b (MI0016748), hsa-mir-1269a (MI0006406), hsa-mir-1269b (MI0016888), hsa-mir-1270-1 (MI0006407), hsa-mir-1270-2 (MI0015976), hsa-mir-1271 (MI0003814), hsa-mir-1272 (MI0006408), hsa-mir-1273a (MI0006409), hsa-mir-1273c (MI0014171), hsa-mir-1273d (MI0014254), hsa-mir-1273e (MI0016059), hsa-mir-1273f (MI0018002), hsa-mir-1273g (MI0018003), hsa-mir-1273h (MI0025512), hsa-mir-1275 (MI0006415), hsa-mir-1276 (MI0006416), hsa-mir-1277 (MI0006419), hsa-mir-1278 (MI0006425), hsa-mir-1279 (MI0006426), hsa-mir-1281 (MI0006428), hsa-mir-1282 (MI0006429), hsa-mir-1283-1 (MI0003832), hsa-mir-1283-2 (MI0006430), hsa-mir-1284 (MI0006431), hsa-mir-1285-1 (MI0006346), hsa-mir-1285-2 (MI0006347), hsa-mir-1286 (MI0006348), hsa-mir-1287 (MI0006349), hsa-mir-1288 (MI0006432), hsa-mir-1289-1 (MI0006350), hsa-mir-1289-2 (MI0006351), hsa-mir-1290 (MI0006352), hsa-mir-1291 (MI0006353), hsa-mir-1292 (MI0006433), hsa-mir-1293 (MI0006355), hsa-mir-1294 (MI0006356), hsa-mir-1295a (MI0006357), hsa-mir-1295b (MI0019146), hsa-mir-1296 (MI0003780), hsa-mir-1297 (MI0006358), hsa-mir-1298 (MI0003938), hsa-mir-1299 (MI0006359), hsa-mir-1301 (MI0003815), hsa-mir-1302-1 (MI0006362), hsa-mir-1302-10 (MI0015979), hsa-mir-1302-11 (MI0015980), hsa-mir-1302-2 (MI0006363), hsa-mir-1302-3 (MI0006364), hsa-mir-1302-4 (MI0006365), hsa-mir-1302-5 (MI0006366), hsa-mir-1302-6 (MI0006367), hsa-mir-1302-7 (MI0006368), hsa-mir-1302-8 (MI0006369), hsa-mir-1302-9 (MI0015978), hsa-mir-1303 (MI0006370), hsa-mir-1304 (MI0006371), hsa-mir-1305 (MI0006372), hsa-mir-1306 (MI0006443), hsa-mir-1307 (MI0006444), hsa-mir-1321 (MI0006652), hsa-mir-1322 (MI0006653), hsa-mir-1323 (MI0003786), hsa-mir-1324 (MI0006657), hsa-mir-1343 (MI0017320), hsa-mir-1468 (MI0003782), hsa-mir-1469 (MI0007074), hsa-mir-1470 (MI0007075), hsa-mir-1471 (MI0007076), hsa-mir-1537 (MI0007258), hsa-mir-1538 (MI0007259), hsa-mir-1539 (MI0007260), hsa-mir-1587 (MI0016905), hsa-mir-1825 (MI0008193), hsa-mir-1827 (MI0008195), hsa-mir-1908 (MI0008329), hsa-mir-1909 (MI0008330), hsa-mir-1910 (MI0008331), hsa-mir-1911 (MI0008332), hsa-mir-1912 (MI0008333), hsa-mir-1913 (MI0008334), hsa-mir-1914 (MI0008335), hsa-mir-1915 (MI0008336), hsa-mir-1972-1 (MI0009982), hsa-mir-1972-2 (MI0015977), hsa-mir-1973 (MI0009983), hsa-mir-1976 (MI0009986), hsa-mir-2052 (MI0010486), hsa-mir-2053 (MI0010487), hsa-mir-2054 (MI0010488), hsa-mir-2110 (MI0010629), hsa-mir-2113 (MI0003939), hsa-mir-2114 (MI0010633), hsa-mir-2115 (MI0010634), hsa-mir-2116 (MI0010635), hsa-mir-2117 (MI0010636), hsa-mir-2276 (MI0011282), hsa-mir-2277 (MI0011284), hsa-mir-2278 (MI0011285), hsa-mir-2355 (MI0015873), hsa-mir-2392 (MI0016870), hsa-mir-2467 (MI0017432), hsa-mir-2681 (MI0012062), hsa-mir-2682 (MI0012063), hsa-mir-2861 (MI0013006), hsa-mir-2909 (MI0013083), hsa-mir-3064 (MI0017375), hsa-mir-3065 (MI0014228), hsa-mir-3074 (MI0014181), hsa-mir-3115 (MI0014127), hsa-mir-3116-1 (MI0014128), hsa-mir-3116-2 (MI0014129), hsa-mir-3117 (MI0014130), hsa-mir-3118-1 (MI0014131), hsa-mir-3118-2 (MI0014132), hsa-mir-3118-3 (MI0014133), hsa-mir-3118-4 (MI0014207), hsa-mir-3118-5 (MI0014243), hsa-mir-3118-6 (MI0015981), hsa-mir-3119-1 (MI0014134), hsa-mir-3119-2 (MI0014135), hsa-mir-3120 (MI0014136), hsa-mir-3121 (MI0014137), hsa-mir-3122 (MI0014138), hsa-mir-3123 (MI0014139), hsa-mir-3124 (MI0014140), hsa-mir-3125 (MI0014142), hsa-mir-3126 (MI0014143), hsa-mir-3127 (MI0014144), hsa-mir-3128 (MI0014145), hsa-mir-3129 (MI0014146), hsa-mir-3130-1 (MI0014147), hsa-mir-3130-2 (MI0014148), hsa-mir-3131 (MI0014151), hsa-mir-3132 (MI0014152), hsa-mir-3133 (MI0014153), hsa-mir-3134 (MI0014155), hsa-mir-3135a (MI0014156), hsa-mir-3135b (MI0016809), hsa-mir-3136 (MI0014158), hsa-mir-3137 (MI0014160), hsa-mir-3138 (MI0014161), hsa-mir-3139 (MI0014162), hsa-mir-3140 (MI0014163), hsa-mir-3141 (MI0014165), hsa-mir-3142 (MI0014166), hsa-mir-3143 (MI0014167), hsa-mir-3144 (MI0014169), hsa-mir-3145 (MI0014170), hsa-mir-3146 (MI0014172), hsa-mir-3147 (MI0014173), hsa-mir-3148 (MI0014175), hsa-mir-3149 (MI0014176), hsa-mir-3150a (MI0014177), hsa-mir-3150b (MI0016426), hsa-mir-3151 (MI0014178), hsa-mir-3152 (MI0014179), hsa-mir-3153 (MI0014180), hsa-mir-3154 (MI0014182), hsa-mir-3155a (MI0014183), hsa-mir-3155b (MI0016839), hsa-mir-3156-1 (MI0014184), hsa-mir-3156-2 (MI0014230), hsa-mir-3156-3 (MI0014242), hsa-mir-3157 (MI0014185), hsa-mir-3158-1 (MI0014186), hsa-mir-3158-2 (MI0014187), hsa-mir-3159 (MI0014188), hsa-mir-3160-1 (MI0014189), hsa-mir-3160-2 (MI0014190), hsa-mir-3161 (MI0014191), hsa-mir-3162 (MI0014192), hsa-mir-3163 (MI0014193), hsa-mir-3164 (MI0014194), hsa-mir-3165 (MI0014195), hsa-mir-3166 (MI0014196), hsa-mir-3167 (MI0014198), hsa-mir-3168 (MI0014199), hsa-mir-3169 (MI0014200), hsa-mir-3170 (MI0014201), hsa-mir-3171 (MI0014202), hsa-mir-3173 (MI0014204), hsa-mir-3174 (MI0014208), hsa-mir-3175 (MI0014209), hsa-mir-3176 (MI0014210), hsa-mir-3177 (MI0014211), hsa-mir-3178 (MI0014212), hsa-mir-3179-1 (MI0014213), hsa-mir-3179-2 (MI0014216; hsa-mir-3179-3 (MI0014221), hsa-mir-3180-1 (MI0014214), hsa-mir-3180-2 (MI0014215; hsa-mir-3180-3 (MI0014217), hsa-mir-3180-4 (MI0016408), hsa-mir-3180-5 (MI0016409), hsa-mir-3181 (MI0014223), hsa-mir-3182 (MI0014224), hsa-mir-3183 (MI0014225), hsa-mir-3184 (MI0014226), hsa-mir-3185 (MI0014227), hsa-mir-3186 (MI0014229), hsa-mir-3187 (MI0014231), hsa-mir-3188 (MI0014232), hsa-mir-3189 (MI0014233), hsa-mir-3190 (MI0014235), hsa-mir-3191 (MI0014236), hsa-mir-3192 (MI0014237), hsa-mir-3193 (MI0014238), hsa-mir-3194 (MI0014239), hsa-mir-3195 (MI0014240), hsa-mir-3196 (MI0014241), hsa-mir-3197 (MI0014245), hsa-mir-3198-1 (MI0014246), hsa-mir-3198-2 (MI0017335), hsa-mir-3199-1 (MI0014247), hsa-mir-3199-2 (MI0014248), hsa-mir-3200 (MI0014249), hsa-mir-3201 (MI0014250), hsa-mir-3202-1 (MI0014252), hsa-mir-3202-2 (MI0014253), hsa-mir-3529 (MI0017351), hsa-mir-3591 (MI0017383), hsa-mir-3605 (MI0015995), hsa-mir-3606 (MI0015996), hsa-mir-3607 (MI0015997), hsa-mir-3609 (MI0015999), hsa-mir-3610 (MI0016000), hsa-mir-3611 (MI0016001), hsa-mir-3612 (MI0016002), hsa-mir-3613 (MI0016003), hsa-mir-3614 (MI0016004), hsa-mir-3615 (MI0016005), hsa-mir-3616 (MI0016006), hsa-mir-3617 (MI0016007), hsa-mir-3618 (MI0016008), hsa-mir-3619 (MI0016009), hsa-mir-3620 (MI0016011), hsa-mir-3621 (MI0016012), hsa-mir-3622a (MI0016013), hsa-mir-3622b (MI0016014), hsa-mir-3646 (MI0016046), hsa-mir-3648 (MI0016048), hsa-mir-3649 (MI0016049), hsa-mir-3650 (MI0016050), hsa-mir-3651 (MI0016051), hsa-mir-3652 (MI0016052), hsa-mir-3653 (MI0016053), hsa-mir-3654 (MI0016054), hsa-mir-3655 (MI0016055), hsa-mir-3656 (MI0016056), hsa-mir-3657 (MI0016057), hsa-mir-3658 (MI0016058), hsa-mir-3659 (MI0016060), hsa-mir-3660 (MI0016061), hsa-mir-3661 (MI0016062), hsa-mir-3662 (MI0016063), hsa-mir-3663 (MI0016064), hsa-mir-3664 (MI0016065), hsa-mir-3665 (MI0016066), hsa-mir-3666 (MI0016067), hsa-mir-3667 (MI0016068), hsa-mir-3668 (MI0016069), hsa-mir-3669 (MI0016070), hsa-mir-3670-1 (MI0016071), hsa-mir-3670-2 (MI0019112), hsa-mir-3671 (MI0016072), hsa-mir-3672 (MI0016073), hsa-mir-3673 (MI0016074), hsa-mir-3674 (MI0016075), hsa-mir-3675 (MI0016076), hsa-mir-3677 (MI0016078), hsa-mir-3678 (MI0016079), hsa-mir-3679 (MI0016080), hsa-mir-3680-1 (MI0016081), hsa-mir-3680-2 (MI0019113), hsa-mir-3681 (MI0016082), hsa-mir-3682 (MI0016083), hsa-mir-3683 (MI0016084), hsa-mir-3684 (MI0016085), hsa-mir-3685 (MI0016086), hsa-mir-3686 (MI0016087), hsa-mir-3687 (MI0016088), hsa-mir-3688-1 (MI0016089), hsa-mir-3688-2 (MI0017447), hsa-mir-3689a (MI0016090), hsa-mir-3689b (MI0016411), hsa-mir-3689c (MI0016832), hsa-mir-3689d-1 (MI0016834), hsa-mir-3689d-2 (MI0016835), hsa-mir-3689e (MI0016836), hsa-mir-3689f (MI0016837), hsa-mir-3690-1 (MI0016091), hsa-mir-3690-2 (MI0023561), hsa-mir-3691 (MI0016092), hsa-mir-3692 (MI0016093), hsa-mir-3713 (MI0016134), hsa-mir-3714 (MI0016135), hsa-mir-3907 (MI0016410), hsa-mir-3908 (MI0016412), hsa-mir-3909 (MI0016413), hsa-mir-3910-1 (MI0016414), hsa-mir-3910-2 (MI0016431), hsa-mir-3911 (MI0016415), hsa-mir-3912 (MI0016416), hsa-mir-3913-1 (MI0016417), hsa-mir-3913-2 (MI0016418), hsa-mir-3914-1 (MI0016419), hsa-mir-3914-2 (MI0016421), hsa-mir-3915 (MI0016420), hsa-mir-3916 (MI0016422), hsa-mir-3917 (MI0016423), hsa-mir-3918 (MI0016424), hsa-mir-3919 (MI0016425), hsa-mir-3920 (MI0016427), hsa-mir-3921 (MI0016428), hsa-mir-3922 (MI0016429), hsa-mir-3923 (MI0016430), hsa-mir-3924 (MI0016432), hsa-mir-3925 (MI0016433), hsa-mir-3926-1 (MI0016434), hsa-mir-3926-2 (MI0016437), hsa-mir-3927 (MI0016435), hsa-mir-3928 (MI0016438), hsa-mir-3929 (MI0016439), hsa-mir-3934 (MI0016590), hsa-mir-3935 (MI0016591), hsa-mir-3936 (MI0016592), hsa-mir-3937 (MI0016593), hsa-mir-3938 (MI0016594), hsa-mir-3939 (MI0016596), hsa-mir-3940 (MI0016597), hsa-mir-3941 (MI0016598), hsa-mir-3942 (MI0016599), hsa-mir-3943 (MI0016600), hsa-mir-3944 (MI0016601), hsa-mir-3945 (MI0016602), hsa-mir-3960 (MI0016964), hsa-mir-3972 (MI0016990), hsa-mir-3973 (MI0016991), hsa-mir-3974 (MI0016992), hsa-mir-3975 (MI0016993), hsa-mir-3976 (MI0016994), hsa-mir-3977 (MI0016995), hsa-mir-3978 (MI0016996), hsa-mir-4251 (MI0015861), hsa-mir-4252 (MI0015864), hsa-mir-4253 (MI0015860), hsa-mir-4254 (MI0015862), hsa-mir-4255 (MI0015863), hsa-mir-4256 (MI0015855), hsa-mir-4257 (MI0015856), hsa-mir-4259 (MI0015858), hsa-mir-4260 (MI0015859), hsa-mir-4261 (MI0015868), hsa-mir-4262 (MI0015872), hsa-mir-4263 (MI0015876), hsa-mir-4264 (MI0015877), hsa-mir-4265 (MI0015869), hsa-mir-4266 (MI0015870), hsa-mir-4267 (MI0015871), hsa-mir-4268 (MI0015874), hsa-mir-4269 (MI0015875), hsa-mir-4270 (MI0015878), hsa-mir-4271 (MI0015879), hsa-mir-4272 (MI0015880), hsa-mir-4273 (MI0015881), hsa-mir-4274 (MI0015884), hsa-mir-4275 (MI0015883), hsa-mir-4276 (MI0015882), hsa-mir-4277 (MI0015886), hsa-mir-4278 (MI0015888), hsa-mir-4279 (MI0015887), hsa-mir-4280 (MI0015889), hsa-mir-4281 (MI0015885), hsa-mir-4282 (MI0015890), hsa-mir-4283-1 (MI0015892), hsa-mir-4283-2 (MI0015982), hsa-mir-4284 (MI0015893), hsa-mir-4285 (MI0015891), hsa-mir-4286 (MI0015894), hsa-mir-4287 (MI0015895), hsa-mir-4288 (MI0015896), hsa-mir-4289 (MI0015898), hsa-mir-4290 (MI0015899), hsa-mir-4291 (MI0015900), hsa-mir-4292 (MI0015897), hsa-mir-4293 (MI0015826), hsa-mir-4294 (MI0015827), hsa-mir-4295 (MI0015822), hsa-mir-4296 (MI0015823), hsa-mir-4297 (MI0015824), hsa-mir-4298 (MI0015830), hsa-mir-4299 (MI0015829), hsa-mir-4300 (MI0015831), hsa-mir-4301 (MI0015828), hsa-mir-4302 (MI0015833), hsa-mir-4303 (MI0015834), hsa-mir-4304 (MI0015832), hsa-mir-4305 (MI0015835), hsa-mir-4306 (MI0015836), hsa-mir-4307 (MI0015838), hsa-mir-4308 (MI0015839), hsa-mir-4309 (MI0015837), hsa-mir-4310 (MI0015840), hsa-mir-4311 (MI0015841), hsa-mir-4312 (MI0015842), hsa-mir-4313 (MI0015843), hsa-mir-4314 (MI0015846), hsa-mir-4315-1 (MI0015844), hsa-mir-4315-2 (MI0015983), hsa-mir-4316 (MI0015845), hsa-mir-4317 (MI0015850), hsa-mir-4318 (MI0015847), hsa-mir-4319 (MI0015848), hsa-mir-4320 (MI0015849), hsa-mir-4321 (MI0015852), hsa-mir-4322 (MI0015851), hsa-mir-4323 (MI0015853), hsa-mir-4324 (MI0015854), hsa-mir-4325 (MI0015865), hsa-mir-4326 (MI0015866), hsa-mir-4327 (MI0015867), hsa-mir-4328 (MI0015904), hsa-mir-4329 (MI0015901), hsa-mir-4330 (MI0015902), hsa-mir-4417 (MI0016753), hsa-mir-4418 (MI0016754), hsa-mir-4419a (MI0016755), hsa-mir-4419b (MI0016861), hsa-mir-4420 (MI0016757), hsa-mir-4421 (MI0016758), hsa-mir-4422 (MI0016759), hsa-mir-4423 (MI0016760), hsa-mir-4424 (MI0016763), hsa-mir-4425 (MI0016764), hsa-mir-4426 (MI0016765), hsa-mir-4427 (MI0016766), hsa-mir-4428 (MI0016767), hsa-mir-4429 (MI0016768), hsa-mir-4430 (MI0016769), hsa-mir-4431 (MI0016771), hsa-mir-4432 (MI0016772), hsa-mir-4433 (MI0016773), hsa-mir-4433b (MI0025511), hsa-mir-4434 (MI0016774), hsa-mir-4435-1 (MI0016775), hsa-mir-4435-2 (MI0016777), hsa-mir-4436a (MI0016776), hsa-mir-4436b-1 (MI0017425), hsa-mir-4436b-2 (MI0019110), hsa-mir-4437 (MI0016778), hsa-mir-4438 (MI0016781), hsa-mir-4439 (MI0016782), hsa-mir-4440 (MI0016783), hsa-mir-4441 (MI0016784), hsa-mir-4442 (MI0016785), hsa-mir-4443 (MI0016786), hsa-mir-4444-1 (MI0016787), hsa-mir-4444-2 (MI0019111), hsa-mir-4445 (MI0016788), hsa-mir-4446 (MI0016789), hsa-mir-4447 (MI0016790), hsa-mir-4448 (MI0016791), hsa-mir-4449 (MI0016792), hsa-mir-4450 (MI0016795), hsa-mir-4451 (MI0016797), hsa-mir-4452 (MI0016798), hsa-mir-4453 (MI0016799), hsa-mir-4454 (MI0016800), hsa-mir-4455 (MI0016801), hsa-mir-4456 (MI0016802), hsa-mir-4457 (MI0016803), hsa-mir-4458 (MI0016804), hsa-mir-4459 (MI0016805), hsa-mir-4460 (MI0016806), hsa-mir-4461 (MI0016807), hsa-mir-4462 (MI0016810), hsa-mir-4463 (MI0016811), hsa-mir-4464 (MI0016812), hsa-mir-4465 (MI0016816), hsa-mir-4466 (MI0016817), hsa-mir-4467 (MI0016818), hsa-mir-4468 (MI0016819), hsa-mir-4469 (MI0016820), hsa-mir-4470 (MI0016821), hsa-mir-4471 (MI0016822), hsa-mir-4472-1 (MI0016823), hsa-mir-4472-2 (MI0016824), hsa-mir-4473 (MI0016825), hsa-mir-4474 (MI0016826), hsa-mir-4475 (MI0016827), hsa-mir-4476 (MI0016828), hsa-mir-4477a (MI0016829), hsa-mir-4477b (MI0016830), hsa-mir-4478 (MI0016831), hsa-mir-4479 (MI0016838), hsa-mir-4480 (MI0016841), hsa-mir-4481 (MI0016842), hsa-mir-4482 (MI0016843), hsa-mir-4483 (MI0016844), hsa-mir-4484 (MI0016845), hsa-mir-4485 (MI0016846), hsa-mir-4486 (MI0016847), hsa-mir-4487 (MI0016848), hsa-mir-4488 (MI0016849), hsa-mir-4489 (MI0016850), hsa-mir-4490 (MI0016852), hsa-mir-4491 (MI0016853), hsa-mir-4492 (MI0016854), hsa-mir-4493 (MI0016855), hsa-mir-4494 (MI0016856), hsa-mir-4495 (MI0016857), hsa-mir-4496 (MI0016858), hsa-mir-4497 (MI0016859), hsa-mir-4498 (MI0016860), hsa-mir-4499 (MI0016862), hsa-mir-4500 (MI0016863), hsa-mir-4501 (MI0016864), hsa-mir-4502 (MI0016865), hsa-mir-4503 (MI0016866), hsa-mir-4504 (MI0016867), hsa-mir-4505 (MI0016868), hsa-mir-4506 (MI0016869), hsa-mir-4507 (MI0016871), hsa-mir-4508 (MI0016872), hsa-mir-4509-1 (MI0016873), hsa-mir-4509-2 (MI0016874), hsa-mir-4509-3 (MI0016875), hsa-mir-4510 (MI0016876), hsa-mir-4511 (MI0016877), hsa-mir-4512 (MI0016878), hsa-mir-4513 (MI0016879), hsa-mir-4514 (MI0016880), hsa-mir-4515 (MI0016881), hsa-mir-4516 (MI0016882), hsa-mir-4517 (MI0016883), hsa-mir-4518 (MI0016884), hsa-mir-4519 (MI0016885), hsa-mir-4520a (MI0016886), hsa-mir-4520b (MI0017358), hsa-mir-4521 (MI0016887), hsa-mir-4522 (MI0016889), hsa-mir-4523 (MI0016890), hsa-mir-4524a (MI0016891), hsa-mir-4524b (MI0019114), hsa-mir-4525 (MI0016892), hsa-mir-4526 (MI0016893), hsa-mir-4527 (MI0016894), hsa-mir-4528 (MI0016895), hsa-mir-4529 (MI0016896), hsa-mir-4530 (MI0016897), hsa-mir-4531 (MI0016898), hsa-mir-4532 (MI0016899), hsa-mir-4533 (MI0016900), hsa-mir-4534 (MI0016901), hsa-mir-4535 (MI0016903), hsa-mir-4536-1 (MI0016906), hsa-mir-4536-2 (MI0019149), hsa-mir-4537 (MI0016908), hsa-mir-4538 (MI0016909), hsa-mir-4539 (MI0016910), hsa-mir-4540 (MI0016911), hsa-mir-4632 (MI0017259), hsa-mir-4633 (MI0017260), hsa-mir-4634 (MI0017261), hsa-mir-4635 (MI0017262), hsa-mir-4636 (MI0017263), hsa-mir-4637 (MI0017264), hsa-mir-4638 (MI0017265), hsa-mir-4639 (MI0017266), hsa-mir-4640 (MI0017267), hsa-mir-4641 (MI0017268), hsa-mir-4642 (MI0017269), hsa-mir-4643 (MI0017270), hsa-mir-4644 (MI0017271), hsa-mir-4645 (MI0017272), hsa-mir-4646 (MI0017273), hsa-mir-4647 (MI0017274), hsa-mir-4648 (MI0017275), hsa-mir-4649 (MI0017276), hsa-mir-4650-1 (MI0017277), hsa-mir-4650-2 (MI0017278), hsa-mir-4651 (MI0017279), hsa-mir-4652 (MI0017280), hsa-mir-4653 (MI0017281), hsa-mir-4654 (MI0017282), hsa-mir-4655 (MI0017283), hsa-mir-4656 (MI0017284), hsa-mir-4657 (MI0017285), hsa-mir-4658 (MI0017286), hsa-mir-4659a (MI0017287), hsa-mir-4659b (MI0017291), hsa-mir-4660 (MI0017288), hsa-mir-4661 (MI0017289), hsa-mir-4662a (MI0017290), hsa-mir-4662b (MI0017293), hsa-mir-4663 (MI0017292), hsa-mir-4664 (MI001729), hsa-mir-4665 (MI0017295), hsa-mir-4666a (MI0017296), hsa-mir-4666b (MI0019299), hsa-mir-4667 (MI0017297), hsa-mir-4668 (MI0017298), hsa-mir-4669 (MI0017300), hsa-mir-4670 (MI0017301), hsa-mir-4671 (MI0017302), hsa-mir-4672 (MI0017303), hsa-mir-4673 (MI0017304), hsa-mir-4674 (MI0017305), hsa-mir-4675 (MI0017306), hsa-mir-4676 (MI0017307), hsa-mir-4677 (MI0017308), hsa-mir-4678 (MI0017309), hsa-mir-4679-1 (MI0017310), hsa-mir-4679-2 (MI0017311), hsa-mir-4680 (MI0017312), hsa-mir-4681 (MI0017313), hsa-mir-4682 (MI0017314), hsa-mir-4683 (MI0017315), hsa-mir-4684 (MI0017316), hsa-mir-4685 (MI0017317), hsa-mir-4686 (MI0017318), hsa-mir-4687 (MI0017319), hsa-mir-4688 (MI0017321), hsa-mir-4689 (MI0017322), hsa-mir-4690 (MI0017323), hsa-mir-4691 (MI0017324), hsa-mir-4692 (MI0017325), hsa-mir-4693 (MI0017326), hsa-mir-4694 (MI0017327), hsa-mir-4695 (MI0017328), hsa-mir-4696 (MI0017329), hsa-mir-4697 (MI0017330), hsa-mir-4698 (MI0017331), hsa-mir-4699 (MI0017332), hsa-mir-4700 (MI0017333), hsa-mir-4701 (MI0017334), hsa-mir-4703 (MI0017336), hsa-mir-4704 (MI0017337), hsa-mir-4705 (MI0017338), hsa-mir-4706 (MI0017339), hsa-mir-4707 (MI0017340), hsa-mir-4708 (MI0017341), hsa-mir-4709 (MI0017342), hsa-mir-4710 (MI0017344), hsa-mir-4711 (MI0017345), hsa-mir-4712 (MI0017346), hsa-mir-4713 (MI0017347), hsa-mir-4714 (MI0017348), hsa-mir-4715 (MI0017349), hsa-mir-4716 (MI0017350), hsa-mir-4717 (MI0017352), hsa-mir-4718 (MI0017353), hsa-mir-4719 (MI0017354), hsa-mir-4720 (MI0017355), hsa-mir-4721 (MI0017356), hsa-mir-4722 (MI0017357), hsa-mir-4723 (MI0017359), hsa-mir-4724 (MI0017361), hsa-mir-4725 (MI0017362), hsa-mir-4726 (MI0017363), hsa-mir-4727 (MI0017364), hsa-mir-4728 (MI0017365), hsa-mir-4729 (MI0017366), hsa-mir-4730 (MI0017367), hsa-mir-4731 (MI0017368), hsa-mir-4732 (MI0017369), hsa-mir-4733 (MI0017370), hsa-mir-4734 (MI0017371), hsa-mir-4735 (MI0017372), hsa-mir-4736 (MI0017373), hsa-mir-4737 (MI0017374), hsa-mir-4738 (MI0017376), hsa-mir-4739 (MI0017377), hsa-mir-4740 (MI0017378), hsa-mir-4741 (MI0017379), hsa-mir-4742 (MI0017380), hsa-mir-4743 (MI0017381), hsa-mir-4744 (MI0017382), hsa-mir-4745 (MI0017384), hsa-mir-4746 (MI0017385), hsa-mir-4747 (MI0017386), hsa-mir-4748 (MI0017387), hsa-mir-4749 (MI0017388), hsa-mir-4750 (MI0017389), hsa-mir-4751 (MI0017390), hsa-mir-4752 (MI0017391), hsa-mir-4753 (MI0017392), hsa-mir-4754 (MI0017394), hsa-mir-4755 (MI0017395), hsa-mir-4756 (MI0017397), hsa-mir-4757 (MI0017398), hsa-mir-4758 (MI0017399), hsa-mir-4759 (MI0017400), hsa-mir-4760 (MI0017401), hsa-mir-4761 (MI0017402), hsa-mir-4762 (MI0017403), hsa-mir-4763 (MI0017404), hsa-mir-4764 (MI0017405), hsa-mir-4765 (MI0017406), hsa-mir-4766 (MI0017407), hsa-mir-4767 (MI0017408), hsa-mir-4768 (MI0017409), hsa-mir-4769 (MI0017410), hsa-mir-4770 (MI0017411), hsa-mir-4771-1 (MI0017412), hsa-mir-4771-2 (MI0017413), hsa-mir-4772 (MI0017414), hsa-mir-4773-1 (MI0017415), hsa-mir-4773-2 (MI0017416), hsa-mir-4774 (MI0017417), hsa-mir-4775 (MI0017418), hsa-mir-4776-1 (MI0017419), hsa-mir-4776-2 (MI0017420), hsa-mir-4777 (MI0017421), hsa-mir-4778 (MI0017422), hsa-mir-4779 (MI0017423), hsa-mir-4780 (MI0017424), hsa-mir-4781 (MI0017426), hsa-mir-4782 (MI0017427), hsa-mir-4783 (MI0017428), hsa-mir-4784 (MI0017429), hsa-mir-4785 (MI0017430), hsa-mir-4786 (MI0017433), hsa-mir-4787 (MI0017434), hsa-mir-4788 (MI0017435), hsa-mir-4789 (MI0017436), hsa-mir-4790 (MI0017437), hsa-mir-4791 (MI0017438), hsa-mir-4792 (MI0017439), hsa-mir-4793 (MI0017440), hsa-mir-4794 (MI0017441), hsa-mir-4795 (MI0017442), hsa-mir-4796 (MI0017443), hsa-mir-4797 (MI0017444), hsa-mir-4798 (MI0017445), hsa-mir-4799 (MI0017446), hsa-mir-4800 (MI0017448), hsa-mir-4801 (MI0017449), hsa-mir-4802 (MI0017450), hsa-mir-4803 (MI0017451), hsa-mir-4804 (MI0017452), hsa-mir-4999 (MI0017865), hsa-mir-5000 (MI0017866), hsa-mir-5001 (MI0017867), hsa-mir-5002 (MI0017868), hsa-mir-5003 (MI0017869), hsa-mir-5004 (MI0017870), hsa-mir-5006 (MI0017873), hsa-mir-5007 (MI0017874), hsa-mir-5008 (MI0017876), hsa-mir-5009 (MI0017877), hsa-mir-5010 (MI0017878), hsa-mir-5011 (MI0017879), hsa-mir-5047 (MI0017932), hsa-mir-5087 (MI0017976), hsa-mir-5088 (MI0017977), hsa-mir-5089 (MI0017978), hsa-mir-5090 (MI0017979), hsa-mir-5091 (MI0017980), hsa-mir-5092 (MI0017981), hsa-mir-5093 (MI0017982), hsa-mir-5094 (MI0017983), hsa-mir-5095 (MI0018001), hsa-mir-5096 (MI0018004), hsa-mir-5100 (MI0019116), hsa-mir-5186 (MI0018165), hsa-mir-5187 (MI0018166), hsa-mir-5188 (MI0018167), hsa-mir-5189 (MI0018168), hsa-mir-5190 (MI0018169), hsa-mir-5191 (MI0018170), hsa-mir-5192 (MI0018171), hsa-mir-5193 (MI0018172), hsa-mir-5194 (MI0018173), hsa-mir-5195 (MI0018174), hsa-mir-5196 (MI0018175), hsa-mir-5197 (MI0018176), hsa-mir-5571 (MI0019115), hsa-mir-5572 (MI0019117), hsa-mir-5579 (MI0019133), hsa-mir-5580 (MI0019135), hsa-mir-5581 (MI0019136), hsa-mir-5582 (MI0019138), hsa-mir-5583-1 (MI0019139), hsa-mir-5583-2 (MI0019140), hsa-mir-5584 (MI0019141), hsa-mir-5585 (MI0019142), hsa-mir-5586 (MI0019143), hsa-mir-5587 (MI0019144), hsa-mir-5588 (MI0019147), hsa-mir-5589 (MI0019148), hsa-mir-5590 (MI0019150), hsa-mir-5591 (MI0019151), hsa-mir-5680 (MI0019280), hsa-mir-5681a (MI0019281), hsa-mir-5681b (MI0019293), hsa-mir-5682 (MI0019282), hsa-mir-5683 (MI0019284), hsa-mir-5684 (MI0019285), hsa-mir-5685 (MI0019287), hsa-mir-5687 (MI0019291), hsa-mir-5688 (MI0019292), hsa-mir-5689 (MI0019294), hsa-mir-5690 (MI0019295), hsa-mir-5691 (MI0019296), hsa-mir-5692a-1 (MI0019297), hsa-mir-5692a-2 (MI0019298), hsa-mir-5692b (MI0019311), hsa-mir-5692c-1 (MI0019288), hsa-mir-5692c-2 (MI0019289), hsa-mir-5693 (MI0019300), hsa-mir-5694 (MI0019301), hsa-mir-5695 (MI0019302), hsa-mir-5696 (MI0019303), hsa-mir-5697 (MI0019304), hsa-mir-5698 (MI0019305), hsa-mir-5699 (MI0019306), hsa-mir-5700 (MI0019307), hsa-mir-5701-1 (MI0019308), hsa-mir-5701-2 (MI0019593), hsa-mir-5702 (MI0019309), hsa-mir-5703 (MI0019310), hsa-mir-5704 (MI0019312), hsa-mir-5705 (MI0019313), hsa-mir-5706 (MI0019314), hsa-mir-5707 (MI0019315), hsa-mir-5708 (MI0019316), hsa-mir-5739 (MI0019412), hsa-mir-5787 (MI0019797), hsa-mir-6068 (MI0020345), hsa-mir-6069 (MI0020346), hsa-mir-6070 (MI0020347), hsa-mir-6071 (MI0020348), hsa-mir-6072 (MI0020349), hsa-mir-6073 (MI0020350), hsa-mir-6074 (MI0020351), hsa-mir-6075 (MI0020352), hsa-mir-6076 (MI0020353), hsa-mir-6077-1 (MI0020354), hsa-mir-6077-2 (MI0023562), hsa-mir-6078 (MI0020355), hsa-mir-6079 (MI0020356), hsa-mir-6080 (MI0020357), hsa-mir-6081 (MI0020358), hsa-mir-6082 (MI0020359), hsa-mir-6083 (MI0020360), hsa-mir-6084 (MI0020361), hsa-mir-6085 (MI0020362), hsa-mir-6086 (MI0020363), hsa-mir-6087 (MI0020364), hsa-mir-6088 (MI0020365), hsa-mir-6089-1 (MI0020366), hsa-mir-6089-2 (MI0023563), hsa-mir-6090 (MI0020367), hsa-mir-6124 (MI0021258), hsa-mir-6125 (MI0021259), hsa-mir-6126 (MI0021260), hsa-mir-6127 (MI0021271), hsa-mir-6128 (MI0021272), hsa-mir-6129 (MI0021273), hsa-mir-6130 (MI0021274), hsa-mir-6131 (MI0021276), hsa-mir-6132 (MI0021277), hsa-mir-6133 (MI0021278), hsa-mir-6134 (MI0021279), hsa-mir-6165 (MI0021472), hsa-mir-6499 (MI0022209), hsa-mir-6500 (MI0022211), hsa-mir-6501 (MI0022213), hsa-mir-6502 (MI0022214), hsa-mir-6503 (MI0022215), hsa-mir-6504 (MI0022216), hsa-mir-6505 (MI0022217), hsa-mir-6506 (MI0022218), hsa-mir-6507 (MI0022219), hsa-mir-6508 (MI0022220), hsa-mir-6509 (MI0022221), hsa-mir-6510 (MI0022222), hsa-mir-6511a-1 (MI0022223), hsa-mir-6511a-2 (MI0023564), hsa-mir-6511a-3 (MI0023565), hsa-mir-6511a-4 (MI0023566), hsa-mir-6511b-1 (MI0022552), hsa-mir-6511b-2 (MI0023431), hsa-mir-6512 (MI0022224), hsa-mir-6513 (MI0022225), hsa-mir-6514 (MI0022226), hsa-mir-6515 (MI0022227), hsa-mir-6516 (MI0025513), hsa-mir-6715a (MI0022548), hsa-mir-6715b (MI0022549), hsa-mir-6716 (MI0022550), hsa-mir-6717 (MI0022551), hsa-mir-6718 (MI0022553), hsa-mir-6719 (MI0022554), hsa-mir-6720 (MI0022555), hsa-mir-6721 (MI0022556), hsa-mir-6722 (MI0022557), hsa-mir-6723 (MI0022558), hsa-mir-6724 (MI0022559), hsa-mir-6726 (MI0022571), hsa-mir-6727 (MI0022572), hsa-mir-6728 (MI0022573), hsa-mir-6729 (MI0022574), hsa-mir-6730 (MI0022575), hsa-mir-6731 (MI0022576), hsa-mir-6732 (MI0022577), hsa-mir-6733 (MI0022578), hsa-mir-6734 (MI0022579), hsa-mir-6735 (MI0022580), hsa-mir-6736 (MI0022581), hsa-mir-6737 (MI0022582), hsa-mir-6738 (MI0022583), hsa-mir-6739 (MI0022584), hsa-mir-6740 (MI0022585), hsa-mir-6741 (MI0022586), hsa-mir-6742 (MI0022587), hsa-mir-6743 (MI0022588), hsa-mir-6744 (MI0022589), hsa-mir-6745 (MI0022590), hsa-mir-6746 (MI0022591), hsa-mir-6747 (MI0022592), hsa-mir-6748 (MI0022593), hsa-mir-6749 (MI0022594), hsa-mir-6750 (MI0022595), hsa-mir-6751 (MI0022596), hsa-mir-6752 (MI0022597), hsa-mir-6753 (MI0022598), hsa-mir-6754 (MI0022599), hsa-mir-6755 (MI0022600), hsa-mir-6756 (MI0022601), hsa-mir-6757 (MI0022602), hsa-mir-6758 (MI0022603), hsa-mir-6759 (MI0022604), hsa-mir-6760 (MI0022605), hsa-mir-6761 (MI0022606), hsa-mir-6762 (MI0022607), hsa-mir-6763 (MI0022608), hsa-mir-6764 (MI0022609), hsa-mir-6765 (MI0022610), hsa-mir-6766 (MI0022611), hsa-mir-6767 (MI0022612), hsa-mir-6768 (MI0022613), hsa-mir-6769a (MI0022614), hsa-mir-6769b (MI0022706), hsa-mir-6770-1 (MI0022615), hsa-mir-6770-2 (MI0026418), hsa-mir-6770-3 (MI0026419), hsa-mir-6771 (MI0022616), hsa-mir-6772 (MI0022617), hsa-mir-6773 (MI0022618), hsa-mir-6774 (MI0022619), hsa-mir-6775 (MI0022620), hsa-mir-6776 (MI0022621), hsa-mir-6777 (MI0022622), hsa-mir-6778 (MI0022623), hsa-mir-6779 (MI0022624), hsa-mir-6780a (MI0022625), hsa-mir-6780b (MI0022681), hsa-mir-6781 (MI0022626), hsa-mir-6782 (MI0022627), hsa-mir-6783 (MI0022628), hsa-mir-6784 (MI0022629), hsa-mir-6785 (MI0022630), hsa-mir-6786 (MI0022631), hsa-mir-6787 (MI0022632), hsa-mir-6788 (MI0022633), hsa-mir-6789 (MI0022634), hsa-mir-6790 (MI0022635), hsa-mir-6791 (MI0022636), hsa-mir-6792 (MI0022637), hsa-mir-6793 (MI0022638), hsa-mir-6794 (MI0022639), hsa-mir-6795 (MI0022640), hsa-mir-6796 (MI0022641), hsa-mir-6797 (MI0022642), hsa-mir-6798 (MI0022643), hsa-mir-6799 (MI0022644), hsa-mir-6800 (MI0022645), hsa-mir-6801 (MI0022646), hsa-mir-6802 (MI0022647), hsa-mir-6803 (MI0022648), hsa-mir-6804 (MI0022649), hsa-mir-6805 (MI0022650), hsa-mir-6806 (MI0022651), hsa-mir-6807 (MI0022652), hsa-mir-6808 (MI0022653), hsa-mir-6809 (MI0022654), hsa-mir-6810 (MI0022655), hsa-mir-6811 (MI0022656), hsa-mir-6812 (MI0022657), hsa-mir-6813 (MI0022658), hsa-mir-6814 (MI0022659), hsa-mir-6815 (MI0022660), hsa-mir-6816 (MI0022661), hsa-mir-6817 (MI0022662), hsa-mir-6818 (MI0022663), hsa-mir-6819 (MI0022664), hsa-mir-6820 (MI0022665), hsa-mir-6821

(MI0022666), hsa-mir-6822 (MI0022667), hsa-mir-6823 (MI0022668), hsa-mir-6824 (MI0022669), hsa-mir-6825 (MI0022670), hsa-mir-6826 (MI0022671), hsa-mir-6827 (MI0022672), hsa-mir-6828 (MI0022673), hsa-mir-6829 (MI0022674), hsa-mir-6830 (MI0022675), hsa-mir-6831 (MI0022676), hsa-mir-6832 (MI0022677), hsa-mir-6833 (MI0022678), hsa-mir-6834 (MI0022679), hsa-mir-6835 (MI0022680), hsa-mir-6836 (MI0022682), hsa-mir-6837 (MI0022683), hsa-mir-6838 (MI0022684), hsa-mir-6839 (MI0022685), hsa-mir-6840 (MI0022686), hsa-mir-6841 (MI0022687), hsa-mir-6842 (MI0022688), hsa-mir-6843 (MI0022689), hsa-mir-6844 (MI0022690), hsa-mir-6845 (MI0022691), hsa-mir-6846 (MI0022692), hsa-mir-6847 (MI0022693), hsa-mir-6848 (MI0022694), hsa-mir-6849 (MI0022695), hsa-mir-6850 (MI0022696), hsa-mir-6851 (MI0022697), hsa-mir-6852 (MI0022698), hsa-mir-6853 (MI0022699), hsa-mir-6854 (MI0022700), hsa-mir-6855 (MI0022701), hsa-mir-6856 (MI0022702), hsa-mir-6857 (MI0022703), hsa-mir-6858 (MI0022704), hsa-mir-6859-1 (MI0022705), hsa-mir-6859-2 (MI0026420), hsa-mir-6859-3 (MI0026421), hsa-mir-6860 (MI0022707), hsa-mir-6861 (MI0022708), hsa-mir-6862-1 (MI0022709), hsa-mir-6862-2 (MI0026415), hsa-mir-6863 (MI0022710), hsa-mir-6864 (MI0022711), hsa-mir-6865 (MI0022712), hsa-mir-6866 (MI0022713), hsa-mir-6867 (MI0022714), hsa-mir-6868 (MI0022715), hsa-mir-6869 (MI0022716), hsa-mir-6870 (MI0022717), hsa-mir-6871 (MI0022718), hsa-mir-6872 (MI0022719), hsa-mir-6873 (MI0022720), hsa-mir-6874 (MI0022721), hsa-mir-6875 (MI0022722), hsa-mir-6876 (MI0022723), hsa-mir-6877 (MI0022724), hsa-mir-6878 (MI0022725), hsa-mir-6879 (MI0022726), hsa-mir-6880 (MI0022727), hsa-mir-6881 (MI0022728), hsa-mir-6882 (MI0022729), hsa-mir-6883 (MI0022730), hsa-mir-6884 (MI0022731), hsa-mir-6885 (MI0022732), hsa-mir-6886 (MI0022733), hsa-mir-6887 (MI0022734), hsa-mir-6888 (MI0022735), hsa-mir-6889 (MI0022736), hsa-mir-6890 (MI0022737), hsa-mir-6891 (MI0022738), hsa-mir-6892 (MI0022739), hsa-mir-6893 (MI0022740), hsa-mir-6894 (MI0022741), hsa-mir-6895 (MI0022742), hsa-mir-7106 (MI0022957), hsa-mir-7107 (MI0022958), hsa-mir-7108 (MI0022959), hsa-mir-7109 (MI0022960), hsa-mir-7110 (MI0022961), hsa-mir-7111 (MI0022962), hsa-mir-7112-1 (MI0022963), hsa-mir-7112-2 (MI0026414), hsa-mir-7113 (MI0022964), hsa-mir-7114 (MI0022965), hsa-mir-7150 (MI0023610), hsa-mir-7151 (MI0023611), hsa-mir-7152 (MI0023612), hsa-mir-7153 (MI0023613), hsa-mir-7154 (MI0023614), hsa-mir-7155 (MI0023615), hsa-mir-7156 (MI0023616), hsa-mir-7157 (MI0023617), hsa-mir-7158 (MI0023618), hsa-mir-7159 (MI0023620), hsa-mir-7160 (MI0023621), hsa-mir-7161 (MI0023619), hsa-mir-7162 (MI0023623), hsa-mir-7515 (MI0024354), hsa-mir-7641-1 (MI0024975), hsa-mir-7641-2 (MI0024976), hsa-mir-7702 (MI0025238), hsa-mir-7703 (MI0025239), hsa-mir-7704 (MI0025240), hsa-mir-7705 (MI0025241), hsa-mir-7706 (MI0025242), hsa-mir-7843 (MI0025510), hsa-mir-7844 (MI0025514), hsa-mir-7845 (MI0025515), hsa-mir-7846 (MI0025516), hsa-mir-7847 (MI0025517), hsa-mir-7848 (MI0025518), hsa-mir-7849 (MI0025519), hsa-mir-7850 (MI0025520), hsa-mir-7851 (MI0025521), hsa-mir-7852 (MI0025522), hsa-mir-7853 (MI0025523), hsa-mir-7854 (MI0025524), hsa-mir-7855 (MI0025525), hsa-mir-7856 (MI0025526), hsa-mir-7973-1 (MI0025748), hsa-mir-7973-2 (MI0025749), hsa-mir-7974 (MI0025750), hsa-mir-7975 (MI0025751), hsa-mir-7976 (MI0025752), hsa-mir-7977 (MI0025753), hsa-mir-7978 (MI0025754), hsa-mir-8052 (MI0025888), hsa-mir-8053 (MI0025889), hsa-mir-8054 (MI0025890), hsa-mir-8055 (MI0025891), hsa-mir-8056 (MI0025892), hsa-mir-8057 (MI0025893), hsa-mir-8058 (MI0025894), hsa-mir-8059 (MI0025895), hsa-mir-8060 (MI0025896), hsa-mir-8061 (MI0025897), hsa-mir-8062 (MI0025898), hsa-mir-8063 (MI0025899), hsa-mir-8064 (MI0025900), hsa-mir-8065 (MI0025901), hsa-mir-8066 (MI0025902), hsa-mir-8067 (MI0025903), hsa-mir-8068 (MI0025904), hsa-mir-8069 (MI0025905), hsa-mir-8070 (MI0025906), hsa-mir-8071-1 (MI0025907), hsa-mir-8071-2 (MI0026417), hsa-mir-8072 (MI0025908), hsa-mir-8073 (MI0025909), hsa-mir-8074 (MI0025910), hsa-mir-8075 (MI0025911), hsa-mir-8076 (MI0025912), hsa-mir-8077 (MI0025913), hsa-mir-8078 (MI0025914), hsa-mir-8079 (MI0025915), hsa-mir-8080 (MI0025916), hsa-mir-8081 (MI0025917), hsa-mir-8082 (MI0025918), hsa-mir-8083 (MI0025919), hsa-mir-8084 (MI0025920), hsa-mir-8085 (MI0025921), hsa-mir-8086 (MI0025922), hsa-mir-8087 (MI0025923), hsa-mir-8088 (MI0025924), hsa-mir-8089 (MI0025925). See, e.g., pre-microRNAs listed on miRBase.org.

In some embodiments, the hybrid molecules comprise the full-length native pre-micro-RNA. In some embodiments, the hybrid molecules comprise fragments or subsequences of the native pre-micro-RNA molecules. Fragments or subsequences of the native pre-micro-RNA molecules that find use will have one or more cleavage sites recognized by and accessible to an endoribonuclease (e.g., Dicer) such that an inserted RNA molecule (e.g., a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), a small activating RNA (saRNA), an aptamer, a catalytic RNA) can be cleaved out of or released from the hybrid tRNA/pre-microRNA molecule.

c. Inserted RNA

In some embodiments, the hybrid tRNA/pre-microRNA molecules contain an inserted RNA sequence and serve as a scaffold, e.g., for the in vivo delivery or the in vitro high-level production of the inserted RNA sequence, which can be cleaved from the hybrid tRNA/pre-microRNA molecule, e.g., by an endoribonuclease, e.g., by Dicer. In some embodiments, the inserted RNA molecule (also referred to as $N^1$, $N^2$, $N^3$, $N^4$ herein) can be from about 18 nucleotides and up to about 200 nucleotides, e.g., at least about 18 nucleotides and up to about 150 nucleotides, e.g., at least about 18 nucleotides and up to about 125 nucleotides, e.g., at least about 18 nucleotides and up to about 100 nucleotides, e.g., at least about 18 nucleotides and up to about 75 nucleotides, e.g., at least about 18 nucleotides and up to about 50 nucleotides, e.g., at least about 18 nucleotides and up to about 40 nucleotides, e.g., at least about 18 nucleotides and up to about 30 nucleotides. In some embodiments, the inserted RNA molecule can be about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

As appropriate or desired, the inserted RNA can be an inhibitory nucleic acid, that prevents, reduces or inhibits the transcription or translation of a target nucleic acid or protein. In some embodiments, the inserted RNA is a noncoding RNA. In some embodiments, the inhibitory nucleic acid is a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), a small activating RNA (saRNA) or a catalytic RNA. In some embodiments, the inserted RNA is a mature miRNA, e.g., that is derived from (e.g., is homologous to) or is heterologous to the pre-microRNA molecule in the hybrid tRNA/pre-microRNA scaffold. In some embodiments, the noncoding RNA is Homeobox (HOX) antisense intergenic RNA (HOTAIR).

In some embodiments, the hybrid tRNA/pre-miRNA molecule comprises one, two or more mature miRNA, e.g., derived from the pre-miRNA identified above and herein. In some embodiments, the hybrid tRNA/pre-miRNA molecule comprises one, two or more mature miRNA selected from the group consisting of let-7c, miR-298, miR-216, miR-34a, miR-124, miR-328, miR-144, miR-126, miR-16, miR-18, miR-125a, miR-195, miR-199a, miR-200, miR-224, miR-1291, miR-429, miR-148, miR-144, miR-1, miR-133, miR-888, miR-6775, miR-374, miR-92, miR-1180, miR-218, miR-7, miR-378, miR-17, miR-18a, miR-22, miR-122, miR-30b, miR-449, miR-506, miR-98, miR-4458, miR-206, miR-519, miR-93, miR-106, miR-373, and miR-520. In some embodiments, the hybrid tRNA/pre-miRNA molecule comprises one, two or more mature miRNA selected from the group consisting of let-7c, miR-1291, miR-200, miR-92, miR-34a and miR-124. In some embodiments, the hybrid tRNA/pre-miRNA molecule comprises one, two or more mature miRNA selected from the group consisting of miR-1291, miR-34, miR-124, miR-200, and miR-216. In hybrid tRNA/dual pre-miRNA molecules, the inserted RNA can be the same or different.

In some embodiments, the target nucleic acid or polypeptide is a biomarker associated with the progression or causative of cancer.

For hepatocellular carcinoma, the inserted RNA comprises one, two or more mature miRNA selected from let-7c, miR-298, miR-216, miR-124, miR-328, miR-144, miR-126, miR-16, miR-18, miR-125a, miR-195, miR-199a, miR-200, and miR-224.

In cases of pancreatic cancer, the inserted RNA comprises one, two or more mature miRNA selected from miR-1291, miR-34, miR-124, miR-200, and miR-216.

In cases of lung cancer, the inserted RNA comprises one, two or more mature miRNA selected from miR-34a and miR-124.

In the case of breast cancer, a target miRNA may be selected from human miRNAs including but not limited to miR-10b, miR-21, miR-29b, miR-17-5p, miR-125b, miR-145, miR-146, and miR-155. For detection of malignant lymphoma, a target miRNA may be selected from human miRNAs including but not limited to miR-155, miR-17, miR-18a, miR-19a, miR-20a, miR-19b, and miR-92. Breast tumors, moreover, comprise heterogeneous miRNA profiles and miRNA signature of, e.g., let-7 family, mir-10b, mir-18a, mir-106a, mir125-a, mir125-b, mir-126, mir-130a, mir-145, mir-155, mir-141, mir-214, mir-205, mir-206, mir-210, mir-126, mir-335, mir-213, mir-203, 17-5p, miR-30, mir-34, and mir-342, have been proposed to affect breast cancer outcomes. See, e.g., Wiemer, Eur. J Cancer 43: 1529-1544 (2007).

In colorectal cancer, a target miRNA may be selected from human miRNAs including but not limited to the let-7 family, miR-10a, miR-20a, miR-24, miR-29b, miR-31, miR-96, miR-133b, miR-135b, miR-143, miR-145, miR-183, miR-17, miR-18a, miR-19a, miR-19b and miR-92.

For prostate cancer, the target miRNA may be selected from human miRNAs including but not limited to let-7d, miR-128a, miR-195, and miR-203.

Further, a number of additional miRNAs are differentially expressed in melanoma cells, and several of the over-expressed miRNAs appear to regulate melanoma cell invasiveness (Ma et al., 2009; Mueller and Bosserhoff, 2009; Mueller et al., 2009; Philippidou et al., 2010; Segura et al., 2010; Stark et al., 2010). The miRNAs miR-221/222 down-regulate p27Kipl/CDKNIB and the c-KIT receptor mRNA levels, thereby controlling the progression of neoplasia, leading to enhanced proliferation and reduced differentiation in such cancers cells (Felicetti et al., 2008). miR-137, moreover, down-regulates the expression of MITF, a master regulator of cell growth, maturation, and pigmentation in melanoma (Bemis et al., 2008). It has recently been shown that several miRNA genes are differentially regulated in melanoma cells, and therefore, lead to cancer. One such miRNA, miR-211, is consistently reduced in melanoma (see Mazar et al, 2010), which is associated with increased invasiveness and high proliferation rates in susceptible cells. A group of epigenetically regulated miRNA genes, moreover, has been associated with melanomas, e.g., miR-34b, -489, -375, -132, -142-3p, -200a, -145, -452, -21, -34c, -496, -let7e, -654, and -519b.

In some embodiments, the inserted RNA is an aptamer that binds to a target molecule or a target polypeptide. Illustrative aptamer targets include without limitation, EpCAM, VEGF, FLT1, theophylline, and malachite green. Illustrative tumor associated antigens on hepatocellular carcinoma cells, and which can be aptamer targets, include without limitation, e.g., HCC-22-5 tumor-associated antigen (Zhou, et al., Clin Chim Acta. 2006 April; 366(1-2):274-80) and KRT23, AHSG and FTL antigens (Wang, et al., Cancer Lett. 2009 Aug. 28; 281(2):144-50). Illustrative tumor associated antigens on lung cancer, e.g., non-small cell lung cancer cells, and which can be aptamer targets, include without limitation, e.g., MAGE-A1, MAGE-A3/4 and NY-ESO-1 (Grah, et al, Tumori. (2014) 100(1):60-8), 14-3-3ζ, c-Myc, MDM2, NPM1, p16, p53 and cyclin B1 (Dai, et al., Lung Cancer. (2016) 99:172-9). Illustrative tumor associated antigens on pancreatic cancer cells, and which can be aptamer targets, include without limitation, e.g., KIF20A (Imai, et al., Br J Cancer. (2011) 104(2):300-7); CA 19-9, DU-PAN-2, and TAG-72 (Toshkov, et al., Int J Pancreatol. (1994) 15(2):97-103); cadherin 3 (CDH3)/P-cadherin (Imai, et al., Clin Cancer Res. (2008) 14(20):6487-95); Receptor-binding cancer antigen expressed on SiSo cells (RCAS1) (Akashi, et al., Pancreas (2003) 26(1):49-55); and SC6 (Liu, et al., World J Gastroenterol. (2005) 11(48):7671-5).

In some embodiments, the target nucleic acid or polypeptide is selected from the group consisting of a fluorescent protein, a cytokine, a growth factor, a hormone, a kinase, a nuclear receptor, a G protein-coupled receptor, an epigenetic regulator, a transcription factor. In some embodiments, the target nucleic acid or polypeptide is a fluorescent protein selected from a violet fluorescent protein, a blue fluorescent protein (BFP), a cyan fluorescent protein, a green fluorescent protein (GFP), a yellow fluorescent protein (YFP), an orange fluorescent protein (OFP), a red fluorescent protein (RFP) and a sapphire-type protein. In some embodiments, the target nucleic acid or polypeptide is a cytokine selected from interleukin (IL)-1α, IL-1β, tumor necrosis factor (TNF)α, interferon (IFN)α, IFNβ, IFNγ, TGFβ1, IL-5, IL-6, IL-8, IL-10, IL-12, IL-17, IL-18, IL-22, IL-23 and migration inhibitory factor (MIF). In some embodiments, the target nucleic acid or polypeptide is a nuclear receptor selected from Peroxisome proliferator-activated receptor gamma (PPAR-γ or PPARG), retinoic acid receptor (RAR), vitamin D receptor, estrogen receptor (ER), androgen receptor (AR), glucocorticoid receptor (GR), thyroid hormone receptor (THR), farnesoid X receptor (FXR) or NR1H4 (nuclear receptor subfamily 1, group H, member 4), a liver X receptor (LXR), constitutive androstane receptor (CAR), and pregnane X receptor (PXR). In some embodiments, the target nucleic acid or polypeptide is a growth factor selected from vascular endothelial growth factor (VEGF), Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Healing factor, Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumor necrosis factor-alpha (TNF-α), wingless-type MMTV integration site (WNT) family members, placental growth factor (PGF), Somatotrophin (growth hormone or GH), IL-2, IL-3, IL-4, IL-5, IL-6, and IL-7.

In some embodiments, the target nucleic acid or polypeptide is selected from the group consisting of miR-1291; AKT2; Cyclin Bl; MeCP2; FOXA2; AMPKal; Anterior gradient homolog 2 (AGR2); Argininosuccinate synthase (ArSS); Chain C, structure of the H3-H4 chaperone ASF1; Ornithine aminotransferase (OAT); Keratin, type II cytoskeletal 8 (KRT8); Phosphoenolpyruvate carboxykinase 2 (PEPCK2); Enoyl-coenzyme A (Co A) hydratase(ECHS1); Phosphoserine aminotransferase isoform 1 (PSAT1); Dihydrolipoamide acetyltransferase (DLAT); Peroxiredoxin 3, isoform CRA a (PRDX3); Cysteine—rich protein 2 (CRIP2); Chain C, human PCNA; Fascin homolog 1, actin-bundling protein, isoform CRA a (FSCN1); Serpin HI precursor; Protein disulfide—isomerase precursor; Chain A, disulfide isomerase related chaperone ERP29; Triosephosphate isomerase isoform 2 (TPII); Peroxiredoxin-4 (PRDX4); and Isocitrate dehydrogenase [NAD] subunit beta (IDH3B); a-fetoprotein (AFP); AFP-L3%, des-gamma-carboxyprothrombin (DCP); CDH1 (E-cadherin); trimethylated lysine 27 of H3 histone (H3K27me3); histone deacetylase—1; histone deacetylase—2; SIRT1; CD44; aldehyde dehydrogenase; KRAS2; or RREB1, an ABC transporter (e.g., ABCC1, ABCG2, ABCB1, ABCC2, ABCC3, and ABCC4) or any combination thereof.

3. Formulation and Administration

The hybrid tRNA/pre-microRNA scaffolds can be administered to a subject in need thereof (e.g., a subject diagnosed as having a cancer, e.g., hepatocellular carcinoma pancreatic cancer, lung cancer) for delivery of an inserted RNA of interest (e.g., an inhibitory nucleic acid, an aptamer) to interior of a target cell. Generally, the subject is a mammal and therefore comprises eukaryotic cells which express endoribonucleases (e.g., Dicer). Once the target eukaryotic cells of the subject have been transfected or transformed with the hybrid tRNA/pre-microRNA scaffolds, the endoribonucleases (e.g., Dicer) within the target cell cleave out or release the inserted RNA of interest.

In some embodiments, the inserted RNA is an inhibitory nucleic acid (e.g., a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), an aptamer). In some embodiments, the inhibitory RNA once released from the hybrid scaffold in a eukaryotic cell reduces the amount and/or activity of the target nucleic acid or polypeptide by at least about 10% to about 100%, 20% to about 100%, 30% to about 100%, 40% to about 100%, 50% to about 100%, 60% to about 100%, 70% to about 100%, 10% to about 90%, 20% to about 85%, 40% to about 84%, 60% to about 90%, including any percent within these ranges, such as but not limited to 15%, 20%, 25%, 30%, 35%, 40%, 45%, 50%, 55%, 60%, 65%, 70%, 75%, 80%, 85%, 90%, 95%, 96%, 97%, 98%, and 99%.

In certain embodiments, the hybrid tRNA/pre-microRNA scaffolds are expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application in a general, illustrative sense, and are not intended to limit the invention.

In one embodiment, an expression vector for expressing the hybrid tRNA/pre-microRNA scaffolds comprises a promoter "operably linked" to a polynucleotide encoding the hybrid tRNA/pre-microRNA scaffolds (e.g., containing an inserted RNA). The phrase "operably linked" or "under transcriptional control" as used herein means that the promoter is in the correct location and orientation in relation to a polynucleotide to control the initiation of transcription by RNA polymerase and expression of the polynucleotide.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III. Illustrative promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences include UTRs which include an Internal Ribosome Entry Site (IRES) present in the leader sequences of picornaviruses such as the encephalomyocarditis virus (EMCV) UTR (Jang et al. J. Virol. (1989) 63:1651-1660. Other picornavirus UTR sequences that will also find use include the polio leader sequence and hepatitis A virus leader and the hepatitis C IRES.

There are a number of ways in which expression vectors may be introduced into cells. In certain embodiments, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the available methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice. The adenovirus may be of any of the 42 different known serotypes or subgroups A-F. Adenovirus type 5 of subgroup C is the preferred starting material in order to obtain the conditional replication-defective adenovirus vector for use. This is because Adenovirus type 5 is a human adenovirus about which a great deal of biochemical and genetic information is known, and it has historically been used for most constructions employing adenovirus as a vector.

The typical vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviral vectors are also suitable for expressing the hybrid tRNA/pre-microRNA scaffolds (e.g., containing an inserted RNA) in cells. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors may be employed as expression constructs. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect cleavage and expression of inserted RNA, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Porter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the hybrid tRNA/pre-microRNA scaffolds, e.g., containing the inserted RNA of interest, may be positioned and expressed at different sites. In certain embodiments, the nucleic acid encoding the hybrid tRNA/pre-microRNA scaffolds may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In some embodiments, the hybrid tRNA/pre-miRNA construct is packaged within and delivered in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ohosh and Bachhawat, 1991). Also contemplated are lipofectamine-DNA complexes. In one embodiment, the hybrid tRNA/pre-miRNA construct is complexed with a polyethylenimine (PEI), e.g., liposomal-branched polyethylenimine (PEI) polyplex (LPP) or in vivo-jetPEI (IPEI). In some embodiments, the tRNA/pre-miRNA construct is complexed with a branched polyethylenimine have an average molecular weight of about 10,000 Da. The complex can then be encapsulated in a lipid bilayer, e.g., comprising a mixture of 1,2-di-O-octadecenyl-3-trimethylammonium propane (DOTMA), cholesterol and 1,2-Dimyristoyl-sn-glycerol, methoxypolyethylene glycol (DMG-PEG2000).

In certain embodiments, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-I) (Kato et al., 1991). In yet further embodiments, the liposome may be complexed or employed in conjunction with both HVJ and HMG-I. In that such expression constructs have been successfully employed in transfer and expression of nucleic acid in vitro and in vivo, then they are applicable. Where a bacterial promoter is employed in the DNA construct, it also will be desirable to include within the liposome an appropriate bacterial polymerase.

Other expression constructs which can be employed to deliver a nucleic acid encoding a particular lncRNA or inhibitor into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise an encapsulating particle and an external targeting ligand, e.g., that specifically binds to a tumor associated antigen. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. Illustrative tumor-associated or surface antigens for delivering the hybrid tRNA/pre-miRNA constructs to HCC cells include without limitation, EpCAM, VEGF, FLT1, theophylline, and malachite green. Illustrative tumor associated antigens on hepatocellular carcinoma cells, and which can be aptamer targets, include without limitation, e.g., HCC-22-5 tumor-associated antigen (Zhou, et al., Clin Chim Acta. 2006 April; 366(1-2):274-80) and KRT23, AHSG and FTL antigens (Wang, et al., Cancer Lett. 2009 Aug. 28; 281(2):144-50). Illustrative tumor associated antigens on lung cancer, e.g., non-small cell lung cancer cells, and which can be aptamer targets, include without limitation, e.g., MAGE-A1, MAGE-A3/4 and NY-ESO-1 (Grah, et al, Tumori. (2014) 100(1): 60-8); 14-3-3ζ, c-Myc, MDM2, NPM1, p16, p53 and cyclin B1 (Dai, et al., Lung Cancer. (2016) 99:172-9). Illustrative tumor associated antigens on pancreatic cancer cells, and which can be aptamer targets, include without limitation, e.g., KIF20A (Imai, et al., *Br J Cancer*. (2011) 104(2):300-7); CA 19-9, DU-PAN-2, and TAG-72 (Toshkov, et al., *Int J Pancreatol*. (1994) 15(2):97-103); cadherin 3 (CDH3)/P-cadherin (Imai, et al., *Clin Cancer Res*. (2008) 14(20):6487-95); Receptor-binding cancer antigen expressed on SiSo cells (RCAS1) (Akashi, et al., *Pancreas* (2003) 26(1):49-55); and SC6 (Liu, et al., *World J Gastroenterol*. (2005) 11(48):7671-5). Other TAAs are known and find use for the formulation and targeted delivery of the hybrid tRNA/pre-microRNA scaffolds.

In a particular example, the oligonucleotide may be administered in combination with a cationic lipid. Examples of cationic lipids include, but are not limited to, lipofectin, DOTMA, DOPE, and DOTAP. The publication of WO00/71096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Also encompassed are pharmaceutical compositions comprising the hybrid tRNA/pre-microRNA scaffolds and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the hybrid tRNA/pre-microRNA scaffolds described herein. Commercially available fat emulsions that are suitable for delivering the nucleic acids to tissues, such as cardiac muscle tissue and smooth muscle tissue, include Intralipid, Liposyn, Liposyn II, Liposyn III, Nutrilipid, and other similar lipid emulsions. One colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are herein incorporated by reference in their entireties.

One will generally desire to employ appropriate salts and buffers to render delivery vehicles stable and allow for uptake by target cells. Buffers also will be employed when recombinant cells are introduced into a patient. Aqueous compositions can comprise an effective amount of the delivery vehicle, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the hybrid tRNA/pre-miRNA scaffolds, its use in therapeutic compositions is contemplated. Supplementary active ingredients also can be incorporated into the compositions, provided they do not inactivate the nucleic acids of the compositions.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous, intrahepatic, intratumoral and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15$^{st}$ Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

The skilled artisan will be able to select and use an appropriate system for delivering the inhibitory nucleic acid or an expression vector to target cells in vitro or in vivo without undue experimentation.

The hybrid tRNA/pre-microRNA scaffolds (e.g., containing an inserted RNA) may be administered to a subject with cancer to enhance or increase the responsiveness to chemotherapy comprising a platinum coordination complex. In alternative embodiments, the cancer is resistant to treatment with a chemotherapy regime. By "resistant to chemotherapy" is meant that the cancer does not substantially respond to treatment with the chemotherapy. Identification of such resistant cancers and cancer In some embodiments, the hybrid tRNA/pre-microRNA scaffolds (e.g., containing an inserted RNA) may be used to treat subjects who have failed (relapsed) after standard chemotherapy or bone marrow transplantation or other emerging or novel targeted therapies. By "treat," "treatment" or "treating" is meant ameliorating symptoms associated with cancer, including preventing or delaying the onset of the disease symptoms and/or lessening the severity or frequency of the disease symptoms and/or prolonging remission and/or decreasing the frequency or severity of relapse. In some embodiments, the hybrid tRNA/pre-microRNA scaffolds (e.g., containing an inserted RNA) can be administered to the subject in conjunction with chemotherapy comprising a platinum coordination complex (e.g., prior to or concurrently with chemotherapy comprising a platinum coordination complex.

The hybrid tRNA/pre-microRNA scaffolds (e.g., containing an inserted RNA) may be provided alone or in combination with other compounds (for example, chemotherapeutics), in the presence of a liposome, an adjuvant, or any pharmaceutically acceptable carrier, in a form suitable for administration to mammals, for example, humans, cattle, sheep, etc. If desired, treatment with the hybrid tRNA/pre-microRNA scaffolds (e.g., containing an inserted RNA) may be combined with traditional and existing, or emerging, therapies for cancer, e.g., targeted chemotherapies using cancer-specific peptides described, e.g., in Intl. Publ. No. 2011/038142.

The hybrid tRNA/pre-microRNA scaffolds (e.g., containing an inserted RNA) may be administered chronically or intermittently. "Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature. In alternative embodiments, the hybrid tRNA/pre-microRNA scaffolds (e.g., containing an inserted RNA) are administered to a subject in need of such inhibitors, e.g., a subject diagnosed with or suspected of having a cancer.

In alternative embodiments, a hybrid tRNA/pre-microRNA scaffold (e.g., containing an inserted RNA) may be effectively delivered to cancer cells, by a variety of methods known to those skilled in the art. Such methods include but are not limited to liposomal encapsulation/delivery, vector-based gene transfer, fusion to peptide or immunoglobulin sequences (peptides described, e.g., in Intl. Publ. No. 2011/038142) for enhanced cell targeting and other techniques. Suitable viral vectors include retroviral vectors such as lentiviral vectors, adenovirus vectors, adeno-associated virus vectors, etc. In alternative embodiments, a hybrid tRNA/pre-microRNA scaffold (e.g., containing an inserted RNA), may also be formulated in pharmaceutical compositions well known to those in the field. These include liposomal formulations and combinations with other agents or vehicles/excipients such as cyclodextrins which may enhance delivery of the inhibitory nucleic acid. In alternative embodiments, suitable carriers include lipid-based carriers such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In alternative embodiments, the carrier system is a cyclodextrin-based carrier system such as a cyclodextrin polymer-nucleic acid complex. In further embodiments, the carrier system is a protein-based carrier system such as a cationic peptide-nucleic acid complex.

Suitable carriers are known in the art and are described in, without limitation, United States Patent Application Nos. 20070173476 published Jul. 26, 2007; 20050008617 published Jan. 13, 2005; 20050014962 published Jan. 20, 2005; 20050064595 published Mar. 24, 2005; 20060008910 published Jan. 12, 2006; 20060051405 published Mar. 9, 2006; 20060083780 published Apr. 20, 2006; 20050008689 published Jan. 13, 2005; 20070172950 published Jul. 26, 2007; U.S. Pat. No. 7,101,995 issued Sep. 5, 2006 to Lewis, et al.; U.S. Pat. No. 7,220,400 issued May 22, 2007, to Monahan, et al.; U.S. Pat. No. 5,705,385 issued Jan. 6, 1998 to Bally, et al.; U.S. Pat. No. 5,965,542 issued Oct. 12, 1999 to Wasan, et al.; U.S. Pat. No. 6,287,591 issued Sep. 11, 2001 to Semple, et al., all of which are hereby incorporated by reference.

In one embodiment, a nucleic acid-lipid particle comprising a hybrid tRNA/pre-microRNA scaffold (e.g., containing an inserted RNA) is provided. In addition to the references described above, suitable nucleic acid-lipid particles and their use are described in U.S. Pat. Nos. 6,815,432, 6,586,410, and 6,534,484.

Conventional pharmaceutical practice may be employed to provide suitable formulations or compositions to administer the hybrid tRNA/pre-microRNA scaffolds (e.g., containing an inserted RNA) to subjects suffering from, at risk of, or presymptomatic for cancer. Suitable pharmaceutical compositions may be formulated by means known in the art and their mode of administration and dose determined by the skilled practitioner. Any appropriate route of administration may be employed, for example, parenteral, intravenous, subcutaneous, intramuscular, intraventricular, intraurethral, intraperitoneal, intrahepatic, intratumoral, intranasal, aerosol, oral administration, or any mode suitable for the selected treatment. Therapeutic formulations may be in the form of liquid solutions or suspensions. For enteral administration, the compound may be administered in a tablet, capsule or dissolved in liquid form. The table or capsule may be enteric coated, or in a formulation for sustained release. For intranasal formulations, in the form of powders, nasal drops, or aerosols. For parenteral administration, a hybrid tRNA/pre-microRNA scaffold (e.g., containing an inserted RNA) may be dissolved in sterile water or saline or a pharmaceutically acceptable vehicle used for administration of non-water soluble hybrid tRNA/pre-microRNA scaffold (e.g., containing an inserted RNA) such as those used for vitamin K. Suitable formulations include those that have desirable pharmaceutical properties, such as targeted delivery to cancer cells, improved serum half-life/stability of a hybrid tRNA/pre-microRNA scaffold (e.g., containing an inserted RNA), improved intracellular penetration and cytoplasmic delivery, improved persistence of in-vivo activity, reduction in dose required for efficacy, reduction in required dosing frequency, etc. In alternative embodiments, a liposomal nanoparticle-based dosing formulation of a hybrid tRNA/pre-microRNA scaffold (e.g., containing an inserted RNA) may be prepared using methods well known to those skilled in the art and currently practiced for the preparation pharmaceutical formulations of other oligonucleotide-based reagents/therapeutics including anti-sense oligonucleotides and/or RNAi (siRNA)-based agents. In alternative embodiments, a gene therapy approach for transduction of hybrid tRNA/pre-microRNA scaffolds (e.g., containing an inserted RNA) to target cells (e.g., cancer cells) using for example lentiviral-based vectors, may be used.

Methods well known in the art for making formulations are found in, for example, Remington: the Science & Practice of Pharmacy, Loyd, et al., eds., $22^{nd}$ ed., Pharmaceutical Press, (2012). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the hybrid tRNA/pre-microRNA scaffolds (e.g., containing an inserted RNA) are administered to an individual in an amount sufficient to stop or slow a cancer, or to promote differentiation, or inhibit or decrease self-renewal, or inhibit or decrease engraftment or metastasis of cancer cells.

An "effective amount" of a hybrid tRNA/pre-microRNA scaffold (e.g., containing an inserted RNA) includes a therapeutically effective amount or a prophylactically effective amount. A "therapeutically effective amount" refers to an amount effective, at dosages and for periods of time necessary, to achieve the desired therapeutic result, such as treatment of a cancer or promotion of differentiation, or inhibition or decrease of self-renewal or inhibition or decrease of engraftment or metastasis of a cancer cell. The increase or decrease may be between 10% and 90%, e.g., 10%, 20%, 30%, 40%, 50%, 60%, 70%, 80%, 90%, or may be over 100%, such as 200%, 300%, 500% or more, when compared with a control or reference subject, sample or compound.

A therapeutically effective amount of a hybrid tRNA/pre-microRNA scaffold (e.g., containing an inserted RNA) may vary according to factors such as the disease state, age, sex, and weight of the individual subject, and the ability of the hybrid tRNA/pre-microRNA scaffolds (e.g., containing an inserted RNA) to elicit a desired response in the individual. Dosage regimens may be adjusted to provide the optimum therapeutic response. A therapeutically effective amount is also one in which any toxic or detrimental effects of the hybrid tRNA/pre-microRNA scaffold (e.g., containing an inserted RNA) are outweighed by therapeutically beneficial effects. A "prophylactically effective amount" refers to an amount effective, at dosages and for periods of time necessary, to achieve the desired prophylactic result, such as prevention or protection against a cancer or promotion of differentiation, inhibition or decrease of self-renewal or inhibition or decrease of engraftment or metastasis of cancer cells. Typically, a prophylactic dose is used in subjects prior to or at an earlier stage of disease, so that a prophylactically effective amount may be less than a therapeutically effective amount. In alternative embodiments, dosages may be adjusted depending on whether the subject is in remission from cancer or not. A preferred range for therapeutically or prophylactically effective amounts of a hybrid tRNA/pre-microRNA scaffolds (e.g., containing an inserted RNA) may be any integer from 0.1 nM-0.1M, 0.1 nM-0.05M, 0.05 nM-15 µM or 0.01 nM-10 µM. In alternative embodiments, a therapeutically or prophylactically effective amount that is administered to a subject may range from about 5 to about 3000 micrograms/kg if body weight of the subject, or any number therebetween.

In alternative embodiments, the hybrid tRNA/pre-microRNA scaffold (e.g., containing an inserted RNA) is provided in an amount that is from 10% to 99% greater than the amount of target nucleic acid or polypeptide present in cancer cells, or more generally at least 10%, 20%, 30%, 40%, 50, 55% or 60%, or at least 65%, 75%, 80%, 85%, 90%, or 95%, or as much as 96%, 97%, 98%, or 99% greater than the amount present in cancer cells. In alternative embodiments, the hybrid tRNA/pre-microRNA scaffold (e.g., containing an inserted RNA) is provided in an amount that is 0.5 to 50 fold greater than the amount present in cancer cells, or more generally at least 0.5, 1, 1.5, 2, 5, 10, 20, 25, 30, 35, 40, 45 fold greater than the amount present in cancer cells. In alternative embodiments, the hybrid tRNA/pre-microRNA scaffold (e.g., containing an inserted RNA) is provided in an amount that is equivalent to the amount present in non-cancerous bladder cells or the amount present in normal bladder cells.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of therapeutic situation. It may be advantageous to formulate parenteral compositions in dosage unit form for ease of administration and uniformity of dosage.

4. Combination Therapies

In various embodiments, the hybrid tRNA/pre-microRNA molecule is co-administered with one or more chemotherapeutic or anticancer agents.

Examples of chemotherapeutic or anticancer agents that can be co-administered with the hybrid tRNA/pre-microRNA molecule are known in the art and include without limitation alkylating agent(s) (e.g., nitrogen mustards, nitrogen ureas, ethylenimines, methylmelamines, alkyl sulfonates, carmustine, triazenes), platinum-coordination complexes (e.g., cisplatin, carboplatin, and oxaliplatin), anti-metabolite(s) (e.g., folic acid analogs (e.g., methotrexate), pyrimidine analogs (e.g., capecitabine, 5-fluorouracil, 5-fluorodeoxyuridine, 5-fluorodeoxyuridine monophosphate, cytosine arabinoside, 5-azacytidine, gemcitabine), purine analogs (e.g., mercaptopurine, thioguanine, azathioprine, pentostatin, erythrohydroxynonyladenine, fludarabine, cladribine)), plant alkaloid(s) and/or terpenoid(s), vinca alkaloid(s) (e.g., vincristine, vinblastine, vinorelbine, and vindesine), podophyllotoxin(s) (e.g., etoposide and teniposide), camptothecin(s) (e.g., irinotecan and topotecan), anthracycline(s), aromatase inhibitor(s), taxane(s) (e.g., paclitaxel (including albumin-bound paclitaxel (nab-paclitaxel)), taxol and docetaxel), topoisomerase inhibitor(s) (e.g., (Type I inhibitors: camptothecins, including irinotecan and topotecan; Type II Inhibitors: amsacrine, etoposide, etoposide phosphate, and teniposide), antibiotic(s) (e.g., dactinomycin, daunorubicin, doxorubincin, idarubicin, epirubicin, bleomycins, mitomycin), hormone(s), differentiating agent(s), kinase inhibitor(s) (e.g., Bevacizumab, BIBW 2992, Cetuximab, Imatinib, Trastuzumab, Gefitinib, Ranibizumab, Pegaptanib, Sorafenib, Dasatinib, Sunitinib, Erlotinib, Nilotinib, Lapatinib, Panitumumab, Vandetanib, E7080, Pazopanib, Mubritinib and Fostamatinib) and antineoplastic agent(s) (e.g., (dactinomycin, doxorubicin, epirubicin, fludarabine and bleomycin). Any chemotherapeutic or anticancer agent being used to treat the cancer of interest can be co-administered in a combination therapy regime with the hybrid tRNA/pre-microRNA molecule. Chemotherapeutic or anticancer agents of use are known in the art and described in reference texts, e.g., Physicians' Desk Reference, 71st Ed., 2017, PDR Network or Brunton and Knollmann, Goodman & Gilman's The Pharmacological Basis of Therapeutics, 13th edition, 2017, McGraw-Hill.

In one embodiment, the hybrid tRNA/pre-microRNA molecule is co-administered with gemcitabine and paclitaxel, e.g., nanoparticle albumin-bound paclitaxel ("nab-paclitaxel").

5. Methods of Monitoring

A variety of methods can be employed in determining efficacy of therapeutic and prophylactic treatment with a hybrid tRNA/pre-microRNA scaffold (e.g., containing an inserted RNA), e.g., in combination with a chemotherapeutic or anticancer agent. Generally, efficacy is the capacity to produce an effect without significant toxicity. Efficacy indicates that therapy provides therapeutic or prophylactic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment. Efficacy of a treatment can be determined using a variety of methods, including pharmacological studies, diagnostic studies, predictive studies and prognostic studies. Examples of indicators of efficacy include but are not limited to inhibition of tumor cell growth and promotion of tumor cell death.

The efficacy of an anti-cancer treatment can be assessed by a variety of methods known in the art. The hybrid tRNA/pre-microRNA scaffold (e.g., containing an inserted RNA), e.g., in combination with a chemotherapeutic or anticancer agent can be screened for prophylactic or therapeutic efficacy in animal models in comparison with untreated or placebo controls. A hybrid tRNA/pre-microRNA scaffold (e.g., containing an inserted RNA), e.g., in combination with a chemotherapeutic or anticancer agent identified by such screens can be then analyzed for the capacity to induce tumor cell death or enhanced immune system activation. For example, multiple dilutions of sera can be tested on tumor cell lines in culture and standard methods for examining cell death or inhibition of cellular growth can be employed. (See, e.g., Green and Sambrook, *Molecular Cloning: A Laboratory Manual*, Cold Spring Harbor Laboratory Press; 4th edition (2012); Ausubel, et al. Editor, *Current Protocols in Molecular Biology, USA*, 1984-2018; and Ausubel, et al. Editor, *Current Protocols in Molecular Biology, USA,* 1984-2018; Bonifacino, et al., Editor, *Current Protocols in Cell Biology, USA, through* 2018; all of which are incorporated herein by reference in their entirety.)

The methods provide for detecting inhibition disease in patient suffering from or susceptible to various cancers. A variety of methods can be used to monitor both therapeutic treatment for symptomatic patients and prophylactic treatment for asymptomatic patients.

Monitoring methods entail determining a baseline value of a tumor burden in a patient before administering a dosage of a hybrid tRNA/pre-microRNA scaffold (e.g., containing an inserted RNA), e.g., in combination with a chemotherapeutic or anticancer agent, and comparing this with a value for the tumor burden after treatment, respectively.

With respect to therapies using a hybrid tRNA/pre-microRNA scaffold (e.g., containing an inserted RNA), e.g., in combination with a chemotherapeutic or anticancer agent, a significant decrease (i.e., greater than the typical margin of experimental error in repeat measurements of the same sample, expressed as one standard deviation from the mean of such measurements) in value of the tumor burden signals a positive treatment outcome (i.e., that administration of a hybrid tRNA/pre-microRNA scaffold (e.g., containing an inserted RNA), e.g., in combination with a chemotherapeutic or anticancer agent has blocked or inhibited, or reduced progression of tumor growth and/or metastasis).

In other methods, a control value of tumor burden (e.g., a mean and standard deviation) is determined from a control population of individuals who have undergone treatment with a hybrid tRNA/pre-microRNA scaffold (e.g., containing an inserted RNA), e.g., in combination with a chemotherapeutic or anticancer agent Measured values of tumor burden in a patient are compared with the control value. If the measured level in a patient is not significantly different (e.g., more than one standard deviation) from the control value, treatment can be discontinued. If the tumor burden level in a patient is significantly above the control value, continued administration of agent is warranted.

In other methods, a patient who is not presently receiving treatment but has undergone a previous course of treatment is monitored for tumor burden to determine whether a resumption of treatment is required. The measured value of tumor burden in the patient can be compared with a value of tumor burden previously achieved in the patient after a previous course of treatment. A significant decrease in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can be analyzed for indication of neoplasia. Neoplasia or tumor burden can be detected using any method known in the art, e.g., visual observation of a biopsy by a qualified pathologist, or other visualization techniques, e.g., radiography, ultrasound, magnetic resonance imaging (MRI).

Further, the level of immune system activity in conjunction with tumor burden in a patient before administering a dosage of a hybrid tRNA/pre-microRNA scaffold (e.g., containing an inserted RNA), e.g., in combination with a chemotherapeutic or anticancer agent, can be compared this with a value for the immune system activity in conjunction with tumor burden after treatment, again respectively.

With respect to therapies involving enhanced immune system activity, a significant increase (i.e., greater than the typical margin of experimental error in repeat measurements of the same sample, expressed as one standard deviation from the mean of such measurements) in value of immune response signals a positive treatment outcome (i.e., that administration of a hybrid tRNA/pre-microRNA scaffold (e.g., containing an inserted RNA), e.g., in combination with a chemotherapeutic or anticancer agent, has achieved or augmented an immune response). Immune response signals can include but are not limited to for example assessing the enhancement of the lymphoma-specific cytotoxic effect of human peripheral blood mononuclear cells (PBMCs). If the value for the immune response signal does not change significantly, or decreases, a negative treatment outcome is indicated. In general, patients undergoing an initial course of treatment with an immunogenic agent are expected to show an increase in immune response activity with successive dosages, which eventually reaches a plateau. Administration of an agent is often continued while the immune response is increasing. Once a plateau is obtained, that is an indicator if the treatment is solely for the immune the administration of the treatment can be discontinued or reduced in dosage or frequency.

6. Kits

Further provided are kits comprising one or more containers comprising one or more hybrid tRNA/pre-microRNA scaffolds (e.g., containing one or more inserted RNA for reducing or inhibiting growth of a cancer cell) described herein. Kits containing multiple containers can have aliquots providing unitary doses of the one or more hybrid tRNA/pre-microRNA molecules in a formulation suitable for administration, e.g., an aqueous solution comprising liposomes encapsulating the tRNA/pre-microRNA scaffolds.

In various embodiments, suitable formulations may be provided in a kit including one or more hybrid tRNA/pre-microRNA (e.g., containing one or more inserted RNA for reducing or inhibiting growth of a cancer cell), together with instructions for using the hybrid tRNA/pre-microRNA molecules to treat cancer (e.g., HCC, pancreatic cancer, lung cancer). The kit may contain additional agents such as a pharmaceutical carrier e.g, a liposomal carrier or additional active ingredients such as a chemotherapeutic or anticancer agent. The additional agents may be provided in the same container as that containing the hybrid tRNA/pre-microRNA scaffolds (e.g., containing one or more inserted RNA) or may be provided in a container separate from that containing the hybrid tRNA/pre-microRNA scaffolds (e.g., containing one or more inserted RNA).

In some embodiments, the one or more hybrid tRNA/pre-microRNA molecules are lyophilized.

SEQUENCES 1-84: human tRNAs with aptamers
85-112: human tRNAs fused to human pre-miR-34a derivative
113-122: human leucine tRNA fused to human pre-miR-34a derivative, with miRNA/siRNAs replacing miR-34a duplex
123-142: human serine tRNA fused to human pre-miR-34a derivative, with miRNA/siRNAs replacing miR-34a duplex
143-170: human tRNAs fused to human pre-miR-1291
171-176: human tRNAs fused to various pre-miRNAs (pre-miR-200b, pre-miR-133a, pre-miR-125a, pre-let-7c, pre-miR-124)
177-182: Human tRNA fragments (tRFs)
183-192: Human tRNA fused to two human pre-miR-34a derivatives, with miRNA/siRNAs replacing miR-34a duplexes
193-210: Human tRNA fused to two human pre-miR-34a derivatives, with miRNA/siRNAs replacing miR-34a duplexes and the addition of aptamers
ANNOTATIONS FOR SEQ ID NOS: 1-210: Underlined are tRNA sequences, and the italic are pre-miRNA sequences. Double underline is the mature miRNA/siRNA sequence, and bold underline is the guide miRNA/siRNA sequence. The boxed are aptamer (e.g., sephadex) sequences.

SEQ ID NO: 1 - htRNA-Ser-TGA-Seph (118nt): A hybrid molecule of human
serine-TGA tRNA and sephadex aptamer.
5'-GCAGCGAUGGCCGAGUGGUUAAGGCGUUGGACUAGUAAUUUACGUCGACGGUGACGUCGAUGGUUGCGG
AAUCCAAUGGGGUCUCCCCGCGCAGGUUCGAACCCUGCUCGCUGCGCCA-3'

SEQ ID NO: 2 - htRNA-Ser-TGA-EpCA (101nt): A hybrid molecule of human
serine-TGA tRNA and EpCAM aptamer
5'-GCAGCGAUGGCCGAGUGGUUAAGGCGUUGGACUGCGACUGGUUACCCGGUCGAAUCCAAUGGGGUCUCC
CCGCGCAGGUUCGAACCCUGCUCGCUGCGCCA-3'

SEQ ID NO: 3 - htRNA-Ser-TGA-Theo (115nt): A hybrid molecule of human
serine-TGA tRNA and theophylline aptamer
5'-GCAGCGAUGGCCGAGUGGUUAAGGCGUUGGACUGGCGAUACCAGCCGAAAGGCCCUUGGCAGCGUCAAU
CCAAUGGGGUCUCCCCGCGCAGGUUCGAACCCUGCUCGCUGCGCCA-3'

SEQ ID NO: 4 - htRNA-Ser-GCT-Seph (118nt): A hybrid molecule of human
serine-GCT tRNA and sephadex aptamer
5'-GACGAGGUGGCCGAGUGGUUAAGGCGAUGGACUAGUAAUUUACGUCGACGGUGACGUCGAUGGUUGCGGA
AUCCAUUGUGCUCUGCACGCGUGGGUUCGAAUCCCACCCUCGUCGCCA-3'

SEQ ID NO: 5 - htRNA-Ser-GCT-EpCA (101nt): A hybrid molecule of human
serine-GCT tRNA and EpCAM aptamer
5'-GACGAGGUGGCCGAGUGGUUAAGGCGAUGGACUGCGACUGGUUACCCGGUCGAAUCCAUUGUGCUCUGCA
CGCGUGGGUUCGAAUCCCACCCUCGUCGCCA-3'

SEQ ID NO: 6 - htRNA-Ser-GCT-Theo (115nt): A hybrid molecule of human
serine-GCT tRNA and theophylline aptamer
5'-GACGAGGUGGCCGAGUGGUUAAGGCGAUGGACUGGCGAUACCAGCCGAAAGGCCCUUGGCAGCGUCAAUC
CAUUGUGCUCUGCACGCGUGGGUUCGAAUCCCACCCUCGUCGCCA-3'

SEQ ID NO: 7 - htRNA-Leu-TAA-Seph aptamer (119nt): A hybrid molecule of
human leucine-TAA ERNA and sephadex aptamer.
5'-ACCAGGAUGGCCGAGUGGUUAAGGCGUUGGACUAGUAAUUUACGUCGACGGUGACGUCGAUGGUUGCGG
GAUCCAAUGGACAUAUGUCCGCGUGGGUUCGAACCCCACUCCUGGUACCA-3'

SEQ ID NO: 8 - htRNA-Leu-TAA-EpCA (102nt): A hybrid molecule of human
leucine-TAA tRNA and EpCAM aptamer
5'-ACCAGGAUGGCCGAGUGGUUAAGGCGUUGGACUGCGACUGGUUACCCGGUCGGAUCCAAUGGACAUAUG
UCCGCGUGGGUUCGAACCCCACUCCUGGUACCA-3'

SEQ ID NO: 9 - htRNA-Leu-TAA-Theo (116nt): A hybrid molecule of human
leucine-TAA ERNA and theophylline aptamer
5'-ACCAGGAUGGCCGAGUGGUUAAGGCGUUGGACUGGCGAUACCAGCCGAAAGGCCCUUGGCAGCGUCGAU
CCAAUGGACAUAUGUCCGCGUGGGUUCGAACCCCACUCCUGGUACCA-3'

SEQ ID NO: 10 - htRNA-Leu-CAA-Seph (120nt): A hybrid molecule of human
leucine-CAA tRNA and sephadex aptamer
5'-GUCAGGAUGGCCGAGUGGUCUAAGGCGCCAGACUAGUAAUUUACGUCGACGGUGACGUCGAUGGUUGCGG
GUUCUGGUCUCCGUAUGGAGGCGUGGGUUCGAAUCCCACUUCUGACACCA-3'

SEQ ID NO: 11 - htRNA-Leu-CAA-EpCA (103nt): A hybrid molecule of human
leucine-CAA ERNA and EpCAM aptamer
5'-GUCAGGAUGGCCGAGUGGUCUAAGGCGCCAGACUGCGACUGGUUACCCGGUCGGUUCUGGUCUCCGUAUG
GAGGCGUGGGUUCGAAUCCCACUUCUGACACCA-3'

SEQ ID NO: 12 - htRNA-Leu-CAA-Theo (117nt): A hybrid molecule of human
leucine-CAA tRNA and theophylline aptamer
5'-GUCAGGAUGGCCGAGUGGUCUAAGGCGCCAGACUGGCGAUACCAGCCGAAAGGCCCUUGGCAGCGUCGUU
CUGGUCUCCGUAUGGAGGCGUGGGUUCGAAUCCCACUUCUGACACCA-3'

SEQ ID NO: 13 - htRNA-Gly-GCC-Seph (107nt): A hybrid molecule of human
glycine-GCC tRNA and sephadex aptamer
5'-GCAUGGGUGGUUCAGUGGUAGAAUUCUCGCCUAGUAAUUUACGUCGACGGUGACGUCGAUGGUUGCGGAC
GCGGGAGGCCCGGGUUCGAUUCCCGGCCCAUGCACCA-3'

SEQ ID NO: 14 - htRNA-Gly-GCC-EpCA (90nt): A hybrid molecule of human
glycine-GCC ERNA and EpCAM aptamer
5'-GCAUGGGUGGUUCAGUGGUAGAAUUCUCGCCUGCGACUGGUUACCCGGUCGACGCGGGAGGCCCGGGUUC
GAUUCCCGGCCCAUGCACCA-3'

SEQ ID NO: 15 - htRNA-Gly-GCC-Theo (104nt): A hybrid molecule of human
glycine-GCC tRNA and theophylline aptamer 5'-<u>GCAUGGGUGGUUCAGUGGUAGAAUUCUCGGCCU</u>GGCGAUACCAGCCGAAAGGCCCUUGGCAGCGUCACGCG
GGAGGCCCGGGUUCGAUUCCCGGCCCAUGCACCA-3'

SEQ ID NO: 16 - htRNA-Gly-TCC-Seph (108nt): A hybrid molecule of human
glycine-TCC tRNA and sephadex aptamer 5'-<u>GCGUUGGUGGUAUAGUGGUUAGCAUAGCUGCCU</u>AGUAAUUUACGUCGACGGUGACGUCGAUGGUUGCGG
AAGCAGUUGACCCGGGUUCGAUUCCCGGCCAACGCACCA-3'

SEQ ID NO: 17 - htRNA-Gly-TCC-EpCA (91nt): A hybrid molecule of human
glycine-TCC tRNA and EpCAM aptamer 5'-<u>GCGUUGGUGGUAUAGUGGUUAGCAUAGCUGCCU</u>GCGACUGGUUACCCGGUCGAAGCAGUUGACCCGGGU
UCGAUUCCCGGCCAACGCACCA-3'

SEQ ID NO: 18 - htRNA-Gly-TCC-Theo (105nt): A hybrid molecule of human
glycine-TCC tRNA and theophylline aptamer 5'-<u>GCGUUGGUGGUAUAGUGGUUAGCAUAGCUGCCU</u>GGCGAUACCAGCCGAAAGGCCCUUGGCAGCGUCAAGC
AGUUGACCCGGGUUCGAUUCCCGGCCAACGCACCA-3'

SEQ ID NO: 19 - htRNA-Glu-CTC-Seph (108nt): A hybrid molecule of human
glutamic acid-CTC tRNA and sephadex aptamer 5'-<u>UCCCUGGUGGUCUAGUGGUUAGGAUUCGGCGCU</u>AGUAAUUUACGUCGACGGUGACGUCGAUGGUUGCGGA
CCGCCGCGGCCCGGGUUCGAUUCCCGGUCAGGGAACCA-3'

SEQ ID NO: 20 - htRNA-Glu-CTC-EpCA (91nt): A hybrid molecule of human
glutamic acid-CTC and EpCAM aptamer 5'-<u>UCCCUGGUGGUCUAGUGGUUAGGAUUCGGCGCU</u>GCGACUGGUUACCCGGUCGACCGCCGCGGCCCGGGUU
CGAUUCCCGGUCAGGGAACCA-3'

SEQ ID NO: 21 - htRNA-Glu-CTC-Theo (105nt): A hybrid molecule of human
glutamic acid-CTC and theophylline aptamer 5'-<u>UCCCUGGUGGUCUAGUGGUUAGGAUUCGGCGCU</u>GGCGAUACCAGCCGAAAGGCCCUUGGCAGCGUCACCG
CCGCGGCCCGGGUUCGAUUCCCGGUCAGGGAACCA-3'

SEQ ID NO: 22 - htRNA-Asp-GTC-Seph (108nt): A hybrid molecule of human
aspartic acid-GTC tRNA and sephadex aptamer 5'-<u>UCCUCGUUAGUAUAGUGGUGAGUAUCCCCGCCU</u>AGUAAUUUACGUCGACGGUGACGUCGAUGGUUGCGGA
CGCGGGAGACCGGGGUUCGAUUCCCCGACGGGGAGCCA-3'

SEQ ID NO: 23 - htRNA-Asp-GTC-EpCA (91nt): A hybrid molecule of human
aspartic acid-GTC tRNA and EpCAM aptamer 5'-<u>UCCUCGUUAGUAUAGUGGUGAGUAUCCCCGCCU</u>GCGACUGGUUACCCGGUCGACGCGGGAGACCGGGGUU
CGAUUCCCGACGGGGAGCCA-3'

SEQ ID NO: 24 - htRNA-Asp-GTC-Theo (105nt): A hybrid molecule of human
aspartic acid-GTC tRNA and theophylline aptamer 5'-<u>UCCUCGUUAGUAUAGUGGUGAGUAUCCCCGCCU</u>GGCGAUACCAGCCGAAAGGCCCUUGGCAGCGUCACGC
GGGAGACCGGGGUUCGAUUCCCCGACGGGGAGCCA-3'

SEQ ID NO: 25 - htRNA-Gln-TTG-Seph (108nt): A hybrid molecule of human
glutamine-TTG tRNA and sephadex aptamer 5'-<u>GGUCCCAUGGUGUAAUGGUUAGCACUCUGGACU</u>AGUAAUUUACGUCGACGGUGACGUCGAUGGUUGCGGA
AUCCAGCGAUCCGAGUUCAAAUCUCGGUGGGACCUCCA-3'

SEQ ID NO: 26 - htRNA-Gln-TTG-EpCA (91nt): A hybrid molecule of human
glutamine-TTG tRNA and EpCAM aptamer 5'-<u>GGUCCCAUGGUGUAAUGGUUAGCACUCUGGACU</u>GCGACUGGUUACCCGGUCGAAUCCAGCGAUCCGAGUU
CAAAUCUCGGUGGGACCUCCA-3'

SEQ ID NO: 27 - htRNA-Gln-TTG-Theo (105nt): A hybrid molecule of human
glutamine-TTG tRNA and theophylline aptamer 5'-<u>GGUCCCAUGGUGUAAUGGUUAGCACUCUGGACU</u>GGCGAUACCAGCCGAAAGGCCCUUGGCAGCGUCAAUC
CAGCGAUCCGAGUUCAAAUCUCGGUGGGACCUCCA-3'

SEQ ID NO: 28 - htRNA-Gln-CTG-Seph (108nt): A hybrid molecule of human
glutamine- CTG tRNA and sephadex aptamer 5'-<u>UGGUUCCAUGGUGUAAUGGUUAGCACUCUGGACU</u>AGUAAUUUACGUCGACGGUGACGUCGAUGGUUGCGGA
AUCCAGCGAUCCGAGUUCAAAUCUCGGUGGAACCUCCA-3'

SEQ ID NO: 29 - htRNA-Gln-CTG-EpCA (91nt): A hybrid molecule of human
glutamine- CTG tRNA and EpCAM aptamer 5'-<u>GGUUCCAUGGUGUAAUGGUUAGCACUCUGGACU</u>GCGACUGGUUACCCGGUCGAAUCCAGCGAUCCGAGUU
CAAAUCUCGGUGGAACCUCCA-3'

-continued

SEQ ID NO: 30 - htRNA-Gln-CTG-Theo (105nt): A hybrid molecule of human
glutamine- CTG tRNA and theophylline aptamer
5'-GGUUCCAUGGUGUAAUGGUUAGCACUCUGGACUGGCGAUACCAGCCGAAAGGCCCUUGGCAGCGUCAAUC
CAGCGAUCCGAGUUCAAAUCUCGGUGGAACCUCCA-3'

SEQ ID NO: 31 - htRNA-Arg-ACG-Seph (109nt): A hybrid molecule of human
arginine-ACG tRNA and sephadex aptamer
5'-GGGCCAGUGGCGCAAUGGAUAACGCGUCUGACUAGUAAUUUACGUCGACGGUGACGUCGAUGGUUGCGGG
AUCAGAAGAUUCCAGGUUCGACUCCUGGCUGGCUCGCCA-3'

SEQ ID NO: 32 - htRNA-Arg-ACG-EpCA (92nt): A hybrid molecule of human
arginine-ACG tRNA and EpCAM aptamer
5'-GGGCCAGUGGCGCAAUGGAUAACGCGUCUGACUGCGACUGGUUACCCGGUCGGAUCAGAAGAUUCCAGGU
UCGACUCCUGGCUGGCUCGCCA-3'

SEQ ID NO: 33 - htRNA-Arg-ACG-Theo (106nt): A hybrid molecule of human
arginine-ACG tRNA and theophylline aptamer
5'-GGGCCAGUGGCGCAAUGGAUAACGCGUCUGACUGGCGAUACCAGCCGAAAGGCCCUUGGCAGCGUCGAUC
AGAAGAUUCCAGGUUCGACUCCUGGCUGGCUCGCCA-3'

SEQ ID NO: 34 - htRNA-Arg-TCT-Seph (109nt): A hybrid molecule of human
arginine-TCT tRNA and sephadex aptamer
5'-GGCUCUGUGGCGCAAUGGAUAGCGCAUUGGACUAGUAAUUUACGUCGACGGUGACGUCGAUGGUUGCGGA
AUUCAAAGGUUGUGGGUUCGAAUCCCACCAGAGUCGCCA-3'

SEQ ID NO: 35 - htRNA-Arg-TCT-EpCA (92nt): A hybrid molecule of human
arginine-TCT tRNA and EpCAM aptamer
5'-GGCUCUGUGGCGCAAUGGAUAGCGCAUUGGACUGCGACUGGUUACCCGGUCGAAUUCAAAGGUUGUGGGU
UCGAAUCCCACCAGAGUCGCCA-3'

SEQ ID NO: 36 - htRNA-Arg-TCT-Theo (106nt): A hybrid molecule of human
arginine-TCT tRNA and theophylline aptamer
5'-GGCUCUGUGGCGCAAUGGAUAGCGCAUUGGACUGGCGAUACCAGCCGAAAGGCCCUUGGCAGCGUCAAUU
CAAAGGUUGUGGGUUCGAAUCCCACCAGAGUCGCCA-3'

SEQ ID NO: 37 - htRNA-Cys-GCA-Seph (108nt): A hybrid molecule of human
cysteine-GCA tRNA and sephadex aptamer
5'-GGGGGAUAGCUCAGUGGUAGAGCAUUUGACUAGUAAUUUACGUCGACGGUGACGUCGAUGGUUGCGGGA
UCAAGAGGUCCCUGGUUCAAAUCCAGGUGCCCCUCCA-3'

SEQ ID NO: 38 - htRNA-Cys-GCA-EpCA (91nt): A hybrid molecule of human
cysteine-GCA tRNA and EpCAM aptamer
5'-GGGGGCAUAGCUCAGUGGUAGAGCAUUUGACUGCGACUGGUUACCCGGUCGGAUCAAGAGGUCCCUGGUU
CAAAUCCAGGUGCCCCUCCA-3'

SEQ ID NO: 39 - htRNA-Cys-GCA-Theo (105nt): A hybrid molecule of human
cysteine-GCA tRNA and theophylline aptamer
5'-GGGGGCAUAGCUCAGUGGUAGAGCAUUUGACUGGCGAUACCAGCCGAAAGGCCCUUGGCAGCGUCGAUCA
AGAGGUCCCUGGUUCAAAUCCAGGUGCCCCUCCA-3'

SEQ ID NO: 40 - htRNA-Lys-CTT-Seph (109nt): A hybrid molecule of human
lysine-CTT tRNA and sephadex aptamer
5'-GCCCGGCUAGCUCAGUCGGUAGAGCAUGGGACUAGUAAUUUACGUCGACGGUGACGUCGAUGGUUGCGGA
AUCCCAGGGUCGUGGGUUCGAGCCCCACGUUGGGCGCCA-3'

SEQ ID NO: 41 - htRNA-Lys-CTT-EpCA (92nt): A hybrid molecule of human
lysine-CTT tRNA and EpCAM aptamer
5'-GCCCGGCUAGCUCAGUCGGUAGAGCAUGGGACUGCGACUGGUUACCCGGUCGAAUCCCAGGGUCGUGGGU
UCGAGCCCCACGUUGGGCGCCA-3'

SEQ ID NO: 42 - htRNA- Lys-CTT-Theo (106nt): A hybrid molecule of human
lysine-CTT tRNA and theophylline aptamer
5'-GCCCGGCUAGCUCAGUCGGUAGAGCAUGGGACUGGCGAUACCAGCCGAAAGGCCCUUGGCAGCGUCAAUC
CCAGGGUCGUGGGUUCGAGCCCCACGUUGGGCGCCA-3'

SEQ ID NO: 43 - htRNA-Lys-TTT-Seph (109nt): A hybrid molecule of human
lysine-TTT tRNA and sephadex aptamer
5'-GCCUGGAUAGCUCAGUUGGUAGAGCAUCAGACUAGUAAUUUACGUCGACGGUGACGUCGAUGGUUGCGGA
AUCUGAGGGUCCAGGGUUCAAGUCCCUGUUCAGGCACCA-3'

SEQ ID NO: 44 - htRNA-Lys-TTT-EpCA (92nt): A hybrid molecule of human lysine-TTT tRNA and EpCAM aptamer
5'-GCCUGGAUAGCUCAGUUGGUAGAGCAUCAGACUGCGACUGGUUACCCGGUCGAAUCUGAGGGUCCAGGGUUCAAGUCCCUGUUCAGGCACCA-3'

SEQ ID NO: 45 - htRNA-Lys-TTT-Theo (106nt): A hybrid molecule of human lysine-TTT tRNA and theophylline aptamer
5'-GCCUGGAUAGCUCAGUUGGUAGAGCAUCAGACUGGCGAUACCAGCCGAAAGGCCCUUGGCAGCGUCAAUCUGAGGGUCCAGGGUUCAAGUCCCUGUUCAGGCACCA-3'

SEQ ID NO: 46 - htRNA-Met-CAT-Seph (109nt): A hybrid molecule of human methionine-CAT tRNA and sephadex aptamer
5'-GCCUCGUUAGCGCAGUAGGUAGCGCGUCAGUCUAGUAAUUUACGUCGACGGUGACGUCGAUGGUUGCGGAAUCUGAAGGUCGUGAGUUCGAUCCUCACACGGGGCACCA-3'

SEQ ID NO: 47 - htRNA-Met-CAT-EpCA (92nt): A hybrid molecule of human methionine-CAT tRNA and EpCAM aptamer
5'-GCCUCGUUAGCGCAGUAGGUAGCGCGUCAGUCUGCGACUGGUUACCCGGUCGAAUCUGAAGGUCGUGAGUUCGAUCCUCACACGGGGCACCA-3'

SEQ ID NO: 48 - htRNA-Met-CAT-Theo (106nt): A hybrid molecule of human methionine-CAT tRNA and theophylline aptamer
5'-GCCUCGUUAGCGCAGUAGGUAGCGCGUCAGUCUGGCGAUACCAGCCGAAAGGCCCUUGGCAGCGUCAAUCUGAAGGUCGUGAGUUCGAUCCUCACACGGGGCACCA-3'

SEQ ID NO: 49 - htRNA-Asn-GTT-Seph (110nt): A hybrid molecule of human asparagine-GTT tRNA and sephadex aptamer
5'-GUCUCUGUGGCGCAAUCGGUUAGCGCGUUCGGCUAGUAAUUUACGUCGACGGUGACGUCGAUGGUUGCGGAACCGAAAGGUUGGUGGUUCGAUCCCACCCAGGGACGCCA-3'

SEQ ID NO: 50 - htRNA-Asn-GTT-EpCA (93nt): A hybrid molecule of human asparagine-GTT tRNA and EpCAM aptamer
5'-GUCUCUGUGGCGCAAUCGGUUAGCGCGUUCGGCUGCGACUGGUUACCCGGUCGAACCGAAAGGUUGGUGGUUCGAUCCCACCCAGGGACGCCA-3'

SEQ ID NO: 51 - htRNA-Asn-GTT-Theo (107nt): A hybrid molecule of human asparagine-GTT tRNA and theophylline aptamer
5'-GUCUCUGUGGCGCAAUCGGUUAGCGCGUUCGGCUGGCGAUACCAGCCGAAAGGCCCUUGGCAGCGUCAACCGAAAGGUUGGUGGUUCGAUCCCACCCAGGGACGCCA-3'

SEQ ID NO: 52 - htRNA-Ala-AGC-Seph (108nt): A hybrid molecule of human alanine-AGC tRNA and sephadex aptamer
5'-GGGGGUGUAGCUCAGUGGUAGAGCGCGUGCUUAGUAAUUUACGUCGACGGUGACGUCGAUGGUUGCGGAUGCACGAGGCCCCGGGUUCAAUCCCCGGCACCUCCACCA-3'

SEQ ID NO: 53 - htRNA-Ala-AGC-EpCA (91nt): A hybrid molecule of human alanine-AGC tRNA and EpCAM aptamer
5'-GGGGGUGUAGCUCAGUGGUAGAGCGCGUGCUUGCGACUGGUUACCCGGUCGAUGCACGAGGCCCCGGGUUCAAUCCCCGGCACCUCCACCA-3'

SEQ ID NO: 54 - htRNA-Ala-AGC-Theo (105nt): A hybrid molecule of human alanine-AGC tRNA and theophylline aptamer
5'-GGGGGUGUAGCUCAGUGGUAGAGCGCGUGCUUGGCGAUACCAGCCGAAAGGCCCUUGGCAGCGUCAUGCACGAGGCCCCGGGUUCAAUCCCCGGCACCUCCACCA-3'

SEQ ID NO: 55 - htRNA-His-GTG-Seph (108nt): A hybrid molecule of human histidine-GTG tRNA and sephadex aptamer
5'-GCCGUGAUCGUAUAGUGGUUAGUACUCUGCGUUAGUAAUUUACGUCGACGGUGACGUCGAUGGUUGCGGGCCGCAGCAACCUCGGUUCGAAUCCGAGUCACGGCACCA-3'

SEQ ID NO: 56 - htRNA-His-GTG-EpCA (91nt): A hybrid molecule of human histidine-GTG tRNA and EpCAM aptamer
5'-GCCGUGAUCGUAUAGUGGUUAGUACUCUGCGUUGCGACUGGUUACCCGGUCGGCCGCAGCAACCUCGGUUCGAAUCCGAGUCACGGCACCA-3'

SEQ ID NO: 57 - htRNA-His-GTG-Theo (105nt): A hybrid molecule of human histidine-GTG tRNA and theophylline aptamer
5'-GCCGUGAUCGUAUAGUGGUUAGUACUCUGCGUUGGCGAUACCAGCCGAAAGGCCCUUGGCAGCGUCGCCGCAGCAACCUCGGUUCGAAUCCGAGUCACGGCACCA-3'

SEQ ID NO: 58 - htRNA-Ile-AAT-Seph (110nt): A hybrid molecule of human isoleucine-AAT tRNA and sephadex aptamer 5'-GGCCGGUUAGCUCAGUUGGUUAGAGCGUGGUGCU AGUAAUUUACGUCGACGGUGACGUCGAUGGUUGCG
GAACGCCAAGGUCGCGGGUUCGAUCCCCGUACUGGCCACCA-3'

SEQ ID NO: 59 - htRNA-Ile-AAT-EpCA (93nt): A hybrid molecule of human
isoleucine-AAT tRNA and EpCAM aptamer 5'-GGCCGGUUAGCUCAGUUGGUUAGAGCGUGGUGCU GCGACUGGUUACCCGGUCG AACGCCAAGGUCGCGG
GUUCGAUCCCCGUACUGGCCACCA-3'

SEQ ID NO: 60 - htRNA-Ile-AAT-Theo (107nt): A hybrid molecule of human
isoleucine-AAT tRNA and theophylline aptamer 5'-GGCCGGUUAGCUCAGUUGGUUAGAGCGUGGUGCU GGCGAUACCAGCCGAAAGGCCCUUGGCAGCGUC AA
CGCCAAGGUCGCGGGUUCGAUCCCCGUACUGGCCACCA-3'

SEQ ID NO: 61 - htRNA-Ile-TAT-Seph (110nt): A hybrid molecule of human
isoleucine-TAT tRNA and sephadex aptamer 5'-GCUCCAGUGGCGCAAUCGGUUAGCGCGCGGUACU AGUAAUUUACGUCGACGGUGACGUCGAUGGUUGCG
GAAUGCCGAGGUUGUGAGUUCGAUCCUCACCUGGAGCACCA-3'

SEQ ID NO: 62 - htRNA-Ile-TAT-EpCA (93nt): A hybrid molecule of human
isoleucine-TAT tRNA and EpCAM aptamer 5'-GCUCCAGUGGCGCAAUCGGUUAGCGCGCGGUACU GCGACUGGUUACCCGGUCG AAUGCCGAGGUUGUGA
GUUCGAUCCUCACCUGGAGCACCA-3'

SEQ ID NO: 63 - htRNA-Ile-TAT-Theo (107nt): A hybrid molecule of human
isoleucine-TAT tRNA and theophylline aptamer 5'-GCUCCAGUGGCGCAAUCGGUUAGCGCGCGGUACU GGCGAUACCAGCCGAAAGGCCCUUGGCAGCGUC AA
UGCCGAGGUUGUGAGUUCGAUCCUCACCUGGAGCACCA-3'

SEQ ID NO: 64 - htRNA-Phe-GAA-Seph (109nt): A hybrid molecule of human
phenylalanine-GAA ERNA and sephadex aptamer 5'-GCCGAAAUAGCUCAGUUGGGAGAGCGUUAGACU AGUAAUUUACGUCGACGGUGACGUCGAUGGUUGCGG
GAUCUAAAGGUCCCUGGUUCGAUCCCGGGUUUCGGCACCA-3'

SEQ ID NO: 65 - htRNA-Phe-GAA-EpCA (92nt): A hybrid molecule of human
phenylalanine-GAA tRNA and EpCAM aptamer 5'-GCCGAAAUAGCUCAGUUGGGAGAGCGUUAGACU GCGACUGGUUACCCGGUCG GAUCUAAAGGUCCCUGG
UUCGAUCCCGGGUUUCGGCACCA-3'

SEQ ID NO: 66 - htRNA- Phe-GAA-Theo (106nt): A hybrid molecule of human
phenylalanine-GAA tRNA and theophylline aptamer 5'-GCCGAAAUAGCUCAGUUGGGAGAGCGUUAGACU GGCGAUACCAGCCGAAAGGCCCUUGGCAGCGUC GAU
CUAAAGGUCCCUGGUUCGAUCCCGGGUUUCGGCACCA-3'

SEQ ID NO: 67 - htRNA- Pro-AGG-Seph (108nt): A hybrid molecule of human
proline-AGG tRNA and sephadex aptamer 5'-GGCUCGUUGGUCUAGGGGUAUGAUUCUCGCUU AGUAAUUUACGUCGACGGUGACGUCGAUGGUUGCGG A
UGCGAGAGGUCCCGGGUUCAAAUCCCGGACGAGCCCCCA-3'

SEQ ID NO: 68 - htRNA- Pro-AGG-EpCA (91nt): A hybrid molecule of human
proline-AGG ERNA and EpCAM aptamer 5'-GGCUCGUUGGUCUAGGGGUAUGAUUCUCGCUU GCGACUGGUUACCCGGUCG AUGCGAGAGGUCCCGGGU
UCAAAUCCCGGACGAGCCCCCA-3'

SEQ ID NO: 69 - htRNA- Pro-AGG-Theo (105nt): A hybrid molecule of human
proline-AGG tRNA and theophylline aptamer 5'-GGCUCGUUGGUCUAGGGGUAUGAUUCUCGCUU GGCGAUACCAGCCGAAAGGCCCUUGGCAGCGUC AUGC
GAGAGGUCCCGGGUUCAAAUCCCGGACGAGCCCCCA-3'

SEQ ID NO: 70 - htRNA-Trp-CCA-Seph (108nt): A hybrid molecule of human
tryptophan-CCA tRNA and sephadex aptamer 5'-GACCUCGUGGCGCAACGGUAGCGCGUCUGACU AGUAAUUUACGUCGACGGUGACGUCGAUGGUUGCGG G
AUCAGAAGGCUGCGUGUUCGAAUCACGUCGGGGUCACCA-3'

SEQ ID NO: 71 - htRNA-Trp-CCA -EpCA (91nt): A hybrid molecule of human
tryptophan-CCA tRNA and EpCAM aptamer 5'-GACCUCGUGGCGCAACGGUAGCGCGUCUGACU GCGACUGGUUACCCGGUCG GAUCAGAAGGCUGCGUGU
UCGAAUCACGUCGGGGUCACCA-3'

SEQ ID NO: 72 - htRNA-Trp-CCA-Theo (105nt): A hybrid molecule of human
tryptophan-CCA tRNA and theophylline aptamer 5'-GACCUCGUGGCGCAACGGUAGCGCGUCUGACU GGCGAUACCAGCCGAAAGGCCCUUGGCAGCGUC GAUC
AGAAGGCUGCGUGUUCGAAUCACGUCGGGGUCACCA-3'

SEQ ID NO: 73 - htRNA- Tyr-GTA-Seph (109nt): A hybrid molecule of human tyrosine-GTA tRNA and sephadex aptamer 5'-CCUUCGAUAGCUCAGUUGGUAGAGCGGAGGACUAGUAAUUUACGUCGACGGUGACGUCGAUGGUUGCGGGAUCCUUAGGUCGCUGGUUCGAAUCCGGCUCGAAGGACCA-3'

SEQ ID NO: 74 - htRNA-Tyr-GTA-EpCA (92nt): A hybrid molecule of human tyrosine-GTA tRNA and EpCAM aptamer 5'-CCUUCGAUAGCUCAGUUGGUAGAGCGGAGGACUGCGACUGGUUACCCGGUCGGAUCCUUAGGUCGCUGGUUCGAAUCCGGCUCGAAGGACCA-3'

SEQ ID NO: 75 - htRNA- Tyr-GTA-Theo (106nt): A hybrid molecule of human tyrosine-GTA tRNA and theophylline aptamer 5'-CCUUCGAUAGCUCAGUUGGUAGAGCGGAGGACUGGCGAUACCAGCCGAAAGGCCCUUGGCAGCGUCGAUCCUUAGGUCGCUGGUUCGAAUCCGGCUCGAAGGACCA-3'

SEQ ID NO: 76 - htRNA- Val-CAC-Seph (109nt): A hybrid molecule of human valine-CAC tRNA and sephadex aptamer 5'-GUUUCCGUAGUGUAGUGGUUAUCACGUUCGCCUAGUAAUUUACGUCGACGGUGACGUCGAUGGUUGCGGACGCGAAAGGUCCCCGGUUCGAAACCGGGCGGAAACACCA-3'

SEQ ID NO: 77 - htRNA-Val-CAC-EpCA (92nt): A hybrid molecule of human valine-CAC tRNA and EpCAM aptamer 5'-GUUUCCGUAGUGUAGUGGUUAUCACGUUCGCCUGCGACUGGUUACCCGGUCGACGCGAAAGGUCCCCGGUUCGAAACCGGGCGGAAACACCA-3'

SEQ ID NO: 78 - htRNA-Val-CAC-Theo (106nt): A hybrid molecule of human valine-CAC tRNA and theophylline aptamer 5'-GUUUCCGUAGUGUAGUGGUUAUCACGUUCGCCUGGCGAUACCAGCGAAAGGCCUUGGCAGCGUCACGCGAAAGGUCCCCGGUUCGAAACCGGGCGGAAACACCA-3'

SEQ ID NO: 79 - htRNA- Thr-TGT-Seph (110nt): A hybrid molecule of human threonine-TGT tRNA and sephadex aptamer 5'-GGUCUAUGGCUUAGUUGGUUAAAGCGCCUGUCUAGUAAUUUACGUCGACCGGUGACGUCGAUGGUUGCGGAAACAGGAGAUCCUGGGUUCGAAUCCCAGUAGAGCCUCCA-3'

SEQ ID NO: 80 - htRNA-Thr-TGT-EpCA (93nt): A hybrid molecule of human threonine-TGT tRNA and EpCAM aptamer 5'-GGCUCUAUGGCUUAGUUGGUUAAAGCGCCUGUCUGCGACUGGUUACCCGGUCGAAACAGCAGAUCCUGGGUUCGAAUCCCAGUAGAGCCUCCA-3'

SEQ ID NO: 81 - htRNA-Thr-TGT-Theo (107nt): A hybrid molecule of human threonine-TGT tRNA and theophylline aptamer 5'-GGCUCUAUGGCUUAGUUGGUUAAAGCGCCUGUCUGGCGAUACCAGCCGAAAGGCCCUUGGCAGCGUCAAACAGGAGAUCCUGGGUUCGAAUCCCAGUAGAGCCUCCA-3'

SEQ ID NO: 82 - htRNA- Thr-AGT-Seph (110nt): A hybrid molecule of human threonine-AGT tRNA and sephadex aptamer 5'-GGCGCCGUGGCUUAGUUGGUUAAAGCGCCUGUCUAGUAAUUUACGUCGACGGUGACGUCGAUGGUUGCGGAAACAGGAGAUCCUGGGUUCGAAUCCCAGCGGUGCCUCCA-3'

SEQ ID NO: 83 - htRNA-Thr-AGT-EpCA (93nt): A hybrid molecule of human threonine-AGT tRNA and EpCAM aptamer 5'-GGCGCCGUGGCUUAGUUGGUUAAAGCGCCUGUCUGCGACUGGUUACCCGGUCGAAACAGGAGAUCCUGGGUUCGAAUCCCAGCGGUGCCUCCA-3'

SEQ ID NO: 84 - htRNA-Thr-TGT-Theo (107nt): A hybrid molecule of human threonine-AGT tRNA and theophylline aptamer 5'-GGCGCCGUGGCUUAGUUGGUUAAAGCGCCUGUCUGGCGAUACCAGCCGAAAGGCCCUUGGCAGCGUCAAACAGGAGAUCCUGGGUUCGAAUCCCAGCGGUGCCUCCA-3'

SEQ ID NO: 85 - htRNA$^{Lys-TTT}$/pre-miR-34a-5p (182nt): A hybrid molecule of human lysine-TTT tRNA and pre-miR-34a 5'-GCCUGGAUAGCUCAGUUGGUAGAGCAUCAGACUGGCCAGCUGUGAGUGUUUCUUUGGCAGUGUCUUAGCUGGUUGUUGUGAGCAAUAGUAAGGAAGCAAUCAGCAAGUAUACUGCCCUAGAAGUGUGCACGUUGUUGGCCCAAUCUGAGGGUCCAGGGUUCAAGUCCCUGUUCAGGCGCCA-3'

SEQ ID NO: 86 - htRNA$^{Lys-CTT}$/pre-miR-34a-5p (182nt): A hybrid molecule of human lysine-CTT tRNA and pre-miR-34a 5'-GCCCGGCUAGCUCAGUCGGUAGAGCAUGGGACUGGCCAGCUGUGAGUGUUUCUUUGGCAGUGUCUUAGCUGGUUGUUGUGAGCAAUAGUAAGGAAGCAAUCAGCAAGUAUACUGCCCUAGAAGUGCUGCACGUUGUUGGCCCAAUCCCAGGGUCGUGGGUUCGAGCCCCACGUUGGGCGCCA-3'

-continued

SEQ ID NO: 87 - htRNA<sup>Gln-TTG</sup>/pre-miR-34a-5p (181nt): A hybrid molecule of human glutamine-TTG tRNA and pre-miR-34a
5'-<u>GGUCCCAUGGUGUAAUGGUUAGCACUGUGGACU</u>GGCCAGCUGUGAGUGUUUCUU<u>UGGCAGUGUCUUAGCU
GGUUGU</u>UGUGAGCAAUAGUAAGGAAG<u>CAAUCAGCAAGUAUACUGCCCU</u>AGAAGUGC<u>ACGUUGUUGGCCCA
AUCCAGCGAUCCGAGUUCAAAUCUCGGUGGGACCUCCA</u>-3'

SEQ ID NO: 88 - htRNA<sup>Gln-CTG</sup>/pre-miR-34a-5p (181nt): A hybrid molecule of human glutamine-CTG tRNA and pre-miR-34a
5'-<u>GGUUCCAUGGUGUAAUGGUUAGCACUCUGGACU</u>GGCCAGCUGUGAGUGUUUCUU<u>UGGCAGUGUCUUAGCU
GGUUGU</u>UGUGAGCAAUAGUAAGGAAG<u>CAAUCAGCAAGUAUACUGCCCU</u>AGAAGUGCUGCACGUUGUUGGCCCA
AUCCAGCGAUCCGAGUUCAAAUCUCGGUGGAACCUCCA-3'

SEQ ID NO: 89 - htRNA<sup>Cys-GCA</sup>/pre-miR-34a-5p (181nt): A hybrid molecule of human cysteine-GCA ERNA and pre-miR-34a
5'-<u>GGGGGCAUAGCUCAGUGGUAGAGCAUUUGACUGGCCAGCUGUGAGUGUUUCUU</u><u>UGGCAGUGUCUUAGCU
GGUUGU</u>UGUGAGCAAUAGUAAGGAAG<u>CAAUCAGCAAGUAUACUGCCCU</u>AGAAGUGCUGCACGUUGUUGGCCCG
AUCAAGAGGUCCCUGGUUCAAAUCCAGGUGCCCCCUCCA-3'

SEQ ID NO: 90 - htRNA<sup>Tyr-GTA</sup>/pre-miR-34a-5p (182nt): A hybrid molecule of human tyrosine-GTA tRNA and pre-miR-34a
5'-<u>CCUUCGAUAGCUCAGUUGGUAGAGCGGAGGACU</u>GGCCAGCUGUGAGUGUUUCU<u>UUGGCAGUGUCUUAGC
UGGUUGU</u>UGUGAGCAAUAGUAAGGAAG<u>CAAUCAGCAAGUAUACUGCCCU</u>AGAAGUGCUGCACGUUGUUGGCCC
GAUCCUUAGGUCGCUGGUUCGAAUCCGGCUCGAAGGACCA-3'

SEQ ID NO: 91 - htRNA<sup>Ser-TGA</sup>/pre-miR-34a-5p (191nt): A hybrid molecule of human serine-TGA tRNA and pre-miR-34a
5'-<u>GCAGCGAUGGCCCGAGUGGUUAAGGCGUUGGACU</u>GGCCAGCUGUGAGUGUUUCU<u>UUGGCAGUGUCUUAGC
UGGUUGU</u>UGUGAGCAAUAGUAAGGAAG<u>CAAUCAGCAAGUAUACUGCCCU</u>AGAAGUGCUGCACGUUGUUGGCCC
AAUCCAAUGGGGUCUCCCCGCGCAGGUUCGAACCUGCUCGCUGCGCCA-3'

SEQ ID NO: 92 - htRNA<sup>Ser-GCT</sup>/pre-miR-34a-5p (191nt): A hybrid molecule of human serine-GCT tRNA and pre-miR-34a
5'-<u>GACGAGGUGGCCGAGUGGUUUAAGGCGAUGGA</u>CU<u>GGCCAGCUGUGAGUGUUUCUU</u><u>UGGCAGUGUCUUAGCU
GGUUGU</u>UGUGAGCAAUAGUAAGGA<u>AGCAAUCAGCAAGUAUACUGCCCU</u>AGAAGUGCUGCACGUUGUUGGCCCA
AUCCAUUGUGCUCUGCACGCGUGGGUUCGAAUCCCACCCUCGUCGCCA-3'

SEQ ID NO: 93 - htRNA<sup>Leu-TAA</sup>/pre-miR-34a-5p (192nt): A hybrid molecule of human leucine-TAA tRNA and pre-miR-34a
5'-<u>ACCAGGAUGGCCGAGUGGUUUAAGGCGUUGGACU</u>GGCCAGCUGUGAGUGUUUCUU<u>UGGCAGUGUCUUAGC
UGGUUGU</u>UGUGAGCAAUAGUAAGGAAG<u>CAAUCAGCAAGUAUACUGCCCU</u>AGAAGUGCUGCACGUUGUUGGCCC
GAUCCAAUGGACAUAUGUCCGCGUGGGUUCGAACCCCACUCCUGGUACCA-3'

SEQ ID NO: 94 - htRNA<sup>Leu-CAA</sup>/pre-miR-34a-5p (193nt): A hybrid molecule of human leucine-CAA tRNA and pre-miR-34a
5'-<u>GUCAGGAUGGCCGAGUGGUCUAAGGCGCCAGACU</u>GGCCAGCUGUGAGUGUUUCUU<u>UGGCAGUGUCUUAGC
UGGUUGU</u>UGUGAGCAAUAGUAAGGAAG<u>CAAUCAGCAAGUAUACUGCCCU</u>AGAAGUGCUGCACGUUGUUGGCCC
GUUCUGGUCUCCGUAUGGAGGCGUGGGUUCGAAUCCCACUUCUGACACCA-3'

SEQ ID NO: 95 - htRNA<sup>Gly-GCC</sup>/pre-miR-34a-5p (180nt): A hybrid molecule of human glycine-GCC tRNA and pre-miR-34a
5'-<u>GCAUGGUGGUUCAGUGGUAGAAUUCUCGCCU</u>GGCCAGCUGUGAGUGUUUCUU<u>UGGCAGUGUCUUAGCUG
GUUGU</u>UGUGAGCAAUAGUAAGGAAGC<u>AAUCAGCAAGUAUACUGCCCU</u>AGAAGUGCUGCACGUUGUUGGCCCAC
GCGGGAGGCCCGGGUUCGAUUCCCGGCCCAUGCACCA-3'

SEQ ID NO: 96 - htRNA<sup>Gly-TCC</sup>/pre-miR-34a-5p (181nt): A hybrid molecule of human glycine-TCC tRNA and pre-miR-34a
5'-<u>GCGUUGGUGGUAUAGUGGUUAGCAUAGCUGCCU</u>GGCCAGCUGUGAGUGUUUCU<u>UUGGCAGUGUCUUAGCU
GGUUGU</u>UGUGAGCAAUAGUAAGGAAG<u>CAAUCAGCAAGUAUACUGCCCU</u>AGAAGUGCUGCACGUUGUUGGCCCA
AGCAGUUGACCCGGUUCGAUUCCCGGCCAACGCACCA-3'

SEQ ID NO: 97 - htRNA<sup>Glu-CTC</sup>/pre-miR-34a-5p (181nt): A hybrid molecule of human glutamic acid-CTC tRNA and pre-miR-34a
5'-<u>UCCCUGGUGGUCUAGUGGUUAGGAUUCGGCGCU</u>GGCCAGCUGUGAGUGUUUCU<u>UUGGCAGUGUCUUAGCU
GGUUGU</u>UGUGAGCAAUAGUAAGGAAG<u>CAAUCAGCAAGUAUACUGCCCU</u>AGAAGUGCUGCACGUUGUUGGCCCA
CCGCCGCGGCCCGGUUCGAUUCCCGGUCAGGGAACCA-3'

SEQ ID NO: 98 - htRNA<sup>Asp-GTC</sup>/pre-miR-34a-5p (181nt): A hybrid molecule of human aspartic acid-GTC tRNA and pre-miR-34a
5'-<u>UCCUCGUUAGUAUAGUGGUGAGUAUCCCCGCCU</u>GGCCAGCUGUGAGUGUUUCU<u>UUGGCAGUGUCUUAGCU
GGUUGU</u>UGUGAGCAAUAGUAAGGAAG<u>CAAUCAGCAAGUAUACUGCCCU</u>AGAAGUGCUGCACGUUGUUGGCCCA
CGCGGGAGACCGGGGUUCGAUUCCCCGACGGGGAGCCA-3'

SEQ ID NO: 99 - htRNA^Arg-ACG/pre-miR-34a-5p (182nt): A hybrid molecule of human arginine-ACG tRNA and pre-miR-34a
5'-GGGCCAGUGGCGCAAUGGAUAACGCGUCUGACUGGCCAGCUGUGAGUGUUUCUUUGGCAGUGUCUUAGCU
GGUUGUUGUGAGCAAUAGUAAGGAAGCAAUCAGCAAGUAUACUGCCCUAGAAGUGCUGCACGUUGUUGGCCCG
AUCAGAAGAUUCCAGGUUCGACUCCUGGCUGGCUCGCCA-3'

SEQ ID NO: 100 - htRNA^Arg-TCT/pre-miR-34a-5p (182nt): A hybrid molecule of human arginine-TCT tRNA and pre-miR-34a
5'-GGCUCUGUGGCGCAAUGGAUAGCCGCAUUGGACUGGCCAGCUGUGAGUGUUUCUUUGGCAGUGUCUUAGCU
GGUUGUUGUGAGCAAUAGUAAGGAAGCAAUCAGCAAGUAUACUGCCCUAGAAGUGCUGCACGUUGUUGGCCCA
AUUCAAAGGUUGUGGGUUCGAAUCCCACCAGAGUCGCCA-3'

SEQ ID NO: 101 - htRNA^Met-CAT/pre-miR-34a-5p (182nt): A hybrid molecule of human methionine-CAT tRNA and pre-miR-34a
5'-GCCUCGUUAGCGCAGUAGGUAGCGGCGUCAGUCUGGCCAGCUGUGAGUGUUUCUUUGGCAGUGUCUUAGCU
GGUUGUUGUGAGCAAUAGUAAGGAAGCAAUCAGCAAGUAUACUGCCCUAGAAGUGCUGCACGUUGUUGGCCCA
AUCUGAAGGUCGUGAGUUCGAUCCUCACACGGGGCACCA-3'

SEQ ID NO: 102 - htRNA^Asn-GTT/pre-miR-34a-5p (183nt): A hybrid molecule of human asparagine-GTT tRNA and pre-miR-34a
5'-GUCUCUGUGGCGCAAUCGGUUAGCGCGUUCGGCUGGCCAGCUGUGAGUGUUUCUUUGGCAGUGUCUUAGC
UGGUUGUUGUGAGCAAUAGUAAGGAAGCAAUCAGCAAGUAUACUGCCCUAGAAGUGCUGCACGUUGUUGGCCC
AACCGAAAGGUUGGUGGUUCGAUCCCACCCAGGGACGCCA-3'

SEQ ID NO: 103 - htRNA^Ala-AGC/pre-miR-34a-5p (181nt): A hybrid molecule of human alanine-AGC tRNA and pre-miR-34a
5'-GGGGGUGUAGCUCAGUGGUAGAGCGCGUGCUUGGCCAGCUGUGAGUGUUUCUUUGGCAGUGUCUUAGCUG
GUUGUUGUGAGCAAUAGUAAGGAAGCAAUCAGCAAGUAUACUGCCCUAGAAGUGCUGCACGUUGUUGGCCCAU
GCACGAGGCCCCGGGUUCAAUCCCCGGCACCUCCACCA-3'

SEQ ID NO: 104 - htRNA^His-GTG/pre-miR-34a-5p (181nt): A hybrid molecule of human histidine-GTG tRNA and pre-miR-34a
5'-GCCGUGAUCGUAUAGUGGUUAGUACUCUGCGUUGGCCAGCUGUGAGUGUUUCUUUGGCAGUGUCUUAGCU
GGUUGUUGUGAGCAAUAGUAAGGAAGCAAUCAGCAAGUAUACUGCCCUAGAAGUGCUGCACGUUGUUGGCCCG
CCGCAGCAACCUCGGUUCGAAUCCGAGUCACGGCACCA-3'

SEQ ID NO: 105 - htRNA^Ile-AAT/pre-miR-34a-5p (183nt): A hybrid molecule of human isoleucine-AAT tRNA and pre-miR-34a
5'-GGCCGGUUAGCUCAGUUGGUUAGAGCGUGGUGCUGGCCAGCUGUGAGUGUUUCUUUGGCAGUGUCUUAGC
UGGUUGUUGUGAGCAAUAGUAAGGAAGCAAUCAGCAAGUAUACUGCCCUAGAAGUGCUGCACGUUGUUGGCCC
AACGCCAAGGUCGCGGGUUCGAUCCCCGUACUGGCCACCA-3'

SEQ ID NO: 106 - htRNA^Ile-TAT/pre-miR-34a-5p (183nt): A hybrid molecule of human isoleucine-TAT tRNA and pre-miR-34a
5'-GCUCCAGUGGCGCAAUCGGUUAGCGCGCGGUACUGGCCAGCUGUGAGUGUUUCUUUGGCAGUGUCUUAGC
UGGUUGUUGUGAGCAAUAGUAAGGAAGCAAUCAGCAAGUAUACUGCCCUAGAAGUGCUGCACGUUGUUGGCCC
AAUGCCGAGGUUGUGAGUUCGAUCCUCACCUGGAGCACCA-3'

SEQ ID NO: 107 - htRNA^Phe-GAA/pre-miR-34a-5p (182nt): A hybrid molecule of human phenylalanine-GAA tRNA and pre-miR-34a
5'-GCCGAAAUAGCUCAGUUUGGGAGAGCGUUAGACUGGCCAGCUGUGAGUGUUUCUUUGGCAGUGUCUUAGCU
GGUUGUUGUGAGCAAUAGUAAGGAAGCAAUCAGCAAGUAUACUGCCCUAGAAGUGCUGCACGUUGUUGGCCCG
AUCUAAAGGUCCCUGGUUCGAUCCCGGGUUUCGGCACCA-3'

SEQ ID NO: 108 - htRNA^Pro-AGG/pre-miR-34a-5p (181nt): A hybrid molecule of human proline-AGG ERNA and pre-miR-34a
5'-GGCUCGUUGGUCUAGGGGUAUGAUUCUCGCUUGGCCAGCUGUGAGUGUUUCUUUGGCAGUGUCUUAGCUG
GUUGUUGUGAGCAAUAGUAAGGAAGCAAUCAGCAAGUAUACUGCCCUAGAAGUGCUGCACGUUGUUGGCCCAU
GCGAGAGGUCCCGGGUUCAAAUCCCGGACGAGCCCCA-3'

SEQ ID NO: 109 - htRNA^Trp-CCA/pre-miR-34a-5p (181nt): A hybrid molecule of human tryptophan-CCA tRNA and pre-miR-34a
5'-GACCUCGUGGCGCAACGGUAGCGCGUCUGACUGGCCAGCUGUGAGUGUUUCUUUGGCAGUGUCUUAGCUG
GUUGUUGUGAGCAAUAGUAAGGAAGCAAUCAGCAAGUAUACUGCCCUAGAAGUGCUGCACGUUGUUGGCCCGA
UCAGAAGGCUGCGUGUUCGAAUCACGUCGGGGUCACCA-3'

SEQ ID NO: 110 - htRNA^Val-CAC/pre-miR-34a-5p (182nt): A hybrid molecule of human valine-CAC tRNA and pre-miR-34a
5'-GUUUCCGUAGUGUAGUGGUUAUCACGUUCGCCUGGCCAGCUGUGAGUGUUUCUUUGGCAGUGUCUUAGCU
GGUUGUUGUGAGCAAUAGUAAGGAAGCAAUCAGCAAGUAUACUGCCCUAGAAGUGCUGCACGUUGUUGGCCCA
CGCGAAAGGUCCCCGGUUCGAAACCGGGCGGAAACACCA-3'

-continued

SEQ ID NO: 111 - htRNA$^{Thr-TGT}$/pre-miR-34a-5p (183nt): A hybrid molecule of human threonine-TGT tRNA and pre-miR-34a 5'-<u>GGGCUCUAUGGCUUAGUUGGUUAAAGCGCCUGUCU</u>GGCCAGCUGUGAGUGUUUCUU<u>UGGCAGUGUCUUAGC UGGUUGUU</u>GUGAGCAAUAGUAAGGAA<u>GCAAUCAGCAAGUAUACUGCCCU</u>AGAAGUGCUGCACGUUGUUGGCCC AAACAGGAGAUCCUGGGUUCGAAUCCCAGUAGAGCCUCCA-3'

SEQ ID NO: 112 - htRNA$^{Thr-AGT}$/pre-miR-34a-5p (183nt): A hybrid molecule of human threonine-AGT tRNA and pre-miR-34a 5'-<u>GGCGCCGUGGCUUAGUUGGUUAAAGCGCCUGUCU</u>GGCCAGCUGUGAGUGUUUCUU<u>UGGCAGUGUCUUAGC UGGUUGUU</u>GUGAGCAAUAGUAAGGAA<u>GCAAUCAGCAAGUAUACUGCCCU</u>AGAAGUGCUGCACGUUGUUGGCCC AAACAGGAGAUCCUGGGUUCGAAUCCCAGCGGUGCCUCCA-3'

SEQ ID NO: 113 - htRNA$^{Leu-TAA}$/pre-miR-34a/Twist-siRNA (192nt): A hybrid molecule of human leucine-TAA tRNA and pre-miR-34a in which miR-34a sequences (mature and guide) are replaced by Twist-siRNA (mature and guide) sequences.

5'-<u>ACCAGGAUGGCCGAGUGGUUUAAGGCGUUGGACU</u>GGCCAGCUGUGAGUGUUUCUU<u>GGUCUGAAUCUUGCU CAGCUUG</u>UGUGAGCAAUAGUAAGGAAC<u>AAGCUGAGAAGUAUUCAGACA</u>UAGAAGUGCUGCACGUUGUUGGCCC GAUCCAAUGGACAUAUGUCCGCGUGGGUUCGAACCCCACUCCUGGUACCA-3'

SEQ ID NO: 114 - htRNA$^{Leu-TAA}$/pre-miR-34a/miR-328-3p (192nt): A hybrid molecule of human leucine-TAA tRNA and pre-miR-34a in which miR-34a sequences (mature and guide) are replaced by miR-328 (mature and guide) sequences.

5'-<u>ACCAGGAUGGCCGAGUGGUUUAAGGCGUUGGACU</u>GGCCAGCUGUGAGUGUUUCUU<u>CUGGCCCUCUCUGCC CUUCCGUU</u>GUGAGCAAUAGUAAGGAAG<u>CGGGGGGGAGAUGGGGGCCA</u>UUAGAAGUGCUGCACGUUGUUGGCCC GAUCCAAUGGACAUAUGUCCGCGUGGGUUCGAACCCCACUCCUGGUACCA-3'

SEQ ID NO: 115 - htRNA$^{Leu-TAA}$/pre-miR-34a/miR-124-3p (192nt): A hybrid molecule of human leucine-TAA tRNA and pre-miR-34a in which miR-34a sequences (mature and guide) are replaced by miR-124 (mature and guide) sequences.

5'-<u>ACCAGGAUGGCCGAGUGGUUUAAGGCGUUGGACU</u>GGCCAGCUGUGAGUGUUUCUUU<u>AAGGCACGCGGUGA AUGCCGUU</u>GUGAGCAAUAGUAAGGAAG<u>CGGUGUUCCCGUCGUGCCUUCU</u>AGAAGUGCUGCACGUUGUUGGCCC GAUCCAAUGGACAUAUGUCCGCGUGGGUUCGAACCCCACUCCUGGUACCA-3'

SEQ ID NO: 116 - htRNA$^{Leu-TAA}$/pre-miR-34a/let-7c-5p (193nt): A hybrid molecule of human leucine-TAA tRNA and pre-miR-34a in which miR-34a sequences (mature and guide) are replaced by let-7c (mature and guide) sequences.

5'-<u>ACCAGGAUGGCCGAGUGGUUUAAGGCGUUGGACU</u>GGCCAGCUGUGAGUGUUUCUU<u>UGAGGUAGUAGGUUG UAUGGUU</u>UGUGAGCAAUAGUAAGGAAG<u>AACUGUACACCUUACUACCUUUC</u>AGAAGUGCUGCACGUUGUUGGCC CGAUCCAAUGGACAUAUGUCCGCGUGGGUUCGAACCCCACUCCUGGUACCA-3'

SEQ ID NO: 117 - htRNA$^{Leu-TAA}$/pre-miR-34a/Nrf2-siRNA (192nt): A hybrid molecule of human leucine-TAA tRNA and pre-miR-34a in which miR-34a sequences (mature and guide) are replaced by Nrf2-siRNA (mature and guide) sequences.

5'-<u>ACCAGGAUGGCCGAGUGGUUUAAGGCGUUGGACU</u>GGCCAGCUGUGAGUGUUUCUUUA<u>AUUGUCAACUAU GUCAGUU</u>UGUGAGCAAUAGUAAGGAA<u>AACUGACAGAGUAUGACAAUUCU</u>AGAAGUGCUGCACGUUGUUGGCCC GAUCCAAUGGACAUAUGUCCGCGUGGGUUCGAACCCCACUCCUGGUACCA-3'

SEQ ID NO: 118 - htRNA$^{Leu-TAA}$/pre-miR-34a/miR-22-3p (192nt): A hybrid molecule of human leucine-TAA tRNA and pre-miR-34a in which miR-34a sequences (mature and guide) are replaced by miR-22 (mature and guide) sequences.

5'-<u>ACCAGGAUGGCCGAGUGGUUUAAGGCGUUGGACU</u>GGCCAGCUGUGAGUGUUUC<u>UUAAGCUGCCAGUUGAA GAACUGUU</u>GUGAGCAAUAGUAAGGAAG<u>CAGUUCUUAGCUUGGCAGCUCU</u>AGAAGUGCUGCACGUUGUUGGCCC GAUCCAAUGGACAUAUGUCCGCGUGGGUUCGAACCCCACUCCUGGUACCA-3'

SEQ ID NO: 119 - htRNA$^{Leu-TAA}$/pre-miR-34a/miR-200b-3p (192nt): A hybrid molecule of human leucine-TAA tRNA and pre-miR-34a in which miR-34a sequences (mature and guide) are replaced by miR-200b (mature and guide) sequences.

5'-<u>ACCAGGAUGGCCGAGUGGUUUAAGGCGUUGGACU</u>GGCCAGCUGUGAGUGUUUC<u>UUAAGCUGCCAGUUGAA GAACUGUU</u>GUGAGCAAUAGUAAGGA<u>AGCAGUUCUUAGCUUGGCAGCUCU</u>AGAAGUGCUGCACGUUGUUGGCCC GAUCCAAUGGACAUAUGUCCGCGUGGGUUCGAACCCCACUCCUGGUACCA-3'

SEQ ID NO: 120 - htRNA$^{Leu-TAA}$/pre-miR-34a/miR-148-3p (192nt): A hybrid molecule of human leucine-TAA tRNA and pre-miR-34a in which miR-34a sequences (mature and guide) are replaced by miR-148 (mature and guide) sequences.

5'-ACCAGGAUGGCCGAGUGGUUAAGGCGUUGGACUGGCCAGCUGUGAGUGUUUCUUAAGCUGCCAGUUGAA
ACUUUGUUGUGAGCAAUAGUAAGGAAGCAAAGUUCGUAUGUGCACUGCUAGAAGUGCUGCACGUUGUUGGCCC
GAUCCAAUGGACAUAUGUCCGCGUGGGUUCGAACCCCACUCCUGGUACCA-3'

SEQ ID NO: 121 - htRNA<sup>Leu-TAA</sup>/pre-miR-34a/miR-6775-3p (192nt): A hybrid
molecule of human leucine-TAA tRNA and pre-miR-34a in which miR-34a
sequences (mature and guide) are replaced by miR-6775 (mature and guide)
sequences.

5'-ACCAGGAUGGCCGAGUGGUUAAGGCGUUGGACUGGCCAGCUGUGAGUGUUUCUUAGGCCCUGUCCUCUG
CCCAGUUGUGAGCAAUAGUAAGGAAGCUGGGGCAAGGCGCAGGGCCCUAGAAGUGCUGCACGUUGUUGGCCC
GAUCCAAUGGACAUAUGUCCGCGUGGGUUCGAACCCCACACCUGGUACCA-3'

SEQ ID NO: 122 - htRNA<sup>Leu-TAA</sup>/pre-miR-34a/miR-1-3p (192nt): A hybrid molecule
of human leucine-TAA tRNA and pre-miR-34a in which miR-34a sequences
(mature and guide) are replaced by miR-1 (mature and guide) sequences.

5'-ACCAGGAUGGCCGAGUGGUUAAGGCGUUGGACUGGCCAGCUGUGAGUGUUUCUUUGGAAUGUAAAGAAG
UAUGUAUUGUGAGCAAUAGUAAGGAAAUACAUACUCUUCUACAUUCCCUAGAAGUGCUGCACGUUGUUGGCCC
GAUCCAAUGGACAUAUGUCCGCGUGGGUUCGAACCCCACUCCUGGUACCA-3'

SEQ ID NO: 123 - htRNA<sup>Leu-TAA</sup>/pre-miR-34a/miR-133a-3p (193nt): A hybrid
molecule of human leucine-TAA tRNA and pre-miR-34a in which miR-34a
sequences (mature and guide) are replaced by miR-133a (mature and guide)
sequences.

5'-ACCAGGAUGGCCGAGUGGUUAAGGCGUUGGACUGGCCAGCUGUGAGUGUUUCUUUUUUGGUCCCUUCAA
CCAGCUGUGUGAGCAAUAGUAAGGAAGCAGCUGGUUAAGUGGGACCAACUAGAAGUGCUGCACGUUGUUGGCC
CGAUCCAAUGGACAUAUGUCCGCGUGGGUUCGAACCCCACUCCUGGUACCA-3'

SEQ ID NO: 124 - htRNA<sup>Leu-TAA</sup>/pre-miR-34a/miR-122-5p (193nt): A hybrid
molecule of human leucine-TAA tRNA and pre-miR-34a in which miR-34a
sequences (mature and guide) are replaced by miR-122 (mature and guide)
sequences.

5'-ACCAGGAUGGCCGAGUGGUUAAGGCGUUGGACUGGCCAGCUGUGAGUGUUUCUUUGGAGUGUGACAAUG
GUGUUUGUGUGAGCAAUAGUAAGGAAGCAAACGCCAUGUACACACUCCCUAGAAGUGCUGCACGUUGUUGGCC
CGAUCCAAUGGACAUAUGUCCGCGUGGGUUCGAACCCCACUCCUGGUACCA-3'

SEQ ID NO: 125 - htRNA<sup>Leu-TAA</sup>/pre-miR-34a/anti-miR-122-5p (193nt): A hybrid
molecule of human leucine-TAA tRNA and pre-miR-34a in which miR-34a
sequences (mature and guide) are replaced by miR-122 antagomir (mature
and guide) sequences.

5'-ACCAGGAUGGCCGAGUGGUUAAGGCGUUGGACUGGCCAGCUGUGAGUGUUUCUUCAAACAACAUUGUCA
CACUCCAUGUGAGCAAUAGUAAGGAAUGGAGUGUGCAAUUGGUGUUUUUAGAAGUGCUGCACGUUGUUGGCCC
GAUCCAAUGGACAUAUGUCCGCGUGGGUUCGAACCCCACUCCUGGUACCA-3'

SEQ ID NO: 126 - htRNA<sup>Leu-TAA</sup>/pre-miR-34a/miR-888-5p (192nt): A hybrid
molecule of human leucine-TAA tRNA and pre-miR-34a in which miR-34a
sequences (mature and guide) are replaced by miR-888 (mature and guide)
sequences.

5'-ACCAGGAUGGCCGAGUGGUUAAGGCGUUGGACUGGCCAGCUGUGAGUGUUUCUUUACUCAAAAAGCUGU
CAGUCAUUGUGAGCAAUAGUAAGGAAGUGACUGACGCUCUUUUGAGUCUAGAAGUGCUGCACGUUGUUGGCCC
GAUCCAAUGGACAUAUGUCCGCGUGGGUUCGAACCCCACUCCUGGUACCA-3'

SEQ ID NO: 127 - htRNA<sup>Ser-TGA</sup>/pre-miR-34a/miR-328-3p (191nt): A hybrid
molecule of human serine-TGA tRNA and pre-miR-34a in which miR-34a
sequences (mature and guide) are replaced by miR-328 (mature and guide)
sequences.

5'-GCAGCGAUGGCCGAGUGGUUAAGGCGUUGGACUGGCCAGCUGUGAGUGUUUCUUCUGGCCCUCUCUGCC
CUUCCGUUGUGAGCAAUAGUAAGGAAGCGGGGGGGAGAUGGGGGCCAUUAGAAGUGCUGCACGUUGUUGGCCC
AAUCCAAUGGGGUCUCCCCGCGCAGGUUCGAACCCUGCUCGCUGCGCCA-3'

SEQ ID NO: 128 - htRNA<sup>Ser-TGA</sup>/pre-miR-34a/miR-124-3p (191nt): A hybrid
molecule of human serine-TGA tRNA and pre-miR-34a in which miR-34a
sequences (mature and guide) are replaced by miR-124 (mature and guide)
sequences.

5'-GCAGCGAUGGCCGAGUGGUUAAGGCGUUGGACUGGCCAGCUGUGAGUGUUUCUUUAAGGCACGCGGUGA
AUGCCGUUGUGAGCAAUAGUAAGGAAGCGGUGUUCCCGUCGUGCCUUCUAGAAGUGCUGCACGUUGUUGGCCC
AAUCCAAUGGGGUCUCCCCGCGCAGGUUCGAACCCUGUCGCUGCGCCA-3'

SEQ ID NO: 129 - htRNA<sup>Ser-TGA</sup>/pre-miR-34a/let-7c-5p (192nt): A hybrid
molecule of human serine-TGA tRNA and pre-miR-34a in which miR-34a
sequences (mature and guide) are replaced by let-7c (mature and guide)
sequences.

5'-<u>GCAGCGAUGGCCGAGUGGUUAAGGCGUUGGACUG</u>GCCAGCUGUGAGUGUUUCUUU<u>GAGGUAGUAGGUUG
UAUGGUUU</u>GUGAGCAAUAGUAAGGAAG<u>AACUGUACACCUUACUACCUUU</u>CAGAAGUGCUGCACGUUGUUGGCC
<u>CAAUCCAAUGGGGUCUCCCCGCGCAGGUUCGAACCCUGCUCGCUGCGCCA</u>-3'

SEQ ID NO: 130 - htRNA<sup>Ser-TGA</sup>/pre-miR-34a/Nrf2-siRNA (191nt): A hybrid
molecule of human serine-TGA tRNA and pre-miR-34a in which miR-34a
sequences (mature and guide) are replaced by Nrf2-siRNA (mature and
guide) sequences.
5'-<u>GCAGCGAUGGCCGAGUGGUUAAGGCGUUGGACU</u>GGCCAGCUGUGAGUGUUUCUUU*AAUUGUCAACUACU
GUCAGUUU*GUGAGCAAUAGUAAGGAA*AACUGACAGAGUAUGACAAUUCU*AGAAGUGCUGCACGUUGUUGGCCC
<u>AAUCCAAUGGGGUCUCCCCGCGCAGGUUCGAACCCUGCUCGCUGCGCCA</u>-3'

SEQ ID NO: 131 - htRNA<sup>Ser-TGA</sup>/pre-miR-34a/PolH-siRNA-20nt (187nt): A hybrid
molecule of human serine-TGA tRNA and pre-miR-34a in which miR-34a
sequences (mature and guide) are replaced by PolH-siRNA-20nt (mature and
guide) sequences.
5'-<u>GCAGCGAUGGCCGAGUGGUUAAGGCGUUGGACU</u>GGCCAGCUGUGAGUGUUUCUUU<u>CGAGCCAUUGAAAU
AAGCC</u>UGUGAGCAAUAGUAAGGAAG<u>GCUUAUUCAUAUGGCUCGCU</u>AGAAGUGCUGCACGUUGUUGGCCC<u>AAUC
CAAUGGGGUCUCCCCGCGCAGGUUCGAACCCUGCUCGCUGCGCCA</u>-3'

SEQ ID NO: 132 - htRNA<sup>Ser-TGA</sup>/pre-miR-34a/PolH-siRNA-22nt (191nt): A hybrid
molecule of human serine-TGA tRNA and pre-miR-34a in which miR-34a
sequences (mature and guide) are replaced by PolH-siRNA-22nt (mature and
guide) sequences.
5'-<u>GCAGCGAUGGCCGAGUGGUUAAGGCGUUGGACUG</u>GCCAGCUGUGAGUGUUUCUUU<u>CGAGCCAUUGAAAU
AAGCCGUU</u>GUGAGCAAUAGUAAGGAAG<u>CGGCUUAUUCAUAUGGCUCGCU</u>AGAAGUGCUGCACGUUGUUGGCCC
<u>AAUCCAAUGGGGUCUCCCCGCGCAGGUUCGAACCCUGCUCGCUGCGCCA</u>-3'

SEQ ID NO: 133 - htRNA<sup>Ser-TGA</sup>/pre-miR-34a/miR-22-3p (191nt): A hybrid
molecule of human serine-TGA tRNA and pre-miR-34a in which miR-34a
sequences (mature and guide) are replaced by miR-22 (mature and guide)
sequences.
5'-<u>GCAGCGAUGGCCGAGUGGUUAAGGCGUUGGACUG</u>GCCAGCUGUGAGUGUUUCUUA<u>AGCUGCCAGUUGAA
GAACUGU</u>GUGAGCAAUAGUAAGGAAG<u>CAGUUCUUAGCUUGGCAGCUCU</u>AGAAGUGCUGCACGUUGUUGGCCC
<u>AAUCCAAUGGGGUCUCCCCGCGCAGGUUCGAACCCUGCUCGCUGCGCCA</u>-3'

SEQ ID NO: 134 - htRNA<sup>Ser-TGA</sup>/pre-miR-34a/miR-200b-3p (191nt): A hybrid
molecule of human serine-TGA tRNA and pre-miR-34a in which miR-34a
sequences (mature and guide) are replaced by miR-200b (mature and guide)
sequences.
5'-<u>GCAGCGAUGGCCGAGUGGUUAAGGCGUUGGACUG</u>GCCAGCUGUGAGUGUUUCUUU<u>AAUACUGCCUGGUA
AUGAUGAU</u>GUGAGCAAUAGUAAGGAA<u>UCAUCAUUAUAGUGCAGUAUUCU</u>AGAAGUGCUGCACGUUGUUGGCCC
<u>AAUCCAAUGGGGUCUCCCCGCGCAGGUUCGAACCCUGCUCGCUGCGCCA</u>-3'

SEQ ID NO: 135 - htRNA<sup>Ser-TGA</sup>/pre-miR-34a/miR-148-3p (191nt): A hybrid
molecule of human serine-TGA tRNA and pre-miR-34a in which miR-34a
sequences (mature and guide) are replaced by miR-148 (mature and guide)
sequences.
5'-<u>GCAGCGAUGGCCGAGUGGUUAAGGCGUUGGACUG</u>GCCAGCUGUGAGUGUUUCUUU<u>UCAGUGCACUACAGA
ACUUUGUU</u>GUGAGCAAUAGUAAGGAAG<u>CAAAGUUCGUAUGUGCACUGCU</u>AGAAGUGCUGCACGUUGUUGGCCC
<u>AAUCCAAUGGGGUCUCCCCGCGCAGGUUCGAACCCUGCUCGCUGCGCCA</u>-3'

SEQ ID NO: 136 - htRNA<sup>Ser-TGA</sup>/pre-miR-34a/miR-6775-3p (191nt): A hybrid
molecule of human serine-TGA tRNA and pre-miR-34a in which miR-34a
sequences (mature and guide) are replaced by miR-6775 (mature and guide)
sequences.
5'-<u>GCAGCGAUGGCCGAGUGGUUAAGGCGUUGGACUG</u>GCCAGCUGUGAGUGUUUCUUA**GGCCCUGUCCUCUG
CCCCAGUUGUGAGCAAUAGUAAGGAAGCUGGGGCAAGGCGCAGGGCCCU**AGAAGUGCUGCACGUUGUUGGCCC
<u>AAUCCAAUGGGGUCUCCCCGCGCAGGUUCGAACCCUGCUCGCUGCGCCA</u>-3'

SEQ ID NO: 137 - htRNA<sup>Ser-TGA</sup>/pre-miR-34a/anti-miR-138-5p (193nt): A hybrid
molecule of human serine-TGA tRNA and pre-miR-34a in which miR-34a
sequences (mature and guide) are replaced by miR-138 antagomir (mature
and guide) sequences.
5'-<u>GCAGCGAUGGCCGAGUGGUUAAGGCGUUGGACUG</u>GCCAGCUGUGAGUGUUUCUU<u>CGGCCUGAUUCACAA
CACCAGCUU</u>GUGAGCAAUAGUAAGGAAAGCUGGUGUUUGAUAUCAGGCCUUAGAAGUGCUGCACGUUGUUGGC
<u>CCAAUCCAAUGGGGUCUCCCCGCGCAGGUUCGAACCCUGCUCGCUGCGCCA</u>-3'

SEQ ID NO: 138 - htRNA<sup>Ser-TGA</sup>/pre-miR-34a/miR-1-3p (191nt): A hybrid molecule
of human serine-TGA tRNA and pre-miR-34a in which miR-34a sequences
(mature and guide) are replaced by miR-1 (mature and guide) sequences.

5'-GCAGCGAUGGCCGAGUGGUUAAGGCGUUGGACUGGCCAGCUGUGAGUGUUUCUUUGGAAUGUAAAGAAG
UAUGUAUUGUGAGCAAUAGUAAGGAAAUACAUACUCUUCUACAUUCCCUAGAAGUGCUGCACGUUGUUGGCCC
AAUCCAAUGGGGUCUCCCCGCGCAGGUUCGAACCCUGCUCGCUGCGCCA-3'

SEQ ID NO: 139 - htRNA<sup>Ser-TGA</sup>/pre-miR-34a/miR-133a-3p (192nt): A hybrid molecule of human serine-TGA tRNA and pre-miR-34a in which miR-34a sequences (mature and guide) are replaced by miR-133a (mature and guide) sequences.

5'-GCAGCGAUGGCCGAGUGGUUAAGGCGUUGGACUGGCCAGCUGUGAGUGUUUCUUUUUGGUCCCCUUCAA
CCAGCUGUGUGAGCAAUAGUAAGGAAGCAGCUGGUUAAGUGGGACCAACUAGAAGUGCUGCACGUUGUUGGCC
CAAUCCAAUGGGGUCUCCCCGCGCAGGUUCGAACCCUGCUCGCUGCGCCA-3'

SEQ ID NO: 140 - htRNA<sup>Ser-TGA</sup>/pre-miR-34a/miR-122-5p (192nt): A hybrid molecule of human serine-TGA tRNA and pre-miR-34a in which miR-34a sequences (mature and guide) are replaced by miR-122 (mature and guide) sequences.

5'-GCAGCGAUGGCCGAGUGGUUAAGGCGUUGGACUGGCCAGCUGUGAGUGUUUCUUUGGAGUGUGACAAUG
GUGUUUGUGUGAGCAAUAGUAAGGAAGCAAACGCCAUGUACACACUCCCUAGAAGUGCUGCACGUUGUUGGCC
CAAUCCAAUGGGGUCUCCCCGCGCAGGUUCGAACCCUGCUCGCUGCGCCA-3'

SEQ ID NO: 141 - htRNA<sup>Ser-TGA</sup>/pre-miR-34a/anti-miR-122-5p (193nt): A hybrid molecule of human serine-TGA tRNA and pre-miR-34a in which miR-34a sequences (mature and guide) are replaced by miR-122 antagomir (mature and guide) sequences.

5'-GCAGCGAUGGCCGAGUGGUUAAGGCGUUGGACUGGCCAGCUGUGAGUGUUUCUUCAAACACCAUUGUCA
CACUCCAUGUGAGCAAUAGUAAGGAAUGGAGUGUGCAAUUGGUGUUUUUAGAAGUGCUGCACGUUGUUGGCCC
AAUCCAAUGGGGUCUCCCCGCGCAGGUUCGAACCCUGCUCGCUGCGCCA-3'

SEQ ID NO: 142 - htRNA<sup>Ser-TGA</sup>/pre-miR-34a/miR-888-5p (192nt): A hybrid molecule of human serine-TGA tRNA and pre-miR-34a in which miR-34a sequences (mature and guide) are replaced by miR-888 (mature and guide) sequences.

5'-GCAGCGAUGGCCGAGUGGUUAAGGCGUUGGACUGGCCAGCUGUGAGUGUUUCUUUACUCAAAAAGCUGU
CAGUCAUUGUGAGCAAUAGUAAGGAAGUGACUGACGCUCUUUUGAGUCUAGAAGUGUGCACGUUGUUGGCCC
AAUCCAAUGGGGUCUCCCCGCGCAGGUUCGAACCCUGCUCGCUGCGCCA-3'

SEQ ID NO: 143 - htRNA<sup>Ser-TGA</sup>/pre-miR-1291 (169nt): A hybrid molecule of human serine-TGA tRNA and pre-miR-1291

5'-GCAGCGAUGGCCGAGUGGUUAAGGCGUUGGACUGGUAGAAUUCCAGUGGCCCUGACUGAAGACCAGCAGU
UGUACUGUGGCUGUUGGUUUCAAGCAGAGGCCUAAAGGACUGUCUUCCUGAAUCCAAUGGGGUCUCCCCGCGC
AGGUUCGAACCCUGCUCGCUGCGCCA-3'

SEQ ID NO: 144 - htRNA<sup>Ser-GCT</sup>/pre-miR-1291 (169nt): A hybrid molecule of human serine-GCT tRNA and pre-miR-1291

5'-GACGAGGUGGCCGAGUGGUUAAGGCGAUGGACUGGUAGAAUUCCAGUGGCCCUGACUGAAGACCAGCAGU
UGUACUGUGGCUGUUGGUUUCAAGCAGAGGCCUAAAGGACUGUCUUCCUGAAUCCAUUGUGCUCUGCACGCGU
GGGUUCGAAUCCCACCCUCGUCGCCA-3'

SEQ ID NO: 145 - htRNA<sup>Leu-TAA</sup>/pre-miR-1291 (170nt): A hybrid molecule of human leucine-TAA tRNA and pre-miR-1291

5'-ACCAGGAUGGCCGAGUGGUUAAGGCGUUGGACUGGUAGAAUUCCAGUGGCCCUGACUGAAGACCAGCAGU
UGUACUGUGGCUGUUGGUUUCAAGCAGAGGCCUAAAGGACUGUCUUCCUGGAUCCAAUGGACAUAUGUCCGCG
UGGGUUCGAACCCCACUCCUGGUACCA-3'

SEQ ID NO: 146 - htRNA<sup>Leu-CAA</sup>/pre-miR-1291 (170nt): A hybrid molecule of human leucine-CAA tRNA and pre-miR-1291

5'-GUCAGGAUGGCCGAGUGGUCUAAGGCGCCAGACUGGUAGAAUUCCAGUGGCCCUGACUGAAGACCAGCAG
UUGUACUGUGGCUGUUGGUUUCAAGCAGAGGCCUAAAGGACUGUCUUCCUGGUUCUGGUCUCCGUAUGGAGGC
GUGGGUUCGAAUCCCACUUCUGACACCA-3'

SEQ ID NO: 147 - htRNA<sup>Gly-GCC</sup>/pre-miR-1291 (158nt): A hybrid molecule of human glycine-GCC tRNA and pre-miR-1291

5'-GCAUGGGUGGUUCAGUGGUAGAAUUCUCGCCUGGUAGAAUUCCAGUGGCCCUGACUGAAGACCAGCAGUU
GUACUGUGGCUGUUGGUUUCAAGCAGAGGCCUAAAGGACUGUCUUCCUGACGCGGGAGGCCCGGGUUCGAUUC
CCGGCCCAUGCACCA-3'

SEQ ID NO: 148 - htRNA$^{Gly\text{-}TCC}$/pre-miR-1291 (159nt): A hybrid molecule of human glycine-TCC tRNA and pre-miR-1291

5'-GCGUUGGUGGUAUAGUGGUUAGCAUAGCUGCCUGGUAGAAUUCCAGUGGCCCUGACUGAAGACCAGCAGU
UGUACUGUGGCUGUUGGUUUCAAGCAGAGGCCUAAAGGACUGUCUUCCUGAAGCAGUUGACCCGGGUUCGAUU
CCCGGCCAACGCACCA-3'

SEQ ID NO: 149 - htRNA$^{Glu\text{-}CTC}$/pre-miR-1291 (159nt): A hybrid molecule of human glutamic acid-CTC tRNA and pre-miR-1291

5'-UCCCUGGUGGUCUAGUGGUUAGGAUUCGGCGCUGGUAGAAUUCCAGUGGCCCUGACUGAAGACCAGCAGU
UGUACUGUGGCUGUUGGUUUCAAGCAGAGGCCUAAAGGACUGUCUUCCUGACCGCCGCGGCCCGGGUUCGAUU
CCCGGUCAGGGAACCA-3'

SEQ ID NO: 150 - htRNA$^{Asp\text{-}GTC}$/pre-miR-1291 (159nt): A hybrid molecule of human aspartic acid-GTC tRNA and pre-miR-1291

5'-UCCUCGUUAGUAUAGUGGUGAGUAUCCCCGCCUGGUAGAAUUCCAGUGGCCCUGACUGAAGACCAGCAGU
UGUACUGUGGCUGUUGGUUUCAAGCAGAGGCCUAAAGGACUGUCUUCCUGACGCGGGAGACCGGGGUUCGAUU
CCCCGACGGGGAGCCA-3'

SEQ ID NO: 151 - htRNA$^{Gln\text{-}TTG}$/pre-miR-1291 (159nt): A hybrid molecule of human glutamine-TTG tRNA and pre-miR-1291

5'-GGUCCCAUGGUGUAAUGGUUAGCACUCUGGACUGGUAGAAUUCCAGUGGCCCUGACUGAAGACCAGCAGU
UGUACUGUGGCUGUUGGUUUCAAGCAGAGGCCUAAAGGACUGUCUUCCUGAAUCCAGCGAUCCGAGUUCAAAU
CUCGGUGGGACCUCCA-3'

SEQ ID NO: 152 - htRNA$^{Gln\text{-}CTG}$/pre-miR-1291 (159nt): A hybrid molecule of human glutamine-CTG tRNA and pre-miR-1291

5'-GGUUCCAUGGUGUAAUGGUUAGCACUCUGGACUGGUAGAAUUCCAGUGGCCCUGACUGAACACCAGCAGU
UGUACUGUGGCUGUUGGUUUCAAGCAGAGGCCUAAAGGACUGUCUUCCUGAAUCCAGCGAUCCGAGUUCAAAU
CUCGGUGGAACCUCCA-3'

SEQ ID NO: 153 - htRNA$^{Arg\text{-}ACG}$/pre-miR-1291 (160nt): A hybrid molecule of human arginine-ACG tRNA and pre-miR-1291

5'-GGGCCAGUGGCGCAAUGGAUAACGCGUCUGACUGGUAGAAUUCCAGUGGCCCUGACUGAAGACCAGCAGU
UGUACUGUGGCUGUUGGUUUCAAGCAGAGGCCUAAAGGACUGUCUUCCUGGAUCAGAAGAUUCCAGGUUCGAC
UCCUGGCUGGCUCGCCA-3'

SEQ ID NO: 154 - htRNA$^{Arg\text{-}TCT}$/pre-miR-1291 (160nt): A hybrid molecule of human arginine-TCT tRNA and pre-miR-1291

5'-GGCUCUGUGGCGCAAUGGAUAGCGCAUUGGACUGGUAGAAUUCCAGUGGCCCUGACUGAAGACCAGCAGU
UGUACUGUGGCUGUUGGUUUCAAGCAGAGGCCUAAAGGACUGUUCCUGAAUUCAAAGGUUGUGGGUUCGAA
UCCCACCAGAGUCGCCA-3'

SEQ ID NO: 155 - htRNA$^{Cys\text{-}GCA}$/pre-miR-1291 (159nt): A hybrid molecule of human cysteine-GCA tRNA and pre-miR-1291

5'-GGGGGCAUAGCUCAGUGGUAGAGCAUUUGACUGGUAGAAUUCCAGUGGCCCUGACUGAAGACCAGGAGCUU
GUACUGUGGCUGUUGGUUUCAAGCAGAGGCCUAAAGGACUGUCUUCCUGGAUCAAGAGGUCCCUGGUUCAAAU
CCAGGUGCCCCCUCCA-3'

SEQ ID NO: 156 - htRNA$^{Lys\text{-}CTT}$/pre-miR-1291 (160nt): A hybrid molecule of human lysine-CTT tRNA and pre-miR-1291

5'-GCCCGGCUAGCUCAGUCGGUAGAGCAUGGGACUGGUAGAAUUCCAGUGGCCCUGACUGAAGACCAGCAGU
UGUACUGUGGCUGUUGGUUUCAAGCAGAGGCCCUAAAGGACUGUCUUCCUGAAUCCCAGGGUCGUGGGUUCGAG
CCCCACGUUGGGCGCCA-3'

SEQ ID NO: 157 - htRNA$^{Lys\text{-}TTT}$/pre-miR-1291 (160nt): A hybrid molecule of human lysine-TTT tRNA and pre-miR-1291

5'-GCCUGGAUAGCUCAGUUGGUAGAGCAUCAGACUGGUAGAAUUCCAGUGGCCCUGACUGAAGACCAGCAGU
UGUACUGUGGCUGUUGGUUUCAAGCAGAGGCCUAAAGGACUGUCUUCCUGAAUCUGAGGGUCCAGGGUUCAAG
UCCCUGUUCAGGCACCA-3'

SEQ ID NO: 158 - htRNA$^{Met\text{-}CAT}$/pre-miR-1291 (160nt): A hybrid molecule of human methionine-CAT tRNA and pre-miR-1291

5'-GCCUCGUUAGCGCAGUAGGUAGCGCGUCAGUCUGGUAGAAUUCCAGUGGCCCUGACUGAAGACCAGCAGU
UGUACUGUGGCUGUUGGUUUCAAGCAGAGGCCAUAAAGGACUGUCUUCCUGAAUCUGAAGGUCGUGAGUUCGAU
CCUCACACGGGGCACCA-3'

SEQ ID NO: 159 - htRNA$^{Asn\text{-}GTT}$/pre-miR-1291 (161nt): A hybrid molecule of human asparagine-GTT tRNA and pre-miR-1291

5'-GUCUCUGUGGCGCAAUCGGUUAGCGCGUUCGGUGGUAGAAUUCCAG<u>UGGCCCUGACUGAAGACCAGCAG
UUGUACUGUG</u><u>GCUGUUGGUUUCAAGCAGAGGCCU</u>AAAGGACUGUCUUCCUG<u>AACCGAAAGGUUGGUGGUUCGA
UCCCACCCAGGGACGCCA</u>-3'

SEQ ID NO: 160 - htRNA<sup>Ala-AGC</sup>/pre-miR-1291 (159nt): A hybrid molecule of
human alanine-AGC tRNA and pre-miR-1291

5'-<u>GGGGUGUAGCUCAGUGGUAGAGCGCGUGCUU</u>GGUAGAAUUCCAG<u>UGGCCCUGACUGAAGACCAGCAGUU
GUACUGUG</u><u>GCVGUUGGUUUCAAGCAGAGGCCU</u>AAAGGACUGUCUUCCUG<u>AUGCACGAGGCCCCGGGUUCAAUC
CCCGGCACCUCCACCA</u>-3'

SEQ ID NO: 161 - htRNA<sup>His-GTG</sup>/pre-miR-1291 (159nt): A hybrid molecule of
human histidine-GTG tRNA and pre-miR-1291

5'-<u>GCCGUGAUCGUAUAGUGGUUAGUACUCUGCGUUG</u>GUAGAAUUCCAG<u>UGGCCCUGACUGAAGACCAGCAGU
UGUACUGUG</u><u>GCUGUUGGUUUCAAGCAGAGGCCU</u>AAAGGACUGUCUUCCUG<u>GCCGCAGCAACCUCGGUUCGAAU
CCGAGUCACGGCACCA</u>-3'

SEQ ID NO: 162 - htRNA<sup>Ile-AAT</sup>/pre-miR-1291 (161nt): A hybrid molecule of
human isoleucine-AAT tRNA and pre-miR-1291

5'-<u>GGCCGGUUAGCUCAGUUGGUUAGAGCGUGGUGCUG</u>GUAGAAUUCCAG<u>UGGCCCUGACUGAAGACCAGCAG
UUGUACUGUG</u><u>GCUGUUGGUUUCAAGCAGAGGCCU</u>AAAGGACUGUCUUCCUG<u>AACGCCAAGGUCGCGGGUUCGA
UCCCCGUACUGGCCACCA</u>-3'

SEQ ID NO: 163 - htRNA<sup>Ile-TAT</sup>/pre-miR-1291 (161nt): A hybrid molecule of
human isoleucine-TAT tRNA and pre-miR-1291

5'-<u>GCUCCAGUGGCGCAAUCGGUUAGCGCGCGGUACU</u>GGUAGAAUUCCAG<u>UGGCCCUGACUGAAGACCAGCAG
UUGUACUGUG</u><u>GCUGUUGGUUUCAAGCAGAGGCCU</u>AAAGGACUGUCUUCCUG<u>AAUGCCGAGGUUGUGAGUUCGA
UCCUCACCUGGAGCACCA</u>-3'

SEQ ID NO: 164 - htRNA<sup>Phe-GAA</sup>/pre-miR-1291 (160nt): A hybrid molecule of
human phenylalanine-GAA tRNA and pre-miR-1291

5'-<u>GCCGAAAUAGCUCAGUUGGGAGAGCGUUAGAC</u>UGGUAGAAUUCCAG<u>UGGCCCUGACUGAAGACCAGCAGU
UGUACUGUG</u><u>GCUGUUGGUUUCAAGCAGAGGCCU</u>AAAGGACUGUCUUCCUG<u>GAUCAAAGGUCCCUGGUUCGAU
CCCGGGUUUCGGCACCA</u>-3'

SEQ ID NO: 165 - htRNA<sup>Pro-AGG</sup>/pre-miR-1291 (159nt): A hybrid molecule of
human proline-AGG ERNA and pre-miR-1291

5'-<u>GGUCGUUGGUCUAGGGGUAUGAUUCUCGCUU</u>GGUAGAAUUCCAG<u>UGGCCCUGACUGAAGACCAGCAGUU
GUACUGUG</u><u>GCUGUUGGUUUCAAGCAGAGGCCU</u>AAAGGACUGUCUUCCUG<u>AUGCGAGAGGUCCCGGGUUCAAAU
CCCGGACGAGCCCCA</u>-3'

SEQ ID NO: 166 - htRNA<sup>Trp-CCA</sup>/pre-miR-1291 (159nt): A hybrid molecule of
human tryptophan-CCA ERNA and pre-miR-1291

5'-<u>GACCUCGUGGCGCAACGGUAGCGCGUCUGACU</u>GGUAGAAUUCCAG<u>UGGCCCUGACUGAAGACCAGCAGUU
GUACUGUG</u><u>GCUGUUGGUUUCAAGCAGAGGCCU</u>AAAGGACUGUCUUCCUG<u>GAUCAGAAGGCUGCGUGAACGAAU
CACGUCGGGGUCACCA</u>-3'

SEQ ID NO: 167 - htRNA<sup>Tyr-GTA</sup>/pre-miR-1291 (160nt): A hybrid molecule of
human tyrosine-GTA ERNA and pre-miR-1291

5'-<u>CCUUCGAUAGGUCAGUUGGUAGAGCGGAGGAC</u>UGGUAGAAUUCCAG<u>UGGCCCUGACUGAAGACCAGCAGU
UGUACUGUG</u><u>GCUGUUGGUUUCAAGCAGAGGCCU</u>AAAGGACUGUCUUCCUG<u>GAUCCUUAGGUCGCUGGUUCGAA
UCCGGCUCGAAGGACCA</u>-3'

SEQ ID NO: 168 - htRNA<sup>Val-CAC</sup>/pre-miR-1291 (160nt): A hybrid molecule of
human valine-CAC tRNA and pre-miR-1291

5'-<u>GUUUCCGUAGUGUAGUGGUUAUCACGUUCGCC</u>UGGUAGAAUUCCAG<u>UGGCCCUGACUGAAGACCAGCAGU
UGUACUGUG</u><u>GCUGUUGGUUUCAAGCAGAGGCCU</u>AAAGGACUGUCUUCCUG<u>ACGCGAAAGGUCCCCGGUUCGAA
ACCGGGCGGAAACACCA</u>-3'

SEQ ID NO: 169 - htRNA<sup>Thr-TGT</sup>/pre-miR-1291 (161nt): A hybrid molecule of
human threonine-TGT tRNA and pre-miR-1291

5'-<u>GCUCUAUGGUUAGUUGGUUAAAGCGCCUGUCUG</u>GUAGAAUUCCAG<u>UGGCCCUGACUGAAGACCAGCAG
UUGUACUGUG</u><u>GCUGUUGGUUUCAAGCAGAGGCCU</u>AAAGGACUGUCUUCCUG<u>AAACAGGAGAUCCUGGGUUCGA
AUCCCAGUAGAGCCUCCA</u>-3'

SEQ ID NO: 170 - htRNA<sup>Thr-AGT</sup>/pre-miR-1291 (161nt): A hybrid molecule of
human threonine-AGT tRNA and pre-miR-1291

5'-<u>GGCGCCGUGGCUUAGUUGGUUAAAGCGCCUGUCUG</u>GUAGAAUUCCAG<u>UGGCCCUGACUGAAGACCAGCAG
UUGUACUGUG</u><u>GCUGUUGGUUUCAAGCAGAGGCCU</u>AAAGGACUGUCUUCCUG<u>AAACAGGAGAUCCUGGGUUCGA
AUCCCAGCGGUGCCUCCA</u>-3'

SEQ ID NO: 171 - htRNA<sup>Leu-TAA</sup>/pre-mir-200b/miR-200b-3p (178nt): A hybrid
molecule of human leucine-TAA tRNA and pre-mir-200b 5'-ACCAGGAUGGCCGAGUGGUUAAGGCGUUGGACUCCAGCUCGGGCAGCCGUGGC<u>CAUCUUACUGGGCAGC
AUUGGA</u>UGGAGUCAGGUCUCU<u>AAUACUGCCUGGUAAUGAUGA</u>CGGCGGAGCCCUGCACGGAUCCAAUGGACAU
AUGUCCGCGUGGGUUCGAACCCCACUCCUGGUACCA-3'

SEQ ID NO: 172 - htRNA^Leu-TAA/pre-mir-133a/miR-133a-5p (168nt): A hybrid
molecule of human leucine-TAA tRNA and pre-mir-133a 5'-<u>ACCAGGAUGGCCGAGUGGUUAAGGCGUUGGACUA</u>CAAUGCUUUGCU<u>AGAGCUGGUAAAAUGGAACCAAA
UCGCCUCUUCAAUGG</u>A<u>UUUGGUCCCCUUCAACCAGCUG</u>UAGCUAUGCAUUGAGAUCCAAUGGACAUAUGUCCG
CGUGGGUUCGAACCCCACUCCUGGUACCA-3'

SEQ ID NO: 173 - htRNA^Ser-TGA/pre-mir-125a/miR-125a-3p (168nt): A hybrid
molecule of human serine-TGA tRNA and pre-mir-125a 5'-<u>GCAGCGAUGGCCGAGUGGUUAAGGCGUUGGACU</u>UGCCAGUCUCUAGG**<u>UCCCUGAGACCCUUUAACCUGU
GA</u>**GGACAUCCAGGGUC<u>ACAGGUGAGGUUCUUGGGAGCC</u>UGGCGUCUGGCC<u>AAUCCAAUGGGGUCUCCCCGCGC
AGGUUCGAACCCUGCUCGCUGCGCCA</u>-3'

SEQ ID NO: 174 - htRNA^Ser-TGA/pre-mir-125a/miR-34a-5p (166nt): A hybrid
molecule of human serine-TGA tRNA and pre-mir-125a in which miR-125a
sequences (mature and guide) are replaced by miR-34a (mature and guide)
sequences.

5'-<u>GCAGCGAUGGCCGAGUGGUUAAGGCGUUGGACU</u>UGCCAGUCUCUAGG<u>UGGCAGUGUCUUAGCUGGUUGU</u>
GGACAUCCAGGGUCC<u>AAUCAGCAAGUAUACUGCCCC</u>UUGGCGUCUGGCC<u>AAUCCAAUGGGGUCUCCCCGCGCAG
GUUCGAACCCUGCUCGCUGCGCCA</u>-3'

SEQ ID NO: 175 - htRNA^Ser-TGA/pre-let-7c (166nt): A hybrid molecule of human
serine-TGA tRNA and pre-let-7c.

5'-<u>GCAGCGAUGGCCGAGUGGUUAAGGCGUUGGACU</u>GCAUCCGGGUU<u>GAGGUAGUAGGUUGUAUGGUU</u>UAGAG
UUACACCCUGGGAGUU<u>AACUGUACAACCUUCUAGCUUUCC</u>UUGGAGC<u>AAUCCAAUGGGGUCUCCCCGCGCAGG
UUCGAACCCUGCUCGCUGCGCCA</u>-3'

SEQ ID NO: 176 - htRNA^Ser-TGA/pre-miR-124 (167nt): A hybrid molecule of human
serine-TGA tRNA and pre-miR-124.

5'-<u>GCAGCCGAUGGCCGAGUGGUUAAGGCGUUGGACU</u>AGGCCUCUCUCU<u>CCGUGUUCACAGCGGACCUUGAUU</u>
UAAAUGUCCAUACAAUUA<u>AAGGCACGCGGUGAAUGCC</u>AAGAAUGGGGCUGA<u>AUCCAAUGGGGUCUCCCCGCGCA
GGUUCGAACCCUGCUCGCUGCGCCA</u>-3'

SEQ ID NO: 177 - htRNA^Glu/5'tRF_miR-34a-5p (93nt): A modified molecule of
human glutamic acid tRNA in which the 5' tRNA fragment (5'tRF) sequence
is replaced by mature miR-34a guide sequence.

5'-<u>UGGCAGUGUCUUAGCUGGUUGUCUAAUCGCCGAGUAAUUUACGCCCGGGUGGUUGCGGCGCGGCCCGGG
UUCGAUUCCCGGCACUGACAACCA</u>-3'

SEQ ID NO: 178 - htRNA^Gly/5'tRF_miR-34a-5p (93nt): A modified molecule of
human glycine tRNA in which the 5' tRNA fragment (5'tRF) sequence is
replaced by mature miR-34a guide sequence.

5'-<u>UGGCAGUGUCUUAGCUGGUUGUCCAGACGCCGAGUAAUUUACGCCCGGGUGGUUGCGGCGUGACCCGGG
UUCGAUUCCCGGCACUGCCAACCA</u>-3'

SEQ ID NO: 179 - htRNA^Leu/5'tRF_miR-34a-5p (103nt): A modified molecule of
human leucine tRNA in which the 5' tRNA fragment (5'tRF) sequence is
replaced by mature miR-34a guide sequence.

5'-<u>UGGCAGUGUCUUAGCUGGUUGUAAUAACCGCCGAGUAAUUUACGCCCGGGUGGUUGCGGCGUCUCUUCG
GGGGCGUGGGUUCAAAUCCCACCACUGCCAACCA</u>-3'

SEQ ID NO: 180 - htRNA^Ser/5'tRF_miR-34a-5p (103nt): A modified molecule of
human serine tRNA in which the 5' tRNA fragment (5'tRF) sequence is
replaced by mature miR-34a guide sequence.

5'-<u>UGGCAGUGUCUUAGCUGGUUGUAUAACCGCCGAGUAAUUUACGCCCGGGUGGUUGCGGCGUGUGCUCUG
CACGCGUGGGUCGAAUCCCCAUCACUGCCAACCA</u>-3'

SEQ ID NO: 181 - htRNA^Leu/pre-miR-34a/miR-34a-5p_5'tRF_anti-miR-21-5p
(191nt): A hybrid molecule of human leucine tRNA and pre-miR-34a in which
the 5' tRNA fragment (tRF) region is replaced by anti-miR-21-5p (mature)
sequence (in bold).

5'-<u>ACCAGGAUGGACUCAACAUCAGUCUGAUAAGCGGCCAGCUGUGAGUGUUUCUU<u>UGGCAGUGUCUUAGCU
GGUUGU</u>UGUGAGUAAGGUAAGCAAUCAGCAAGUAUACUGCCCUAGAAGUGCUGCACGUUGUUGGCCCG
AUUAUCAGGACAUAUGUCCGCGUGGGUUCGAACCCCACUCCUGGUACCA</u>-3'

SEQ ID NO: 182 - htRNA^Leu/pre-miR-34a/miR-34a-5p_3'tRF_anti-miR-21-5p
(191nt): A hybrid molecule of human leucine tRNA and pre-miR-34a in which
the 3' tRNA fragment (tRF) region is replaced by anti-miR-21-5p (mature)
sequence (in bold).

5'-UCAGACUUGGCCGAGUGGUUAAGGCGUUGGACUGGCCAGCUGUGAGUGUUUCUU**UGGCAGUGUCUUAGC
UGGUUGUUGUGAGCAAUAGUAAGGAAGCAAUCAGCAAGUAUACUGCCCU**AGAAGUGCUGCACGUUGUUGGCCC
GAUCCAAUGGACAUAUGUCCGCGAUGUCCGUCAACAUCAGCUGAUAAG-3'

SEQ ID NO: 183 - htRNA^(Leu-TAA)/pre-miR-34a/anti-miR-21-5p/pre-miR-34a/miR-34a-
5p (294nt) (htRNA^Leu/miR-34a/anti-miR-21): A hybrid molecule of human
leucine-TAA tRNA and two pre-miR-34a molecules in which miR-34a sequences
(mature and guide) are replaced in the first precursor by miR-21
antagomir (mature and guide) sequences and in the second precursor by
miR-34a (mature and guide) sequences [in bold].
5'-ACCAGGAUGGCCGAGUGGUUAAGGCGUUGGACUGGCCAGCUGUGAGUGUUUCUU**UCAACAUCAGUCUGA
UAAGCUAUGUGAGCGGCCAGCUGUGAGUGUUUCUUUGGCAGUGUCUUAGCUGGUUGU**UGUGAGCAAUAGUAAC
GAAGCAAUCAGCAAGUAUACUGCCCUAGAAGUGCUGCACGUUGUUGGCCCGUAAGGAAG**UAGCUUAUAAGAAU
GAUGUUGC**AGAAGUGCUGCACGUUGUUGGCCCGAUCCAAUGGACAUAUGUCCGCGUGGGUUCGAACCCCACUC
CUGGUACCA-3'

SEQ ID NO: 184 - htRNA^(Leu-TAA)/pre-miR-34a/miR-34a-5p/pre-miR-34a/miR-124-3p
(297nt) (htRNA^Leu/miR-34a/miR-124): A hybrid molecule of human leucine-TAA
tRNA and two pre-miR-34a molecules in which miR-34a sequences (mature and
guide) are replaced in the first precursor by miR-34a (mature and guide)
sequences and in the second precursor by miR-124 (mature and guide)
sequences [in bold].
5'-ACCAGGAUGGCCGAGUGGUUAAGGCGUUGGACUGGCCAGCUGUGAGUGUUUCUU**UGGCAGUGUCUUAGC
UGGUUGUGUGUAGCGGCCAGCUGUGAGUGUUUCUUUAAGGCACGCGGUGAAUGCCGU**UGUGAGCAAUAGUAAG
GAAGCGGUGUUCCCGUCGUGCCUUCUAGAAGUGCUGCACGUUGUUGGCCCGUAAGGAAG**CAAUCAGCAAGUAU
ACUGCCCU**AGAAGUGCUGCACGUUGUUGGCCCGAUCCAAUGGACAUAUGUCCGCGUGGGUUCGAACCCCACUC
CUGGUACCA-3'

SEQ ID NO: 185 - htRNA^(Leu-TAA)/pre-miR-34a/let-7c-5p/pre-miR-34a/miR-124-3p
(298nt) (htRNA^Leu/let-7c/miR-1241): A hybrid molecule of human leucine-TAA
tRNA and two pre-miR-34a molecules in which miR-34a sequences (mature and
guide) are replaced in the first precursor by let-7c (mature and guide)
sequences and in the second precursor by miR-124 (mature and guide)
sequences [in bold].
5'-ACCAGGAUGGCCGAGUGGUUAAGGCGUUGGACUGGCCAGCUGUGAGUGUUUCU**UUGAGGUAGUAGGUUG
UAUGGUUUGUGAGCGGCCAGCUGUGAGUGUUUCUUUAAGGCACGCGGUGAAUGCCGU**UGUGAGCAAUAGUAAG
GAAGCGGUGUUCCCGUCGUGCCUUCUAGAAGUGCUGCACGUUGUUGGCCCGUAAGGAAA**AACUGUACACCUUA
CUACCUUUC**AGAAGUGCUGCACGUUGUUGGCCCGAUCCAAUGGACAUAUGUCCGCGUGGGUUCGAACCCCACU
CCUGGUACCA-3'

SEQ ID NO: 186 - htRNA^(Leu-TAA)/pre-miR-34a/miR-124-3p/pre-miR-34a/miR-34a-5p
(297nt) (htRNA^Leu/miR-124/miR-34a): A hybrid molecule of human leucine-TAA
tRNA and two pre-miR-34a molecules in which miR-34a sequences (mature and
guide) are replaced in the first precursor by miR-124 (mature and guide)
sequences and in the second precursor by miR-34a (mature and guide)
sequences [in bold].
5'-ACCAGGAUGGCCGAGUGGUUAAGGCGUUGGACUGGCCAGCUGUGAGUGUUUCU**UUAAGGCACGCGGUGA
AUGCCGUUGUGAGCGGCCAGCUGUGAGUGUUUCUUUGGCAGUGUCUUAGCUGGU**UGUUGUGAGCAAUAGUAAG
GAAGCAAUCAGCAAGUAUACUGCCCUAGAAGUGCUGCACGUUGUUGGCCCGUAAGGAAG**CGUGUUCCCGUCG
UGCCUUCU**AGAAGUGCUGCACGUUGUUGGCCCGAUCCAAUGGACAUAUGUCCGCGUGGGUUCGAACCCCACUC
CUGGUACCA-3'

SEQ ID NO: 187 - htRNA^(Ser-TGA)/pre-miR-34a/Nrf2-siRNA/pre-miR-34a/miR-34a-5p
(296nt) (htRNA^Ser/NRF2-siRNA/miR-34a): A hybrid molecule of human serine-
TGA tRNA and two pre-miR-34a molecules in which miR-34a sequences (mature
and guide) are replaced in the first precursor by Nrf2-siRNA (mature and
guide) sequences and in the second precursor by miR-34a (mature and
guide) sequences [in bold].
5'-GCAGCGAUGGCCGAGUGGUUAAGGCGUUGGACUGGCCAGCUGUGAGUGUUUCUU**AAVVGUCAACUACU
GUCAGUUUGUGAGCGGCCAGCUGUGAGUGUUUCUUUGGCAGUGUCUUAGCUGGU**UGUUGUGAGCAAUAGUAAG
GAAGCAAUCAGCAAGUAUACUGCCCUAGAAGUGCUGCACGUUGUUGGCCCGUAAGGAA**AACUGACAGAGUAUG
ACAAUUCU**AGAAGUGCUGCACGUUGUUGGCCCAAUCCAAUGGGGUCUCCCCGCGCAGGUUCGAACCCUGCUCG
CUGCGCCA-3'

SEQ ID NO: 188 - htRNA^(Leu-TAA)/pre-miR-34a/let-7c-5p/pre-miR-34a/miR-34a-5p
(298nt) (htRNA^Leu/let-7c/miR-34a): A hybrid molecule of human leucine-TAA
tRNA and two pre-miR-34a molecules in which miR-34a sequences (mature and
guide) are replaced in the first precursor by let-7c (mature and guide)
sequences and in the second precursor by miR-34a (mature and guide)
sequences [in bold].

5'-ACCAGGAUGGCCGAGUGGUUAAGGCGUUGGACUGGCCAGCUGUGAGUGUUUCUUUGAGGUAGUAGGUUG
UAUGGUUUGUGAGCGGCCAGCUGUGAGUGUUUCUUUGGCAGUGUCUUAGCUGGUUGUUGUGAGCAAUAGUAAG
GAAGCAAUCAGCAAGUAUACUGCCCUAGAAGUGGUGCACGUUGUUGGCCCGUAAGGAAGAACUGUACACCUUA
CUACCUUUCAGAAGUGCUGCACGUUGUUGGCCCGAUCCAAUGGACAUAUGUCCGCGUGGGUUCGAACCCCACU
CCUGGUACCA-3'

SEQ ID NO: 189 - htRNA<sup>Ser-TGA</sup>/pre-miR-34a/miR-124-3p/pre-miR-34a/miR-34a-5p
(296nt) (htRNA<sup>Ser</sup>/miR-124/miR-34a): A hybrid molecule of human serine-TGA
tRNA and two pre-miR-34a molecules in which miR-34 sequences (mature and
guide) are replaced in the first precursor by miR-124 (mature and guide)
sequences and in the second precursor by miR-34a (mature and guide)
sequences [in bold].
5'-GCAGCGAUGGCCGAGUGGUUAAGGCGUUGGACUGGCCAGCUGUGAGUGUUUCUUUAAGGCACGCGGUGA
AUGCCGUUGUGAGCGGCCAGCUGUGAGUGUUUCUUUGGCAGUGUCUUAGCUGGUUGUUGUGAGCAAUAGUAAG
GAAGCAAUCAGCAAGUAUACUGCCCUAGAAGUGCUGCACGUUGUUGGCCCGUAAGGAACGGUGUUCCCGUCG
UGCCUUCUAGAAGUGCUGCACGUUGUUGGCCCAAUCCAAUGGGGUCUCCCCGCGCAGGUUCGAACCCUGGCUCG
CUGCGCCA-3'

SEQ ID NO: 190 - htRNA<sup>Ser-TGA</sup>/pre-miR-34a/let-7c-5p/pre-miR-34a/miR-124-3p
(297nt) (htRNA<sup>Ser</sup>/let-7c/ miR-124): A hybrid molecule of human serine-TGA
tRNA and two pre-miR-34a molecules in which miR-34a sequences (mature and
guide) are replaced in the first precursor by let-7c (mature and guide)
sequences and in the second precursor by miR-124 (mature and guide)
sequences [in bold].
5'-GCAGCGAUGGCCGAGUGGUUAAGGCGUUGGACUGGCCAGCUGUGAGUGUUUCUUUGAGGUAGUAGGUUG
UAUGGUUUGUGAGCGGCCAGCUGUGAGUGUUUCUUUAAGGCACGCGGUGAAAUGCCGUUGUGAGCAAUAGUAAG
GAAGCGGUGUUCCCGUCGUGCCUUCUAGAAGUGCUGCACGUUGUUGGCCCGUAAGGAAGAACUGUACACCUUA
CUACCUUUCAGAAGUGCUGCACGUUGUUGGCCCAAUCCAAUGGGGUCUCCCCGCGCAGGUUCGAACCCUGCUC
GCUGCGCCA-3'

SEQ ID NO: 191 - htRNA<sup>Ser-TGA</sup>/pre-miR-34a/let-7c-5p/pre-miR-34a/miR-34a-5p
(297nt) (htRNA<sup>Ser</sup>/let-7c/miR-34a): A hybrid molecule of human serine-TGA
tRNA and two pre-miR-34a molecules in which miR-34a sequences (mature and
guide) are replaced in the first precursor by let-7c (mature and guide)
sequences and in the second precursor by miR-34a (mature and guide)
sequences [in bold].
5'-GCAGCGAUGGCCGAGUGGUUAAGGCGUUGGACUGGCCAGCUGUGAGUGUUUCUUUGAGGUAGUAGGUUG
UAUGGUUUGUGAGCGGCCAGCUGUGAGUGUUUCUUUGGCAGUGUCUUAGCUGGUUGUUGUGAGCAAUAGUAAC
GAAGCAAUCAGCAAGUAUACUGCCCUAGAAGUGCUGCACGUUGUUGGCCCGUAAGGAAGAACUGUACACCUUA
CUACCUUUCAGAAGUGCUGCACGUUGUUGGCCCAAUCCAAUGGGGUCUCCCCGCGCAGGUUCGAACCUGCUC
GCUGCGCCA-3'

SEQ ID NO: 192 - htRNA<sup>Leu-TAA</sup>/pre-miR-34a/Nrf2-siRNA/pre-miR-34a/miR-34a-5p
(297nt) (htRNA<sup>Leu</sup>/NRF2-siRNA/miR-34a): A hybrid molecule of human leucine-
TAA tRNA and two pre-miR-34a molecules in which miR-34a sequences (mature
and guide) are replaced in the first precursor by Nrf2-siRNA (mature and
guide) sequences and in the second precursor by miR-34a (mature and
guide) sequences [in bold].
5'-ACCAGGAUGGCCCGAGUGGUUAAGGCGUUGGACUGGCCAGCUGUGAGUGUUUCUUUAAUUGUCAACUACU
GUCAGUUUGUGAGCGGCCAGCUGUGAGUGUUUCUUUGGCAGUGUCUUAGCUGGUUGUUGUGAGCAAUAGUAAG
GAAGCAAUCAGCAAGUAUACUGCCCUAGAAGUGCUGCACGUUGUUGGCCCCGUAAGGAAAACUGACAGAGUAUG
ACAAUUCUAGAAGUGCUGCACGUUGUUGGCCCGAUCCAAUGGACAUAUGUCCGCGUGGGUUCGAACCCCACUC
CUGGUACCA-3'

SEQ ID NO: 193 - htRNA<sup>Leu-TAA</sup>/5'TPA/pre-miR-34a/let-7c-5p/pre-miR-34a/miR-
124-3p (331nt): A hybrid molecule of human leucine-TAA tRNA and two pre-
miR-34a molecules in which miR-34a sequences (mature and guide) are
replaced in the first precursor by let-7c (mature and guide) sequences
and in the second precursor by miR-124 (mature and guide) sequences [in
bold], with the addition a theophylline aptamer (5') upstream of the
first pre-miR-34a.
5'-ACCAGGAUGGCCGAGUGGUUAAGGCGUUGGACUGGCGAUACCAGCCGAAAGGCCCUUGGCAGCGUCGGC
CAGCUGUGAGUGUUUCUUUGAGGUAGUAGGUUGUAUGGUUUGUGAGCGGCCAGCUGUGAGUGUUUCUUUAAGG
CACGCGGUGAAUGCCGUUGUGAGCAAUAGUAAGGAAGCGGUGUUCCCGUCGUGCCUUCUAGAAGUGCUGCACG
UUGUUGGCCCGUAAGGAAGAACUGUACACCUUACUACCUUUCAGAAGUGCUGCACGUUGUUGCCCGAUCCAA
UGGACAUAUGUCCGCGUGGGUUCGAACCCCACUCCUGGUACCA-3'

SEQ ID NO: 194 - htRNA<sup>Leu-TAA</sup>/5'TPA/pre-mir-34a/miR-124-3p/pre-mir-34a/miR-
34a-5p (330nt): A hybrid molecule of human leucine-TAA tRNA and two pre-
miR-34a molecules in which miR-34a sequences (mature and guide) are
replaced in the first precursor by miR-124 (mature and guide) sequences
and in the second precursor by miR-34a (mature and guide) sequences [in
bold], with the addition of a theophylline aptamer (5') upstream of the
first pre-miR-34a.

5'-ACCAGGAUGGCCGAGUGGUUAAGGCGUUGGACUGGCGAUACCAGCCGAAAGGCCCUUGGCAGCGUCGGC
CAGCUGUGAGUGUUUCUUUUAAGGCACGCGGUGAAUGCCGUUGUGAGCGGCCAGCUGUGAGUGUUUCUU**UGGCA
GUGUCUUAGCUGGUUGUUGUGAGCAAUAGUAAGGAAGCAAUCAGCAAGUAUACUGCCCU**AGAAGUGCUGCACG
UUGUUGGCCCGUAAGGAAGCGGUGUUCCCGUCGUGCCUUCUAGAAGUGCUGCACGUUGUUGGCCCGAUCCAAU
GGACAUAUGUCCGCGUGGGUUCGAACCCCACUCCUGGUACCA-3'

SEQ ID NO: 195 - htRNA$^{Leu-TAA}$/5'TPA/pre-mir-34a/miR-34a-5p/pre-mir-34a/miR-124-3p (330nt): A hybrid molecule of human leucine-TAA tRNA and two pre-miR-34a molecules in which miR-34a sequences (mature and guide) are replaced in the first precursor by miR-34a (mature and guide) sequences and in the second precursor by miR-124 (mature and guide) sequences [in bold], with the addition of a theophylline aptamer (5') upstream of the first pre-miR-34a.

5'-ACCAGGAUGGCCGAGUGGUUAAGGCGUUGGACUGGCGAUACCAGCCGAAAGGCCCUUGGCAGCGUCGGC
CAGCUGUGAGUGUUUCUUUGGCAGUGUCUUAGCUGGUUGUUGUGAGCGGCCAGCUGUGAGUGUUUCUU**UAAGG
CACGCGGUGAAUGCCGUUGUGAGCAAUAGUAAGGAAGCGGUGUUCCCGUCGUGCCUUCU**AGAAGUGCUGCACG
UUGUUGGCCCGUAAGGAAGCAAUCAGCAAGUAUACUGCCCUAGAAGUGCUGCACGUUGUUGGCCCGAUCCAAU
GGACAUAUGUCCGCGUGGGUUCGAACCCCACUCCUGGUACCA-3'

SEQ ID NO: 196 - htRNA$^{Leu-TAA}$/3'TPA/pre-mir-34a/let-7c-5p/pre-mir-34a/miR-124-3p (331nt): A hybrid molecule of human leucine-TAA tRNA and two pre-miR-34a molecules in which miR-34a sequences (mature and guide) are replaced in the first precursor by let-7c (mature and guide) sequences and in the second precursor by miR-124 (mature and guide) sequences [in bold], with the addition of a theophylline aptamer (3') downstream of the first pre-miR-34a.

5'-ACCAGGAUGGCCGAGUGGUUAAGGCGUUGGACUGGCCAGCUGUGAGUGUUUCUUUGAGGUAGUAGGUUG
UAUGGUUUGUGAGCGGCCAGCUGUGAGUGUUUCUUUAAGGCACGCGGUGAAUGCCGUUGUGAGCAAUAGUAAG
GAAGCGGUGUUCCCGUCGUGCCUUCUAGAAGUGCUGCACGUUGUUGGCCCGUAAGGAAGAACUGUACACCUUA
CUACCUUUCAGAAGUGCUGCACGUUGUUGGCCCGGCGAUACCAGCCGAAAGGCCCUUGGCAGCGUCGAUCCAA
UGGACAUAUGUCCGCGUGGGUUCGAACCCCACUCCUGGUACCA-3'

SEQ ID NO: 197 - htRNA$^{Leu-TAA}$/3'TPA/pre-mir-34a/miR-124-3p/pre-mir-34a/miR-34a-5p (330nt): A hybrid molecule of human leucine-TAA tRNA and two pre-miR-34a molecules in which miR-34a sequences (mature and guide) are replaced in the first precursor by miR-124 (mature and guide) sequences and in the second precursor by miR-34a (mature and guide) sequences [in bold], with the addition of a theophylline aptamer (3') downstream of the first pre-miR-34a.

5'-ACCAGGAUGGCCGAGUGGUUAAGGCGUUGGACUGGCCAGCUGUGAGUGUUUCUU**UAAGGCACGCGGUGA
AUGCCGUUGUGAGCGGCCAGCUGUGAGUGUUUCUUUGGCAGUGUCUUAGCUGGUUGU**UGUGAGCAAUAGUAAG
GAAGCAAUCAGCAAGUAUACUGCCCUAGAAGUGCUGCACGUUGUUGGCCCGUAAGGAA**GCGGUGUUCCCGUCG
UGCCUUCU**AGAAGUGCUGCACGUUGUUGGCCCGCGAUACCAGCCGAAAGGCCCUUGGCAGCGUCGAUCCAAU
GGACAUAUGUCCGCGUGGGUUCGAACCCCACUCCUGGUACCA-3'

SEQ ID NO: 198 - htRNA$^{Leu-TAA}$/3'TPA/pre-mir-34a/miR-34a-5p/pre-mir-34a/miR-124-3p (330nt): A hybrid molecule of human leucine-TAA tRNA and two pre-miR-34a molecules in which miR-34a sequences (mature and guide) are replaced in the first precursor by miR-34a (mature and guide) sequences and in the second precursor by miR-124 (mature and guide) sequences [in bold], with the addition of a theophylline aptamer (3') downstream of the first pre-miR-34a.

5'-ACCAGGAUGGCCGAGUGGUUAAGGCGUUGGACUGGCCAGCUGUGAGUGUUUCUUUGGCAGUGUCUUAGC
UGGUUGUUGUGAGCGGCCAGCUGUGAGUGUUUCUUUAAGGCACGCGGUGAAUGCCGUUGUGAGCAAUAGUAAG
GAAGCGGUGUUCCCGUCGUGCCUUCUAGAAGUGCUGCACGUUGUUGGCCCGUAAGGAAGCAAUCAGCAAGUAU
ACUGCCCUAGAAGUGCUGCACGUUGUUGGCCCGCGAUACCAGCCGAAAGGCCCUUGGCAGCGUCGAUCCAAU
GGACAUAUGUCCGCGUGGGUUCGAACCCCACUCCUGGUACCA-3'

SEQ ID NO: 199 - htRNA$^{Leu-TAA}$/5' + 3'TPA/pre-miR-34a/let-7c-5p/pre-miR-34a/miR-124-3p (364nt): A hybrid molecule of human leucine-TAA tRNA and two pre-miR-34a molecules in which miR-34a sequences (mature and guide) are replaced in the first precursor by let-7c (mature and guide) sequences and in the second precursor by miR-124 (mature and guide) sequences [in bold], with the addition of two theophylline aptamers (5' and 3') upstream and downstream of the first pre-miR-34a.

5'-ACCAGGAUGGCCGAGUGGUUAAGGCGUUGGACUGGCGAUACCAGCCGAAAGGCCCUUGGCAGCGUCGGC
CAGCUGUGAGUGUUUCUUUGAGGUAGUAGGUUGUAUGGUUUGUGAGCGGCCAGCUGUGAGUGUUUCUU**UAAGG
CACGCGGUGAAUGCCGUUGUGAGCAAUAGUAAGGAAGCGGUGUUCCCGUCGUGCCUUCU**AGAAGUGCUGCACG
UUGUUGGCCCGUAAGGAAGAACUGUACACCUUACUACCUUUCAGAAGUGCUGCACGUUGUUGGCCCGGCGAUA
CCAGCCGAAAGGCCCUUGGCAGCGUCGAUCCAAUGGACAUAUGUCCGCGUGGGUUCGAACCCCACUCCUGGUA
CCA-3'

SEQ ID NO: 200 - htRNA$^{Leu-TAA}$/5' + 3'TPA/pre-miR-34a/miR-124-3p/pre-miR-34a/miR-34a-5p (364nt): A hybrid molecule of human leucine-TAA tRNA and two pre-miR-34a molecules in which miR-34a sequences (mature and guide)

are replaced in the first precursor by miR-124 (mature and guide)
sequences and in the second precursor by miR-34a (mature and guide)
sequences [in bold], with the addition of two theophylline aptamers (5'
and 3') upstream and downstream of the first pre-miR-34a.

5'-ACCAGGAUGGCCGAGUGGUUAAGGCGUUGGACUGGCGAUACCAGCCGAAAGGCCCUUGGCAGCGUCGGC
CAGCUGUGAGUGUUUCUUUAAGGCACGCGGUGAAUGCCGUUGUGAGCGGCCAGCUGUGAGUGUUUCUU**UGGCA
GUGUCUUAGCUGGUUGU**UGUGACAAUAGUAAGGAAGCAAUCAGCAAGUAUACUGCCCUAGAAGUGCUGCACG
UUGUUGGCCCGUAAGGAAGCGGUGUUCCCGUCGUGCCUUCUAGAAGUGCUGCACGUUGUUGGCCCGGCGAUAC
CAGCCGAAAGGCCCUUGGCAGCGUCGAUCCAAUGGACAUAUGUCCGCGUGGGUUCGAACCCCACUCCUGGUAC
CA-3'

SEQ ID NO: 201 - htRNA$^{Leu-TAA}$/5' + 3'TPA/pre-miR-34a/miR-34a-5p/pre-miR-
34a/miR-124-3p (363nt): A hybrid molecule of human leucine-TAA tRNA and
two pre-miR-34a molecules in which miR-34a sequences (mature and guide)
are replaced in the first precursor by miR-34a (mature and guide)
sequences and in the second precursor by miR-124 (mature and guide)
sequences [in bold], with the addition of two theophylline aptamers (5'
and 3') upstream and downstream of the first pre-miR-34a.

5'-ACCAGGAUGGCCGAGUGGUUAAGGCGUUGGACUGGCGAUACCAGCCGAAAGGCCCUUGGCAGCGUCGGC
CAGCUGUGAGUGUUUCUUUGGCAGUGUCUUAGCUGGUUGUGUGAGCAAUAGUAAGGAAGCGGUGUUCCCGUCGUGCCUUCUAGAAGUGCUGCACG
UUGUUGGCCCGUAAGGAAGCAAUCAGCAAGUAUACUGCCCUAGAAGUGCUGCACGUUGUUGGCCCGGCGAUAC
CAGCCGAAAGGCCCUUGGCAGCGUCGAUCCAAUGGACAUAUGUCCGCGUGGGUUCGAACCCCACUCCUGGUAC
CA-3'

SEQ ID NO: 202 - htRNA$^{Leu-TAA}$/pre-mir-34a/let-7c-5p/5'TPA/pre-mir-34a/miR-
124-3p (331nt): A hybrid molecule of human leucine-TAA tRNA and two pre-
miR-34a molecules in which miR-34a sequences (mature and guide) are
replaced in the first precursor by let-7c (mature and guide) sequences
and in the second precursor by miR-124 (mature and guide) sequences [in
bold], with the addition of a theophylline aptamer (5') upstream of the
second pre-miR-34a.

5'-ACCAGGAUGGCCGAGUGGUUAAGGCGUUGGACUGGCCAGCUGUGAGUGUUUCUUUGAGGUAGUAGGUUG
UAUGGUUUGUGAGCGGCGAUACCAGCCGAAAGGCCCUUGGCAGCGUCGGCCAGCUGUGAGUGUUUCUUUAAGG
CACGCGGUGAAUGCCGUUGUGAGCAAUAGUAAGGAAGCGGUGUUCCCGUCGUGCCUUCUAGAAGUGCUGCACG
UUGUUGGCCCGUAAGGAAGAACUGUACACCCUUACUACCUUUCAGAAGUGCUGCACGUUGUUGGCCCGAUCCAA
UGGACAUAUGUCCGCGUGGGUUCGAACCCCACUCCUGGUACCA-3'

SEQ ID NO: 203 - htRNA$^{Leu-TAA}$/pre-mir-34a/miR-124-3p/5'TPA/pre-mir-34a/miR-
34a-5p (330nt): A hybrid molecule of human leucine-TAA tRNA and two pre-
miR-34a molecules in which miR-34a sequences (mature and guide) are
replaced in the first precursor by miR-124 (mature and guide) sequences
and in the second precursor by miR-34a (mature and guide) sequences [in
bold], with the addition of a theophylline aptamer (5') upstream of the
second pre-miR-34a.

5'-ACCAGGAUGGCCGAGUGGUUAAGGCGUUGGACUGGCCAGCUGUGAGUGUUUCUUUAAGGCACGCGGUGA
AUGCCGUUGUGAGCGGCGAUACCAGCCGAAAGGCCCUUGGCAGCGUCGGCCAGCUGUGAGUGUUUCUU**UGGCA
GUGUCUUAGCUGGUUGU**UGUGACAAUAGUAAGGAAGCAAUCAGCAAGUAUACUGCCCUAGAAGUGCUGCACG
UUGUUGGCCCGUAAGGAAGCGGUGUUCCCGUCGUGCCUUCUAGAAGUGCUGCACGUUGUUGGCCCGAUCCAAU
GGACAUAUGUCCGCGUGGGUUCGAACCCCACUCCUGGUACCA-3'

SEQ ID NO: 204 - htRNA$^{Leu-TAA}$/pre-mir-34a/miR-34a-5p/5'TPA/pre-mir-34a/miR-
124-3p (330nt): A hybrid molecule of human leucine-TAA tRNA and two pre-
miR-34a molecules in which miR-34a sequences (mature and guide) are
replaced in the first precursor by miR-34a (mature and guide) sequences
and in the second precursor by miR-124 (mature and guide) sequences [in
bold], with the addition of a theophylline aptamer (5') upstream of the
second pre-miR-34a.

5'-ACCAGGAUGGCCGAGUGGUUAAGGCGUUGGACUGGCCAGCUGUGAGUGUUUCUUUGGCAGUGUCUUAGC
UGGUUGUUGUGAGCGGCGAUACCAGCCGAAAGGCCCUUGGCAGCGUCGGCCAGCUGUGAGUGUUUCUU**UAAGG
CACGCGGUGAAUGCCGUUGUGAGCAAUAGUAAGGAAGCGGUGUUCCCGUCGUGCCUUCU**AGAAGUGCUGCACG
UUGUUGGCCCGUAAGGAAGCAAUCAGCAAGUAUACUGCCCUAGAAGUGCUGCACGUUGUUGGCCCGAUCCAAU
GGACAUAUGUCCGCGUGGGUUCGAACCCCACUCCUGGUACCA-3'

SEQ ID NO: 205 - htRNA$^{Leu-TAA}$/pre-mir-34a/let-7c-5p/3'TPA/pre-mir-34a/miR-
124-3p (331nt): A hybrid molecule of human leucine-TAA tRNA and two pre-
miR-34a molecules in which miR-34a sequences (mature and guide) are
replaced in the first precursor by let-7c (mature and guide) sequences
and in the second precursor by miR-124 (mature and guide) sequences [in
bold], with the addition of a theophylline aptamer (3') downstream of the
second pre-miR-34a.

5'-ACCAGGAUGGCCGAGUGGUUAAGGCGUUGGACUGGCCAGCUGUGAGUGUUUCUUUGAGGUAGUAGGUUG
UAUGGUUUGUGAGCGGCCAGCUGUGAGUGUUUCUUUAAGGCACGCGGUGAAUGCCGUUGUGAGCAAUAGUAAG
GAAGCGGUGUUCCCGUCGUGCCUUCUAGAAGUGCUGCACGUUGUUGGCCCGGCGAUACCAGCCGAAAGGCCCU
UGGCAGCGUCGUAAGGAAGAACUGUACACCUUACUACCUUUCAGAAGUGCUGCACGUUGUUGGCCCGAUCCAA
UGGACAUAUGUCCGCGUGGGUUCGAACCCCACUCCUGGUACCA-3'

SEQ ID NO: 206 - htRNA$^{Leu-TAA}$/pre-mir-34a/miR-124-3p/3'TPA/pre-mir-34a/miR-
34a-5p (330nt): A hybrid molecule of human leucine-TAA tRNA and two pre-
miR-34a molecules in which miR-34a sequences (mature and guide) are
replaced in the first precursor by miR-124 (mature and guide) sequences
and in the second precursor by miR-34a (mature and guide) sequences [in
bold], with the addition of a theophylline aptamer (3') downstream of the
second pre-miR-34a.
5'-ACCAGGAUGGCCGAGUGGUUAAGGCGUUGGACUGGCCAGCUGUGAGUGUUUCUUUAAGGCACGCGGUGA
AUGCCGUUGUGAGCGGCCAGCUGUGAGUGUUUCUUUUGGCAGUGUCUUAGCUGGUUGUUGUGAGCAAUAGUAAG
GAAGCAAUCAGCAAGUAUACUGCCCUAGAAGUGCUGCACGUUGUUGGCCCGGCGAUACCAGCCGAAAGGCCCU
UGGCAGCGUCGUAAGGAAGCGGUGUUCCCGUCGUGCCUUCUAGAAGUGCUGCACGUUGUUGGCCCGAUCCAAU
GGACAUAUGUCCGCGUGGGUUCGAACCCCACUCCUGGUACCA-3'

SEQ ID NO: 207 - htRNA$^{Leu-TAA}$/pre-mir-34a/miR-34a-5p/3'TPA/pre-mir-34a/miR-
124-3p (330nt): A hybrid molecule of human leucine-TAA tRNA and two pre-
miR-34a molecules in which miR-34a sequences (mature and guide) are
replaced in the first precursor by miR-34a (mature and guide) sequences
and in the second precursor by miR-124 (mature and guide) sequences [in
bold], with the addition of a theophylline aptamer (3') downstream of the
second pre-miR-34a.
5'-ACCAGGAUGGCCGAGUGGUUAAGGCGUUGGACUGGCCAGCUGUGAGUGUUUCUUUGGCAGUGUCUUAGC
UGGUUGUUGUGAGCGGCCAGCUGUGAGUGUUUCUUUAAGGCACGCGGUGAAUGCCGUUGUGAGCAAUAGUAAG
GAAGCGGUGUUCCCGUCGUGCCUUCUAGAAGUGCUGCACGUUGUUGGCCCGGCGAUACCAGCCGAAAGGCCCU
UGGCAGCGUCGUAAGGAAGCAAUCAGCAAGUAUACUGCCCUAGAAGUGCUGCACGUUGUUGGCCCGAUCCAAU
GGACAUAUGUCCGCGUGGGUUCGAACCCCACUCCUGGUACCA-3'

SEQ ID NO: 208 - htRNA$^{Leu-TAA}$/pre-mir-34a/let-7c-5p/5' + 3'TPA/pre-mir-34a/miR-
124-3p (364nt): A hybrid molecule of human leucine-TAA tRNA and two pre-
miR-34a molecules in which miR-34a sequences (mature and guide) are
replaced in the first precursor by let-7c (mature and guide) sequences
and in the second precursor by miR-124 (mature and guide) sequences [in
bold], with the addition of two theophylline aptamers (5' and 3')
upstream and downstream of the second pre-miR-34a.
5'-ACCAGGAUGGCCGAGUGGUUAAGGCGUUGGACUGGCCAGCUGUGAGUGUUUCUUUGAGGUAGUAGGUUG
UAUGGUUUGUGAGCGGCGAUACCAGCCGAAAGGCCCUUGGCAGCGUCGGCCAGCUGUGAGUGUUUCUUUAAGG
CACGCGGUGAAUGCCGUUGUGAGCAAUAGUAAGGAAGCGGUGUUCCCGUCGUGCCUUCUAGAAGUGCUGCACG
UUGUUGGCCCGGCGAUACCAGCCGAAAGGCCCUUGGCAGCGUCGUAAGGAAGAACUGUACACCUUACUACCUU
UCAGAAGUGCUGCACGUUGUUGGCCCGAUCCAAUGGACAUAUGUCCGCGUGGGUUCGAACCCCACUCCUGGUA
CCA-3'

SEQ ID NO: 209 - htRNA$^{Leu-TAA}$/pre-mir-34a/miR-124-3p/5' + 3'TPA/pre-mir-
34a/miR-34a-5p (363nt): A hybrid molecule of human leucine-TAA ERNA and
two pre-miR-34a molecules in which miR-34a sequences (mature and guide)
are replaced in the first precursor by miR-124 (mature and guide)
sequences and in the second precursor by miR-34a (mature and guide)
sequences [in bold], with the addition of two theophylline aptamers (5'
and 3') upstream and downstream of the second pre-miR-34a.
5'-ACCAGGAUGGCCGAGUGGUUAAGGCGUUGGACUGGCCAGCUGUGAGUGUUUCUUUAAGGCACGCGGUGA
AUGCCGUUGUGAGCGGCGAUACCAGCCGAAAGGCCCUUGGCAGCGUCGGCCAGCUGUGAGUGUUUCUUUGGCA
GUGUCUUAGCUGGUUGUUGUGAGCAAUAGUAAGGAAGCAAUCAGCAAGUAUACUGCCCUAGAAGUGCUGCACG
UUGUUGGCCCGGCGAUACCAGCCGAAAGGCCCUUGGCAGCGUCGUAAGGAAGCGGUGUUCCCGUCGUGCCUUC
UAGAAGUGCUGCACGUUGUUGGCCCGAUCCAAUGGACAUAUGUCCGCGUGGGUUCGAACCCCACUCCUGGUAC
CA-3'

SEQ ID NO: 210 - htRNA$^{Leu-TAA}$/pre-mir-34a/miR-34a-5p/5' + 3'TPA/pre-mir-
34a/miR-124-3p (363nt): A hybrid molecule of human leucine-TAA ERNA and
two pre-miR-34a molecules in which miR-34a sequences (mature and guide)
are replaced in the first precursor by miR-34a (mature and guide)
sequences and in the second precursor by miR-124 (mature and guide)
sequences [in bold], with the addition of two theophylline aptamers (5'
and 3') upstream and downstream of the second pre-miR-34a.
5'-ACCAGGAUGGCCGAGUGGUUAAGGCGUUGGACUGGCCAGCUGUGAGUGUUUCUUUGGCAGUGUCUUAGC
UGGUUGUUGUGAGCGGCGAUACCAGCCGAAAGGCCCUUGGCAGCGUCGGCCAGCUGUGAGUGUUUCUUUAAGG
CACGCGGUGAAUGCCGUUGUGAGCAAUAGUAAGGAAGCGGUGUUCCCGUCGUGCCUUCUAGAAGUGCUGCACG
UUGUUGGCCCGGCGAUACCAGCCGAAAGGCCCUUGGCAGCGUCGUAAGGAAGCAAUCAGCAAGUAUACUGCCC
UAGAAGUGCUGCACGUUGUUGGCCCGAUCCAAUGGACAUAUGUCCGCGUGGGUUCGAACCCCACUCCUGGUAC
CA-3'

ANNOTATIONS FOR SEQ ID NOS: 211-256: (underlined, tRNA sequence; italic, pre-miRNA sequence; bold underlined, mature miRNA; italic underlined, passenger sequence)

SEQ ID NO: 211 nCAR<sup>Met</sup>/miR-34a-5p (180 nt)
5'-<u>GGCUACGUAGCUCAGUUGGUUAGAGCAG</u>*CGGCCGGGCCAGCUGUGAGUGUU UCUU*UGGCAGUGUCUUAGCUGGUUGU*UGUGAGCAAUAGUAAGGAAG*<u>*CAAUCAGCAAGUAUACUGCCCU*</u>*AGAAG UGCUGCACGUUGUUGGCCCCCGCGG*<u>GUCACAGGUUCGAAUCCCGUCGUAGCCACCA</u>-3'

SEQ ID NO: 212 hCAR<sup>Leu</sup>/miR-34a-5p (192 nt)
5'-<u>ACCAGGAUGGCCGAGUGGUUAAGGCGUUGGACU</u>*GGCCAGCUGUGAGUGUUU CUU*UGGCAGUGUCUUAGCUGGUUGU*UGUGAGCAAUAGUAAGGAAG*<u>*CAAUCAGCAAGUAUACUGCCCU*</u>*AGAAGU GCUGCACGUUGUUGGCCCGA*<u>UCCAAUGGACAUAUGUCCGCGUGGGUUCGAACCCCACUCCUGGUACCA</u>-3'

SEQ ID NO: 213 hCAR<sup>Ser</sup>/miR-34a-5p (191 nt)
5'-<u>GCAGCGAUGGCCGAGUGGUUAAGGCGUUGGACU</u>*GGCCAGCUGUGAGUGUU UCUU*UGGCAGUGUCUUAGCUGGUUGU*UGUGAGCAAUAGUAAGG**<u>*AAGCAAUCAGCAAGUAUACUGCCCU*</u>*AGAAG UGCUGCACGUUGUUGGCCC*<u>AAUCCAAUGGGGUCUCCCCGCGCAGGUUCGAACCCUGCUCGCUGCGCCA</u>-3'

SEQ ID NO: 214 hCAR<sup>Lys</sup>/miR-34a-5p (182 nt)
5'-<u>GCCUGGAUAGCUCAGUUGGUAGAGCAUCAGACU</u>*GGCCAGCUGUGAGUGUUU CUU*UGGCAGUGUCUUAGCUGGU*UGUUGUGAGCAAUAGUAAGGAAG*<u>*CAAUCAGCAAGUAUACUGCCCU*</u>*AGAAGU GCUGCACGUUGUUGCCCAA*<u>UCUGAGGGUCCAGGGUUCAAGUCCCUGUUCAGGCGCCA</u>-3'

SEQ ID NO: 215 hCAR<sup>Gln</sup>/miR-34a-5p (181 nt)
5'-<u>GGUCCCAUGGUGUAAUGGUUAGCACUCUGGACU</u>*GGCCAGCUGUGAGUGUUU CUU*UGGCAGUGUCUUAGCUGGU*UGUUGUGAGCAAUAGUAAGGAAGC*<u>*AAUCAGCAAGUAUACUGCCCU*</u>*AGAAGU GCUGCACGUUGUUGGCCC*<u>AAUCCAGCGAUCCGAGUUCAAAUCUCGGUGGGACCUCCA</u>-3'

SEQ ID NO: 216 hCAR<sup>Cys</sup>/miR-34a-5p (181 nt)
5'-<u>GGGGGCAUAGCUCAGUGGUAGAGCAUUUGACU</u>*GGCCAGCUGUGAGUGUUUC UU*UGGCAGUGUCUUAGCUGGU*UGUUGUGAGCAAUAGUAAGGAAG*<u>*CAAUCAGCAAGUAUACUGCCCU*</u>*AGAAGUG CUGCACGUUGUUGGCCC*<u>GAUCAAGAGGUCCCUGGUUCAAAUCCAGGUGCCCCUCCA</u>-3'

SEQ ID NO: 217 htRNA<sup>Leu</sup>/miR-124-3p (167 nt)
5'-<u>ACCAGGAUGGCCGAGUGGUUAAGGCGUUGGACA</u>*GGCCUCUCUCUC*CGUGU UCACAGCGGACCUUGAU*UUAAAUGUCCAUACAAUU*<u>*AAGGCACGCGGUGAAUGCC*</u>*AAGAAUGGGGCUG*<u>GAUCCA AUGGACAUAUGUCCGCGUGGGUUCGAACCCCACUCCUGGUACCA</u>-3'

SEQ ID NO: 218 htRNA<sup>Ser</sup>/miR-124-3p (167 nt)
5'-<u>GCAGCGAUGGCCGAGUGGUUAAGGCGUUGGACU</u>*AGGCCUCUCUCUC*CGUGU UCACAGCGGACCUUGAU*UUAAAUGUCCAUACAAUU*<u>*AAGGCACGCGGUGAAUGCC*</u>*AAGAAUGGGGCUG*<u>AAUCCA AUGGGGUCUCCCCGCGCAGGUUCGAACCCUGCUCGCUGCGCCA</u>-3'

SEQ ID NO: 219 htRNA<sup>Lys</sup>/miR-124-3p (158 nt)
5'-<u>GCCUGGAUAGCUCAGUUGGUAGAGCAUCAGACU</u>*AGGCCUCUCUCUC*CGUGU UCACAGCGGACCUUGAU*UUAAAUGUCCAUACAAUU*<u>*AAGGCACGCGGUGAAUGCC*</u>*AAGAAUGGGGCUG*<u>AAUCUG AGGGUCCAGGGUUCAAGUCCCUGUUCAGGCGCCA</u>-3'

SEQ ID NO: 220 htRNA<sup>Gln</sup>/miR-124-3p (157 nt)
5'-<u>GGUCCCAUGGUGUAAUGGUUAGCACUCUGGACU</u>*AGGCCUCUCUCUC*CGUGU UCACAGCGGACCUUGAU*UUAAAUGUCCAUACAAUU*<u>*AAGGCACGCGGUGAAUGCC*</u>*AAGAAUGGGGCUG*<u>AAUCCA GCGAUCCGAGUUCAAAUCUCGGUGGGACCUCCA</u>-3'

SEQ ID NO: 221 htRNA<sup>Cys</sup>/miR-124-3p (157 nt)
5'-<u>GGGGGCAUAGCUCAGUGGUAGAGCAUUUGACU</u>*AGGCCUCUCUCUC*CGUGU UCACAGCGGACCUUGAU*UUAAAUGUCCAUACAAUU*<u>*AAGGCACGCGGUGAAUGCC*</u>*AAGAAUGGGGCUG*<u>GAUCAA GAGGUCCCUGGUUCAAAUCCAGGUGCCCCUCCA</u>-3'

SEQ ID NO: 222 nCAR<sup>Met</sup>/let-7c-5p (181 nt)
5'-<u>GGCUACGUAGCUCAGUUGGUUAGAGCAG</u>*CGGCCGGGCCAGCUGUGAGUGUU UCUU*UGAGGUAGUAGGUUGUAUGGUU*UGUGAGCAAUAGUAAGGAAG*<u>*AACUGUACACCUUACUACCUUUC*</u>*AGAA GUGCUGCACGUUGUUGGCCCCCGCGG*<u>GUCACAGGUUCGAAUCCCGUCGUAGCCACCA</u>-3'

-continued

SEQ ID NO: 223 hCAR<sup>Leu</sup>/let-7c-5p (193 nt)
5'-<u>ACCAGGAUGGCCGAGUGGUUUAAGG</u>CGUUGGACUGGCCAGCUGUGAGUGUUU
CUUUGAGGUAGUAGGUUGUAUGGUUUGUGAGCAAUAGUAAGGAAG<u>AACUGUACACCUUACUACCUUUC</u>AGAAG
UGCUGCACGUUGUUGGCCC<u>GAUCCAAUGGACAUAUGUCCGCGUGGGUUCGAACCCCACUCCUGGUACCA</u>-3'

SEQ ID NO: 224 hCAR<sup>Ser</sup>/let-7c-5p (192 nt)
5'-<u>GCAGCGAUGGCCGAGUGGUUAAGGCGUUGGACU</u>GGCCAGCUGUGAGUGUUU
CUUUGAGGUAGUAGGUUGUAUGGUUUGUGAGCAAUAGUAAGGAAG<u>AACUGUACACCUUACUACCUUUC</u>AGAAG
UGCUGCACGUUGUUGGCCC<u>AAUCCAAUGGGGUCUCCCCGCGCAGGUUCGAACCCUGCUCGCUGCGCCA</u>-3'

SEQ ID NO: 225 hCAR<sup>Lys</sup>/let-7c-5p (183 nt)
5'-<u>GCCUGGAUAGCUCAGUUGGUAGAGCAU</u>CAGACUGGCCAGCUGUGAGUGUUU
CUUUGAGGUAGUAGGUUGUAUGGUUUGUGAGCAAUAGUAAGGAAG<u>AACUGUACACCUUACUACCUUUC</u>AGAAG
UGCUGCACGUUGUUGGCCC<u>AAUCUGAGGGUCCAGGGUUCAAGUCCCUGUUCAGGCGCCA</u>-3'

SEQ ID NO: 226 hCAR<sup>Gln</sup>/let-7c-5p (182 nt)
5'-<u>GGUCCCAUGGUGUAAUGGUUAGCACUCUGGACU</u>GGCCAGCUGUGAGUGUUU
CUUUGAGGUAGUAGGUUGUAUGGUUUGUGAGCAAUAGUAAGGAAG<u>AACUGUACACCUUACUACCUUUC</u>AGAAG
UGCUGCACGUUGUUGGCCC<u>AAUCCAGCGAUCCGAGUUCAAAUCUCGGUGGGACCUCCA</u>-3'

SEQ ID NO: 227 hCAR<sup>Cys</sup>/let-7c-5p (182 nt)
5'-<u>GGGGGCAUAGCUCAGUGGUAGAGCAUUUGACU</u>GGCCAGCUGUGAGUGUUUC
UUUGAGGUAGUAGGUUGUAUGGUUUGUGAGCAAUAGUAAGGAAG<u>AACUGUACACCUUACUACCUUUC</u>AGAAGU
GCUGCACGUUGUUGGCC<u>CGAUCAAGAGGUCCCUGGUUCAAAUCCAGGUGCCCCCUCCA</u>-3'

SEQ ID NO: 228 htRNA<sup>Ser</sup>/pre-let-7c-5p (166 nt)
5'-<u>GCAGCGAUGGCCGAGUGGUUAAGGCGUUGGACU</u>GCAUCCGGGUUGAGGUA

GUAGGUUGUAUGGUUUAGAGUUACACCCUGGGAGUUAA<u>CUGUACAACCUUCUAGCUUUCC</u>UUGGAGCA<u>AUCCA
AUGGGGUCUCCCCGCGCAGGUUCGAACCCUGCUCGCUGCGCCA</u>-3'

SEQ ID NO: 229 htRNA<sup>Leu</sup>/pre-let-7c-5p (168 nt)
5'-<u>ACCAGGAUGGCCGAGUGGUUUAAGGCGUUGGACU</u>GCAUCCGGGUUGAGGUA

GUAGGUUGUAUGGUUUAGAGUUACACCCUGGGAGUUAA<u>CUGUACAACCUUCUAGCUUUCC</u>UUGGAGC<u>AGAUCC
AAUGGACAUAUGUCCGCGUGGGUUCGAACCCCACUCCUGGUACCA</u>-3'

SEQ ID NO: 230 htRNA<sup>Lys</sup>/pre-let-7c-5p (152 nt)
5'-GCCUGGAUAGCUCAGUUGGUAGAGCAUGCAUCCGGGUUGAGGUA
GUAGGUUGUAUGGUUUAGAGUUACACCCUGGGAGUUAA<u>CUGUACAACCUUCUAGCUUUCC</u>UUGGAGCA<u>AAUCU
GAGGGUCCAGGGUUCAAGUCCCUGUUCAGGCGCCA</u>-3'

SEQ ID NO: 231 htRNA<sup>Cys</sup>/pre-let-7c-5p (157 nt)
5'-<u>GGGGGCAUAGCUCAGUGGUAGAGCAUUUGACU</u>GCAUCCGGGUUGAGGUA

GUAGGUUGUAUGGUUUAGAGUUACACCCUGGGAGUUAA<u>CUGUACAACCUUCUAGCUUUCC</u>UUGGAGC<u>AGAUCA
AGAGGUCCCUGGUUCAAAUCAGGUGCCCCCUCCA</u>-3'

SEQ ID NO: 232 htRNA<sup>Gln</sup>/pre-let-7c-5p (157 nt)
5'-<u>GGUCCCAUGGUGUAAUGGUUAGCACUCUGGACU</u>GCAUCCGGGUUGAGGUA

GUAGGUUGUAUGGUUUAGAGUUACACCCUGGGAGUUAA<u>CUGUACAACCUUCUAGCUUUCC</u>UUGGAGCA<u>AAUCC
AGCGAUCCGAUUCAAAUCUCGGGACCUCCA</u>-3'

SEQ ID NO: 233 nCAR<sup>Met</sup>/miR-328-3p (180 nt)
5'-<u>GGCUACGUAGCUCAGUUGGUUAGAGCAG</u>CGGCCGGGCCAGCUGUGAGUGUU
UCUUCUGGCCCUCUCUGCCCUUCCGUUGUGAGCAAUAGUAAGGAAG<u>CGGGGGGGAGAUGGGGGCCAUUA</u>GAAG
UGCUGCACGUUGUUGGCCCCGCGGG<u>UCACAGGUUCGAAUCCCGUCUAGCCACCA</u>-3'

SEQ ID NO: 234 hCAR<sup>Leu</sup>/miR-328-3p (192 nt)
5'-<u>ACCAGGAUGGCCGAGUGGUUUAAGG</u>CGUUGGACUGGCCAGCUGUGAGUGUUU
CUUCUGGCCCUCUCUGCCCUUCCGUUGUGAGCAAUAGUAAGGAAG<u>CGGGGGGAGAUGGGGGCCAUUA</u>GAAGU
GCUGCACGUUGUUGGCCC<u>GAUCCAAUGGACAUAUGUCCGCGUGGGUUCGAACCCCACUCCUGGUACCA</u>-3'

SEQ ID NO: 235 hCAR<sup>Ser</sup>/miR-328-3p (191 nt)
5'-<u>GCAGCGAUGGCCGAGUGGUUAAGGCGUUGGACU</u>GGCCAGCUGUGAGUGUUU
CUUCUGGCCCUCUCUGCCCUUCCGUUGUGAGCAAUAGUAAGGAAG<u>CGGGGGGAGAUGGGGGCCAUUA</u>GAAGU
GCUGCACGUUGUUGGCCCAAU<u>CCAAUGGGGUCUCCCCGCGCAGGUUCGAACCCUGCUCGCUGCGCCA</u>-3'

SEQ ID NO: 236 hCAR<sup>Lys</sup>/miR-328-3p (182 nt)
5'-<u>GCCUGGAUAGCUCAGUUGGUAGAGCAUCAGACU</u>GGCCAGCUGUGAGUGUUU
CUUCUGGCCCUCUCUGCCCUUCCGUUGUGAGCAAUAGUAAGGAA<u>GCGGGGGGAGAUGGGGGCCAUUAGA</u>AGU
GCUGCACGUUGUUGGCCC<u>AAUCUGAGGGUCCAGGGUUCAAGUCCCUGUUCAGGCGCCA</u>-3'

SEQ ID NO: 237 hCAR<sup>Gln</sup>/miR-328-3p (181 nt)
5'-<u>GGUCCCAUGGUGUAAUGGUUAGCACUCUGGACU</u>GGCCAGCUGUGAGUGUUU
CUUCUGGCCCUCUCUGCCCUUCCGUUGUGAGCAAUAGUAAGGAA<u>GCGGGGGGAGAUGGGGGCCAUUAGA</u>AGU
GCUGCACGUUGUUGGCCC<u>AAUCCAGCGAUCCGAGUUCAAAUCUCGGUGGGACCUCCA</u>-3'

SEQ ID NO: 238 hCAR<sup>Cys</sup>/miR-328-3p (181 nt)
5'-<u>GGGGGCAUAGCUCAGUGGUAGAGCAUUUGACUG</u>GCCAGCUGUGAGUGUUUC
UUCUGGCCCUCUCUGCCCUUCCGUUGUGAGCAAUAGUAAGGAA<u>GCGGGGGGAGAUGGGGGCCAUUAGA</u>AGUG
CUGCACGUUGUUGGCCC<u>GAUCAAGAGGUCCCUGGUUCAAUCCAGGUGCCCCUCCA</u>-3'

SEQ ID NO: 239 nCAR<sup>Met</sup>/miR-124-3p (180 nt)
5'-<u>GGCUACGUAGCUCAGUUGGUUAGAGCAG</u>CGGCCGGGCCAGCUGUGAGUGUU
UCUUUAAGGCACGCGGUGAAUGCCGUUGUGAGCAAUAGUAGGAAG<u>CGGUGUUCCCGUCGUGCCUUCU</u>AGAAG
UGCUGCACGUUGUUGGCCCCCGCGG<u>GUCACAGGUUCGAAUCCCGUCGUAGCCACCA</u>-3'

SEQ ID NO: 240 hCAR<sup>Leu</sup>/miR-124-3p (192 nt)
5'-<u>ACCAGGAUGGCCGAGUGGUUAAGGCGUUGGACU</u>GGCCAGCUGUGAGUGUUU
CUUUAAGGCACGCGGUGAAUGCCGUUGUGAGCAAUAGUAAGGAAG<u>CGGUGUUCCCGUCGUGCCUUCU</u>AGAAGU
GCUGCACGUUGUUGGCCC<u>GAUCCAAUGGACAUAUGUCCGCGUGGGUUCGAACCCCACUCCUGGUACCA</u>-3'

SEQ ID NO: 241 hCAR<sup>Ser</sup>/miR-124-3p (191 nt)
5'-<u>GCAGCGAUGGCCGAGUGGUUAAGGCGUUGGACU</u>GGCCAGCUGUGAGUGUUU
CUUUAAGGCACGCGGUGAAUGCCGUUGUGAGCAAUAGUAAGGAAG<u>CGGUGUUCCCGUCGUGCCUUCU</u>AGAAGU
GCUGCACGUUGUUGGCCC<u>AAUCCAAUGGGGUCUCCCCGCGCAGGUUCGAACCCUGCUCGCUGCGCCA</u>-3'

SEQ ID NO: 242 hCAR<sup>Lys</sup>/miR-124-3p (182 nt)
5'-<u>GCCUGGAUAGCUCAGUUGGUAGAGCAU</u>CAGACUGGCCAGCUGUGAGUGUUU
CUUUAAGGCACGCGGUGAAUGCCGUUGUGAGCAAUAGUAAGGAAG<u>CGGUGUUCCCGUCGUGCCUUCU</u>AGAAGU
GCUGCACGUUGUUGGCCC<u>AAUCUGAGGGUCCAGGGUUCAAGUCCCUGUUCAGGCGCCA</u>-3'

SEQ ID NO: 243 hCAR<sup>Gln</sup>/miR-124-3p (181 nt)
5'-<u>GGUCCCAUGGUGUAAUGGUUAGCACUCUGGACU</u>GGCCAGCUGUGAGUGUUU
CUUUAAGGCACGCGGUGAAUGCCGUUGUGAGCAAUAGUAAGGAAG<u>CGGUGUUCCCGUCGUGCCUUCU</u>AGAAGU
GCUGCACGUUGUUGGCCC<u>AAUCCAGCGAUCCGAGUUCAAAUCUCGGUGGGACCUCCA</u>-3'

SEQ ID NO: 244 hCAR<sup>Cys</sup>/miR-124-3p (181 nt)
5'-<u>GGGGGCAUAGCUCAGUGGUAGAGCAUUUGACU</u>GGCCAGCUGUGAGUGUUUC
UUUAAGGCACGCGGUGAAUGCCGUUGUGAGCAAUAGUAAGGAA<u>GCGGUGUUCCCGUCGUGCCUUCU</u>AGAAGUG
CUGCACGUUGUUGGCCC<u>GAUCAACAGGUCCCUGGUUCAAUCCAGGUGCCCCUCCA</u>-3'

SEQ ID NO: 245 nCAR<sup>Met</sup>/miR-126-3p (180 nt)
5'-<u>GGCUACGUAGCUCAGUUGGUUAGAGCAG</u>CGGCCGGGCCAGCUGUGAGUGUU
UCUUUCGUACCGUGAGUAAUAAUGCGUGUGAGCAAUAGUAAGGAA<u>GUGCAUUAUUCUCUAUGGUACGC</u>AGAAG
UGUGCACGUUGUUGGCCCCCGCGGGU<u>CACAGGUUCGAAUCCCGUCGUAGCCACCA</u>-3'

SEQ ID NO: 246 hCAR<sup>Leu</sup>/miR-126-3p (192 nt)
5'-<u>ACCAGGAUGGCCGAGUGGUUAAGGCGUUGGACUGGC</u>CAGCUGUGAGUGUUU
CUUUCGUACCGUGAGUAAUAAUGCGUGUGAGCAAUAGUAAGGAA<u>GGUGCAUUAUUCUCUAUGGUACG</u>AGAAGU
GCUGCACGUUGUUGGCCC<u>GAUCCAAUGGACAUAUGUCCGCGUGGGUUCGAACCCCACUCCUGGUACCA</u>-3'

SEQ ID NO: 247 hCAR<sup>Ser</sup>/miR-126-3p (191 nt)
5'-<u>GCAGCGAUGGCCGAGUGGUUAAGGCGUUGGACU</u>GGCCAGCUGUGAGUGUUU
CUUUCGUACCGUGAGUAAUAAUGCGUGUGAGCAAUAGUAAGGAA<u>GGUGCAUUAUUCUCUAUGGUACG</u>AGAAGU
GCUGCACGUUGUUGGCCAA<u>UCCAAUGGGGUCUCCCCGCGCAGGUUCGAACCCUGCUCGCUGCGCCA</u>-3'

SEQ ID NO: 248 hCAR<sup>Lys</sup>/miR-126-3p (182 nt)
5'-<u>GCCUGGAUAGCUCAGUUGGUAGAGCAUCAGACU</u>GGCCAGCUGUGAGUGUUU
CUUUCGUACCGUGAGUAAUAAUGCGUGUGAGCAAUAGUAAGGAAG<u>GUGCAUUAUUCUCUAUGGUACG</u>AGAAGU
GCUGCACGUUGUUGGCCC<u>AAUCUGAGGGUCCAGGGUUCAAGUCCCUGUUCAGCGCCA</u>-3'.

SEQ ID NO: 249 hCAR<sup>Gln</sup>/miR-126-3p (181 nt)
5'-<u>GGUCCCAUGGUGUAAUGGUUAGCACUCUGGACU</u>GGCCAGCUGUGAGUGUUU
CUUUCGUACCGUGAGUAAUAAUGCGUGUGAGGCAAUAGUAAGGAAG<u>GUGCAUUAUUCUCUAUGGUACG</u>AGAAGU
GCUGCACGUUGUUGGCCC<u>AAUCCAGCGAUCCGAGUUCAAAUCUCGGUGGGACCUCCA</u>-3'

-continued

SEQ ID NO: 250 hCAR$^{Cys}$/miR-126-3p (181 nt)
5'-*GGGGGCAUAGCUCAGUGGUAGAGCAUUUGACU*GGCCAGCUGUGAGUGUUUC
UUUCGUACCGUGAGUAAUAAUGCGUGUGAGCAAUAGUAAGGAAG<u>GUGCAUUAUUCUCUAUGGUACG</u>AGAAGUG
CUGCACGUUGUUGGCCCGA<u>UCAAGAGGUCCCUGGUUCAAAUCCAGGUGCCCCUCCA</u>-3'

SEQ ID NO: 251 nCAR$^{Met}$/miR-298-5p (180 nt)
5'-<u>GGCUACGUAGCUCAGUUGGUUAGAGCAG</u>*CGGCCGGGCCAGCUGUGAGUGUU*
*UCUU*AGCAGAAGCAGGGAGGUUCUCCCA*UGAGCAAUAGUAAGGAG*<u>GGAGAACCCCAUGCUUUUGACA</u>*GAAG*
*UGCUGCACGUUGUUGGCCCCGCGGGU*<u>CACAGGUUCGAAUCCCGUCGUAGCCACCA</u>-3'

SEQ ID NO: 252 hCAR$^{Leu}$/miR-298-5p (194 nt)
5'-<u>ACCAGGAUGGCCGAGUGGUUAAGGCGUUGGACUGGC</u>*CAGCUGUGAGUGUUU*
*CUU*AGCAGAAGCAGGGAGGUUCUCCCA*UGUGAGCAAUAGUAAGGAAG*<u>GGAGAACCCCCAUGCUUUUGACAG</u>*AA*
*GUGCUGCACGUUGUUGGCCCGA*<u>UCCAAUGGACAUAUGUCCGCGUGGGUUCGAACCCCACUCCUGGUACCA</u>-3'

SEQ ID NO: 253 hCAR$^{Ser}$/miR-298-5p (193 nt)
5'-<u>GCAGCGAUGGCCGAGUGGUUAAGGCGUUGGACU</u>*GGCCAGCUGUGAGUGUUU*
*CUU*AGCAGAAGCAGGGAGGUUCUCCCA*UGUGAGCAAUAGUAAGGAAG*<u>GGAGAACCCCCAUGCUUUUGACA</u>*GAA*
*GUGCUGCACGUUGUUGGCCC*<u>AAUCCAAUGGGGUCUCCCCGCGCAGGUUCGAACCCUGCUCGCUGCGCCA</u>-3'

SEQ ID NO: 254 hCAR$^{Lys}$/miR-298-5p (184 nt)
5' - <u>GCCUGGAUAGCUCAGUUGGUAGAGCAUCAGACUGGCC</u>*AGCUGUGAGUGUUU*
*CUU*AGCAGAAGCAGGGAGGUUCUCCCA*UGUGAGCAAUAGUAAGGAAG*<u>GGAGAACCCCCAUGCUUUUGACA</u>*GAA*
*GUGCUGCACGUUGUUGGCCC*<u>AAUCUGAGGGUCCAGGGUUCAAGUCCCUGUUCAGGCGCCA</u>-3'

SEQ ID NO: 255 hCAR$^{Gln}$/miR-298-5p (183 nt)
5' - <u>GGUCCCAUGGUGUAAUGGUUAGCACUCUGGACUGGCC</u>*AGCUGUGAGUGUUU*
*CUU*AGCAGAAGCAGGGAGGUUCUCCCA*UGUGAGCAAUAGUAAGGAAG*<u>GGAGAACCCCCAUGCUUUUGACA</u>*GAA*
*GUGCUGCACGUUGUUGGCCC*<u>AAUCCAGCGAUCCGAGUUCAAAUCUCGGUGGGACCUCCA</u>-3'

SEQ ID NO: 256 hCAR$^{Cys}$/miR-298-5p (183 nt)
5' - GGGGGCAUAGCUCAGUGGUAGAGCAUUUGACU*GGCCAGCUGUGAGUGUUUC*
*UU*AGCAGAAGCAGGGAGGUUCUCCCA*UGUGAGCAAUAGUAAGGAAG*<u>GGAGAACCCCCAUGCUUUUGACA</u>*GAAG*
*UGCUGCACGUUGUUGGCCC*<u>GAUCAAGAGGUCCCUGGUUCAAAUCCAGGUGCCCCUCCA</u>-3'

ANNOTATIONS FOR SEQ ID NOS: 257-288 Underlined are tRNA sequences, and the italic are pre-miRNA sequences. Double underline is the mature miRNA/siRNA sequence, and bold underline is the guide miRNA/siRNA sequence. The boxed are aptamer (e.g., sephadex) sequences.
257-259: Bacterial tRNA fused to human pre-miR-34a derivative, with miRNA/siRNAs replacing miR-34a duplex
260-263: Bacterial tRNA fragments (tRFs)
264: bacterial tRNA fused to human pre-miR-1291
265-270: Bacterial tRNA fused to two human pre-miR-34a derivatives, with miRNA/siRNAs replacing miR-34a duplexes
271-288: Bacterial tRNA fused to two human pre-miR-34a derivatives, with miRNA/siRNAs replacing miR-34a duplexes and the addition of aptamers SEQ ID NO: 257 - btRNA$^{Met-CAT}$/pre-miR-34a (180 nt): A hybrid molecule of bacterial methionine-CAT tRNA and pre-miR-34a 5'-<u>GGCUACGUAGCUCAGUUGGUUAGAGCAGCGGCCGGGCC</u>AGCUGUGAGUGUUUCUUUGGCAGUGUCUUAGC
UGGUUGUUGUGAGCAAUAGUAAGGAAGCAAUCAGCAAGUAUACUGCCCUAGAAGUGCUGCACGUUGUUGGCCC
CCGCGGGUCACAGGUUCGAAUCCCGUCGUAGCCACCA-3'

SEQ ID NO: 258 - btRNA$^{Met-CAT}$/pre-miR-34a/miR-124a-3p (180 nt): A hybrid molecule of bacterial methionine-CAT tRNA and pre-miR-34a in which miR-34a sequences (mature and guide) are replaced by miR-124 (mature and guide) sequences.

5'-<u>GGCUACGUAGCUCAGUUGGUUAGAGCAGCGGCCGGGCC</u>AGCUGUGAGUGUUUCUU<u>UAAGGCACGCGGUGA</u>
<u>AUGCC</u>GUUGUGAGCAAUAGUAAGGAAG<u>CGGUGUUCCCGUCGUGCCUUCU</u>AGAAGUGCUGCACGUUGUUGGCCC
CCGCGGGUCACAGGUUCGAAUCCCGUCGUAGCCACCA-3'

SEQ ID NO: 259 - btRNA$^{Met-CAT}$/pre-miR-34a/let-7c-5p (181 nt): A hybrid molecule of bacterial methionine-CAT tRNA and pre-miR-34a in which miR-34a sequences (mature and guide) are replaced by let-7c (mature and guide) sequences.

5'-<u>GGCUACGUAGCUCAGUUGGUUAGAGCAGCGGCCGGGCC</u>AGCUGUGAGUGUUUCUUUG<u>AGGUAGUAGGUUG</u>
<u>UAUGGUU</u>UGUGAGCAAUAGUAAGGAAGAACUGUACACCUUACUACCUUUCAGAAGUGCUGCACGUUGUUGGCC
CCCGCGGGUCACAGGUUCGAAUCCCGUCGUAGCCACCA-3'

-continued

SEQ ID NO: 260 - btRNA<sup>Met-CAT</sup>/pre-miR-34a/miR-34a-5p_5'tRF_anti-miR-21-5p
(180 nt): A hybrid molecule of bacterial methionine-CAT tRNA and pre-miR-34a
in which the 5' tRNA fragment (tRF) region is replaced by anti-miR-21-5p (mature) sequence (in bold).

5'-GGCUACGUAAGACUCAACAUCAGUCUGAUAAGCGGGCCAGCUGUGAGUGUUUCUUUGGCAGUGUCUUAGC
UGGUUGUUGUGAGCAAUAGUAAGGAAGCAAUCAGCAAGUAUACUGCCCUAGAAGUGCUGCACGUUGUUGGCCC
UUAUGGGUCACAGGUUCGAAUCCCGUCGUAGCCACCA-3'

SEQ ID NO: 261 - btRNA<sup>Met-CAT</sup>/pre-miR-34a/miR-34a-5p_3'tRF_anti-miR-21-5p
(180 nt): A hybrid molecule of bacterial methionine-CAT tRNA and pre-miR-34a
in which the 3' tRNA fragment (tRF) region is replaced by anti-miR-21-5p (mature) sequence (in bold).

5'-UCAGACUUAGCUCAGUUGGUUAGAGCAGCGGCCGGGCCAGCUGUGAGUGUUUCUUUGGCAGUGUCUUAGC
UGGUUGUUGUGAGCAAUAGUAAGGAAGCAAUCAGCAAGUAUACUGCCCUAGAAGUGCUGCACGUUGUUGGCCC
CCGCUGUACACAGGUUCGUCAACAUCAGUCUGAUCCA-3'

SEQ ID NO: 262 - btRNA<sup>Met-CAT</sup>/pre-miR-34a/anti-miR-21-5p_5'tRF_miR-34a-5p
(180 nt): A hybrid molecule of bacterial methionine-CAT tRNA and pre-miR-34a
in which miR-34a sequences (mature and guide) are replaced by anti-miR-21
(mature and guide) sequences and the 5' tRNA fragment (tRF) region
is replaced by miR-34a-5p (mature) sequence (in bold).

5'-GGCUACGUAUAAGUGGCAGUGUCUUAGCUGGUUGGGCCAGCUGUGAGUGUUUCUUUCAACAUCAGUCUGA
UAAGCUAUGUGAGCAAUAGUAAGGAAGUAGCUUAUAAGAAUGAUGUUGCAGAAGUGCUGCACGUUGUUGGCCC
CCAGGGGUCACAGGUUCGAAUCCCGUCGUAGCCACCA-3'

SEQ ID NO: 263 - btRNA<sup>Met-CAT</sup>/pre-miR-34a/anti-miR-21-5p_3'tRF_miR-34a-5p
(180 nt): A hybrid molecule of bacterial methionine-CAT tRNA and pre-miR-34a in
which miR-34a sequences (mature and guide) are replaced by anti-miR-21
(mature and guide) sequences and the 3' tRNA fragment (tRF) region
is replaced by miR-34a-5p (mature) sequence (in bold).

5'-GCUAAGAUAGCUCAGUUGGUUAGAGCAGCGGCCGGGCCAGCUGUGAGUGUUUCUUUCAACAUCAGUCUGA
UAAGCUAUGUGAGCAAUAGUAAGGAAGUAGCUUAUAAGAAUGAUGUUGCAGAAGUGCUGCACGUUGUUGGCCC
CCGCCUGACACAGGUUCGUGGCAGUGUCUUAGCUCCA-3'

SEQ ID NO: 264 - btRNA<sup>Met-CAT</sup>/pre-miR-1291 (227 nt): A hybrid molecule of
bacteria methionine tRNA and pre-miR-1291 with 36nt forward and backward
sequence (SNOR34, italic and bold)

5'-GGCUACGUAGCUCAGUUGGUUAGAGCAG*CGGCCGAGUAAUUUACGUCGAC**GAGUUCUGUCCGUGAGCCUU
GGGUAGAAUUCCAG**UGGCCCUGACUGAAGACCAGCAGUUGUACUGUGGCUGUUGGUUUCAAGCAGAGGCCUAA
AGGACUGUCUUCCUGUGGUCUGUUGGCUGUGACGUCGAUGGUUGCGGCCGCGG*GUCACAGGUUCGAAUCCCGU
CGUAGCCACCA -3'

SEQ ID NO: 265 - btRNA<sup>Met-CAT</sup>/pre-miR-34a/anti-miR-21-5p/pre-miR-34a/miR-34a-5p (285 nt):
A hybrid molecule of bacterial methionine-CAT tRNA and two pre-miR-34a molecules in which
miR-34a sequences (mature and guide) are replaced in the first precursor by miR-21 antagomir
(mature and guide) sequences and in the second precursor by miR-34a (mature and guide)
sequences [in bold].

5'- GGCUACGUAGCUCAGUUGGUUAGAGCAGCGGCCGGGCCAGCUGUGAGUGUUUCUUUCAACAUCAGUCUG
AUAAGCUAUGUGAGCGGCCAGCUGUGAGUGUUUCUUUGGCAGUGUCUUAGCUGGUUGUUGUGAGCAAUAGUAA
GGAAGCAAUCAGCAAGUAUACUGCCCUAGAAGUGCUGCACGUUGUUGGCCCGUAAGGAAGUAGCUUAUAAGAA
UGAUGUUGCAGAAGUGCUGCACGUUGUUGGCCCCCGCGGGUCACAGGUUCGAAUCCCGUCGUAGCCACCA-3'

SEQ ID NO: 266 - btRNA<sup>Met-CAT</sup>/pre-miR-34a/miR-34a-5p/pre-miR-34a/miR-124-3p (285 nt):
A hybrid molecule of bacterial methionine-CAT tRNA and two pre-miR-34a molecules
in which miR-34a sequences (mature and guide) are replaced in the first precursor by
miR-34a (mature and guide) sequences and in the second precursor by miR-124
(mature and guide) sequences [in bold].

5'- GGCUACGUAGCUCAGUUGGUUAGAGCAGCGGCCGGGCCAGCUGUGAGUGUUUCUUUGGCAGUGUCUUAG
CUGGUUGUUGUGAGCGGCCAGCUGUGAGUGUUUCUUUAAGGCACGCGGUGAAUGCCGUUGUGAGCAAUAGUAA
GGAAGCGGUGUUCCCGUCGUGCCUUCUAGAAGUGCUGCACGUUGUUGGCCCGUAAGGAAGCAAUCAGCAAGUA
UACUGCCCUAGAAGUGCUGCACGUUGUUGGCCCCCGCGGGUCACAGGUUCGAAUCCCGUCGUAGCCACCA-3'

SEQ ID NO: 267 - btRNA<sup>Met-CAT</sup>/pre-miR-34a/let-7c-5p/pre-miR-34a/miR-124-3p
(286 nt): A hybrid molecule of bacterial methionine-CAT and two pre-miR-
34a molecules in which miR-34a sequences (mature and guide) are replaced
in the first precursor by let-7c (mature and guide) sequences and in the
second precursor by miR-124 (mature and guide) sequences [in bold].

5'- GGCUACGUAGCUCAGUUGGUUAGAGCAGCGGCCGGGCCAGCUGUGAGUGUUUCUUUGAGGUAGUAGGUU
GUAUGGUUUGUGAGCGGCCAGCUGUGAGUGUUUCUUUAAGGCACGCGGUGAAUGCCGUUGUGAGCAAUAGUAA
GGAAGCGGUGUUCCCGUCGUGCCUUCUAGAAGUGCUGCACGUUGUUGGCCCGUAAGGAAGAACUGUACACCUU
ACUACCUUUCGAAGUGCUGCACGUUGUUGGCCCCCGCCGGUCACAGGUUCGAAUCCCGUCGUAGCCACCA-
3'

SEQ ID NO: 268 - btRNA<sup>Met-CAT</sup>/pre-miR-34a/miR-124-3p/pre-miR-34a/miR-34a-5p
(285 nt): A hybrid molecule of bacterial methionine-CAT tRNA and two pre-miR-34a
molecules in which miR-34a sequences (mature and guide) arer eplaced in the first
precursor by miR-124 (mature and guide) sequences and in the second precursor
by miR-34a (mature and guide) sequences [in bold].

5'- GGCUACGUAGCUCAGUUGGUUAGAGCAGCGGCCGGGCCAGCUGUGAGUGUUUCUUUAAGGCACGCGGUG
AAUGCCGUUGUGAGCGGCCAGCUGUGAGUGUUUCUUUUGGCAGUGUCUUAGCUGGUUGUUGUGAGCAAUAGUAA
GGAAGCAAUCAGCAAGUAUACUGCCCUAGAAGUGCUGCACGUUGUUGGCCCGUAAGGAAGCGGUGUUCCCGUC
GUGCCUUCUAGAAGUGCUGCACGUUGUUGGCCCCCGCGGUCACAGGUUCGAAUCCCGUCGUAGCCACCA-3'

SEQ ID NO: 269 - btRNA<sup>Met-CAT</sup>/pre-miR-34a/let-7c-5p/pre-miR-34a/miR-34a-5p
(286 nt): A hybrid molecule of bacterial methionine-CAT tRNA and two pre-
miR-34a molecules in which miR-34a sequences (mature and guide) are
replaced in the first precursor by let-7c (mature and guide) sequences
and in the second precursor by miR-34a (mature and guide) sequences [in bold].

5'- GGCUACGUAGCUCAGUUGGUUAGAGCAGCGGCCGGGCCAGCUGUGAGUGUUUCUUUGAGGUAGUAGGUU
GUAUGGUUUGUGAGCGGCCAGCUGUGAGUGUUUCUUUUGGCAGUGUCUUAGCUGGUUGUUGUGAGCAAUAGUAA
GGAAGCAAUCAGCAAGUAUACUGCCCUAGAAGUGCUGCACGUUGUUGGCCCGUAAGGAAGAACUGUACACCUU
ACUACCUUUCAGAAGUGCUGCACGUUGUUGGCCCCCGCGGUCACAGGUUCGAAUCCCGUCGUAGCCACCA-
3'

SEQ ID NO: 270 - btRNA<sup>Met-CAT</sup>/pre-miR-34a/Nrf2-siRNA/pre-miR-34a/miR-34a-5p
(285 nt): A hybrid molecule of bacterial methionine-CAT tRNA and two pre-
miR-34a molecules in which miR-34a sequences (mature and guide) are
replaced in the first precursor by Nrf2-siRNA (mature and guide)
sequences and in the second precursor by miR-34a (mature and guide)
sequences [in bold].

5'- GGCUACGUAGCUCAGUUGGUUAGAGCAGCGGCCGGGCCAGCUGUGAGUGUUUCUUUAAUUGUCAACUAC
UGUCAGUUUGUGAGCGGCCAGCUGUGAGUGUUUCUUUUGGCAGUGUCUUAGCUGGUUGUUGUGAGCAAUAGUAA
GGAAGCAAUCAGCAAGUAUACUGCCCUAGAAGUGCUGCACGUUGUUGGCCCGUAAGGAAAACUGACAGAGUAU
GACAAUUCUAGAAGUGCUGCACGUUGUUGGCCCCCGCGGUCACAGGUUCGAAUCCCGUCGUAGCCACCA-3'

SEQ ID NO: 271 - btRNA<sup>Met-CAT</sup>/5' TPA/pre-miR-34a/let-7c-5p/pre-miR-34a/miR-
124-3p (319 nt): A hybrid molecule of bacterial methionine-CAT tRNA and
two pre-miR-34a molecules in which miR-34a sequences (mature and guide)
are replaced in the first precursor by let-7c (mature and guide)
sequences and in the second precursor by miR-124 (mature and guide)
sequences [in bold], with the addition a theophylline aptamer (5')
upstream of the first pre-miR-34a.

5'- GGCUACGUAGCUCAGUUGGUUAGAGCAGCGGCCGGGCGAUACCAGCCGAAAGGCCCUUGGCAGCGUCGG
CCAGCUGUGAGUGUUUCUUUGAGGUAGUAGGUUGUAUGGUUUGUGAGCGGCCAGCUGUGAGUGUUUCUUU**AAG
GCACGCGGUGAAUGCCGUUGUGAGCAAUAGUAAGGAAGCGGUGUUCCCGUCGUGCCUUCU**AGAAGUGCUGCAC
GUUGUUGGCCCGUAAGGAAGAACUGUACACCUUACUACCUUUCAGAAGUGCUGCACGUUGUUGGCCCCCGCGG
GUCACAGGUUCGAAUCCCGUCGUAGCCACCA-3'

SEQ ID NO: 272 - btRNA<sup>Met-CAT</sup>/5' TPA/pre-miR-34a/miR-124-3p/pre-miR-34a/miR-34a-5p
(318 nt): A hybrid molecule of bacterial methionine-CAT tRNA and two pre-miR-34a molecules
in which miR-34a sequences (mature and guide) are replaced in the first precursor by miR-124
(mature and guide) sequences and in the second precursor by miR-34a (mature and guide)
sequences [in bold], with the addition of a theophylline aptamer (5') upstream of the first
pre-miR-34a.

5'- GGCUACGUAGCUCAGUUGGUUAGAGCAGCGGCCGGGCGAUACCAGCCGAAAGGCCCUUGGCAGCGUCGG
CCAGCUGUGAGUGUUUCUUUAAGGCACGCGGUGAAUGCCGUUGUGAGCGGCCAGCUGUGAGUGUUUCUUU**UGGC
AGUGUCUUAGCUGGUUGUUGUGAGCAAUAGUAAGGAAGCAAUCAGCAAGUAUACUGCCCU**AGAAGUGCUGCAC
GUUGUUGGCCCGUAAGGAAGCGGUGUUCCCGUCGUGCCUUCUAGAAGUGCUGCACGUUGUUGGCCCCCGCGGG
UCACAGGUUCGAAUCCCGUCGUAGCCACCA-3'

SEQ ID NO: 273 - btRNA<sup>Met-CAT</sup>/5' TPA/pre-miR-34a/miR-34a-5p/pre-miR-34a/miR-124-3p
(318 nt): A hybrid molecule of bacterial methionine-CAT tRNA and two pre-miR-34a
molecules in which miR-34a sequences (mature and guide) are replaced in the first
precursor by miR-34a (mature and guide) sequences and in the second precursor
by miR-124 (mature and guide) sequences [in bold], with the addition of a theophylline
aptamer (5') upstream of the first pre-miR-34a.

5'- GGCUACGUAGCUCAGUUGGUUAGAGCAGCGGCCGGGCGAUACCAGCCGAAAGGCCCUUGGCAGCGUCGG
CCAGCUGUGAGUGUUUCUUUGGCAGUGUCUUAGCUGGUUGUUGUGAGCGGCCAGCUGUGAGUGUUUCUUU**AAG
GCACGCGGUGAAUGCCGUUGUGAGCAAUAGUAAGGAAGCGGUGUUCCCGUCGUGCCUUCU**AGAAGUGCUGCAC
GUUGUUGGCCCGUAAGGAAGCAAUCAGCAAGUAUACUGCCCUAGAAGUGCUGCACGUUGUUGGCCCCCGCGGG
UCACAGGUUCGAAUCCCGUCGUAGCCACCA-3'

SEQ ID NO: 274 - btRNA<sup>Met-CAT</sup>/3' TPA/pre-miR-34a/let-7c-5p/pre-miR-124-3p
(319 nt): A hybrid molecule of bacterial methionine-CAT tRNA and two pre-miR-34a molecules in which miR-34a sequences (mature and guide) are replaced in the first
precursor by let-7c (mature and guide) sequences and in the second precursor by miR-124
(mature and guide) sequences [in bold], with the addition of a theophylline aptamer (3')
downstream of the first pre-miR-34a.

5'- GGCUACGUAGCUCAGUUGGUUAGAGCAGCGGCCGGGCCAGCUGUGAGUGUUUCUUUGAGGUAGUAGGUU
GUAUGGUUUGUGAGCGGCCAGCUGUGAGUGUUUCUUUAAGGCACGCGGUGAAUGCCGUUGUGAGCAAUAGUAA
GGAAGCGGUGUUCCCGUCGUGCCUUCUAGAAGUGCUGCACGUUGUUGGCCCGUAAGGAAGAACUGUACACCUU
ACUACCUUUCAGAAGUGCUGCACGUUGUUGGCCCGGCGAUACCAGCCGAAAGGCCCUUGGCAGCGUCCGCGG
GUCACAGGUUCGAAUCCCGUCGUAGCCACCA-3'

SEQ ID NO: 275 - btRNA$^{Met-CAT}$/3' TPA/pre-miR-34a/miR-124-3p/pre-miR-34a/miR-34a-5p
(318 nt): A hybrid molecule of bacterial methionine-CAT tRNA and two pre-miR-34a
molecules in which miR-34a sequences (mature and guide) are replaced in the first
precursor by miR-124 (mature and guide) sequences and in the second precursor
by miR-34a (mature and guide) sequences [in bold], with the addition of a theophylline
aptamer (3') downstream of the first pre-miR-34a.

5'- GGCUACGUAGCUCAGUUGGUUAGAGCAGCGGCCGGGCCAGCUGUGAGUGUUUCUUUAAGGCACGCGGUG
AAUGCCGUUGUGAGCGGCCAGCUGUGAGUGUUUCUUUGGCAGUGUCUUAGCUGGUUGUUGUGAGCAAUAGUAA
GGAAGCAAUCAGCAAGUAUACUGCCCUAGAAGUGCUGCACGUUGUUGGCCCGUAAGGAAGCGGUGUUCCCGUC
GUGCCUUCUAGAAGUGCUGCACGUUGUUGGCCCGGCGAUACCAGCCGAAAGGCCCUUGGCAGCGUCCGCGGG
UCACAGGUUCGAAUCCCGUCGUAGCCACCA-3'

SEQ ID NO: 276 - btRNA$^{Met-CAT}$/3' TPA/pre-miR-34a/miR-34a-5p/pre-miR-34a/miR-
124-3p (318 nt): A hybrid molecule of bacterial methionine-CAT tRNA and
two pre-miR-34a molecules in which miR-34a sequences (mature and guide)
are replaced in the first precursor by miR-34a (mature and guide)
sequences and in the second precursor by miR-124 (mature and guide)
sequences [in bold], with the addition of a theophylline aptamer (3')
downstream of the first pre-miR-34a.

5'- GGCUACGUAGCUCAGUUGGUUAGAGCAGCGGCCGGGCCAGCUGUGAGUGUUUCUU**UGGCAGUGUCUUAG
CUGGUUGUUGUGAGCGGCCAGCUGUGAGUGUUUCUUUAAGGCACGCGGUGAAUGCCG**UUGUGAGCAAUAGUAA
GGAAGCGGUGUUCCCGUCGUGCCUUCUAGAAGUGCUGCACGUUGUUGGCCCGUAAGGAAG**CAAUCAGCAAGUA
UACUGCCCU**AGAAGUGCUGCACGUUGUUGGCCCGGCGAUACCAGCCGAAAGGCCCUUGGCAGCGUCCGCGGG
UCACAGGUUCGAAUCCCGUCGUAGCCACCA-3'

SEQ ID NO: 277 - btRNA$^{Met-CAT}$/5' + 3' TPA/pre-miR-34a/let-7c-5p/pre-miR-34a/miR-
124-3p (352 nt) : A hybrid molecule of bacterial methionine-CAT RNA and
two pre-miR-34a molecules in which miR-34a sequences (mature and guide)
are replaced in the first precursor by let-7c (mature and guide)
sequences and in the second precursor by miR-124 (mature and guide)
sequences [in bold], with the addition of two theophylline aptamers (5' and 3' )
upstream and downstream of the first pre-miR-34a.

5'- GGCUACGUAGCUCAGUUGGUUAGAGCAGCGGCCGGGCGAUACCAGCCGAAAGGCCCUUGGCAGCGUCGG
CCAGCUGUGAGUGUUUCUUUGAGGUAGUAGGUUGUAUGGUUUGUGAGCGGCCAGCUGUGAGUGUUUCUU**UAAG
GCACGCGGUGAAUGCCGUUGUGAGCAAUAGUAAGGAAGCGGUGUUCCCGUCGUGCCUUCU**AGAAGUGCUGCAC
GUUGUUGGCCCGUAAGGAAGAACUGUACACCUUACUACCUUUCAGAAGUGCUGCACGUUGUUGGCCCGGCGAU
ACCAGCCGAAAGGCCCUUGGCAGCGUCCGCGGGUCACAGGUUCGAAUCCCGUCGUAGCCACCA-3'

SEQ ID NO: 278 - btRNA$^{Met-CAT}$/5' + 3' TPA/pre-miR-34a/miR-124-3p/pre-miR-
34a/miR-34a-5p (351 nt): A hybrid molecule of bacterial methionine-CAT
tRNA and two pre-miR-34a molecules in which miR-34a sequences (mature and
guide) are replaced in the first precursor by miR-124 (mature and guide)
sequences and in the second precursor by miR-34a (mature and guide)
sequences [in bold], with the addition of two theophylline aptamers (5' and 3')
upstream and downstream of the first pre-miR-34a.

5'- GGCUACGUAGCUCAGUUGGUUAGAGCAGCGGCCGGGCGAUACCAGCCGAAAGGCCCUUGGCAGCGUCGG
CCAGCUGUGAGUGUUUCUUUAAGGCACGCGGUGAAUGCCGUUGUGAGCAAUAGUAAGGAAG**UGGC
AGUGUCUUAGCUGGUUGUUGUGAGCAAUAGUAAGGAAGCAAUCAGCAAGUAVACUGCCCU**AGAAGUGCUGCAC
GUUGUUGGCCCGUAAGGAAGCGGUGUUCCCGUCGUGCCUUCUAGAAGUGCUGCACGUUGUUGGCCCGGCGAUA
CCAGCCGAAAGGCCCUUGGCAGCGUCCGCGGGUCACAGGUUCGAAUCCCGUCGUAGCCACCA-3'

SEQ ID NO: 279 - btRNAMet-CAT/5' + 3' TPA/pre-miR-34a/miR-34a-5p/pre-miR-
34a/miR-124-3p (351 nt): A hybrid molecule of bacterial methionine-CAT
tRNA and two pre-miR-34a molecules in which miR-34a sequences (mature and
guide) are replaced in the first precursor by miR-34a (mature and guide)
sequences and in the second precursor by miR-124 (mature and guide)
sequences [in bold], with the addition of two theophylline aptamers (5' and 3')
upstream and downstream of the first pre-miR-34a.

5'- GGCUACGUAGCUCAGUUGGUUAGAGCAGCGGCCGGGCGAUACCAGCCGAAAGGCCCUUGGCAGCGUCGG
CCAGCUGUGAGUGUUUCUUUGGCAGUGUCUUAGCUGGUUGUUGUGAGCGGCCAGCUGUGAGUGUUUCUU**UAAG
GCACGCGGUGAAUGCCGUUGUGAGCAAUAGUAAGGAAGCGGUGUUCCCGUCGUGCCUUCU**AGAAGUGCUGCAC
GUUGUUGGCCCGUAAGGAAGCAAUCAGCAAGUAUACUGCCCUAGAAGUGCUGCACGUUGUUGGCCCGGCGAUA
CCAGCCGAAAGGCCCUUGGCAGCGUCCGCGGGUCACAGGUUCGAAUCCCGUCGUAGCCACCA-3'

SEQ ID NO: 280 - btRNA^(Met-CAT)/pre-miR-34a/let-7c-5p/5'TPA/pre-miR-34a/miR-
124-3p (319 nt): A hybrid molecule of bacterial methionine-CAT tRNA and
two pre-miR-34a molecules in which miR-34a sequences (mature and guide)
are replaced in the first precursor by let-7c (mature and guide)
sequences and in the second precursor by miR-124 (mature and guide)
sequences [in bold], with the addition of a theophylline aptamer (5')
upstream of the second pre-miR-34a.

5'- GGCUACGUAGCUCAGUUGGUUAGAGCAGCGGCCGGGCCAGCUGUGAGUGUUUCUUUGAGGUAGUAGGUU
GUAUGGUUUGUGAGCGGCGAUACCAGCCGAAAGGCCCUUGGCAGCGUCGGCCAGCUGUGAGUGUUUCUU**UAAG
GCACGCGGUGAAUGCCGUUGUGAGCAAUAGUAAGGAAGCGGUGUUCCCGUCGUGCCUUCU**AGAAGUGCUGCAC
GUUGUUGGCCCGUAAGGAAGAACUGUACACCUUACUACCUUUCAGAAGUGCUGCACGUUGUUGGCCCCCGCGG
GUCACAGGUUCGAAUCCCGUCGUAGCCACCA-3'

SEQ ID NO: 281 - btRNA^(Met-CAT)/pre-miR-34a/miR-124-3p/5'TPA/pre-miR-
34a-5p (318 nt): A hybrid molecule of bacterial methionine-CAT tRNA and
two pre-miR-34a molecules in which miR-34a sequences (mature and guide)
are replaced in the first precursor by miR-124 (mature and guide)
sequences and in the second precursor by miR-34a (mature and guide)
sequences [in bold], with the addition of a theophylline aptamer (5')
upstream of the second pre-miR-34a.

5'- GGCUACGUAGCUCAGUUGGUUAGAGCAGCGGCCGGGCCAGCUGUGAGUGUUUCUUUAAGGCACGCGGUG
AAUGCCGUUGUGAGCGGCGAUACCAGCCGAAAGGCCCUUGGCAGCGUCGGCCAGCUGUGAGUGUUUCUU**UGGC
AGUGUCUUAGCUGGUUGUUGUGAGCAAUAGUAAGGAAGCAAUCAGCAAGUAUACUGCCCU**AGAAGUGCUGCAC
GUUGUUGGCCCGUAAGGAAGCGGUGUUCCCGUCGUGCCUUCUAGAAGUGCUGCACGUUGUUGGCCCCCGCGG
UCACAGGUUCGAAUCCCGUCGUAGCCACCA-3'

SEQ ID NO: 282 - btRNA^(Met-CAT)/pre-miR-34a/miR-34a-5p/5'TPA/pre-miR-34a/miR-
124-3p (318 nt): A hybrid molecule of bacterial methionine-CAT tRNA and
two pre-miR-34a molecules in which miR-34a sequences (mature and guide)
are replaced in the first precursor by miR-34a (mature and guide)
sequences and in the second precursor by miR-124 (mature and guide)
sequences [in bold], with the addition of a theophylline aptamer (5')
upstream of the second pre-miR-34a.

5'- GGCUACGUAGCUCAGUUGGUUAGAGCAGCGGCCGGGCCAGCUGUGAGUGUUUCUUUGGCAGUGUCUUAG
CUGGUUGUUGUGAGCGGCGAUACCAGCCGAAAGGCCCUUGGCAGCGUCGGCCAGCUGUGAGUGUUUCUU**UAAG
GCACGCGGUGAAUGCCGUUGUGAGCAAUAGUAAGGAAGCGGUGUUCCCGUCGUGCCUUCU**AGAAGUGCUGCAC
GUUGUUGGCCCGUAAGGAAGCAAUCAGCAAGUAUACUGCCCUAGAAGUGCUGCACGUUGUUGGCCCCCGCGGG
UCACAGGUUCGAAUCCCGUCGUAGCCACCA-3'

SEQ ID NO: 283 - btRNA^(Met-CAT)/pre-miR-34a/let-7c-5p/3'TPA/pre-miR-34a/miR-
124-3p (319 nt): A hybrid molecule of bacterial methionine-CAT tRNA and
two pre-miR-34a molecules in which miR-34a sequences (mature and guide)
are replaced in the first precursor by let-7c (mature and guide)
sequences and in the second precursor by miR-124 (mature and guide)
sequences [in bold], with the addition of a theophylline aptamer (3')
downstream of the second pre-miR-34a.

5'- GGCUACGUAGCUCAGUUGGUUAGAGCAGCGGCCGGGCCAGCUGUGAGUGUUUCUUUGAGGUAGUAGGUU
GUAUGGUUUGUGAGCGGCCAGCUGUGAGUGUUUCUUUAAGGCACGCGGUGAAUGCCGUUGUGAGCAAUAGUAA
GGAAGCGGUGUUCCCGUCGUGCCUUCUAGAAGUGCUGCACGUUGUUGGCCCGGCGAUACCAGCCGAAAGGCCC
UUGGCAGCGUCGUAAGGAAGAACUGUACACCUUACUACCUUUCAGAAGUGCUGCACGUUGUUGGCCCCCGCGG
GUCACAGGUUCGAAUCCCGUCGUAGCCACCA-3'

SEQ ID NO: 284 - btRNA^(Met-CAT)/pre-miR-34a/miR-124-3p/3'TPA/pre-miR-34a/miR-
34a-5p (318 nt): A hybrid molecule of bacterial methionine-CAT tRNA and
two pre-miR-34a molecules in which miR-34a sequences (mature and guide)
are replaced in the first precursor by miR-124 (mature and guide)
sequences and in the second precursor by miR-34a (mature and guide)
sequences [in bold], with the addition of a theophylline aptamer (3')
downstream of the second pre-miR-34a.

5'- GGCUACGUAGCUCAGUUGGUUAGAGCAGCGGCCGGGCCAGCUGUGAGUGUUUCUUUAAGGCACGCGGUG
AAUGCCGUUGUGAGCGGCCAGCUGUGAGUGUUUCUUUGGCAGUGUCUUAGCUGGUUGUUGUGAGCAAUAGUAA
GGAAGCAAUCAGCAAGUAUACUGCCCUAGAAGUGCUGCACGUUGUUGGCCCGGCGAUACCAGCCGAAAGGCCC
UUGGCAGCGUCGUAAGGAAGCGGUGUUCCCGUCGUGCCUUCUAGAAGUGCUGCACGUUGUUGGCCCCCGCGGG
UCACAGGUUCGAAUCCCGUCGUAGCCACCA-3'

-continued

SEQ ID NO: 285 - btRNA^(Met-CAT)/pre-miR-34a/miR-34a-5p/3'TPA/pre-miR-34a/miR-124-3p (318 nt): A hybrid molecule of bacterial methionine-CAT tRNA and two pre-miR-34a molecules in which miR-34a sequences (mature and guide) are replaced in the first precursor by miR-34a (mature and guide) sequences and in the second precursor by miR-124 (mature and guide) sequences [in bold], with the addition of a theophylline aptamer (3') downstream of the second pre-miR-34a.

5'- GGCUACGUAGCUCAGUUGGUUAGAGCAGCGGCCGGGCCAGCUGUGAGUGUUUCUUUGGCAGUGUCUUAG
CUGGUUGUUGUGAGCGGCCAGCUGUGAGUGUUUCUUUAAGGCACGCGGUGAAUGCCGUUGUGAGCAAUAGUAA
GGAAGCGGUGUUCCCGUCGUGCCUUCUAGAAGUGCUGCACGUUGUUGGCCCGGCGAUACCAGCCGAAAGGCCC
UUGGCAGCGUCGUAAGGAAGCAAUCAGCAAGUAUACUGCCCUAGAAGUGCUGCACGUUGUUGGCCCCCGCGGG
UCACAGGUUCGAAUCCCGUCGUAGCCACCA-3'

SEQ ID NO: 286 - btRNA^(Met-CAT)/pre-miR-34a/let-7c-5p/5' + 3' TPA/pre-miR-34a/miR-124-3p (352 nt): A hybrid molecule of bacterial methionine-CAT tRNA and two pre-miR-34a molecules in which miR-34a sequences (mature and guide) are replaced in the first precursor by let-7c (mature and guide) sequences and in the second precursor by miR-124 (mature and guide) sequences [in bold], with the addition of two theophylline aptamers (5' and 3') upstream and downstream of the second pre-miR-34a.

5'- GGCUACGUAGCUCAGUUGGUUAGAGCAGCGGCCGGGCCAGCUGUGAGUGUUUCUUUGAGGUAGUAGGUU
GUAUGGUUUGUGAGCGGCGAUACCAGCCGAAAGGCCCUUGGCAGCGUCGGCCAGCUGUGAGUGUUUCUU**AAG
GCACGCGGUGAAUGCCGUUGUGAGCAAUAGUAAGGAAGCGGUGUUCCCGUCGUGCCUUCU**AGAAGUGCUGCAC
GUUGUUGGCCCGGCGAUACCAGCCGAAAGGCCCUUGGCAGCGUCGUAAGGAAGAACUGUACACCUUACUACCU
UUCAGAAGUGCUGCACGUUGUUGGCCCCCGCGGGUCACAGGUUCGAAUCCCGUCGUAGCCACCA-3'

SEQ ID NO: 287 - btRNA^(Met-CAT)/pre-miR-34a/miR-124-3p/5' + 3' TPA/pre-miR-34a/miR-34a-5p (351 nt): A hybrid molecule of bacterial methionine-CAT tRNA and two pre-miR-34a molecules in which miR-34a sequences (mature and guide) are replaced in the first precursor by miR-124 (mature and guide) sequences and in the second precursor by miR-34a (mature and guide) sequences [in bold], with the addition of two theophylline aptamers (5' and 3') upstream and downstream of the second pre-miR-34a.

5'- GGCUACGUAGCUCAGUUGGUUAGAGCAGCGGCCGGGCCAGCUGUGAGUGUUUCUUUAAGGCACGCGGUG
AAUGCCGUUGUGAGCGGCGAUACCAGCCGAAAGGCCCUUGGCAGCGUCGGCCAGCUGUGAGUGUUUCUU**UGGC
AGUGUCUUAGCUGGUUGUUGUGAGCAAUAGUAAGGAAGCAAUCAGCAAGUAVACUGCCCU**AGAAGUGCUGCAC
GUUGUUGGCCCGGCGAUACCAGCCGAAAGGCCCUUGGCAGCGUCGUAAGGAAGCGGUGUUCCCGUCGUGCCUU
CUAGAAGUGCUGCACGUUGUUGGCCCCCGCGGGUCACAGGUUCGAAUCCCGUCGUAGCCACCA-3'

SEQ ID NO: 288 - btRNA^(Met-CAT)/pre-miR-34a/miR-34a-5p/5' + 3' TPA/pre-miR-34a/miR-124-3p (351 nt): A hybrid molecule of bacterial methionine-CAT tRNA and two pre-miR-34a molecules in which miR-34a sequences (mature and guide) are replaced in the first precursor by miR-34a (mature and guide) sequences and in the second precursor by miR-124 (mature and guide) sequences [in bold], with the addition of two theophylline aptamers (5' and 3') upstream and downstream of the second pre-miR-34a.

5'-GGCUACGUAGCUCAGUUGGUUAGAGCAGCGGCCGGGCCAGCUGUGAGUGUUUCUUUGGCAGUGUCUUAG
CUGGUUGUUGUGAGCGGCGAUACCAGCCGAAAGGCCCUUGGCAGCGUCGGCCAGCUGUGAGUGUUUCUU**UAAG
GCACGCGGUGAAUGCCGUUGUGAGCAAUAGUAAGGAAGCGGUGUUCCCGUCGUGCCUUCU**AGAAGUGCUGCAC
GUUGUUGGCCCGGCGAUACCAGCCGAAAGGCCCUUGGCAGCGUCGUAAGGAAGCAAUCAGCAAGUAUACUGCC
CUAGAAGUGCUGCACGUUGUUGGCCCCCGCGGGUCACAGGUUCGAAUCCCGUCGUAGCCACCA-3'

SEQ ID NO: 289 - stabilized pre-miR-34a G138U/139AG derivative shell/scaffold; tRNA sequences provided in Table 8; N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths):

5'-1$^{st}$ or 5' tRNA portion [- optional aptamer, small activating RNA (saRNA) or catalytic RNA -]
GGCCAGCUGUGAGUGUUUCUU [N$^1_{18-200}$] UGUGAGCAAUAGUAAGGAAG [N$^2_{18-200}$] AGAAGUGCUGCACGUUG
UUGGCCC [- optional aptamer, small activating RNA (saRNA) or catalytic RNA -]
2$^{nd}$ or 3' tRNA portion - 3'

SEQ ID NO: 290 - pre-miR-1291 shell/scaffold; tRNA sequences provided in Table 8; N1 and N2 are substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths):

-continued

```
5'-1st or 5' tRNA portion - optional aptamer, small activating RNA(saRNA)
or catalytic RNA - GGUAGAAUUCCAG[N¹₁₈₋₂₀₀]UGUACUGUG[N²₁₈₋₂₀₀]AAAGGACUGUCUUCCUG -
optional aptamer, small activating RNA (saRNA) or catalytic RNA - 2nd or
3' tRNA portion - 3'
```

SEQ ID NO: 291 - pre-mir-200b shell/scaffold; tRNA sequences provided in
Table 8; N1 and N2 are substantially complementary (e.g., at least 85%,
86%, 87%, 88%, 89%, 90%, 91%, 92%, 93%, 94%, 95%, 96%, 97%, 98%, 99% or
100% complementary) and of substantially equal length (e.g., of equal
length or within 3 nucleotide bases if different lengths):

```
5'-1st or 5' tRNA portion - optional aptamer, small activating RNA (saRNA)
or catalytic RNA -
CCAGCUCGGGCAGCCGUGGC[N¹₁₈₋₂₀₀]UGGAGUCAGGUCUC[N²₁₈₋₂₀₀]UGACGGCGGAGCCCUGCACG -
optional aptamer, small activating RNA (saRNA) or catalytic RNA - 2nd or
3' tRNA portion - 3'
```

SEQ ID NO: 292 - pre-mir-133a shell/scaffold; tRNA sequences provided in
Table 8; N1 and N2 are substantially complementary (e.g., at least 85%,
86%, 87%, 88%, 89%, 90%, 91%, 92%, 93%, 94%, 95%, 96%, 97%, 98%, 99% or
100% complementary) and of substantially equal length (e.g., of equal
length or within 3 nucleotide bases if different lengths):

```
5'-1st or 5' tRNA portion - optional aptamer, small activating RNA (saRNA)
or catalytic RNA -
ACAAUGCUUUGCUAG[N¹₁₈₋₂₀₀]CGCCUCUUCAAUGGA[N²₁₈₋₂₀₀]UAGCUAUGCAUUGA - optional
aptamer, small activating RNA (saRNA) or catalytic RNA - 2nd or 3' tRNA
portion - 3'
```

SEQ ID NO: 293 - pre-mir-125a shell/scaffold; tRNA sequences provided in
Table 8; N1 and N2 are substantially complementary (e.g., at least 85%,
86%, 87%, 88%, 89%, 90%, 91%, 92%, 93%, 94%, 95%, 96%, 97%, 98%, 99% or
100% complementary) and of substantially equal length (e.g., of equal
length or within 3 nucleotide bases if different lengths):

```
5'-1st or 5' tRNA portion - optional aptamer, small activating RNA (saRNA)
or catalytic RNA -
UGCCAGUCUCUAGG[N¹₁₈₋₂₀₀]GGACAUCCAGGGUC[N²₁₈₋₂₀₀]UGGCGUCUGGCC - optional
aptamer, small activating RNA (saRNA) or catalytic RNA - 2nd or 3' tRNA
portion - 3'
```

SEQ ID NO: 294 - pre-let-7c shell/scaffold; RNA sequences provided in
Table 8; N1 and N2 are substantially complementary (e.g., at least 85%,
86%, 87%, 88%, 89%, 90%, 91%, 92%, 93%, 94%, 95%, 96%, 97%, 98%, 99% or
100% complementary) and of substantially equal length (e.g., of equal
length or within 3 nucleotide bases if different lengths):

```
5'-1st or 5' tRNA portion - optional aptamer, small activating RNA (saRNA)
or catalytic RNA -

GCAUCCGGGU[N¹₁₈₋₂₀₀]UAGAGUUACACCCUGGGAGUUAA[N²₁₈₋₂₀₀]UUGGAGC - optional
aptamer, small activating RNA (saRNA) or catalytic RNA - 2nd or 3' tRNA
portion - 3'
```

SEQ ID NO: 295 - pre-miR-124 shell/scaffold; tRNA sequences provided in
Table 8; N1 and N2 are substantially complementary (e.g., at least 85%,
86%, 87%, 88%, 89%, 90%, 91%, 92%, 93%, 94%, 95%, 96%, 97%, 98%, 99% or
100% complementary) and of substantially equal length (e.g., of equal
length or within 3 nucleotide bases if different lengths):

```
5'-1st or 5' tRNA portion - optional aptamer, small activating RNA (saRNA)
or catalytic RNA -

AGGCCUCUCUCUC[N¹₁₈₋₂₀₀]UUAAAUGUCCAUACAAU[N²₁₈₋₂₀₀]AAGAAUGGGCUG - optional
aptamer, small activating RNA (saRNA) or catalytic RNA - 2nd or 3' tRNA
portion - 3'
``` two pre-miR-34a molecule shell/scaffolds; tRNA sequences provided in
Table 8; N1 and N2 are substantially complementary (e.g., at least 85%,
86%, 87%, 88%, 89%, 90%, 91%, 92%, 93%, 94%, 95%, 96%, 97%, 98%, 99% or
100% complementary) and of substantially equal length (e.g., of equal
length or within 3 nucleotide bases if different lengths) ; N3 and N4 are
substantially complementary (e.g., at least 85%, 86%, 87%, 88%, 89%, 90%, 91%, 92%, 93%, 94%, 95%, 96%, 97%, 98%, 99% or 100% complementary) and of substantially equal length (e.g., of equal length or within 3 nucleotide bases if different lengths):

SEQ ID NO: 296 -
5'- 1$^{st}$ or 5' tRNA portion -
GGCCAGCUGUGAGUGUUUCUU [N$^1_{18-200}$] UGUGAGCGGCCAGCUGUGAGUGUUUCUU [N$^3_{18-200}$] UGUGAGCAA
UAGUAAGGAAG [N$^4_{18-200}$] AGAAGUGCUGCACGUUGUUGGCCCGUAAGGAAG [N$^2_{18-200}$] AGAAGUGCUGCACG
UUGUUGGCCC - 2$^{nd}$ or 3' tRNA portion -3'

SEQ ID NO: 297 -
5'- 1$^{st}$ or 5' tRNA portion - optional aptamer, small activating RNA (saRNA) or catalytic RNA -
GGCCAGCUGUGAGUGUUUCUU [N$^1_{18-200}$] UGUGAGCGGCCAGCUGUGAGUGUUUCUU [N$^3_{18-200}$] UGUGAGCAA
UAGUAAGGAAG [N$^4_{18-200}$] AGAAGUGCUGCACGUUGUUGGCCCGUAAGGAAG [N$^2_{18-200}$] AGAAGUGCUGCACG
UUGUUGGCCC - optional aptamer, small activating RNA (saRNA) or catalytic RNA - 2$^{nd}$ or 3' tRNA portion -3'

SEQ ID NO: 298 -
5'- 1$^{st}$ or 5' tRNA portion GGCCAGCUGUGAGUGUUUCUU [N$^1_{18-200}$] UGUGAGC - optional aptamer, small activating RNA (saRNA) or catalytic RNA -
GGCCAGCUGUGAGUGUUUCUU [N$^3_{18-200}$] UGUGAGCAAUAGUAAGGAAG [N$^4_{18-200}$] AGAAGUGCUGCACGUUG
UUGGCCC - optional aptamer, small activating RNA (saRNA) - or catalytic RNA -
GUAAGGAAG [N$^2_{18-200}$] AGAAGUGCUGCACGUUGUUGGCCC2$^{nd}$ or 3' tRNA portion -3'

SEQ ID NO: 299: - intentionally left blank

TABLE 8 human tRNA (htRNA) sequences

| Amino acid | Anti codon | SEQ ID NO: | 5' tRNA portion | SEQ ID NO: | 3' tRNA portion |
|---|---|---|---|---|---|
| Ser | TGA | 300 | GCAGCGAUGGCCGAGUGGUUAAGGCGUUGGACU | 301 | AAUCCAAUGGGGUCUCCCCGCGCAGGUUCGAACCCUGCUCGCUGCGCCA |
| Ser | GCT | 302 | GACGAGGUGGCCGAGUGGUUAAGGCGAUGGACU | 303 | AAUCCAUUGUGCUCUGCACGCGUGGGUUCGAAUCCCACCCUCGUCGCCA |
| Leu | TAA | 304 | ACCAGGAUGGCCGAGUGGUUAAGGCGUUGGACU | 305 | GAUCCAAUGGACAUAUGUCCGCGUGGGUUCGAACCCCACUCCUGGUACCA |
| Leu | CAA | 306 | GUCAGGAUGGCCGAGUGGUCUAAGGCGCCAGACU | 307 | GUUCUGGUCUCCGUAUGGAGGCGUGGGUUCGAAUCCCACUUCUGACACCA |
| Gly | GCC | 308 | GCAUGGGUGGUUCAGUGGUAGAAUUCUCGCCU | 309 | ACGCGGGAGGCCCGGGUUCGAUUCCCGGCCCAUGCACCA |
| Gly | TCC | 310 | GCGUUGGUGGUAUAGUGGUUAGCAUAGCUGCCU | 311 | AAGCAGUUGACCCGGGUUCGAUUCCCGGCCAACGCACCA |
| Glu | CTC | 312 | UCCCUGGUGGUCUAGUGGUUAGGAUUCGGCGCU | 313 | ACCGCCGCGGCCCGGGUUCGAUUCCCGGUCAGGGAACCA |
| Asp | GTC | 314 | UCCUCGUUAGUAUAGUGGUGAGUAUCCCCGCCU | 315 | ACGCGGGAGACCGGGGUUCGAUUCCCCGACGGGAGCCA |
| Gln | TTG | 316 | GGUCCCAUGGUGUAAUGGUUAGCACUCUGGACU | 317 | AAUCCAGCGAUCCGAGUUCAAAUCUCGGUGGGACCUCCA |
| Gln | CTG | 318 | GGUUCCAUGGUGUAAUGGUUAGCACUCUGGACU | 319 | AAUCCAGCGAUCCGAGUUCAAAUCUCGGUGGAACCUCCA |
| Arg | ACG | 320 | GGGCCAGUGGCGCAAUGGAUAACGCGUCUGACU | 321 | GAUCAGAAGAUUCCAGGUUCGACUCCUGGCUGGCUCGCCA |
| Arg | TCT | 322 | GGCUCUGUGGCGCAAUGGAUAGCGCAUUGGACU | 323 | AAUUCAAAGGUUGUGGGUUCGAAUCCCACCAGAGUCGCCA |
| Cys | GCA | 324 | GGGGGCAUAGCUCAGUGGUAGAGCAUUUGACU | 325 | GAUCAAGAGGUCCCUGGUUCAAAUCCAGGUGCCCCUCCA |

TABLE 8-continued human tRNA (htRNA) sequences

| Amino acid | Anti codon | SEQ ID NO: | 5' tRNA portion | SEQ ID NO: | 3' tRNA portion |
|---|---|---|---|---|---|
| Lys | CTT | 326 | GCCCGGCUAGCUCAGUCGGUAGAGCAUGGGACU | 327 | AAUCCCAGGGUCGUGGGUUCGAGCCCCACGUUGGGCGCCA |
| Lys | TTT | 328 | GCCUGGAUAGCUCAGUUGGUAGAGCAUCAGACU | 329 | AAUCUGAGGGUCCAGGGUUCAAGUCCCUGUUCAGGCACCA |
| Met | CAT | 330 | GCCUCGUUAGCGCAGUAGGUAGCGCGUCAGUCU | 331 | AAUCUGAAGGUCGUGAGUUCGAUCCUCACACGGGGCACCA |
| Asn | GTT | 332 | GUCUCUGUGGCGCAAUCGGUUAGCGCGUUCGGCU | 333 | AACCGAAAGGUUGGUGGUUCGAUCCCACCCAGGGACGCCA |
| Ala | AGC | 334 | GGGGGUGUAGCUCAGUGGUAGAGCGCGUGCUU | 335 | AUGCACGAGGCCCCGGGUUCAAUCCCCGGCACCUCCACCA |
| His | GTG | 336 | GCCGUGAUCGUAUAGUGGUUAGUACUCUGCGUU | 337 | GCCGCAGCAACCUCGGUUCGAAUCCGAGUCACGGCACCA |
| Ile | AAT | 338 | GGCCGGUUAGCUCAGUUGGUUAGAGCGUGGUGCU | 339 | AACGCCAAGGUCGCGGGUUCGAUCCCCGUACUGGCCACCA |
| Ile | TAT | 340 | GCUCCAGUGGCGCAAUCGGUUAGCGCGCGGUACU | 341 | AAUGCCGAGGUUGUGAGUUCGAUCCUCACCUGGAGCACCA |
| Phe | GAA | 342 | GCCGAAAUAGCUCAGUUGGGAGAGCGUUAGACU | 343 | GAUCUAAAGGUCCCUGGUUCGAUCCCGGGUUUCGGCACCA |
| Pro | AGG | 344 | GGCUCGUUGGUCUAGGGGUAUGAUUCUCGCUU | 345 | AUGCGAGAGGUCCCGGGUUCAAAUCCCGGACGAGCCCCA |
| Trp | CCA | 346 | GACCUCGUGGCGCAACGGUAGCGCGUCUGACU | 347 | GAUCAGAAGGCUGCGUGUUCGAAUCACGUCGGGGUCACCA |
| Tyr | GTA | 348 | CCUUCGAUAGCUCAGUUGGUAGAGCGGAGGACU | 349 | GAUCCUUAGGUCGCUGGUUCGAAUCCGGCUCGAAGGACCA |
| Val | CAC | 350 | GUUUCCGUAGUGUAGUGGUUAUCACGUUCGCCU | 351 | ACGCGAAAGGUCCCCGGUUCGAAACCGGGCGGAAACACCA |
| Thr | TGT | 352 | GGCUCUAUGGCUUAGUUGGUUAAAGCGCCUGUCU | 353 | AAACAGGAGAUCCUGGGUUCGAAUCCCAGUAGAGCCUCCA |
| Thr | AGT | 354 | GGCGCCGUGGCUUAGUUGGUUAAAGCGCCUGUCU | 355 | AAACAGGAGAUCCUGGGUUCGAAUCCCAGCGGUGCCUCCA |

TABLE 10

APTAMER/TARGETING SEQUENCES

| Aptamer Target | RNA Sequence (5' - 3') | SEQ ID NO: |
|---|---|---|
| Sephadex | AGUAAUUUACGUCGACGGUGACGUCGAUGGUUGCGG | 356 |
| Theophylline Aptamer (TPA) | GGCGAUACCAGCCGAAAGGCCCUUGGCAGCGUC | 357 |
| Pegaptanib (anti-VEGF) | CGGAAUCAGUGAAUGCUUAUACAUCCG | 358 |
| EpCAM Aptamer (EpCAMA) | GCGACUGGUUACCCGGUCG | 359 |
| Apolipoprotein B-siRNA (ApoB-siRNA) | GCCUCAGUCUGCUUCGCACC | 360 |
| ICAM1-siRNA | GCCCAAGCUGGCAUCCGUCA | 361 |
| Nrf2-siRNA | UAAUUGUCAACUUCUGUCA | 362 |
| ARV7-siRNA | GUAGUUGUAAGUAUCAUGA | 363 |
| GFP-siRNA | AGUUGUACUCCAGCUUGUGCCC | 364 |
| Scramble-1 (scrm-1) | GUGUAACACGUCUAUACGCCCA | 365 |

TABLE 10-continued

APTAMER/TARGETING SEQUENCES

| Aptamer Target | RNA Sequence (5' - 3') | SEQ ID NO: |
| --- | --- | --- |
| Scramble-2 (scrm-2) | GUUCGUCUGUAGACGGUUGUUG | 366 |
| Scramble-3 (scrm-3) | UUCUCCGAAGCUGUCACGUUU | 367 |
| Scramble-4 (scrm-4) | AAGCGCGCUUUGUAGGAUUCGU | 368 |
| Scramble-5 (scrm-5) | GGUGUCGUUUCUCUGGUGAGUA | 369 |

EXAMPLES

The following examples are offered to illustrate, but not to limit the claimed invention.

Example 1

Bioengineered ncRNAs Selectively Change Cellular miRNome Profiles for Cancer Therapy Materials and Methods Bacterial culture. DH5u (Thermo Fisher Scientific, Rockford, IL) and HST08 (Clontech Laboratories, Mountain View, CA) were grown at 37° C. in LB supplemented with 100 μg/ml ampicillin for plasmid preparation and amplification. To produce RNA, 2×YT media supplemented with 100 μg/ml ampicillin was used for enriched growth of HST08 E. coli.

Human cell culture. Human lung carcinoma cell lines A549 H23, H1650, H1299 and H1975 were purchased from American Type Culture Collection (Manassas, VA, USA). HEK293T and Dicer-KO (4-25) cell lines were kindly provided by Prof. Bryan R. Cullen (Duke University, Durham, NC) (Bogerd et al., 2014). Luciferase and GFP-expressing A549-Luc-GFP cells were generated by transduction with pCCLc-Luc-EGFP lentiviral constructs (Vector Core, UC Davis Medical Center, Sacramento, CA). Lung carcinoma cell lines were maintained in RPMI 1640 supplemented with 10% fetal bovine serum and 293T cells were maintained in DMEM supplemented with 10% fetal bovine serum and Gentamicin (10 μg/mL), both grown at 37° C. in a humidified atmosphere with 5% CO2 and 95% air.

Construction of ncRNA expression plasmids. Sequences of individual miRNAs and pre-miR-34a were obtained from miRBase (mirbase.org/), while siRNA and RNA aptamer sequences were gathered from previously reported studies (Table 1). Inserts coding target ncRNA sequences (Table 2) were generated by PCR amplification using primers (IDT, San Diego, CA) (Table 2). Amplicons were annealed into pBSTNAV (Ponchon et al., 2009) linearized by SacII and EagI (New England Biolabs, Ipswich, MA) via Seamless Recombination (Clontech Laboratories). Plasmids were propagated in DH5u cells and confirmed by sequencing analyses (Genscript, Piscataway, NJ).

TABLE 1

List of siRNA and RNA aptamer sequences obtained from literature for bioengineering of target ncRNA agents

| Name | RNA Sequence (5' - 3') | Reference |
| --- | --- | --- |
| Apolipoprotein B-siRNA (ApoB-siRNA) | GCCUCAGUCUGCUUCGCACC (SEQ ID NO: 360) | (Raal et al., 2010) |
| ICAM1-siRNA | GCCCAAGCUGGCAUCCGUCA (SEQ ID NO: 361) | (Miner et al., 2004) |
| Nrf2-siRNA | UAAUUGUCAACUUCUGUCA (SEQ ID NO: 362) | (Feinstein, 2013) |
| ARV7-siRNA | GUAGUUGUAAGUAUCAUGA (SEQ ID NO: 363) | (Liu et al., 2014) |
| GFP-siRNA | AGUUGUACUCCAGCUUGUGCCC (SEQ ID NO: 364) | (Chen et al., 2015) |
| Theophylline Aptamer (TPA) | GGCGAUACCAGCCGAAAGGCCCUUGGCAGCGUC (SEQ ID NO: 357) | (Zimmermann et al., 2000) |
| Pegaptanib | CGGAAUCAGUGAAUGCUUAUACAUCCG (SEQ ID NO: 358) | (Ng et al., 2006) |
| EpCAM Aptamer (EpCAMA) | GCGACUGGUUACCCGGUCG (SEQ ID NO: 359) | (Shigdar et al., 2011) |
| scrm-1 | GUGUAACACGUCUAUACGCCCA (SEQ ID NO: 365) | (Schober et al., 2014) |
| scrm-2 | GUUCGUCUGUAGACGGUUGUUG (SEQ ID NO: 366) | genscript.com/siRNA_target_finder.html |
| scrm-3 | UUCUCCGAAGCUGUCACGUUU (SEQ ID NO: 367) | (Luan et al., 2010) |
| scrm-4 | AAGCGCGCUUUGUAGGAUUCGU (SEQ ID NO: 368) | (Nakatsu et al., 2013) |
| scrm-5 | GGUGUCGUUUCUCUGGUGAGUA (SEQ ID NO: 369) | invivogen.com/sirnawizard/ |

TABLE 2A

| Name | # nts | RNA Sequence | pre-miR-34a derivatives | MW (Da) | Primers (5'-3') to clone corresponding coding sequence |
|---|---|---|---|---|---|
| MSA/mir-34a-129nt | 233 | GGCUACGUAGCUCAGUUGGUUAGAGCAGCGGCCGAGUAAUUUACGUCGACCUGGACCCGGCCAGCU GUGAGUGUUCUUUGGCAGUGUCUUAGCUGGUUGUGUGAGCGAUUGGUUGUGAGCAAUAGAAGCAAG UAUACUGCCCUAGAAGUGCUGACACGUUGUGGGGCCCAAGAGGGAAGAUGACGUCGAUGGUUGCGG CCGCGGGUCACAGGUUCGAAUCCCGUCGUAGCCACCA (SEQ ID NO: 383) | | 75,604 | F AGTAATTTACGTCGACGTGGACC GGCCAGCTGTGAGTGTT (SEQ ID NO: 388) CGGCCGCAACCATCGACGTCAT<br>R CTTCCCTCTTGGGCCCCACAACG (SEQ ID NO: 389) |
| tRNA/mir-34a-110nt 144AC | 180 | GGCUACGUAGCUCAGUUGGUUAGAGCAGCGGCCGGCCAGCUGUGAGUGUUUCUU UGGCAGUGUC UUAGCUGGUUGUGUGAGCAAUAGUAAGGAAG CAAUCAGCAAGUAUACUGCCCUAGAAGUGCUGCA CGUUGUGGGGCCCCGGUCACAGGUUCGAAUCCCGUCGUAGCCACCA (SEQ ID NO: 384) | | 58,322 | F GTTAGAGCAGCGGCCGGCCAG CTGTGAGTGTTTCTTTG (SEQ ID NO: 390)<br>R TCGAACCTGTGACCGCGGGGC CCCACAACGTGCAG (SEQ ID NO: 391) |
| tRNA/mir-34a-110nt Wild type | 181 | GGCUACGUAGCUCAGUUGGUUAGAGCAGCGGCCGGGCCAGCUGUGAGUGUUUCUUUGGCAGUGUC UUAGCUGGUUGUGUGAGCAAUAGUAAGGAAGCAAUCAGCAAGUAUACUGCCCUAGAAGUGCUGCA CGUUGUGGGGCCCCGGGUCACAGGUUCGAAUCCCGUCGUAGCCACCA (SEQ ID NO: 385) | | 58,627 | R GTTAGAGCAGCGGCCGGCCAG CTGTGAGTGTTTCTTTG (SEQ ID NO: 390) TCGAACCTGTGACCCGCGGGGG CCCCACAACGTGCAG (SEQ ID NO: 393) |
| tRNA/mir-34a-110nt G138U/139AG | 180 | GGCUACGUAGCUCAGUUGGUUAGAGCAGCGGCCGGGCCAGCUGUGAGUGUUUCUU UGGCAGUGUC UUAGCUGGUUGUGUGAGCAAUACUGCCCUAGAAGUGCUGCA CGUUGUGGCCCCGCGGUCACAGGUUCGAAUCCCGUCGUAGCCACCA (SEQ ID NO: 257) | | 58,243 | F GTTAGAGCAGCGGCCGGCCAG CTGTGAGTGTTTCTTTG (SEQ ID NO: 390)<br>R TCGAACCTGTGACCGCGGGGG CCAACAACGTGCAGC (SEQ ID NO: 395) |
| tRNA/mir-34a-110nt A39CC | 182 | GGCUACGUAGCUCAGUUGGUUAGAGCAGCAAUAGUAAGGAAG CUUAUCAGCAAGUAUACUGCCUAGAAGUGCUGC CAAUCAGCAAGUAUACUGCCCUAGAAGUGCUGC ACGUUGUGGGGCCCCGCGGUUCACAGGUUCGAAUCCCGUCGUAGCCACCA (SEQ ID NO: 387) | | 58,908 | F GTTAGAGCAGCGGCCGCGGCCCC GCTGTGAGTGTTTC (SEQ ID NO: 396)<br>R TCGAACCTGTGACCGCGGGGG CCAACAACGTGCAGC (SEQ ID NO: 393) |

TABLE 2B

| Name | # nts | RNA Sequence | nCAR/sRNAs MW (Da) | | Primers (5'-3') |
|---|---|---|---|---|---|
| miR-27 a-3p | 181 | GGCUACGUAGCUCAGUUGGUUAGAGCAGCGGCCGGGCCAGCUGUGAG UGUUUCUUUCACAGUUGGCUAAGUUCCGCUGUGAGCAAUAGUAAGG AAGGCAGGGCUUAGCUGCUUGUGAGCUAGAAGUGCUGCACGUUGUGG CCCCGCGGGUCACAGGUUCGAAUCCCGUCGUAGCCACCA (SEQ ID NO: 398) | 58,580 | F | GTTAGAGCAGCGGCCGGGCCAGCTGTGAGTGTTTCTTTCA CAGTGGCTAAGTTCCGCTGTGAGCAATAGTAA (SEQ ID NO: 442) |
| | | | | R | TCGAACCTGTGACCCGCGGGGCCAACAACGTGCAGCACTT CTAGTCACAAGCAGCTAAGCCCTGCCTTCCTTACTATTGC (SEQ ID NO: 443) |
| miR-27b-3p | 180 | GGCUACGUAGCUCAGUUGGUUAGAGCAGCGGCCGGGCCAGCUGUGAG UGUUUCUUUCACAGUUGGCUAAGUUCUGCUUGUGAGCAAUAGUAAGG AAGGCAGAGCUAGCUACCAUGUGACCAGAAGUGCUGCACGUUGUGC CCCGCGGGUCACAGGUUCGAAUCCCGUCGUAGCCACCA (SEQ ID NO: 399) | 58,242 | F | GTTAGAGCAGCGGCCGGGCCAGCTGTGAGTGTTTCTTTCA CAGTGGCTAAGTTCTGCTTGTGAGCAATAGTAA (SEQ ID NO: 444) |
| | | | | R | TCGAACCTGTGACCCGCGGGGCCAACAACGTGCAGCACTT CTGGTCACAGTGAGCTAGCTCTGCCTTCCTTACTATTGC (SEQ ID NO: 445) |
| miR-892b-3p | 180 | GGCUACGUAGCUCAGUUGGUUAGAGCAGCGGCCGGGCCAGCUGUGAG UGUUUCUUCACUGGCUCCUUUCUGGUAGAUGUGAGCAAUAGUAAGG AAUCUACUGACAAGUGAGCCAGUUUAGAAGUGCUGCACGUUGUGGC CCCGCGGGUCACAGGUUCGAAUCCCGUCGUAGCCACCA (SEQ ID NO: 400) | 58,203 | F | GTTAGAGCAGCGGCCGGGCCAGCTGTGAGTGTTTCTTCACT GGCTCCTTTCTGGTAGATGTGAGCAATAGTAA (SEQ ID NO: 446) |
| | | | | R | TCGAACCTGTGACCCGCGGGGCCAACAACGTGCAGCACTT CTAAACTGGCTCACTTCTGAGTAGATTCCTTACTATTGC (SEQ ID NO: 447) |
| miR-451a-5p | 180 | GGCUACGUAGCUCAGUUGGUUAGAGCAGCGGCCGGGCCAGCUGUGAG UGUUUCUUAAACCGUUACCAUUACUGAGUUUGUGAGCAAUAGUAAGGA AGACUUAGUAUGGUUAAUUGGUUCUAGAAGUGCUGCACGUUGUGGCC CCCGCGGGUCACAGGUUCGAAUCCCGUCGUAGCCACCA (SEQ ID NO: 401) | 58,198 | F | GTTAGAGCAGCGGCCGGGCCAGCTGTGAGTGTTTCTTAAAC CGTTACCATTACTGAGTTTGTGAGCAATAGTAA (SEQ ID NO: 448) |
| | | | | R | CTAGAACCATTAACCATACTAAGTCTTCCTTACTATTGC (SEQ ID NO: 449) |
| ApoB-siRNA | 180 | GGCUACGUAGCUCAGUUGGUUAGAGCAGCGGCCGGGCCAGCUGUGAG UGUUUCUGCUUCGCACCUGUGAGCAAUAGUAAGG AAGGGUGCGAACAGUACUGGCCUAGAAGUGCUGCACGUUGUGGC CCCCGCGGGUCACAGGUUCGAAUCCCGUCGUAGCCACCA (SEQ ID NO: 402) | 58,232 | F | GTTAGAGCAGCGGCCGGGCCAGCTGTGAGTGTTTCTTTGCC TCAGTCTGCTTCGCACCTGTGAGCAATAGTAA (SEQ ID NO: 450) |
| | | | | R | TCGAACCTGTGACCCGCGGGGCCAACAACGTGCAGCACTT CTAGGCCTCAGTACTGTTCGCACCCTTCCTTACTATTGC (SEQ ID NO: 451) |
| anti-miR-33a-5p | 180 | GGCUACGUAGCUCAGUUGGUUAGAGCAGCGGCCGGGCCAGCUGUGAG UGUUUCUUACCACCAGAACAUGCAAUGCCAAUGUGAGCAAUGUAGAAGGA AUUGCAUUGGUAUUCUGGUUGUGGAAGUGCUGCACGUUGUGGCC CCCGCGGGUCACAGGUUCGAAUCCCGUCGUAGCCACCA (SEQ ID NO: 403) | 58,273 | F | GTTAGAGCAGCGGCCGGGCCAGCTGTGAGTGTTTCTTACCA CCAGAACATGCAATGCAATGTGAGCAAT (SEQ ID NO: 452) |
| | | | | R | TCGAACCTGTGACCCGCGGGGCCAACAACGTGCAGCACTT CTACCACCAGAATATCGCAATGCAATTCCTTA (SEQ ID NO: 453) |
| anti-miR-126-3p | 180 | GGCUACGUAGCUCAGUUGGUUAGAGCAGCGGCCGGGCCAGCUGUGAG UGUUUCUUAGCAUGGCACUCAUUAUUACGCUGUGAGCAAUAGUAAGGA AGCGUAAUAAAGAGUGCCAUGCCUAGAAGUGCUGCACGUUGUGGCC CCCGGGUCACAGGUUCGAAUCCCGUCGUAGCCACCA (SEQ ID NO: 404) | 58,233 | F | GTTAGAGCAGCGGCCGGGCCAGCTGTGAGTGTTTCTTAGCA TGGCACTCATTATTACGCTGTGAGCAATAGTAA (SEQ ID NO: 454) |
| | | | | R | TCGAACCTGTGACCCGCGGGGCCAACAACGTGCAGCACTT CTAGGCCATGGCAACTCTTATTACGCTTCCTTACTATTGC (SEQ ID NO: 455) |
| ICAM1-siRNA | 180 | GGCUACGUAGCUCAGUUGGUUAGAGCAGCGGCCGGGCCAGCUGUGAG UGUUUCUUGCCCAAGCUGGCAUCGUCAUUGUGAGCAAUAGUAAGG AAGUGGAUCCAUGCUUGGCCUAGAAGUGCUGCACGUUGUGGC CCCGCGGGUCACAGGUUCGAAUCCCGUCGUAGCCACCA (SEQ ID NO: 405) | 58,232 | F | GTTAGAGCAGCGGCCGGGCCAGCTGTGAGTGTTTCTTTGCC CAAGCTGGCATCGTCATTGTGAGCAATAGTAA (SEQ ID NO: 456) |
| | | | | R | TCGAACCTGTGACCCGCGGGGCCAACAACGTGCAGCACTT CTAGGGCCAAGCATGGATCCGTCACTTCCTTACTATTGC (SEQ ID NO: 457) |
| miR-298-5p | 180 | GGCUACGUAGCUCAGUUGGUUAGAGCAGCGGCCGGGCCAGCUGUGAG UGUUUCUUAGGAAGAAGCAGGTUCCCAUGAGCAAUAAGA GGGGAGAACCCCAUGGUUCGACAGAAGUGCUGCACGUUGGCC CCCGCGGGUCACAGGUUCGAAUCCCGUCGUAGCCACCA (SEQ ID NO: 406) | 58,364 | F | GTTAGAGCAGCGGCCGGGCCAGCTGTGAGTGTTTCTTAGCA GAAGGAGGTTCTCCATGAGCAATAGTAA (SEQ ID NO: 458) |
| | | | | R | TCGAACCTGTGACCCGCGGGGCCAACAACGTGCAGCACTT CTGTCAAAAGCATGGGGTTCTCCCCTTCCTTACTATTGC (SEQ ID NO: 459) |
| miR-519c-5p | 180 | GGCUACGUAGCUCAGUUGGUUAGAGCAGCGGCCGGGCCAGCUGUGAG UGUUUCUCUCUAGAGGAAGCGUUUCUGUGGAGCUUUCCAUUAGCAUAA AACAGAAAGUCAUCUUUUAGAUUAGAAGUGCUGCACGUUGUGGCC CCCGCGGGUCACAGGUUCGAAUCCCGUCGUAGCCACCA (SEQ ID NO: 407) | 58,252 | F | GTTAGAGCAGCGGCCGGGCCAGCTGTGAGTGTTTCTCTCT AGAGGGAAGCGCTTTCTGTGGAGCAATAGTAA (SEQ ID NO: 460) |
| | | | | R | TCGAACCTGTGACCCGCGGGGCCAACAACGTGCAGCACTT CTAATCTAAAAGATGACACTTTCGTTCCTTACTATTGC (SEQ ID NO: 461) |
| miR-122-5p | 180 | GGCUACGUAGCUCAGUUGGUUAGAGCAGCGGCCGGGCCAGCUGUGAG UGUUUCUUUGGAGUGUGACAAUGGUGUUUGUGUGAGCAAUAGUAAGG | 58,249 | F | GTTAGAGCAGCGGCCGGGCCAGCTGTGAGTGTTTCTTTGGA GTGTGACAATGGTGTTTGTGAGCAATAGTAA (SEQ ID NO: 462) |

TABLE 2B-continued

| Name | # nts | RNA Sequence | nCAR/sRNAs MW (Da) | | Primers (5'-3') |
|---|---|---|---|---|---|
| Nrf2-siRNA | 180 | AACAAACGCCAUGUACACUCCCUAGAAGUGCUGCACGUUGUUGGCC CCCGCGGGUCACAGGUUCGAAUCCCGUCGUAGCCACCA (SEQ ID NO: 408) | 58,188 | R | TCGAACCTGTGACCGCGGGGGCCAACAACGTGCAGCACTT CTAGGGAGTGTGTACATGGCGTTTGTTCCTTACTATT (SEQ ID NO: 463) |
| miR-335-5p | 181 | GGCUACGUAGCUCAGUUGGUUAGAGCAGCGGCCGCUGAUAAUCUGUUCACUCUGUCCAGUUGUGAGCAAUAGUAAGGAAACUGACAGAGUAUGACAAUUCUAGAAGAGUGCACGUUGUUGGCCC CCGCGGGUCACAGGUUCGAAUCCCGUCGUAGCCACCA (SEQ ID NO: 409) | 58,470 | F | GTTAGAGCAGCGGCCGCTGTGAGTGTTTCTTCAA GTCAACTACTGTCAGTTTGTGAGCAATAGTA (SEQ ID NO: 464) |
| | | | | R | TCGAACCTGTGACCGCGGGGGCCAACAACGTGCAGCACTT CTAGAATTGTCATACTCTGTCAGTTTTCCTTACTAT (SEQ ID NO: 465) |
| miR-126-3p | 180 | GGCUACGUAGCUCAGUUGGUUAGAGCAGCGGCCGCUGAUAG UGUUUCUUUCAGAGCAAUAAACAUGUGUGAGCAAUAGUAAGG AACCGUUUUUCAUUAAUGCUCUUGCAAUCCGUCGUAGCCACCA (SEQ ID NO: 410) | 58,228 | F | GTTAGAGCAGCGGCCGCTGTGAGTGTTTCTTCAA GAGCAATAACGAAAAATGTTGTGAGCAA (SEQ ID NO: 466) |
| | | | | R | TCGAACCTGTGACCGCGGGGGCCAACAACGTGCAGCACTT CTAGCAAGAGCAATAATGAAAAACGGTTCCTTAC (SEQ ID NO: 467) |
| miR-144-5p | 180 | GGCUACGUAGCUCAGUUGGUUAGAGCGGCCGCUGAUGUGAG UGUUUCUUCGACCGUGAGUAAUAAUGCGUGUGAGCAAUAGUAAGGA AGUGCAUAUAUCUCUAUGUACGCAGAAUUCGUCGUAGCCACCA (SEQ ID NO: 411) | 58,214 | F | GTTAGAGCAGCGGCCGCTGTGAGTGTTTCTTCGT ACCGTGAGTAATAATGCGTGTGAGCAA (SEQ ID NO: 468) |
| | | | | R | TCGAACCTGTGACCGCGGGGGCCAACAACGTGCAGCACTT CTGCGTACCATAGAGAATAATGCACTTCCTTACT (SEQ ID NO: 469) |
| ARV7-siRNA | 180 | GGCUACGUAGCUCAGUUGGUUAGAGCAGCGGCCGCUGUGAG UGUUUCUUGGAUAUCAUAUACUGUAAGUGUAAUAUCAUAUACGAGAUUACAGUAACGUAGAAUGCUCUACAACUAAUCCGUCGUAGCCACCA (SEQ ID NO: 412) | 58,252 | F | GTTAGAGCAGCGGCCGCTGTGAGTGTTTCTTGGAT ATCATCATATACTGTAAGTGTGAGCAATAGTA (SEQ ID NO: 470) |
| | | | | R | TCGAACCTGTGACCGCGGGGGCCAACAACGTGCAGCACTT CTATGATATCATACATTACTGTAAATTCCTTACTATTG (SEQ ID NO: 471) |
| miR-200c-5p | 180 | GGCUACGUAGCUCAGUUGGUUAGAGCAGCGGCCGCUGUGAG UGUUUCUGUAAGUAAUGUAAUGAAUGUGUGAGCAAUAGUAAGG AGCAUCAUGAACUAAUCAACUAAAUCCGUCGUAGCCACCA (SEQ ID NO: 413) | 58,186 | F | GTTAGAGCAGCGGCCGCTGTGAGTGTTTCTGTAG TTGTAAGTATCATGATGTTTGGTGTGAGCAATAGTAA (SEQ ID NO: 472) |
| | | | | R | TCGAACCTGTGACCGCGGGGGCCAACAACGTGCAGCACTT CTATTAGTTGTATAGTTCATGATGCTTCCTTACTATTGC (SEQ ID NO: 473) |
| GFP-siRNA | 180 | CCCGCGGGUCACAGGUUCGAAUCCCGUCGUAGCCACCA (SEQ ID NO: 414) UGUUUCGUCCUACCCAGAGTTGATUGAGCAGCGGCCGCUGUGAG AAUCAAACACUCUGUGAAGACCCUAGAAGUGCUGCACCACCA | | F | GTTAGAGCAGCGGCCGCTGTGAGTGTTTCTTGAGT TTACCCAGTGTTCTTACCACAGAGTGTTTGGTGAGCAATAGTAA (SEQ ID NO: 474) |
| | | | | R | TCGAACCTGTGACCGCGGGGGCCAACAACGTGCAGCACTT CTAGGTCTTACCACAGAGTGTTTGATTCCTTACTATTG (SEQ ID NO: 475) |
| let-7c-5p | 180 | GGCUACGUAGCUCAGUUGGUUAGAGCAGCGGCCGCUGUGAG UGUUUCUUGAGGUAGUAGGUUGUAUGGUUUGUGAGCAAUAGUAAGG AAGGGCACAAGGUGUAGUACAACCUAGUGCUGCACGUUGUUGGCCC CCCGCGGGUCACAGGTTCGAATCCCGTCGTAGCCACCA (SEQ ID NO: 415) | 58,264 | F | GTTAGAGCAGCGGCCGCTGTGAGTGTTTCTTAGTT GTACTCCAGCTTGTGCCCTGTGAGCAATAGTAA (SEQ ID NO: 476) |
| | | | | R | TCGAACCTGTGACCGCGGGGGCCAACAACGTGCAGCACTT CTAGGTTGTACTACCACTTGTGCCCTTCCTTACTATTGC (SEQ ID NO: 477) |
| miR-127-3p | 181 | GGCUACGUAGCUCAGUUGGUUAGAGCAGCGGCCGCUGAG UGUUUCUACGGUGUUGGCGGUAUAGGTTTTGTGAGCAA AAGAACUGUACACCUUACUAGGUCCGCUGUGAGCAAUAGUGAAGG CCGCGGGGUCACAGGUUCGAAUCCCGUCGUAGCCACCA (SEQ ID NO: 259) | 58,535 | F | GTTAGAGCAGCGGCCGCTGTGAGTGTTTCTTGAG GTAGTAGGTTGTATGGTTTGTGAGCAA (SEQ ID NO: 478) |
| | | | | R | TCGAACCTGTGACCGCGGGGGCCAACAACGTGCAGCACTT CTGAAAGGTAGTAAGGTGTACAGTTCTTCCTTACT (SEQ ID NO: 479) |
| miR-34a-5p | 185 | GGCUACGUAGCUCAGUUGGUUAGAGCAGCGGCCGCUGUGAG UGUUUCUUUGGCAGUGUCUUAGCUGGUUGUGUGGAAGUGCUGAAGGCUGGAAAAGCUGGAAAGCUCAGAGCAUUUCCGUCGUAGCCACCA (SEQ ID NO: 417) | 59,927 | F | GTTAGAGCAGCGGCCGCTGTGAGTGTTTCTATCGG ATCCGTCTGAGCTTGGCTTGCAGTTGAGCAAT (SEQ ID NO: 480) |
| | | | | R | TCGAACCTGTGACCGCGGGGGCCAACAACGTGCAGCACTT CTATCAGAGCCCTCTGAGCTTCAGCAGGCTTTCCTTA (SEQ ID NO: 481) |
| miR-124-3p | 180 | GGCUACGUAGCUCAGUUGGUUAGAGCAGCGGCCGCUGUGAG UGUUUCUUAAGGCACGCGGUGAAUGCCAAGAAUGGGUGUUCCGUGGUUCCCGUGUCCGUUCUCUAGAAAGUGCUGCACGUUGUUGGCCC CCGCGGGTCACAGGTTCGAATCCCGTCGTAGCCACCA (SEQ ID NO: 257) | 58,243 | F | GTTAGAGCAGCGGCCGCTGTGAGTGTTTCTTTAAG GCACGCGGTGAATGCCAAGAA (SEQ ID NO: 390) |
| | | | | R | TCGAACCTGTGACCGCGGGGGCCAACAACGTGCAGC (SEQ ID NO: 483) |
| miR-124-3p | 180 | GGCUACGUAGCUCAGUUGGUUAGAGCAGCGGCCGCUGUGAG UGUUUCUUUAAGGCACGCGGUGAAUGCCAAGAAUGGGUGUGAGCAAUAGUAAGGAAGGCCUUUAAGGCACGCGGUGAAUGCCUUCGUUCCGUCGUAGCCACCA (SEQ ID NO: 258) | 58,265 | F | GTTAGAGCAGCGGCCGCTGTGAGTGTTTCTTTAAG GCACGCGGTGAATGCCAAGAA (SEQ ID NO: 484) |
| | | | | R | TCGAACCTGTGACCGCGGGGGCCAACAACGTGCAGCACTT CTAGAAGGCACGCGGAACACCGCTTCCTTACTAT (SEQ ID NO: 485) |
| miR-328-3p | 180 | GGCUACGUAGCUCAGUUGGUUAGAGCAGCGGCCGCUGUGAG UGUUUCUUCUGGCCCUCUCUGCCCUUCCGUGUGAGCAAUAGUAAGG | 58,335 | F | GTTAGAGCAGCGGCCGCTGTGAGTGTTTCTTCTGG CCCTCTGCCCTTCCGTGTGTGAGCAATAGTAA (SEQ ID NO: 486) |

TABLE 2B-continued

| Name | # nts | RNA Sequence | nCAR/sRNAs MW (Da) | | Primers (5'-3') |
|---|---|---|---|---|---|
| | | AAGCGGGGGGAGAUGGGGCCAUUAGAAGUGCUGCACGUGUGGC CCCGCGGGUCACAGGUUCGAAUCCCGUCGUAGCCACCA (SEQ ID NO: 420) | | R | TCGAACCTGTGACCCGCGGGGGCCAACAACGTGCAGCACTT CTAATGCCCCCATCTCCCCCCGCTTCCTTACTATGC (SEQ ID NO: 487) |
| anti-miR-451b-5p | 180 | GGCUACGUAGCUCAGUUGGUUAGAGCAGCGGCCGGGCCAGCUGUGAG UGUUCUUCCGUUCCUUGGCAAUGGUAAUUGUGAGCAAUAGUAAGG AAAUUACCAUUCGAACCAUUAAGAAGCGUCUGCACGUGUUGGCC CCCGCGGGUCACAGGUUCGAAUCCCGUCGUAGCCACCA (SEQ ID NO: 421) | 58,156 | F | GTTAGAGCAGCGGCCGGGCCAGCTGTGAGTGTTCTTCCGT TCCTTGGCAATGGTAATTGTGAGCAATAGTA (SEQ ID NO: 488) |
| | | | | R | TCGAACCTGTGACCCGCGGGGGCCAACAACGTGCAGCACTT CTAACGTTCCTTATGGAATTGGTAATTTCCTTACTA (SEQ ID NO: 489) |
| tRNAMet | 75 | GGCUACGUAGCUCAGUUGGUUAGAGCAGCGGCCGGAUCCCGCGGGUC ACAGGUUCGAAUCCCGUCGUAGCCACCA (SEQ ID NO: 422) | 24,344 | F | TTGTAACGCTGAATTCGGCTACGAGCTCAGTTGGTTAGAGC AGCGGCCGGATATCCGCGGGTCACAGGT (SEQ ID NO: 490) |
| | | | | R | CTTTCGCTAAGGATCTGCAGTGGTTGGCTACGACGGGATTCG AACCTGTGACCCGCGGATAT (SEQ ID NO: 491) |
| MSA | 107 | GGCUACGUAGCUCAGUUGGUUAGAGCAGCGGCCGAGUAAUUUACGUC GACGGUGACGUCGAUGGUUGGGCCGGCGCGGGUCACAGGUUCGAAUCCC GUCGUAGCCACCUUAGCGAAAGCUAAGGAUUUUUUUU AAGCUU (SEQ ID NO: 423) | 47,870 | | |
| miR-206-3p | 180 | GGCUACGUAGCUCAGUUGGUUAGAGCAGCGGCCGGGCCAGCUGUGAG UGUUCUUUGGAAUGUAAGGAAGUGUGUGUGUGAGCAAUAGUAAGG AACCAUGCAUUCUCUUACAGGUCACACUGUUGGGCACUAUAUCCCCAAGAAGUGCUGCACGUUGUGGCC CCCGCGGGUCACAGGUUCGAAUCCCGUCGUAGCCACCA (SEQ ID NO: 424) | 58,251 | F | GTTAGAGCAGCGGCCGGGCCAGCTGTGAGTGTTCTTTGGA ATGTAAGGAAGTGTGTGTGTGAGCAA (SEQ ID NO: 492) |
| | | | | R | TCGAACCTGTGACCCGCGGGGGCCAACAACGTGCAGCACTT CTTGGGAATATAAAGAAGCATGTTGGTTCCTTACTA (SEQ ID NO: 493) |
| anti-miR-21-5p-3 | 180 | GGCUACGUAGCUCAGUUGGUUAGAGCAGCGGCCGGGCCAGCUGUGAG UGUUUGCAUGAGAUUUUGUGAGCAAUAUUUGACUGGUUGCAUGAGAUUUUGUGAGCAAUA AGAAUCUCACAAUGCAUACACCAGUAAGAGUGCUGCACGUUGUGGCC CCCGCGGGUCACAGGUUCGAAUCCCGUCGUAGCCACCA (SEQ ID NO: 425) | 58,235 | F | GTTAGAGCAGCGGCCGGGCCAGCTGTGAGTGTTTCTTGACT GGTTGTTGCATGAGATTTTGTGAGCAATA (SEQ ID NO: 494) |
| | | | | R | TCGAACCTGTGACCCGCGGGGGCCAACAACGTGCAGCACTT CTATACTGGTGTATGCATGAGATTCTTCCTTAC (SEQ ID NO: 495) |
| miR-33a-5p | 180 | GGCUACGUAGCUCAGUUGGUUAGAGCAGCGGCCGGGCCAGCUGUGAG UGUUUGUGCAUUGUAGUUGCAUUGUGAGCAAUAGUAAGG AAGGUGCAAUGAAACGACAAUGCAAAGAAGUGCUGCACGUUGUGGCC CCCGCGGGUCACAGGUUCGAAUCCCGUCGUAGCCACCA (SEQ ID NO: 426) | 58,361 | F | GTTAGAGCAGCGGCCGGGCCAGCTGTGAGTGTTTCTTGTGC ATTGTAGTTGCATTGTGAGCAAT (SEQ ID NO: 496) |
| | | | | R | TCGAACCTGTACCCGCGGGGGCCAACAACGTGCAGCACTT CTTTGTGCATTGTCGTTTCATTGCACCTTCCTTACT (SEQ ID NO: 497) |
| miR-130b-3p | 180 | GGCUACGUAGCUCAGUUGGUUAGAGCAGCGGCCGGGCCAGCUGUGAG UGUUUCUUCAGUGCAAUGAUGAAAGGGCAUUGUGAGCAAUAUGAAGGA AGUGCGUCUUCCGUUGCAACUAUAGAAGUGCUGCACGUUGUGGCC CCCGCGGGUCACAGGUUCGAAUCCCGUCGUAGCCACCA (SEQ ID NO: 427) | 58,226 | F | GTTAGAGCAGCGGCCGGGCCAGCTGTGAGTGTTTCTTCAGT GCAATGATGAAAGGGCATTGTGAGCAATAGTAA (SEQ ID NO: 498) |
| | | | | R | TCGAACCTGTGACCCGCGGGGGCCAACAACGTGCAGCACTT CTAAGTGCAACAGGGAAAGAGCACTTCCTTACTATGC (SEQ ID NO: 499) |
| anti-miR-21-5p-2 | 180 | GGCUACGUAGCUCAGUUGGUUAGAGCAGCGGCCGGGCCAGCUGUGAG UGUUCUUGAUUCAAACAGUCAUCAGUCTGTGAGCAATAAGGA AGACUGAUGUGACUGUUGAAAUAUGAAGUGCUGCACGUUGUGGCC CCCGCGGGUCACAGGUUCGAAUCCCGUCGUAGCCACCA (SEQ ID NO: 428) | 58,243 | F | GTTAGAGCAGCGGCCGGGCCAGCTGTGAGTGTTTCTTGATT CAACAGTCAACATCAGTCTGTGAGCAATAGT (SEQ ID NO: 500) |
| | | | | R | TCGAACCTGTGACCCGCGGGGGCCAACAACGTGCAGCACTT CTATATTCAACAAGTCACATCAGTCTTCCTTAC (SEQ ID NO: 501) |
| anti-miR-122-5p | 180 | GGCUACGUAGCUCAGUUGGUUAGAGCAGCGGCCGGGCCAGCUGUGAG UGUUCUUUUACCACAAACACAGAUUGAUUGTGAGCAGCAAUAGUAAGGA AAUCAAAUCUGUGUUUGUGGUAAUCCCGUCGUAGCCACCA (SEQ ID NO: 429) | 58,125 | F | GTTAGAGCAGCGGCCGGGCCAGCTGTGAGTGTTTCTTTAC CACAAACACAGATTTGATTGTGAGCAATAGTA (SEQ ID NO: 502) |
| | | | | R | TCGAACCTGTGACCCGCGGGGGCCAACAACGTGCAGCACTT CTAGTACCAACAAGACAAAGATTTGATTTCCTTACTA (SEQ ID NO: 503) |
| scrm-5 | 180 | GGCUACGUAGCUCAGUUGGUUAGAGCAGCGGCCGGGCCAGCUGUGAG UGUUUCUGGUAGUAUGUGAGCAAUAGUAAGG AAGUACUACCAUAUGAAACGACACAAGAAGUGCUGCACGUUGUGGCC CCCGCGGGUCACAGGUUCGAAUCCCGUCGUAGCCACCA (SEQ ID NO: 430) | 58,273 | F | GTTAGAGCAGCGGCCGGGCCAGCTGTGAGTGTTTCTTGGTG TCGTTTCTCTGGTAGTATGTGAGCAAT (SEQ ID NO: 504) |
| | | | | R | TCGAACCTGTGACCCGCGGGGGCCAACAACGTGCAGCACTT CTTGTGTCGTTTCTATGGTGAGTACTTCCTTACTA (SEQ ID NO: 505) |

TABLE 2B-continued

| Name | # nts | RNA Sequence | nCAR/sRNAs MW (Da) | | Primers (5'-3') |
|---|---|---|---|---|---|
| scrm-4 | 180 | GGCUACGUAGCUCAGUUGGUUAGAGCAGCGGCCGGGCCAGCUGUGAG UGUUCUUAAGCGCGCUUUGUAGGAUUCGUUGUGAGCAAUAGUAAGG AAGCGAAUCCCGUCACAGGUUCGAAUCCCGUCGUAGCCACCA (SEQ ID NO: 431) | 58,281 | F | GTTAGAGCAGCGGCCGGGCCAGCTGTGAGTGTTCTTAAGC GCGCTTGTAGGATTCGTTGTGAGCAA (SEQ ID NO: 506) |
| | | | | R | TCGAACCTGTGACCCGCGGGGCCAACAACGTGCAGCACTT CTACAGCGCGCTATTGAGGATTCGCTTCCTTACTAT (SEQ ID NO: 507) |
| scrm-2 | 180 | GGCUACGUAGCUCAGUUGGUUAGAGCAGCGGCCGGGCCAGCUGUGAG UGUUCUUGACGGUUGUUGUUGUGAGCAAUAGUAAGG AAGCAACAACCUUCUCCGACGAAAAGAAGUGCUGCACGUUGUUGGCC CCCGGGUCACAGGUUCGAAUCCCGUCGUAGCCACCA (SEQ ID NO: 432) | 58,249 | F | GTTAGAGCAGCGGCCGGGCCAGCTGTGAGTGTTCTTGTTC GTCTGTAGACGGTTGTTGTTGTGAGCAAT (SEQ ID NO: 508) |
| | | | | R | TCGAACCTGTGACCCGCGGGGCCAACAACGTGCAGCACTT CTTTTCGTCTGGAAAGGTTGTTGCTTCCTTACTA (SEQ ID NO: 509) |
| scrm-3 | 180 | GGCUACGUAGCUCAGUUGGUUAGAGCAGCGGCCGGGCCAGCUGUGAG UGUUCUUUUUCUCCGAAGCGUCACGUUUUGUAGAGCAAUAGUAAGG AAGAAUCGUGUAGCUUUCGGAAGCUAGAAGUGCUGCACGUUGUUGGCC CCCGGGUCACAGGUUCGAAUCCCGUCGUAGCCACCA (SEQ ID NO: 433) | 58,181 | F | GTTAGAGCAGCGGCCGGGCCAGCTGTGAGTGTTCTTTTCTC CGAAGCTGTCACGTTTTTGTGAGCAAT (SEQ ID NO: 510) |
| | | | | R | TCGAACCTGTGACCCGCGGGGCCAACAACGTGCAGCACTT CTAGTCTCCGAAAGCTACACGATTCTTCCTTACTAT (SEQ ID NO: 511) |
| scrm-1 | 180 | GGCUACGUAGCUCAGUUGGUUAGAGCAGCGGCCGGGCCAGCUGUGAG UGUUUCUGUGUAACACGUCUAUACGCCCAUGUGAGCAAUAGUAAGGA | 58,335 | F | GTTAGAGCAGCGGCCGGGCCAGCTGTGAGTGTTCTTGTGT AACACGTCTATACGCCCATGTGAGCAA (SEQ ID NO: 512) |
| | | AGUGGGGCUACAGAAGAAGUGUUACAAAGAAGUGCUGCACGUUGGCC CCCGGCGGGUCACAGGUUCGAAUCCCGUCGUAGCCACCA (SEQ ID NO: 434) | | R | TCGAACCTGTGACCCGCGGGGCCAACAACGTGCAGCACTT CTTTGTAACACTTCTGTACGCCCACTTCCTTACTATTG (SEQ ID NO: 513) |
| miR-21-5p | 180 | GGCUACGUAGCUCAGUUGGUUAGAGCAGCGCGGCCGGGCCAGCUGUGAG UGUUUCUUAGCUUAUCAGACUGAUGUUGAUGUGAGCAAUAGUAAGGA AGUACUGAUCCGUCACGGUUCGAAGUUGCUGCACGUUGUUGGCC CCGCGGGUCACAGGUUCGAAUCCCGUCGUAGCCACCA (SEQ ID NO: 435) | 58,267 | F | GTTAGAGCAGCGGCCGGGCCAGCTGTGAGTGTTCTTAGC TTATCAGACTGATGTTGATGTGAGCAAT (SEQ ID NO: 514) |
| | | | | R | TCGAACCTGTGACCCGCGGGGCCAACAACGTGCAGCACTT CTACAGCCCATCGACGATGTTGACTTCCTTACTA (SEQ ID NO: 515) |
| anti-miR-21-5p | 180 | GGCUACGUAGCUCAGUUGGUUAGAGCAGCGGCCGGGCCAGCUGUGAG UGUUUCUUCAACAUCAGUCUGAUAAGCUAUGUGAGCAAUAGUAAGGA AGUAGCUUAUAGAAUGAUUCAGAAGUGCUGCACGUUGUUGCC CCCGGGUCACAGGUUCGAAUCCCGUCGUAGCCACCA (SEQ ID NO: 436) | 58,267 | F | GTTAGAGCAGCGGCCGGGCCAGCTGTGAGTGTTCTTCAA CATCAGTCTGATAAGCTATGTGAGCAA (SEQ ID NO: 516) |
| | | | | R | TCGAACCTGTGACCCGCGGGGCCAACAACGTGCAGCACTT CTGCAACATCATTCTTATAAGCTACTTCCTTACTA (SEQ ID NO: 517) |
| miR-34a/TPA3' | 213 | GGCUACGUAGCUCAGUUGGUUAGAGCAGCGGCCGGGCCAGCUGUGAG UGUUCUGCAGUUCUUAGCUGUUGUUAGAAGUGCUGCACGUUGUUGGCC AAGAAUCACAAGUAUACUCCCUAGAAGUGCUGCACGUUGUUGGCC GGCGAUACCAGGCCCUUGGCCAGCGUCCCGCGGGUCACAG GUUCGAAUCCCGUCGUAGCCACCA (SEQ ID NO: 437) | 68,926 | F | GTTAGAGCAGCGGCCGGGCCAGCTGTGAGTGTTTCT (SEQ ID NO: 390) |
| | | | | R | TCGAACCTGTGACCCGCGGGGACGCTGCCAAGGGCCTTTCGG CTGTATCGCCGGACCAACAACGTGCAGC (SEQ ID NO: 519) |
| miR-34a/TPA3'+TPA5' | 246 | GGCUACGUAGCUCAGUUGGUUAGAGCAGCGCGGCCGGCCGGCGAUACCAGGCC CAAAGGCCCUUGGCCAGCGUCGGCCAGCUGUGAGUGUUCUUUGGCAG UGUCUUUAGCUGGUUGUUGUUGUGAGCAAUAGAAGCAACAGCAAGU AUACUGCCCUAGAAGUGCUGCACGUUGUUGGCCGGGAUACCAGCC CAAAGGCCCUUGGCCAGCGUCCGCGGGUCACAGGUUCGAAUCCCGUC GUAGCCACCA (SEQ ID NO: 438) | 79,610 | F | GTTAGAGCAGCGGCCGGGCCGGCGATACCAGGCCGAAAGGCCCTTG GCAGCGTCGGCCAGCTGTGAGTGTTT (SEQ ID NO: 520) |
| | | | | R | TCGAACCTGTGACCCGCGGGACCGTGCCAAGGGCCTTTCGG CTGGTATCGCCGGCCAACAACGTGCAGC (SEQ ID NO: 519) |

TABLE 2B-continued

| | | nCAR/sRNAs | | | |
|---|---|---|---|---|---|
| Name | # nts | RNA Sequence | MW (Da) | | Primers (5'-3') |
| miR-888/ pegaptanib3' | 207 | GGCUACGUAGCUCAGUUGGUUAGAGCAGCGGCCGGGCCAGCUGUGAG UGUUUCUUUACUCAAAAGCUGUCAGUCAUUGUGAGCAAUAGUAAGGA AGUGACUGACGCCUUUUUGGGUCUAGAAGUGCUGCACGUUGUUGGCC CCGGAAUCAGUGAAUGCUUAUACAUCCGCCGCGGGUCACAGGUUCGA AUCCCGUCGUAGCCACCA (SEQ ID NO: 439) | 66,868 | F R | GTTAGAGCAGCGGCCGGGCCAGCTGTGAGTGTTTCTTTACT CAAAAGCTGTCAGTCATTGTGAGCAATAGTAA (SEQ ID NO: 522) TCGAACCTGTGACCCGCGGCGGATGTATAAGCATTCACTGAT TCCGGGCCAACAACGTGCAGCACTTCTAGACCCAAAAAG CGTCAGTCACTTCCTTACTATTGC (SEQ ID NO: 523) |
| miR-34a/ pegaptanib5' | 207 | GGCUACGUAGCUCAGUUGGUUAGAGCAGCGGCCGCCGGAAUCAGUGAA UGCUUAUAUACAUCCGGGCCAGCUGUGAGUGUUUCUUUGGCAGUGUCUU AGCUGGUUGUGUGAGCAAUAGUAAGGAAGCAAUCAGCAAGUAAUACUG CCCUAGAAGUGCUGCACGUUGUUGGCCCCCGCGGGUCACAGGUUCGA AUCCCGUCGUAGCCACCA (SEQ ID NO: 440) | 66,922 | F R | GTTAGAGCAGCGGCCGCCGGAATCAGTGAATGCTTATACATCC GGGCCAGCTGTGAGTGTTTCTTTGGCAGTGTCTTAGCTGGTT GTTGTGAGCAATAGTAA (SEQ ID NO: 524) GCATTCACTGATTCCGGCGGGGCCAACAACGTGCAGCACTT CTAGGGCAGTATACTTGCTGATTGCTTCCTTACTATTGC (SEQ ID NO: 525) |
| miR-34a/ EpCAMA3' | 199 | GGCUACGUAGCUCAGUUGGUUAGAGCAGCAGCGGCCGGGCCAGCUGAG UGUUUCUUUGGCAGUGUCUUAGCUGGUUGUUGGUGAGCAAUAGUAAGG AAGCAAUCAGCAAGUAUACUGCCCUAGAAGUGCUGCACAGGUUCGAAUCCCGUC GCGACUGGUUACCCGGUCGCGCGGGUCACAGGUUCGAAUCCCGUC GUAGCCACCA (SEQ ID NO: 441) | 64,373 | F R | GTTAGAGCAGCGGCCGGGCCAGCTGTGAGTGTTTCT (SEQ ID NO: 390) TCGAACCTGTGACCCGGGCGACCGGGTAACCAGTCGCGG GCCAACAACGTGCAGCAC (SEQ ID NO: 527) |

Expression of recombinant RNAs in E. coli. HST08 competent cells were transformed with target plasmids and then grown either on small scale (5-50 mL) or large scale (500-600 mL). Total RNAs were isolated by phenol extraction, quantitated with a NanoDrop 2000 Spectrophotometer (Thermo Fisher Scientific, Rockford, IL), and analyzed by denaturing urea (8 M) polyacrylamide (8%) gel electrophoresis (PAGE). Images were acquired with ChemiDoc MP Imaging System (Bio-Rad, Hercules, CA). Band intensities were used to roughly estimate target RNA expression relative to total RNAs. Precise calculation of the fraction of target RNA in total RNAs was achieved by dividing the area of target RNA peak by total areas of all peaks in chromatograph during FPLC purification, as shown below.

Small- and large-scale purification of nCAR/sRNAs. Target bioengineered RNA agent ("BERA") was purified on small scale using spin columns: RNA Clean & Concentrator and Select-a-Size DNA Clean & Concentrator (Zymo Research, Irvine, CA). RNA was isolated following the protocols suggested for >200 nt (RNA Clean & Concentrator) sequentially followed by a 50 bp cutoff protocol (Select-a-Size DNA Clean & Concentrator). Large-scale purification of target BERA was performed with a NGC QUEST 10PLUS fast protein liquid chromatography system (Bio-Rad) equipped with an anion exchange Enrich-Q 10×100 column (Bio-Rad). Separation of nCAR/sRNA from total RNAs was achieved on an Enrich-Q 10×100 column that was first equilibrated with Buffer A (10 mM sodium phosphate, pH 7.0) at a constant flow rate of 2.5 ml/min for 2 min and then followed by a gradient elution at the same flow rate: 55% Buffer B (Buffer A+1 M sodium chloride, pH 7.0) for 4.8 min, 55-75% Buffer B for 20.4 min, and then 100% Buffer B for 9.6 min. FPLC traces were monitored at 260/280 nm using a UV/Vis detector and individual fractions were collected for urea-PAGE analyses. After confirmation of purity and expected size, fractions containing target BERA were pooled, precipitated by ethanol, desalted and concentrated/dissolved in nuclease-free water with an Amicon ultra-2 mL centrifugal filter (30 kDa; EMD Millipore, Billerica, MA).

Determination of RNA purity. RNA purity was quantitated by HPLC analysis as previously described (Wang et al., 2015) and endotoxin activity was determined using the Pyrogent-5000 kinetic LAL assay (Lonza, Walkersville, MD) by following manufacturer's instructions, prior to in vitro and in vivo functional studies. The majority of nCAR/sRNAs purified by FPLC were >98% pure (Table 3) with minimal endotoxin levels (<1 EU/μg RNA).

TABLE 3

Yields and purities of individual BERAs produced on a large scale using the nCAR platform and isolated by FPLC method

| nCAR | Yield (mg RNA/L fermentation) | Purity (%; by HPLC) |
|---|---|---|
| miR-27a-3p | 10.1 | 99.4 |
| miR-27b-3p | 10.2 | 99.4 |
| miR-451a-5p | 18.8 | 98.9 |
| ApoB-siRNA | 17.0 | 99.0 |
| anti-miR-126-3p | 20.0 | 99.2 |
| ICAM1-siRNA | 12.0 | 98.6 |
| miR-298-5p | 15.4 | 97.2 |
| miR-519c-5p | 16.0 | 99.3 |
| miR-122-5p | 9.80 | 87.0 |
| Nrf2-siRNA | 18.7 | 98.3 |
| miR-126-3p | 11.6 | 99.8 |
| miR-144-5p | 10.6 | 98.7 |
| ARV7-siRNA | 17.0 | 99.3 |
| GFP-siRNA | 12.0 | 99.3 |
| let-7c-5p | 8.70 | 92.4 |
| miR-127-3p | 3.83 | 95.5 |
| miR-34a-5p | 16.6 | 98.3 |
| miR-124-3p | 8.34 | 98.3 |
| miR-328-3p | 14.8 | 99.7 |
| anti-miR-451b-5p | 11.3 | 99.3 |
| MSA | 5.72 | 99.6 |
| anti-miR-21-5p-3 | 7.48 | 98.2 |
| miR-33a-5p | 7.54 | 96.0 |
| anti-miR-21-5p-2 | 9.41 | 96.9 |
| anti-miR-122-5p | 7.67 | 99.3 |
| scrm-5 | 7.54 | 53.5 |
| scrm-4 | 7.43 | 98.2 |
| scrm-3 | 8.54 | 99.3 |
| anti-miR-21-5p | 11.7 | 99.4 |
| miR-34a/TPA3'+TPA5' | 18.2 | 99.5 |
| miR-888/pegaptanib3' | 16.0 | 98.3 |
| miR-34a/EpCAMA3' | 12.7 | 99.0 |

RNA sequencing and data analyses. 293T and Dicer-KO cells were transfected with 20 nM of nCAR/miR-34a-5p, nCAR/miR-124-3p or control tRNA. Cells were treated in triplicate and processed and sequenced separately. Total RNAs were isolated using TRIzol-chloroform protocol (Abcam) at 48 hr post-transfection and RNA integrity was assessed by 1% standard agarose gel electrophoresis.

Small RNAs: Library construction was prepared by BGI, where small RNAs less than 30 nt were collected through gel separation (15% Urea-PAGE) starting with 1 μg of total RNA. Small RNA fragments were ligated to adenylated 3' adapters annealed to unique barcodes, followed by the ligation of 5' adapters and reverse transcription (RT). After synthesis of the first strand cDNA, the product was expanded by 15 cycles of PCR amplification. A second size selection operation was carried out to purify the PCR amplicons from nonspecific products, selecting 103-115 bp fragments by gel separation. After gel purification, PCR yield was quantified by Qubit 3.0 Fluorometer (Invitrogen, Carlsbad, CA) and samples were pooled to make a single strand DNA circle (ssDNA circle) to yield the final small RNA library. DNA nanoballs (DNBs) were generated with the ssDNA circle by rolling circle replication (RCR) to enlarge fluorescent signals at the sequencing process. The DNBs were loaded into the patterned nanoarrays and single-end reads of 50 bp were read on the BGISEQ-500 platform (Shenzhen, China). The FASTQ-formatted sequence data were analyzed using the miRDeep module (An et al., 2013) to obtain the read counts of known miRNAs. To compute the read counts derived from transfected nCAR/miR-34a-5p or nCAR/miR-124-3p, a PERL script was developed to map sequence reads from FASTQ-formatted sequence data to the corresponding constructor, followed by counting isoform reads in individual samples. Read counts of known miRNAs and sRNAs derived from nCAR/miR-34a-5p or nCAR/miR-124-3p among individual samples were thus used for the analysis of significantly, differentially expressed miRNAs (P<0.05 and log 2CPM>6) between phenotype using EdgeR (Robinson et al., 2010).

Messenger RNAs: mRNAs were purified using poly-T oligo-attached magnetic beads. Following purification, the mRNA was fragmented into small pieces using divalent cations under elevated temperature. The cleaved RNA fragments were copied into first strand cDNA using random primers by reverse transcription, followed by second strand cDNA synthesis using DNA Polymerase I and RNase H. These cDNA fragments contain an additional 'A' at the 3' end to allow subsequent ligation of the adapter. The products were then purified and enriched with PCR amplification, quantified with Qubit and used to create DNB-based nanoarrays by RCR. Stepwise sequencing was performed using the combinatorial Probe-Anchor (cPAL) ligation approach and read on the BGISEQ-500 system. The FASTQ-formatted sequence data were analyzed using a BWA-RSEM-EdgeR workflow (Li and Durbin, 2009; Robinson et al., 2010; Li and Dewey, 2011), with sequence reads mapped to the reference human-genome assembly (February 2009, GRCh37/hg19) with BWA software. Sequence read counts for individual genes were computed using RSEM, and the resulting read counts from individual samples were subjected to the detection of differentially expressed mRNAs (log 2FC>1.2 or log 2FC<0.8, P<0.05, and log 2CPM>5) between phenotypes using EdgeR package. Networks, functions, and pathways analyses were generated using Ingenuity Pathway Analysis (Ingenuity Systems; Qiagen, Redwood City, CA), primarily based on experimentally demonstrated interactions in human and rodent studies.

Enrichment analysis. miRNA target enrichment analyses of significantly downregulated genes (log 2FC<0.8, P<0.05, and log 2CPM>5) were undertaken using miRNA targets predicted by TargetScan (Lewis et al., 2005), and enrichment P-values were computed by Fisher's exact test.

Reverse transcription quantitative real-time PCR. Cells were transfected with 20 nM of nCAR/miR-34a, nCAR/miR-124, or control using Lipofectamine 3000 (Life Technologies, Carlsbad, CA) and harvested at 48 h post transfection. Total RNAs were extracted using Direct-zol RNA isolation kit (Zymo Research) and 500 ng of total RNAs were used for cDNA synthesis with random hexamers or respective stem-loop primers (Table 4). RT was conducted with NxGen M-MuLV reverse transcriptase (Lucigen, Middleton, WI), and qPCR analysis was carried out on a CFX96 Touch real-time PCR system (Bio-Rad) using quantitative RT-PCR master mix and respective primers (Table 4). Levels of miRNA were normalized to U6 snRNA and levels of mRNA were normalized to 18S rRNA (N=9) in corresponding samples, determined using the formula 2-ΔΔCT. Reactions were run in triplicate in three independent experiments and similar results were obtained.

TABLE 4

| nCAR | Method | Yield (% of total RNA) | Yield (μg/mL bacterial culture) | Purity (%; by HPLC) |
|---|---|---|---|---|
| miR-34a-5p | Single-column | 42.5 | 18.9 | 88.5% |
| | Double-column | 33.0 | 14.8 | 97.8% |
| miR-124-3p | Single | 44.3 | 15.4 | 94.8% |
| | Double | 40.4 | 14.0 | 98.3% |

Cell viability assay. Cells were transfected with various doses of nCAR/miR-34a-5p, nCAR/miR-124-3p, or control tRNA. Cell viability was determined with CellTiter-Glo 2.0 assay kit (Promega, Madison, WI) at 72 post-transfection, according to manufacturer's protocol. Luminescence was recorded using a SpectraMax Microplate Reader (Molecular Devices, Sunnyvale, CA) at an integration time of 250 ms. Inhibition was calculated by adjusting vehicle control to 0% and dose response curves were established by plotting inhibition versus RNA concentration. Data were fit into a normalized inhibitory dose-response model with variable slope (Y=100/(1+10^((Log EC50−X)*HillSlope))); GraphPad Prism, San Diego, CA) for the estimation of EC50 and Hill slope values (Table 5). All experiments were performed in triplicates.

TABLE 5

| Target | | Primer Sequence |
|---|---|---|
| U6 | Forward | 5'-CTCGCTTCGGCAGCACA-3' (SEQ ID NO: 528) |
| | Reverse | 5'-AACGCTTCACGAATTTGCGT-3' (SEQ ID NO: 529) |
| miR-34a | RT | 5'-GTCGTATCCAGTGCAGGGTCCGAGGTATTCGCACTGGATA CGACACAACC-3' (SEQ ID NO: 530) |
| | Forward | 5'-CGCGCTGGCAGTGTCTTAGCT-3' (SEQ ID NO: 531) |
| | Reverse | 5'-GTGCAGGGTCCGAGGT-3' (SEQ ID NO: 532) |
| miR-124 | RT | 5'- GTCGTATCCAGTGCAGGGTCCGAGGTATTCGCACTGGAT ACGACGGCATT-3' (SEQ ID NO: 533) |
| | Forward | 5'-GCGCTAAGGCACGCGGTG-3' (SEQ ID NO: 534) |
| | Reverse | 5'-GTGCAGGGTCCGAGGT-3' (SEQ ID NO: 532) |
| 18S | Forward | 5'-GTAACCCGTTGAACCCCATT-3' (SEQ ID NO: 536) |
| | Reverse | 5'-CCATCCAATCGGTAGTAGCG-3' (SEQ ID NO: 537) |
| AMER1 | Forward | 5'-GCGAATTCGGAGACCCAAAAGGATGAAGCTGCTCAG-3' (SEQ ID NO: 538) |
| | Reverse | 5'-CCTTGCTCTTCCGGTGACGGCGGATACTGC-3 (SEQ ID NO: 539) |
| BAG2 | Forward | 5'-AGCCACATTAGGCGCTCGGTCT-3' (SEQ ID NO: 540) |
| | Reverse | 5'-AGTTAGAGGTTCGCGAGCCACACG-3' (SEQ ID NO: 541) |
| BCL6B | Forward | 5'-GCTTTGTACAGGTGGCACATC-3' (SEQ ID NO: 542) |
| | Reverse | 5'-GAACGTGGCTCTTGAGGGTC-3' (SEQ ID NO: 543) |
| CLUH | Forward | 5'-GGTAGCGGGCACGGTACA-3' (SEQ ID NO: 544) |
| | Reverse | 5'-GCATTGAGCACCCCAACAC-3' (SEQ ID NO: 545) |
| GAS1 | Forward | 5'-CTGGGGTTTGTTACCAGTTG-3' (SEQ ID NO: 546) |
| | Reverse | 5'-GGGGGAAAGGTGTAATATGG-3' (SEQ ID NO: 547) |

TABLE 5-continued

| Target | | Primer Sequence |
|---|---|---|
| IQGAP1 | Forward | 5'-GAAAGCCCAGGAAATCCAG-3' (SEQ ID NO: 548) |
| | Reverse | 5'-TCCATACAAGCCAACATCAG-3' (SEQ ID NO: 549) |
| KCTD12 | Forward | 5'-GCTCGGGCTACATCACCATCGG-3' (SEQ ID NO: 550) |
| | Reverse | 5'-GGGTCCCGGCTTTCGTTCAG-3' (SEQ ID NO: 551) |
| NECTIN1 | Forward | 5'-ACCAACCCCATCGGTACAC-3' (SEQ ID NO: 552) |
| | Reverse | 5'-GGGGTGTAGGGGAATTCTGT-3' (SEQ ID NO: 553) |
| NID1 | Forward | 5'-CGGGGATGACTTCGTCTCTC-3' (SEQ ID NO: 554) |
| | Reverse | 5'-GTGGTGACGTAGACTGCGT-3' (SEQ ID NO: 555) |
| NRAS | Forward | 5'-CCTCTACAGGGAGCAGATTAAGCGA-3' (SEQ ID NO: 556) |
| | Reverse | 5'-CCCTGTCTGGTCTTGGCTGAGGT-3' (SEQ ID NO: 557) |
| SNAI2 | Forward | 5'-TGGTTGCTTCAAGGACACAT-3' (SEQ ID NO: 558) |
| | Reverse | 5'-GCAGATGAGCCCTCAGATTT-3' (SEQ ID NO: 559) |
| TMEM109 | Forward | 5'-ACACTGGATGCCTGGATTGGGC-3' (SEQ ID NO: 560) |
| | Reverse | 5'-AAGCCGAGGAGCAGAGACAGCA-3' (SEQ ID NO: 561) |
| VAMP3 | Forward | 5'-GCAGCCAAGTTGAAGAGGAA-3' (SEQ ID NO: 562) |
| | Reverse | 5'-CAGTTTTGAGTTCCGCTGGT-3' (SEQ ID NO: 563) |
| VIM | Forward | 5'-GAGAACTTTGCCGTTGAAGC-3' (SEQ ID NO: 564) |
| | Reverse | 5'-TCCAGCAGCTTCCTGTAGGT-3' (SEQ ID NO: 565) |

Western blot assay. A549, 293T, and Dicer-KO 293T cells were seeded at 0.25×10$^6$ cells/well and treated with 30 nM nCAR/miR-34a-5p, nCAR/miR-124-3p, or tRNA control. Cultured cells were harvested at 48 h and lysed with RIPA lysis buffer (Sigma Aldrich, St. Louis, MO) containing protease inhibitor cocktail (Roche Diagnostics, Mannheim, Germany). Total cell lysate (30 µg) was resolved by 10% SDS-PAGE gel, transferred to PVDF membranes (250 mA for 2 hours), and probed with target antibodies. Antibodies against CDK6 (C-21), cMET (C-28), Dicer (H-212), GAPDH (FL-335) and SIRT1 (H-300) were obtained from Santa Cruz Biotechnology (Santa Cruz, CA), p-STAT3 (Tyr705) and STAT3 (124H6) were acquired from Cell Signaling Technology (Beverly, MA), β-actin (AC-15) from Sigma-Aldrich (St Louis, MO) and MRP4 (M4I-10) from Abcam (Cambridge, MA). Subsequently, secondary antibodies linked with peroxidase were anti-rabbit (Jackson ImmunoResearch Inc., West Grove, PA), anti-mouse IgG or anti-rat IgG (Cell Signaling). Protein bands were captured by a luminescent image analyzer (ChemiDoc MP Imaging System).

Metastatic lung xenograft mouse models and therapy studies. All animal procedures were approved by the Institutional Animal Care and Use Committee of University of California, Davis, and all animal studies were conducted in accordance with the relevant national and international guidelines. Five week old female non-obese diabetic/severe combined immunodeficient (NOD/SCID) mice (NOD.CB17-Prkdcscid/J) were purchased from Jackson Laboratory and adaptively fed at least one week before experiments.

A549 metastatic xenograft mouse models were established by injecting 3.5×10$^6$ A549-luc/GFP cells via tail vein. Tumor growth was monitored using bioluminescence imaging by injecting D-luciferin potassium salt solution (150 mg/kg) intraperitoneally 10 min post-anesthesia. Images were acquired with the ChemiDoc MP Imaging System. 14 days after inoculation, 27 mice were randomly divided into 3 three groups (N=9 per group). Mice were treated intravenously with 30 µg of control tRNA, nCAR/miR-34a-5p or nCAR/miR-124-3p, formulated with in vivo-jetPEI (Polyplus Transfection), three times per week for three weeks. At the end of the study, all mice were sacrificed and lungs were dissected, weighed, and imaged ex vivo for GFP signals. Lung tissues were further fixed with 10% formalin and subjected to hematoxylin and eosin (H&E) staining for histopathological evaluation in the Histology Facility at Roswell Park Cancer Institute (Buffalo, N.Y., USA). H&E-staining images (100×) were captured using an Olympus camera (DP25) and CellSens software (Olympus, Center Valley, PA).

Induction of cytokine release. Female BALB/c mice at five to six weeks of age (Jackson Laboratory) were administered intravenously via tail vein with 30 µg of in vivo-jetPEI-formulated control tRNA, nCAR/miR-34a-5p or nCAR/miR-124-3p. Separate groups of animals without any treatment or treated intravenously with 20 µg of lipopolysaccharide (LPS) were used as controls. Blood was collected 1 h after administration and serum was isolated for the quantification of cytokine IL-6 and TNFα levels using mouse ELISA assay kits (Thermo Fisher Scientific).

Statistical analysis. Data are presented as mean±SD. Statistics analysis was performed using unpaired Student's t-test, one-way ANOVA, or two-way ANOVA (GraphPad Prism, San Diego, CA). $P<0.05$ was considered to be statistically significant.

Results

Figure 1B:
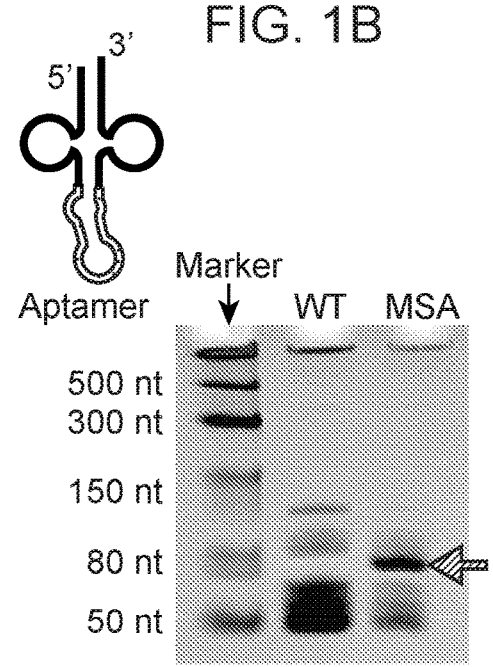
Figure 1C:
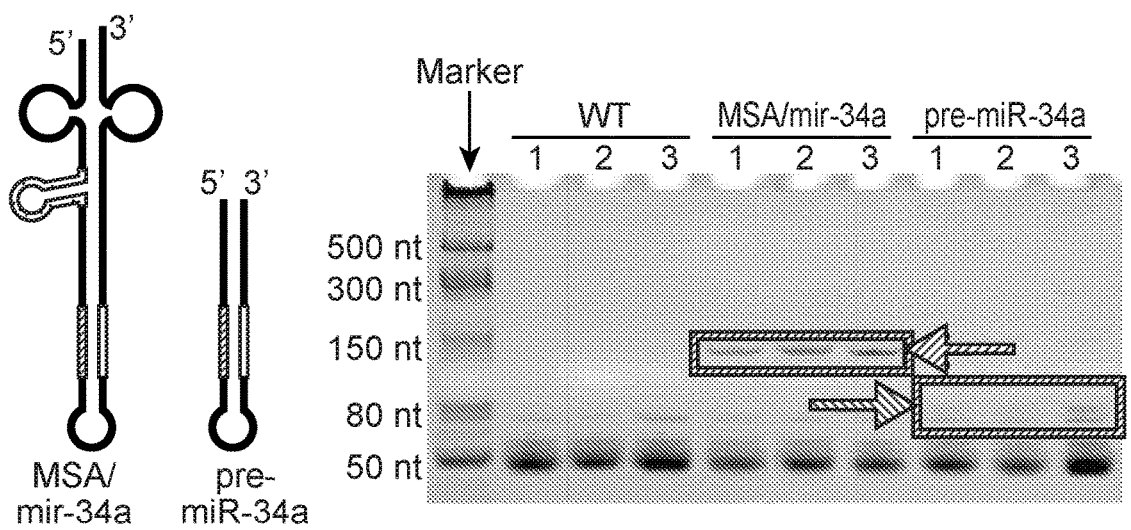

Identification of pre-miR-34a G138U/139ΔG derivative for ncRNA carrier. To enable heterogeneous expression of recombinant ncRNAs in bacteria, we sought to assess the foundational basis for chimeric ncRNA design. We first found that tRNAMet standalone showed no obvious expression in E. coli (FIG. 1A). In sharp contrast, tRNAMet fused Sephadex aptamer (MSA) was overexpressed, indicating the importance of Sephadex aptamer for accumulation of the chimera (FIG. 1B). Furthermore, human pre-miR-34a itself was noticeably expressed in bacteria (≤2% of total RNAs) and hybrid MSA/mir-34a showed an improved accumulation (10-20% of total RNAs) (FIG. 1C), demonstrating the stabilities of pre-miR-34a and chimeric ncRNA for the success of heterogeneous expression.

Figure 1D:
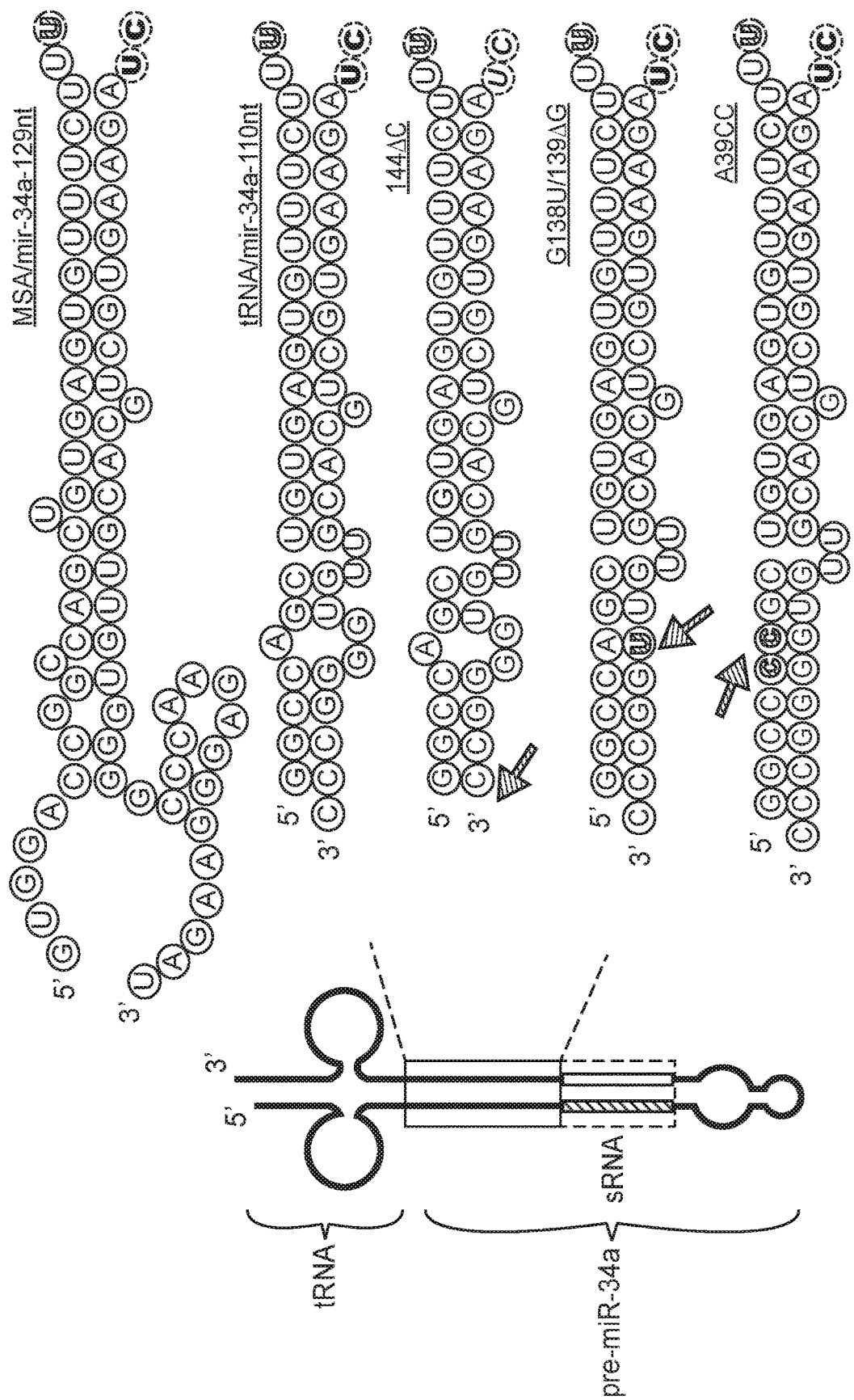
Figure 1D:
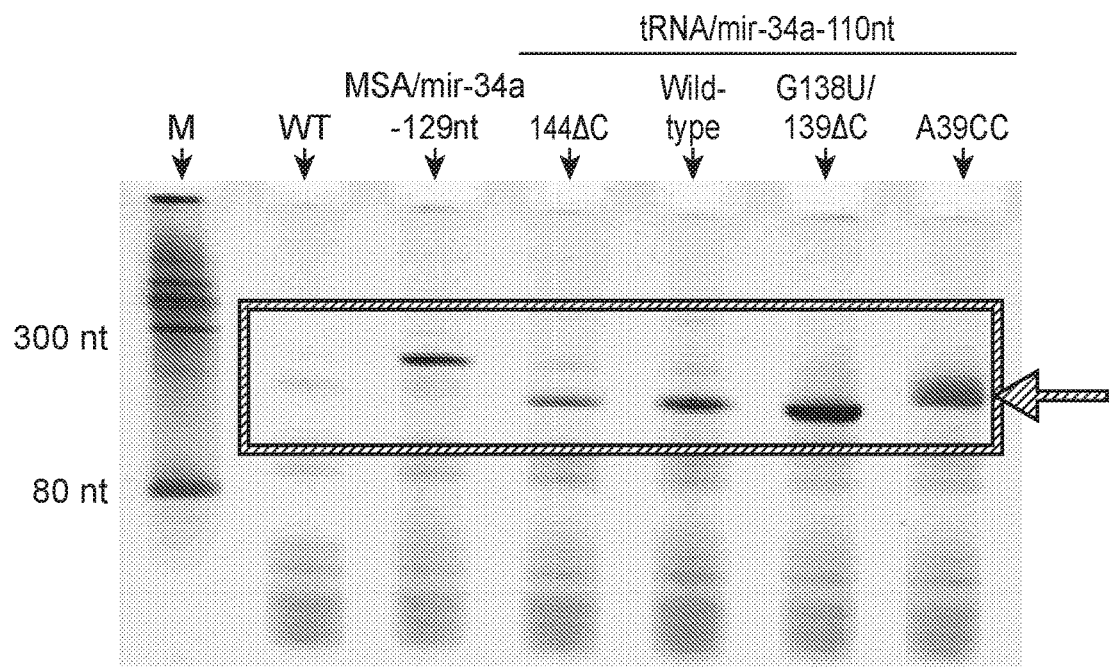
Figure 1E:
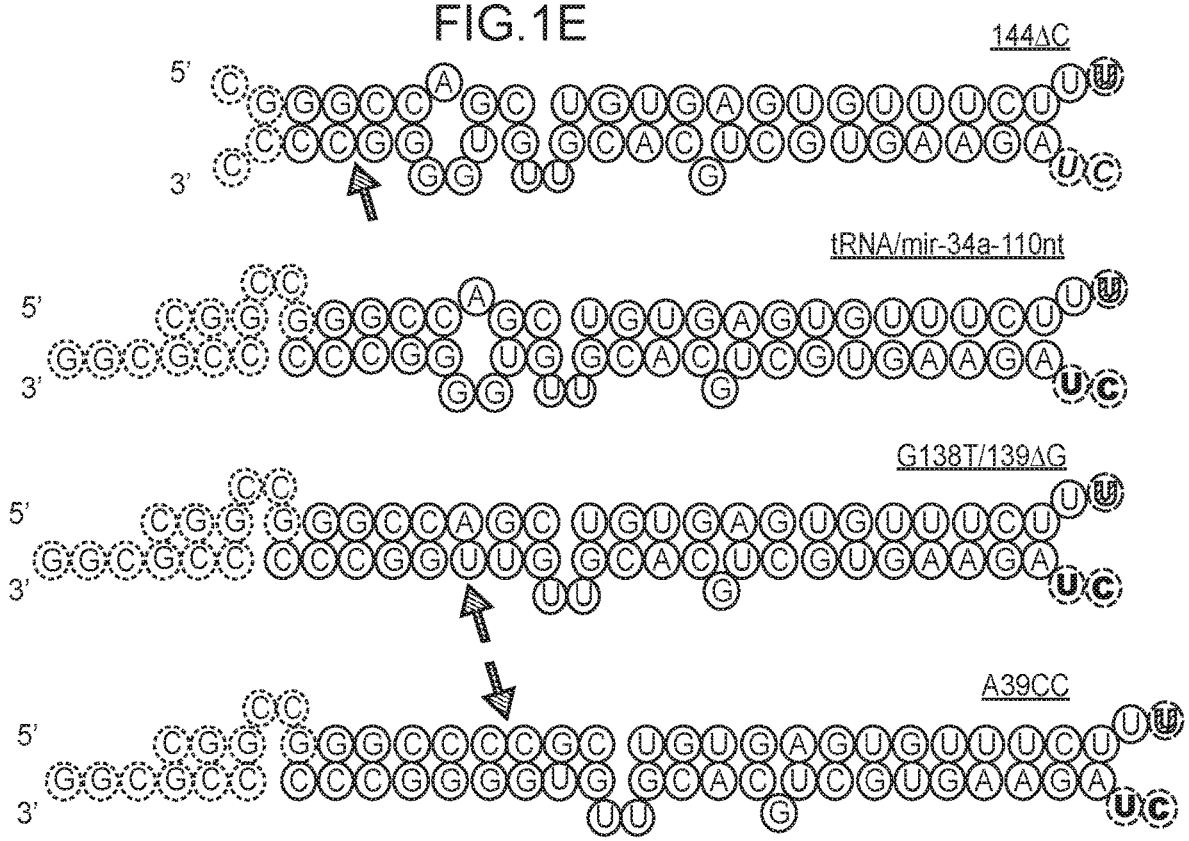
Figure 2:
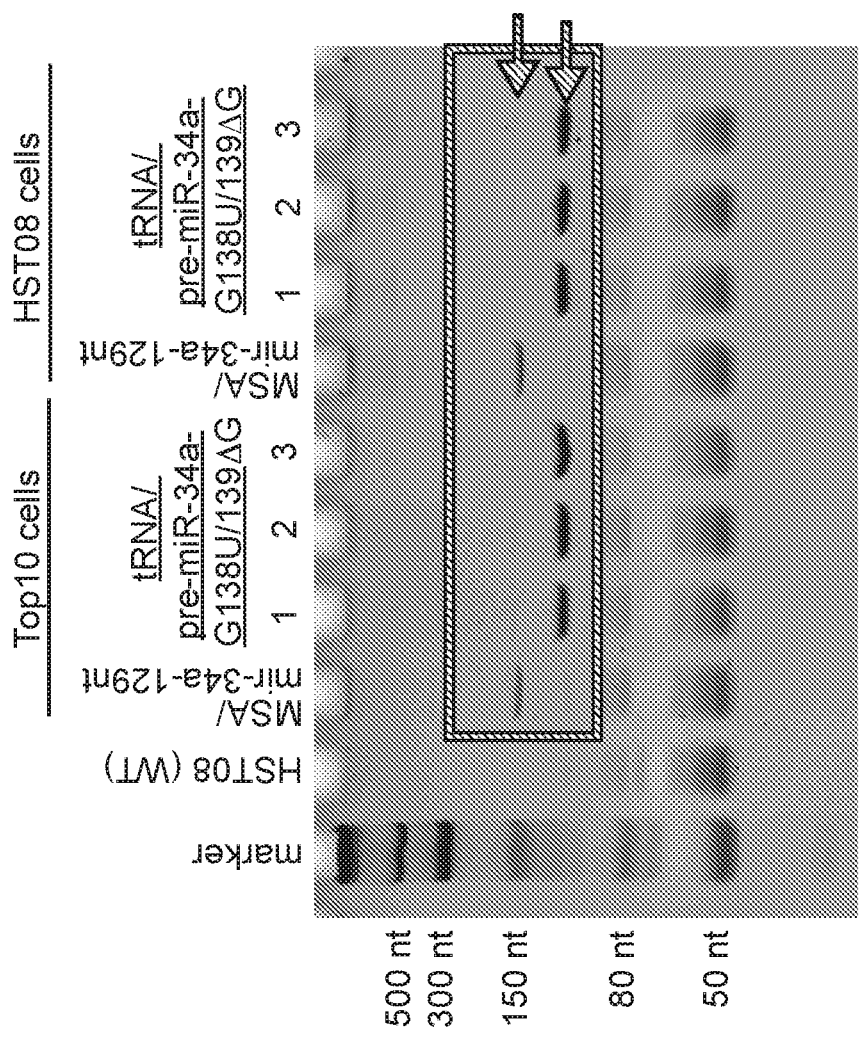
FIG. 2 illustrates independence on Sephadex aptamer for heterogeneous expression of ncRNAs in *E. coli*. The refined pre-miR-34a G138U/139ΔG fused to standalone tRNA is expressed at higher level than MSA/mir-34a-129nt in both HST08 and Top10 cells. Total RNAs were analysed by urea-PAGE.
Figure 2:
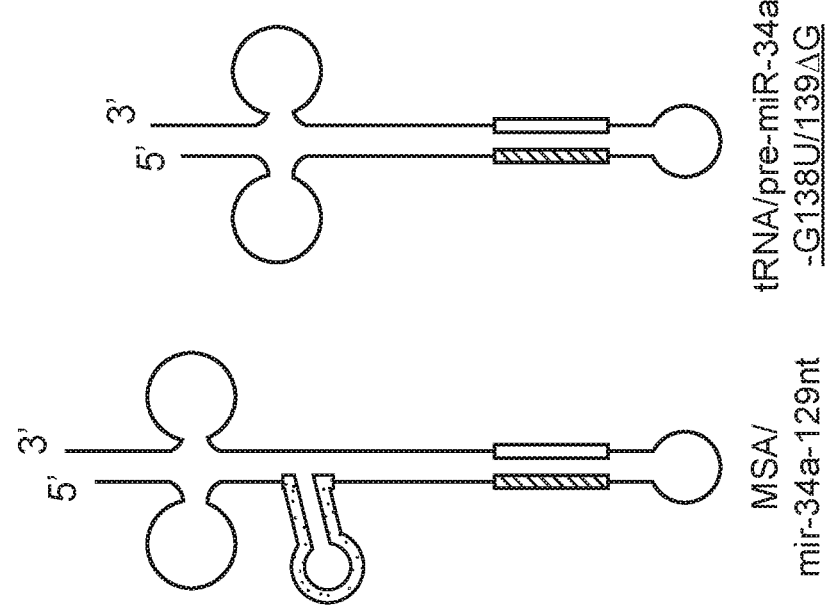
Figure 3B:
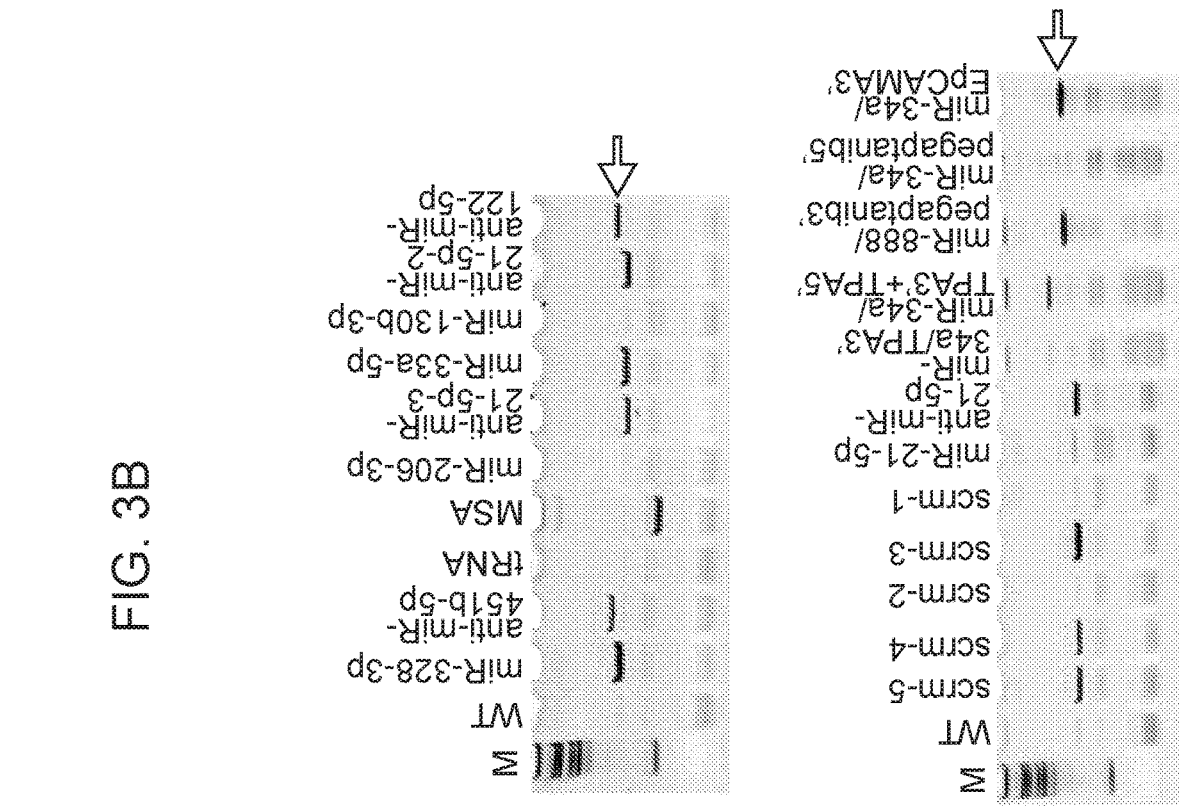
Figure 3B:
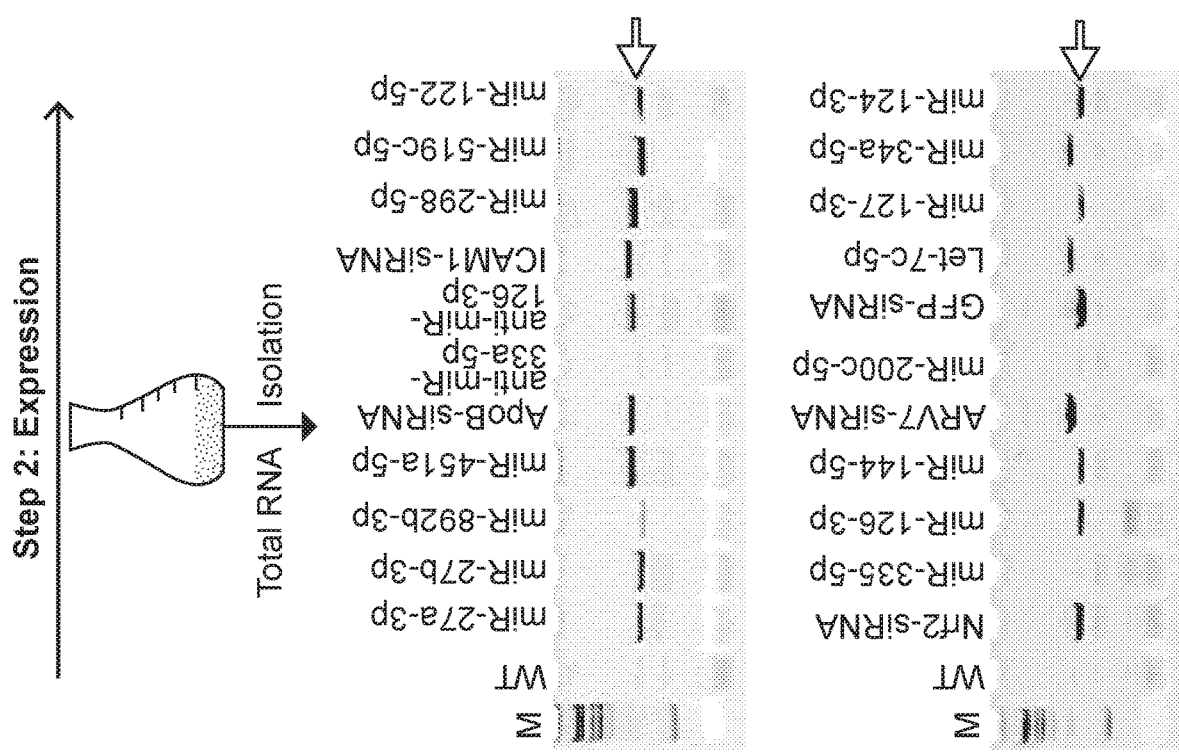
Figure 4:
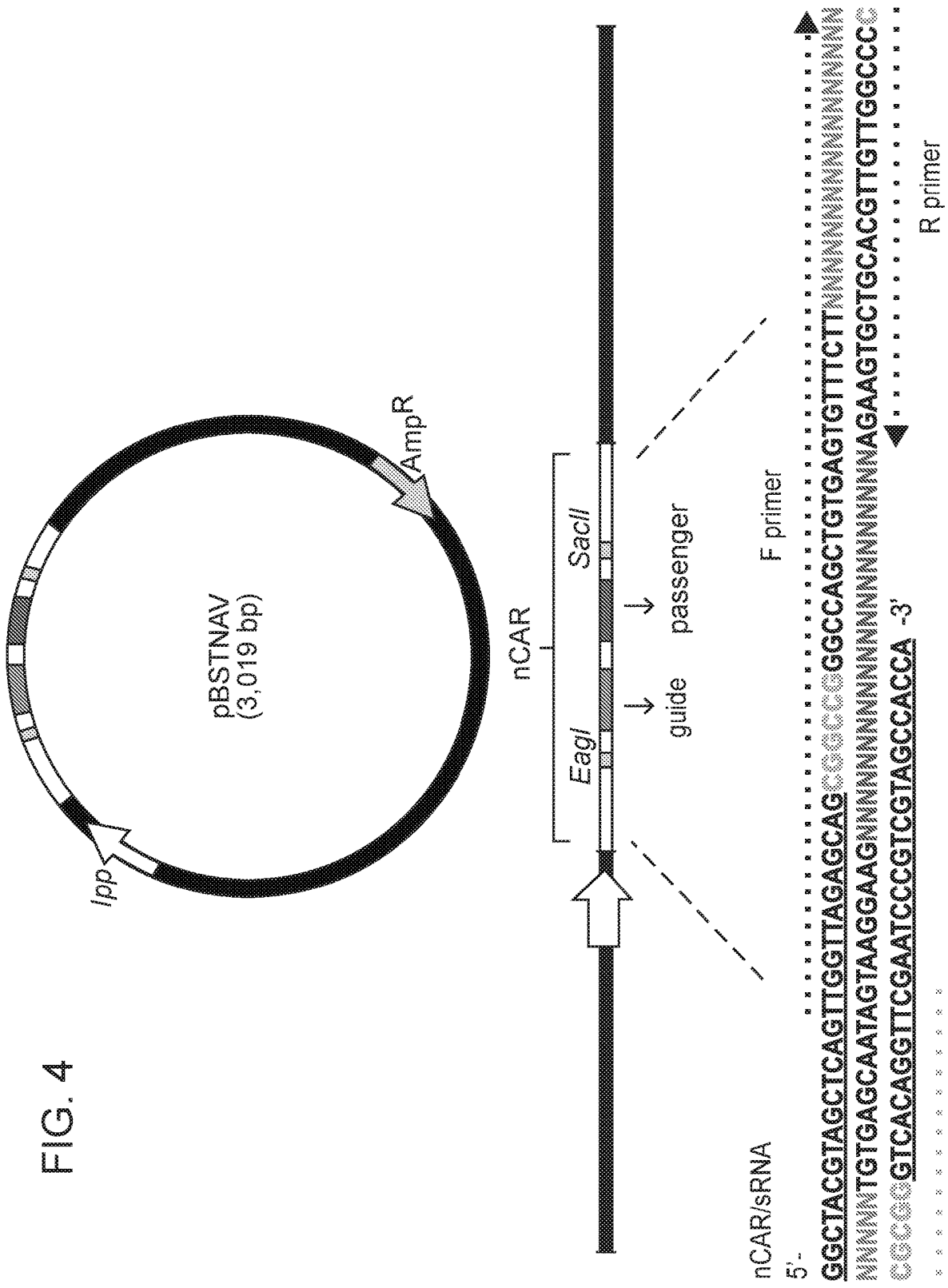
FIG. 4 illustrates Map of nCAR-based plasmid for the production of BERAs. nCAR (SEQ ID NO:588) was placed into the pBSTNAV vector, driven under Ipp promoter and selected via ampicillin resistance (AmpR). The mature miRNA and complementary sequences (the first "NN . . . NN" and second "NN . . . NN" sequence, respectively) within nCAR may be substituted by a miRNA/siRNA of interest. Cloning primers (dotted lines) are thus designed to span the 15-nt from restriction site (Eag I and Sac II), partially overlapping pre-miR-34a spanning towards the target ncRNA on both ends.
Figure 5:
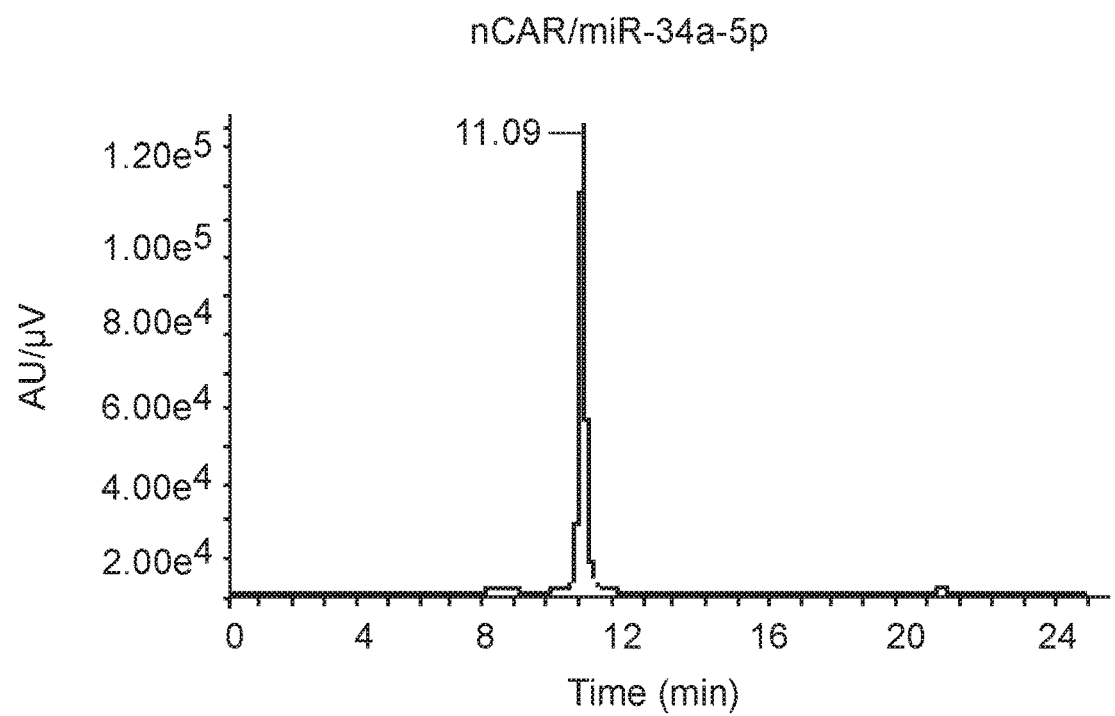
FIG. 5 illustrates HPLC determination of the purity of isolated BERAs. Shown are the HPLC traces of nCAR/miR-34a-5p and nCAR/miR-124-3p purified by anion exchange FPLC on a large scale, which are both over 98% pure.
Figure 5:
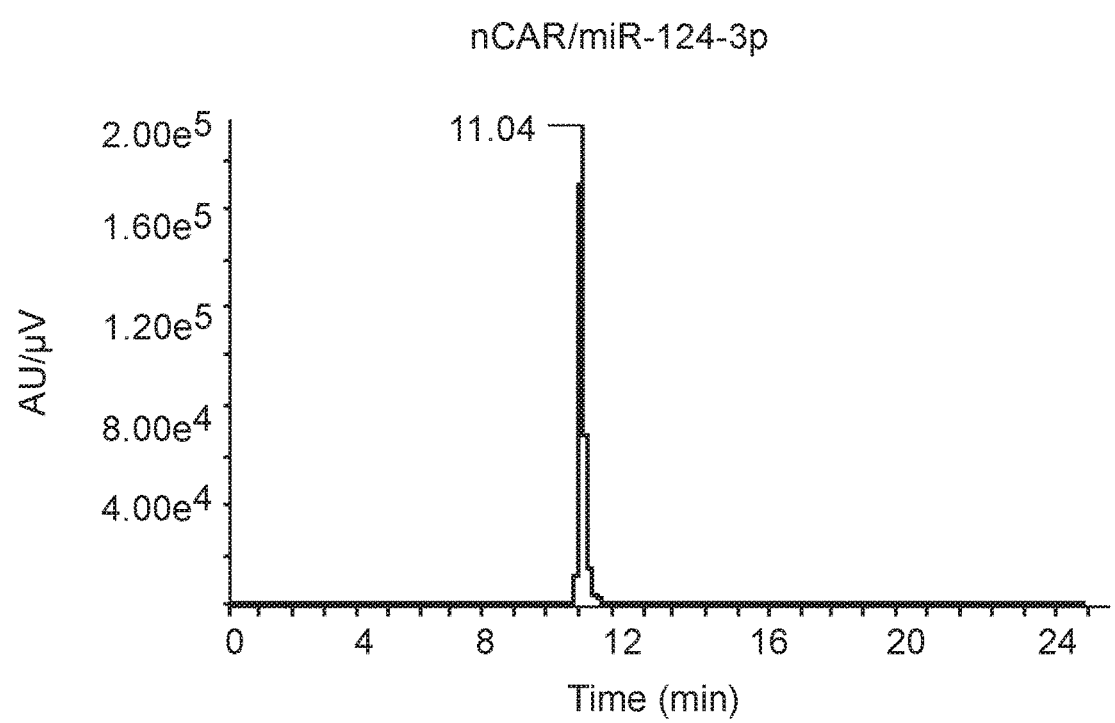

Therefore, we aimed at refining pre-miR-34a to achieve a more stable and higher level of expression, and assessed the dependence on Sephadex aptamer. Our approach was to use pre-miR-34a (110 nt) and rationally modify small bulges and kinks to yield more stable stems (FIG. 1D), which might lead to greater degree of RNA stability and accumulation in the host. Among five pre-miR-34a derivatives evaluated experimentally, we found that construct G138U/139ΔG showed the highest level of expression (>50% of total RNAs), which was also independent of Sephadex aptamer (FIG. 1D). Supporting this observation, the positional entropy of pre-miR-34a G138U/139ΔG was 4.6 Kcal/mol lower than its wild type counterpart (tRNA/mir-34a-110 nt). In addition, the increased expression of tRNA-fused pre-miR-34a G138U/139ΔG derivative, as compared to MSA/pre-miR-34a (Chen et al., 2015), was shown in both HST08 and Top10 common $E.$ $coli$ stains (FIG. 2). As a result, the pre-miR-34a G138U/139ΔG derivative was selected to fuse to a tRNA (e.g., tRNAMet) as ncRNA carrier (nCAR) for bioengineering RNAi agents.

nCAR permits a remarkable high-level production of target ncRNAs at a high success rate. The nCAR was applied for the assembly of target RNAi agents, where small RNAs (sRNAs) such as miRNAs, siRNAs and aptamers substituted miR-34a sequences or were directly added to designated locations (FIG. 3A). Considering the 5' counting rule (Park et al., 2011), a total of 42 nCAR/sRNA agents were designed (Tables 1 and 2). The coding sequences of individual target bioengineered ncRNA agents (BERA) were thus cloned into a target vector (FIG. 4). Following transformation and fermentation, we assessed the expression of target BERAs by urea-PAGE analysis of total RNAs isolated from $E.$ $coli$. Excitingly, we found that 33 BERAs were successfully expressed at a remarkably high level (40-80% of total RNAs; FIG. 3B), which gave a success rate of 80% (33 out of 42 target ncRNAs). The results demonstrate the robustness of nCAR for an improved higher level, heterogeneous expression of target RNAi agents.

On-demand small- and large-scale purification of bioengineered ncRNAs. We next sought for methods to isolate target BERAs from total RNAs. While the utility of the nCAR platform is purposed for large-scale production of milligrams of BERAs, we did examine the practicality of purifying microgram quantities that may be used for initial or high-throughput screening. Since the nCAR system generally offers BERAs (e.g., nCAR/miR-34a-5p and nCAR/miR-124-3p, etc.) around a length of 180 nt, we assessed whether target BERAs could be isolated with commercially available Select-a-Size DNA Clean & Concentrator (FIG. 3C) based on similar physicochemical properties of nucleic acids. The 50-bp selection was able to produce >88% pure BERA (determined by HPLC method) with a yield of 15-20 μg/ml culture (Table 4). When used in combination with the RNA Clean & Concentrator spin columns that remove large RNAs (FIG. 3C), the purity of isolated BERAs was over 97% (Table 4). Although the two-column method unsurprisingly offered a lower yield than the single-column, overall yield (~14 μg/ml culture or 30-40% of total RNAs) was still tremendously high, owing to the remarkable high-level expression.

Figure 3C:
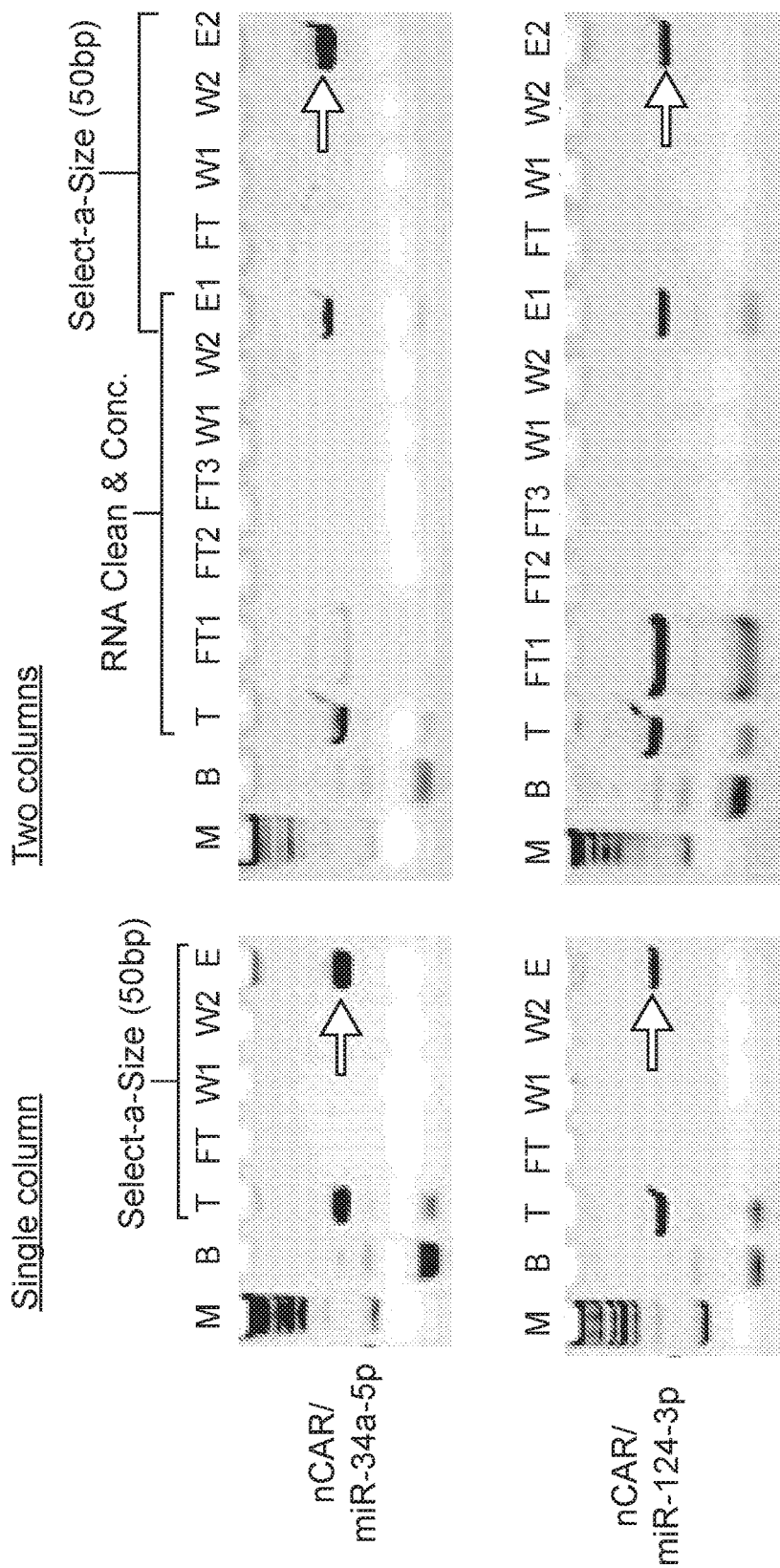
Figure 3C:
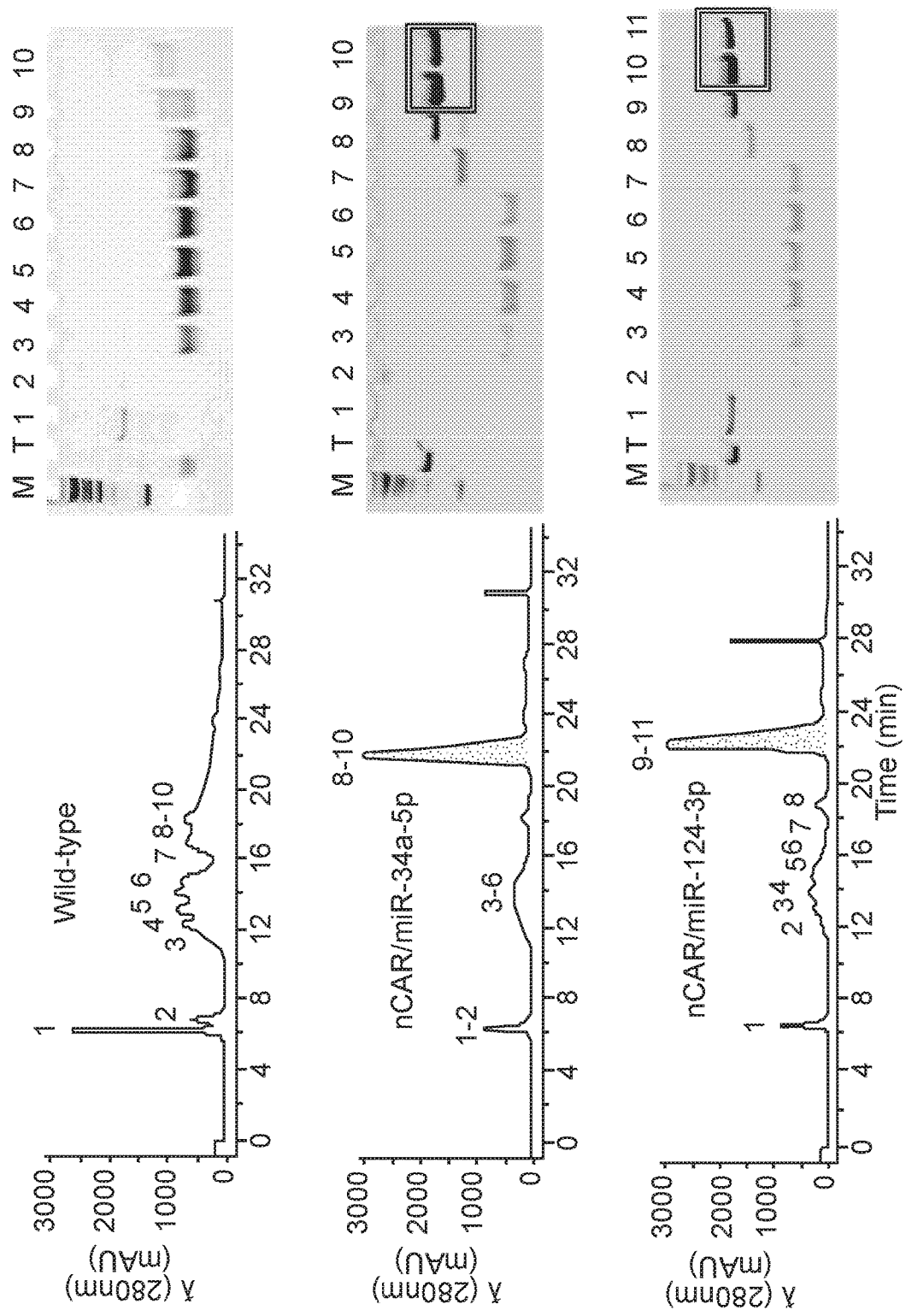

To achieve large-scale purification, we established a new anion exchange FPLC method. Up to 15 mg of total RNAs were loaded onto an Enrich-Q 10×100 column and separated by a single-run, salt-gradient elution (FIG. 3C). The majority of FPLC-isolated BERAs displayed a high degree of homogeneity (>98%; Table 3), as determined by HPLC method (FIG. 6). Given such enhanced expression and purification yield, we readily obtained up to 10 mg of target BERAs in a single run and 4-20 mg of pure BERAs from 1 L bacterial fermentation (Table 3). In addition, endotoxin was flushed through this process and the endotoxin activities of final BERAs were minimal (e.g., nCAR/miR-34a-5p: 0.85 EU/μg RNA; nCAR/miR-124-3p: 0.1 EU/μg RNA), which are much lower than the reported levels (2,000 EU/μg DNA) to induce cytotoxicity (Butash et al., 2000) and that (<5 EU/mg of body weight at a rate of 30 μg RNA/h; see the following animal studies) recommended for mouse studies (Malyala and Singh, 2008), and thus ensure endotoxin-free BERAs for functional studies.

Figure 6A:
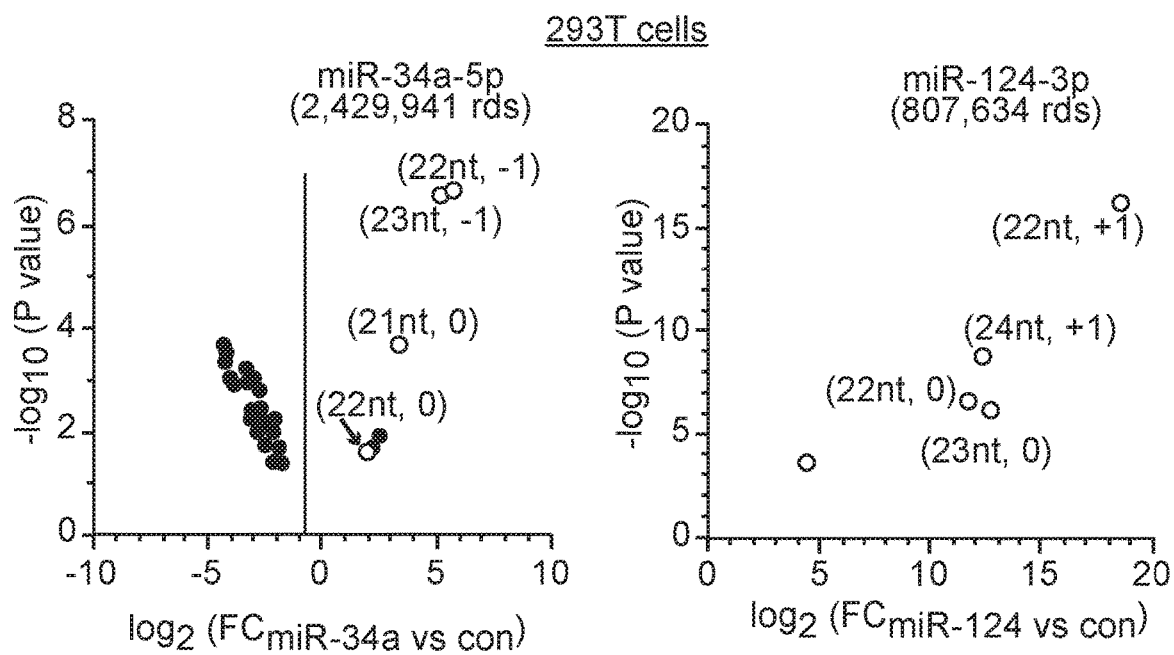
FIGS. 6A-6B illustrate selective release of target miRNAs from nCAR/miRNAs in human cells, in a Dicer dependent (miR-34a) and independent (miR-124) manner, changes miRNome profiles.
Figure 6A:
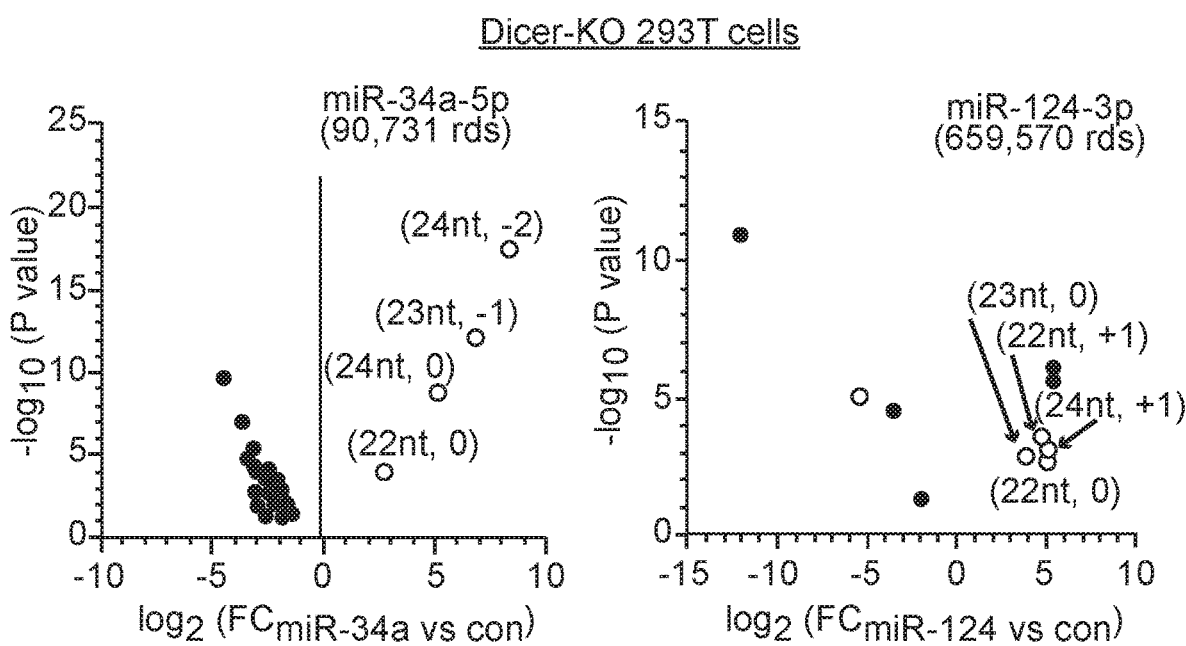

Selective release of target miRNAs from bioengineered ncRNAs in human cells rewrites miRNome, dependent (miR-34a-5p) or independent (miR-124-3p) on endoribonuclease Dicer. To examine whether target miRNAs can be specifically generated from BERAs in human cells and whether this process is Dicer dependent, we conducted a small RNA sequencing study on human 293T cells and Dicer-knockout (Dicer-KO) counterparts (Bogerd et al., 2014) treated with nCAR/miR-34a-5p, nCAR/miR-124-3p, and control RNA. The result showed that nCAR/miR-34a-5p was selectively processed to miR-34a-5p as its dominant isoform (22-nt; starting site 0) in 293T cells, as well as to lower reads of other isoforms (FIG. 6A). However, miR-34a-5p levels were 27-fold lower in Dicer-KO 293T cells than wild type 293T cells, demonstrating a critical role for Dicer in the production of miR-34a-5p from nCAR/miR-34a-5p. Surprisingly, nCAR/miR-124-3p was mainly processed to a 23-nt isoform starting at position 0 in wild type 293T cells whereas a 22-nt specie from position +1 in Dicer-KO cells. Since miR-124-3p naturally exists as 20-nt, additional nucleotides carried over from pre-miR-34a at the 3' end of the carrier indicates a unique cleavage of nCAR/miR-124-3p to offer miR-124-3p. Most interestingly, comparable levels of miR-124-3p were generated from nCAR/miR-124-3p in wild type and Dicer-KO 293T cells (FIG. 6A), indicating the independence of Dicer for the production of miR-124-3p.

Figure 6B:
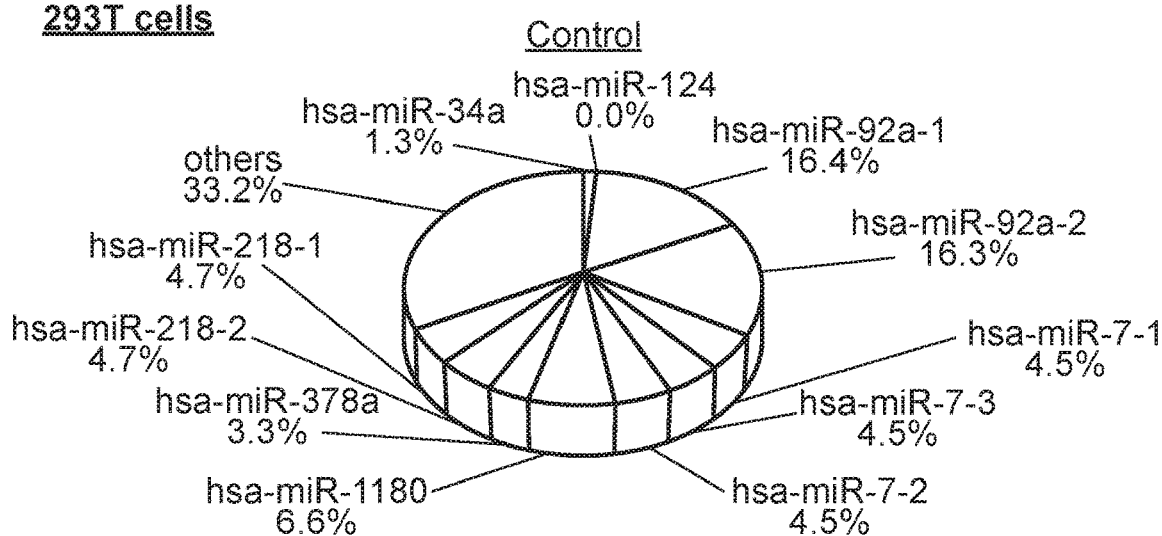
Figure 6B:
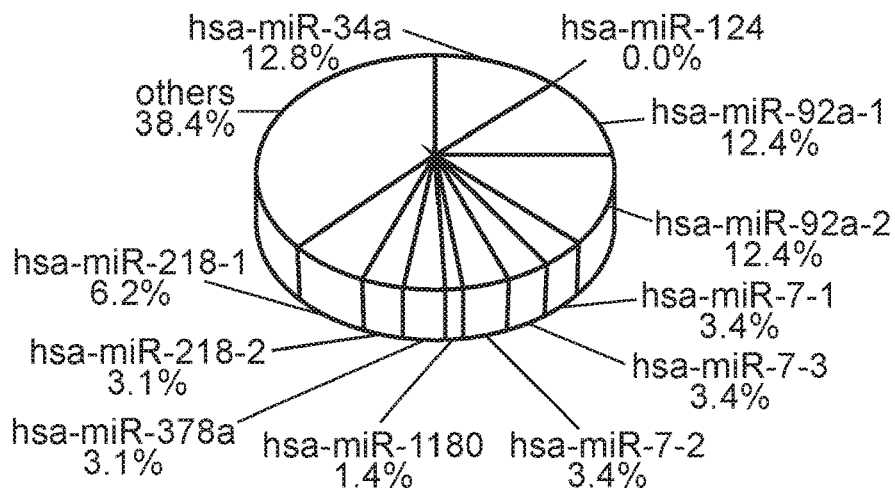
Figure 6B:
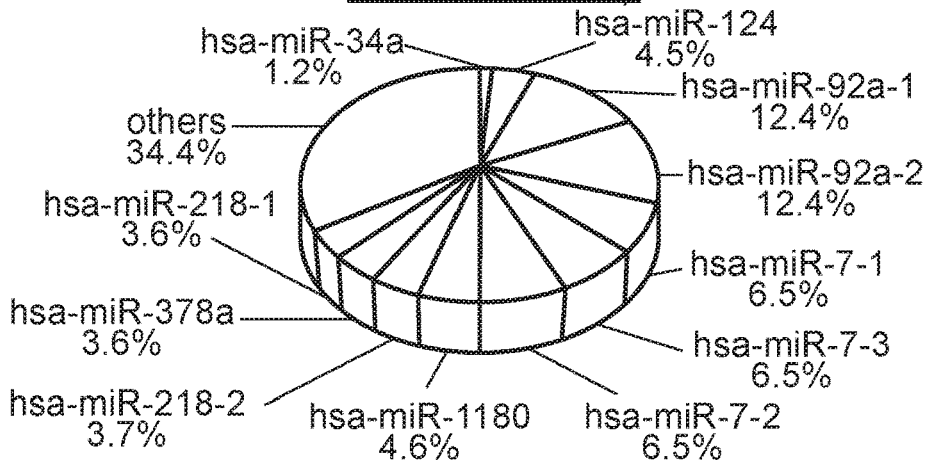
Figure 6B:
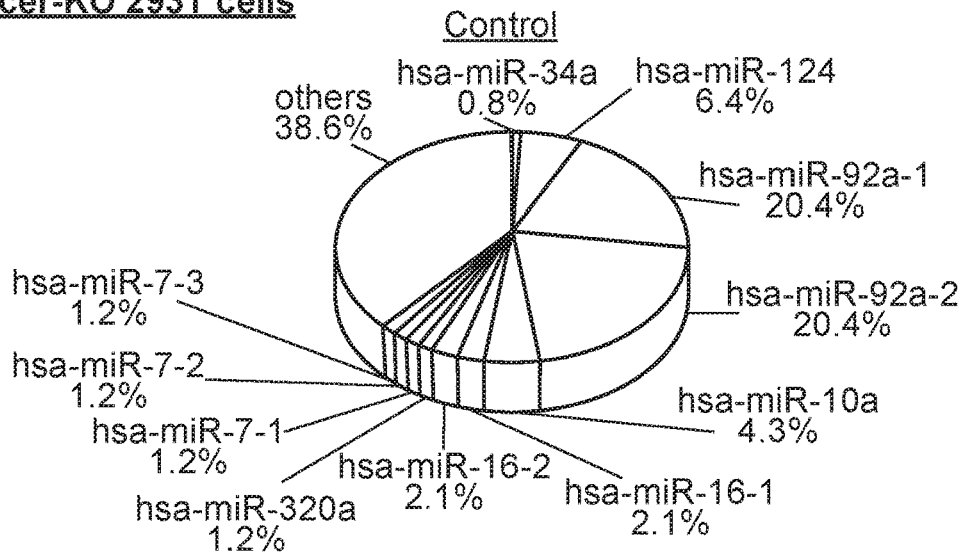
Figure 6B:
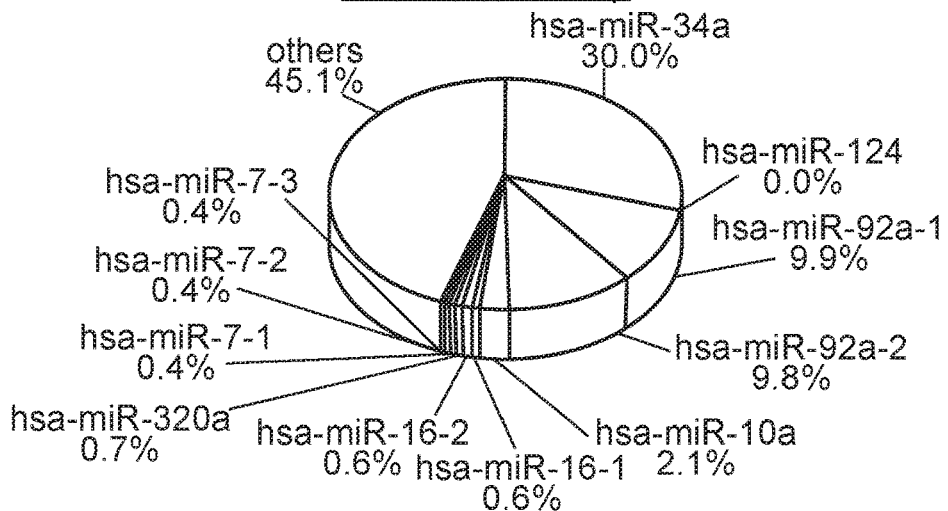
Figure 6B:
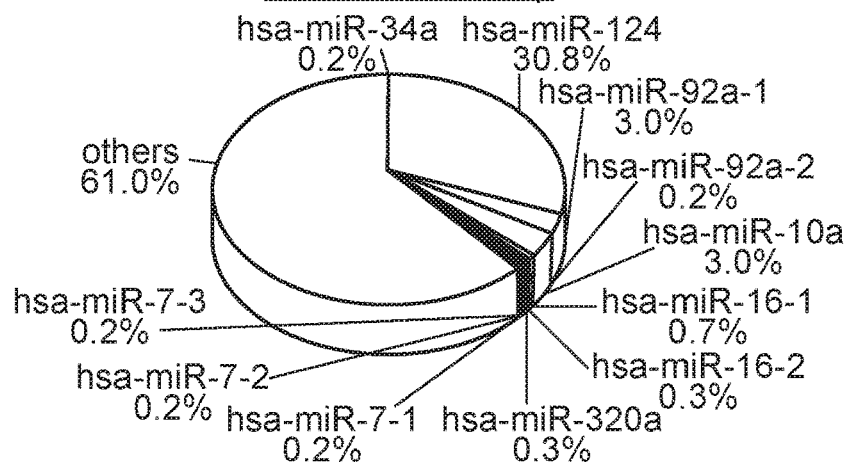
Figure 7A:
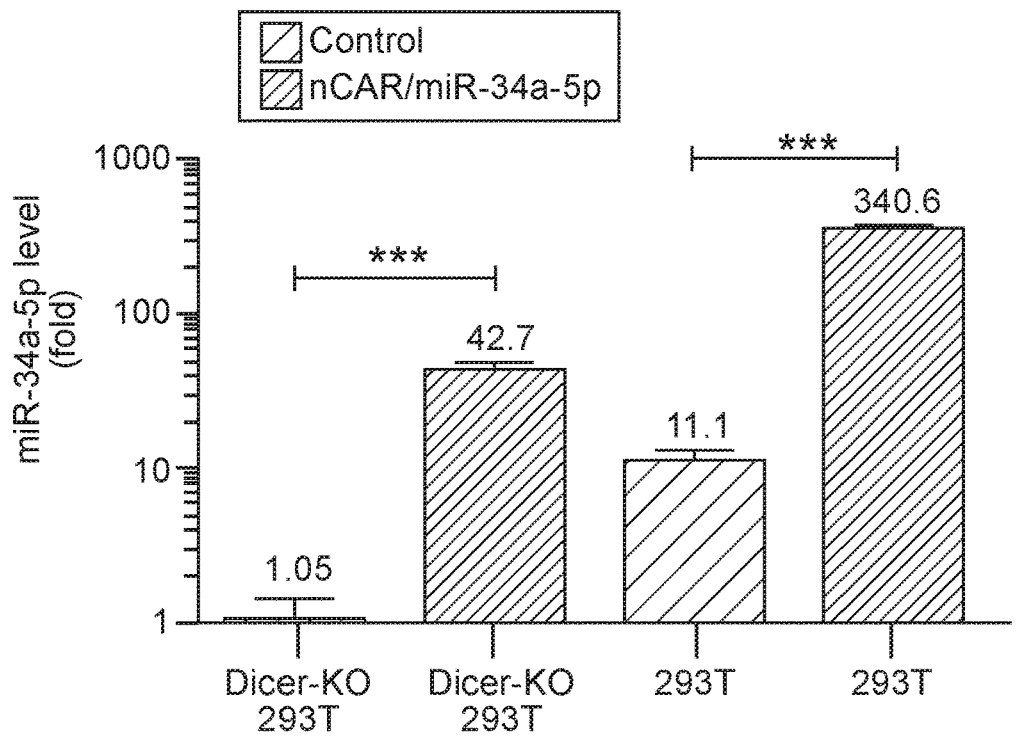
FIGS. 7A-7C illustrate qPCR verification of the degree of changes in target miRNAs and some mRNAs identified by RNA sequencing study.
Figure 7A:
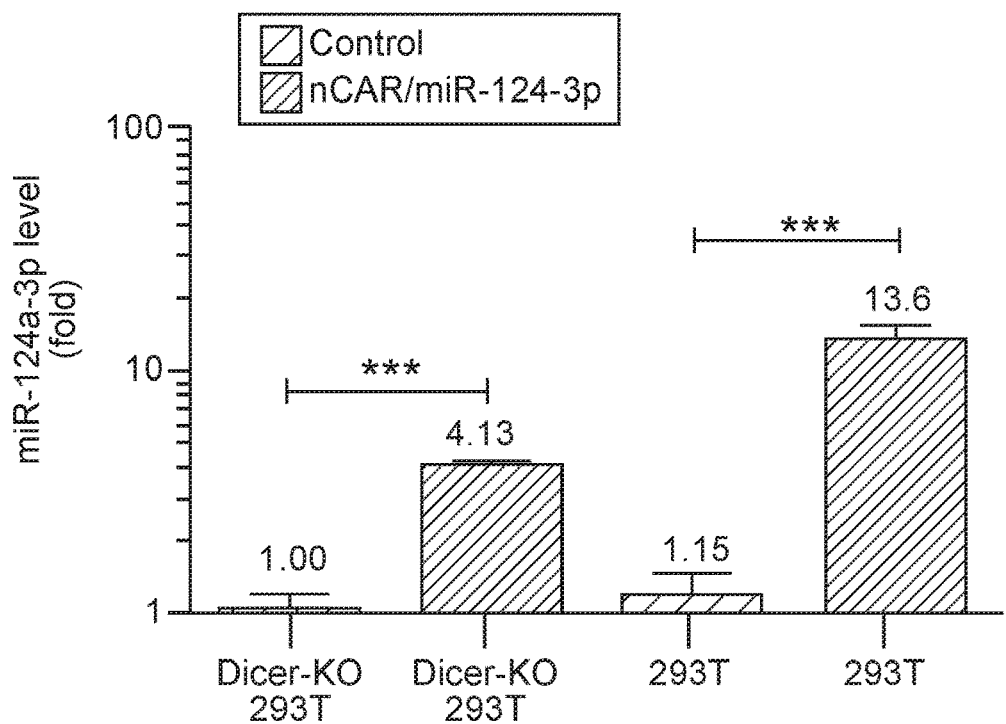

The selective release of target miR-34a-5p from nCAR/miR-34a-5p in human cells led to a specific change of miRNome profiles, where miR-34a-5p became the most abundant miRNA in both wild type 293T cells (>16 million reads of all miRNAs) and Dicer-KO cells (<0.5 million of reads) (FIG. 6B). Likewise, miR-124-3p became the seventh-most and most abundant miRNA in wild type and Dicer-KO 293T cells, respectively, post treatment with nCAR-miR-124-3p. The increase in target miRNA levels among miRNome was further confirmed by qPCR analyses (FIG. 7A). Although the fold of increase in miR-34a-5p levels was "surprisingly" higher in the Dicer-KO cells than wild type 293T cells, this scenario is simply attributable to the low basal expression level of miR-34a-5p in Dicer-KO cells (FIG. 6A). Together, our results demonstrate that a large number of target miRNAs can be selectively generated from BERAs in human cells, in a Dicer dependent (e.g., miR-34a-5p) or independent (e.g., miR-124-3p) manner, which subsequently rewrites cellular miRNome profiles.

Figure 7B:
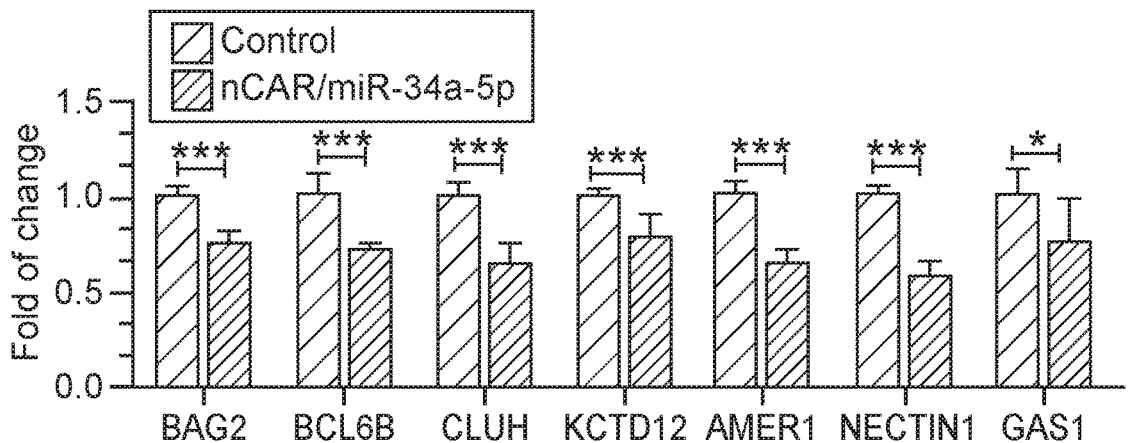
Figure 7B:
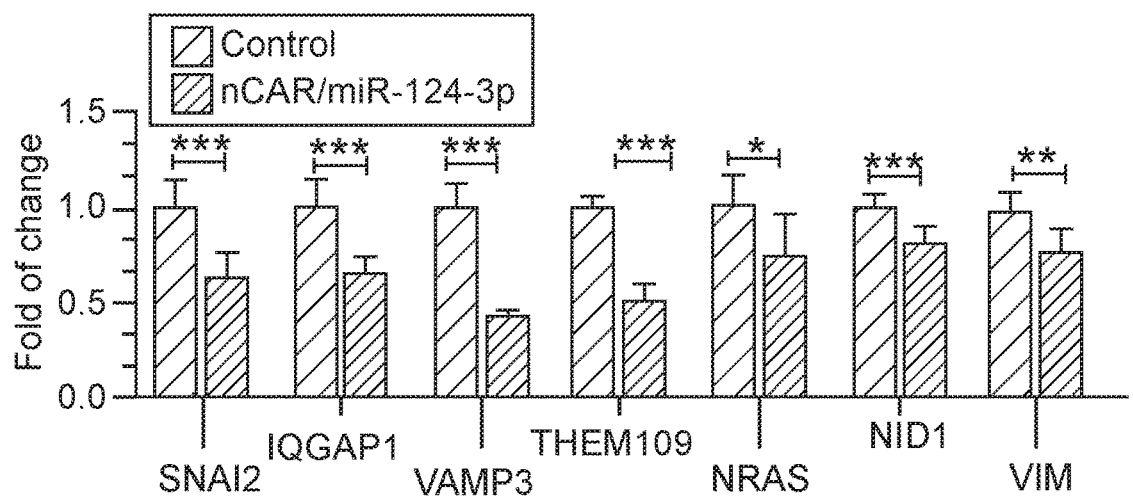
Figure 7C:
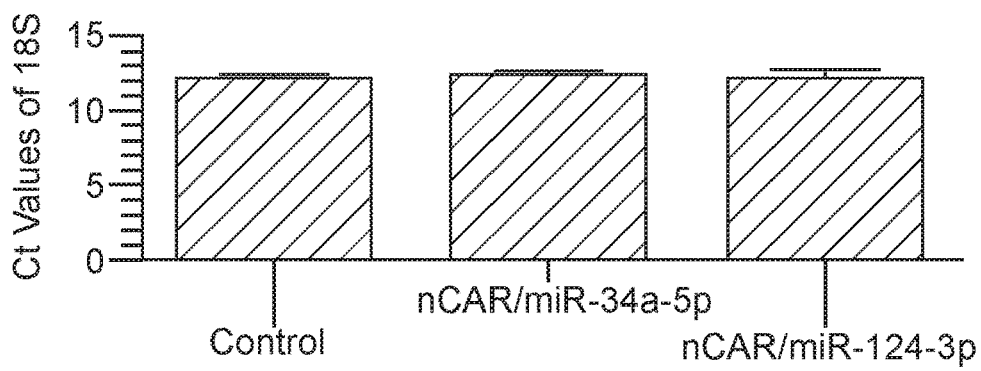
Figure 8A:
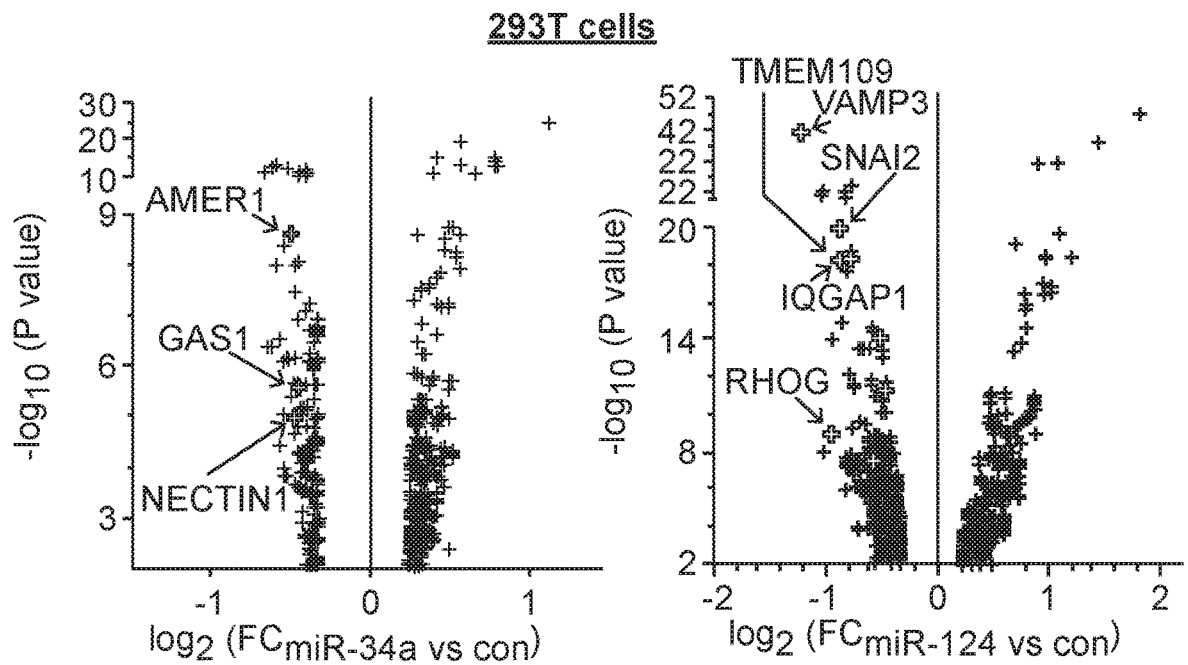
FIGS. 8A-8D illustrate specificity of nCAR/miRNA in the regulation of miRNA target gene expression.
Figure 8A:
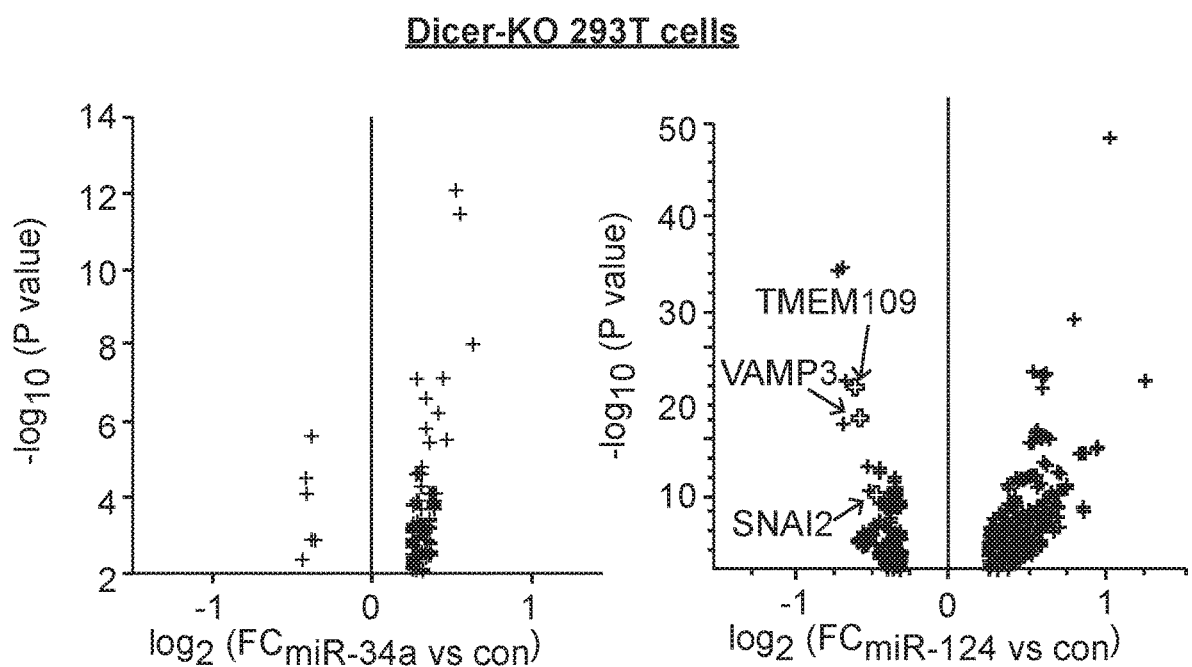

Bioengineered miRNAs specifically modulate the transcriptome profiles in human cells. To delineate the effects of BERA on miRNA target gene expression and assess its specificity, we processed the same set of RNA samples for mRNA sequencing study. The results showed that 112 genes were significantly downregulated and 193 upregulated in nCAR/miR-34a-treated 293T cells, as well as 260 genes downregulated and 290 upregulated in nCAR/miR-124-treated 293T cells (FIG. 8A). These downregulated genes include many well-documented targets for specific miRNA (e.g., AMER1, GAS1, and NECTIN1 for miR-34a; VAMP3, SNAI2, IQGAP1, TMEM109, and RHOG for miR-124) (Chang et al., 2007; Karginov et al., 2007; Chi et al., 2009; Kaller et al., 2011), as well as some genes that have not been reported before (e.g., BAG2 and BCL6B for miR-34a; NID1 and VIM for miR-124). The suppression of several transcripts was further verified by qPCR analyses (FIG. 7B) with gene selective primers (Table 5), where housekeeping gene levels were not altered (FIG. 7C).

Figure 8B:
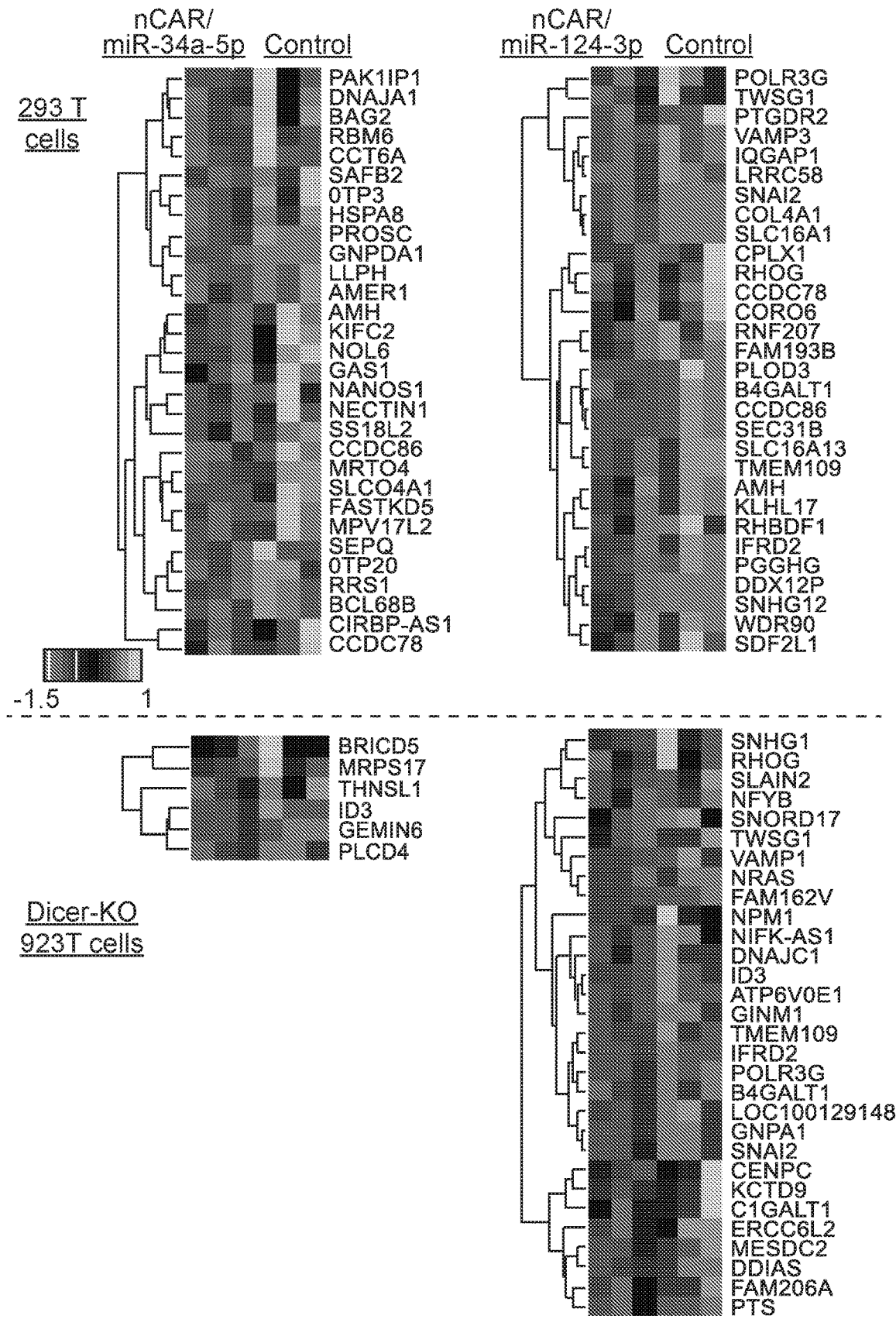

On the other hand, only six genes were significantly downregulated in Dicer-KO 293T cells by nCAR/miR-34a-5p (FIG. 8B), which have not been connected to miR-34a, again supporting the dependence on Dicer for miR-34a-5p production as well as the selectivity of nCAR/miR-34a-5p in the regulation of miR-34a target gene expression. In sharp contrast, nCAR/miR-124-3p significantly reduced the expression of 68 genes in Dicer-KO cells, among which many (e.g., VAMP3, SNAI2, and RHOG) are known miR-124 targets and show good overlap with targets identified in wild type 293T cells (FIG. 8B). This is in agreement with the independence on Dicer in generating comparable high levels of miR-124-3p isoforms from nCAR/miR-124-3p in cells, whereas the major isoforms differed in length and position.

Figure 8C:
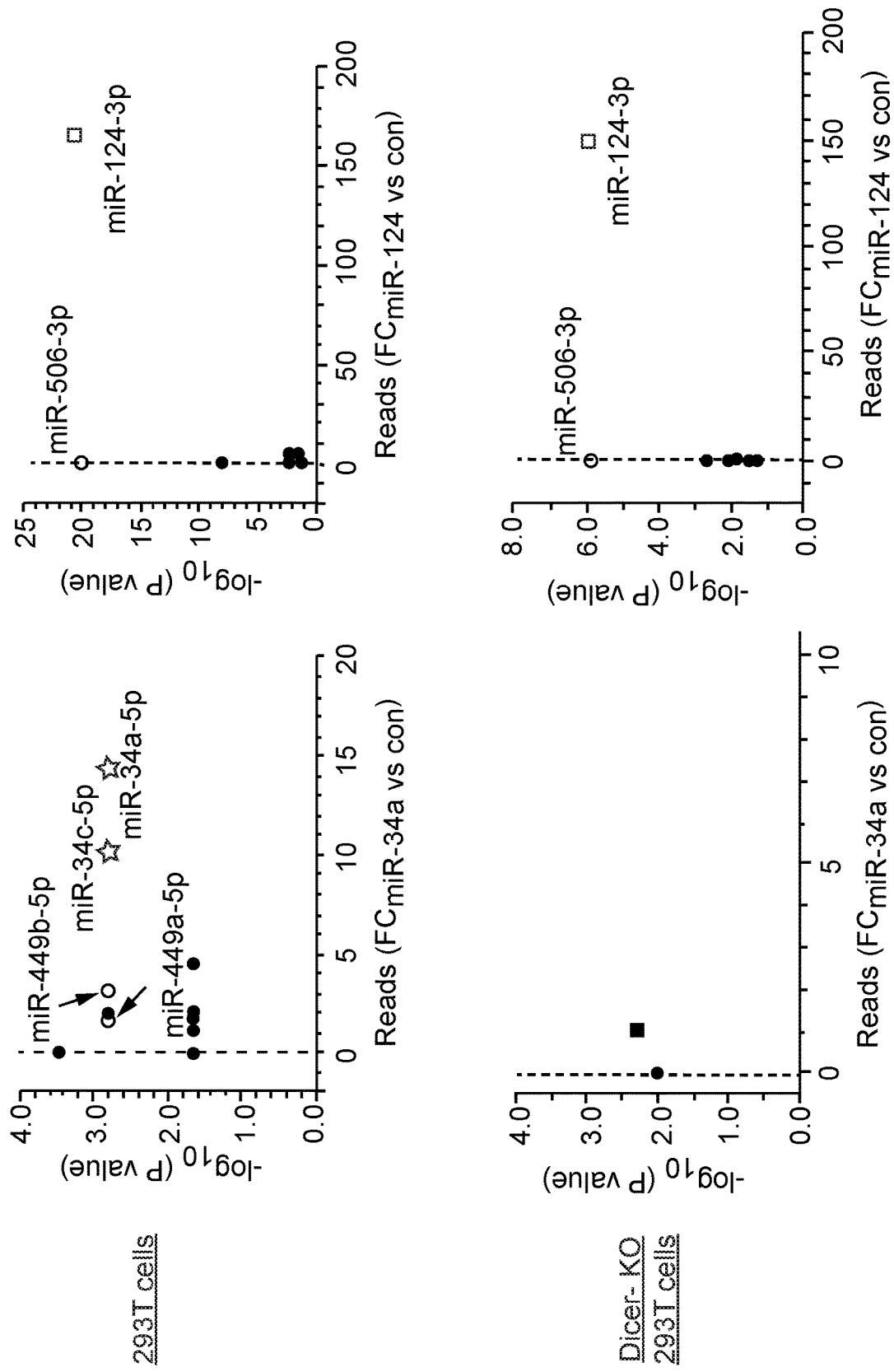
Figure 8D:
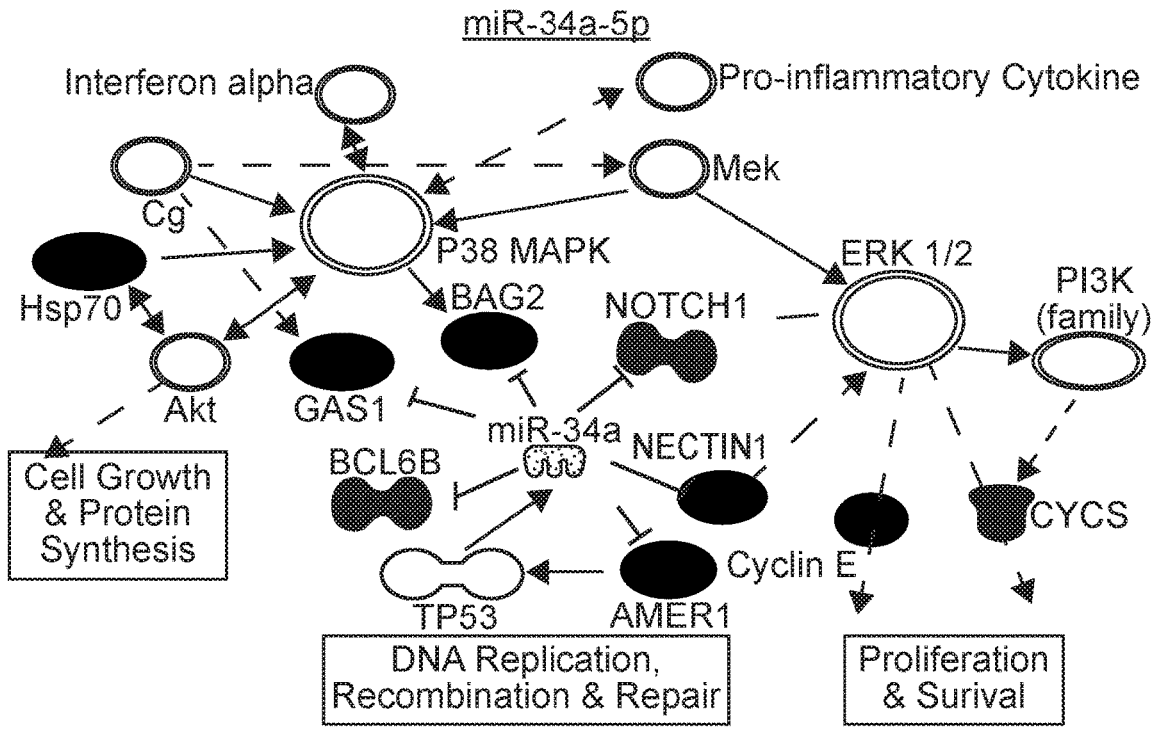
Figure 8D:
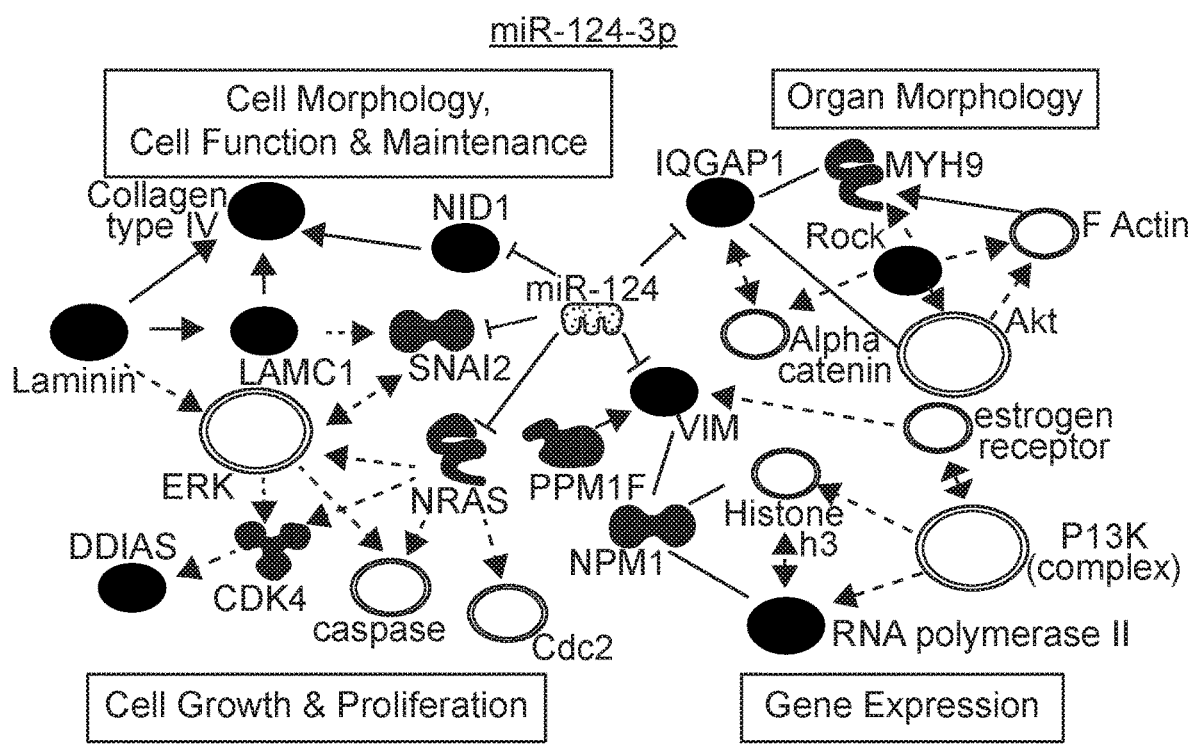

The selectivity of nCAR/miRNA in the regulation of miRNA target gene expression was further demonstrated by miRNA enrichment analyses. MiR-34a-5p was highly enriched from nCAR/miR-34a-5p-downregulated genes in 293T cells while the same did not hold true for Dicer KO cells (FIG. 8C), interweaving the specific effects on target gene expression due to Dicer-dependent excision of miR-34a-5p from nCAR/miR-34a-5p. Unsurprisingly, miR-449/34c within the same miR-34/449 family was also enriched from nCAR/miR-34a-5p-downregulated genes in 293T cells, supporting the similarity of their functions in gene regulation. However, miR-449/34c showed a low abundance (log 2CPM<6) and/or no significant (P>0.05) change in its expression after BERA treatment, and thus unlikely had any contribution to the change of transcriptome. Interestingly, miR-124-3p was highly enriched for nCAR/miR-124-3p-downregulated genes in both wild type and Dicer-KO 293T cells (FIG. 8C), which not only supports the selectivity of nCAR/miR-124-3p in the regulation of miR-124 target gene expression but also demonstrates the independence of miR-124-3p formation on Dicer. Likewise, miR-506 within the miR-124/506 family was enriched, although miR-506 was absent (0 reads) in all genotype and treatment cells. Additionally, we employed ingenuity pathway analysis to investigate the biological pathways affected by BERA-downregulated genes. Gene regulation networks regulated by miR-34a were linked to cell growth, DNA replication, and cell proliferation and survival, while miR-124 was associated with cell morphology, maintenance, and gene expression (FIG. 8D). Taken together, these results demonstrate that nCAR/miRNAs displayed a high selectivity in gene regulation in human cells.

Figure 9A:
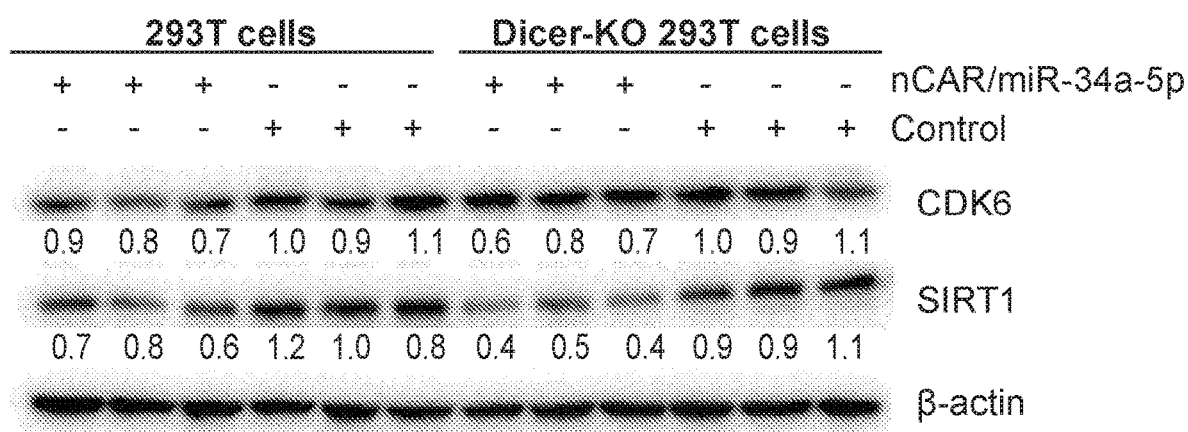
FIGS. 9A-9B illustrate impact of Dicer status on the control of protein levels of target genes by bioengineered miR-34a and miR-124.
Figure 9B:
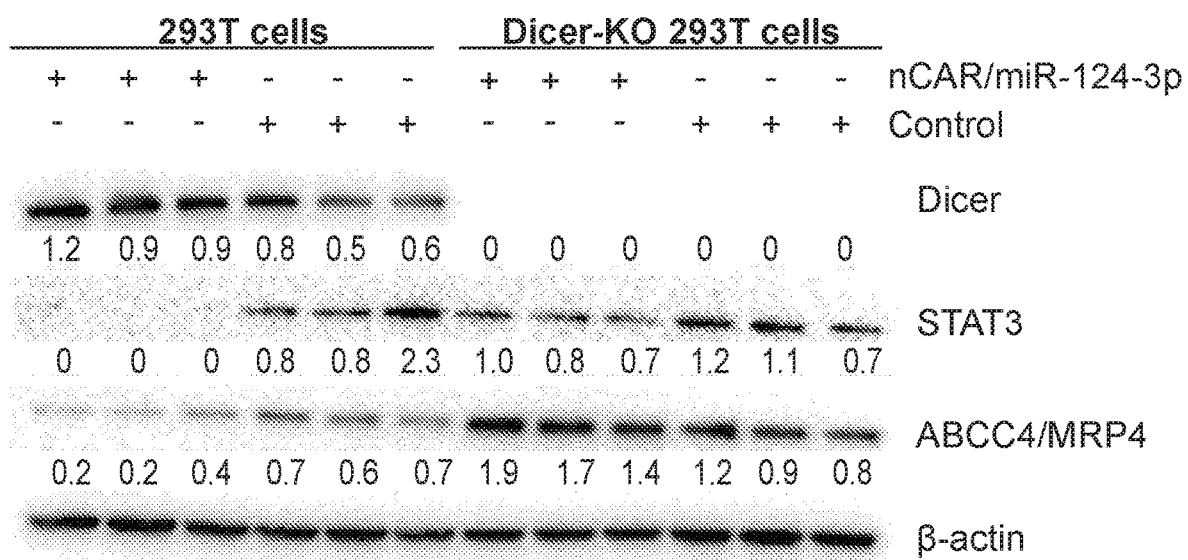

Biologic miRNAs reduce the protein levels of target genes in human cells. We further chose a few well-established targets for miR-34a (e.g., CDK6 and SIRT1) (Sun et al., 2008; Yamakuchi et al., 2008) and miR-124 (e.g., STAT3 and ABCC4/MRP4) (Hatziapostolou et al., 2011; Markova and Kroetz, 2014) to delineate the impact of bioengineered miRNAs on protein expression levels. Immunoblot analyses revealed a consistent suppression of CDK6 and SIRT1 protein levels by nCAR/miR-34a-5p in 293T cells (FIG. 9A), as a result of high levels of released miR-34a-5p (FIG. 6A) However, in Dicer-KO cells, CDK6 protein levels were unchanged while SIRT1 levels were steadily reduced by nCAR/miR-34a-5p, which could be due to a much lower level of miR-34a-5p produced in the absence of Dicer (FIG. 6A). This interesting observation might also indicate distinct sensitivities of different targets to the absolute amounts or extents of change of cellular miR-34a levels (FIG. 6A). Similarly, variable degrees of impact of nCAR/miR-124-3p on the protein levels of miR-124-3p targeted STAT3 and MRP4/ABCC4 (FIG. 9B) were identified in wild type and Dicer-KO 293T cells, which might be attributable to the difference in the most abundant miR-124-3p isoforms produced in those cells (FIG. 6A) with slightly-altered seed sequences or nucleotides.

Figure 10A:
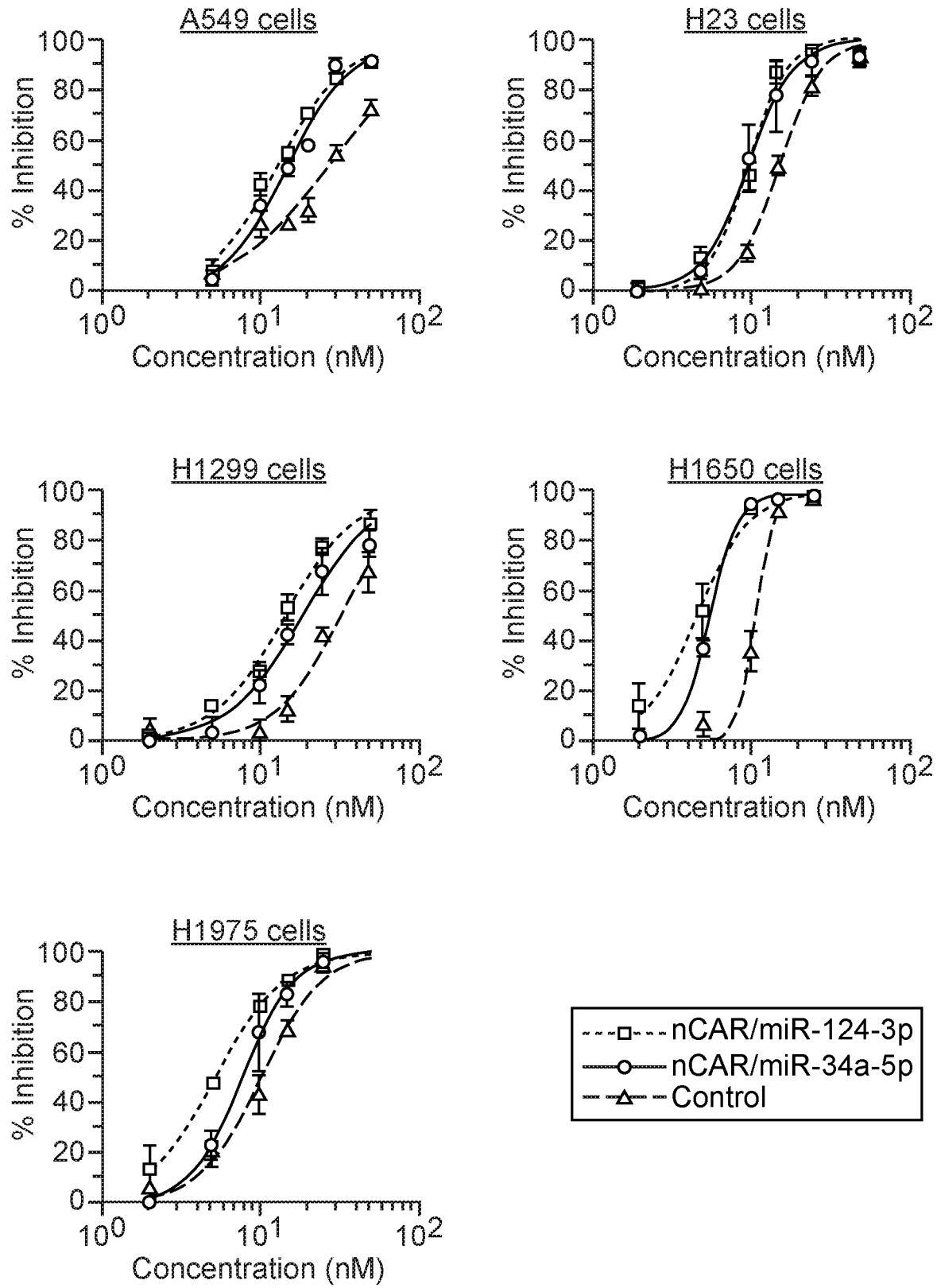
FIGS. 10A-10C illustrate bioengineered miR-34a and miR-124 inhibit human lung cancer cell proliferation via the suppression of (proto-)oncogene expression.
Figures 10B, 10C:
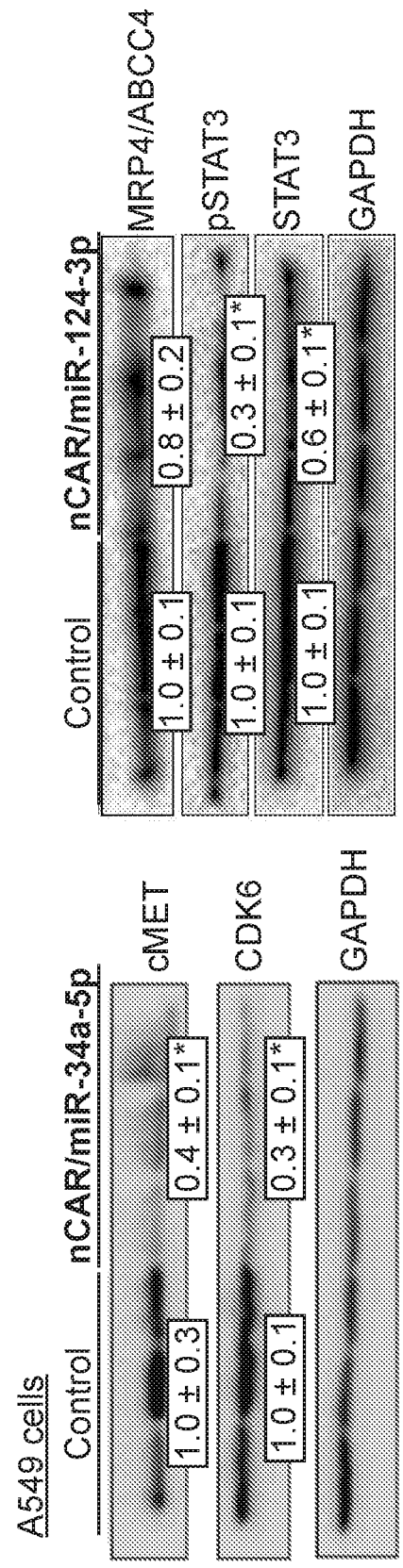

Bioengineered nCAR/miR-34a-5p and miR-124-3p are active in suppressing human lung carcinoma cell proliferation in vitro. To further evaluate the utility of BERAs, we investigated the dose-dependent anti-proliferation activities of two model BERAs, nCAR/miR-34a-5p and nCAR/miR-124-3p, against a variety of human lung carcinoma cells with different p53 and EGFR status as lung cancer remains the most lethal cancer in the United States (Siegel et al., 2017), and restoration of miR-34a and miR-124 expression or function is effective to inhibit lung cancer cell growth (Wiggins et al., 2010; Kasinski and Slack, 2012; Cho et al., 2016; Yang et al., 2017). Compared to the control, both nCAR/miR-34a-5p and nCAR/miR-124-3p inhibited cell proliferation to a significantly greater degree (FIG. 10A), which was also demonstrated by the estimated EC50 and Hill Slope values. Interestingly, H1299 cells (mutant p53) were more sensitive to nCAR/miR-34a-5p than A549 (wild type p53), under which the p53-miR-34a positive feedback loop confers an additional tumor suppressive effect when p53 is haploinsufficient (Okada et al., 2014). Similarly, H1650 and H1975 (mutant EGFR) cells carrying constitutively active EGFR were more sensitive to nCAR/miR-124-3p than A549 (wild type EGFR). In addition, the suppression of A549 cell proliferation was associated with reduced protein levels of miR-34a targets (cMET and CDK6) and miR-124 targets (STAT3, pSTAT3 and MRP4/ABCC4) (FIG. 10B), supporting the presence of multiple targets/pathways for these miRNAs in reducing cancer cell proliferation.

Figure 11A:
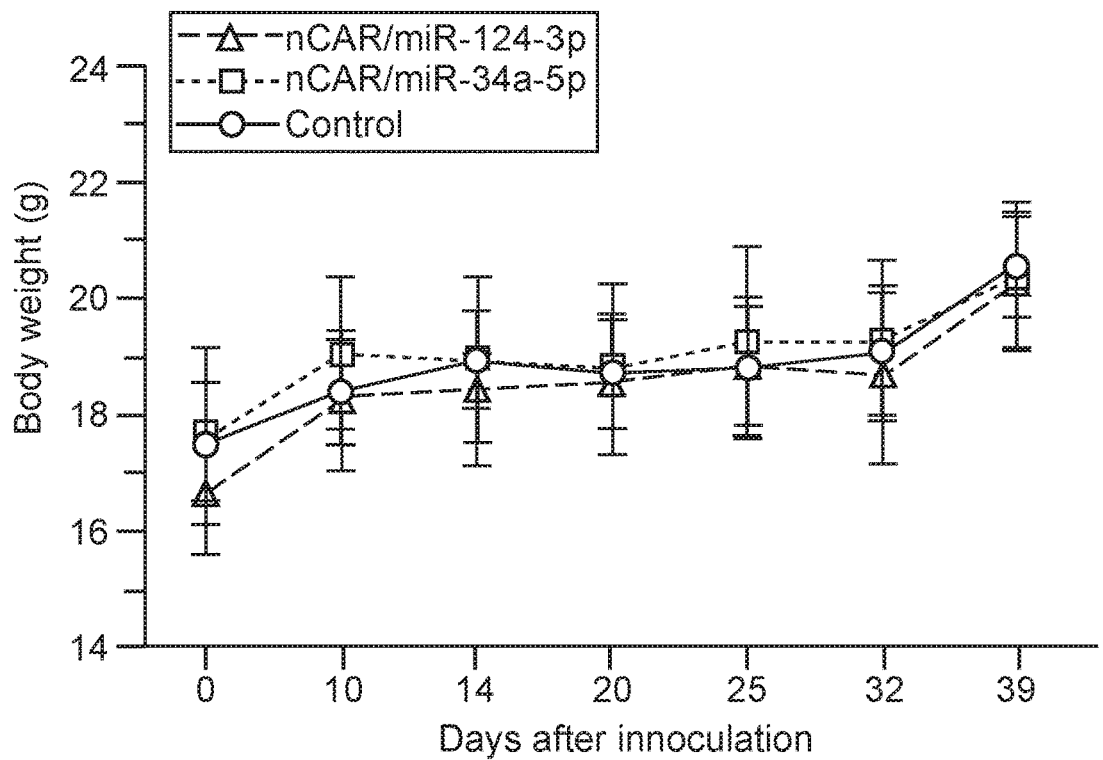
FIGS. 11A-11B.
Figure 11B:
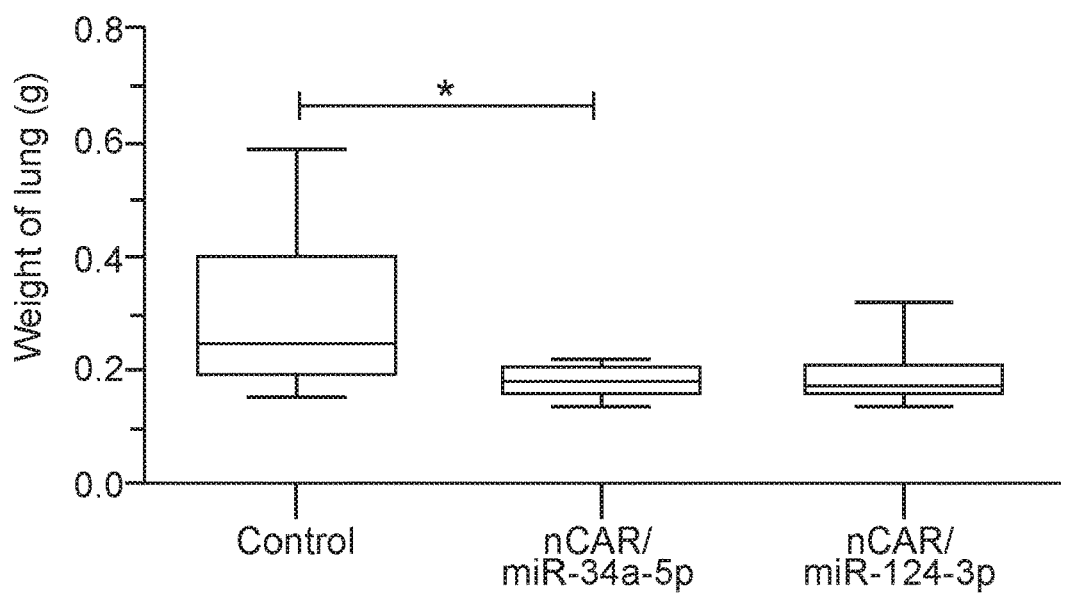
Figure 12A:
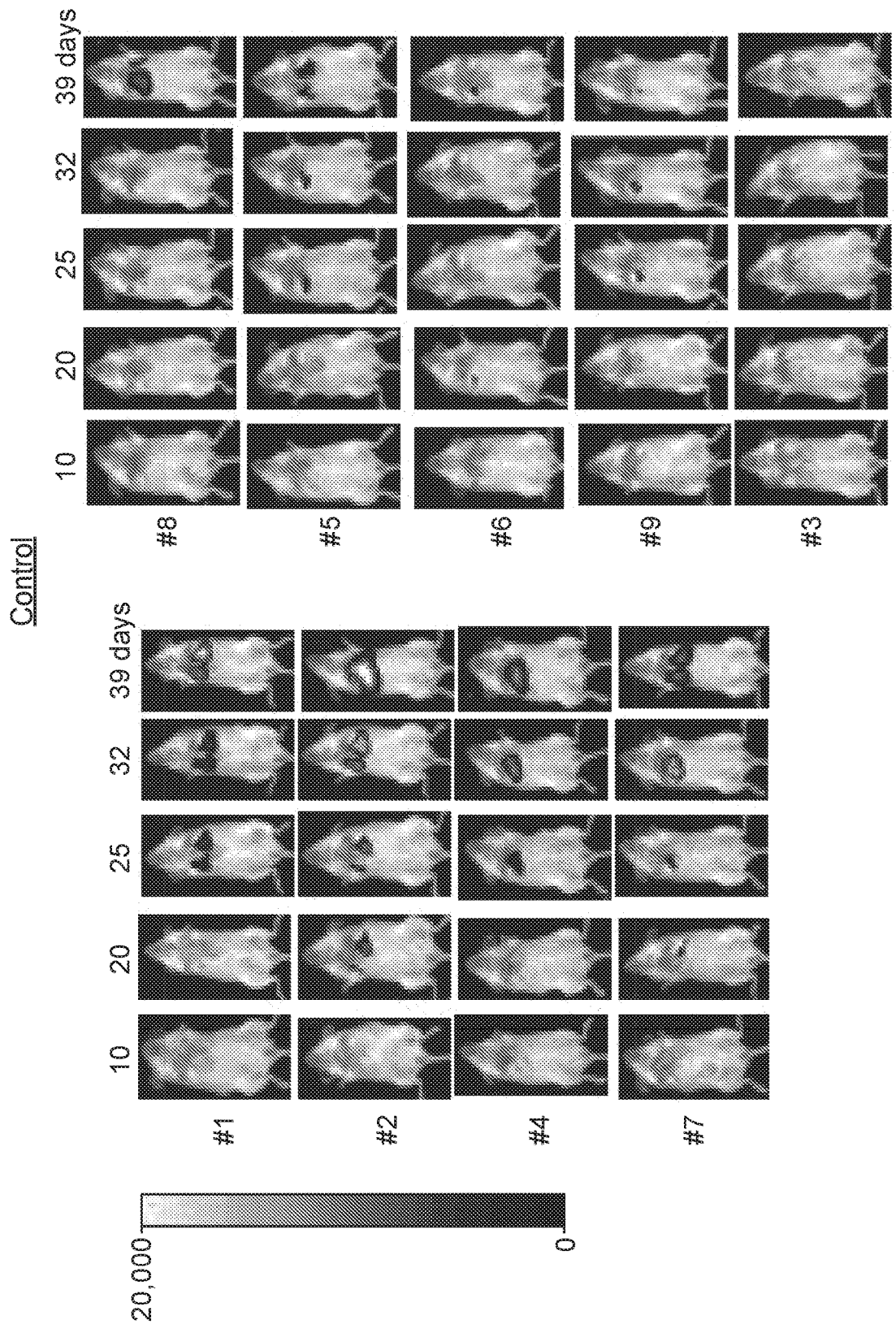
FIGS. 12A-12C illustrate application of bioengineered miRNAs to control lung xenograft tumor progression in vivo.
Figure 12A:
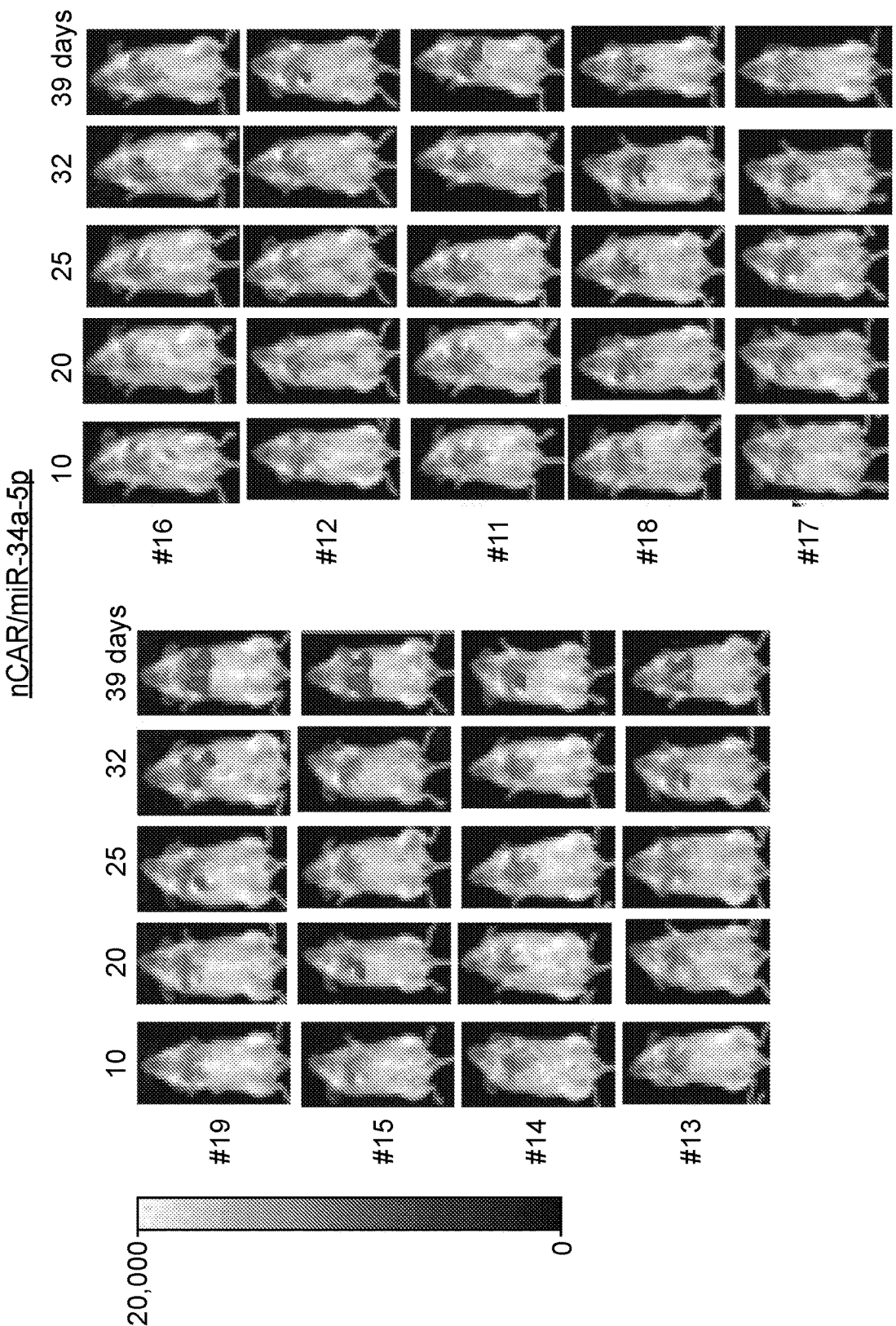
Figure 12B:
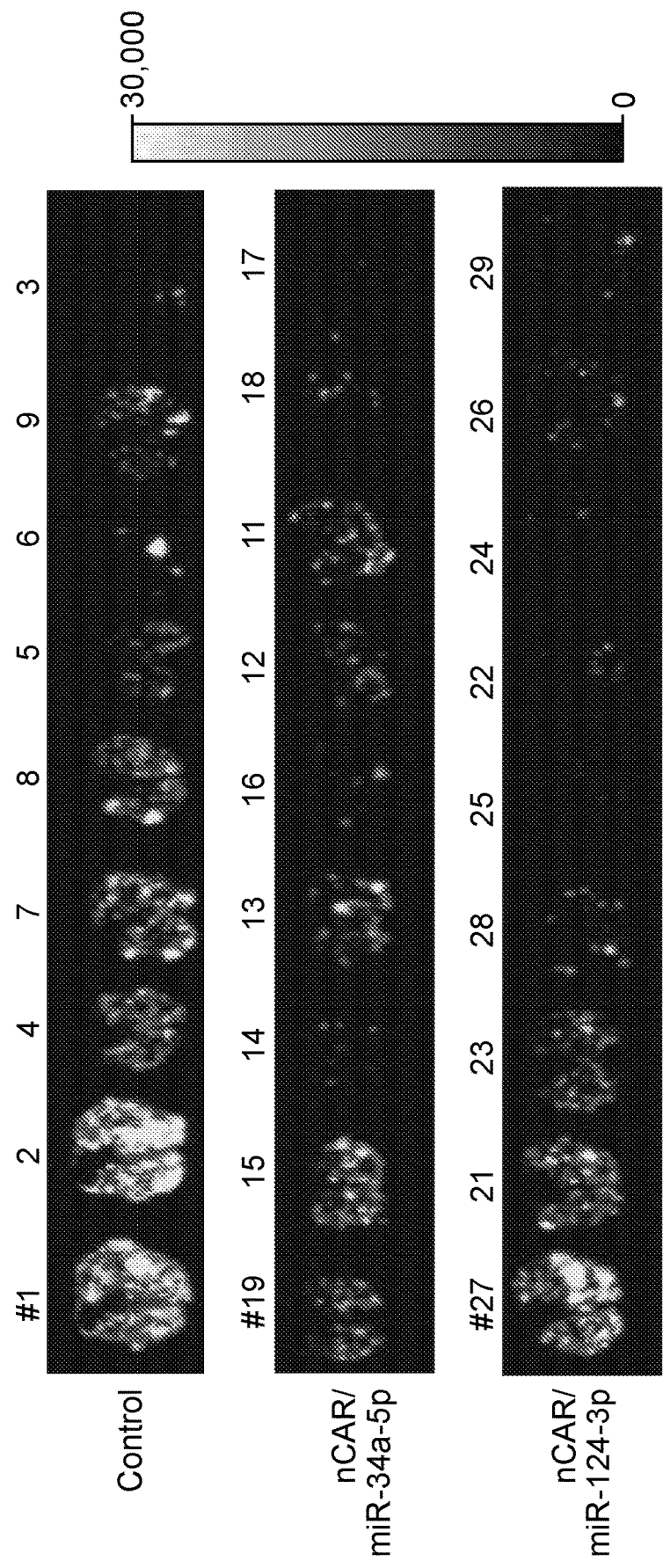
Figure 12C:
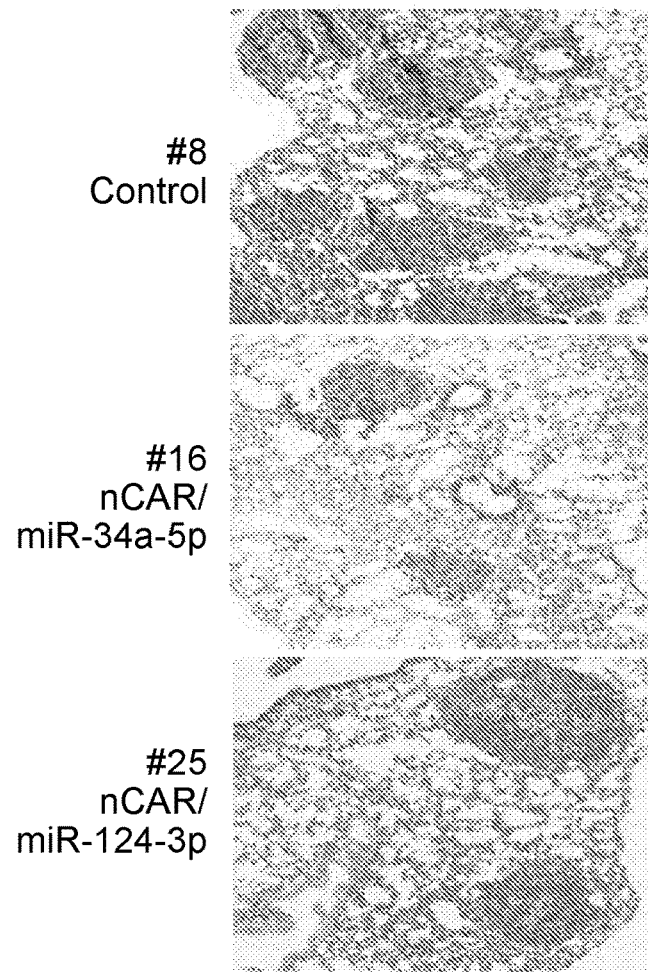
Figure 12C:
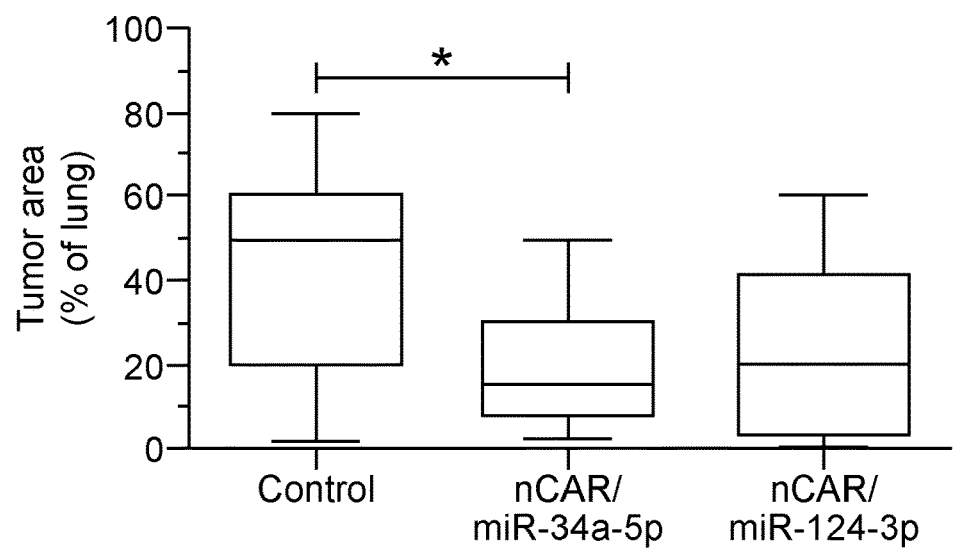
Figure 13A:
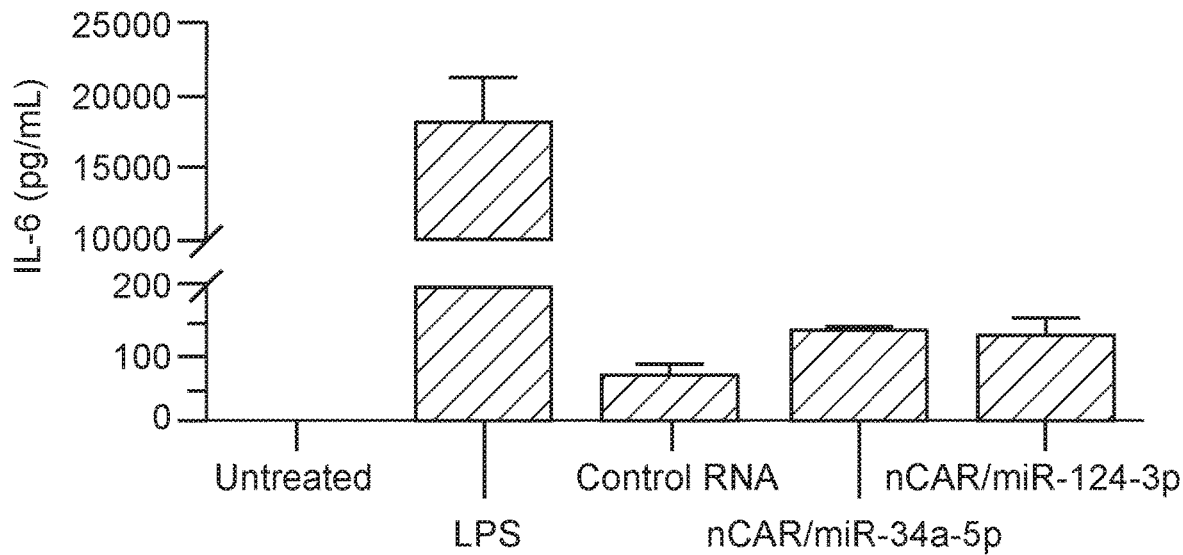
FIGS. 13A-13B illustrate that bioengineered RNAs have minor effects on cytokine release in immunocompetent BALB/c mice, as indicated by minimal changes of serum IL-6 (FIG. 13A) and TNFα (FIG. 13B) levels. Untreated mice and mice treated with lipopolysaccharide (LPS) were used as controls, and cytokine levels were determined by ELISA. IL-6 and TNFα levels in LPS-treated mice are significantly (P<0.01; 1-way ANOVA) higher than all other groups, whereas none of the RNA treatment group is statistically different from untreated mice. Values are mean±SD (N=4 mice per group).
Figure 13B:
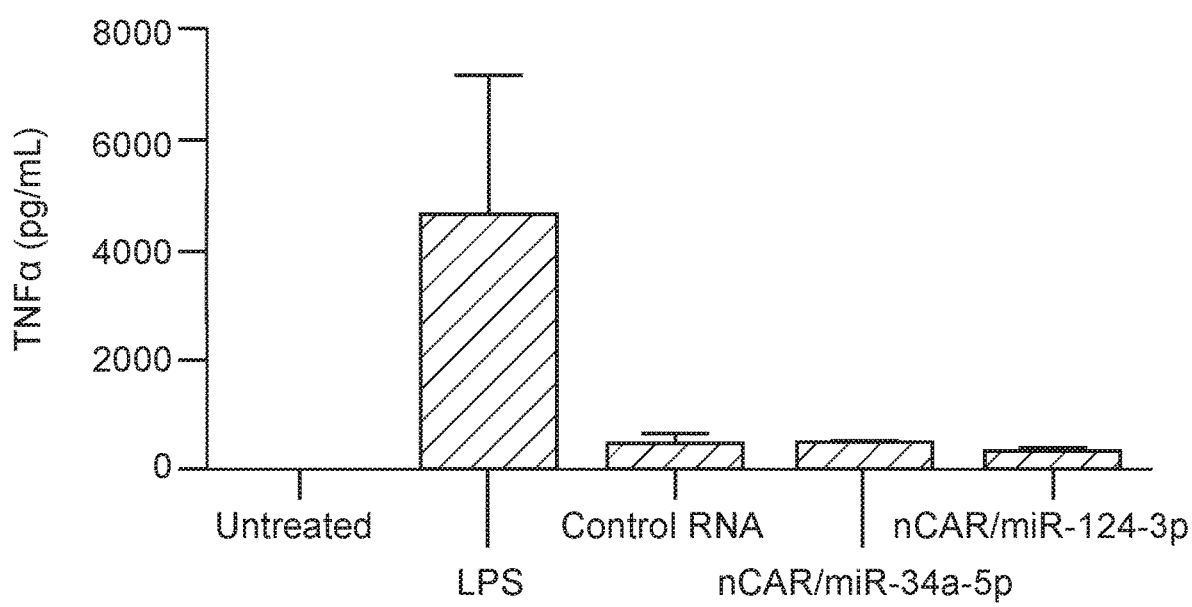

Bioengineered nCAR/miR-34a-5p significantly reduces metastatic lung xenograft tumor growth in vivo. Lastly we determined the effectiveness of BERA miR-34a-5p and miR-124-3p in the suppression of lung tumor progression in vivo. Metastatic lung xenograft mouse models were established via tail vein injection of luciferase/GFP-expressing A549 cells and then treated intravenously with in vivo-jetPEI-formulated nCAR/miR-34a-5p, nCAR/miR-124-3p, or control RNA (30 µg, three times per week for three weeks). BERAs appeared to be well tolerated in mice because, in addition to normal behaviors, all mice showed a steady increase in body weights that did not differ between treatments (FIG. 11A). Tumor growth was monitored over the course of 6 weeks by bioluminescent imaging; and control mice showed stronger signals compared to mice treated with nCAR/miR-34a-5p and nCAR/miR-124-3p (FIG. 12A). At the end of the study, whole lung tissues were excised, weighed, and imaged ex vivo (FIG. 12B). As expected, tumors were obvious by visual inspection of lungs collected from mice that showed strong bioluminescent signals, which were indicated by more apparent ex vivo GFP signals. Lung tissues from mice treated with nCAR/miR- 34a-5p were also found to be significantly lighter than the control group (FIG. 11B). Furthermore, we performed histopathological analyses of all excised lung tissues to verify xenograft tumors and quantitatively determine the effectiveness of BERA therapy (FIG. 12C). In agreement with the observations from live animal and ex vivo lung images, we found that mice treated with nCAR/miR-34a-5p had significantly lower degrees of lung tumor nodules. These results demonstrate the effectiveness of biologic miR-34a-5p in the control of lung cancer progression in metastatic xenograft mouse models.

Bioengineered have minimal impact on cytokine release in immunocompetent mice in vivo. Lastly, we assessed possible immunogenicity of biologic ncRNAs in immunocompetent BALB/c mouse models by measuring the most sensitive cytokines IL-6 and TNFα around the peak time point (1 h after treatment). Our data showed that LPS induced an immediate cytokine release syndrome in mice, as manifested by sharp increase in blood IL-6 and TNFα levels (FIG. 11C). In contrast, compared to untreated mice, administration of in vivo-jetPEI-formulated nCAR/miR-34a-5p, nCAR/miR-124-3p, and control RNA just led to insignificant increase of serum IL-6, TNFα levels that are remarkably and significantly lower than LPS treatment. The results indicate that biologic ncRNAs are tolerable in mice with minimal effects on cytokine release.

Discussion

We established a novel ncRNA bioengineering technology following the identification of a stable pre-miR-34a G138U/139ΔG derivative fused to tRNA molecule as a versatile carrier. This platform included the development of new complementary small- and large-scale purification methods. This approach offered a remarkable high-yield (40-80% of total RNAs) and large-scale (4-20 mg from 1 L bacterial fermentation) production of target ncRNAs in E. coli, with a high success rate (80%; 33 ncRNAs out of 42). Using two bioengineered ncRNAs as examples, we further demonstrated a selective release of target miRNAs from nCAR/miRNAs and thus specific regulation of target genes, leading to altered miRNome and transcriptome profiles in human cells. In addition, we showed that the introduction of tumor suppressive miR-34a-5p and miR-124-3p with corresponding nCAR/miRNA prodrugs was proven to be effective for the control of human lung cancer cell proliferation in vitro and metastatic xenograft tumor progression in vivo. These results support the robustness of this new ncRNA bioengineering pipeline and broad applications of biologic ncRNA agents (BERAs) to basic research and experimental therapy.

In sharp contrast to the studies on protein functions and therapeutics using recombinant proteins produced and folded within live cells rather than those made by peptide synthesis, current research on ncRNA macromolecules rely heavily on chemically synthesized ncRNA mimics containing extensive artificial modifications. Although chemical modifications may increase ncRNA stability and thus offer more favorable pharmacokinetic properties (e.g., longer half-life) and even higher potency, synthetic ncRNA agents are fundamentally different molecules that undoubtedly have distinct higher order structures as well as altered chemical and biological properties. Therefore, the relevance of chemo-engineered ncRNAs to cellular ncRNAs needs reconsideration. In addition, synthetic ncRNA agents from different manufacturers vary largely in the type, site and degree of artificial modifications, which create another layer of uncertainty. Conversely, ncRNAs produced by the bioengineering platform presented in this report resemble the biogenesis of natural ncRNAs in live cells and thus offer highly structured, stable macromolecules without or just with necessary posttranscriptional modifications (Li et al., 2015; Wang et al., 2015). Since recombinant ncRNAs are produced in live cells to tolerable levels, biologic ncRNAs unlikely trigger any severe immune response (Wang et al., 2015; Zhao et al., 2016). Most importantly, the present approach displays substantial advantages over existing recombinant RNA methods (Ponchon and Dardel, 2007; Ponchon et al., 2009; Huang et al., 2013; Chen et al., 2015) because it achieves a remarkable high-level expression of target ncRNA molecules (40-80% of total RNAs) at a high success rate (80%). The resultant ncRNA molecules are also different from viral or non-viral vector/plasmid based ncRNA expression materials that are truly DNA reagents (Ho and Yu, 2016). Therefore, the nCAR-based technology represents a more practical and cost-effective endeavor that can be easily adapted by a general biomedical research lab for the production of ncRNA agents of interest, either in microgram or milligram quantities.

Besides the confirmation of a selective release of target miRNAs from bioengineered nCAR/miRNA agents in human cells, our small RNA sequencing results show that intracellular miRNAs are present as various isoforms, consistent with other studies (Ebhardt et al., 2009; Llorens et al., 2013). This may affect the binding affinity of miRNAs to Ago proteins (Elkayam et al., 2012) or turnover in the cell (Chatterjee and Grosshans, 2009). In particular, nCAR/miR-34a-5p was predominately processed into mature miR-34a-5p as a 22-nt isoform, while other species (21- and 23-nt, shifts in cleavage start site) were produced at much lower abundance. However, nCAR/miR-124-3p was predominantly processed to a 23-nt form in 293T cells, whereas the other 22-nt specie shifted one nt to the right in Dicer-KO cells, whose levels were rather comparable levels. The lack of significant increase of other miRNAs also supports the selectivity in producing target miRNAs from nCAR/miR-NAs, while the proportional decrease of some high-abundance miRNAs could be a result of sharp increase of miR-34a-5p. Moreover, the dependence (miR-34a-5p) and independence (miR-124-3p) on Dicer for processing the nCAR/miRNAs indicate the versatility of using nCAR/miRNAs to introduce particular miRNAs into human cells to selectively change intracellular miRNome. Although it is unknown whether genetic background in Dicer-KO cells remains unchanged or not, our RNA sequencing results support the presence of Dicer-independent factors and pathways for miRNA biogenesis that might be altered in Dicer-KO cells and/or induced by nCAR/miR-124-3p treatment.

Upon the introduction of target miRNA into human cells, bioengineered ncRNA was effective to modulate target gene expression, leading to a specific change of transcriptome profile. Particularly, nCAR/miR-34a-5p and nCAR/miR-124-3p downregulated many well-documented targets (Chang et al., 2007; Karginov et al., 2007; Chi et al., 2009; Kaller et al., 2011) in 293T cells, as well as others (BAG2 and BCL6B for miR-34a; NID1 and VIM for miR-124) not reported before, although synthetic miRNA reagents were not included for comparison in present study. Although those genes have not been experimentally identified or verified by others, many are tentative targets (e.g., BCL6B for miR-34a-5p; and NID1 and VIM for miR-124-3p) predicted by various algorisms such as miRanda (microrna.org), TargetScan (targetscan.org/) and miRWalk (zmf.umm.uni-heidelberg.de/apps/zmf/mirwalk/micrornapredictedtarget.html). Some genes (e.g., BAG2) are not predicted targets, whose changes could be consequent or spatially-controlled effects of the changes of primary target gene expression while we cannot rule out possible off-target effects. Nevertheless, the specificity of nCAR/miRNA in the modulation of target gene expression is further demonstrated by "unbiased" enrichment analyses, which identified specific miRNAs behind corresponding downregulated genes. A step towards understanding ncRNAs as biologic macromolecules may advance our knowledge of these regulators in their natural forms to enable the progression of new discoveries.

As the altered transcriptomes were redefined for multiple intercalating pathways underlying cell growth, proliferation and survival, the antiproliferative activities of nCAR-carried miR-34a-5p and miR-124-3p were observed in multiple human lung carcinoma cell lines. Cells with mutant p53 or constitutively active EGFR backgrounds seem to be more sensitive to miRNA treatment. Since naked biologic RNAs are degradable by serum RNases, formulation is necessary for therapeutic applications (Wang et al., 2015; Jilek et al., 2017). Further studies with in vivo-jetPEI-formulated RNAs in metastatic lung xenograft mouse models not only support the effectiveness of bioengineered miRNA agents in vivo but also establish the feasibility of developing biologic ncRNAs as therapeutics. While the sample size was relatively small and nCAR/miR-124-3p treatment group was more variable, the suppression of xenograft tumor growth by nCAR/miR-34a-5p was identified statistically significant than control treatment. Moreover, we demonstrate that biologic ncRNAs are well tolerated in immunocompetent mice, as indicated by minimal impact on cytokine release. Rather, the assessment of biologic ncRNAs for cancer therapy should be challenged by more comprehensive studies with larger sample sizes and different models.

Limited by the array of possible directions, downstream in depth studies were carried out for two of many bioengineered ncRNAs to exemplify their biologic and pharmacological actions in the present study, but warrants additional investigations for bioengineered siRNA and RNA aptamer agents. While we focused on establishing the robust ncRNA bioengineering platform and assessing miRNA replacement strategy (Bader et al., 2010; Rupaimoole and Slack, 2017) with biologic miR-34a-5p and miR-124-3p molecules for lung cancer therapy, the utilities of BERAs cannot be underestimated. As supported by current studies, ncRNA bioengineering technology and the resulting biologic ncRNA agents (BERAs) should have direct impact on basic biomedical research and development of ncRNA therapies, although current ncRNA carriers may not be extended for the production of long ncRNAs playing important roles in various diseases (Cech and Steitz, 2014; Liu et al., 2017) since longer RNAs are more susceptible for degradation by bacterial RNases (Li et al., 2014; Li et al., 2015).

In summary, we established a novel ncRNA bioengineering technology that can be easily adapted for the production of ncRNA agents bearing sRNAs of interest. Our findings indicate that bioengineered ncRNAs represent unique biologic materials and can be an invaluable addition to current tools for broad biomedical research including the development of ncRNA therapeutics. While we cannot exclude the possibility that more superior ncRNA carriers would be expanded, the principle of producing biologic ncRNA macromolecules for basic and translational research will remain.

REFERENCES FOR BACKGROUND AND EXAMPLE 1

An, J., J. Lai, M. L. Lehman and C. C. Nelson (2013). miRDeep*: an integrated application tool for miRNA identification from RNA sequencing data. Nucleic Acids Res 41: 727-737.
Bader, A. G., D. Brown and M. Winkler (2010). The promise of microRNA replacement therapy. Cancer Res 70: 7027-7030.
Beckert, B. and B. Masquida (2011). Synthesis of RNA by in vitro transcription. Methods Mol Biol 703: 29-41.
Beg, M. S., A. J. Brenner, J. Sachdev, M. Borad, Y. K. Kang, J. Stoudemire, S. Smith, A. G. Bader, S. Kim and D. S. Hong (2017). Phase I study of MRX34, a liposomal miR-34a mimic, administered twice weekly in patients with advanced solid tumors. Invest New Drugs 35: 180-188.
Bogerd, H. P., A. W. Whisnant, E. M. Kennedy, O. Flores and B. R. Cullen (2014). Derivation and characterization of Dicer- and microRNA-deficient human cells. RNA 20: 923-937.
Bramsen, J. B. and J. Kjems (2012). Development of Therapeutic-Grade Small Interfering RNAs by Chemical Engineering. Front Genet 3: 154.
Butash, K. A., P. Natarajan, A. Young and D. K. Fox (2000). Reexamination of the effect of endotoxin on cell proliferation and transfection efficiency. Biotechniques 29: 610-614, 616, 618-619.
Cech, T. R. and J. A. Steitz (2014). The noncoding RNA revolution-trashing old rules to forge new ones. Cell 157: 77-94.
Chang, T. C., E. A. Wentzel, O. A. Kent, K. Ramachandran, M. Mullendore, K. H. Lee, G. Feldmann, M. Yamakuchi, M. Ferlito, C. J. Lowenstein, D. E. Arking, M. A. Beer, A. Maitra and J. T. Mendell (2007). Transactivation of miR-34a by p53 broadly influences gene expression and promotes apoptosis. Mol Cell 26: 745-752.
Chatterjee, S. and H. Grosshans (2009). Active turnover modulates mature microRNA activity in Caenorhabditis elegans. Nature 461: 546-549.
Chen, Q. X., W. P. Wang, S. Zeng, S. Urayama and A. M. Yu (2015). A general approach to high-yield biosynthesis of chimeric RNAs bearing various types of functional small RNAs for broad applications. Nucleic Acids Res 43: 3857-3869.
Chi, S. W., J. B. Zang, A. Mele and R. B. Darnell (2009). Argonaute HITS-CLIP decodes microRNA-mRNA interaction maps. Nature 460: 479-486.
Cho, C. Y., J. S. Huang, S. G. Shiah, S. Y. Chung, J. D. Lay, Y. Y. Yang, G. M. Lai, A. L. Cheng, L. T. Chen and S. E. Chuang (2016). Negative feedback regulation of AXL by miR-34a modulates apoptosis in lung cancer cells. RNA 22: 303-315.
Corey, D. R. (2007). Chemical modification: the key to clinical application of RNA interference? J Clin Invest 117: 3615-3622.
Ebhardt, H. A., H. H. Tsang, D. C. Dai, Y. Liu, B. Bostan and R. P. Fahlman (2009). Meta-analysis of small RNA-sequencing errors reveals ubiquitous post-transcriptional RNA modifications. Nucleic Acids Res 37: 2461-2470.
Elkayam, E., C. D. Kuhn, A. Tocilj, A. D. Haase, E. M. Greene, G. J. Hannon and L. Joshua-Tor (2012). The structure of human argonaute-2 in complex with miR-20a. Cell 150: 100-110.
Fang, P. Y., L. M. Gomez Ramos, S. Y. Holguin, C. Hsiao, J. C. Bowman, H. W. Yang and L. D. Williams (2017). Functional RNAs: combined assembly and packaging in VLPs. Nucleic Acids Res 45: 3519-3527.
Hatziapostolou, M., C. Polytarchou, E. Aggelidou, A. Drakaki, G. A. Poultsides, S. A. Jaeger, H. Ogata, M. Karin, K. Struhl, M. Hadzopoulou-Cladaras and D. Iliopoulos (2011). An HNF4alpha-miRNA inflammatory feedback circuit regulates hepatocellular oncogenesis. Cell 147: 1233-1247.

Ho, P. Y. and A. M. Yu (2016). Bioengineering of noncoding RNAs for research agents and therapeutics. Wiley Interdiscip Rev RNA 7: 186-197.

Hornung, V., M. Guenthner-Biller, C. Bourquin, A. Ablasser, M. Schlee, S. Uematsu, A. Noronha, M. Manoharan, S. Akira, A. de Fougerolles, S. Endres and G. Hartmann (2005). Sequence-specific potent induction of IFN-alpha by short interfering RNA in plasmacytoid dendritic cells through TLR7. Nat Med 11: 263-270.

Huang, L., J. Jin, P. Deighan, E. Kiner, L. McReynolds and J. Lieberman (2013). Efficient and specific gene knockdown by small interfering RNAs produced in bacteria. Nat Biotechnol 31: 350-356.

Jilek, J. L., Y. Tian and A. M. Yu (2017). Effects of MicroRNA-34a on the Pharmacokinetics of Cytochrome P450 Probe Drugs in Mice. Drug Metab Dispos 45: 512-522.

Kaller, M., S. T. Liffers, S. Oeljeklaus, K. Kuhlmann, S. Roh, R. Hoffmann, B. Warscheid and H. Hermeking (2011). Genome-wide characterization of miR-34a induced changes in protein and mRNA expression by a combined pulsed SILAC and microarray analysis. Mol Cell Proteomics 10: M1111 010462.

Karginov, F. V., C. Conaco, Z. Xuan, B. H. Schmidt, J. S. Parker, G. Mandel and G. J. Hannon (2007). A biochemical approach to identifying microRNA targets. Proc Natl Acad Sci USA 104: 19291-19296.

Kasinski, A. L. and F. J. Slack (2012). miRNA-34 prevents cancer initiation and progression in a therapeutically resistant K-ras and p53-induced mouse model of lung adenocarcinoma. Cancer Res 72: 5576-5587.

Khvorova, A. and J. K. Watts (2017). The chemical evolution of oligonucleotide therapies of clinical utility. Nat Biotechnol 35: 238-248.

Lewis, B. P., C. B. Burge and D. P. Bartel (2005). Conserved seed pairing, often flanked by adenosines, indicates that thousands of human genes are microRNA targets. Cell 120: 15-20.

Li, B. and C. N. Dewey (2011). RSEM: accurate transcript quantification from RNA-Seq data with or without a reference genome. BMC Bioinformatics 12: 323.

Li, H. and R. Durbin (2009). Fast and accurate short read alignment with Burrows-Wheeler transform. Bioinformatics 25: 1754-1760.

Li, M. M., B. Addepalli, M. J. Tu, Q. X. Chen, W. P. Wang, P. A. Limbach, J. M. LaSalle, S. Zeng, M. Huang and A. M. Yu (2015). Chimeric MicroRNA-1291 Biosynthesized Efficiently in Escherichia coli Is Effective to Reduce Target Gene Expression in Human Carcinoma Cells and Improve Chemosensitivity. Drug Metab Dispos 43: 1129-1136.

Li, M. M., W. P. Wang, W. J. Wu, M. Huang and A. M. Yu (2014). Rapid Production of Novel Pre-MicroRNA Agent hsa-mir-27b in Escherichia coli Using Recombinant RNA Technology for Functional Studies in Mammalian Cells. Drug Metab Dispos 42: 1791-1795.

Li, P. C., M. J. Tu, P. Y. Ho, J. L. Jilek, Z. Duan, Q. Y. Zhang, A. X. Yu and A. M. Yu (2018). Bioengineered NRF2-siRNA Is Effective to Interfere with NRF2 Pathways and Improve Chemosensitivity of Human Cancer Cells. Drug Metab Dispos 46: 2-10.

Liu, C., Z. Yang, J. Wu, L. Zhang, S. Lee, D. J. Shin, M. Tran and L. Wang (2017). lncRNA H19 interacts with polypyrimidine tract-binding protein 1 to reprogram hepatic lipid homeostasis. Hepatology.

Llorens, F., M. Hummel, L. Pantano, X. Pastor, A. Vivancos, E. Castillo, H. Mattlin, A. Ferrer, M. Ingham, M. Noguera, R. Kofler, J. C. Dohm, R. Pluvinet, M. Bayes, H. Himmelbauer, J. Antonio del Rio, E. Marti and L. Sumoy (2013). Microarray and deep sequencing cross-platform analysis of the mirRNome and isomiR variation in response to epidermal growth factor. BMC Genomics 14.

Malyala, P. and M. Singh (2008). Endotoxin limits in formulations for preclinical research. J Pharm Sci 97: 2041-2044.

Markova, S. M. and D. L. Kroetz (2014). ABCC4 is regulated by microRNA-124a and microRNA-506. Biochem Pharmacol 87: 515-522.

Okada, N., C. P. Lin, M. C. Ribeiro, A. Biton, G. Lai, X. He, P. Bu, H. Vogel, D. M. Jablons, A. C. Keller, J. E. Wilkinson, B. He, T. P. Speed and L. He (2014). A positive feedback between p53 and miR-34 miRNAs mediates tumor suppression. Genes Dev 28: 438-450.

Park, J. E., I. Heo, Y. Tian, D. K. Simanshu, H. Chang, D. Jee, D. J. Patel and V. N. Kim (2011). Dicer recognizes the 5' end of RNA for efficient and accurate processing. Nature 475: 201-205.

Pereira, P., A. Q. Pedro, J. A. Queiroz, A. R. Figueiras and F. Sousa (2017). New insights for therapeutic recombinant human miRNAs heterologous production: Rhodovolum sulfidophilum vs Escherichia coli. Bioengineered: 1-8.

Pereira, P. A., J. F. Tomas, J. A. Queiroz, A. R. Figueiras and F. Sousa (2016). Recombinant pre-miR-29b for Alzheimer s disease therapeutics. Sci Rep 6: 19946.

Ponchon, L., G. Beauvais, S. Nonin-Lecomte and F. Dardel (2009). A generic protocol for the expression and purification of recombinant RNA in Escherichia coli using a tRNA scaffold. Nat Protoc 4: 947-959.

Ponchon, L. and F. Dardel (2007). Recombinant RNA technology: the tRNA scaffold. Nat Methods 4: 571-576.

Robbins, M., A. Judge and I. MacLachlan (2009). siRNA and innate immunity. Oligonucleotides 19: 89-102.

Robinson, M. D., D. J. McCarthy and G. K. Smyth (2010). edgeR: a Bioconductor package for differential expression analysis of digital gene expression data. Bioinformatics 26: 139-140.

Rupaimoole, R. and F. J. Slack (2017). MicroRNA therapeutics: towards a new era for the management of cancer and other diseases. Nat Rev Drug Discov 16: 203-222.

Siegel, R. L., K. D. Miller and A. Jemal (2017). Cancer Statistics, 2017. CA Cancer J Clin 67: 7-30.

Sun, F., H. Fu, Q. Liu, Y. Tie, J. Zhu, R. Xing, Z. Sun and X. Zheng (2008). Downregulation of CCND1 and CDK6 by miR-34a induces cell cycle arrest. FEBS Lett 582: 1564-1568.

Thyagarajan, A., A. Shaban and R. P. Sahu (2018). MicroRNA-Directed Cancer Therapies: Implications in Melanoma Intervention. J Pharmacol Exp Ther 364: 1-12.

Wang, W. P., P. Y. Ho, Q. X. Chen, B. Addepalli, P. A. Limbach, M. M. Li, W. J. Wu, J. L. Jilek, J. X. Qiu, H. J. Zhang, T. Li, T. Wun, R. D. White, K. S. Lam and A. M. Yu (2015). Bioengineering Novel Chimeric microRNA-34a for Prodrug Cancer Therapy: High-Yield Expression and Purification, and Structural and Functional Characterization. J Pharmacol Exp Ther 354:131-141.

Wiggins, J. F., L. Ruffino, K. Kelnar, M. Omotola, L. Patrawala, D. Brown and A. G. Bader (2010). Development of a lung cancer therapeutic based on the tumor suppressor microRNA-34. Cancer Res 70: 5923-5930.

Yamakuchi, M., M. Ferlito and C. J. Lowenstein (2008). miR-34a repression of SIRT1 regulates apoptosis. Proc Natl Acad Sci USA 105: 13421-13426.

Yang, Q., L. Wan, C. Xiao, H. Hu, L. Wang, J. Zhao, Z. Lei and H. T. Zhang (2017). Inhibition of LHX2 by miR-124 suppresses cellular migration and invasion in non-small cell lung cancer. Oncol Lett 14: 3429-3436.

Zhao, Y., M. J. Tu, W. P. Wang, J. X. Qiu, A. X. Yu and A. M. Yu (2016). Genetically engineered pre-microRNA-34a prodrug suppresses orthotopic osteosarcoma xenograft tumor growth via the induction of apoptosis and cell cycle arrest. Sci Rep 6: 26611.

Example 2

Bioengineered Let-7c Loaded Lipopolyplex Inhibits Hepatocellular Carcinoma (HCC) and Improves Overall Survival with Minimal Immunogenicity Abstract Hepatocellular carcinoma (HCC) remains a leading cause of cancer-related deaths and warrants more effective therapies. Restoration of multi-targeting microRNA (miRNA) depleted in HCC represents a new therapeutic strategy. In this study, we sought to identify potent miRNA agent that could alleviate HCC tumor burden and improve survival. Among a collection of unique bioengineered non-coding RNA molecules purified from bacterial fermentation, we have identified let-7c agent as the most potent inhibitor against both Huh7 and Sk-Hep-1 cell proliferation in vitro. We present further studies to demonstrate the mechanistic actions of bioengineered let-7c in selective modulation of target gene expression (Lin28B, ARID3B, Bcl-xl, and c-Myc), induction of apoptosis, and inhibition of tumorsphere growth. Biologic let-7c formulated with liposomal-branched polyethylenimine (PEI) polyplex (LPP) exhibited much higher serum stability than in vivo-jetPEI (IPEI). Furthermore, LPP/let-7c nanotherapeutics was revealed to be more effective than IPEI/let-7c in the control of tumor progression in orthotopic HCC Huh7 xenograft mouse models, manifested by a more ubiquitous and greater degree of reduction of tumor burden determined by live animal and ex vivo tissue imaging as well as histopathological examination and blood chemistry profiling (e.g., α-fetoprotein and bilirubin levels). In addition, LPP/let-7c significantly extended overall survival of orthotopic HCC mice, whereas elicited no or minimal immune responses in immunocompetent mice and human peripheral blood mononuclear cells. These results demonstrate that bioengineered let-7c is a promising molecule for the treatment of advanced HCC and LPP is a superior modality for in vivo RNA delivery.

Materials and Methods

Materials. In vivo-jetPEI (linear 22 kDa PEI; IPEI) was purchased from Polyplus Transfection (Illkirch, France). Branched polyethylenimine with molecular weight 10,000 Da (bPEI10k) was bought from Alfa Aesar (Wardhill, MA). 1,2-di-O-octadecenyl-3-trimethylammonium propane (DOTMA) and cholesterol were purchased from Avanti Polar Lipids (Alabaster, AL). 1,2-Dimyristoyl-sn-glycerol, methoxypolyethylene glycol (DMG-PEG2000) was purchased from NOF America Corporation (White Plains, NY). Lipofectamine 3000 (LF3000), TRIzol RNA isolation reagent, and BCA protein assay kit were purchased from Thermo Fisher Scientific (Waltham, MA). Direct-zol RNA MiniPrep Kit was from Zymo Research (Irvine, CA). Cell-titer-Glo assay was purchased from Promega (Madison, WI). Matrigel was purchased from Corning (Corning, NY). Human α-fetoprotein ELISA kit was purchased from R&D Systems (San Diego, CA). All other chemicals and organic solvents of analytical grade were purchased from Sigma Aldrich or Thermo Fisher Scientific.

Cell Culture. Sk-Hep-1 cells were obtained from American Type Culture Collection and grown in Eagle's minimal essential medium (Cellgro, Manassas, VA), and Huh7 cells were bought from Japanese Collection of Research Biore-sources and grown in Dulbecco's modified Eagle medium (Gibco, Grand Island, NY). Both cell lines were supplemented with 10% fetal bovine serum (Gibco, Grand Island, NY) and 1% antibiotic/antimycotic (Cellgro, Manassas, VA). GFP/luciferase-expressing cell lines were established after transduction of parental cells with pCCLc-Luc-EGFP lentiviral constructs (Vector Core, UC Davis Medical Center, Sacramento, CA). All cells were transfected with Lipofectamine 3000 (Invitrogen, Carlsbad, CA) per the manufacturer's instructions for in vitro RNA delivery, unless otherwise indicated.

Figure 15A:
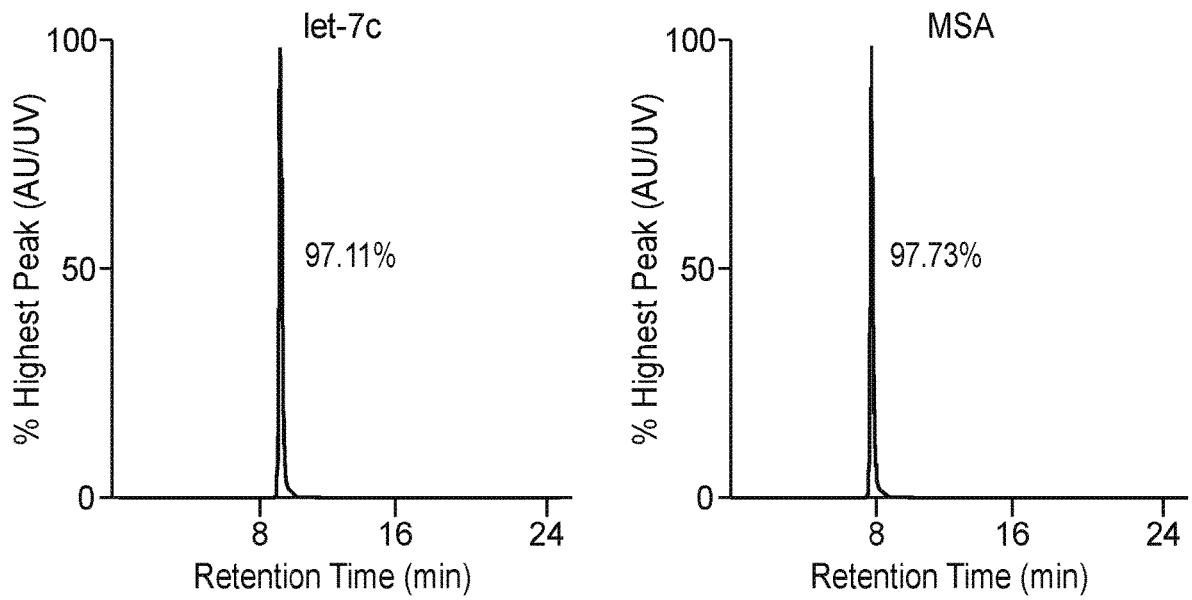
FIGS. 15A-B illustrate that isolated let-7c and control MSA agents are >97% pure with an endotoxin level <3 EU/μg RNA, which were determined by HPLC and Pyrogent-5000 kinetic LAL assay, respectively.
Figure 15B:
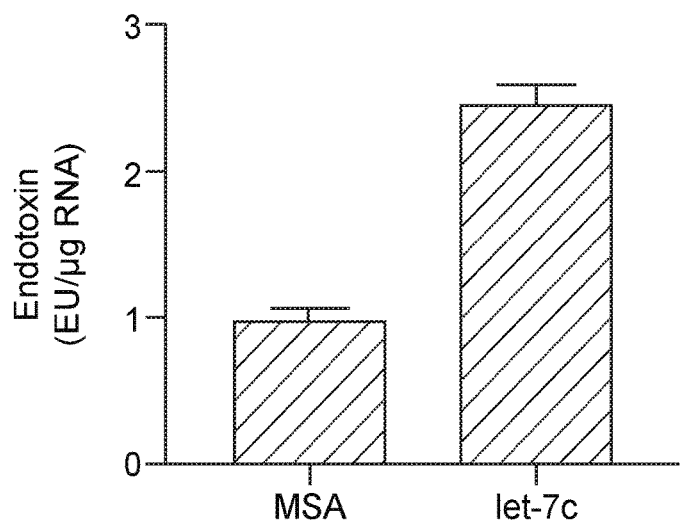

Production of Recombinant miRNA Agents. Bioengineering of miRNA molecules was conducted as described very recently (21). Briefly, inserts encoding target miRNA-containing ncRNAs were cloned into a pBSMrna vector using In-Fusion cloning technology and transformed into HST08 *Escherichia coli*. Recombinant ncRNAs were purified by anion exchange fast protein liquid chromatography (FPLC) to >96% purity that was determined by a high performance liquid chromatography (HPLC) assay (23). Bioengineered let-7c less than 95% pure was re-purified by the same FPLC method to reach >96% homogeneity (FIG. 15). Endotoxin activity was examined with Pyrogent-5000 kinetic LAL assay (Lonza, Walkersville, MD).

Cell Viability Assay. GFP/luciferase-expressing Sk-Hep-1 and Huh7 cells (5,000 cells/well) were seeded in 96-well plates and grown overnight. let-7c or MSA was administered in triplicate with either Lipofectamine 3000 or LPP. Cell viability was measured using Cell Titer-Glo kit. Inhibition of cell viability was determined as relative to vehicle control (0% inhibition) and pharmacodynamics parameters were estimated by fitting the data to fitting the data to a normalized dose response equation with variable slope:

$$Y = 100/(1+(10)\char`\^((\text{Log}(EC)\_50-X)*\text{Hill Slope}))$$

Given low efficacy, MSA (Emax, Emin=100, 20.64%) and miR-144 (Emax, Emin=44.42, 17.27%) in Huh7 cells were best fit to the full dose response equation equation:

$$Y = E\_\min + (E\_\max - E\_\min)/(1+(10)\char`\^((\text{Log}(EC)\_50-X)*\text{Hill Slope}))$$

Immunoblot and Immunofluorescence Analyses. Huh7 and Sk-Hep-1 cells were seeded in 6-well plate at 300,000 cells/well and transfected with 15 nM RNA. After 72 h, cells were harvested and lysed in RIPA buffer with protease inhibitor (Pierce, Rockford, IL). Protein levels were determined by BCA assay (Pierce, Rockford, IL). After separated on a 12% SDS-PAGE gel (Bio-Rad, Hercules, CA), proteins were transferred onto a polyvinylidene difluoride membrane, and blocked in 5% milk/I % Tween-20 in tris-buffered saline. Total immobilized protein was imaged per the manufacturer's instructions. Membranes were incubated with primary antibodies (Bcl-xl rabbit mAb [CST 2764], c-Myc rabbit mAb [CST 13987], and LIN28B rabbit mAb [CST 11965] from Cell Signaling Inc.; ARID3B rabbit pAb [AB 92328] from Abcam) overnight at 4° C. at 1:1,000 dilution in 5% bovine serum albumin in TBS-T, followed by horseradish peroxidase-conjugated goat-anti-rabbit secondary antibody (1:10,000 dilution) for 2 h at room temperature prior to chemiluminescent imaging with Clarity ECL (Bio-Rad, Hercules, CA). Relative band intensity was normalized to total immobilized protein.

To assay HMGA2 expression, Huh7 and Sk-Hep-1 cells were grown on glass chamber slides and transfected with MSA or let-7c. After 72 h, cells were fixed with 10% formalin, permeabilized with 1% Triton X-100, and incubated with HMGA2 rabbit mAb [CST 8179] (1:400 dilution in 5% bovine serum albumin) overnight at 4° C. Antigen was detected with Alexa 488-conjugated anti-rabbit IgG Fab fragment [CST 4412] and nuclei were counterstained with DAPI [CST 4803].

Flow Cytometry. Huh7 and Sk-Hep-1 cells were plated in 6-well plates at a density of 150,000 cells/well and transfected with 5 nM RNA. After 48 h, cells were stained with propidium iodide and Annexin V-FITC per manufacturer's instructions (Trevigen, Gaithersburg, MD). Cell count and fluorophore intensity was measured using a BD Biosciences Fortessa 20 color cytometer. Total event count was gated at 10,000 events and quadrant gating was set relative to vehicle control.

Tumorsphere Assay. Huh7 cells were seeded under adherent conditions at a density of 300,000 cells/well in 6-well plates and transfected with 15 nM RNA. After 48 hours, live cells were transferred to 24-well ultra-low attachment plates (Corning, Kennebunk, ME) at a density of 2,500 cells/well and grown in DMEM/F12+B27 with penicillin/streptomycin, GlutaMax (Gibco, Grand Island, NY), 20 ng/ml human epidermal growth factor, and 10 ng/ml human basic-fibroblast growth factor (Peprotech, Rocky Hill, NJ). After 7 days, primary tumorspheres (>10 μm diameter) were counted, sphere diameter was measured in ImageJ, and dissociated with trypsin to single cell. After all cells were transferred to new wells in ultra-low attachment/serum free conditions, cells were transfected again with 15 nM RNA. After 7 days, secondary tumorspheres were again counted, diameter was measured, and dissociated to count individual cells. Sphere formation efficiency (%) was calculated relative to total single cells seeded from the previous generation.

followed by further intermittent sonication by a Probe Sonicator (Thermo Fisher Scientific) for 100 s. The resultant liposomes were sterilized by passing through 0.22-μm sterile filter. Polyplex was formed by mixing 250 μL of purified RNA (1 mg/mL) and 250 μL bPEI10k (250 μg/mL) by pipetting, followed by incubation at room temperature for 5 min. LPP was produced by adding 500 μL freshly prepared polyplex into 500 μL liposomes through vigorous pipetting and incubating for 30 min. Zeta potentials and particle sizes of RNA-loaded LPP were measured by dynamic light scattering (Malvern Zetasizer Nano ZS90 instrument, Malvern instruments Ltd. U. K.). The morphology of LPP/let-7c was observed on a Philips CM-120 transmission electron microscope (TEM) after staining with phosphotungstic acid on copper grid.

Serum stability. To determine stability in serum, 500 μL RNA-loaded formulations were mixed with 500 μL FBS or human serum and incubated at 37° C. At different time points, 100 μL of samples were subjected to total RNA isolation using TRIzol and analyzed by denaturing urea polyacrylamide (8%) gel electrophoresis (PAGE) to assess RNA integrity.

In Vitro knockdown of GFP-mRNA by GFP-siRNA in SK-Hep-Luc-GFP cells. SK-Hep1-Luc-GFP was seeded in 12-well plate and grown overnight at the density of $5\times10^4$ cells/well. BERA/GFP-siRNA-loaded LPP nanocomplex was added into each well to a final concentration of 5 nM. LP3000 and IVJ-PEI formulations were included for comparison. After 72 h of treatment, cells were collected and total RNA was extracted with Trizol and Direct-zol RNA MiniPrep Kit (Zymo Research). cDNA was synthesized from 500 ng total RNA using NxGen M-MuLV reverse transcriptase (Lucigen, Middleton, Wis., USA), with random hexamers. Levels of GFP-mRNA were determined by using 18S as the internal standard. Primers used in this study are listed in Table 6. All real-time qPCR experiments were performed using iTaq Universal SYBR Green Supermix on a CFX96 Touch real-time PCR system (Bio-Rad, Hercules, Calif., USA). Cells were treated in triplicate and assayed separately. The comparative threshold cycle (Ct) approach with the formula $2^{-\Delta\Delta Ct}$ was utilized to calculate the relative gene expression.

TABLE 6

| | List of Primers |
|---|---|
| Let-7c (RT) | 5'-GTCGTATCCAGTGCAGGGTCCCAGGTATTCGCACTGGATAC GACAACCAT-3' (SEQ ID NO: 566) |
| Let-7c (PCR) | Reverse: 5'-GCGCTAAGGCACGCGGTG-3' (SEQ ID NO: 534) Forward 5'-CGCGCTGAGGTAGTAGGTTGT-3' (SEQ ID NO: 568) |
| GFP | Forward 5'-ACGTAAACGGCCACAAGTTC-3' (SEQ ID NO: 569) Reverse 5'-AAGTCGTGCTGCTTCATGTG-3' (SEQ ID NO: 570) |
| 18S | Forward 5'-GTAACCCGTTGAACCCCATT-3' (SEQ ID NO: 536) Reverse 5'-CCATCCAATCGGTAGTAGCG-3' (SEQ ID NO: 537) |
| U6 | Forward 5'-CTCGCTTCGGCAGCACA-3' (SEQ ID NO: 528) Reverse 5'-AACGCTTCACGA ATTTGCGT-3' (SEQ ID NO: 529) |

Formulation and Characterization of LPP Nanocomplex. 5.07 mg DOTMA, 2.92 mg cholesterol and 0.38 mg DMG-PEG2000 (molar ratio=50:50:1) were dissolved in chloroform in a round-bottom flask. The organic solvent was removed by rotary evaporation, and the thin lipid film formed at the bottom of flasks was hydrated in 1 mL diethylpyrocarbonate-treated water using bath sonication, In Vitro Delivery of let-7c and Inhibition of Cell Growth. To assess in vitro let-7c delivery, GFP/luciferase-transduced Sk-Hep-1 or Huh7 cells (50,000 cells/well) were seeded in 12-well plate and grown overnight. LPP nanocomplex or LF3000-formulated let-7c was added into each well to a final concentration of 15 nM RNA. After 72 h, cells were lysed with Trizol, RNA was collected with Direct-zol RNA MiniPrep Kit (Zymo Research, Irvine, CA), and subject to RT-qPCR evaluation of let-7c and precursor let-7c levels. Primers used in this study are listed in Table 6. All real-time qPCR experiments were performed using iTaq Universal SYBR Green Supermix on a CFX96 real-time thermocycler (Bio-Rad, Hercules, Calif., USA). Amplicon abundance was reported relative to U6 small nucleolar RNA and vehicle control by the $2^{-\Delta\Delta C_t}$ method.

Therapy Studies in Orthotopic HCC Xenograft Mouse Models. All animal procedures were approved by the Institutional Animal Care and Use Committee of the University of California, Davis.

Establishment of Orthotopic HCC Xenograft Mouse Model. Luciferase/GFP-expressing Huh7 cells were mixed with Matrigel to a final concentration of $1\times10^8$ cells/ml. 4-week-old male athymic nude mice (Jackson Laboratory, Bar Harbor, ME) were anesthetized and an incision (~1 cm) along the linea alba in the midline of the abdominal muscle layer was made. 20 μL of Huh7 cells in Matrigel suspension ($2\times10^6$ cells) were injected into the left lobe of liver. Successful engraftment of Huh7 cells was confirmed by bioluminescent imaging using ChemiDoc™ MP Imaging System (BioRad, Hercules, CA), following the intraperitoneal injection of D-luciferin (150 mg/kg) (BioVision, Inc. Milpitas, CA).

Tumor Progression Study. One-week post-inoculation, mice were assigned into 5 groups (Untreated, lPEI/MSA, LPP/MSA, 1PEI/let-7c and LPP/let-7c) according to tumor sizes determined by in vivo bioluminescence imaging, and treated (40 μg RNA) three times per week. Mice were imaged once per week to monitor tumor growth. Mice were sacrificed 2 h after the last dose on day 15. Livers with engrafted tumors were harvested and imaged for GFP fluorescence using ChemiDoc™ MP Imaging System. RNA was extracted from healthy livers and HCC tumors and the levels of let-7c were quantified using stem loop RT-qPCR using gene selective primers (Table 6). Blood was collected for blood chemistry profiling (Comparative Pathology Laboratory, UC Davis) and serum α-fetoprotein (AFP) was examined by ELISA (R&D Systems, Minneapolis, MN). Hematoxylin and eosin (H&E) histopathological study was performed by the Clinical Immunohistochemistry Laboratory at Roswell Park Cancer Institute (Buffalo, NY).

Survival Study. One-week post-inoculation, a separate batch of tumor-bearing mice were assigned into 2 groups (LPP/MSA and LPP/let-7c) according to tumor sizes determined by bioluminescence imaging, and treated with (40 μg RNA) three times per week continuously for 3 weeks. Body weights were recorded twice a week to assess animal health. Survival was analyzed by Kaplan-Meier method and compared by log-rank (Mantel-Cox) test.

Induction of Cytokine Release. Human PMCs were purchased from Lonza (Walkerville, MD) and maintained in RPMI 1640 supplemented with 10% human AB serum (Sigma, St. Louis, MO). PBMCs were seeded onto a 96-well plate at a density of $2\times10^5$ cells/well and allowed to grow overnight. Cells were treated with 10 ng/mL or 100 ng/mL LPS (positive control), LPP/MSA (5 nM), LPP/let-7c (5 nM), or LPP vehicle. Twenty-four hours post-treatment, medium was harvested and cell debris was removed by centrifugation. IL-6, TNF-α, IL-4 and IL-10 levels were quantified using corresponding human cytokine ELISA assay kit (Invitrogen, Carlsbad, CA).

Healthy Balb/c and CD-1 mice (5-6 weeks old) were randomly assigned into different groups (3 female and 3 male per group) and injected with 40 μg of either MSA or let-7c loaded LPP nanocomplex, or 20 μg LPS (positive control), or LPP vehicle (negative control). Blood was collected 1 h post treatment and serum IL-6 and IL-4 levels were quantified using a mouse IL-6 and IL-4 ELISA assay kit (Invitrogen, Carlsbad, CA).

Statistical Analysis. All values are mean±standard deviation (SD). Statistical analysis was performed using 1- or 2-way ANOVA with Bonferroni's post-hoc test or Student's t-test where appropriate (GraphPad Prism, San Diego, CA).

Results

Figure 14A:
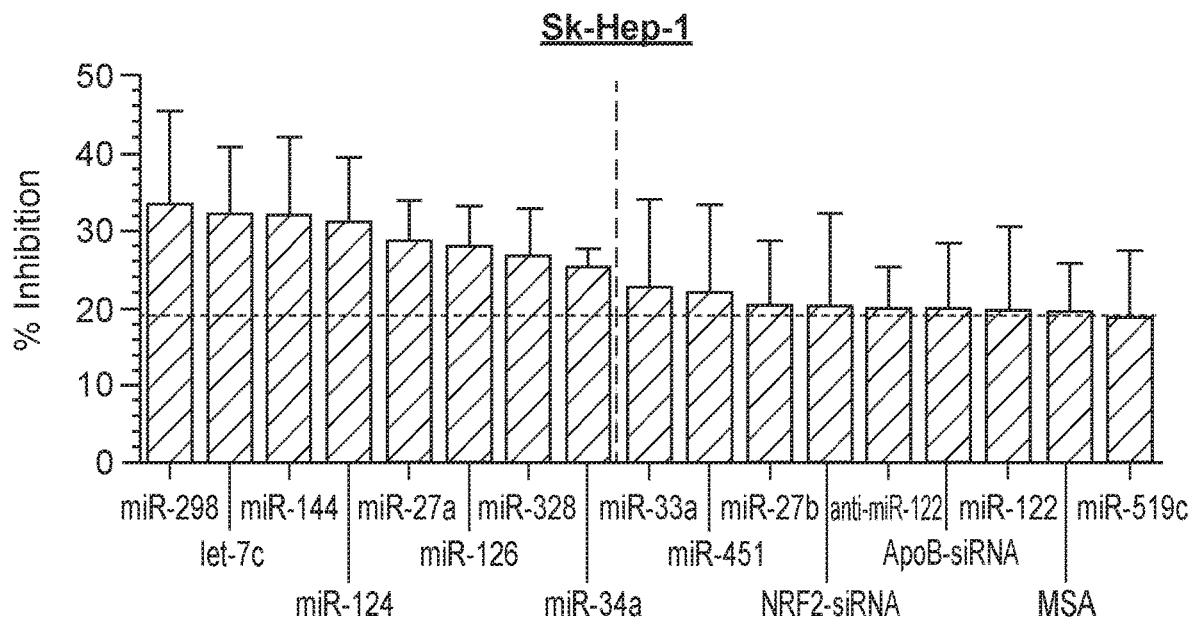
FIGS. 14A-14C illustrates bioengineered let-7c is identified as the most potent inhibitor against HCC cell proliferation among a small collection of ncRNAs.
Figure 14A:
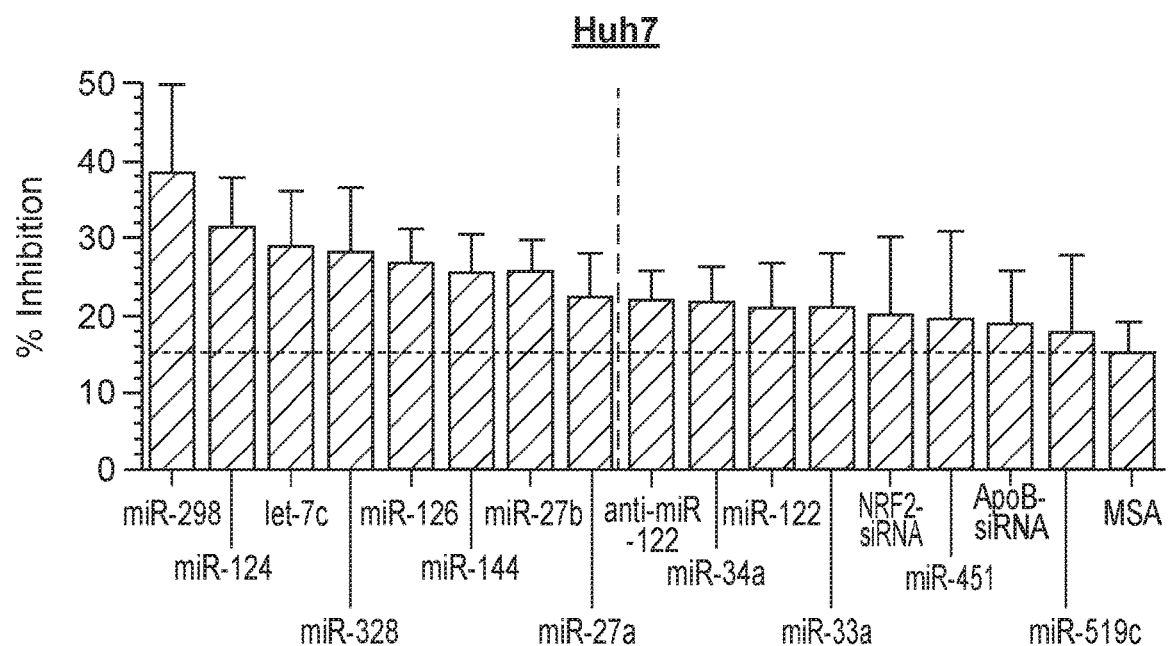
Figure 14B:
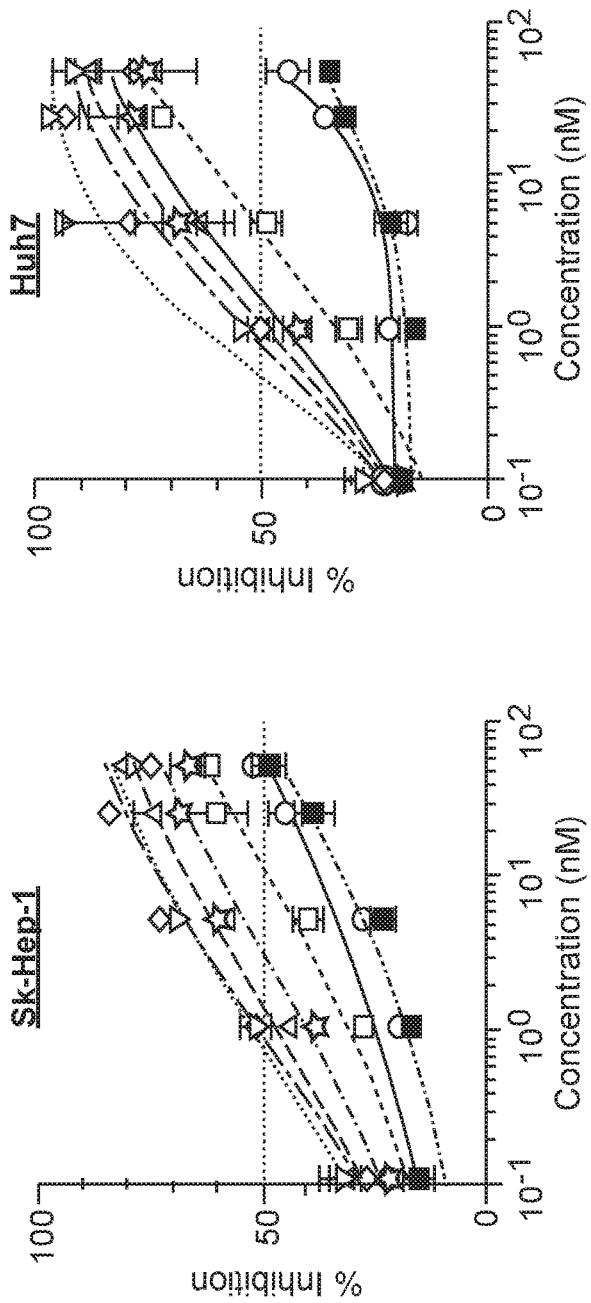
Figure 14C:
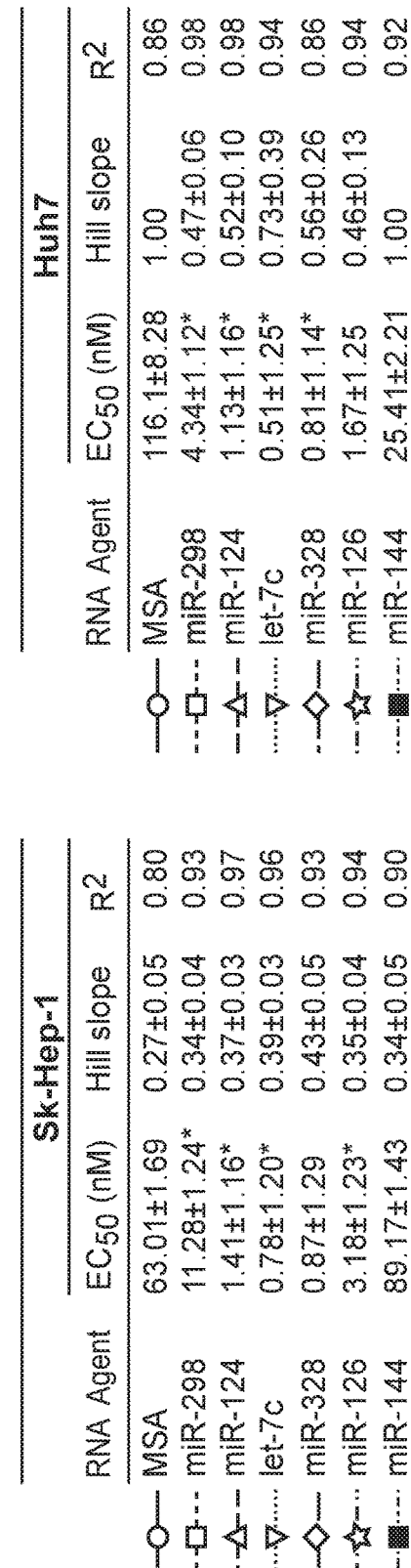

Bioengineered let-7c is the most potent inhibitor against HCC cell proliferation among a collection of ncRNA agents. Screening of a small collection of bioengineered miRNA agents was predictive for their anti-proliferative activities, as control RNA (MSA) consistently yielded the least inhibition of cell viability (FIG. 14A). A number of miRNA agents showing overlapped and greater antiproliferative activities in both cell lines, including miR-298, miR-124, let-7c, miR-328, miR-144, and miR-126, were pursued for dose response study (FIG. 14B). Let-7c was revealed as the most potent ncRNA, with EC50 values of 0.78 and 0.51 nM in Sk-Hep-1 and Huh7 cells, respectively (FIG. 14C). Furthermore, let-7c was as pure (>97%, by HPLC) as other tested ncRNAs (FIG. 14) purified by the same anion exchange FPLC method (21) and had a low endotoxin level (FIG. 15), suggesting a minimal interference by impurities.

Figure 16A:
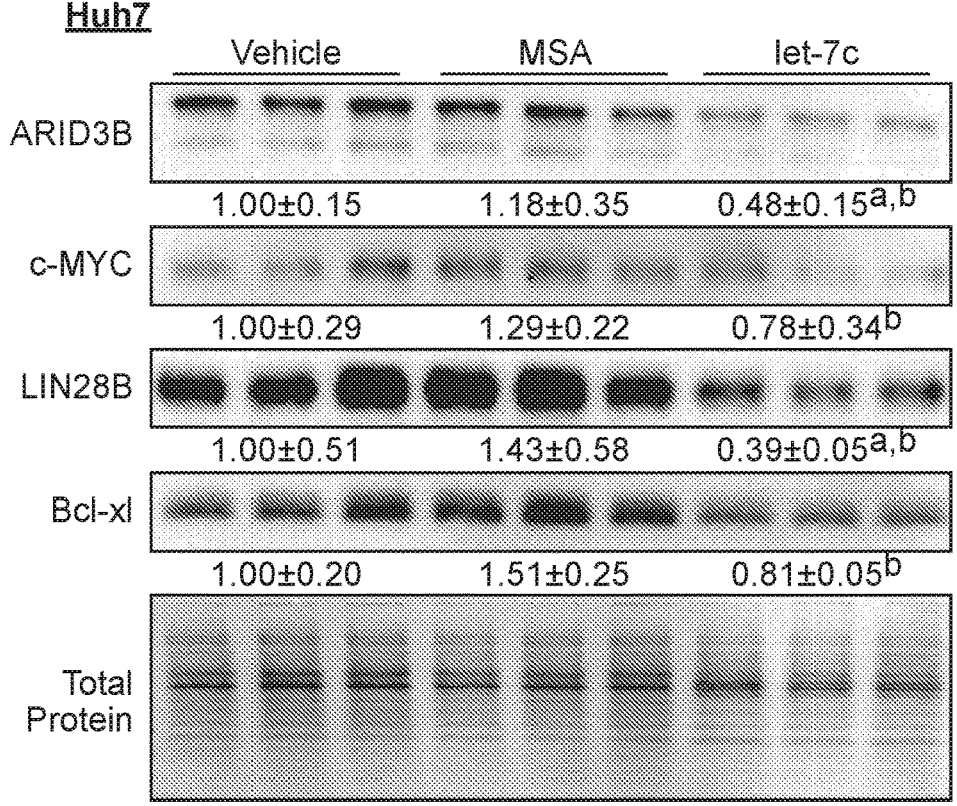
FIGS. 16A-B illustrates suppression of protein levels of target genes by bioengineered let-7c in HCC cell lines. (A) Immunoblot analyses of let-7 targeted ARID3B, c-MYC, LIN28B and Bcl-xl protein levels and (B) immunofluorescent analysis of HMGA2 in Huh7 and Sk-Hep-1 cells treated with 15 nM let-7c or control MSA. Immunoblot intensity was normalized to total protein and vehicle control for comparison between groups; P<0.05 compared to vehicle (a) or MSA (b) (1-way ANOVA with Bonferroni's post-hoc test). Immunofluorescent intensity of HMGA2 staining was normalized to total DAPI-positive cells. *P<0.05 compared to MSA (Student's t-test).
Figure 16A:
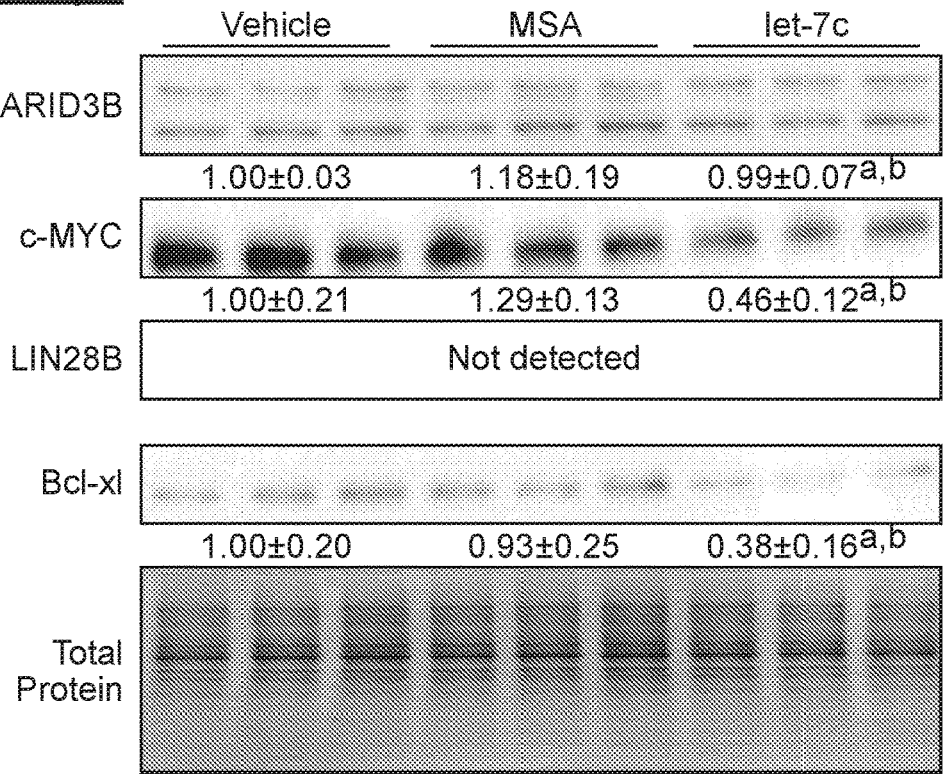
Figure 16B:
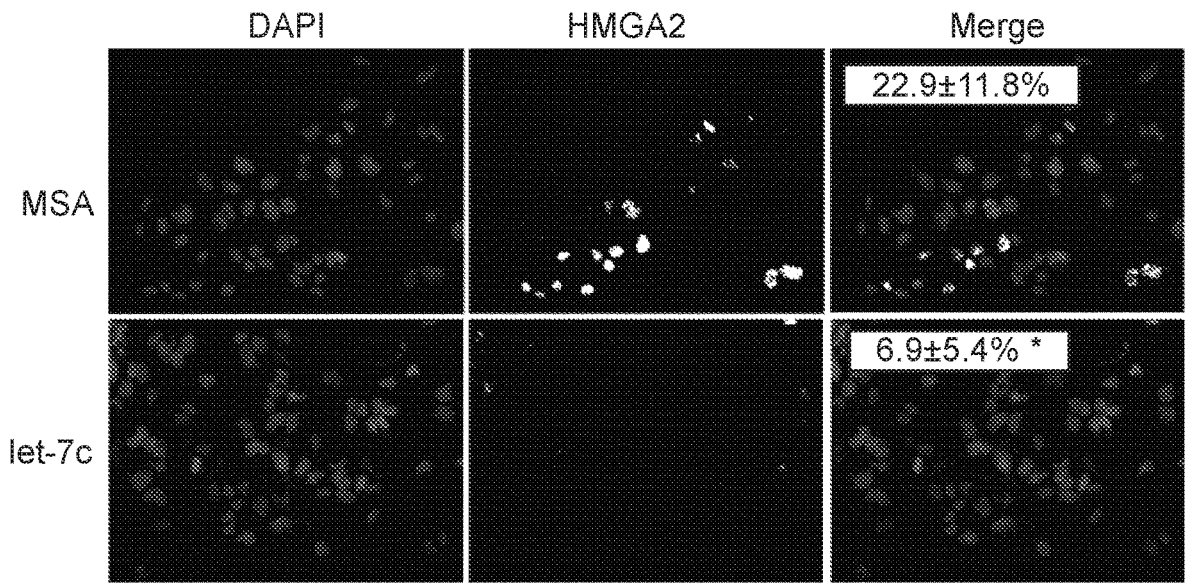
Figure 16B:
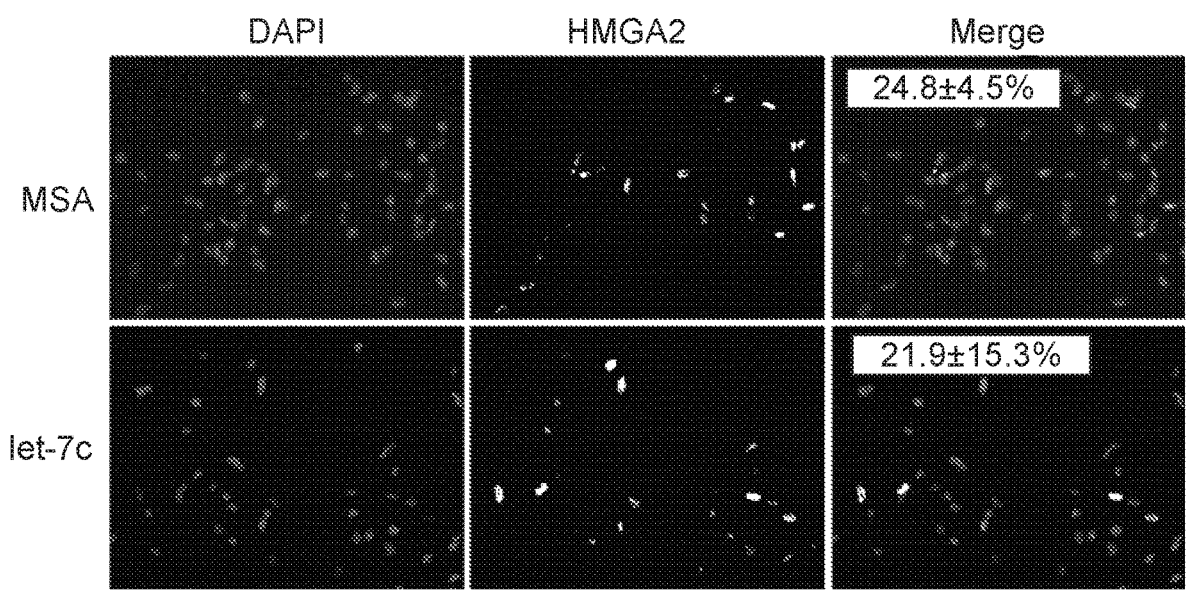

Bioengineered let-7c reduces protein levels of target genes. To verify the actions of recombinant let-7c, we examined protein levels of several known let-7c targets important in cancer. LIN28B, a canonical target of let-7 family miRNAs, was reduced by let-7c over 60% in Huh7 cells, while it was not detected in Sk-Hep-1 cells by immunoblot (FIG. 16A). This was associated with much higher levels of let-7c in cells treated with biologic let-7c—than control MSA. Furthermore, Bcl-xl and c-Myc protein levels were suppressed consistently by let-7c in both Huh7 and Sk-Hep-1 cells, whereas downregulation of ARID3B was only observed in Huh7 cells. In addition, immunofluorescence study demonstrated that HMGA2 expression was reduced significantly in Huh7 cells, whereas it was not significantly in Sk-Hep-1 cells (FIG. 16B).

Induction of apoptosis of HCC cells by bioengineered let-7c. Let-7 family miRNAs have been shown to induce apoptosis via targeting of Bcl-xl, among other mechanisms (32). Likewise, our data showed that a low dose (5 nM) of let-7c induced a modest yet robust increase in early and late apoptotic cell populations in both Huh7 and Sk-Hep-1 cells (FIG. 17), compared to vehicle- and MSA treatments. Additionally, necrotic cell populations were not altered following the transfection of let-7c and MSA.

Biologic let-7c suppresses HCC cell stemness. Negative feedback between let-7 and LIN28 influences the stemness of cancer cells (33) critical for therapeutic outcomes. As such, we evaluated cancer stem cell (CSC) growth using a tumorsphere assay in Huh7 cells; Sk-Hep-1 cells did not form tumorspheres under similar conditions. Following transfection in adherent conditions and subsequent growth in ultra-low attachment/serum-free conditions, we observed a significant half-diameter reduction in primary tumorsphere size, but not tumorsphere count, in let-7c-treated cells (FIG. 18). Upon subsequent dissociation, transfection, and growth in ultra-low attachment/serum-free conditions to form secondary tumorspheres, a similar 50% reduction in diameter was observed in let-7c-treated cells. While sphere formation efficiency from primary tumorspheres was not significantly reduced, sphere count and individual cell number were significantly reduced in secondary tumorspheres by let-7c treatment (FIG. 18).

Figure 19A:
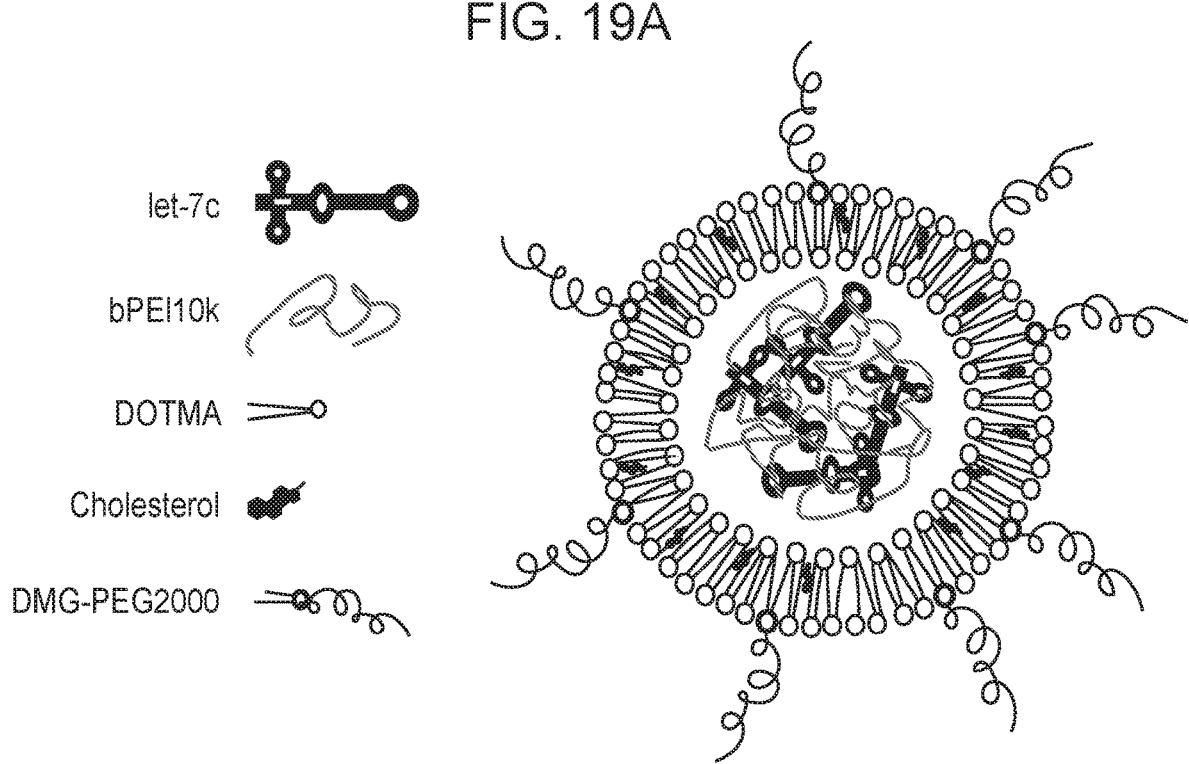
FIGS. 19A-F illustrate that Let-7c is efficiently delivered into HCC cells by LPP nanocomplex to control cell proliferation. (A) Schematic illustration of let-7c-loaded lipopolyplex (LPP). (B) TEM image of let-7c-loaded LPP (indicated by red arrows) nanocomplex, as well as the size and zeta potential measured by dynamic light scattering. Bar indicates 500 nm. (C and E) Efficient delivery of let-7c (15 nM) led to sharp suppression of Huh7 and Sk-Hep-1 cell growth (D and F). Lipofectamine 3000 (LF3000) treatments were used for comparison. Values are mean±SD of triplicate treatments (N=3 per group). P<0.01 and *P<0.001 (1- or 2-way ANOVA with Bonferroni's post-hoc test).
Figure 19B:
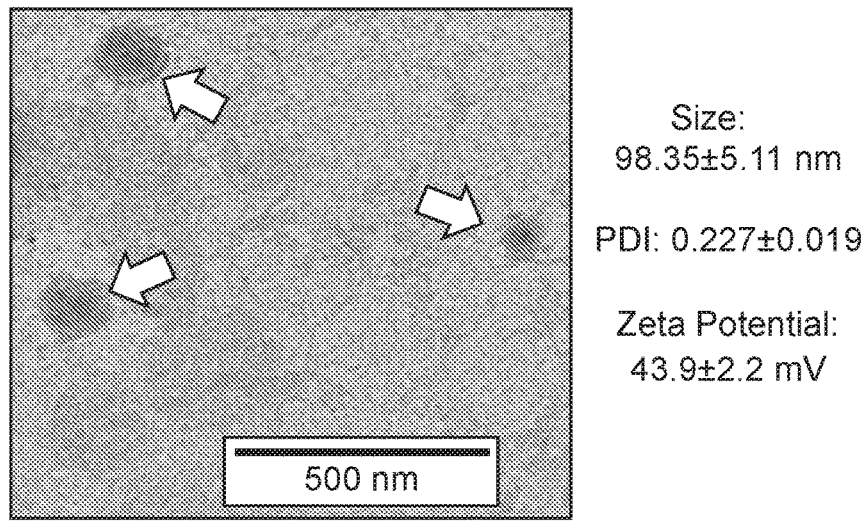
Figure 20:
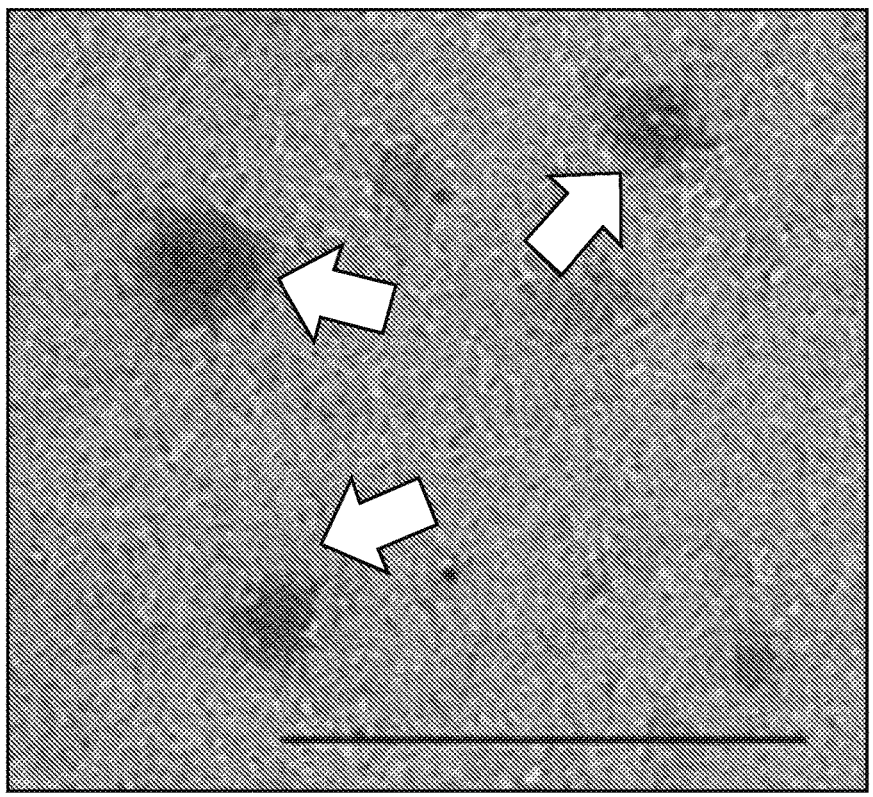
FIG. 20 illustrates transmission electron microscopy (TEM) examination of LPP/MSA nanocomplex. Particle size and zeta potential were measured by dynamic light scattering.
Figure 21A:
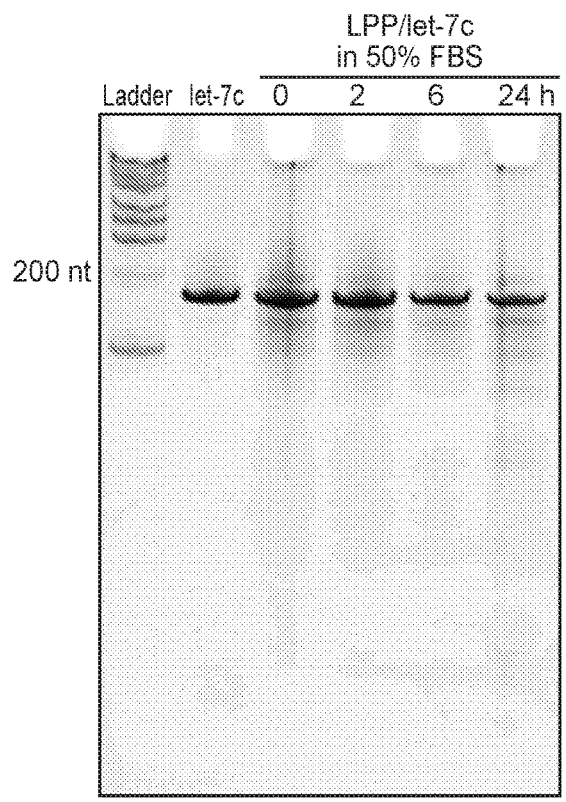
FIGS. 21A-C illustrate serum stability of LPP-let-7c nanocomplex, in comparison to IPEI/let-7c formulation. Shown are urea-PAGE analyses of isolated let-7c after different let-7c formulations were incubated in serum for 0, 2, 6 and 24 h under 37° C.
Figure 21B:
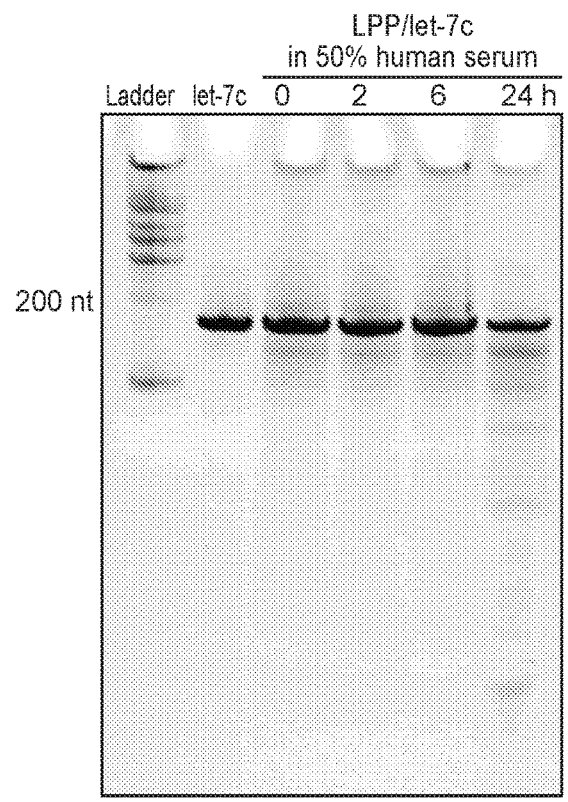
Figure 21C:
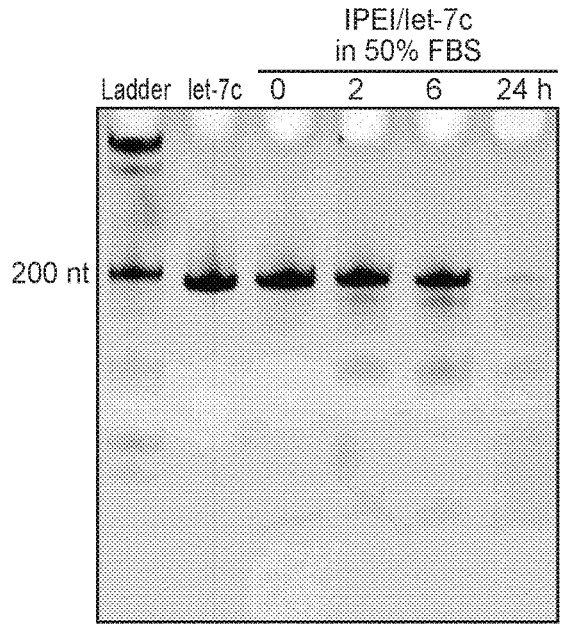

Preparation and characterization of let-7c-loaded LPP nanocomplex. We thus employed LPP to load bioengineered let-7c molecule (FIG. 19A) towards therapy study in animal models. The size of let-7c-loaded LPP was 98.35±5.11 nm with a zeta potential value of 43.9±2.2 mV, which was complemented by TEM examination (FIG. 19B). Control RNA MSA was formulated in the same manner and LPP/MSA nanocomplex showed similar size (102.4±5.9 nm) and zeta potential (45.1±1.2 mV) (FIG. 20). In addition, LPP could effectively protect let-7c from degradation in both FBS and human serum up to 24 h (FIG. 21A-B), to a greater degree than polyplex (FIG. 21C).

Figure 19C:
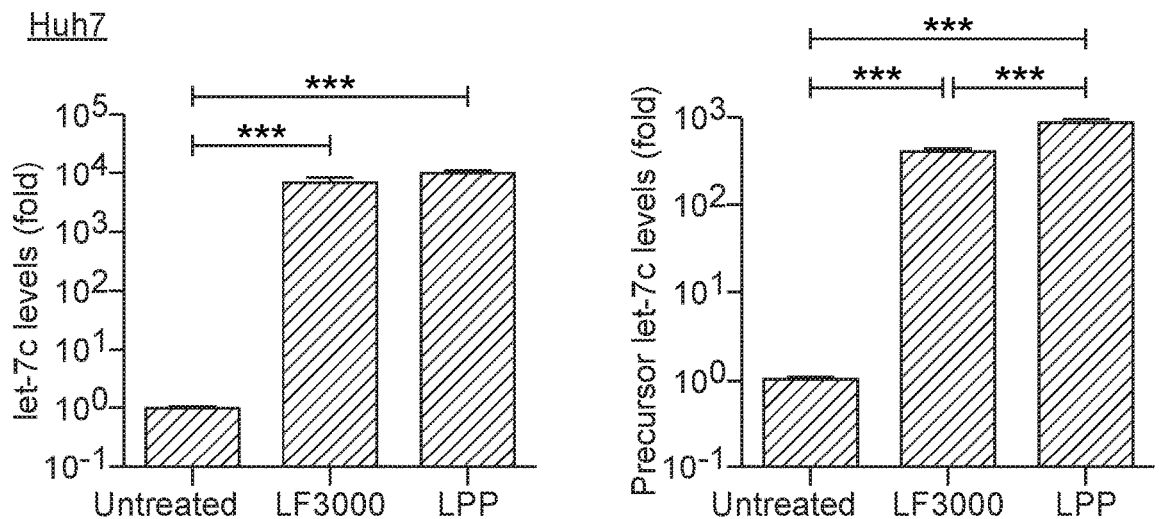
Figure 19D:
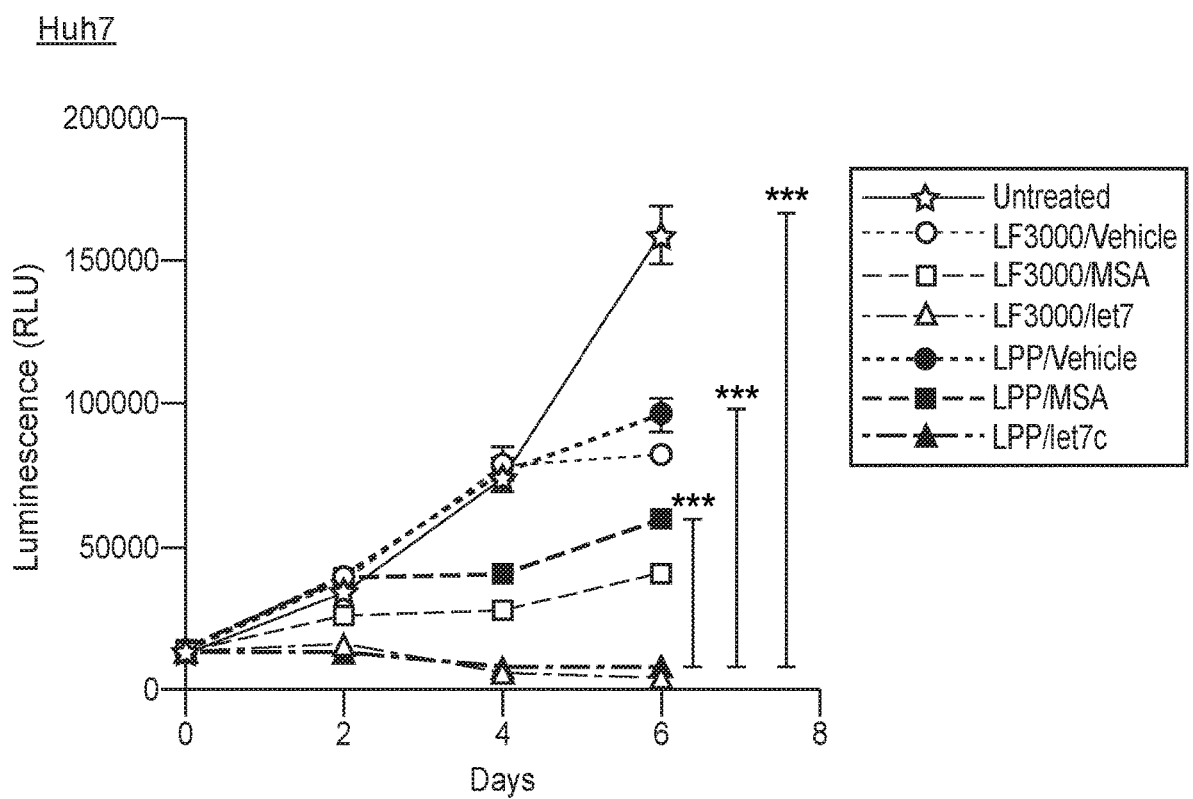
Figure 19E:
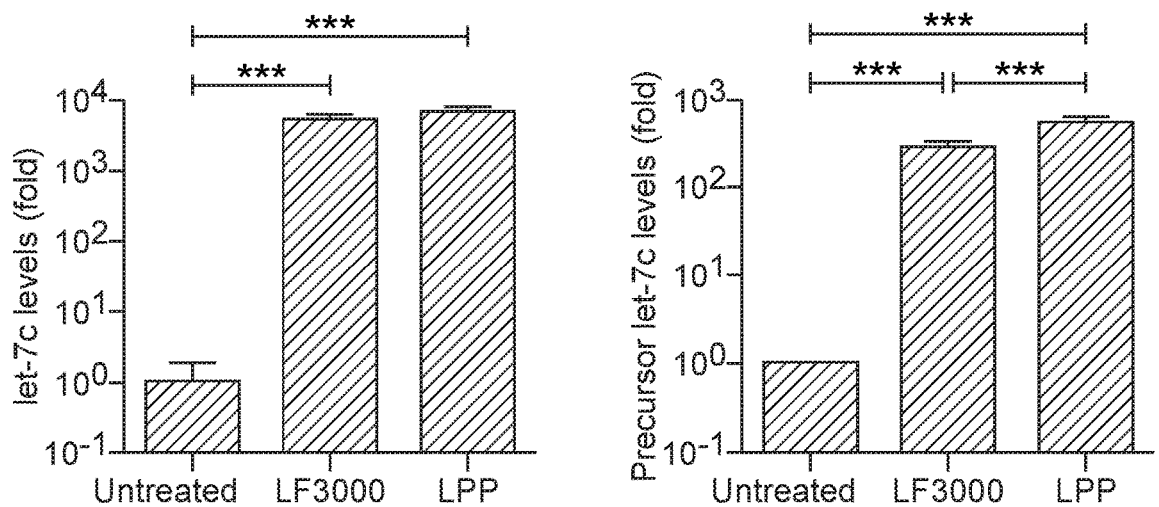
Figure 19F:
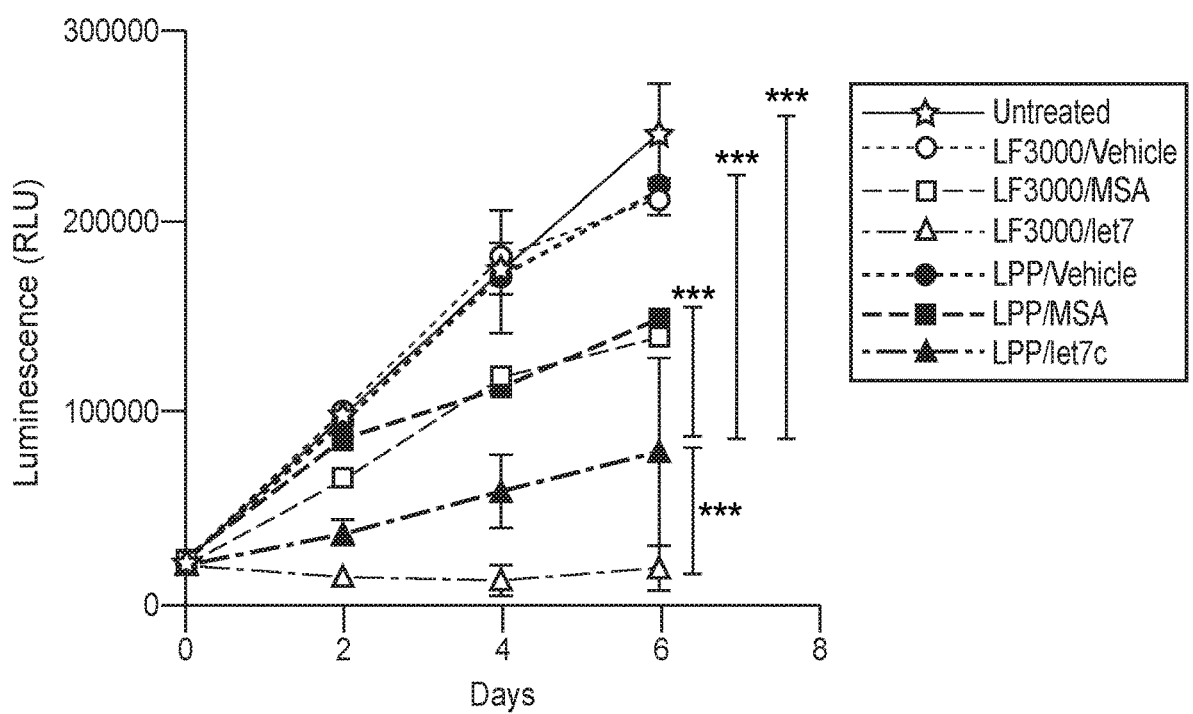
Figure 22:
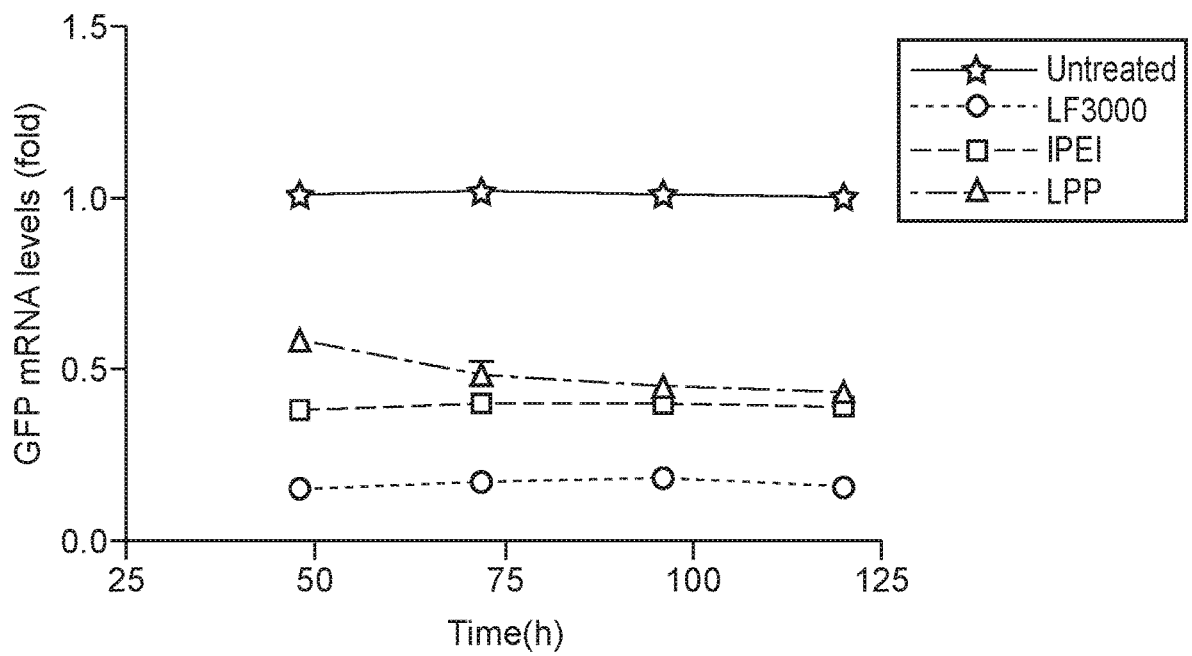
FIG. 22 illustrates LPP is effective to delivery bioengineered ncRNA for target gene regulation, as demonstrated by the delivery of bioengineered GFP-siRNA (5 nM) and effective reduction of target GFP mRNA levels in GFP/luciferase-expressing SK-Hep1 cells. Lipofectamine 3000 (LP3000) and in vivo-jetPEI (IPEI) formulations were used for comparison. GFP mRNA levels were determined by selective RT-qPCR assay. Values are mean±SD of triplicate treatments (N=3 per group).

LPP efficiently delivers let-7c into HCC cells to elicit inhibition of cell growth. We further assessed delivery efficiency by LPP in both Huh7 and Sk-Hep-1 cells, in parallel to Lipofectamine 3000 (LF3000). Our data demonstrated that let-7c was efficiently delivered into Huh7 cells by LPP nanocomplex, as manifested by the increase in comparable level of let-7c as LF3000 formulations (FIG. 19C), which led to a sharp suppression of cell proliferation (FIG. 19D). Similar results were observed for LF3000- and LPP-formulated let-7c in Sk-Hep-1 cells (FIG. 19E-F). These data were also complemented by efficient delivery of another bioengineered ncRNA molecule, GFP-siRNA (20, 21), by LPP nanoparticles, as indicated by the knockdown of target GFP levels in GFP/luciferase-expressing Huh7 cells (FIG. 22).

Figure 23A:
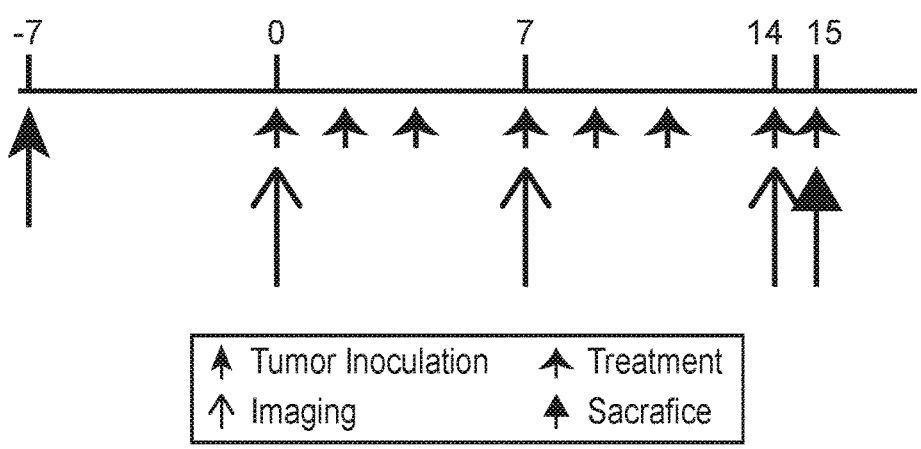
Figure 23C:
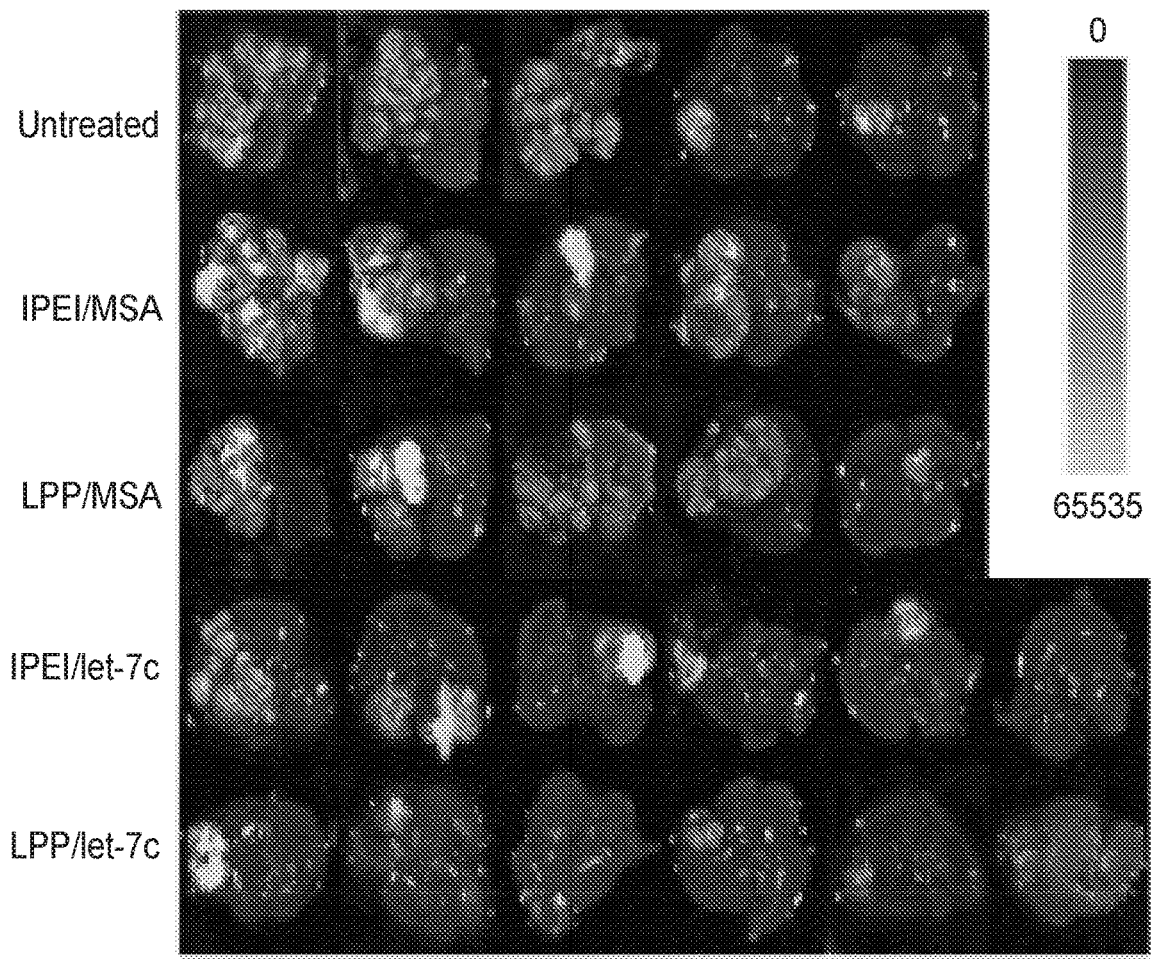
Figure 23C:
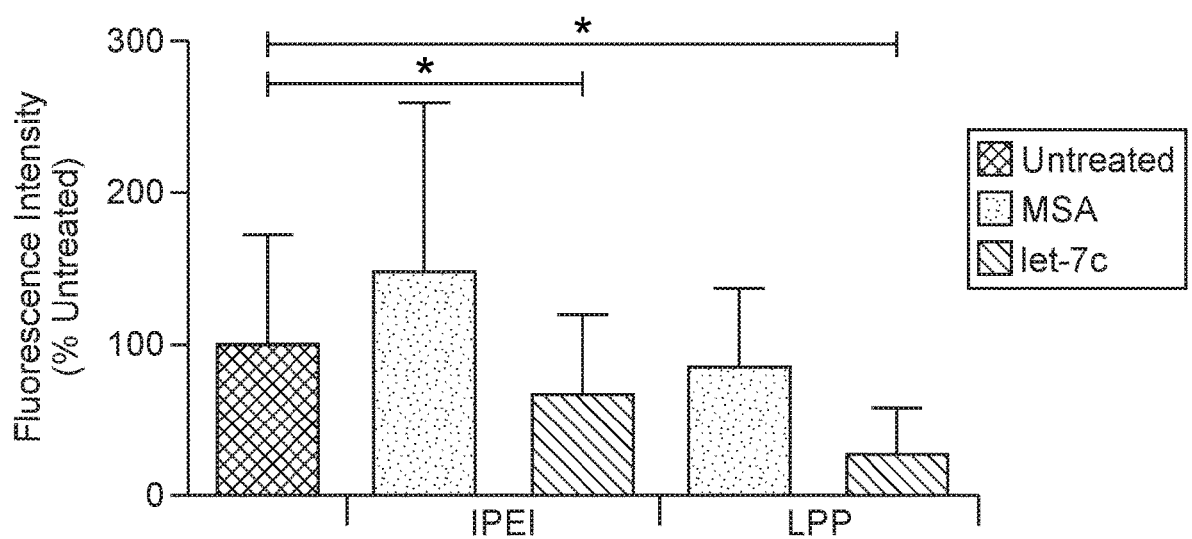
Figure 23D:
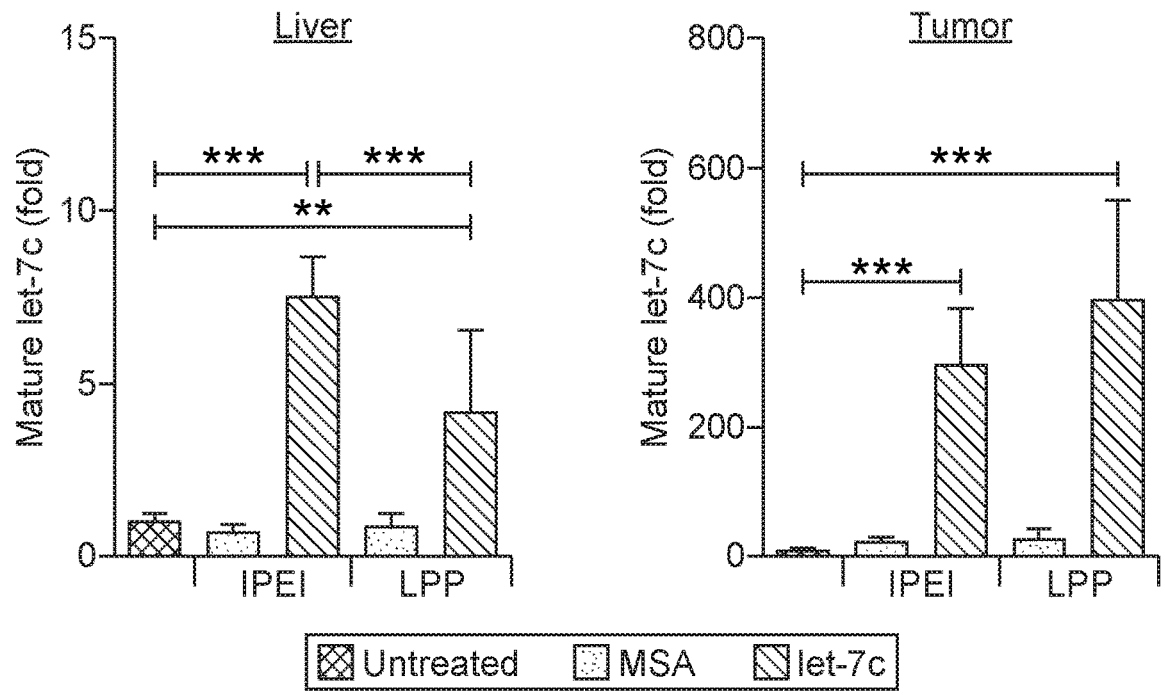
Figure 23E:
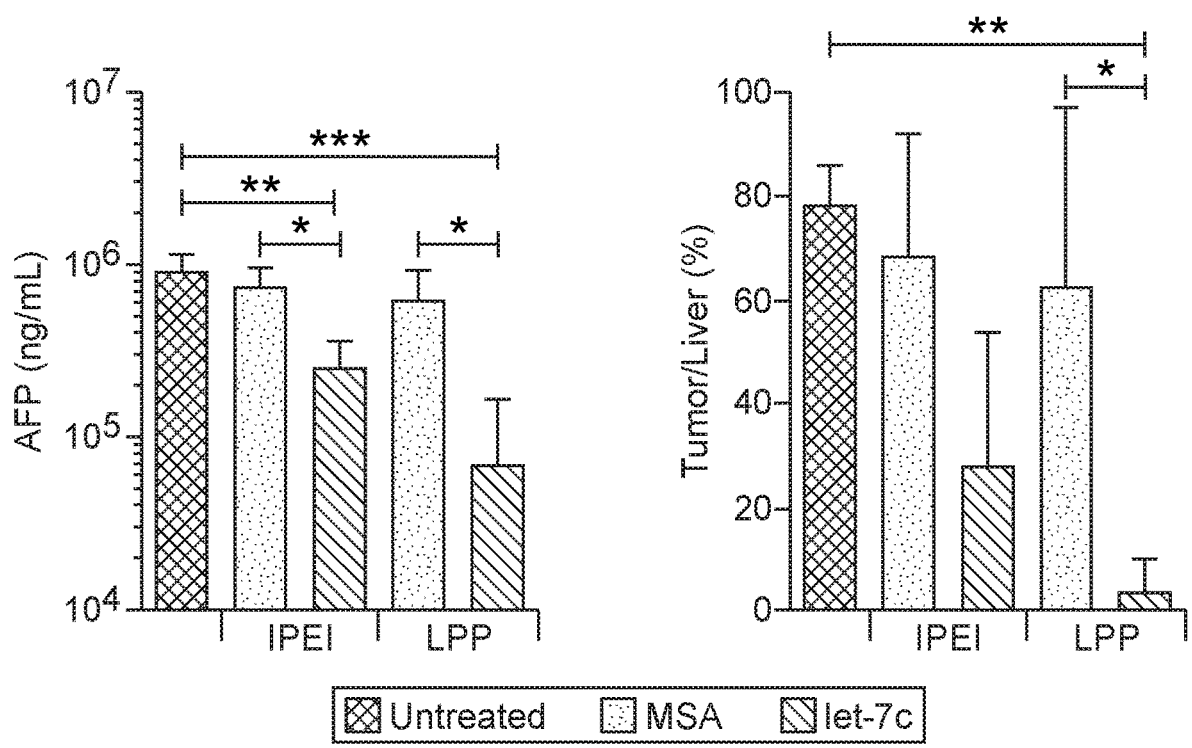
Figure 23F:
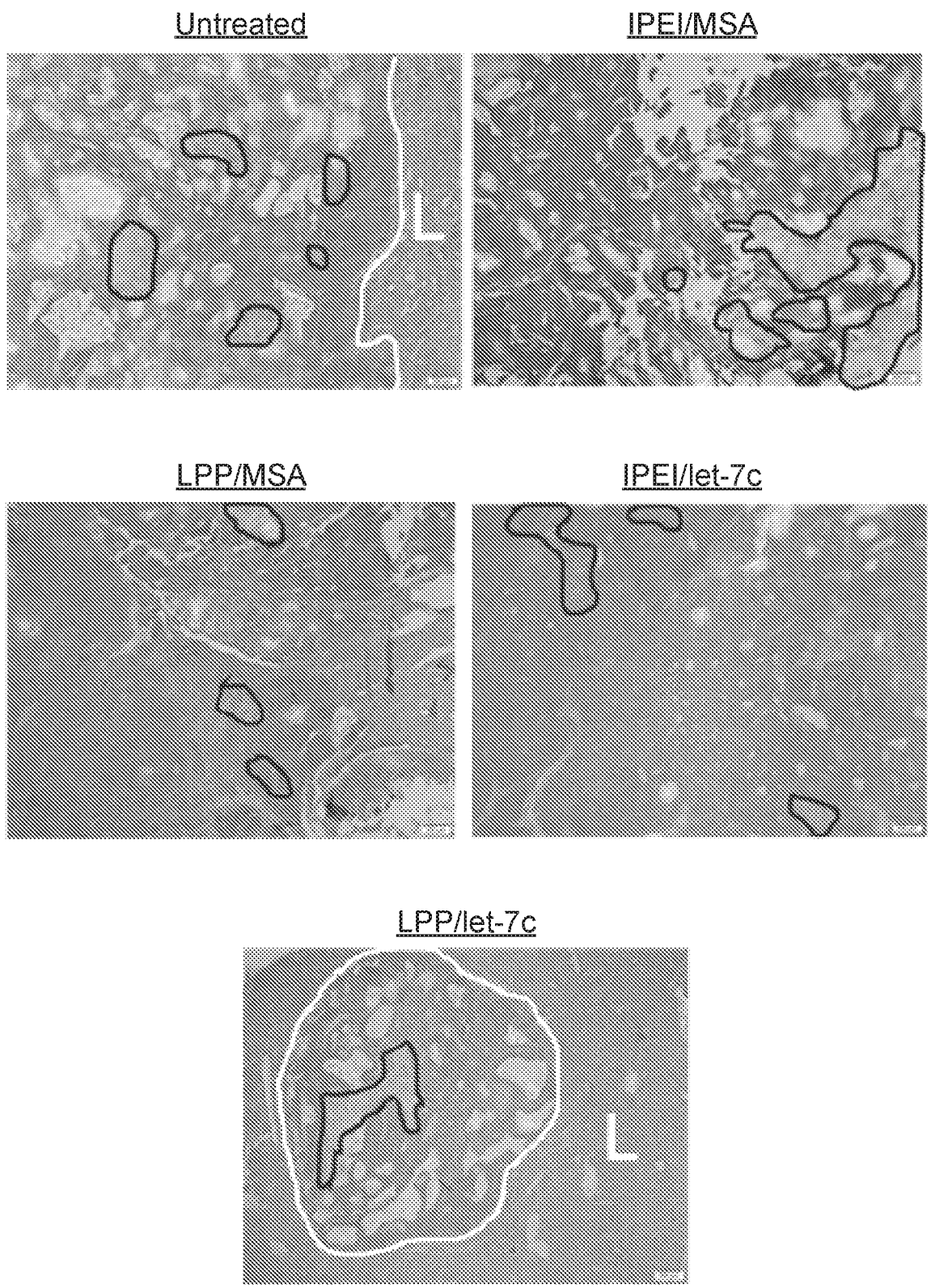

Bioengineered let-7c significantly reduces HCC tumor progression in orthotopic xenograft mouse models and it is well tolerated. We thus established orthotopic HCC xenograft mouse models with luciferase/GFP-expressing Huh7 cells to investigate the efficacy of let-7c therapy (FIG. 23A). As revealed by bioluminescent imaging in live animals (FIG. 23B), HCC tumor burden was inhibited by approximately 50% by both LPP- and IPEI-delivered let-7c, compared to untreated mice; whereas control MSA had no impact. Ex vivo imaging of liver tumoral GFP signals (FIG. 23C) further demonstrated the effectiveness of let-7c for the control of HCC, which was reduced over 70% by LPP/let-7c and around 33% by IPEI/let-7c as compared with untreated mice. Suppression of HCC was associated with higher levels of let-7c in both healthy livers and tumors isolated from let-7c treated mice (FIG. 23D). In addition, efficacy of let-7c therapy in the inhibition of orthotopic HCC was supported significant lower serum AFP levels in let-7c-treated mice (FIG. 23E), as well as histopathological examination of HCC tissues (FIG. 23F). It is also noteworthy that, consistent with a greater serum stability (FIG. 21), LPP/let-7c was more effective than IPEI/let-7c in the control of HCC, as indicated by a more ubiquitous and significantly greater degree of reduction of tumor burden (FIG. 23).

Figure 24A:
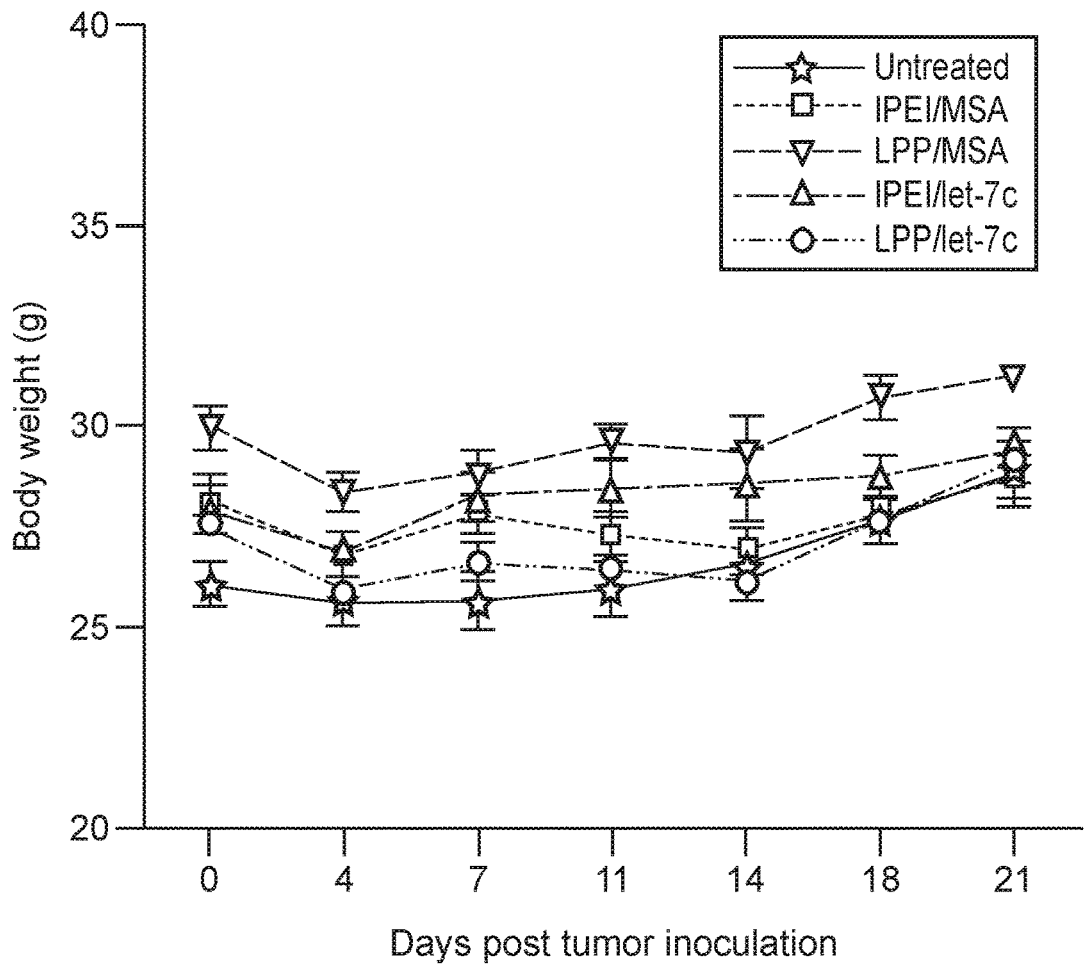
FIGS. 24A-F illustrate treatments are well tolerated in orthotopic HCC xenograft mice, as indicated the lack of differences in animal body weights during therapy (A) as well as blood chemistry profiles including blood urea nitrogen (BUN; B), creatinine (C), alanine transaminase (ALT; D), aspartate transaminase (AST; E). Interestingly, total bilirubin (F) levels were high in untreated and MSA-treated mice, whereas they are within normal range in let-7c-treated mice. Values are mean±SD (N=4-6 in each group). The ranges of individual blood chemistry biomarkers (derived from BALB/c mice; Comparative Pathology Laboratory at UC-Davis) were marked as references.
Figure 24B:
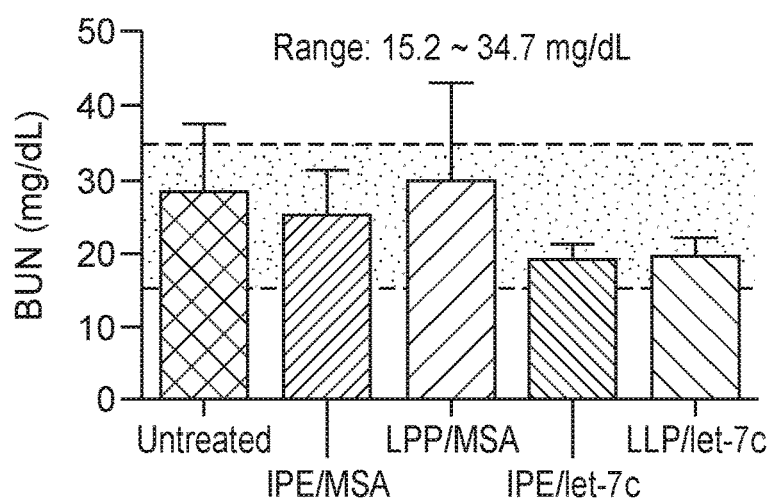
Figure 24C:
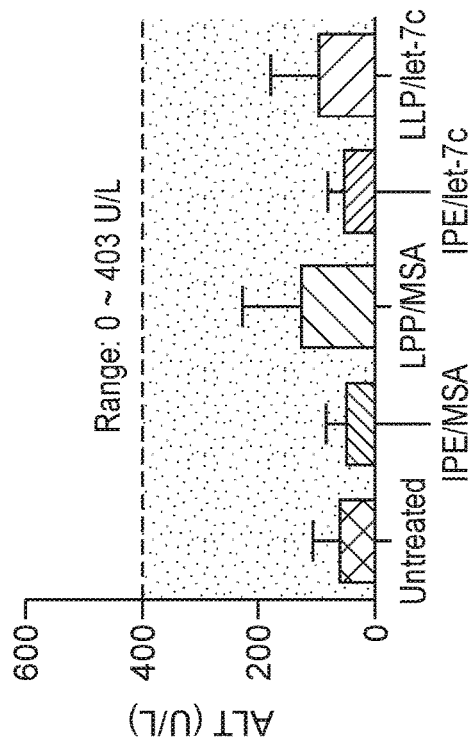
Figure 24D:
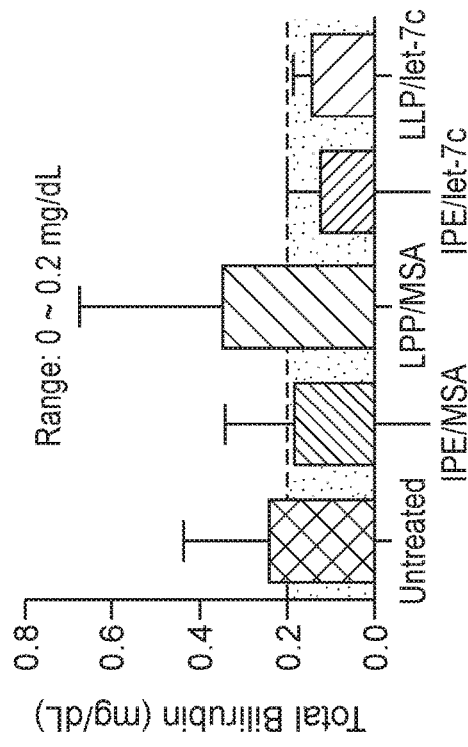
Figure 24E:
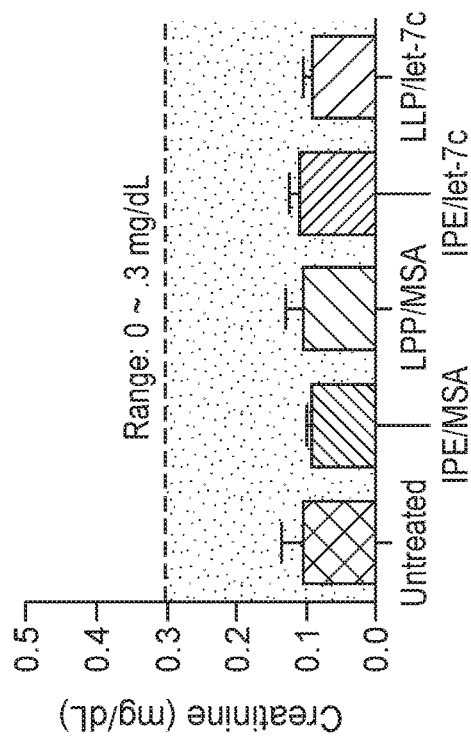
Figure 24F:
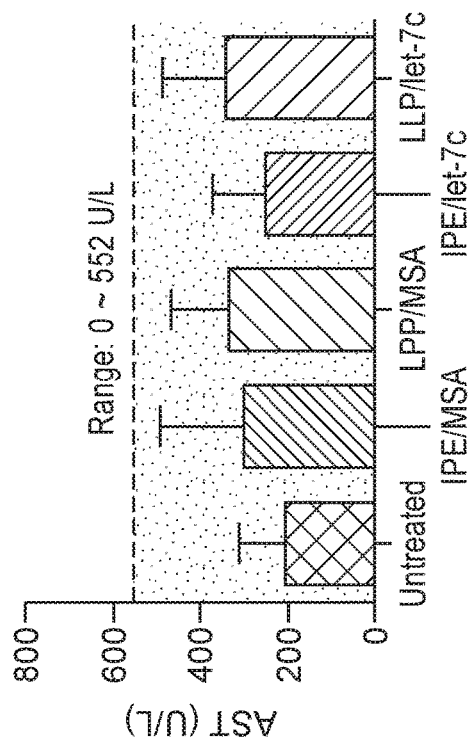

All treatments were well tolerated as body weights of all mice showed steady increases over time (FIG. 24A). To further investigate the safety of let-7c, blood biochemistry profiles were determined (FIG. 22B-F). Biomarkers of hepatic and renal functions including alanine aminotransferase (ALT), aspartate aminotransferase (AST), blood urea nitrogen (BUN) and creatinine were all within the normal ranges. To our surprise, blood total bilirubin levels in untreated and MSA-treated mice were highly variable and inclined to be above normal range, whereas they retained within normal range in let-7c-treated mice, which may be another indication of effectiveness of let-7c in the control of HCC.

Figure 25A:
FIGS. 25A-C illustrate that LPP/let-7c nanotherapeutics significantly improves overall survival of orthotopic HCC xenograft tumor-bearing mice. (A) Bioluminescence images of HCC tumor-bearing animals before the treatment with LPP/let-7c and control LPP/MSA, and quantitative measurement of bioluminescent intensities. (B) Survival analysis showed that LPP/let-7c-treated mice lived much longer than the control (**P<0.01; N=10 per group; Log-rank (Mantel-Cox) Test). The median survival was 26.0 days for LPP/let-7c-treated mice and 19.5 days for LPP/MSA-treated animals. (C) Mouse body weights during the treatment. ▼ indicates days on which mice received treatments.
Figure 25A:
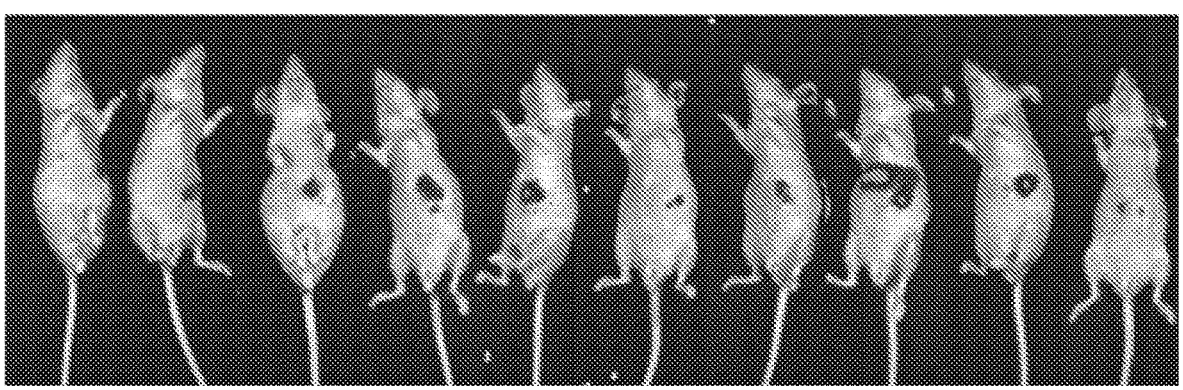
Figure 25A:
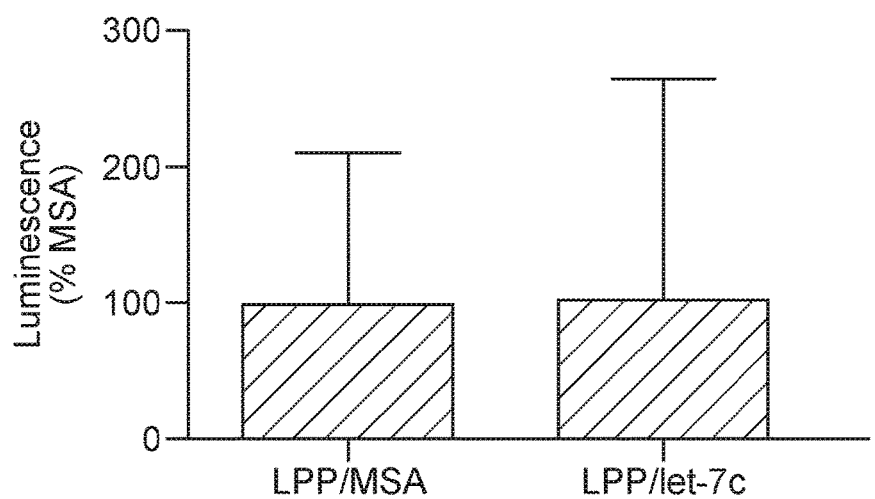
Figure 25B:
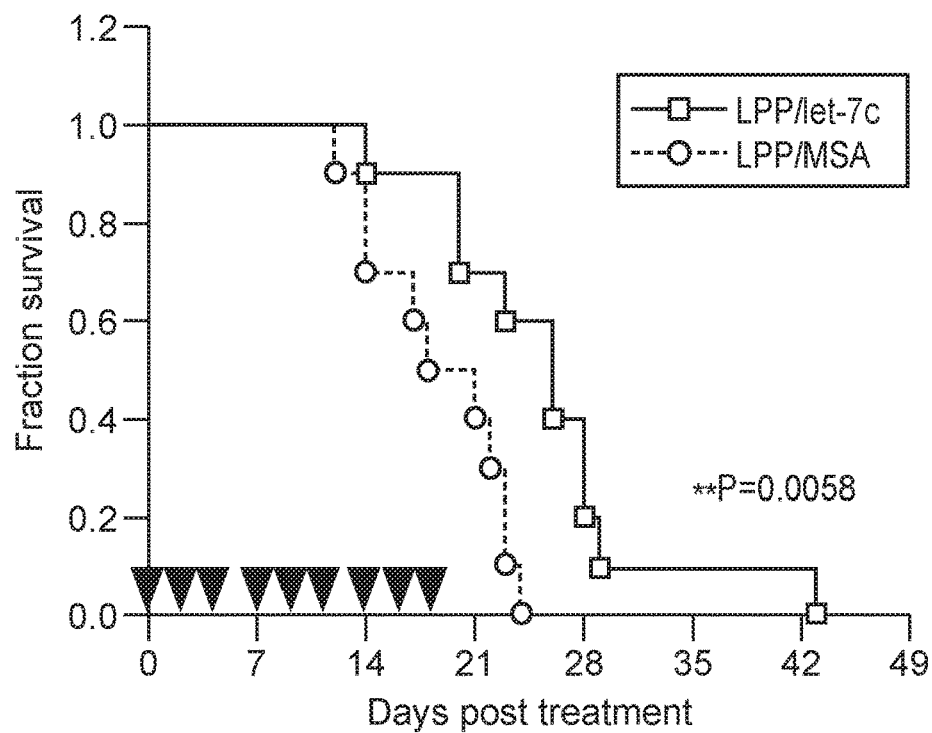
Figure 25C:
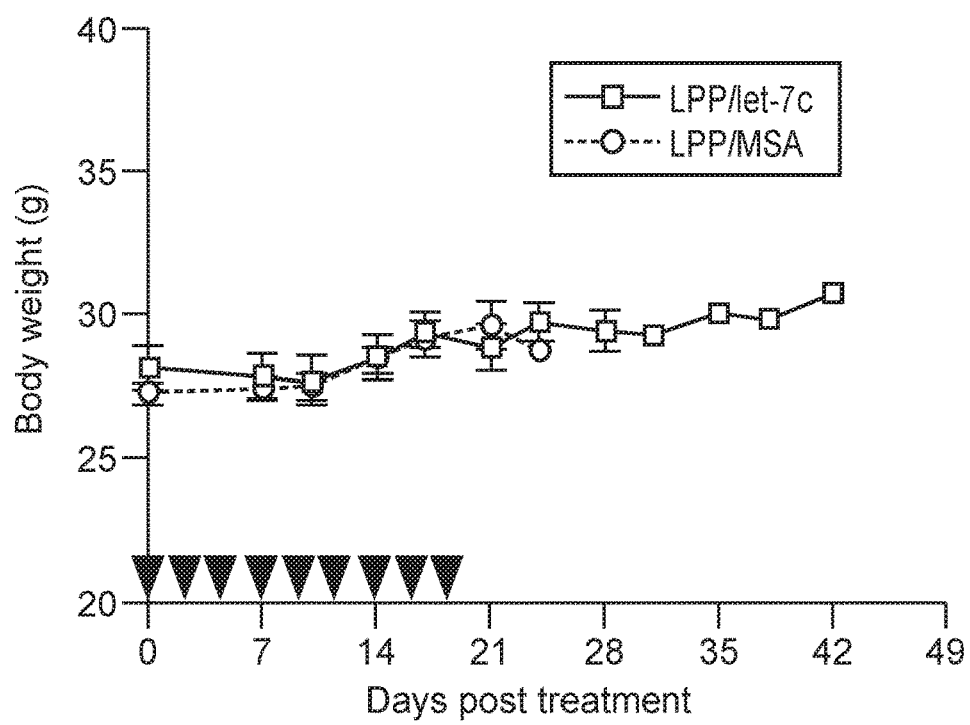

LPP/let-7c nanotherapeutics significantly improves the overall survival of orthotopic HCC tumor-bearing mice. A separate cohort of orthotopic HCC Huh7 xenograft mice was further produced to define the magnitude of benefit of LPP/let-7c nanotherapeutics on overall survival. After the development of HCC was confirmed by quantitative bioluminescence imaging of live mice, subjects showing the same degrees of tumor burden were randomized for LPP/let-7c and control LPP/MSA treatments (FIG. 25A). Survival analysis showed that, compared to LPP/MSA, LPP/let-7c therapy significantly improved overall survival of HCC tumor-bearing mice (FIG. 25B). This was also indicated by a longer median survival of LPP/let-7c-treated mice (26.0 days) than LPP/MSA controls (19.5 days). In agreement with the safety profiles of let-7c treatment in the other therapy study (FIG. 24), LPP/let-7c treatment did not alter mouse body weights compared to LPP/MSA (FIG. 25C).

Figure 26A:
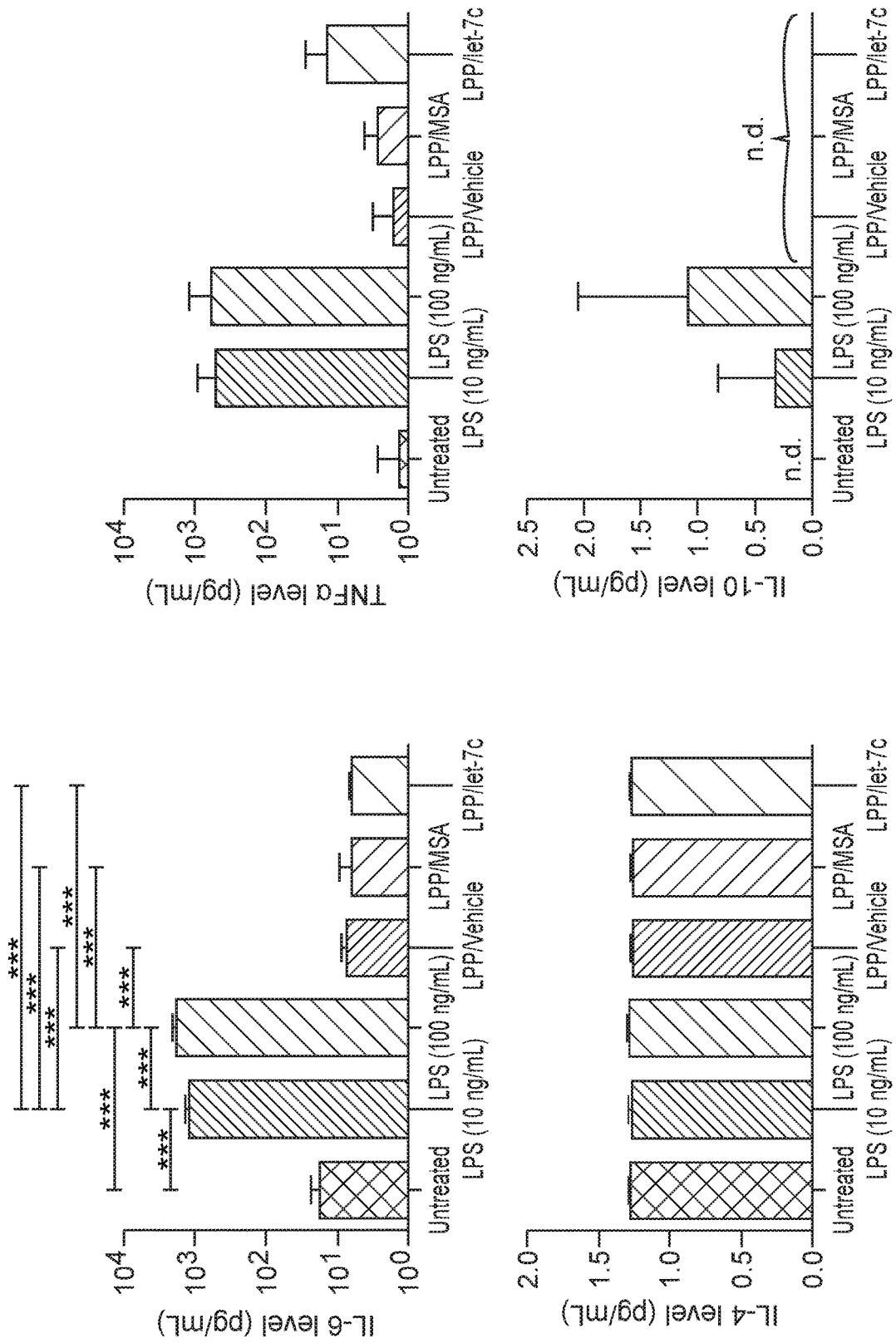

LPP/let-7c produces no or minimal immunogenicity in human PBMCs and immunocompetent mice. Lastly we assessed if LPP/let-7c nanotherapeutics induces any immune response in human PBMCs and two different strains of healthy immunocompetent mice (Balb/c and CD-1). As expected, LPS treatment provoked a cytokine release syndrome in both human PBMCs (FIG. 26A) and Balb/c (FIG. 26B) and CD-1 (FIG. 26C) mice, as indicated by a significantly sharp elevation of IL-6 levels as well as increase in TNFα and IL-10 levels. By contrast, LPP/let-7c treatment did not alter the levels of IL-6, IL-4 or IL-10 in human PBMCs while it slighted increased TNFα level that is not statistically significant different from untreated cells. Although LPP/vehicle, LPP/MSA and LPP/let-7c all caused a mild increase in serum IL-6 levels in Balb/c and CD-1 mice, the elevated IL-6 levels were still significantly, two to three orders of magnitude lower than those induced by LPS. These results suggest that LPP/let-7c is not immunogenic.

Discussion

MiRNA replacement therapy represents a novel promising strategy for the control of tumor progression given the findings on a loss of expression/function of tumor suppressive miRNAs in cancerous cells. However, due to the complexity in dysregulation of miRNAs as well as other regulatory factors and pathways, reintroduction of functional miRNAs may not necessarily coincide with optimal efficacy. As such, while miR-122 is the most abundant hepatic miRNA and a number of miRNAs are associated with HCC progression, we found that bioengineered let-7c showed the highest antiproliferative activity against HCC cells among a small collection of ncRNA agents including miR-122. Although the in vivo efficacy of other miRNAs is not compared with let-7c herein, this screening method is predictive of potential benefits of let-7c in relieving HCC tumor burden and improving overall survival revealed in this study.

Current miRNA research and drug development primarily uses miRNA mimics synthesized in test tubes, which are comprised of extensive chemical modifications expected to improve metabolic stability and display more favorable pharmacokinetic properties. However, such synthetic miRNA agents or oligonucleotides from different manufacturers are widely variable in terms of the types, positions and degrees of artificial modifications. These miRNA agents, which are thought to retain "the same sequences", are literally different molecules and inevitably have distinct secondary and higher-order structures as well as physicochemical and biological activities. Moreover, synthetic RNA agents pose high risk of the induction of cytokine release syndrome (34-36). This is also in sharp contrast to protein research and therapy that is proven successful by using recombinant proteins produced and folded in living cells rather than synthetic polypeptides/proteins. Bioengineered miRNA molecules presented in this study represent a novel class of biologic miRNA agents, which are folded and tolerated in living cells and thus may better capture the properties of cellular RNA macromolecules (22). With minimal natural modifications and exhibiting favorable stability in human cells (23, 37), recombinant miRNA agents are selectively processed to target mature miRNAs that rewrite cellular miRNome profile and execute regulatory functions (21).

The pleiotropic nature of miRNA-controlled gene regulation behind cancer cellular processes warrants extensive validation. The interplay between LIN28 and let-7 family miRNAs (33, 38) is a critical component in the regulation of pluripotency as well as HCC and other liver diseases (39). LIN28 that has been shown to be upregulated in stem-like cells can reprogram cells into an undifferentiated state (40) and thus LIN28 may be a druggable target for the suppression of CSCs and tumor initiation. By contrast, LIN28-regulatory let-7 family miRNAs shown to inhibit pluripotency and favor differentiation may be employed to manage CSC maintenance and replication (41, 42). This study demonstrated a consistent action of bioengineered let-7c agent in the inhibition of tumorsphere growth, which is likely attributable to the strong suppression of LIN28B expression in Huh7 cells, and provides an explanation for the greater sensitivity of Huh7 cells to let-7c agent over Sk-Hep-1 cells. Moreover, induction of apoptosis is a common mechanism of antineoplastic agents, and resistance to apoptosis is a common feature of CSCs. let-7 family miRNAs have also been shown to either induce or sensitize cells to apoptosis via attenuation of anti-apoptotic proteins, including Bcl-xl (32, 43). In this study, we found the suppression of Bcl-xl expression by let-7c in both HCC cell lines, which is consistent with the induction of apoptotic, but not necrotic cell populations by a low dose of let-7c.

RNA drugs for systemic administration currently under clinical investigation are mainly delivered by lipid-based systems (e.g., liposomes), given their excellent biocompatibility and favorable lipid composition (44-46). As an example, a Phase I trial is underway to evaluate a small activating, double stranded RNA targeting the transcription factor C/EBP-α formulated in SMARTICLES® liposomal nanoparticle for advanced HCC (https://clinicaltrials.gov/ct2/show/NCT02716012). Among lipid-based delivery systems, LPPs convey the favorable properties of both liposomes and polyplexes (28, 29, 47). Our recent studies have demonstrated that IPEI is able to deliver biologic RNAs to livers to achieve target gene knockdown (20) as well as tumor tissues to control disease (21, 24, 26) in a whole body system. In the present study, we identified an improvement of serum stability for let-7c formulated in LPP nanocomplex as compared to IPEI, owing to the outer PEGylated lipid coating of polyplex. As a result, LPP showed high in vitro delivery efficiency in HCC cell lines. Most importantly, LPP/let-7c provided significantly greater extent suppression of orthotopic HCC tumor burden in vivo, consistently indicated by multiple independent endpoints including live animal luciferase bioluminescent signal, ex vivo GFP intensity, serum AFP level, and histological tumor area. In addition, we revealed that LPP/let-7c nanotherapeutics significantly improved the median survival of orthotopic HCC mice by 6.5-day, which seems to be small. However, considering the difference in lifespans between mice and humans and their possible correlation (48), this would be equivalent to an approximately 9-month extension of survival benefit for HCC patients, which warrants clinical investigation.

Consistent with our previous findings (23), current study demonstrated that highly-purified low-endotoxin recombinant RNAs were well tolerated in HCC tumor-bearing immunodeficient mice and caused no or minimal degree of cytokine release in immunocompetent mice. Interestingly, serum bilirubin level, an indicator of liver damage, fell within normal range in let-7c-treated mice only. This is likely attributable to the effectiveness of let-7c therapy in the control of HCC tumor growth, leading to the suppression of further liver damage, which highlights the aggressive nature of this HCC model (49). Moreover, the present study showed for the first time that bioengineered RNAs are not immunogenic in human PBMCs, an addition to the safety profile of recombinant miRNA molecules produced in living cells.

In conclusion, we have demonstrated the efficacy of LPP/let-7c nanotherapeutics in an aggressive HCC tumor mouse model, showing no or minimal immunogenicity in mice and human PBMCs. The first-of-a-kind biologic let-7c agent was identified as the most potent among a small set of miRNAs in inhibiting HCC cell viability via interference of specific targets and critical cell functions. Our findings suggest that LPP-formulated biologic let-7c serveS as an effective and safe treatment for HCC which deserves clinical verification.

REFERENCES FOR EXAMPLE 2

1. Siegel R L, Miller K D, Jemal A. Cancer statistics, 2018. CA Cancer J Clin 2018; 68:7-30.
2. Kim N G, Nguyen P P, Dang H, Kumari R, Garcia G, Esquivel C O, Nguyen M H. Temporal trends in disease presentation and survival of patients with hepatocellular carcinoma: A real-world experience from 1998 to 2015. Cancer 2018.
3. Sun W, Cabrera R. Systemic Treatment of Patients with Advanced, Unresectable Hepatocellular Carcinoma: Emergence of Therapies. J Gastrointest Cancer 2018.
4. Gbolahan O B, Schacht M A, Beckley E W, LaRoche T P, O'Neil B H, Pyko M. Locoregional and systemic therapy for hepatocellular carcinoma. J Gastrointest Oncol 2017; 8:215-228.
5. Galle P R, Tovoli F, Foerster F, Worns M A, Cucchetti A, Bolondi L. The treatment of intermediate stage tumours beyond TACE: From surgery to systemic therapy. J Hepatol 2017; 67:173-183.
6. Llovet J M, Ricci S, Mazzaferro V, Hilgard P, Gane E, Blanc J F, de Oliveira A C, et al. Sorafenib in advanced hepatocellular carcinoma. N Engl J Med 2008; 359:378-390.
7. Bruix J, Qin S, Merle P, Granito A, Huang Y H, Bodoky G, Pracht M, et al. Regorafenib for patients with hepatocellular carcinoma who progressed on sorafenib treatment (RESORCE): a randomised, double-blind, placebo-controlled, phase 3 trial. Lancet 2017; 389:56-66.
8. Inarrairaegui M, Melero I, Sangro B. Immunotherapy of Hepatocellular Carcinoma: Facts and Hopes. Clin Cancer Res 2018; 24:1518-1524.
9. Torre L A, Siegel R L, Ward E M, Jemal A. Global Cancer Incidence and Mortality Rates and Trends—An Update. Cancer Epidemiol Biomarkers Prev 2016; 25:16-27.
10. Ambros V. The functions of animal microRNAs. Nature 2004; 431:350-355.
11. Bader A G, Brown D, Winkler M. The promise of microRNA replacement therapy. Cancer Res 2010; 70:7027-7030.

12. Rupaimoole R, Slack F J. MicroRNA therapeutics: towards a new era for the management of cancer and other diseases. Nat Rev Drug Discov 2017; 16:203-222.
13. Yu A M, Tian Y, Tu M J, Ho P Y, Jilek J L. MicroRNA Pharmacoepigenetics: Posttranscriptional Regulation Mechanisms behind Variable Drug Disposition and Strategy to Develop More Effective Therapy. Drug Metab Dispos 2016; 44:308-319.
14. Kota J, Chivukula R R, O'Donnell K A, Wentzel E A, Montgomery C L, Hwang H W, Chang T C, et al. Therapeutic microRNA Delivery Suppresses Tumorigenesis in a Murine Liver Cancer Model. Cell 2009; 137: 1005-1017.
15. Fu X, Rivera A, Tao L, De Geest B, Zhang X. Construction of an oncolytic herpes simplex virus that precisely targets hepatocellular carcinoma cells. Mol Ther 2012; 20:339-346.
16. Sandbothe M, Buurman R, Reich N, Greiwe L, Vajen B, Gurlevik E, Schaffer V, et al. The microRNA-449 family inhibits TGF-beta-mediated liver cancer cell migration by targeting SOX4. J Hepatol 2017; 66:1012-1021.
17. Wu H, Tao J, Li X, Zhang T, Zhao L, Wang Y, Zhang L, et al. MicroRNA-206 prevents the pathogenesis of hepatocellular carcinoma by modulating expression of met proto-oncogene and cyclin-dependent kinase 6 in mice. Hepatology 2017; 66:1952-1967.
18. Zhang J, Yang Y, Yang T, Yuan S, Wang R, Pan Z, Yang Y, et al. Double-negative feedback loop between microRNA-422a and forkhead box (FOX)G1/Q1/E1 regulates hepatocellular carcinoma tumor growth and metastasis. Hepatology 2015; 61:561-573.
19. Lu Y, Yue X, Cui Y, Zhang J, Wang K. MicroRNA-124 suppresses growth of human hepatocellular carcinoma by targeting STAT3. Biochem Biophys Res Commun 2013; 441:873-879.
20. Chen Q X, Wang W P, Zeng S, Urayama S, Yu A M. A general approach to high-yield biosynthesis of chimeric RNAs bearing various types of functional small RNAs for broad applications. Nucleic Acids Res 2015; 43:3857-3869.
21. Ho P Y, Duan Z, Batra N, Jilek J L, Tu M J, Qiu J X, Hu Z, et al. Bioengineered ncRNAs selectively change cellular miRNome profiles for cancer therapy. J Pharmacol Exp Ther 2018.
22. Ho P Y, Yu A M. Bioengineering of noncoding RNAs for research agents and therapeutics. Wiley Interdisciplinary Reviews: RNA 2016; 7:186-197.
23. Wang W P, Ho P Y, Chen Q X, Addepalli B, Limbach P A, Li M M, Wu W J, et al. Bioengineering Novel Chimeric microRNA-34a for Prodrug Cancer Therapy: High-Yield Expression and Purification, and Structural and Functional Characterization. Journal Of Pharmacology And Experimental Therapeutics 2015; 354:131-141.
24. Jian C, Tu M J, Ho P Y, Duan Z, Zhang Q, Qiu J X, DeVere White R W, et al. Co-targeting of DNA, RNA, and protein molecules provides optimal outcomes for treating osteosarcoma and pulmonary metastasis in spontaneous and experimental metastasis mouse models. Oncotarget 2017; 8:30742-30755.
25. Li P C, Tu M J, Ho P Y, Jilek J L, Duan Z, Zhang Q Y, Yu A X, et al. Bioengineered NRF2-siRNA Is Effective to Interfere with NRF2 Pathways and Improve Chemosensitivity of Human Cancer Cells. Drug Metab Dispos 2018; 46:2-10.
26. Zhao Y, Tu M J, Yu Y F, Wang W P, Chen Q X, Qiu J X, Yu A X, et al. Combination therapy with bioengineered miR-34a prodrug and doxorubicin synergistically suppresses osteosarcoma growth. Biochem Pharmacol 2015; 98:602-613.
27. Lv H T, Zhang S B, Wang B, Cui S H, Yan J. Toxicity of cationic lipids and cationic polymers in gene delivery. Journal Of Controlled Release 2006; 114:100-109.
28. Rezaee M, Oskuee R K, Nassirli H, Malaekeh-Nikouei B. Progress in the development of lipopolyplexes as efficient non-viral gene delivery systems. Journal Of Controlled Release 2016; 236:1-14.
29. Ewe A, Panchal O, Pinnapireddy S R, Bakowsky U, Przybylski S, Temme A, Aigner A. Liposome-polyethylenimine complexes (DPPC-PEI lipopolyplexes) for therapeutic siRNA delivery in vivo. Nanomedicine 2017; 13:209-218.
30. Schafer J, Hobel S, Bakowsky U, Aigner A. Liposome-polyethylenimine complexes for enhanced DNA and siRNA delivery. Biomaterials 2010; 31:6892-6900.
31. Ewe A, Schaper A, Barnert S, Schubert R, Temme A, Bakowsky U, Aigner A. Storage stability of optimal liposome-polyethylenimine complexes (lipopolyplexes) for DNA or siRNA delivery. Acta biomaterialia 2014; 10:2663-2673.
32. Shimizu S, Takehara T, Hikita H, Kodama T, Miyagi T, Hosui A, Tatsumi T, et al. The let-7 family of microRNAs inhibits Bcl-xL expression and potentiates sorafenib-induced apoptosis in human hepatocellular carcinoma. Journal of hepatology 2010; 52:698-704.
33. Nam Y, Chen C, Gregory R I, Chou J J, Sliz P. Molecular basis for interaction of let-7 microRNAs with Lin28. Cell 2011; 147:1080-1091.
34. Robbins M, Judge A, MacLachlan I. siRNA and innate immunity. Oligonucleotides 2009; 19:89-102.
35. Yu H, Wang Z, Sun G, Yu Y. Recognition of nucleic acid ligands by toll-like receptors 7/8: importance of chemical modification. Curr Med Chem 2012; 19:1365-1377.
36. Bramsen J B, Kjems J. Development of Therapeutic-Grade Small Interfering RNAs by Chemical Engineering. Front Genet 2012; 3:154.
37. Li M-M, Addepalli B, Tu M-J, Chen Q-X, Wang W-P, Limbach P A, LaSalle J M, et al. Chimeric microRNA-1291 biosynthesized efficiently in *Escherichia coli* is effective to reduce target gene expression in human carcinoma cells and improve chemosensitivity. Drug Metabolism and Disposition 2015; 43:1129-1136.
38. Guo Y, Chen Y, Ito H, Watanabe A, Ge X, Kodama T, Aburatani H. Identification and characterization of lin-28 homolog B (LIN28B) in human hepatocellular carcinoma. Gene 2006; 384:51-61.
39. McDaniel K, Hall C, Sato K, Lairmore T, Marzioni M, Glaser S, Meng F, et al. Lin28 and let-7: roles and regulation in liver diseases. Am J Physiol Gastrointest Liver Physiol 2016; 310:G757-765.
40. Yu J, Vodyanik M A, Smuga-Otto K, Antosiewicz-Bourget J, Frane J L, Tian S, Nie J, et al. Induced pluripotent stem cell lines derived from human somatic cells. Science 2007; 318:1917-1920.
41. Reinhart B J, Slack F J, Basson M, Pasquinelli A E, Bettinger J C, Rougvie A E, Horvitz H R, et al. The 21-nucleotide let-7 RNA regulates developmental timing in *Caenorhabditis elegans*. Nature 2000; 403:901-906.
42. Viswanathan S R, Daley G Q. Lin28: A microRNA regulator with a macro role. Cell 2010; 140:445-449.
43. Tian N, Han Z, Li Z, Zhou M, Fan C. Lin28/let-7/Bcl-xL pathway: the underlying mechanism of drug resistance in Hep3B cells. Oncol Rep 2014; 32:1050-1056.

44. Xue H Y, Guo P B, Wen W C, Wong H L. Lipid-Based Nanocarriers for RNA Delivery. Current Pharmaceutical Design 2015; 21:3140-3147.
45. Sullenger B A, Nair S. From the RNA world to the clinic. Science 2016; 352:1417-1420.
46. Kim H J, Kim A, Miyata K, Kataoka K. Recent progress in development of siRNA delivery vehicles for cancer therapy. Advanced Drug Delivery Reviews 2016; 104:61-77.
47. Xia Y, Tian J, Chen X. Effect of surface properties on liposomal siRNA delivery. Biomaterials 2016; 79:56-68.
48. Dutta S, Sengupta P. Men and mice: Relating their ages. Life Sci 2016; 152:244-248.
49. Carr B I, Guerra V, Giannini E G, Farinati F, Ciccarese F, Rapaccini G L, Di Marco M, et al. Association of abnormal plasma bilirubin with aggressive hepatocellular carcinoma phenotype. In: Seminars in oncology; 2014: Elsevier; 2014. p. 252-258.

Example 3

Bioengineered miRNA-1291 Prodrug Therapy in Pancreatic Cancer Cells and Patient-Derived Xenograft Mouse Models Abstract Purpose: Our recent studies have revealed that microRNA-1291 (miR-1291) is downregulated in pancreatic cancer (PC) specimens and restoration of miR-1291 inhibits tumorigenesis of PC cells. We have also bioengineered a miR-1291 prodrug. This study is to assess the efficacy of miR-1291 prodrug monotherapy and combined treatment with chemotherapy.

Experimental design: Sensitivity of PC cells to drug treatment was determined by CellTiter-Glo assay. Mechanisms of drug actions were verified by monitoring specific markers or targets. PANC-1 and patient-derived xenograft (PDX) mouse models were established to define anti-tumor effects of miR-1291 mono- and combination therapy with gemcitabine plus nab-paclitaxel (Gem-nP). To explore miR-1291 based therapeutic strategies for the treatment of PC, we have successfully established a novel approach to producing large quantities of pre-miR-1291 (or mir-1291) agents in bacteria by using a sephadex aptamer tagged methionyl-tRNA (MSA) scaffold (23). Further studies demonstrated that chimeric MSA/mir-1291 or "miR-1291 prodrug" was precisely processed into mature miR-1291 in human cells, and subsequently regulated target protein expression and suppressed the growth of PC cells (23). It is noteworthy that bioengineered miRNA agents produced in living cells are distinguished from conventional miRNA agents made in test tubes by chemical synthesis or enzymatic reactions (24). Most importantly, synthetic RNA agents or oligonucleotides from different manufacturers/vendors differ widely in the types, positions and degrees of modifications, which, although are thought to have "the same sequences", are literally different molecules and inevitably have distinct secondary and higher-order structures as well as biological activities. Therefore, our biologic miRNA agents, given the fact that they are folded and tolerated within living cells, may better capture the natural characteristics of cellular RNA molecules (24).

Results: ARID3B was verified as a new target for miR-1291, and bioengineered miR-1291 prodrug was selectively processed to mature miR-1291 in PC cells which surprisingly upregulated ARID3B mRNA and protein levels. Co-administration of miR-1291 with Gem-nP largely increased the levels of apoptosis (cleaved caspase-3/7), DNA damage ($\gamma$H2A.X) and mitotic arrest (H3PS10) in PC cells, compared with miR-1291 or Gem-nP alone. Consequently, miR-1291 prodrug improved PANC-1 and AsPC-1 cell sensitivity to Gem-nP. Furthermore, systemic administration of in vivo-jetPEI-formulated miR-1291 prodrug suppressed tumor growth in both PANC-1 xenograft and three PDX mouse models to comparable degrees as Gem-nP alone, while combination treatment reduced tumor growth more ubiquitously and to the greatest degrees (70-90%) than monotherapy in all models. All treatments were well tolerated in mice in vivo.

Conclusion: Biologic miR-1291 prodrug has therapeutic potential as a monotherapy for PC, as well as a sensitizing agent to chemotherapy.

Materials and Methods

Materials. RPMI 1640 medium, Dulbecco's modified Eagle medium (DMEM), Fetal bovine serum (FBS), trypsin, Lipofectamine 3000 and Trizol reagent were purchased from Life Technologies (Carlsbad, CA). Gemcitabine hydrochloride salt was purchased from LC Laboratories (Woburn, MA). RIPA lysis buffer and the complete protease inhibitor cocktail were bought from Sigma-Aldrich (St. Louis, MO). BCA Protein Assay Kit was bought from Thermo Scientific (Rockford, IL). The primary antibodies against $\gamma$H2A.X, cleaved-caspase-3, and cleaved-caspase-7 were purchased from Cell Signaling Technology (Danvers, MA), the antibodies against ARID3B and H3PS10 were purchased from Abcam (Cambridge, MA), and the antibody against $\beta$-actin was obtained from Sigma-Aldrich (St. Louis, MO). The horseradish peroxidase goat anti-rabbit and mouse secondary antibodies were supplied by Jackson Immuno-Research Laboratories (West Grove, PA) and Cell Signaling Technology (Danvers, MA), respectively. ECL substrate and PVDF membrane were obtained from Bio-Rad (Hercules, CA). All other reagents were purchased from commercial sources and were of the analytical grade.

Production of biologic miR-1291 prodrug (MSA/mir-1291) and control RNA MSA. Expression of recombinant MSA/mir-1291 and control tRNA MSA was conducted as described recently (23, 25), while purification was performed with an improved anion exchange fast protein liquid chromatograph (FPLC) method (26). In brief, MSA/mir-1291- and MSA-expressing plasmids were transformed into HST08 E. coli competent cells, respectively. Separation of target RNAs from total bacterial RNA was achieved on an Enrich-Q 10×100 column by using a NGC QUEST 10PLUS FPLC system (Bio-Rad), which was first equilibrated with Buffer A (10 mM sodium phosphate, pH 7.0) at a constant flow rate of 2.5 ml/min for 4.4 min and then a gradient elution: 64% Buffer B (Buffer A+1 M sodium chloride, pH 7.0) for 10 min, 64-78% Buffer B for 8 min, and then 100% Buffer B for 3 min. FPLC traces were monitored at 260/280 nm using a UV/Vis detector. After the confirmation of target RNA by urea-PAGE analyses, fractions were pooled, precipitated by ethanol, desalted and concentrated/dissolved in nuclease-free water with an Amicon ultra-2 mL centrifugal filter (30 kDa; EMD Millipore, Billerica, MA). RNA purities were verified by a high performance liquid chromatography (HPLC) assay (25), and recombinant RNAs over 97% pure were used in this study.

Figure 27A:
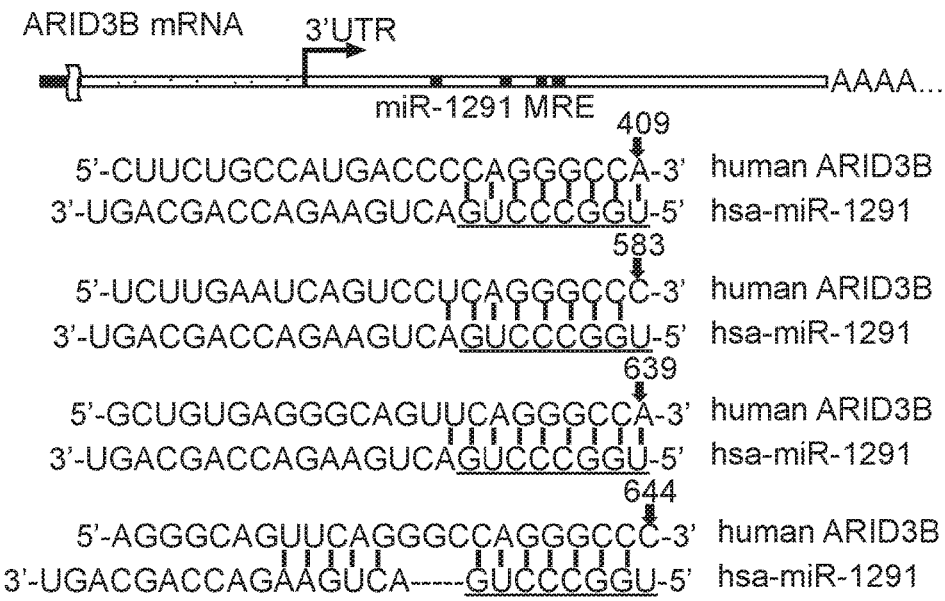
FIGS. 27A-27E illustrate that MiR-1291 targets ARID3B and upregulates its expression in human pancreatic cancer cells.

Plasmids construction and luciferase reporter gene assay. The 3'UTR segment (0-972 bp from stop codon) of human ARID3B containing the predicted hsa-miR-1291 response elements (MREs; FIG. 27A) was amplified from human genome by PCR with the following primers: forward: 5'-CCG CTC GAG GTC CGT CTG TCC AGG CTC CAT TCA GGT CCT GCT G-3' (SEQ ID NO: 575), reverse: 5'-TTG CGG CCG CGG GGC CGG GTT ACC CAA TCA CTT GCT TGG CTT T-3' (SEQ ID NO: 576), and then inserted downstream of *Renilla luciferase* gene within psi-CHECK-II vector (Promega, Madison, WI) at XhoI and NotI restriction sites. Sequence was confirmed by DNA sequencing.

Luciferase reporter assay was conducted as previously reported (27). Briefly, HEK-293 cells and AsPC-1 cells were co-transfected with ARID3B-3'UTR luciferase reporter plasmids (psiCHECK-ARID3B-3'UTR) or psiCHECK empty vector (0.1 µg) plus MSA or MSA/mir-1291 (0, 5, 20 nM), or miR-1291-expressing plasmid or control vector (20), or miR-1291 antagomir or control oligo using Lipofectamine 3000. 48 h post-transfection, luciferase activities were determined by a Dual-Luciferase Reporter Assay kit (Promega, Madison, WI) using a SpectraMax® M3 microplate reader (Molecular Devices, Sunnyvale, CA). Activity of *Renilla luciferase* was normalized to firefly luciferase and then calculated as a percentage of corresponding control.

Cell culture and treatments. AsPC-1, PANC-1, and HEK293 cells were obtained from ATCC and maintained in RPMI or DMEM media containing 10% fetal bovine serum (GIBICO), 100 U/ml penicillin and 100 mg/ml streptomycin at 37° C. with 5% CO2 in a humidified incubator. For cell viability assays, cells were seeded in 96-well plates at a density of 5,000 cells/well, incubated overnight, and then transfected with MSA or MSA/mir-1291 (1 nM for AsPC-1 cells, 5 nM for PANC-1 cells) in the presence of various concentrations of gemcitabine (Gem, 0-10 µM) plus nab-paclitaxel (at a fixed ratio Gem/nP=8/1). Forty-eight hours later, the viability of cells was determined by CellTiter-Glo® Luminescent Cell Viability Assay (Promega, Madison, WI). Pharmacodynamic parameters were estimated by fitting the data to an inhibitory dose-response model with variable slope, $Y=Bottom+(Top-Bottom)/(1+10\string^((Log\ IC50-X)*HillSlope))$.

RNA isolation and reverse transcription quantitative real-time PCR (RT-qPCR). PANC-1 or AsPC-1 cells seeded in 24-well plates were transfected with MSA/mir-1291, control MSA, or vehicle using Lipofectamine 3000. Total RNA was extracted at 48 h and 72 h post-transfection using a Direct-zol RNA MiniPrep kit (Zymo Research, Irvine, CA), and reverse-transcribed with NxGen M-MuLV reverse transcriptase (Lucigen, Middleton, WI). RT-qPCR was performed on a CFX96 Touch real-time PCR system (Bio-Rad, Hercules, CA) by using TaqMan small RNA assay kit (Thermo Fisher Scientific) for mature miR-1291, or gene-specific primers for U6 (Forward: 5'-CTC GCT TCG GCA GCA CA-3' (SEQ ID NO: 528), Reverse: 5'-AAC GCT TCA CGA ATT TGC GT-3' (SEQ ID NO: 529), internal standard for miR-1291), ARID3B (Forward: 5'-GTG GCA CCC ATG TCC AAT CTA-3' (SEQ ID NO: 579), Reverse: AGG ATC ACC GTC CAG TTC ATA-3' (SEQ ID NO: 580)), and GAPDH (Forward: 5'-ATC ACC ATC TTC CAG GAG CGA-3' (SEQ ID NO: 581), Reverse: 5'-GCT TCA CCA CCT TCT TGA TGT-3' (SEQ ID NO: 582), internal standard for ARID3B). The relative expression of target gene was calculated using comparative threshold cycle (Ct) method with the formula $2-\Delta\Delta Ct$.

Protein isolation and immunoblot analysis. PANC-1 and AsPC-1 cells were treated with MSA/mir-1291 (10 or 20 nM for PANC-1 cells, 3 or 5 nM for AsPC-1 cells), Gem-nP (160 nM-20 nM for PANC-1 cells, 100 nM-12.5 nM for AsPC-1 cells), or the combination of MSA/mir-1291 and Gem-nP. Cells were harvested after 48 h or 72 h, and lysed with RIPA buffer supplemented with protease inhibitor cocktail (Sigma-Aldrich, St. Louis, MO) whose protein concentrations were determined by a BCA kit (Thermo Fisher Scientific, Rockford, IL). Proteins (30 µg/lane) were separated on a 10% or 12% SDS-PAGE gel and transferred to a polyvinylidene difluoride (PVDF) membrane, followed by blocking with 5% milk. The membranes were incubated with selective anti-ARID3B (1:1500, Abcam), anti-γH2A.X (1:1000, Cell Signaling Technology), anti-cleaved caspase-7 (1: 1000, Cell Signaling Technology), anti-histone H3 (phospho S10, 1:1000, Cell Signaling Technology) or anti-p-actin (1:5000, Sigma-Aldrich) primary antibodies, and then incubated with horseradish peroxidase-conjugated anti-rabbit (1:10000, Jackson ImmunoResearch Inc., West Grove, Pa., USA) or anti-mouse (1:3000, Cell Signaling Technology) IgG (Table 7). After washed three times, the membranes were incubated with ECL substrates, subsequently visualized and imaged by a ChemiDoc MP Imaging System (Bio-Rad). Protein band intensities were quantified by Image Lab software (Bio-Rad) and normalized to β-actin levels in corresponding samples.

TABLE 7

Antibodies Used For Western Blots And Immunofluorescence Analyses.

| Antibodies | Manufacture | Catalog No. |
| --- | --- | --- |
| ARID3B | Abcam | ab92328 |
| γH2A.X | Cell Signaling | 2577 |
| Cleaved Caspase-7 | Cell signaling | 9491 |
| Cleaved Caspase-3 | Cell signaling | 9579 |
| Histone H3 (phospho S10) | Abcam | ab5176 |
| Peroxidase-conjugated goat anti-rabbit IgG | Jackson ImmunoReseach | 111-035-003 |
| Anti-mouse IgG, HRP-linked Antibody | Cell signaling | 7076 |
| Alexa Fluor ® 488-conjugated goat anti-rabbit IgG | Cell signaling | 4412 |

Immunofluorescence. Cells were plated on 8-well chamber slides and incubated overnight for attachment. Then the cells were treated with regular medium (blank), MSA/mir-1291, Gem-nP, or the combination of MSA/mir-1291 with Gem-nP. After 48-h incubation, the medium was removed, and cells were fixed with 4% paraformaldehyde, permeabilized and blocked by 5% BSA supplemented with 0.5% Triton X-100. The blocked cells were then incubated overnight at 4° C. with a primary antibody, anti-cleaved-caspase-3, anti-cleaved-caspase-7, anti-γH2A.X, or anti-H3PS10, followed by the incubation with fluorescent secondary antibody, anti-rabbit IgG Alexa Fluor® 488 Conjugate (1:500, #4412, Cell signaling Technology). DAPI (#8961, Cell signaling Technology) were incubated with the cells to stain nuclei. The images were obtained by using a Zeiss Axio Observer.zl Microscope coupled to a Zeiss LSM 710 Scanning Device (Zeiss, Oberkochen, Germany).

Animals. All animal experiments were performed according to our protocol approved by the Institutional Animal Care and Use Committee at UC Davis. 5- to 6-week-old female athymic nude mice (NU/J) and NOD.CB17-Prkdcscid/J mice (The Jackson Laboratory, Bar Harbor, ME) were used to establish PANC-1 xenograft mouse models and pancreatic carcinoma patient derived xenograft (PDX) mouse models, respectively. The mice were maintained in sterile cages at constant temperature and humidity, with free access to food and water. Mice were anesthetized through intraperitoneal injection of a combination of ketamine (80 mg/kg) and xylazine (7 mg/kg) in PBS before cell/tissue implantation.

PANC-1 xenograft mouse model. PANC-1 cells were trypsinized, resuspended in PBS, and mixed with Matrigel (BD Biosciences, San Jose, CA) in a 1:1 ratio (v/v). Cells ($7.5 \times 10^6$) in 100 μL of PBS/Matrigel solution were injected subcutaneously into the left lower back region of the nude mice for the production of PANC-1 xenograft tumor mouse models.

Pancreatic carcinoma PDX mouse models. Fresh, de-identified surgical pancreatic carcinoma specimens were obtained from Comprehensive Cancer Center Biorepository at UC Davis. None of the patients have received preoperative chemotherapy or radiotherapy. The PDX mouse model was thus established as previously described with minor modifications (28, 29). Briefly, patients' tumor specimens were minced into 2-3 $mm^3$ pieces in antibiotics-containing RPMI and implanted subcutaneously into the SCID mice (F1). When the size reaches 1 cm in dimeter, PDX was harvested, cut into 2-3 $mm^3$, and expanded into 4 new SCID mice (F2). Three PDX models derived from different patients, PA-0387, PA-0375, and PA-0327, were successfully engrafted, and subsequently passaged into P3 (PA-0387, PA-0375) and P4 (PA-0327) which were used in therapy studies.

Therapy studies. The tumor-bearing mice, when tumor sizes reached 70-120 $mm^3$, were randomized into 5 treatment groups (5-6 mice/group). The mice were treated intravenously with buffer (group 1), MSA (10 μg/mouse, group 2), MSA/mir-1291 (10 μg/mouse, group 3), Gem (300 μg/mouse) plus nP (40 μg/mouse) (group 4), or the combination of MSA/mir-1291 (10 μg/mouse) with Gem (300 μg/mouse) plus nP (40 μg/mouse) (group 5) every three days for 10 times. Body weights and tumor sizes of individual animals were monitored 1-2 times per week. Tumor size was calculated by the following formula: $V=0.5 \times Length \times Width^2$. The animals were sacrificed on day 29 from the first treatment, and tumors were dissected and fixed with 10% formalin for histological analysis. Serum samples were also prepared for blood chemistry analyses.

Immunohistochemistry. The histological features of tumor tissues and the expression of caspase-3 and Ki-67 were determined by H&E staining and immunohistochemistry assay, respectively, as previously reported (18, 30). In brief, the fixed tumor tissues were embedded with paraffin. The paraffin slides were stained with anti-cleaved-caspase-3, anti-Ki-67 antibody or hematoxylin and eosin (H&E), and then photographed by using an Olympus camera (DP25) and CellSens software (Olympus, Center Valley, PA).

Blood chemistry profiles. Blood chemistry profiles were determined in the Comparative Pathology Laboratory at UC Davis.

Statistical analysis. Values are mean±standard deviation (SD). According to the numbers of groups and variants, data were analyzed by Student's t-test, 1-way or 2-way ANOVA using GraphPad Prism. Difference was considered as significant when P value was less than 0.05 ($P<0.05$).

Results

ARID3B is a direct target of miR-1291. Our recent studies have demonstrated that miR-1291 suppresses proliferation and tumorigenesis of PC cells (18). To further delineate the molecular mechanisms through which miR-1291 controls PC cell growth, computational analysis was conducted to predict potential targets of miR-1291. Among a set of putative targets, the DNA binding protein ARID3B was a top candidate consisting of four miRNA response elements (MREs) for miR-1291 within its 3'UTR (FIG. 27A). An ARID3B 3'UTR luciferase reporter plasmid was thus constructed to evaluate the interactions between miR-1291 and ARID3B 3'UTR. Surprisingly, treatment with bioengineered miR-1291 significantly increased ARID3B-3'UTR-luciferase reporter activities in AsPC-1 (FIG. 27B) and HEK293 cells, as compared to controls. Introduction of miR-1291 into cells with miR-1291-expressing plasmid showed the same results (FIG. 28A), whereas ARID3B-3'UTR-luciferase reporter activities were decreased in cells treated with miR-1291 antagomir (FIG. 28B). These experiments using different tools to interfere with miR-1291 expression/functions are consistent, and the results suggest that miR-1291 targets ARID3B 3'UTR and may positively regulate the expression of ARID3B.

MiR-1291 upregulates the mRNA and protein levels of ARID3B in PC cells. To define the effects of miR-1291 on the expression of ARID3B, we first verified the production of high levels of mature miR-1291 from bioengineered MSA/mir-1291 prodrug in PANC-1 and AsPC-1 cells with TaqMan stem-loop RT-qPCR assay kit (FIG. 27C). We then compared ARID3B mRNA levels in PC cells treated with MSA/mir-1291 and control MSA. Compared to vehicle control treatments, MSA did not alter ARID3B mRNA levels. Treatment with MSA/mir-1291 (20 nM) led to a 1.2- and 1.4-fold increase in ARID3B mRNA levels in PANC-1 cells, as compared to MSA or vehicle control, at 48 h and 72 h post-treatment, respectively (FIG. 27D). Similarly, MSA/mir-1291 (5 nM) caused a 4.7-fold and 3.2-fold upregulation of ARID3B mRNA levels in AsPC-1 cells (FIG. 27D), at 48 h and 72 h post-treatment, respectively.

We further conducted Western blots to examine the impact of miR-1291 on ARID3B protein levels in PC cells. As found in other types of human carcinoma cell lines by other investigators (31), we observed two different ARID3B bands in both PANC-1 and AsPC-1 cells which are designated as full-length ARID3B (ARID3B-Fl, ~61 kD) and short-form ARID3B (ARID3B-sh, ~28 kD), respectively (FIG. 27E). Our data showed that ARID3B-FL protein levels increased around 50% in PANC-1 cells at 72 h post-transfection with 20 nM miR-1291 prodrug. A higher degree of increase of ARID3B-FL protein levels was found in AsPC-1 cells at both 48 h (80%) and 72 h (200%) post-treatment with 5 nM miR-1291. Interestingly, impact of miR-1291 on ARID3B-Sh protein levels appeared to follow the same pattern as ARID3B-Fl in both PANC-1 and AsPC-1 cells (FIG. 27E). These results indicate that miR-1291 upregulates ARID3B expression in PC cells.

Figure 29A:
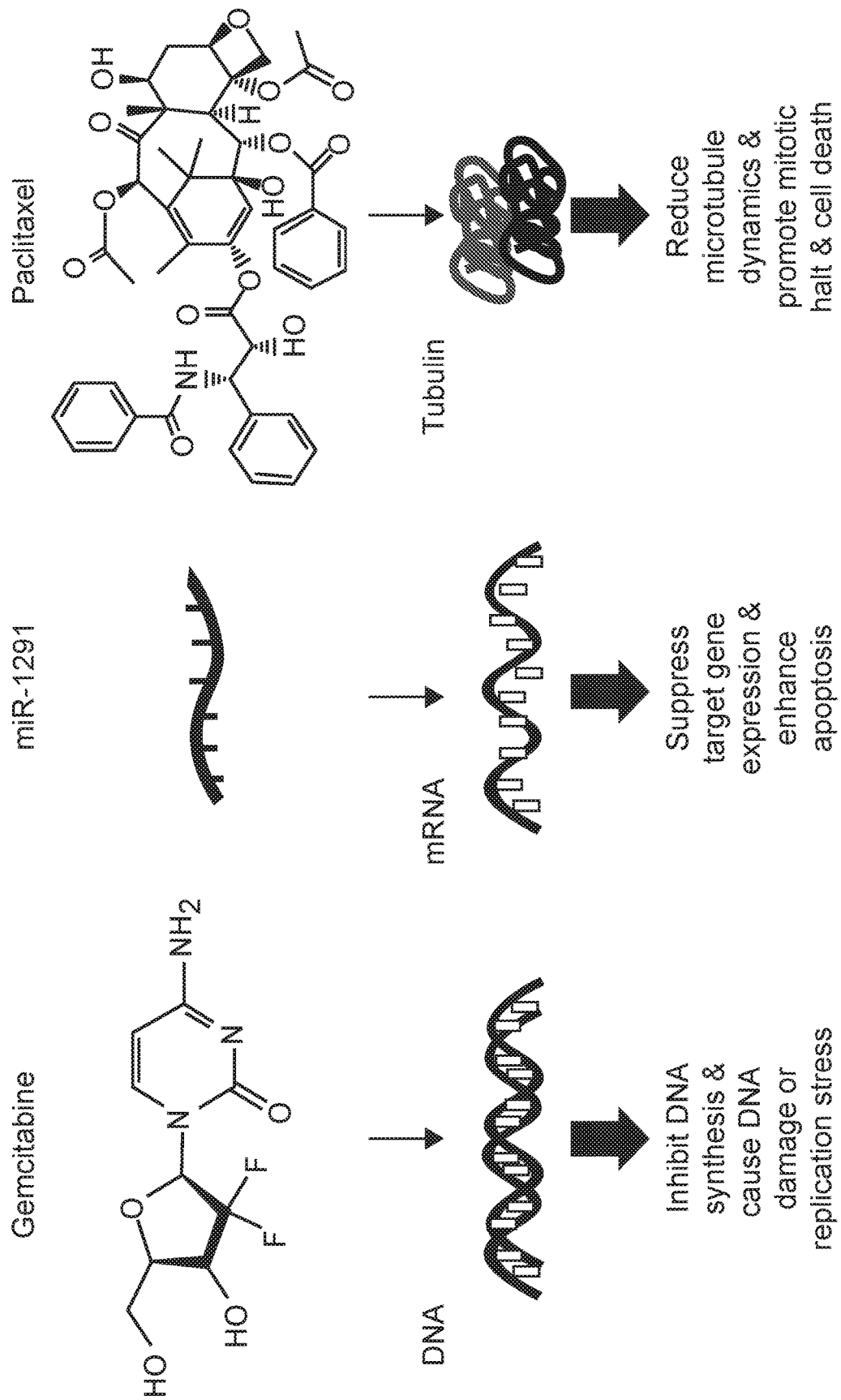
FIGS. 29A-F illustrate independent and combined actions of miR-1291 and gemcitabine plus nab-paclitaxel (Gem-nP) in human pancreatic cancer cells. A, Gemcitabine, miR-1291 and paclitaxel may act on specific targets and thus interfere with particular cellular processes. Immunoblot (B and C) and immunofluorescence (D, E and F; scale bar, 20 μm) studies showed that combination (combo) treatment with miR-1291 prodrug and Gem-nP exhibited the greatest degrees of DNA damage, mitosis and apoptosis in PANC-1 and AsPC-1 cells, which were indicated by γH2A.X, H3PS10, and cleaved caspase-3/7 (C-caspase-3/7), respectively. β-actin was used as a loading control. C-caspase-7 images in PANC-1 cells are provided in FIG. 30, and individual biomarkers in AsPC-1 cells are shown in FIG. 31.
Figure 29B:
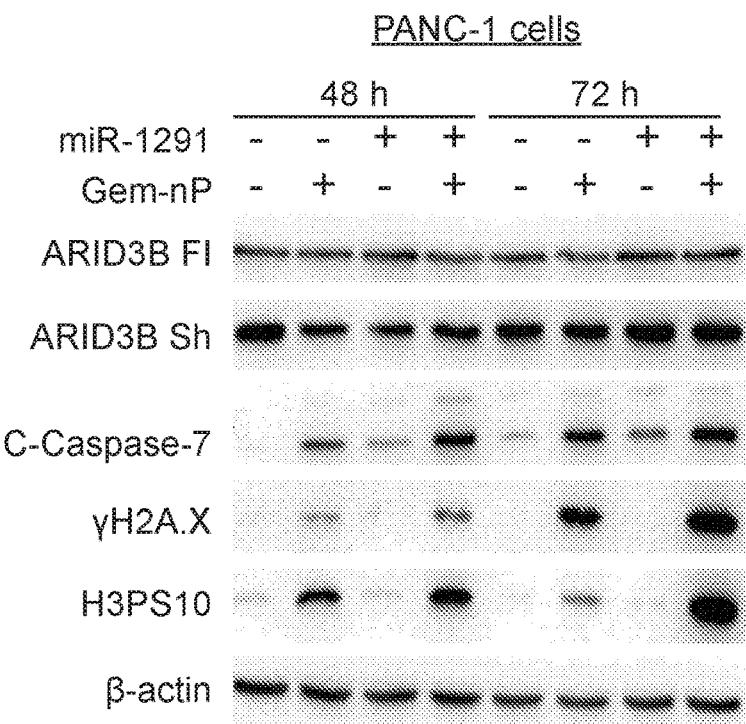
Figure 29C:
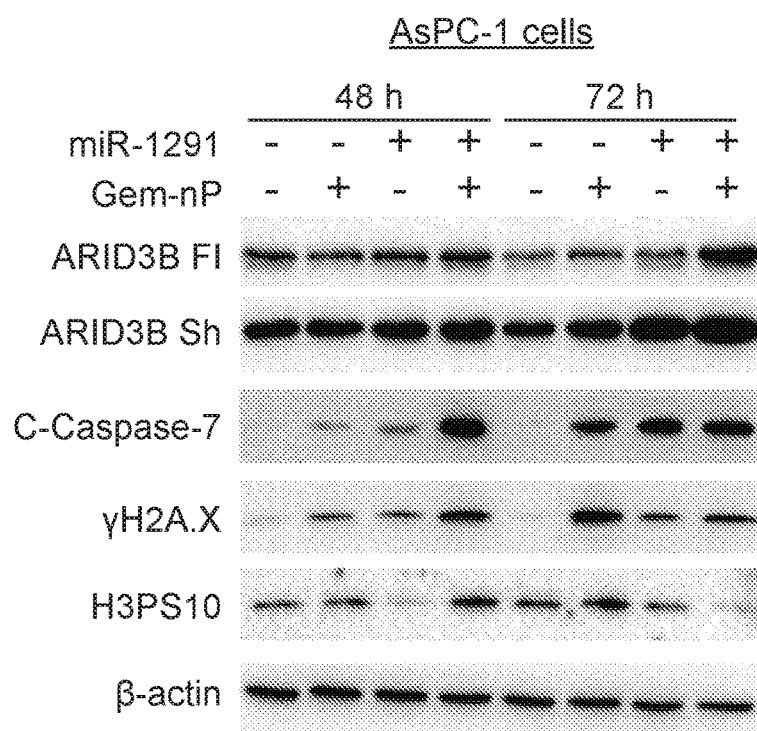
Figure 29D:
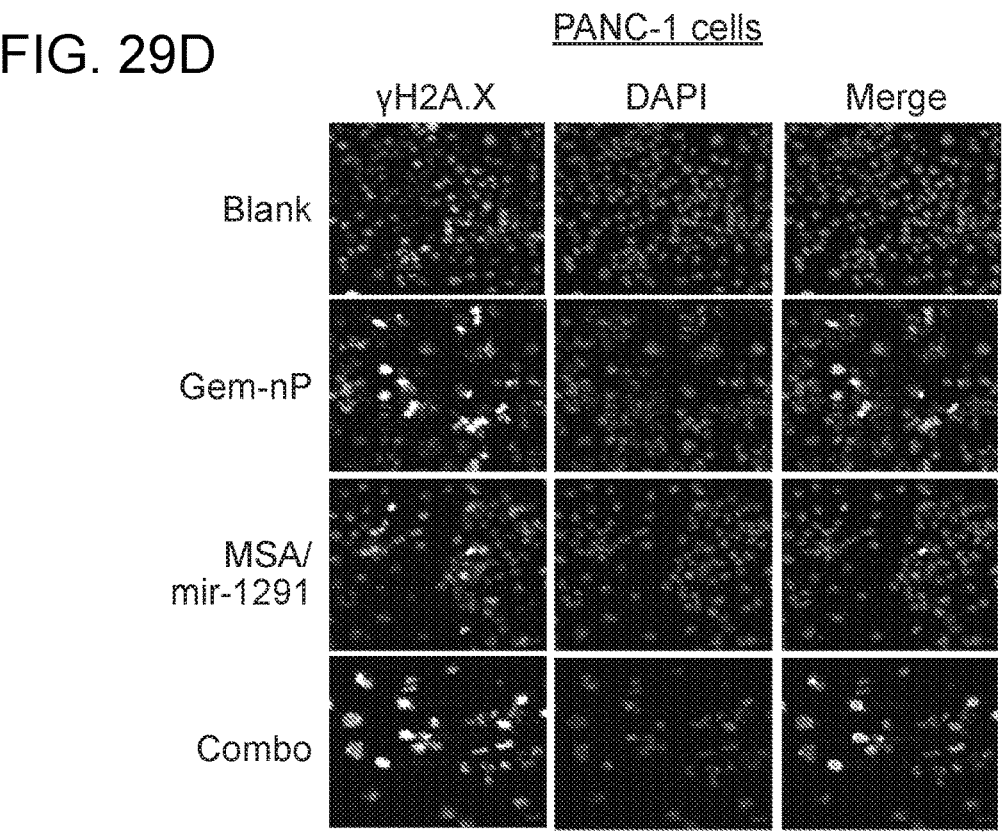
Figure 29E:
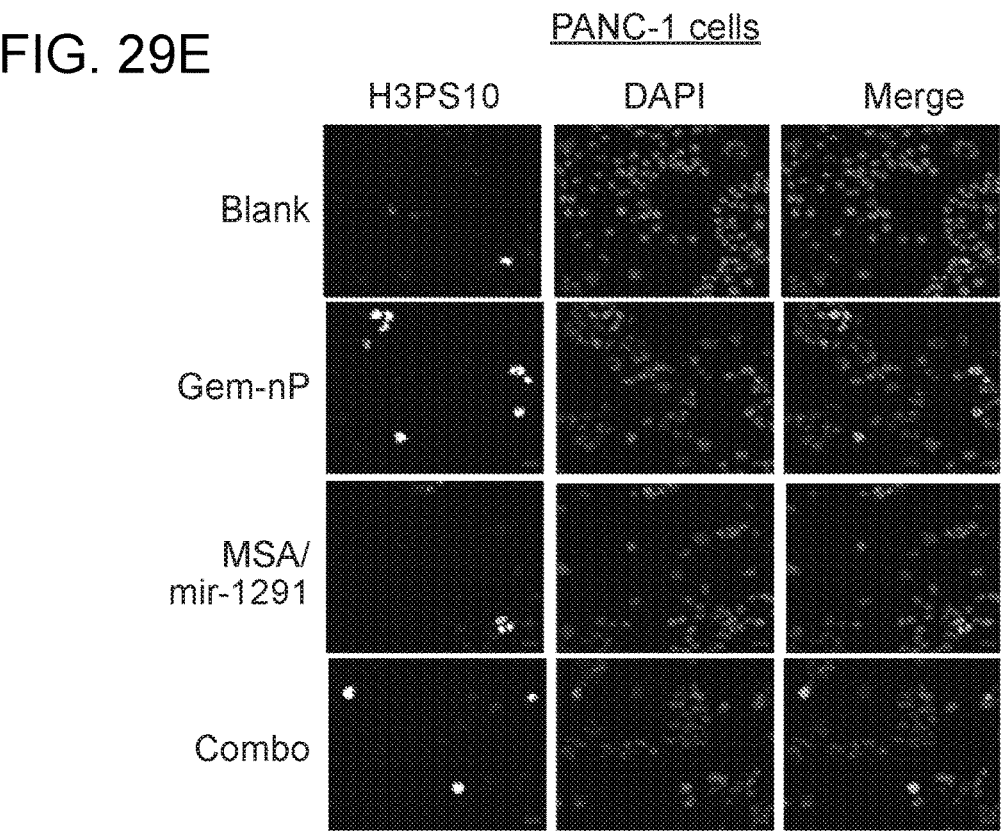
Figure 29F:
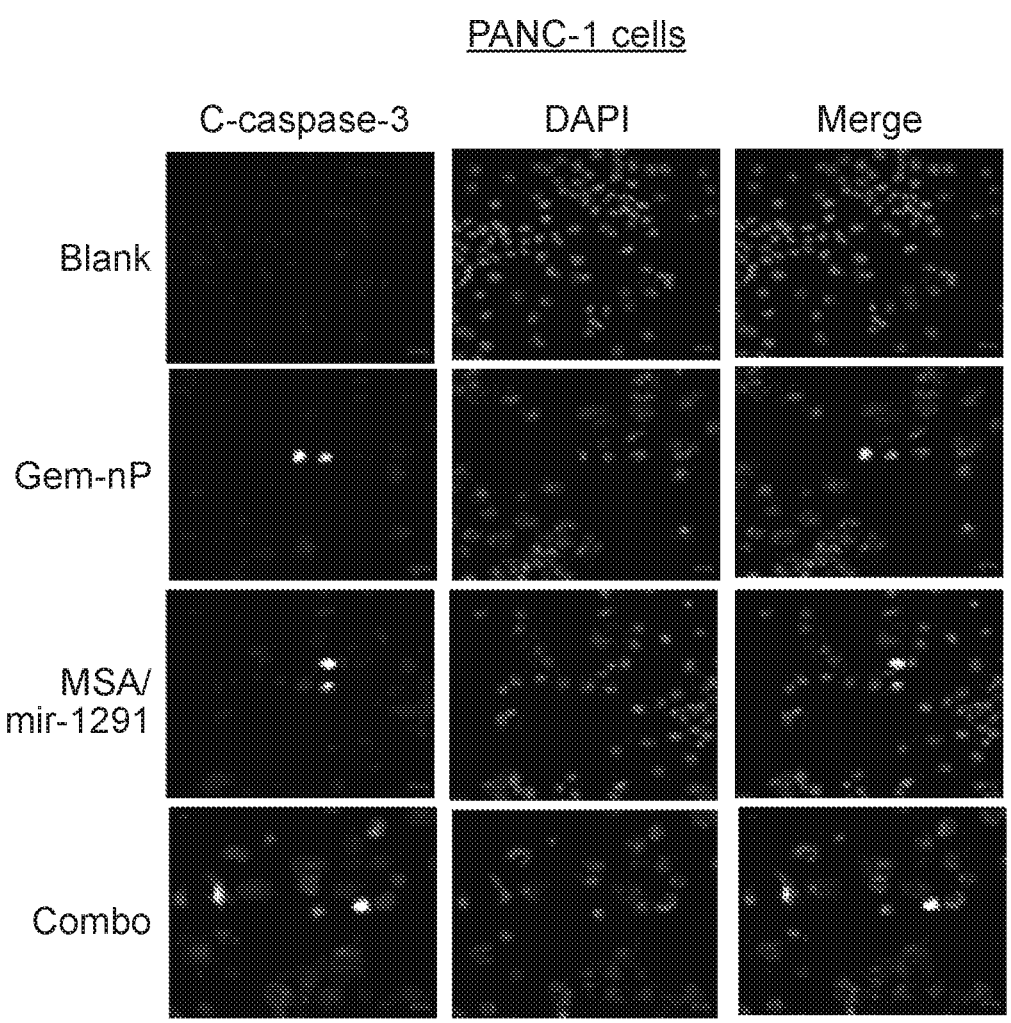
Figure 30:
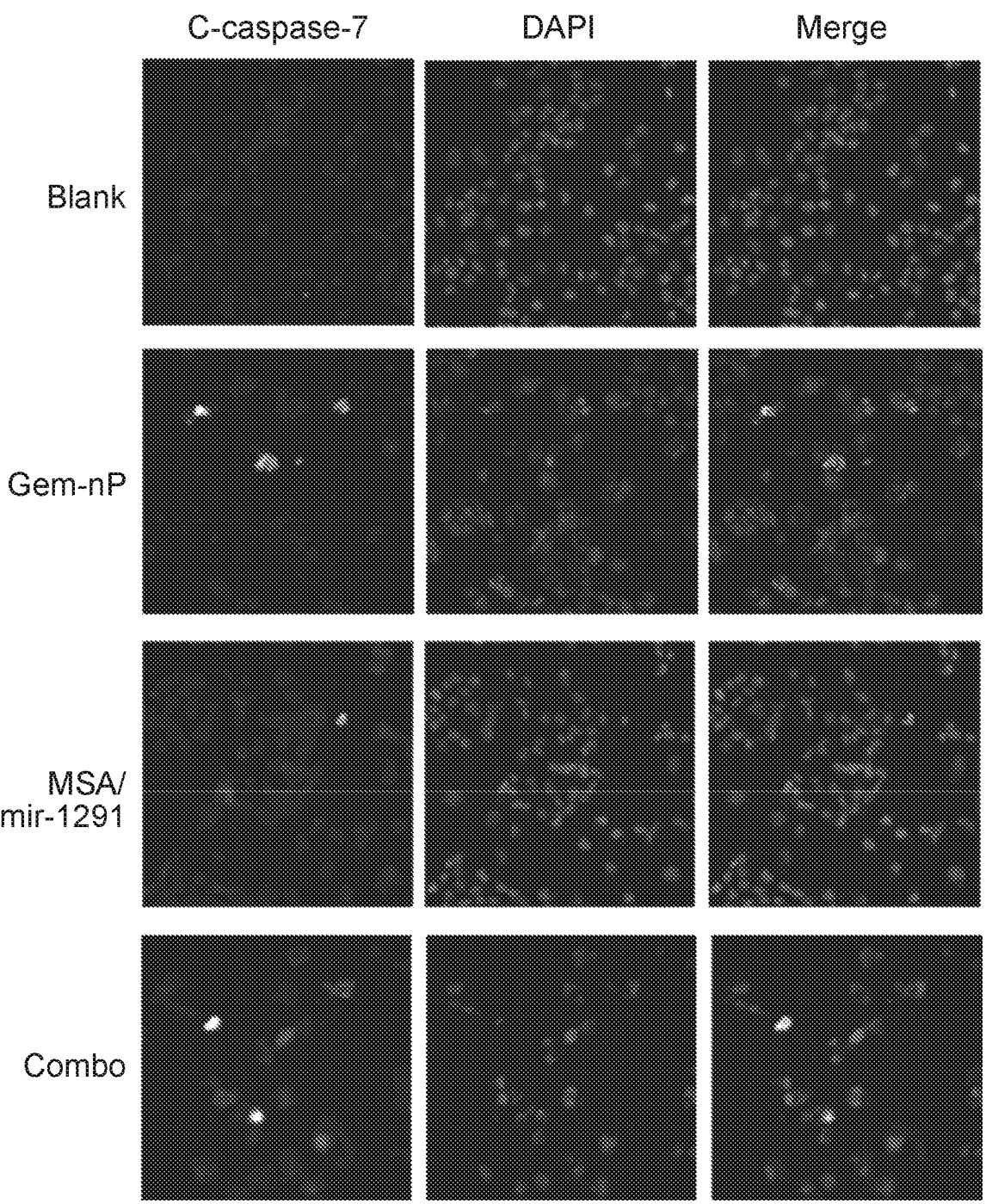
FIG. 30 illustrates immunofluorescence of another apoptosis marker, cleaved caspase-7, in PANC-1 cells. Compared to the control, miR-1291 or Gem-nP treatment alone led to an increase of cleaved caspase-7 levels, and combination treatment (combo) induced apoptosis to the greatest degree. Scale bar indicates 20 μm.
Figure 31A:
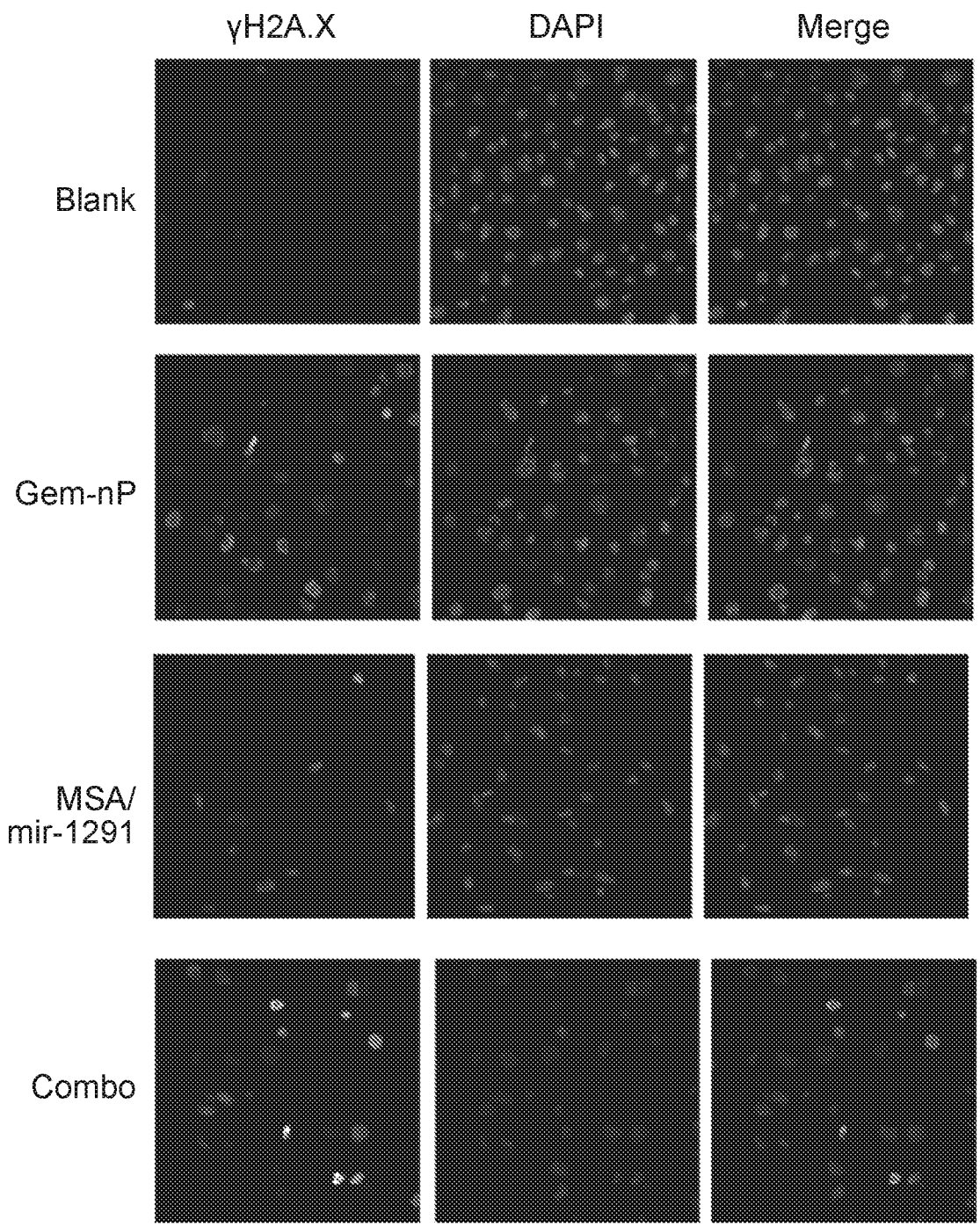
FIGS. 31A-C illustrate immunofluorescence study on the effects of individual and combined drugs on DNA damage (γH2A.X; A), mitosis inhibition (H3PS10; B), and apoptosis markers (cleaved caspase 3/7; C) in AsPC-1 cells. Combination treatment (combo) with miR-1291 prodrug and Gem-nP induced a higher level of cleaved caspase 3/7, and γH2A.X than single drug treatment or blank control. Scale bar indicates 20 μm
Figure 31B:
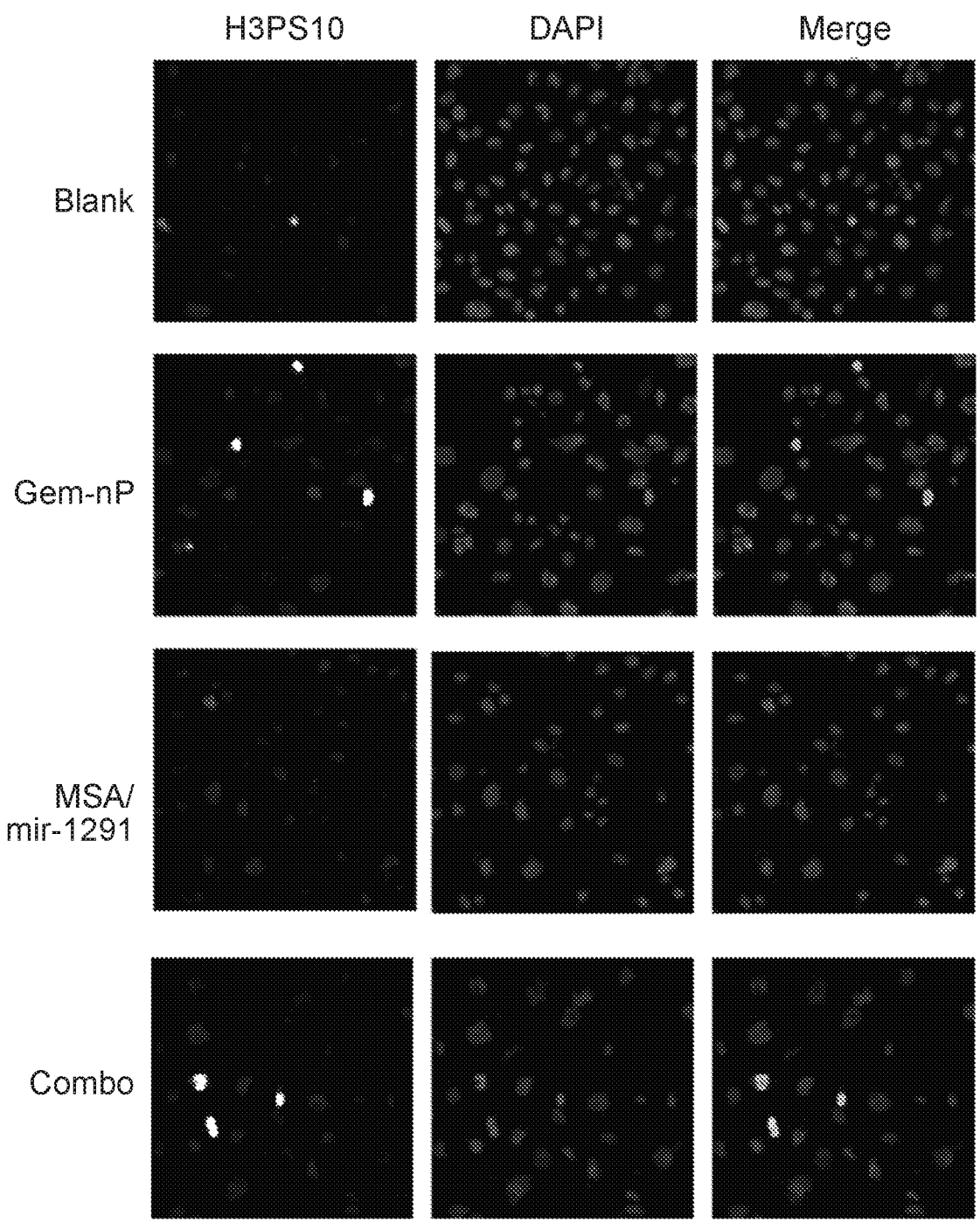
Figure 31C:
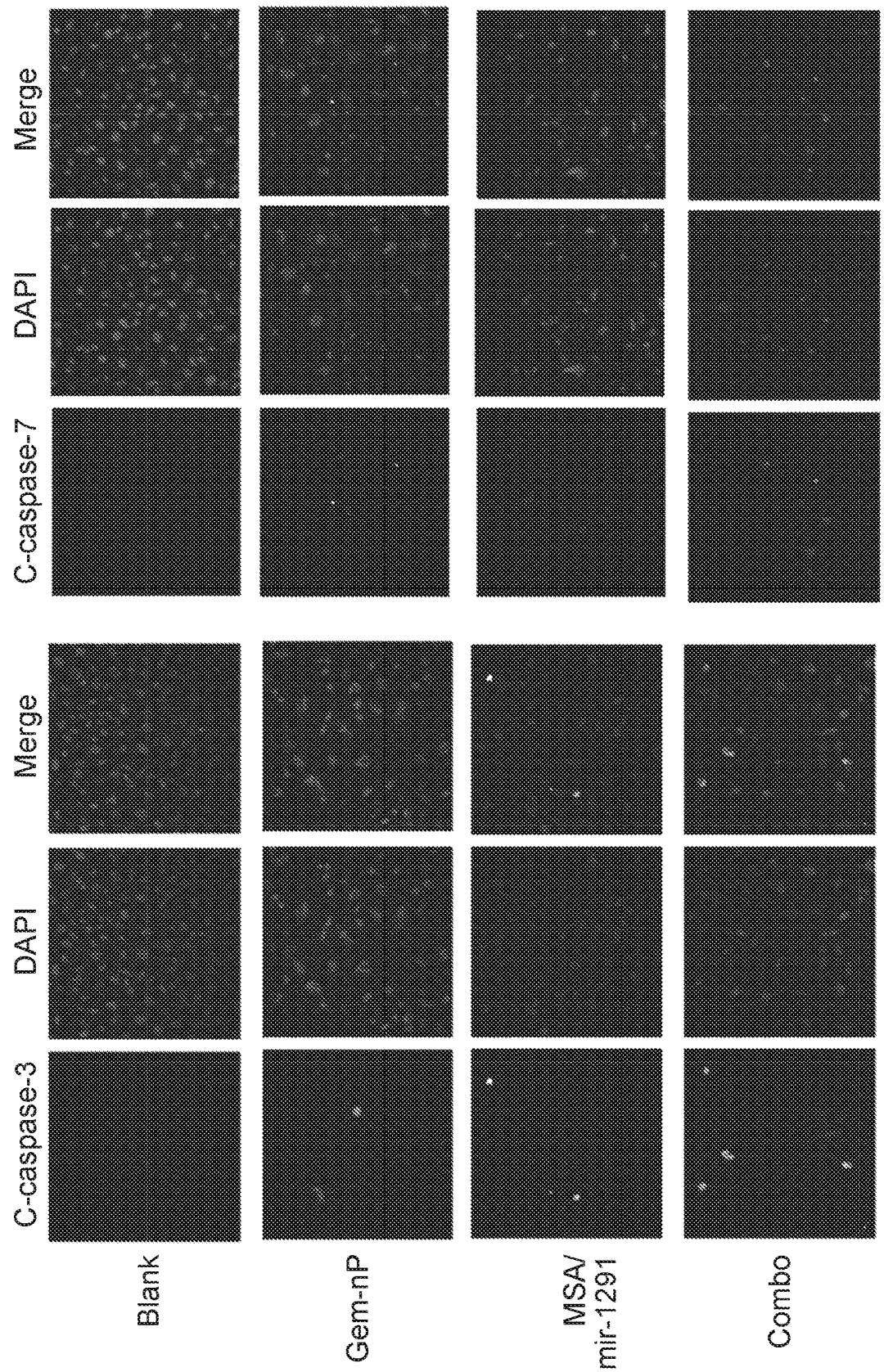

Individual and combined actions of miR-1291 prodrug and Gem-nP on DNA damage, mitosis arrest, and apoptosis. Historically, single drug exerted very limited efficacy for the treatment of PC. Therefore, we aimed at examining combination effects (FIG. 29A) while assessing miR-1291 monotherapy and comparing it to Gem-nP, the first-line chemotherapy for PC. Individual and combined actions of miR-1291 prodrug (10 nM in PANC-1 cells, 3 nM in AsPC-1 cells) and Gem-nP on their corresponding target or marker proteins were first investigated in PANC-1 and AsPC-1 cells by Western blots (FIG. 29B-C). Our data showed that co-administration of Gem-nP did not alter miR-1291-controlled upregulation of ARID3B in PANC-1 cells but enhanced the effects in AsPC-1 cells, again suggesting distinct sensitivities of the two cell lines. Immunoblot (FIG. 29B-C) and immunofluorescence studies were further conducted to determine single and combined drug effects on DNA damage (γ-H2A.X foci), apoptosis (cleaved caspase-3/7) and mitotic arrest (H3PS10) (FIG. 29D-F; FIG. 30, FIG. 31). The results showed that, in addition to the induction of apoptosis (caspase-3/7) in both PANC-1 and AsPC-1 cell lines, miR-1291 alone surprisingly elicited obvious DNA damage (formation of γ-H2A.X foci) in AsPC-1 cells. On the other hand, Gem-nP largely provoked DNA damage and mitotic arrest in both PC cell lines, as manifested by an upregulation of γ-H2A.X and H3PS10, respectively. Most importantly, combination treatment with miR-1291 prodrug and Gem-nP caused the greatest extents of DNA damage, mitosis and apoptosis in both PANC-1 and AsPC-1 cells, which were indicated by γH2A.X, H3PS10, and cleaved caspase-3/7 (C-caspase-3/7), respectively. These results demonstrate that miR-1291 induces apoptosis and possibly DNA damage, and suggest that combination therapy with miR-1291 and Gem-nP may produce optimal outcomes.

Figure 32B:
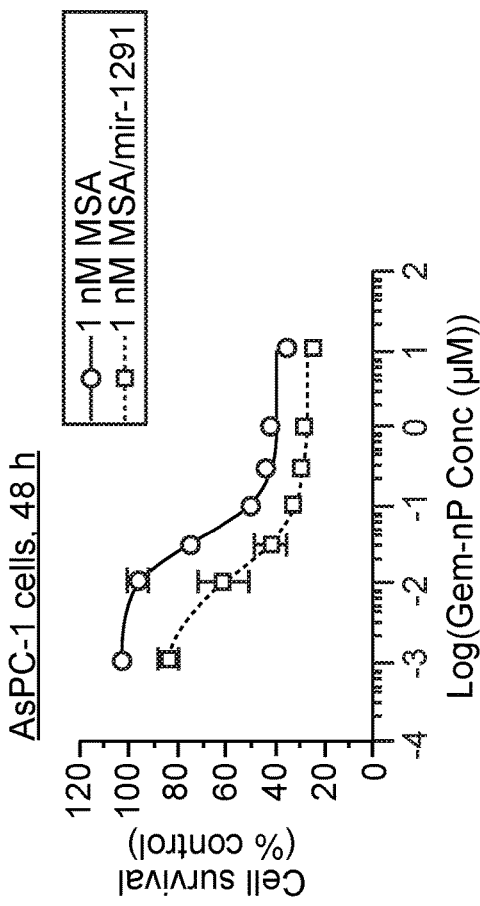
Figure 32D:
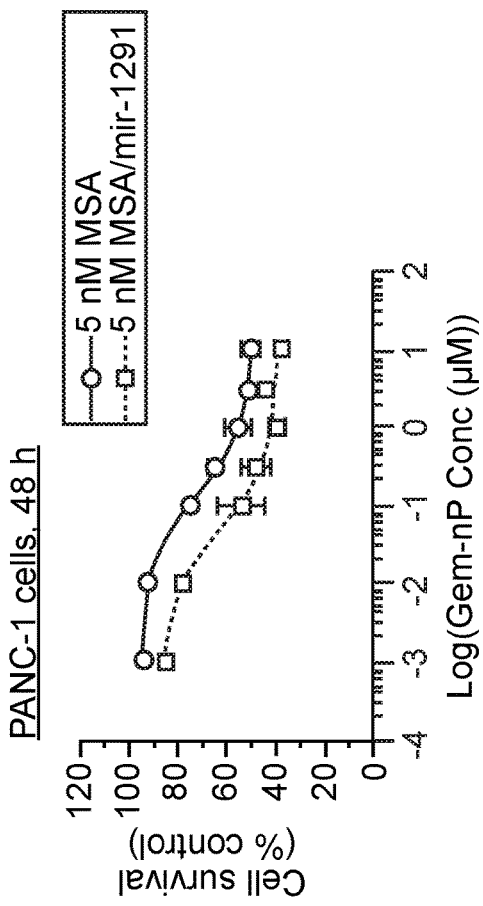
Figure 32A:
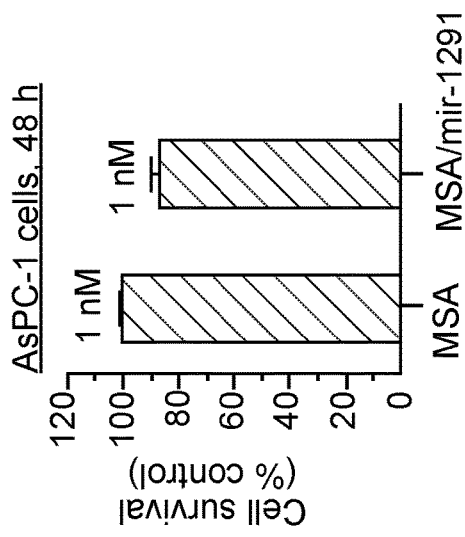
Figure 32C:
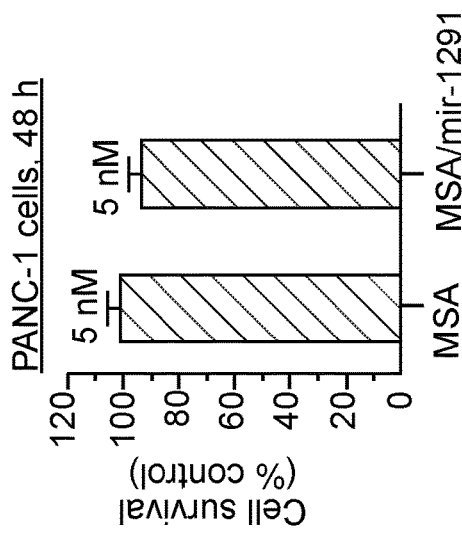

Bioengineered miR-1291 prodrug enhances the sensitivity of PC cells to chemotherapeutic drugs. To assess whether miR-1291 prodrug could increase the sensitivity of pancreatic cancer cells to Gem-nP, the anti-proliferative activity of Gem-nP in the presence of mir-1291 prodrug or control MSA was evaluated in PANC-1 and AsPC-1 cells by Cell-titer-Glo assay. The results showed that miR-1291 treated PANC-1 and AsPC-1 cells were much more sensitive to Gem-nP, as compared to MSA treated cells (FIG. 32). The enhanced sensitivity was also manifested by the lower EC50 value in miR-1291 treated PANC-1 cells (155±33 nM) than that in MSA treated cells (52.3±20.3 nM, *P<0.05). In addition, miR-1291 transfected AsPC-1 cells also showed a significantly lower EC50 value (40.4±1.8 nM) than MSA treated cells (14.6±5.5 nM, **P<0.01) (FIG. 32E). These results show that co-administration of miR- is able to sensitize PC cells to chemotherapies.

Figure 33D:
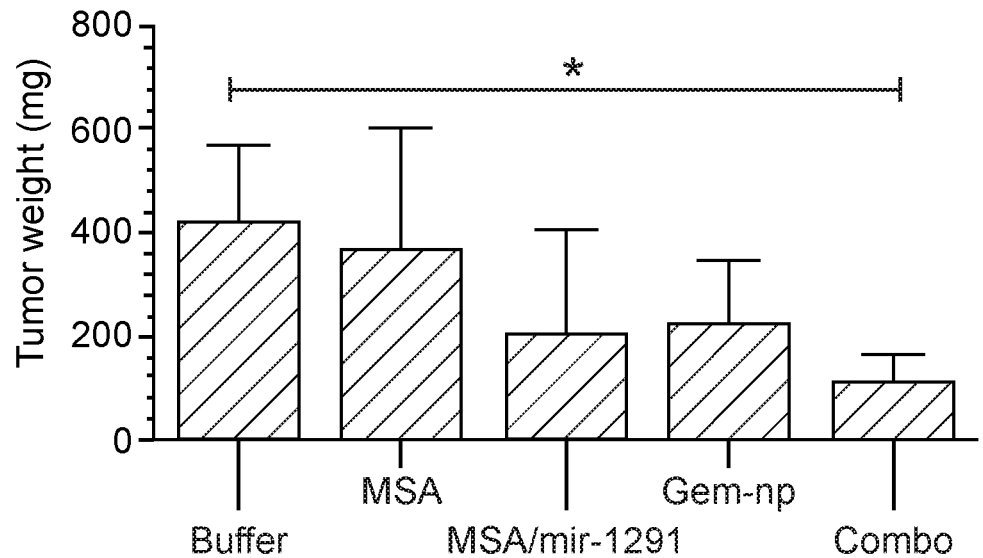

Bioengineered miR-1291 prodrug monotherapy and combination therapy with Gem-nP are effective to control tumor growth in PANC-1 xenograft mouse models, while they are well tolerated in mice. To determine the anti-tumor efficacy of bioengineered miR-1291 prodrug monotherapy and combination therapy with Gem-nP in vivo, we first established PANC-1 xenograft mouse models (FIG. 33A). Systematic administration of a single dose of in vivo-jetPEI formulated miR-1291 prodrug was distributable to PANC-1 xenograft tumor tissues, as indicated by high levels of tumoral miR-1291 at 24 h after drug administration (FIG. 33A). Compared to buffer or MSA treatment, miR-1291 prodrug alone significantly suppressed PANC-1 tumor growth to a similar degree as Gem-nP, while combination treatment with miR-1291 and Gem-nP inhibited tumor growth to the greatest extent (FIG. 33B). Visual inspection and weights of the dissected tumors (FIG. 33C-D) further demonstrated the remarkably optimal tumor suppressive effects for combination therapy. Interestingly, sizes of final tumors among miR-1291 prodrug treatment group were relatively variable where 50% were highly responsive and 50% were less responsive (FIG. 33C). By contrast, all tumors were ubiquitously reduced to similar sizes by combination treatment. These results demonstrated the effectiveness of miR-1291 prodrug monotherapy in the control of PANC-1 xenograft tumor progression as well as an optimal outcome for combination therapy with miR-1291 and Gem-nP.

Figure 33E:
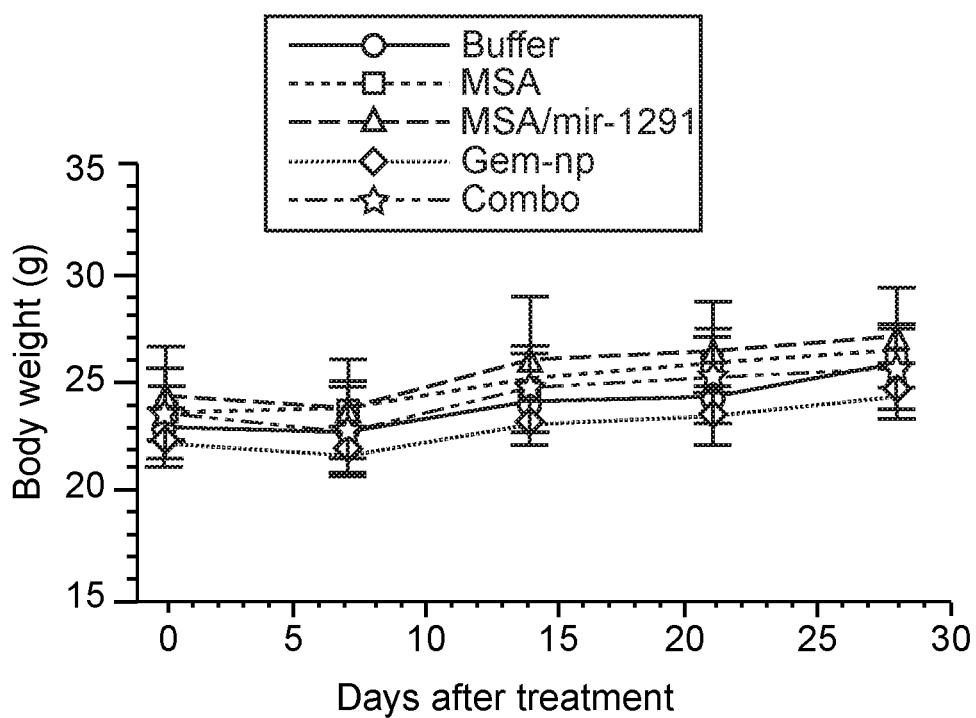
Figure 33F:
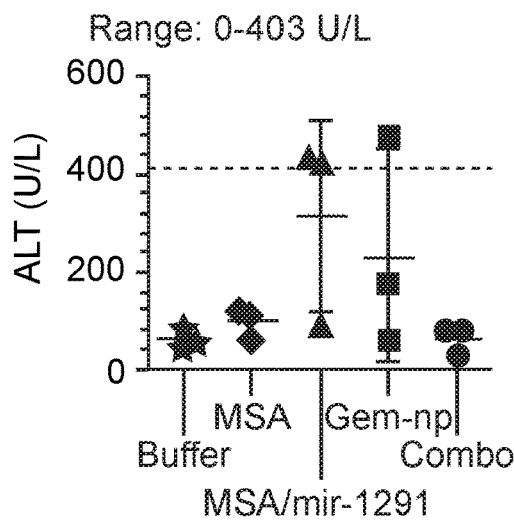
Figure 33F:
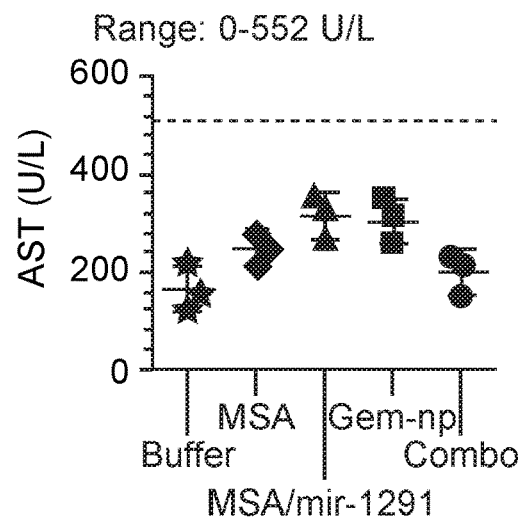
Figure 33F:
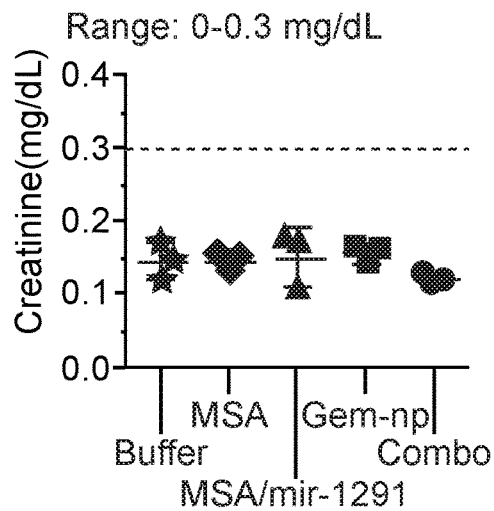
Figure 33F:
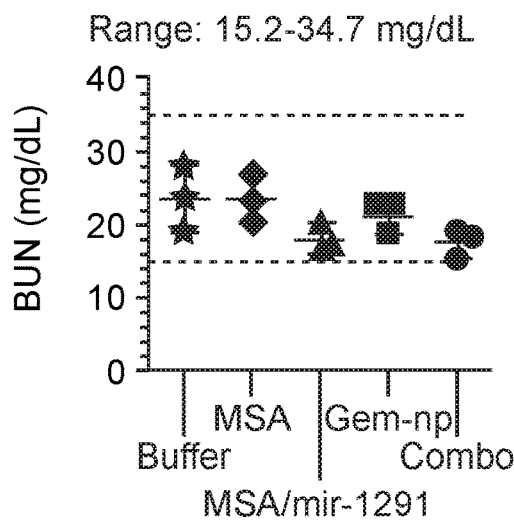
Figure 33F:
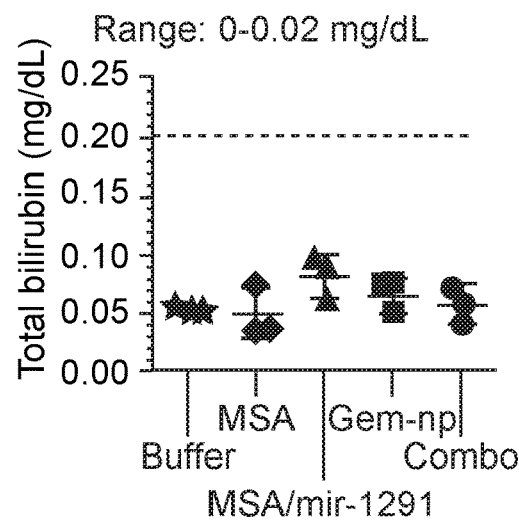

All treatments were well tolerated in mice as animal body weights showed no significant differences among different groups (FIG. 33E). To further examine the safety of drug treatments, blood biochemistry profiles were determined (FIG. 33F). All markers of liver and kidney functions including alanine aminotransferase (ALT), aspartate aminotransferase (AST), total bilirubin, blood urea nitrogen (BUN) and creatinine were within the normal ranges, except ALT levels in two mice, in which one from miR-1291 monotherapy and one from Gem-nP treatment group, slightly exceeded the normal range. However, there was no significant difference in each blood biomarker between any treatment groups, suggesting that therapies did not cause any hepatic or renal toxicity. Together, the results indicate that systemic administration of therapeutic doses of miR-1291 prodrug or Gem-nP alone, or in combination are well tolerated in PANC-1 xenograft mouse models.

Figure 34A:
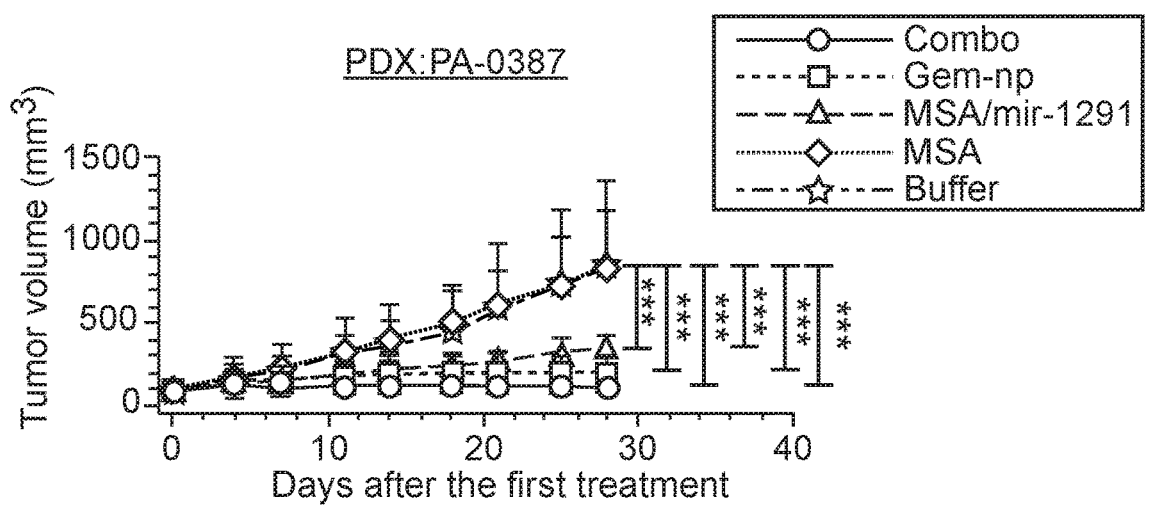
FIGS. 34A-F illustrate bioengineered miR-1291 prodrug monotherapy and combination therapy with Gem-nP in PDX mouse model derived from clinical PDAC tissues (PA-0387). A, PDX tumor growth was significantly suppressed by miR-1291 monotherapy or combination therapy, as compared to MSA or buffer control. *P<0.05, P<0.01, and *P<0.001 (2-way ANOVA with Bonferroni post-tests). B, Comparison of dissected tumor from mice with different treatments. C, Weights of the dissected xenograft tumors. P<0.01, *P<0.001 (1-way ANOVA). D, Representative IHC (100×) of PDX tumors stained with Ki-67 or cleaved caspase-3 antibodies. Combination treatment induced the highest degree of apoptosis (Red arrow: caspase-3 staining) while cell proliferation did not differ much among different treatment groups. E, Body weights were not different from each treatment. F, Blood biochemistry profiles were not altered by any drug treatment. Values are mean±SD (N=5 per group, except N=3 for blood chemistry profiles). The ranges of individual markers were marked as references.
Figure 34B:
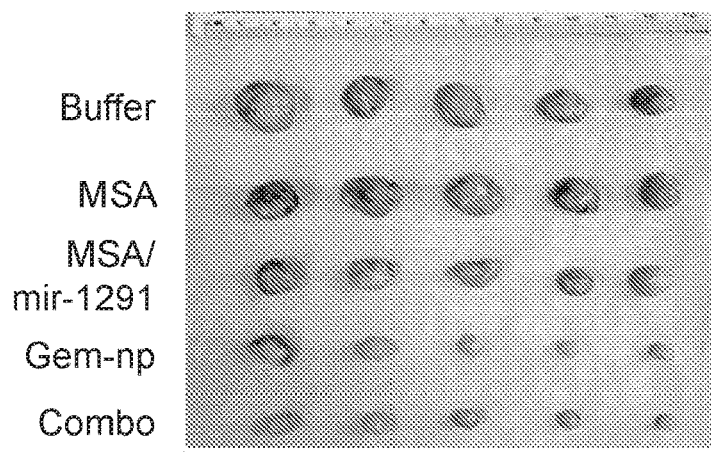
Figure 34C:
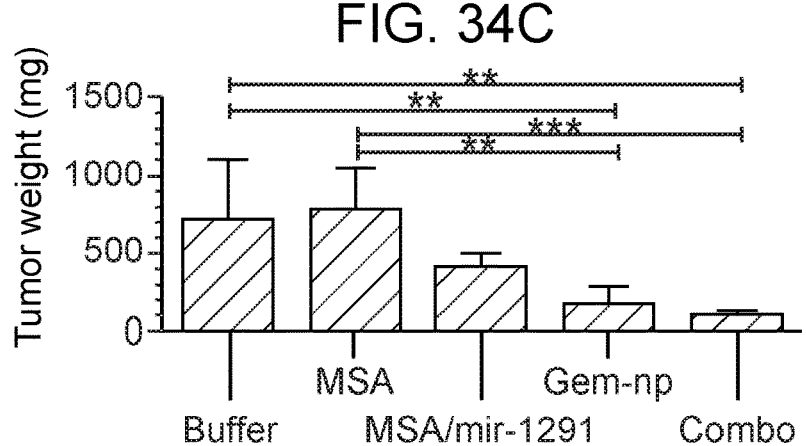
Figure 34D:
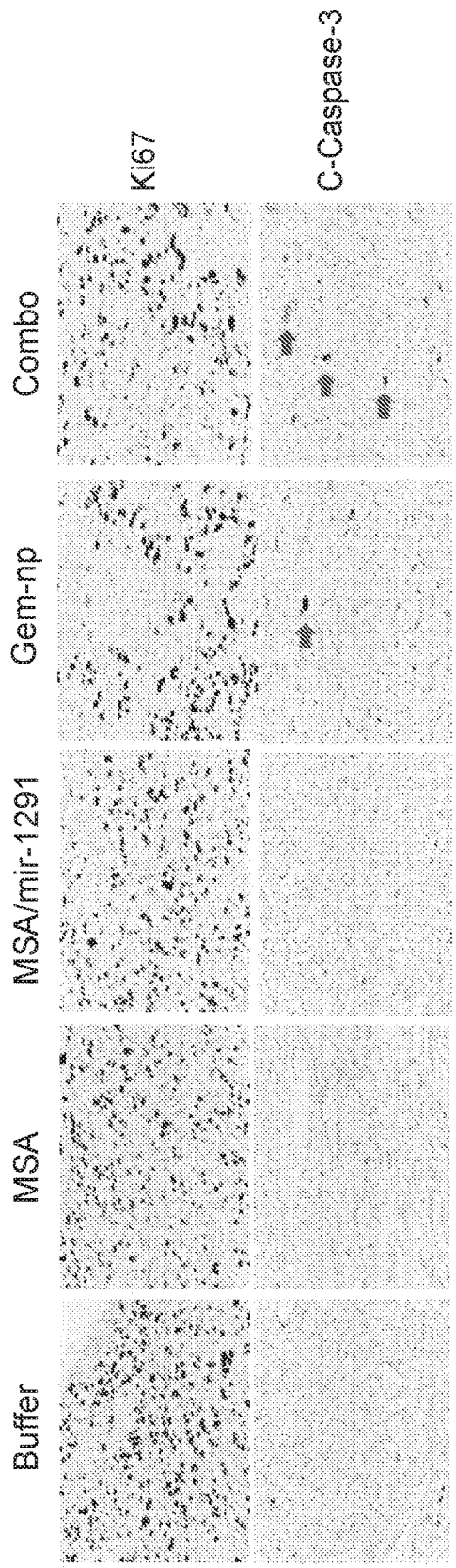
Figure 34E:
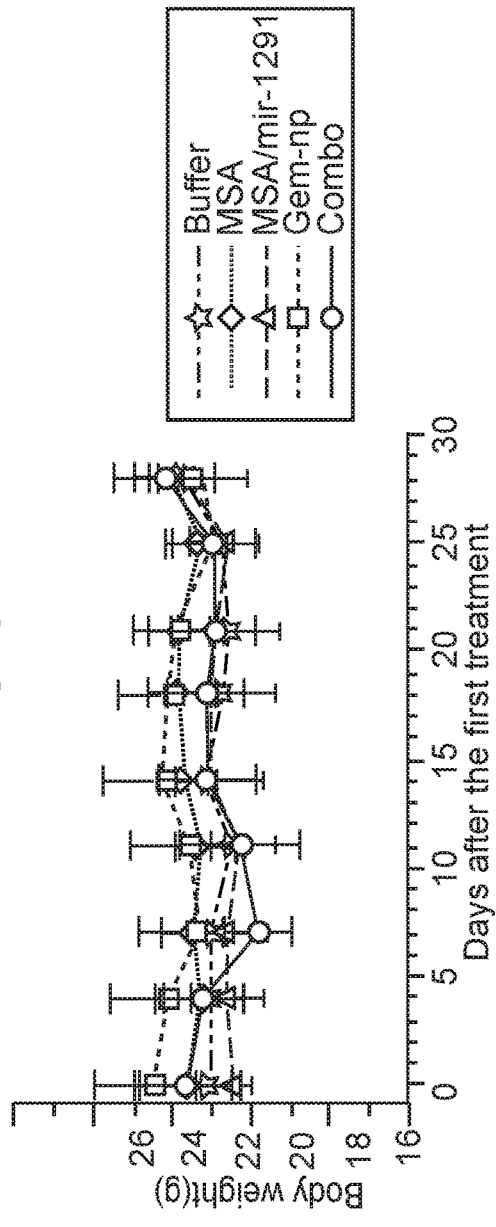
Figure 34F:
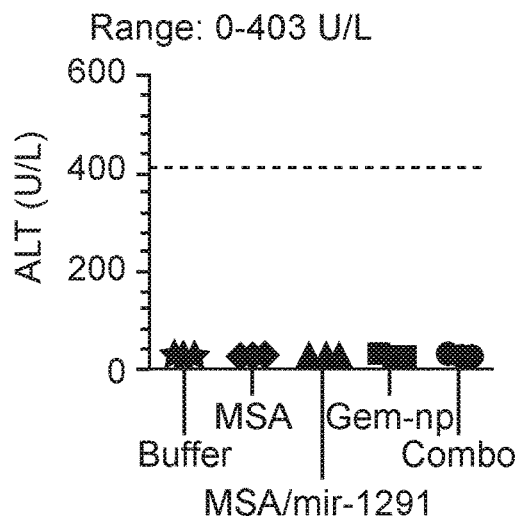
Figure 34F:
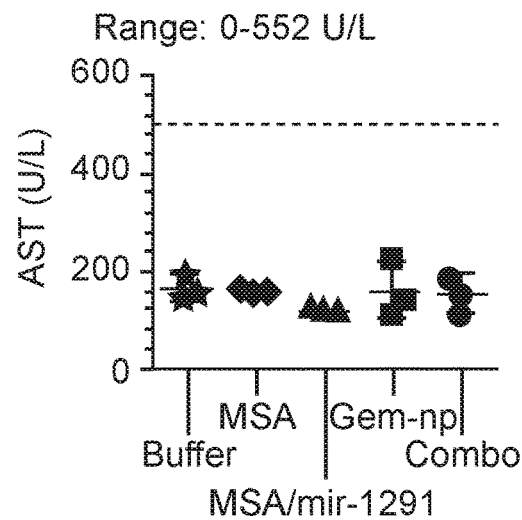
Figure 34F:
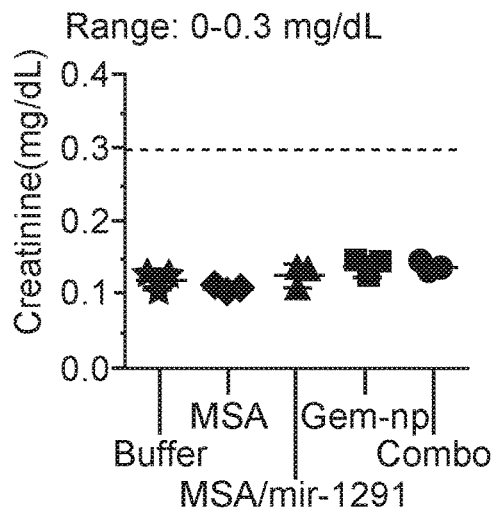
Figure 34F:
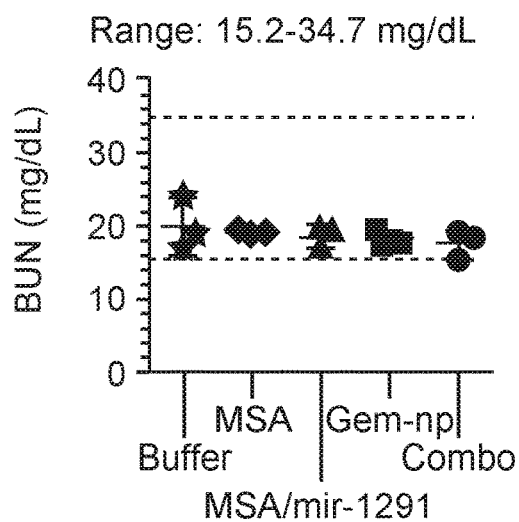
Figure 34F:
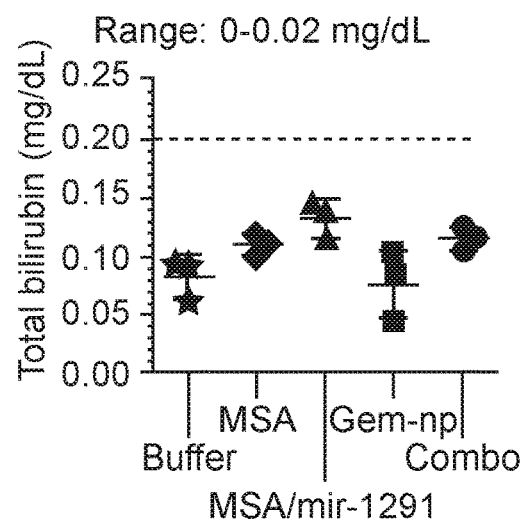
Figure 35A:
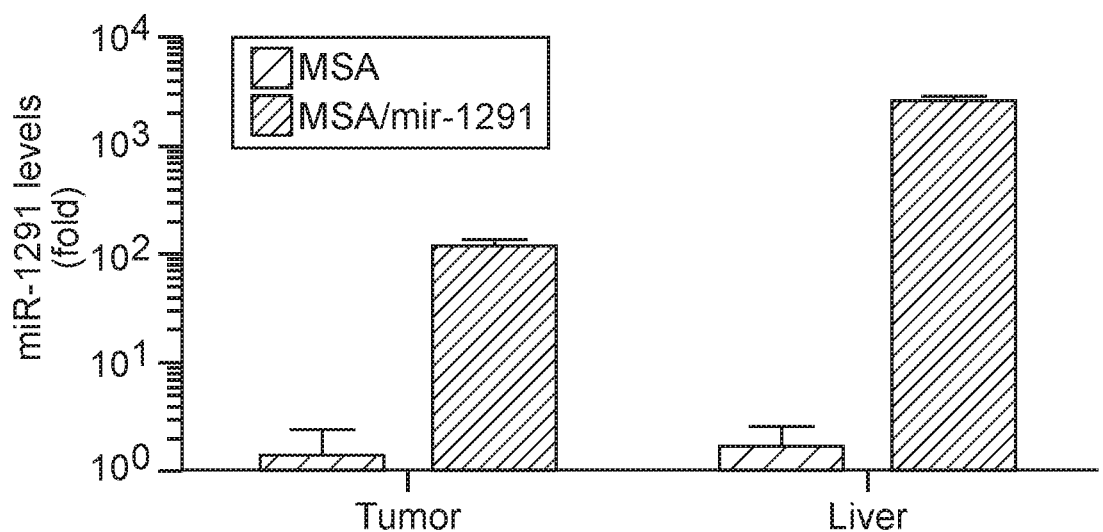
FIGS. 35A-B illustrate that in vivo-jetPEI-formulated miR-1291 prodrug is distributable to PANC-1 xenograft and PDX tumors in mouse models. Tumor-bearing mice were treated intravenously with a single dose of in vivo-jetPEI-formulated miR-1291 prodrug (25 μg/mouse). 24-h later, tumor and liver tissues were harvested and total RNAs were isolated. Levels of miR-1291 were determined with TaqMan stem-loop RT-qPCR assay, which were much higher in livers and tumors isolated from MSA/mir-1291-treated PANC-1 xenograft (A) and PDX (B) mice, as compared with MSA control (N=2 mice per group in PANC-1 xenograft model, and N=3 mice per group in PDX model).
Figure 35B:
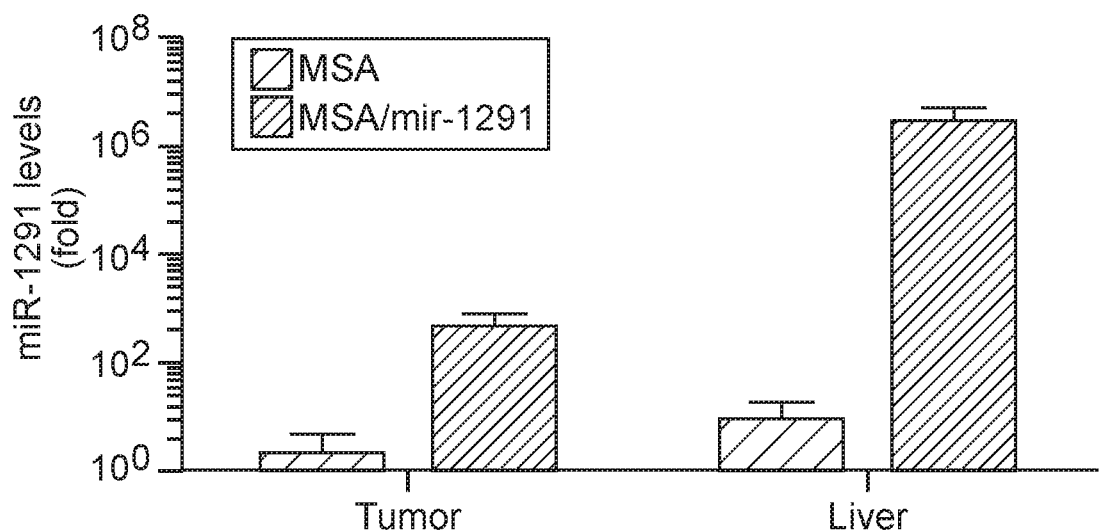
Figure 36:
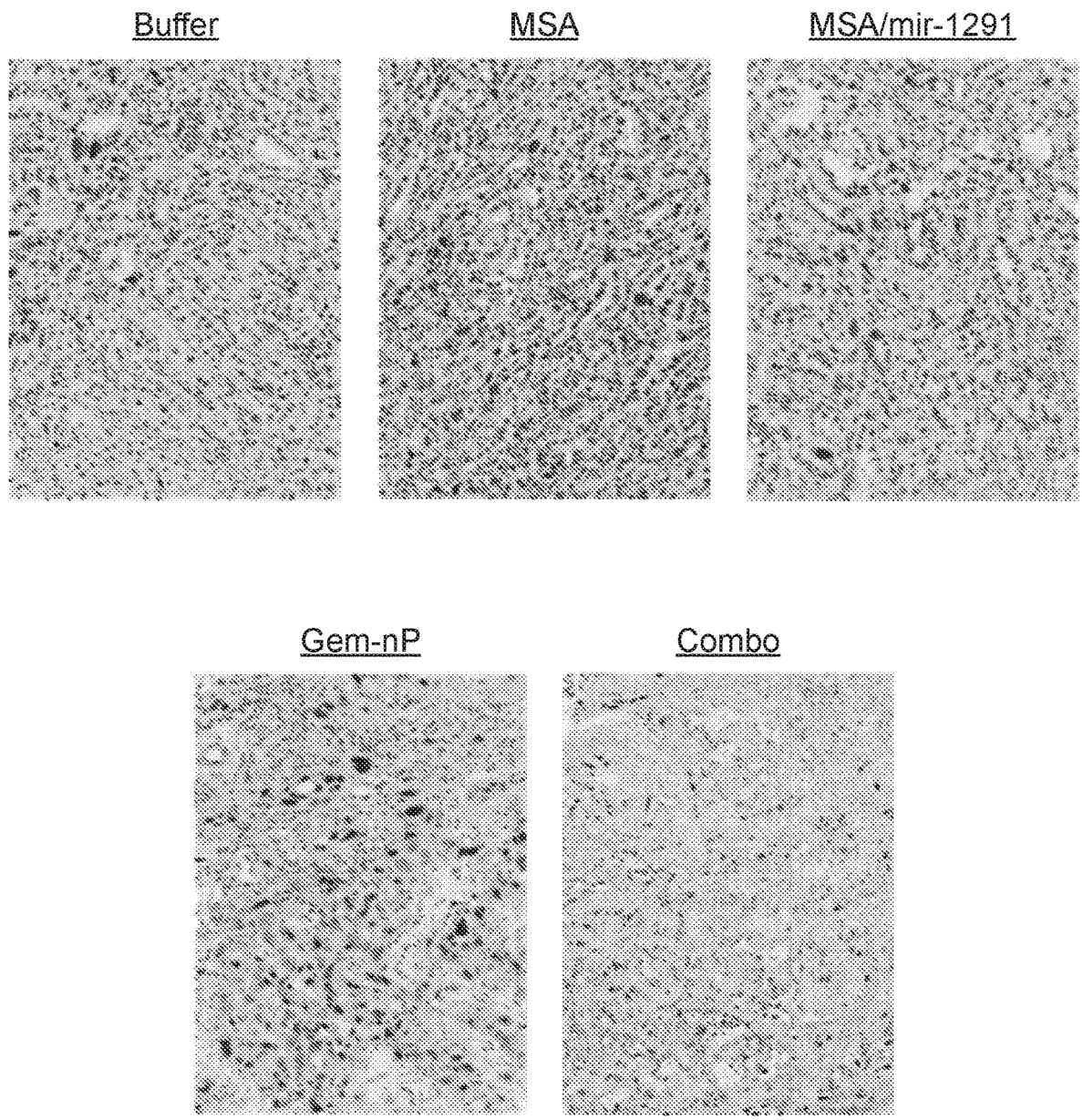
FIG. 36 illustrates representative H&E images of PDX-PA-0387 tumors. There is not any remarkable difference in the morphology of survived tumors between different treatment groups (100×).

Efficacy of biologic miR-1291 prodrug treatment alone and in combination with Gem-nP chemotherapy in three different PDX mouse models. Compared xenograft models derived from cancer cell lines, PDX tumor models may better preserve the heterogeneity and histological characteristics of the original tumors and thus provide greater representative accuracy and fidelity to human diseases (32-34). Therefore, we established three PDX models from clinical PC samples and employed them to further assess miR-1291 prodrug therapies. The first PDX model (PA-0387, FIG. 34) was subjected to the same dose regimens as those used in PANC-1 xenograft mouse models. Similarly, RT-qPCR analyses confirmed high levels of miR-1291 in PDX tissues at 24 h after systemic administration of a single dose of miR-1291 prodrug (FIG. 35B). Therapy data showed that treatment with miR-1291 prodrug or Gem-nP alone significantly reduced PDX PA-0387 tumor growth, as compared to buffer or MSA control; and combination treatment showed the highest degree of inhibition (FIG. 34A). Likewise, visual inspection of dissected tumors (FIG. 34B) and examination of final tumor weights (FIG. 34C) supported the effectiveness of miR-1291 prodrug alone, Gem-nP alone, and their combination in the control of PDX PA-0387, while there was no statistical difference between mono- and combination therapy. H&E staining further demonstrated that PDXs indeed showed the histologic phenotypic characteristics close to clinical pancreatic adenocarcinomas (FIG. 36). Furthermore, immunohistochemistry studies showed that there was no difference in cell proliferation (Ki-67 staining) between different treatment groups, while tumors from combination treatment group showed the highest levels of apoptosis (cleaved-caspase-3) (FIG. 34D), supporting the induction of apoptosis as a major mechanism behind their anti-tumor activities. In addition, none of animals showed any signs of stress, and there was no significant difference in body weights (FIG. 34D) and blood biochemistry profiles (FIG. 34F) among different treatments, suggesting that all drug treatments were safe to PDX-bearing mice.

Another PDX model, PA-0375, was utilized to critically assess the efficacy of miR-1291 prodrug monotherapy and combination therapy with Gem-nP, by following the same dosing regimens for PNAC-1 (FIG. 33A) and PA-0387 PDX. Our data showed that treatment with wither bioengineered miR-1291 prodrug or Gem-nP, alone or in combination, was able to significantly suppress PA-0375 PDX tumor growth in mice (FIG. 37A-C). While it was not statistically significant different between mono- and combination therapy, combination therapy obviously produced the greatest extent of inhibition.

Figure 37E:
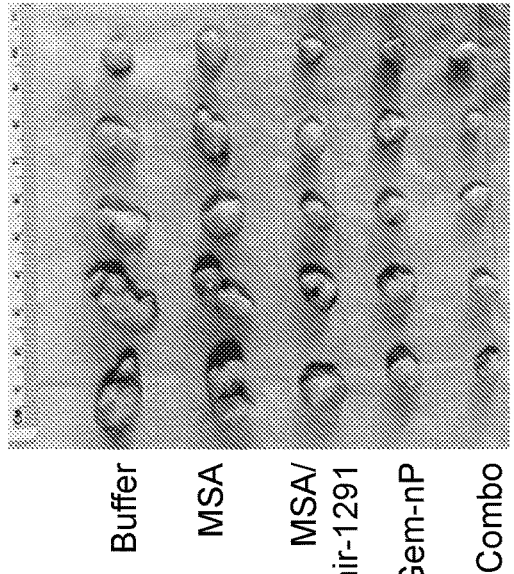
Figure 37F:
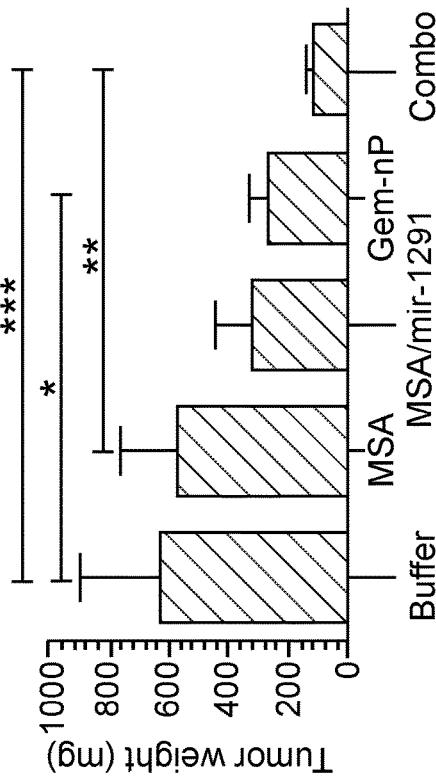
Figure 37D:
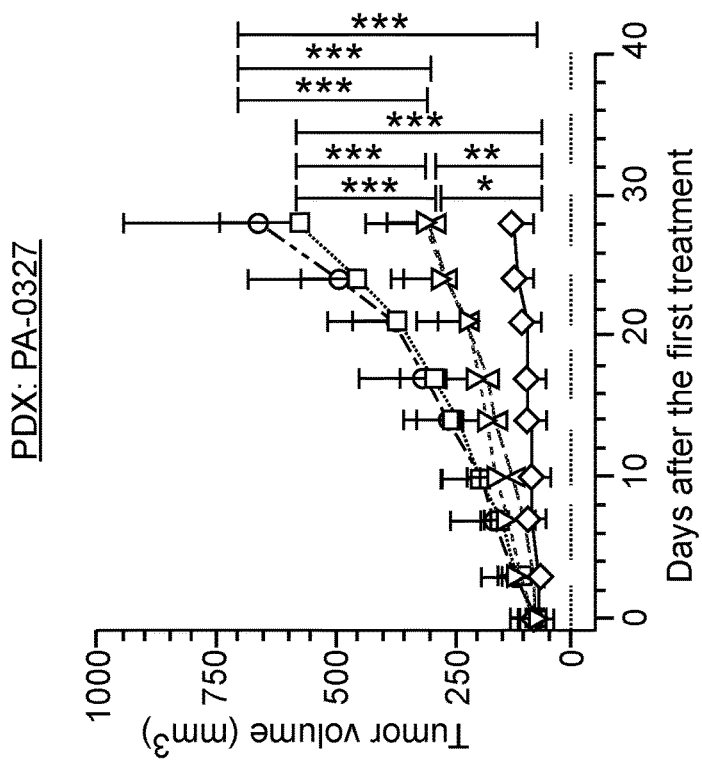
Figure 38A:
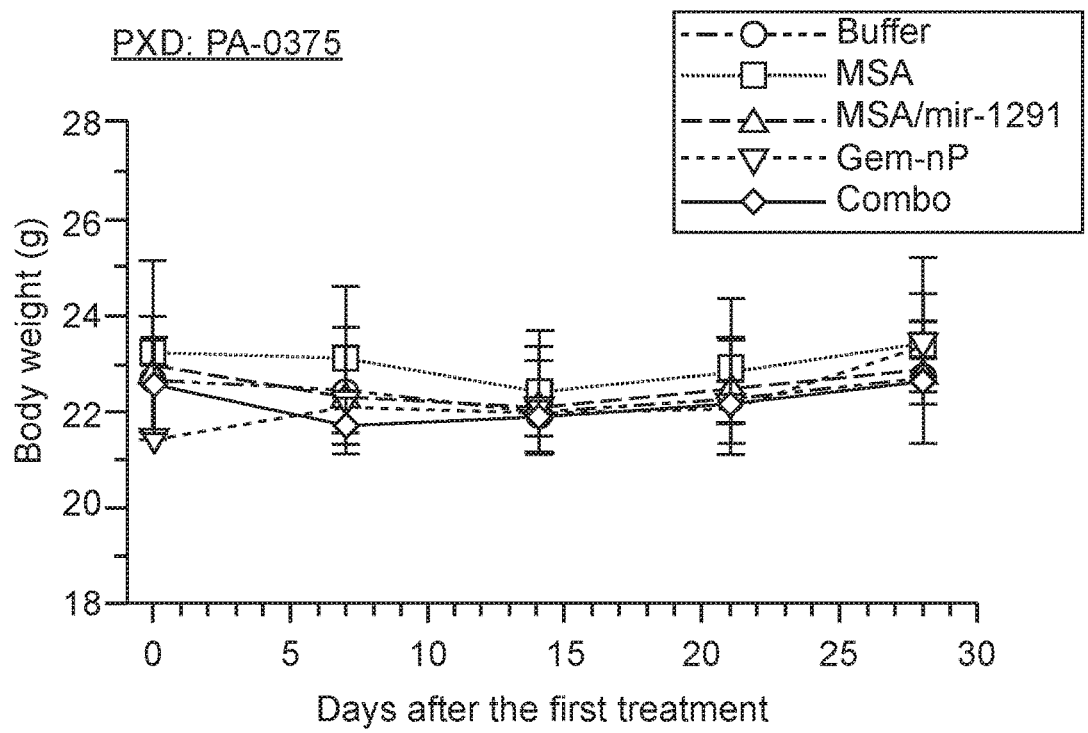
FIGS. 38A-B illustrate miR-1291 prodrug monotherapy and combination therapy are tolerated in PDX mouse models. Body weights of the mice showed no difference between different treatments.
Figure 38B:
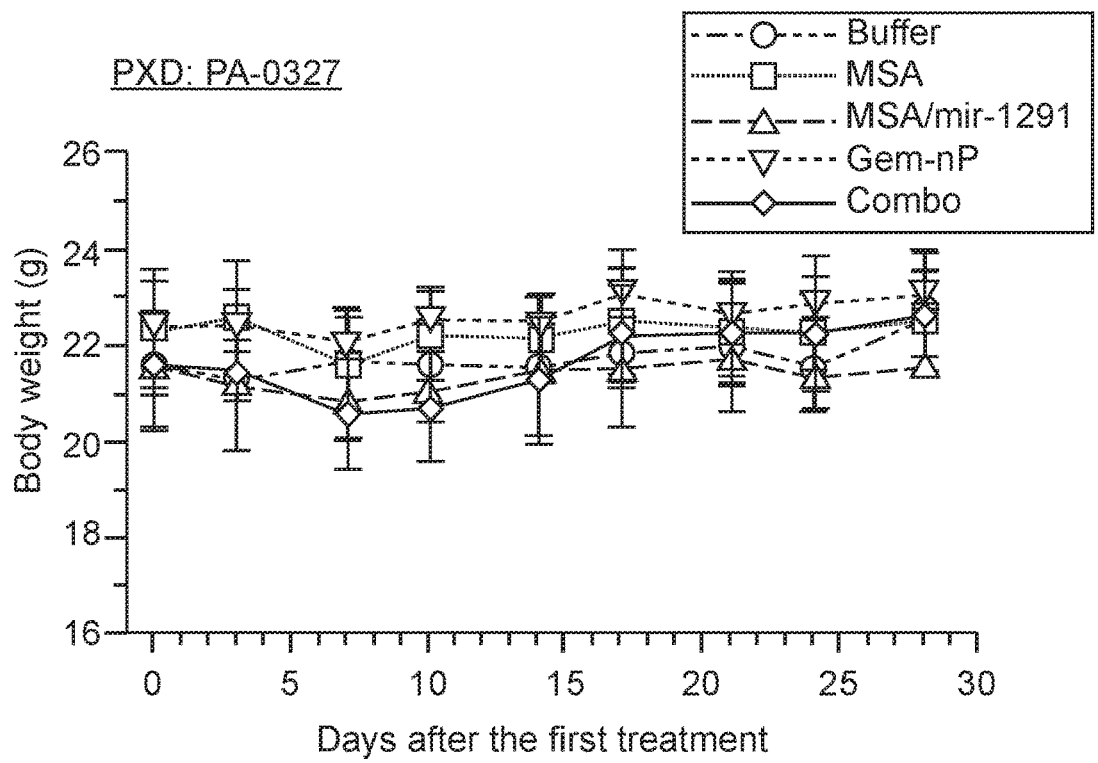

Because the third PDX model, PA-0327, was more aggressive than the other two PDX models, we refined the dosing regimens by increasing miR-1291 prodrug dose to 20 µg/mouse for both mono- and combination therapy, while using the same dose of Gem-nP. Optimal outcomes were surprisingly observed (FIG. 37D-F). Compared to buffer and MSA treatment, monotherapy with miR-1291 prodrug significantly reduced PA-0327 PDX progression by 50%, the same level as Gem-nP chemotherapy, which was indicated by tumor growth over time (FIG. 37D), as well as visual inspection of dissected tumors (FIG. 37E) and quantitative measurement of tumor weights (FIG. 37F) at the end of the study. Most importantly, co-administration of miR-1291 prodrug and Gem-nP chemotherapeutics could suppress PDX progression to the greatest degree (>80%) that was also significantly different from monotherapy (FIG. 37D). The strongest anti-tumor effects of combination therapy were also demonstrated by visual inspection (FIG. 37E) and weighting (FIG. 37F) of the dissected tumors. In addition, body weight of PDX-bearing animals did not show any significant difference among different treatment groups (FIG. 38), indicating that all treatments were well tolerated in mice.

Discussion

Despite several decades of investigation into biology and treatment of PC, there is still a lack of deep understanding of the causes and pathogenesis of PC and more effective therapeutics, making PC one of the most lethal malignancies. Recent findings on functional noncoding miRNAs as well as the association of dysregulation of miRNAs with pathogenesis and progression of pancreatic adenocarcinoma offer clue to developing miRNA based therapies (13-15, 35). After revealing a significant downregulation of miR-1291 in human pancreatic adenocarcinoma tissues and a tumor suppressive action of miR-1291 (18), we demonstrated in the present study that miR-1291 monotherapy (10-20 µg/mouse or 0.5-1 mg/kg, i.v.) was as effective as Gem-nP (300-40 µg/mouse; 7.5/1 ratio; i.v.) for the control of PC growth in PANC-1 xenograft and three different PDX tumor mouse models, while combination therapy offered the greatest degrees of suppression. The optimal outcome of combination treatment with miR-1291 and Gem-nP was associated with an increased level of apoptosis.

MiRNA based therapy represents a novel strategy for the treatment of cancer. However, research and development of new miRNA therapeutics are limited to the use of miRNA mimics made in test tubes by chemical synthesis, as well as the access to large quantities of miRNA agents required for animal and human studies (24). This is also in sharp contrast to protein research and therapy that uses recombinant/ bioengineered proteins produced in living cells instead of synthetic polypeptides/proteins. Distinguished from the conventional synthetic miRNA agents used by others, the present study investigated the efficacy of a bioengineered miR-1291 prodrug that was produced, folded and tolerated in living cells, and purified by FPLC method to high degree of homogeneity on large scale (e.g., multi-milligrams from 0.5-1 liter fermentation) (23, 36). Biologic miR-1291 prodrug was selectively processed to mature miR-1291 in human PC cells and xenograft tumor tissues, which consequently modulated target gene expression and improved the efficacy of Gme-nP.

Because PANC-1 cells are relatively more resistant to Gem-nP or miR-1291 than AsPC-1 cells, PANC-1 cells were utilized to establish xenograft mouse models for the evaluation of miR-1291 mono- and combination therapy. While both miR-1291 and Gem-nP monotherapy showed an overall effectiveness in controlling PANC-1 xenograft tumor growth, intra-individual variation was obvious. Even with a small sample size of six mice per group, three subjects were sensitive to miR-1291 and Gem-nP monotherapy, whereas the other three showed relatively poor responses. In contrast, combination therapy with miR-1291 and Gem-nP, while well tolerated in mice, was able to ubiquitously suppress tumor growth and to a greater extent than either Gem-nP or miR-1291 alone, demonstrating the advantage of combination treatment than monotherapy.

While cell line derived xenograft models are useful for cancer research and therapy studies, commercialized cell lines having been cultured for many passages under an artificial environment may exhibit many genetic changes and new characteristics that are different from original tissues (34, 37). To better recapitulate the properties of original patient tumors and reflect the efficiency of new therapies in patients, an increasing number of PDX models have been used for studying cancer biology and assessing new drugs (16, 28, 32, 38-40). In current study, PDX models from three different PC patients were established and utilized to evaluate miR-1291 monotherapy and combination treatment with Gem-nP. Consistent with findings from PANC-1 xenograft mouse models, biologic miR-1291 prodrug was effective to reduce PDX tumor growth and improve the efficacy of Gem-nP, while histopathology analysis indicated that PDX tumor indeed better preserved the histological features of clinical PC than xenograft tumors derived from PANC-1 cells (data no shown). As manifested by the increase in caspase-3 levels, reduction of PDX progression by combination therapy was attributable to the induction of apoptosis, which is also in accordance with in vitro data. Moreover, different PDX tumor models unsurprisingly showed variable sensitivities to miR-1291 and Gem-nP treatment alone. PA-0387 was relatively more sensitive to Gem-nP than miR-1291 while PA-0375 was equally responsive to miR-1291 and Gem-nP. The third PDX, PA-0327, seemed to be the most invasive, showed lower sensitivities to both Gem-nP and miR-1291 monotherapy. Rather, combination treatment with miR-1291 and Gem-nP reduced the final tumor sizes of PA-0327 by >80%, supporting combination treatment including dose tailoring as an optimal strategy to combat PC.

Improved outcomes of miR-1291 plus Gem-nP combination treatment are inevitably due to multi-targeting in PC cells. Consistent with our previous findings (18), current study showed that miR-1291 alone enhanced apoptosis, as manifested by higher caspase-3/7 levels, which increased to even greater degrees when Gem-nP was co-administered. Gemcitabine is a nucleoside analogue that is converted to an activated metabolite, gemcitabine triphosphate, and subsequently inhibits DNA synthesis by incorporating into DNA, leading to G1/S cell cycle arrest and apoptosis (41, 42). Paclitaxel reduces cell mitosis through stabilization of microtubes (43). As indicated by the increase in γH2A.X and H3PS10 levels, actions of Gem-nP on DNA damage and mitotic arrest were obvious in PC cell lines. Likewise, co-administration of miR-1291 enhanced the levels of DNA damage and mitotic arrest, providing a good explanation of the sensitization of PC cells to Gem-nP by miR-1291. It is also notable that AsPC-1 cells were more sensitive to miR-1291 and chemotherapies than PANC-1 cells, in agreement with the finding on more striking increases in the expression of marker proteins at earlier time points (48 h post-treatment) in AsPC-1 cells.

The present study also validated a new target for miR-1291, ARID3B, an addition to those (e.g., MRP1, GLUT1, MUC1, FOXA2, and MeCP2) reported previously (18, 20-23). While a miRNA generally reduces target gene expression, ARID3B was rather upregulated in PC cells by miR-1291. Although the precise mechanisms are unknown, there is growing evidence that miRNAs are also able to stimulate the expression of target genes through direct or indirect actions (44). In addition, the role of ARID3B in cancer remains controversial although there are only a limited number of reports. Some studies showed that ARID3B promoted cancer cell proliferation, invasiveness, stemness or tumorigenesis (45-48), whereas other studies demonstrated that ARID3B played an important role in the activation of pro-apoptotic p53-target genes and induction of apoptosis (31, 49). These studies differ much in the types of cancer cells investigated and reagents used, as well as study designs. Our studies, the first to investigate ARID3B in PC cells, are consistent with the report on the presence of full-length and short-length (splice form) ARID3B proteins in human cancer cells (31). The upregulation of ARID3B by miR-1291 not only agrees with the function of ARID3B in the induction of apoptosis showed by others (31, 49) but also the role of miR-1291 in the enhancement of apoptosis in PC cells reported by us very recently (18). Therefore, the upregulation of anti-apoptotic ARID3B is likely another possible mechanism behind the antitumor function of miR-1291.

In summary, the present study demonstrated that a first-of-a-kind biologic miR-1291 prodrug was effective as Gem-nP in the control of PC tumor growth in PNAC-1 xenograft and different PDX tumor mouse models, while combination therapy with miR-1291 and Gem-nP suppressed xenograft tumor growth to the greatest degrees. Furthermore, all treatments were well tolerated in mice without any signs of hepatic and renal toxicity. Optimal efficacy of combination treatment was attributable to the enhanced induction of apoptosis, DNA damage and mitotic arrest. In addition, the induction of apoptosis by miR-1291 was associated with upregulation of ARID3B. These results are consistent with the conclusion that biologic miR-1291 prodrug can be developed as a new anti-tumor agent for the treatment of PC, and co-administration of miR-1291 augments the efficacy of current standard chemotherapy Gem-nP.

REFERENCES FOR EXAMPLE 3

1. Siegel R L, Miller K D, Jemal A. Cancer statistics, 2018. CA: a cancer journal for clinicians. 2018; 68:7-30.
2. Tempero M A, Malafa M P, Al-Hawary M, Asbun H, Bain A, Behrman S W, et al. Pancreatic Adenocarcinoma, Version 2.2017, NCCN Clinical Practice Guidelines in Oncology. J Natl Compr Canc Netw. 2017; 15:1028-61.
3. Hidalgo M. Pancreatic cancer. New England Journal of Medicine. 2010; 362:1605-17.
4. Burris 3rd H, Moore M J, Andersen J, Green M R, Rothenberg M L, Modiano M R, et al. Improvements in survival and clinical benefit with gemcitabine as first-line therapy for patients with advanced pancreas cancer: a randomized trial. Journal of clinical oncology. 1997; 15:2403-13.
5. Von Hoff D D, Ervin T, Arena F P, Chiorean E G, Infante J, Moore M, et al. Increased survival in pancreatic cancer with nab-paclitaxel plus gemcitabine. New England Journal of Medicine. 2013; 369:1691-703.
6. Mohammed A, Janakiram N B, Madka V, Li M, Asch A S, Rao C V. Current Challenges and Opportunities for Chemoprevention of Pancreatic Cancer. Curr Med Chem. 2017.
7. Tsai S, Evans D B. Therapeutic Advances in Localized Pancreatic Cancer. JAMA Surg. 2016; 151:862-8.
8. Krantz B A, O'Reilly E M. Biomarker-Based Therapy in Pancreatic Ductal Adenocarcinoma: An Emerging Reality? Clin Cancer Res. 2017.
9. Manji G A, Olive K P, Saenger Y M, Oberstein P. Current and Emerging Therapies in Metastatic Pancreatic Cancer. Clin Cancer Res. 2017; 23:1670-8.
10. Narayanan V, Weekes C D. Molecular therapeutics in pancreas cancer. World J Gastrointest Oncol. 2016; 8:366-79.
11. Ambros V. The functions of animal microRNAs. Nature. 2004; 431:350-5.
12. Bartel D P. MicroRNAs: genomics, biogenesis, mechanism, and function. Cell. 2004; 116:281-97.
13. Bader A G, Brown D, Winkler M. The promise of microRNA replacement therapy. Cancer research. 2010; 70:7027-30.
14. Rupaimoole R, Slack F J. MicroRNA therapeutics: towards a new era for the management of cancer and other diseases. Nature reviews Drug discovery. 2017; 16:203-22.
15. Yu A M, Tian Y, Tu M J, Ho P Y, Jilek J L. MicroRNA Pharmacoepigenetics: Posttranscriptional Regulation Mechanisms behind Variable Drug Disposition and Strategy to Develop More Effective Therapy. Drug metabolism and disposition: the biological fate of chemicals. 2016; 44:308-19.
16. Gilles M E, Hao L, Huang L, Rupaimoole R, Lopez-Casas P P, Pulver E, et al. Personalized RNA Medicine for Pancreatic Cancer. Clin Cancer Res. 2018; 24:1734-47.
17. Sicard F, Gayral M, Lulka H, Buscail L, Cordelier P. Targeting miR-21 for therapy of pancreatic cancer. Mol Ther. 2013; 21:986-94.
18. Tu M-J, Pan Y-Z, Qiu J-X, Kim E J, Yu A-M. MicroRNA-1291 targets the FOXA2-AGR2 pathway to suppress pancreatic cancer cell proliferation and tumorigenesis. Oncotarget. 2016; 7:45547.
19. Bi H-C, Pan Y-Z, Qiu J-X, Krausz K W, Li F, Johnson C H, et al. N-methylnicotinamide and nicotinamide N-methyltransferase are associated with microRNA-1291-altered pancreatic carcinoma cell metabolome and suppressed tumorigenesis. Carcinogenesis. 2014; 35:2264-72.
20. Pan Y-Z, Zhou A, Hu Z, Yu A-M. Small nucleolar RNA-derived microRNA hsa-miR-1291 modulates cellular drug disposition through direct targeting of ABC transporter ABCC1. Drug Metabolism and Disposition. 2013; 41:1744-51.
21. Yamasaki T, Seki N, Yoshino H, Itesako T, Yamada Y, Tatarano S, et al. Tumor-suppressive microRNA-1291 directly regulates glucose transporter 1 in renal cell carcinoma. Cancer science. 2013; 104:1411-9.
22. Luo H, Guo W, Wang F, You Y, Wang J, Chen X, et al. miR-1291 targets mucin 1 inhibiting cell proliferation and invasion to promote cell apoptosis in esophageal squamous cell carcinoma. Oncology reports. 2015; 34:2665-73.
23. Li M M, Addepalli B, Tu M J, Chen Q X, Wang W P, Limbach P A, et al. Chimeric MicroRNA-1291 Biosynthesized Efficiently in *Escherichia coli* Is Effective to Reduce Target Gene Expression in Human Carcinoma Cells and Improve Chemosensitivity. Drug metabolism and disposition: the biological fate of chemicals. 2015; 43:1129-36.
24. Ho P Y, Yu A M. Bioengineering of noncoding RNAs for research agents and therapeutics. Wiley Interdisciplinary Reviews: RNA. 2016; 7:186-97.
25. Wang W-P, Ho P Y, Chen Q-X, Addepalli B, Limbach P A, Li M-M, et al. Bioengineering novel chimeric microRNA-34a for prodrug cancer therapy: high-yield expression and purification, and structural and functional characterization. Journal of Pharmacology and Experimental Therapeutics. 2015; 354:131-41.
26. Ho P, Duan Z, Batra N, Jilek J, Tu M, Qiu J, et al. Bioengineered ncRNAs selectively change cellular miR-Nome profiles for cancer therapy. The Journal of pharmacology and experimental therapeutics. 2018.

27. Pan Y-Z, Morris M E, Yu A-M. MicroRNA-328 negatively regulates the expression of breast cancer resistance protein (BCRP/ABCG2) in human cancer cells. Molecular pharmacology. 2009; 75:1374-9.
28. Rubio-Viqueira B, Jimeno A, Cusatis G, Zhang X, Iacobuzio-Donahue C, Karikari C, et al. An in vivo platform for translational drug development in pancreatic cancer. Clinical cancer research. 2006; 12:4652-61.
29. Kim M P, Evans D B, Wang H, Abbruzzese J L, Fleming J B, Gallick G E. Generation of orthotopic and heterotopic human pancreatic cancer xenografts in immunodeficient mice. Nature protocols. 2009; 4:1670-80.
30. Zhao Y, Tu M-J, Yu Y-F, Wang W-P, Chen Q-X, Qiu J-X, et al. Combination therapy with bioengineered miR-34a prodrug and doxorubicin synergistically suppresses osteosarcoma growth. Biochemical pharmacology. 2015; 98:602-13.
31. Joseph S, Deneke V E, Dahl K D C. ARID3B induces tumor necrosis factor alpha mediated apoptosis while a novel ARID3B splice form does not induce cell death. PloS one. 2012; 7:e42159.
32. Tentler J J, Tan A C, Weekes C D, Jimeno A, Leong S, Pitts T M, et al. Patient-derived tumour xenografts as models for oncology drug development. Nature reviews Clinical oncology. 2012; 9:338-50.
33. Siolas D, Hannon G J. Patient-derived tumor xenografts: transforming clinical samples into mouse models. Cancer research. 2013; 73:5315-9.
34. Voskoglou-Nomikos T, Pater J L, Seymour L. Clinical predictive value of the in vitro cell line, human xenograft, and mouse allograft preclinical cancer models. Clinical Cancer Research. 2003; 9:4227-39.
35. Rachagani S, Macha M A, Heimann N, Seshacharyulu P, Haridas D, Chugh S, et al. Clinical implications of miRNAs in the pathogenesis, diagnosis and therapy of pancreatic cancer. Advanced drug delivery reviews. 2015; 81:16-33.
36. Chen Q X, Wang W P, Zeng S, Urayama S, Yu A M. A general approach to high-yield biosynthesis of chimeric RNAs bearing various types of functional small RNAs for broad applications. Nucleic acids research. 2015; 43:3857-69.
37. Daniel V C, Marchionni L, Hierman J S, Rhodes J T, Devereux W L, Rudin C M, et al. A primary xenograft model of small-cell lung cancer reveals irreversible changes in gene expression imposed by culture in vitro. Cancer research. 2009; 69:3364-73.
38. Rajeshkumar N V, Yabuuchi S, Pai S G, De Oliveira E, Kamphorst J J, Rabinowitz J D, et al. Treatment of Pancreatic Cancer Patient-Derived Xenograft Panel with Metabolic Inhibitors Reveals Efficacy of Phenformin. Clin Cancer Res. 2017; 23:5639-47.
39. Knudsen E S, Balaji U, Mannakee B, Vail P, Eslinger C, Moxom C, et al. Pancreatic cancer cell lines as patient-derived avatars: genetic characterisation and functional utility. Gut. 2018; 67:508-20.
40. D'Costa Z, Jones K, Azad A, van Stiphout R, Lim S Y, Gomes A L, et al. Gemcitabine-Induced TIMP1 Attenuates Therapy Response and Promotes Tumor Growth and Liver Metastasis in Pancreatic Cancer. Cancer Res. 2017; 77:5952-62.
41. Yip-Schneider M T, Sweeney C J, Jung S-H, Crowell P L, Marshall M S. Cell cycle effects of nonsteroidal anti-inflammatory drugs and enhanced growth inhibition in combination with gemcitabine in pancreatic carcinoma cells. Journal of Pharmacology and Experimental Therapeutics. 2001; 298:976-85.
42. Huang P, Plunkett W. Induction of apoptosis by gemcitabine. Seminars in oncology; 1995. p. 19-25.
43. Horwitz S B, Cohen D, Rao S, Ringel I, Shen H-J, Yang C. Taxol: mechanisms of action and resistance. Journal of the National Cancer Institute Monographs. 1993:55-61.
44. Vasudevan S. Posttranscriptional upregulation by microRNAs. Wiley Interdiscip Rev RNA. 2012; 3:311-30.
45. Kobayashi K, Era T, Takebe A, Jakt L M, Nishikawa S. ARID3B induces malignant transformation of mouse embryonic fibroblasts and is strongly associated with malignant neuroblastoma. Cancer Res. 2006; 66:8331-6.
46. Cowden Dahl K D, Dahl R, Kruichak J N, Hudson L G. The epidermal growth factor receptor responsive miR-125a represses mesenchymal morphology in ovarian cancer cells. Neoplasia. 2009; 11:1208-15.
47. Bobbs A, Gellerman K, Hallas W M, Joseph S, Yang C, Kurkewich J, et al. ARID3B Directly Regulates Ovarian Cancer Promoting Genes. PLoS One. 2015; 10:e0131961.
48. Liao T T, Hsu W H, Ho C H, Hwang W L, Lan H Y, Lo T, et al. let-7 Modulates Chromatin Configuration and Target Gene Repression through Regulation of the ARID3B Complex. Cell Rep. 2016; 14:520-33.
49. Pratama E, Tian X, Lestari W, Iseki S, Ichwan S J, Ikeda M-A. Critical role of ARID3B in the expression of pro-apoptotic p53-target genes and apoptosis. Biochemical and biophysical research communications. 2015; 468:248-54.

Example 4

Bioengineering of Single ncRNA Molecule for Carrying Multiple Small RNAs

We have recently established a high-yield and cost-effective method of producing bioengineered or biologic ncRNA agents (BERAs) through bacterial fermentation, which is based on a stable tRNA/pre-miR-34a carrier (~180 nt) that accommodates target small RNAs. Nevertheless, it remains a challenge to heterogeneously express longer ncRNAs (e.g., >260 nt) and it is unknown if single BERA may carry multiple small RNAs. To address this issue, we hypothesized that an additional human pre-miR-34a could be attached to the tRNA/pre-miR-34a scaffold to offer a new tRNA/pre-miR-34a/pre-miR-34a carrier (~296 nt) for the accommodation of multiple small RNAs. We thus designed ten different combinatorial BERAs (CO-BERAs) that include different combinations of miRNAs, siRNAs, and antagomirs. Our data showed that all target CO-BERAs were successfully expressed in *Escherichia coli* at high levels, greater than 40% in total bacterial RNAs. Furthermore, recombinant CO-BERAs were purified to a high degree of homogeneity by fast protein liquid chromatography methods. In addition, CO-BERAs exhibited strong anti-proliferative activities against a variety of human non-small cell lung cancer cell lines. These results support the production of long ncRNA molecules carrying different warhead small RNAs for multi-targeting which may open avenues for developing new biologic RNAs as experimental, diagnostic, and therapeutic tools.

Lung cancer is the second most common cancer among both men and women in the United States. The majority of lung cancer cases are classified as non-small cell lung cancer (NSCLC). Current NSCLC treatments include resection surgery, radiation, and pharmacotherapy which all provide some benefits and have limitations. As a result, lung cancer caused deaths account for about 27% of all cancer deaths in the US. Therefore, new therapeutic agents are highly demanded for NSCLC. MicroRNAs (miRNA or miR) are a class of genome-derived, small noncoding RNAs (ncRNA) in cells that govern target gene expression through mRNA degradation or translational inhibition. Some miRNAs such as miR-34a, miR-124 and let-7c are commonly downregulated in NSCLC tissues/cells and target various oncogenes such as CDK6, STAT3, and Ras. Restoring the expression or function of such dysregulated, tumor suppressive miRNAs represents a new strategy for cancer therapy. Aiming at simultaneously introducing multiple miRNAs in NSCLC cells for multi-targeting, we employed our ncRNA bioengineering technology to produce a single ncRNA molecule bearing multiple miRNAs. The CO-BERAs construct design, expression and treatment results are shown in FIGS. 39-44.

Our data showed that multi-targeting ncRNA agents were successfully expressed in E. coli. We were able to purify recombinant ncRNAs to a high degree of homogeneity using FPLC methods. The ncRNA are effective in inhibiting human NSCLC cell viability in a variety of cell lines and htRNALeu/let-7c/miR-124 and htRNALeu/miR-124/miR-34a were chosen as the best candidates for further testing. We demonstrated that treatment of human NSCLC cells with bioengineered ncRNAs elevated cellular miR-34a, miR-124 and let-7c levels and reduced protein levels of target genes including CDK6, STAT3 and Ras. LPP loaded with ncRNA was more effective in inhibiting cell proliferation than Lipofectamine 3000, therefore LPP was used in the animal model. htRNALeu/let-7c/miR-124 and htRNALeu/miR-124/miR-34a may be effective in controlling the growth of xenograft NSCLC in mice as evidenced by the increase in signal after treatment was withdrawn. Therefore, using single ncRNA agent for multi-targeting provides an effective treatment of NSCLC.

Materials and Methods
Bacterial Culture

E. coli strains DH5u (Thermo Fisher Scientific, Waltham, MA) and HST08 (Clontech Laboratories, Mountain View, CA) were grown in Luria Broth (LB) for plasmid preparation and 2×YT media for RNA production, respectively. The media were supplemented with 100 µg/ml ampicillin.

Human Cell Culture

Human lung carcinoma cell lines A549 (ATCC: CRM-CCL-185), H1975 (ATCC: CRL-5908), H23 (ATCC: CRL-5800), H1650 (ATCC: CRL-5883), and H1299 (ATCC: 5803) were purchased from American Type Culture Collection (Manassas, VA). Cell lines were maintained in RPMI 1640 (Thermo Fisher Scientific) supplemented with 10% fetal bovine serum, 100 U/ml penicillin sodium, and 100 µg/ml streptomycin sulfate (Thermo Fisher Scientific) grown at 37° C. in a humidified atmosphere with 5% $CO_2$.

Construction of CO-BERA Expression Plasmids

Figure 39A:
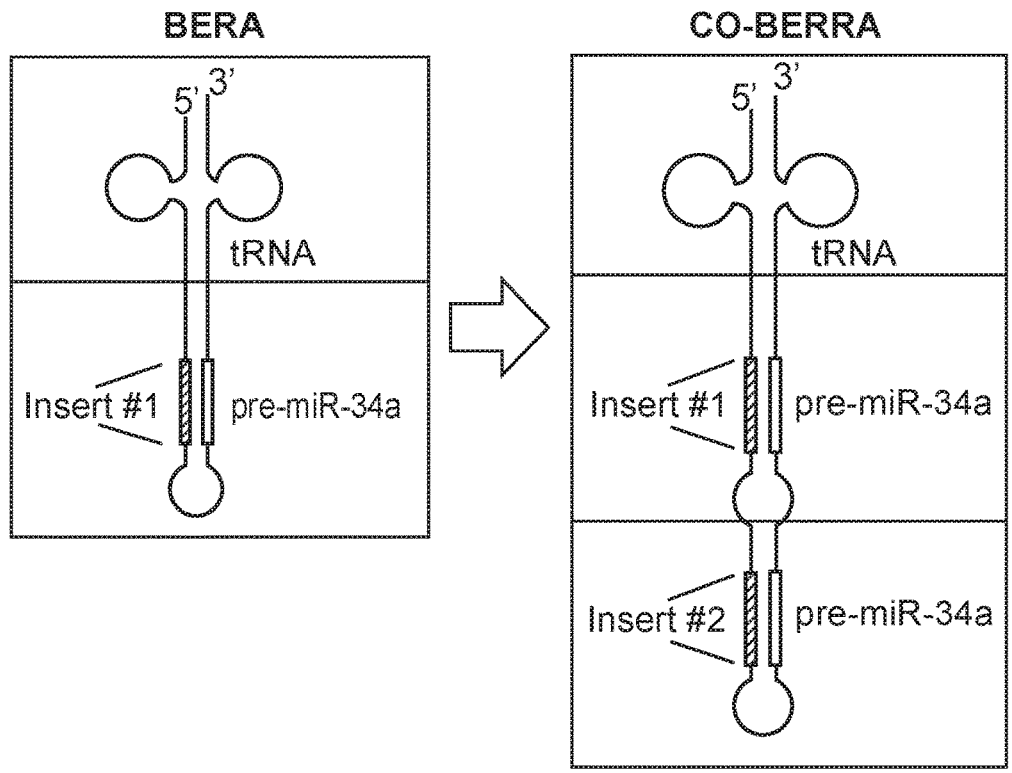
FIG. 39. Novel combinatorial bioengineered RNA agent (CO-BERA) is highly expressed in E. coli. a) Illustration of the designed CO-BERA (~297-nt in length) which includes two optimized pre-miR-34a sequences preceding each of the inserts, different from BERA (~180-nt in length) that includes only one pre-miR-34a. Each insert included a target sequence and a complementary sequence. b) Denaturing urea PAGE analysis of total RNA extracted from the E. coli HST08 cells transformed with plasmids encoding individual CO-BERAs, with a ladder and wild-type (WT) HST08 cells for references. Successful overexpression of each target CO-BERA is demonstrated by the appearance of a new strong band in transformed HST08 cells, as compared to the WT cells.
Figure 39B:
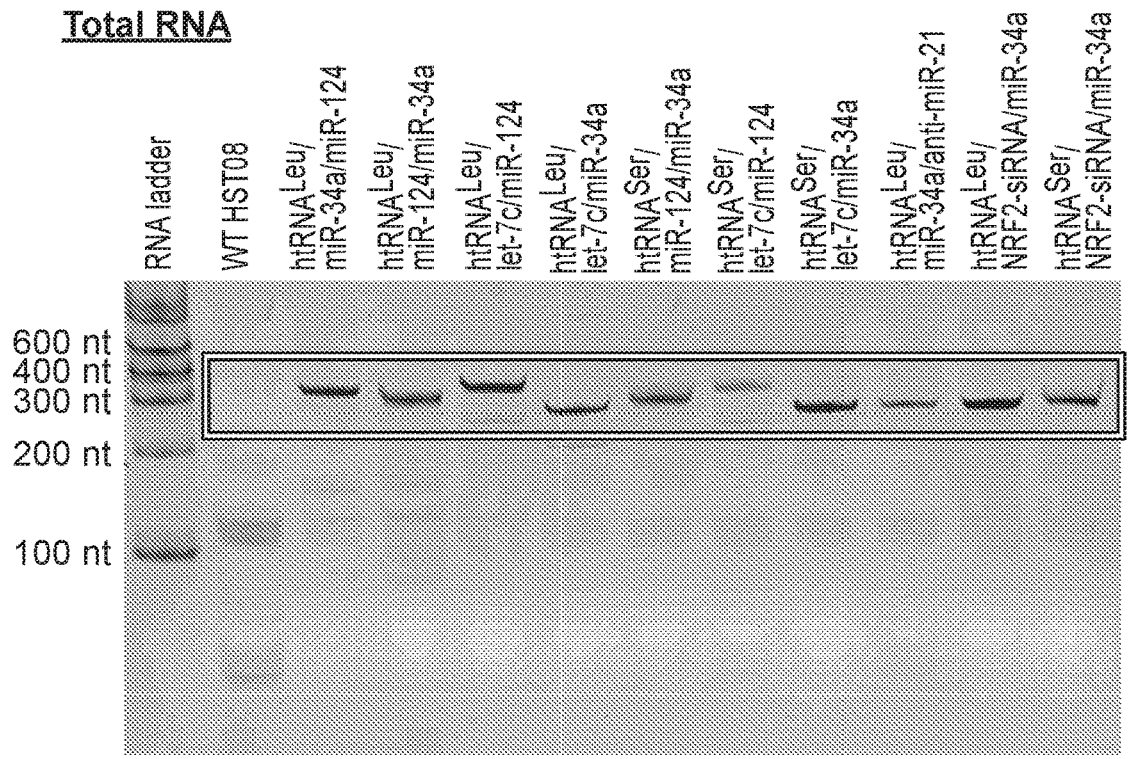

The sequences of all miRNAs were obtained from miR-Base, and the optimized pre-miR-34a as well as anti-miR-21, NRF2-siRNA, let-7c, and miR-124 sequences were adopted from our recently study (Ho et al. 2018; Li et al. 2018). CO-BERA sequences (SEQ ID NOs:183, 184, 185, 186, 187, 188, 189, 190, 191, and 192) were generated by substituting miR-34a duplexes with target miRNA or siRNA sequences, as illustrated in FIG. 39a, and corresponding coding sequences were synthesized in the pUC57 vector by GenScript Corporation (Piscataway, NJ). Target inserts were released from the plasmids after digestion with EcoRI and PstI (New England Biolabs, Ipswitch, MA). Following gel purification using USB PrepEase Gel Extraction Kit (Affymetrix, Inc. Cleveland, Ohio), each insert was ligated to the EcoRI and PstI digested vector pBSTNAV (Ho et al. 2018; Ponchon et al. 2009) with T4 Rapid Ligation Kit (Thermo Fisher Scientific). The plasmids were then transformed into DH5u competent cells and selected with ampicillin. Colonies were expanded, and CO-BERA expression plasmids were isolated with a Miniprep Kit (Qiagen, Hilden, Germany). All target CO-BERA expression plasmids were confirmed by sequencing analysis (GenScript, Piscataway, NJ).

Expression of Recombinant CO-BERA in E. coli

Plasmids with confirmed sequences were transformed into HST08 as previously described (Ho et al. 2018; Li et al. 2014; Wang et al. 2015). Total RNAs were extracted by Tris-HCl-saturated phenol extraction method, quantified with a NanoDrop 2000 spectrophotometer (Thermo Fisher Scientific), and analyzed for recombinant CO-BERA expression by separating 0.1 µg total bacterial RNA per lane on a denaturing urea (8 M) PAGE (8%) gel with a RiboRuler low range RNA ladder (Thermo Fisher Scientific) for reference. PAGE gels were stained with ethidium bromide and imaged using ChemiDoc MP Imaging System (BioRad, Hercules, CA).

Purification of CO-BERAs by Fast Protein Liquid Chromatography

CO-BERAs were purified from total RNAs using an NGC Quest 10 Plus Chromatography fast protein liquid chromatography (FPLC) system (BioRad, Hercules, CA). All CO-BERAs were initially purified using Enrich-Q 10×100 (Bio-Rad, Hercules, CA). FPLC fractions were analyzed by urea-PAGE to verify RNA separation and purity. Fractions containing target CO-BERA were pooled, precipitated in ethanol, and desalted/concentrated in nuclease-free water using an Amicon ultra-2 ml centrifugal filter (30 kDa; EMD Millipore, Billerica, MA). In some cases, the concentrated CO-BERAs contained some impurities and were subjected for a second purification using either Enrich-Q 10×100, Bio-Scale Mini Macro-Prep DEAE, or Bio-Scale Mini CHT Type II (BioRad, Hercules, CA) depending on which column yielded the purest product. Likewise, the fractions were assessed by urea-PAGE analysis, and target fractions were thus combined, desalted and concentrated.

RNA separation on Enrich-Q 10×100 and Bio-Scale Mini Macro-Prep DEAE were conducted with Buffer A (10 mM sodium phosphate, pH 7.0) and Buffer B (Buffer A+1 M sodium chloride, pH 7.0) while Bio-Scale Mini CHT Type II was achieved by using Buffer C (5 mM sodium phosphate, pH 7.0) and Buffer D (150 mM sodium phosphate, pH 7.0). FPLC traces were monitored at 260/280 nm using a UV-visible detector, and fractions were collected accordingly. Specifically, around 5-10 mg of RNA was loaded onto the Enrich-Q column and separated through a gradient elution at a flow rate of 2 ml/min, i.e., 100% Buffer A for 4 min, followed by 55% Buffer B for 10 min, a gradient of 55-72% Buffer B for 20 min, 72-74% Buffer B for 8 min, 100% Buffer B for 10 min, and then 100% Buffer A for 10 min. Around 5 mg of RNA was loaded onto the Bio-Scale Mini Macro-Prep DEAE for separation by gradient elution at 2 ml/min, i.e., 100% Buffer A for 12 min, then switched to 50% Buffer B for 5 min, a gradient of 50-60% Buffer B for 25 min, 60-75% Buffer B for 10 min, 100% Buffer B for 5 min, and finally 100% Buffer A for 5 min. Lastly, around 0.5 mg RNA was loaded onto the Bio-Scale Mini CHT Type II for separation by gradient elution at 2.5 ml/min, i.e., 100% Buffer C for 2 min, followed by 73-90% Buffer D for 18 min, 100% Buffer D for 5 min, then 100% Buffer C for 5 min.

Quantitative Measurement of the Purity of FPLC-Isolated CO-BERA

The purity of FPLC-isolated RNA was quantitatively determined by an optimal high performance liquid chromatography (HPLC) method with a XBridge® Oligonucleotide BEH Cis column (2.1×50 mm, 2.5 µm particle size; Waters, Milford, MA) on a Shimadzu LC-20AD HPLC system, as we described previously (Wang et al. 2015).

Endotoxin Quantification

Endotoxin levels in FPLC-purified CO-BERAs were quantitated by using Limulus Amebocyte Lysate Pyrogent-5000 kinetic assay (Lonza, Walkersville, MD), following the manufacturer's instructions. In brief, a SpectraMax3 plate reader (Molecular Devices, Sunnyvale, CA) was used to measure the absorbance at 340 nm wavelength. Endotoxin standards provided in the kit were used to generate a standard curve, and endotoxin levels were calculated as endotoxin units (EU)/µg RNA.

Cell Viability Assay

Cells were seeded at 3,000 or 5,000 cells per well in a 96-well pate and after overnight incubation cells were transfected with 15 nM ncRNA or control tRNA using Lipofectamine 3000 (Thermo Fisher Scientific) as well as empty Lipofectamine 3000 as vehicle control. Cell viability was measured using MTT assay 72 h post-transfection, as we described (Ho et al. 2018; Jilek et al. 2019; Wang et al. 2015). All experiments were carried out in triplicate and repeated at least once in separate cultures.

Results

Design of CO-BERAs and Construction of Plasmids

Using the novel tRNA/pre-miRNA-based ncRNA bioengineering technology, we were able to produce a variety of target BERAs in milligram quantities from one liter of bacterial culture (Chen et al. 2015; Ho et al. 2018; Li et al. 2014; Li et al. 2019; Wang et al. 2015). However, it was unknown if this technology would allow us to produce an RNA molecule longer than 260 nt that carries multiple target small RNAs. To address this issue, we designed ten new CO-BERA molecules (SEQ ID NOs:183-192) based on our BERA technology, where another pre-miR-34a was fused consecutively onto the tRNA/pre-miR-34a carrier, and the resulting tRNA/pre-miR-34a/pre-miR-34a carrier, around 296 nt in length, permitted the loading of two target small RNAs through substituting intrinsic miR-34a duplexes (FIG. 39a). To increase the diversity of CO-BERAs, our designs included either a human serine or leucine tRNA followed by two optimized human pre-miR-34a (Ho et al. 2018) carrying different combinations of NRF2-siRNA, anti-miR-21-5p, let-7c-5p, miR-124-3p and miR-34a-3p (SEQ ID NOs:183-192). Corresponding coding sequences were synthesized and cloned into the pUC57 vector, and consequently subcloned into the target pBSTNAV vector (Ho et al. 2018; Li et al. 2014; Ponchon et al. 2009; Ponchon and Dardel 2007), which were confirmed by sequencing before proceeding to heterogeneous expression in HST08 E. coli.

All Target CO-BERAs are Highly Expressed in E. coli

To determine if long ncRNA CO-BERA can be overexpressed heterogeneously, total RNA was extracted from E. coli transformed with individual CO-BERA expression plasmids and analyzed by urea-PAGE. The results (FIG. 39b) showed that all ten CO-BERAs were successfully expressed in bacteria, as manifested by the appearance of new corresponding RNA bands when compared to the wild-type bacteria. Interestingly, these CO-BERAs in similar lengths (SEQ ID NOs:183-192) undoubtedly contain different secondary and higher-order structures as exhibited by variable levels of PAGE mobility (FIG. 39b), similar to our findings on BERAs (Ho et al. 2018; Jilek et al. 2019). While the expression levels of these CO-BERAs also varied slightly, each accounted for over 40% of total bacterial RNAs, as estimated from the intensities of RNA bands (FIG. 39b) as well as more quantitatively from the FPLC peak areas (FIG. 40a). In addition, the amounts of total RNAs extracted from one liter of bacterial culture were variable between CO-BERAs, ranging from approximately 50 mg for htRNA$^{Leu}$/miR-124/miR-34a to 12.6 mg for htRNA$^{Ser}$/let-7c/miR-124 (Table 9).

TABLE 9

Yields, purities, and endotoxin levels of individual FPLC-isolated CO-BERAs
The yield was defined as the amount of purified CO-BERA per liter bacterial culture, and the purity of isolated CO-BERA was quantified by an optimal HPLC method (Wang et al. 2015). The molecular weights of individual CO-BERAs were calculated with OligoCalc. Endotoxin levels were determined by using the Limulus Amebocyte Lysate Pyrogent-5000 kinetic assay.

|   | Name | Length (nt) | Molecular Weight (g/mol) | Total RNA extracted from 1 L culture (mg) | Target CO-BERA purified from 1 L culture (mg) | Purity (%) | Endotoxin activity (EU/µg RNA) |
|---|------|-------------|--------------------------|-------------------------------------------|-----------------------------------------------|------------|-------------------------------|
| 1 | htRNA$^{Leu}$/miR-34a/miR-124$^a$ | 297 | 96,008.1 | 48.4 | 21.3 | 99.0 | 0.15 |
| 2 | htRNA$^{Leu}$/miR-124/miR-34a$^a$ | 297 | 96,583.4 | 50.0 | 22.0 | 99.0 | 3.31 |
| 3 | htRNA$^{Leu}$/let-7c/miR-124$^b$ | 298 | 96,300.3 | 21.6 | 4.3 | 96.7 | 1.60 |
| 4 | htRNA$^{Leu}$/let-7c/miR-34a$^c$ | 298 | 96,278.3 | 21.3 | 10.7 | 95.6 | 1.34 |
| 5 | htRNA$^{Ser}$/miR-124/miR-34a$^a$ | 296 | 95,684.9 | 22.2 | 4.4 | 99.4 | 1.44 |
| 6 | htRNA$^{Ser}$/let-7c/miR-124$^d$ | 297 | 95,977.0 | 12.6 | 0.5 | 92.3 | 0.33 |
| 7 | htRNA$^{Ser}$/let-7c/miR-34a$^a$ | 297 | 95,955.1 | 22.0 | 13.2 | 99.6 | 0.71 |
| 8 | htRNA$^{Leu}$/miR-34a/anti-miR-21$^e$ | 294 | 96,010.2 | 17.6 | 0.2 | 95.1 | 1.11 |
| 9 | htRNA$^{Leu}$/NRF2-siRNA/miR-34a$^a$ | 297 | 95,931.1 | 20.0 | 6.4 | 99.6 | 0.19 |

TABLE 9-continued

Yields, purities, and endotoxin levels of individual FPLC-isolated CO-BERAs
The yield was defined as the amount of purified CO-BERA per liter bacterial culture, and
the purity of isolated CO-BERA was quantified by an optimal HPLC method (Wang et al.
2015). The molecular weights of individual CO-BERAs were calculated with OligoCalc.
Endotoxin levels were determined by using the Limulus Amebocyte Lysate Pyrogent-5000
kinetic assay.

| | Name | Length (nt) | Molecular Weight (g/mol) | Total RNA extracted from 1 L culture (mg) | Target CO-BERA purified from 1 L culture (mg) | Purity (%) | Endotoxin activity (EU/μg RNA) |
|---|---|---|---|---|---|---|---|
| 10 | htRNA$^{Ser}$/NRF2-siRNA/miR-34a$^a$ | 296 | 95,607.9 | 13.3 | 1.3 | 99.0 | 6.32 |

$^a$ENrich Q only;
$^b$ENrich Q then CHT Type II;
$^c$ENrich Q then DEAE;
$^d$Enrich Q the nEnrich Q.

CO-BERAs are Purified to a High Degree of Homogeneity by FPLC Methods

Figure 41B:
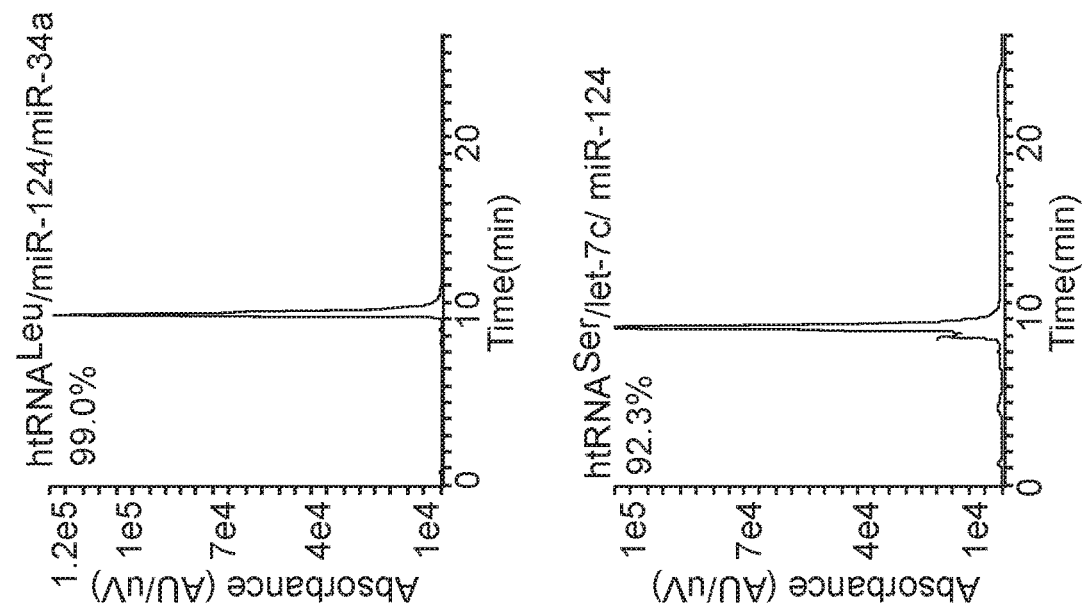
FIG. 41. Verification of the purity of FPLC-isolated CO-BERAs. a) PAGE analysis showed that majority of the isolated CO-BERAs are very pure with no or minimal impurity. B) HPLC analysis quantitatively determined the purities of individual CO-BERAs, among which, most CO-BERAs are around 99% pure and only one CO-BERA is <95% pure (see Table xxx for details).
Figure 41A:
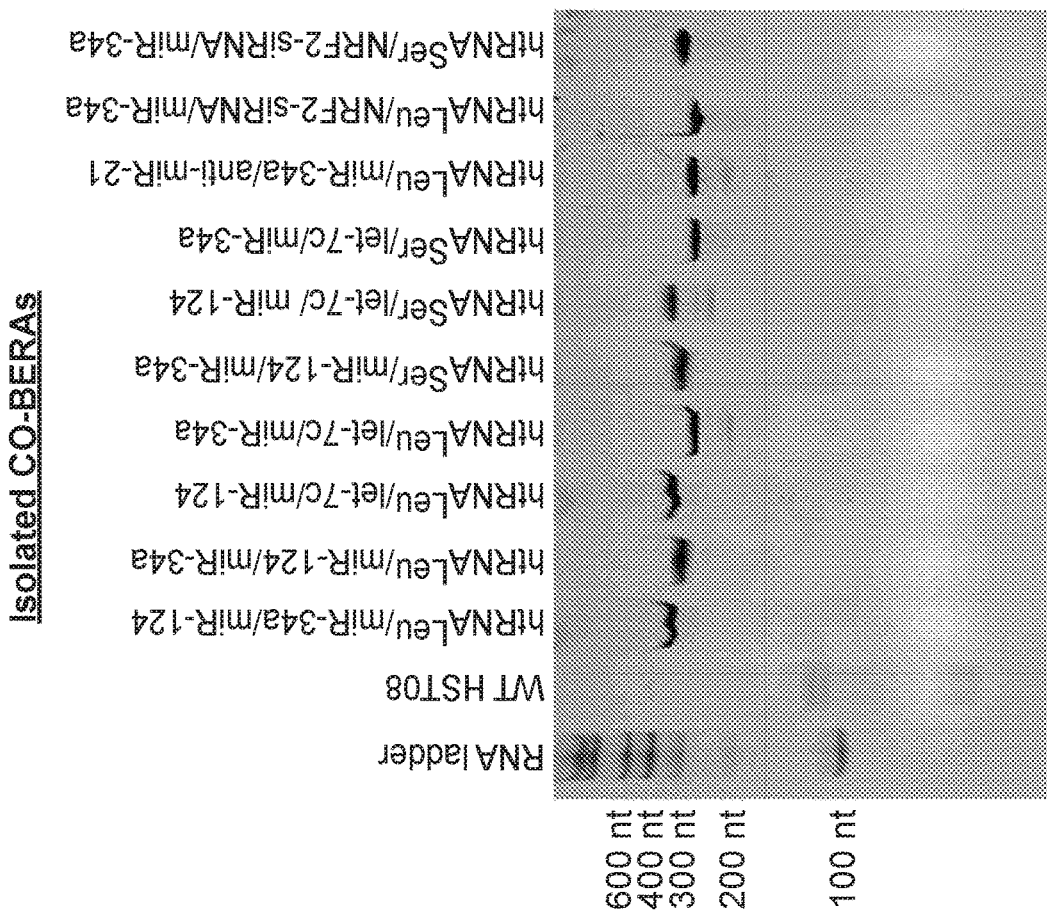

To isolate recombinant CO-BERAs from bacterial RNAs, we sought to optimize the anion-exchange FPLC method utilized for the purification of BERAs (Ho et al. 2018). Through elution with a refined salt-gradient for a longer period of time (FIG. 40a), we were able to purify target CO-BERAs from bacterial RNAs to a high degree of homogeneity in a single run with six out of ten CO-BERAs were greater than or equal to 99.0% pure (Table 9), as quantitatively determined by HPLC method and evaluated by urea-PAGE analysis (FIG. 41). Nevertheless, the other four CO-BERAs were less than 90% pure after single-run FPLC separation with the strong anion-exchange column and thus processed for further purification. Re-purification using either the same strong anion-exchange column or a weak anion-exchange column (FIG. 40b-c) offered satisfactory 95-97% pure CO-BERAs (Table 9). CO-BERAs htRNA$^{Ser}$/let-7c/miR-124 and htRNA$^{Leu}$/let-7c/miR-124 turned out be extremely hard to purify; and re-purification with a strong anion exchange (FIG. 40b) or ceramic hydroxyapatite column (FIG. 40d) resulted in 96.7% pure htRNA$^{Leu}$/let-7c/miR-124 and 92.3% pure htRNA$^{Ser}$/let-7c/miR-124 molecules (Table 9). Meanwhile, overall yields were also lower following two-column purifications, in addition to its association with a lower amount of total RNA from one liter of bacterial fermentation (Table 9). By contrast, the majority of target CO-BERAs purified with single-run strong anion-exchange FPLC method were over 10 mg from one liter of bacterial culture, and 4-7 mg were usually obtained when re-purification was conducted (Table 9). In addition, FPLC-purified CO-BERAs exhibited low endotoxin activities (Table 9), as measured by the Limulus Amebocyte Lysate Pyrogent-5000 kinetic assay. As one CO-BERA htRNA$^{Ser}$/NRF2-siRNA/miR-34a had an endotoxin level of 6.32 EU/μg RNA, all other CO-BERAs showed an endotoxin activity less than 4 EU/μg RNA. Together, these results demonstrated a successful large-scale purification of recombinant CO-BERAs by single- or multi-column FPLC methods that generally offer multi-milligrams of over 95% pure CO-BERAs with minimal endotoxin activities from one liter of bacterial fermentation.

Biologic CO-BERA Molecules Inhibit Human NSCLC Cell Viability

Figure 42C:
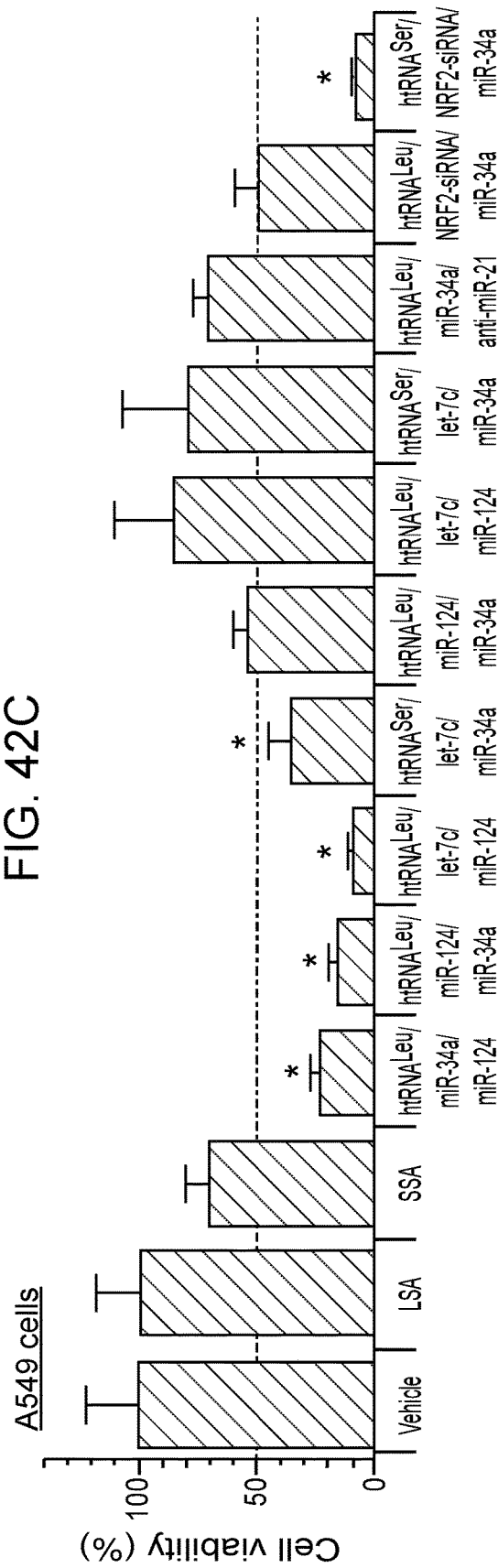
FIG. 42. Anti-proliferative activities of CO-BERAs against various human NSCLC cell lines. Cell viability of five different NSCLC cell lines (a-e) was reduced by 15 nM of purified CO-BERAs to various degrees, as compared to lipofectamine 3000 only (vehicle), leucine (LSA), or serine (SSA) tRNA controls. Data were normalized to vehicle control. Values are mean±SD (N=3). * P<0.05, as compared to vehicle, LSA, and SSA control (1-way ANOVA with Bonferroni post-tests).
Figure 42D:
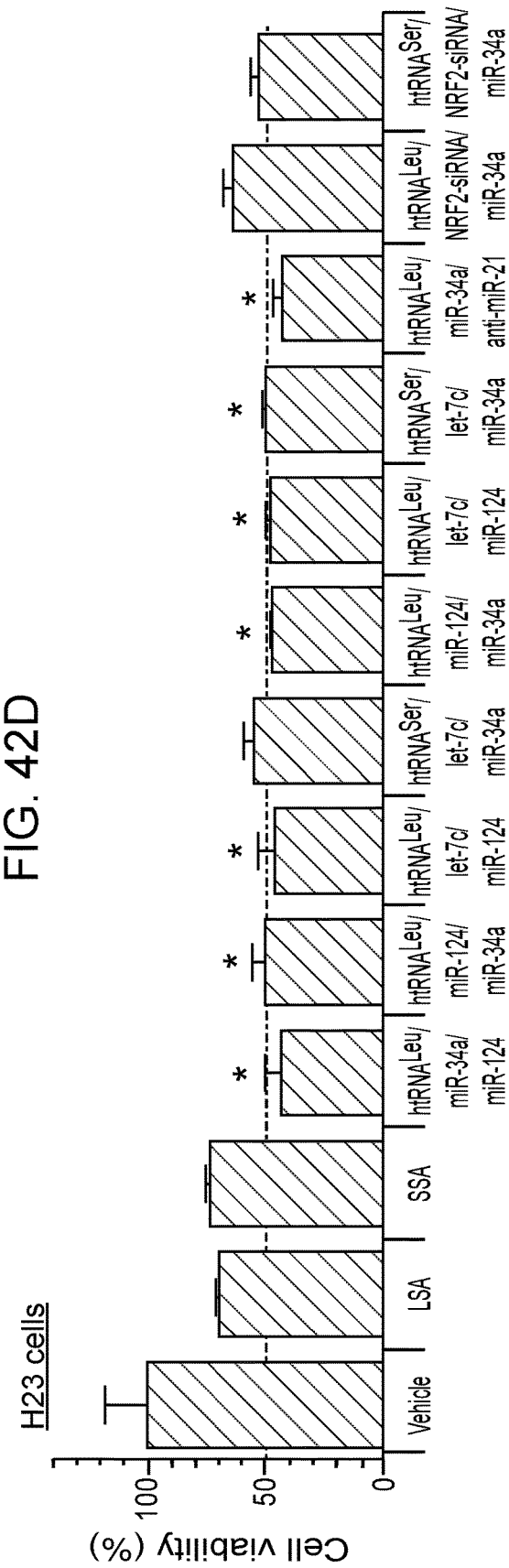
Figure 42E:
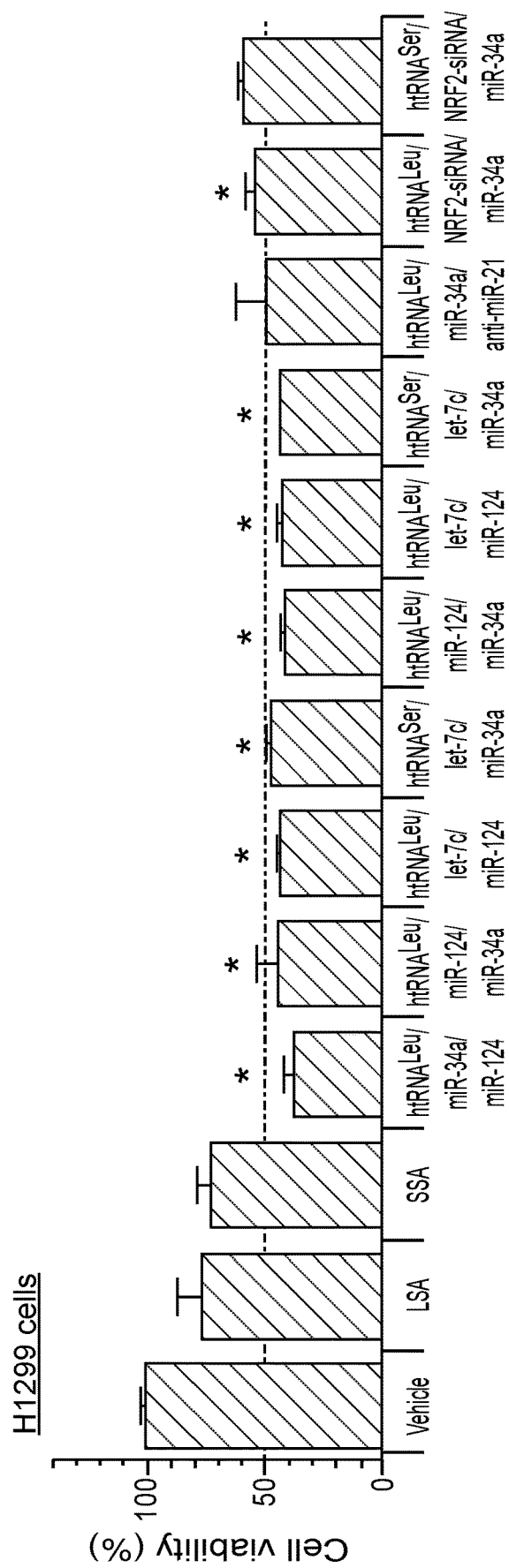
Figure 43:
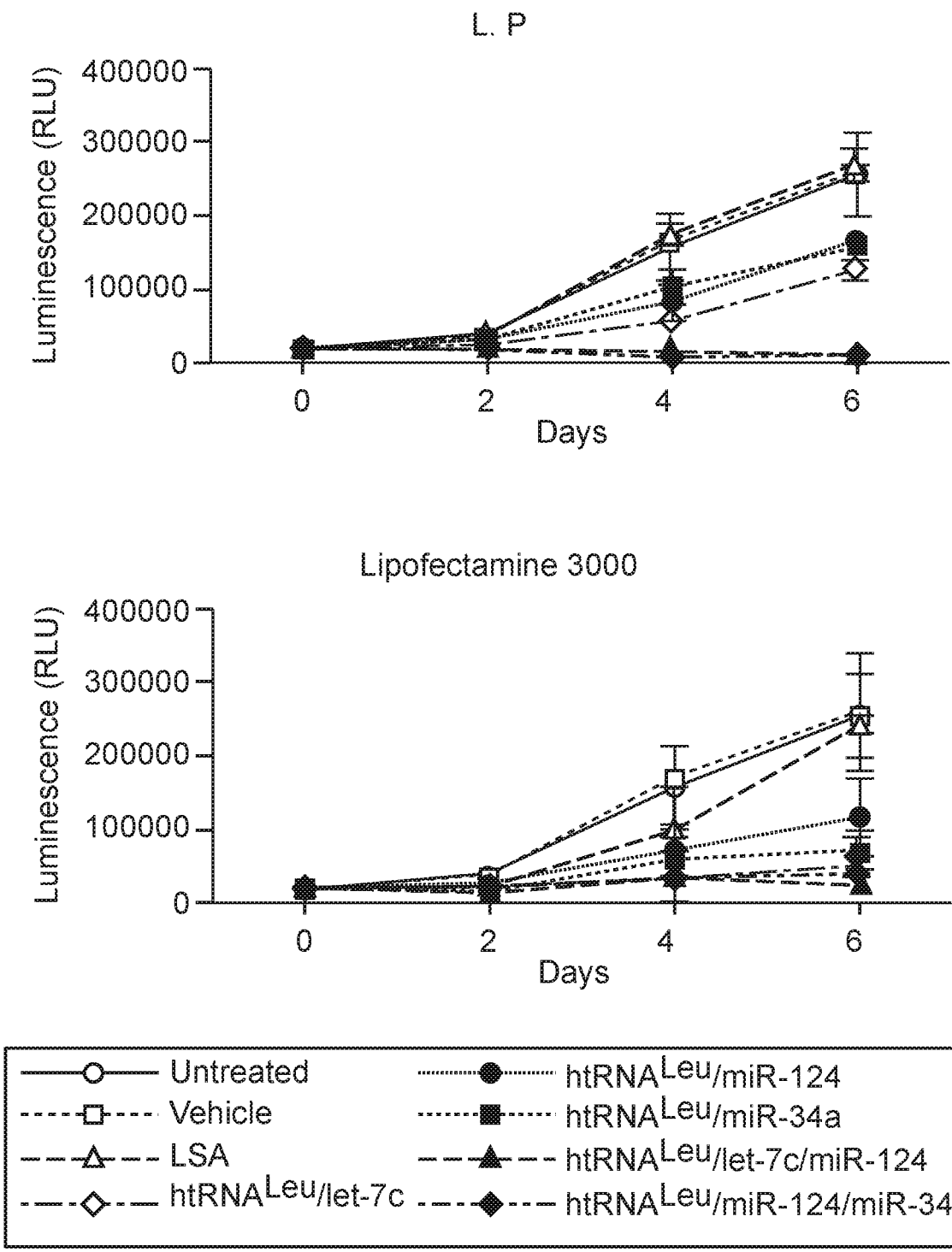
FIG. 43 illustrates cell proliferation measured by ATP luminescent assay of A549 cells transfected with lipopolyplex (LPP) or Lipofectamine 3000 loaded with ncRNA.
Figure 44:
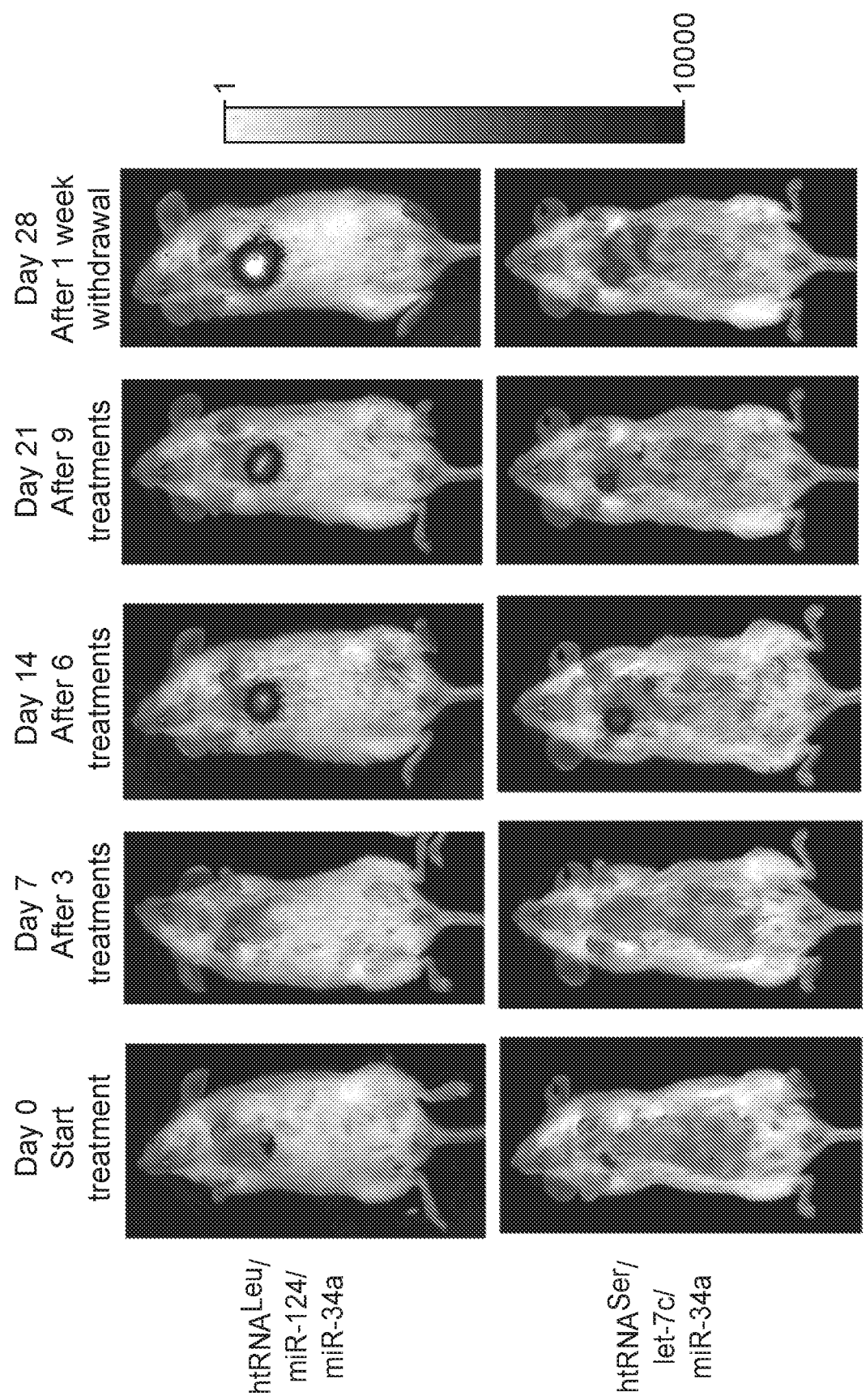
FIG. 44 illustrates treatment of mice having lung tumor burden. Mice were inoculated with luciferase expressing A459 cells through the tail vein, imaged with D-luciferin once a week, and began treatment when signal is visible. The mice were treated with LPP loaded with 30 ng ncRNA in the tail vein three times a week for three weeks. After the third week the treatment was withdrawn.

We thus assessed and compared the anti-proliferation activities of these recombinant CO-BERAs against human NSCLC cells. A panel of five different NSCLC cell lines, namely A549, H1975, H23, H1650, and H1299, was chosen to represent a variety of genetic backgrounds and simulate the heterogeneity of NSCLC. Cell variability was determined at 72 h after transfection with 15 nM of individual CO-BERAs, control tRNA (namely LSA and SSA), or vehicle. Our data (FIG. 42a-e) showed that all CO-BERAs showed remarkable anti-proliferation activities in these NSCLC cell lines, as compared to vehicle and tRNA controls. The same CO-BERA exhibited variable levels of suppression of the viability of different cell lines, while different CO-BERAs demonstrated variable degrees of inhibition of the same cell line (FIG. 42). Among them htRNA$^{Leu}$/miR-34a/miR-124 and htRNA$^{Leu}$/let-7c/miR-124 consistently exhibited the greatest extents of anti-proliferation activities against all NSCLC cell lines (e.g., >80% inhibition of A549 cells, and >50% suppression of all others), which may be pursued for future studies.

Discussion

A new microbial fermentation-based method was established in this study which for the first time achieved high-level heterogeneous expression of novel long ncRNA molecules around 300 nt in length, namely CO-BERAs, carrying two small RNAs warheads. CO-BERAs were designed by utilizing the unique stable tRNA/pre-miR-34a scaffold, which we identified recently (Chen et al. 2015; Ho et al. 2018), to assemble another human pre-miRNA for the accommodation of additional small RNAs for multi-targeting purposes. All ten CO-BERAs, consisting of different combinations of NRF2-siRNA, miR-34a, miR-124, let-7c, and anti-miR-21, were successfully expressed in the common E. coli strain HST08, each accounting for greater than 40% of total bacterial RNA. These small RNAs were chosen for their tumor suppressive properties in NSCLC, and our results suggest that this approach may be employed to accommodate other small RNAs of interest. The majority of recombinant CO-BERAs could be purified to a high degree of homogeneity, generally greater than 99% pure as quantified by HPLC and less than 3 EU/μg RNA endotoxin activity as determined by Limulus Amebocyte Lysate kinetic assay, through single-run strong anion-exchange FPLC method while some others required re-purification and thus showed variable overall yields. While biologic CO-BERAs exhibited potent anti-proliferative activities against a panel of human NSCLC cell lines, further studies are highly warranted to define their multi-targeting mechanisms and effectiveness in controlling tumor progression in animal models.

Bioengineered or recombinant RNA molecules as well as CO-BERAs described in this study are made and folded in living cells, distinguished from chemo-engineered RNA mimics with extensive and various modifications (Bramsen and Kjems 2012; Ho and Yu 2016; Khvorova and Watts 2017; Yu et al. 2019) that have been dominating RNA research and drug development. Interestingly, protein research has been directly ruled by bioengineered or recombinant proteins produced and folded in living cells rather than synthetic polypeptides or proteins, which has proved to be extremely successful in understanding protein structures and functions and developing novel protein therapeutics (Leader et al. 2008). It is also noted that synthetic DNAs or genes, which has become popular in genetic research (Schindler et al. 2018), are actually not comprised of any chemical modifications. Therefore, there is a need to develop novel technologies, especially microbial fermentation based methods, for the production of biologic RNA molecules (Ho and Yu 2016; Pereira et al. 2017; Yu et al. 2019) that allow for cellular machineries to recognize and perform post-transcriptional modification and processing to necessary structures and folding. Indeed, recombinant RNAs or BERAs have none or just minimal post-transcriptional modifications, such as pseudouridine (Gaudin et al. 2003; Li et al. 2015; Nelissen et al. 2012; Ponchon et al. 2009; Ponchon and Dardel 2007; Ranaei-Siadat et al. 2014; Wang et al. 2015) which are necessary to resemble natural RNAs and pose intrinsic secondary and high-order structures. Furthermore, bioengineered RNA molecules produced heterogeneously in microbial fermentation have been demonstrated to be biologically functional in vitro and in vivo by various studies (Chen et al. 2015; Ho et al. 2018; Jian et al. 2017; Jilek et al., 2019; Li et al. 2014, 2015, 2018, 2019; Liu et al. 2010; Nelissen et al. 2012; Paige et al. 2011, 2012; Pereira et al. 2016a, 2016b; Pitulle et al. 1995; Tu et al. 2019; Wang et al. 2015; Zhang et al. 2009; Zhao et al. 2016). In addition, although we cannot have a direct comparison of the costs in producing the same amounts of equally pure (e.g., >98%) chemo- and bio-engineered RNA agents, RNA bioengineering technology is proved to be cost-effective in consistent large-scale production of high-purity target RNAi molecules for research and development (Yu et al. 2019).

In this study we were able to achieve consistent, high-level expression of long ncRNA molecules around 300 nt in length via bacterial fermentation as previous research only offered ncRNAs less than 260 nt. The approach also allowed us to assemble two targeted small RNAs into a single long CO-BERA that may be employed for multi-targeting. Five warhead small RNAs, miR-34a, miR-124, let-7c, NRF2-siRNA, and anti-miR-21, were selected for their anti-tumor activities in NSCLC. Tumor suppressive miRNAs, miR-124, miR-34a and let-7c that target many oncogenes such as STAT3, CDK4/6, and RAS (Hatziapostolou et al. 2011; Johnson et al. 2005; Sun et al. 2008) are commonly dysregulated in NSCLC tissues or cells due to chromosomal aberrations or methylations (Hermeking 2010; Lin et al. 2010). In contrast, miR-21 that targets tumor suppressive genes such as PTEN and PDCD4 (Asangani et al. 2008; Meng et al. 2007) is usually overexpressed in NSCLC. Nuclear factor erythroid-2-related factor-2 (NRF2) is constitutively activated in NSCLC through a variety of mechanisms and plays an important role in cell proliferation and chemosensitivity (Bar-Peled et al. 2017; Yamadori et al. 2012). Restoration of tumor suppressive miRNAs and inhibition of tumor promoting RNAs through miRNA and antagomir agents, respectively, represent new strategies to treat cancer. Indeed, these CO-BERAs showed strong anti-proliferative activities against all human NSCLC cell lines tested, whereas the underlying multi-targeting mechanisms warrant further verification.

As each CO-BERA accounted for greater than 40% of total bacterial RNA, individual CO-BERAs led to variable amounts of total RNA from the same volume of microbial fermentation, which may be related to CO-BERAs' structures, stabilities, and biological properties. An interesting observation is that, besides the docked small RNAs, tRNA seems to influence the yield of total RNA. Six CO-BERAs were produced with a leucine tRNA scaffold and four with serine tRNA. The average amount of total RNA extracted for the leucine tRNA-assembled CO-BERAs was 29.8 mg/L bacterial culture while the average amount for the serine tRNA-containing CO-BERAs was 17.5 mg/L. This is presumably due to the difference in their stabilities and/or possible toxicities to host bacteria as CO-BERAs are accumulated in E. coli. Furthermore, the order of small RNAs in a CO-BERA does not seem to affect the yield of total RNA as htRNA$^{Leu}$/miR-34a/miR-124 and htRNA$^{Leu}$/miR-124/miR-34a offered similar amounts of total RNAs per liter bacterial culture. Understanding the impact of different factors and their underlying mechanisms would facilitate improvement of RNA bioengineering technology and production of CO-BERAs.

Purification of CO-BERAs was achieved by using single or multi-column FPLC methods. Most CO-BERAs were 99% pure after single-run FPLC separation, yielding multi-milligrams of ready-to-use CO-BERAs from one liter of bacterial culture. As others required further purification on additional column, their overall yields were also lower. An extra band was obvious in the urea-PAGE gel in some of the less pure CO-BERAs, which was not visible in the untransformed E. coli. This band might represent an altered form of CO-BERA such as a truncated, post-transcriptionally modified, or alternately-folded specie, or simply a bacterial RNA that is upregulated due to the transformation with CO-BERA expression plasmid. Further investigation, such as RNA sequencing, may be needed to identify the nature of such "impurities". Alternative methods may be explored or current methods may be refined to yield purer products required for more extensive structural and functional studies.

In summary, we have established a new approach to produce novel single ncRNA molecule around 300 nt in length bearing multiple warhead small RNAs that holds promise for multi-targeting. This method can be readily adapted for the production of milligram quantities of target CO-BERAs from one liter of bacterial culture within a few days. Most importantly, CO-BERAs are produced and folded in living cells and thus may better capture the properties of cellular RNAs. As such, this unique multiplexing of biologic RNAs shall be an invaluable addition to current tools for broad biomedical research including but not limited to the investigation of cellular regulatory mechanisms and development of ncRNA therapeutics.

REFERENCES FOR EXAMPLE 4

Alegre F, Ormonde A R, Snider K M, Woolard K, Yu A M, Wittenburg L A (2018) A genetically engineered microRNA-34a prodrug demonstrates anti-tumor activity in a canine model of osteosarcoma. PLoS One 13(12): e0209941
Ambros V (2004) The functions of animal microRNAs. Nature 431(7006):350-5
Asangani I A, Rasheed S A, Nikolova D A, Leupold J H, Colburn N H, Post S, Allgayer H (2008) MicroRNA-21

(miR-21) post-transcriptionally downregulates tumor suppressor Pdcd4 and stimulates invasion, intravasation and metastasis in colorectal cancer. Oncogene 27(15): 2128-36

Bar-Peled L, Kemper E K, Suciu R M, Vinogradova E V, Backus K M, Horning B D, Paul T A, Ichu T A, Svensson R U, Olucha J, Chang M W, Kok B P, Zhu Z, Ihle N T, Dix M M, Jiang P, Hayward M M, Saez E, Shaw R J, Cravatt B F (2017) Chemical proteomics identifies druggable vulnerabilities in a genetically defined cancer. Cell 171(3):696-709 e23

Bramsen J B, Kjems J (2012) Development of therapeutic-grade small interfering RNAs by chemical engineering. Front Genet 3:154

Chen Q X, Wang W P, Zeng S, Urayama S, Yu A M (2015) A general approach to high-yield biosynthesis of chimeric RNAs bearing various types of functional small RNAs for broad applications. Nucleic Acids Res 43(7):3857-69

Esteller M (2011) Non-coding RNAs in human disease. Nat Rev Genet 12(12):861-74

Gaudin C, Nonin-Lecomte S, Tisné C, Corvaisier S, Bordeau V, Dardel F, Felden B (2003) The tRNA-like domains of E. coli and A. aeolicus transfer-messenger RNA: structural and functional studies. J Mol Biol 331(2):457-471

Hatziapostolou M, Polytarchou C, Aggelidou E, Drakaki A, Poultsides G A, Jaeger S A, Ogata H, Karin M, Struhl K, Hadzopoulou-Cladaras M, Iliopoulos D (2011) An HNF4a-miRNA inflammatory feedback circuit regulates hepatocellular oncogenesis. Cell 147(6):1233-47

Hermeking H (2010) The miR-34 family in cancer and apoptosis. Cell Death Differ 17(2):193-9

Ho P Y, Duan Z, Batra N, Jilek J L, Tu M J, Qiu J X, Hu Z, Wun T, Lara P N, DeVere White R W, Chen H W, Yu A M (2018) Bioengineered noncoding RNAs selectively change cellular miRNome profiles for cancer therapy. J Pharmacol Exp Ther 365(3):494-506

Ho P Y, Yu A M (2016) Bioengineering of noncoding RNAs for research agents and therapeutics. Wiley Interdiscip Rev RNA 7(2):186-97

Hutchinson C R (1998) Combinatorial biosynthesis for new drug discovery. Curr Opin Microbiol 1(3):319-29

Jian C, Tu M J, Ho P Y, Duan Z, Zhang Q, Qiu J X, DeVere White R W, Wun T, Lara P N, Lam K S, Yu A X, Yu A M (2017) Co-targeting of DNA, RNA, and protein molecules provides optimal outcomes for treating osteosarcoma and pulmonary metastasis in spontaneous and experimental metastasis mouse models. Oncotarget 8(19): 30742-30755

Jilek J L, Zhang Q Y, Tu M J, Ho P Y, Duan Z, Qiu J X, Yu A M (2019) Bioengineered let-7c inhibits orthotopic hepatocellular carcinoma and improves overall survival with minimal immunogenicity. Mol Ther Nucleic Acids 14:498-508

Johnson S M, Grosshans H, Shingara J, Byrom M, Jarvis R, Cheng A, Labourier E, Reinert K L, Brown D, Slack F J (2005) RAS is regulated by the let-7 microRNA family. Cell 120(5):635-47

Khvorova A, Watts J K (2017) The chemical evolution of oligonucleotide therapies of clinical utility. Nat Biotechnol 35(3):238-248

Knight V, Sanglier J J, DiTullio D, Braccili S, Bonner P, Waters J, Hughes D, Zhang L (2003) Diversifying microbial natural products for drug discovery. Appl Microbiol Biotechnol 62(5-6):446-58

Leader B, Baca Q J, Golan D E (2008) Protein therapeutics: a summary and pharmacological classification. Nat Rev Drug Discov 7(1):21-39

Levin A A (2019) Treating disease at the RNA level with oligonucleotides. N Engl J Med 380(1):57-70

Li M M, Addepalli B, Tu M J, Chen Q X, Wang W P, Limbach P A, LaSalle J M, Zeng S, Huang M, Yu A M (2015) Chimeric microRNA-1291 biosynthesized efficiently in Escherichia coli is effective to reduce target gene expression in human carcinoma cells and improve chemosensitivity. Drug Metab Dispos 43(7):1129-36

Li M M, Wang W P, Wu W J, Huang M, Yu A M (2014) Rapid production of novel pre-microRNA agent hsa-mir-27b in Escherichia coli using recombinant RNA technology for functional studies in mammalian cells. Drug Metab Dispos 42(11):1791-5

Li P C, Tu M J, Ho P Y, Jilek J L, Duan Z, Zhang Q Y, Yu A X, Yu A M (2018) Bioengineered NRF2-siRNA is effective to interfere with NRF2 pathways and improve chemosensitivity of human cancer cells. Drug Metab Dispos 46(1):2-10

Li X, Tian Y, Tu M J, Ho P Y, Batra N, Yu A M (2019) Bioengineered miR-27b-3p and miR-328-3p modulate drug metabolism and disposition via the regulation of target ADME gene expression. Acta Pharm Sin B [ePub ahead of print]

Lin P Y, Yu S L, Yang P C (2010) MicroRNA in lung cancer. Br J Cancer 103(8):1144-8 Liu Y, Stepanov V G, Strych U, Willson R C, Jackson G W, Fox G E (2010) DNAzyme-mediated recovery of small recombinant RNAs from a 5S rRNA-derived chimera expressed in Escherichia coli. BMC biotechnology 10:85

Liu Y P, Berkhout B (2011) miRNA cassettes in viral vectors: problems and solutions. Biochimica et biophysica acta 1809(11-12):732-45

Meng F, Henson R, Wehbe-Janek H, Ghoshal K, Jacob S T, Patel T (2007) MicroRNA-21 regulates expression of the PTEN tumor suppressor gene in human hepatocellular cancer. Gastroenterology 133(2):647-58

Nelissen F H T, Leunissen E H P, van de Laar L, Tessari M, Heus H A, Wijmenga S S (2012) Fast production of homogeneous recombinant RNA-towards large-scale production of RNA. Nucleic Acids Res 40(13)

Paige J S, Nguyen-Duc T, Song W, Jaffrey S R (2012) Fluorescence imaging of cellular metabolites with RNA. Science 335(6073):1194

Paige J S, Wu K Y, Jaffrey S R (2011) RNA mimics of green fluorescent protein. Science 333(6042):642-6

Pereira P, Pedro A Q, Queiroz J A, Figueiras A R, Sousa F (2017) New insights for therapeutic recombinant human miRNAs heterologous production: Rhodovolum sulfidophilum vs Escherichia coli. Bioengineered 8(5):670-677

Pereira P, Pedro A Q, Tomas J, Maia C J, Queiroz J A, Figueiras A, Sousa F (2016a) Advances in time course extracellular production of human pre-miR-29b from Rhodovulum sulfidophilum. Appl Microbiol Biotechnol 100(8):3723-34

Pereira P A, Tomas J F, Queiroz J A, Figueiras A R, Sousa F (2016b) Recombinant pre-miR-29b for Alzheimer s disease therapeutics. Sci Rep 6:19946

Pitulle C, Hedenstierna K O, Fox G E (1995) A novel approach for monitoring genetically engineered microorganisms by using artificial, stable RNAs. Appl Environ Microbiol 61(10):3661-6

Ponchon L, Beauvais G, Nonin-Lecomte S, Dardel F (2009) A generic protocol for the expression and purification of recombinant RNA in *Escherichia coli* using a tRNA scaffold. Nat Protoc 4(6):947-59

Ponchon L, Dardel F (2007) Recombinant RNA technology: the tRNA scaffold. Nat Methods 4(7):571-6

Ranaei-Siadat E, Merigoux C, Seijo B, Ponchon L, Saliou J M, Bemauer J, Sanglier-Cianferani S, Dardel F, Vachette P, Nonin-Lecomte S (2014) In vivo tmRNA protection by SmpB and pre-ribosome binding conformation in solution. RNA 20(10):1607-20

Rosano G L, Ceccarelli E A (2014) Recombinant protein expression in *Escherichia coli*: advances and challenges. Front Microbiol 5:172

Schindler D, Dai J, Cai Y (2018) Synthetic genomics: a new venture to dissect genome fundamentals and engineer new functions. Curr Opin Chem Biol 46:56-62

Sun F, Fu H, Liu Q, Tie Y, Zhu J, Xing R, Sun Z, Zheng X (2008) Downregulation of CCND1 and CDK6 by miR-34a induces cell cycle arrest. FEBS letters 582(10):1564-8

Tu M J, Ho P Y, Zhang Q Y, Jian C, Qiu J X, Kim E J, Bold R J, Gonzalez F J, Bi H, Yu A M (2019) Bioengineered miRNA-1291 prodrug therapy in pancreatic cancer cells and patient-derived xenograft mouse models. Cancer Lett 442:82-90

Wang W P, Ho P Y, Chen Q X, Addepalli B, Limbach P A, Li M M, Wu W J, Jilek J L, Qiu J X, Zhang H J, Li T, Wun T, White R D, Lam K S, Yu A M (2015) Bioengineering novel chimeric microRNA-34a for prodrug cancer therapy: High-yield expression and purification, and structural and functional characterization. J Pharmacol Exp Ther 354(2):131-41

Yamadori T, Ishii Y, Homma S, Morishima Y, Kurishima K, Itoh K, Yamamoto M, Minami Y, Noguchi M, Hizawa N (2012) Molecular mechanisms for the regulation of Nrf2-mediated cell proliferation in non-small-cell lung cancers. Oncogene 31(45):4768-77

Yu A M, Jian C, Yu A H, Tu M J (2019) RNA therapy: Are we using the right molecules? Pharmacol Ther 196:91-104

Zhang K, Lu X, Li Y, Jiang X, Liu L, Wang H (2019) New technologies provide more metabolic engineering strategies for bioethanol production in *Zymomonas mobilis*. Appl Microbiol Biotechnol Zhang X, Potty A S, Jackson G W, Stepanov V, Tang A, Liu Y, Kourentzi K, Strych U, Fox G E, Willson R C (2009) Engineered 5S ribosomal RNAs displaying aptamers recognizing vascular endothelial growth factor and malachite green. J Mol Recognit 22(2):154-61

Zhao Y, Tu M J, Wang W P, Qiu J X, Yu A X, Yu A M (2016) Genetically engineered pre-microRNA-34a prodrug suppresses orthotopic osteosarcoma xenograft tumor growth via the induction of apoptosis and cell cycle arrest. Sci Rep 6:26611

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polynucleotide comprising a tRNA operably linked to a first pre-microRNA 34a (pre-miRNA-34a) and a second pre-miRNA-34a, wherein all or part of the stem-loop anticodon of the tRNA is replaced with the first pre-miRNA-34a and the second pre-miRNA-34a, wherein the first pre-miRNA-34a is operably linked to a first inserted RNA molecule, and the second pre-miRNA-34a is operably linked to a second inserted RNA molecule, wherein the first and second inserted RNA molecules are heterologous to the first pre-miRNA-34a and the second pre-miRNA-34a, wherein the first inserted RNA molecule is inserted at, abutted with, or operably linked to:

the 5' end of the first pre-miRNA-34a;
the 3' end of the first pre-miRNA-34a;
of a dicer or RNase cleavage site of the first pre-miRNA-34a; or
3' of a dicer or RNase cleavage site of the first pre-miRNA-34a; and wherein the second inserted RNA molecule is inserted at, abutted with, or operably linked to:

the 5' end of the second pre-miRNA-34a;
the 3' end of the second pre-miRNA-34a;
of a dicer or RNase cleavage site of the second pre-miRNA-34a; or
3' of a dicer or RNase cleavage site of the second pre-miRNA-34a.

2. The polynucleotide of claim 1, wherein the polynucleotide is from 275 nucleotides to 400 nucleotides in length.

3. The polynucleotide of claim 1, wherein the tRNA is a mammalian tRNA.

4. The polynucleotide of claim 1, wherein the first pre-miRNA-34a and the second pre-miRNA-34a are human pre-miRNA-34a molecules.

5. The polynucleotide of claim 1, wherein the inserted RNA is selected from the group consisting of a noncoding RNA (ncRNA), mature microRNA (miRNA), a small interfering RNA (siRNA), a short hairpin RNA (shRNA), a Piwi-interacting RNA (piRNA), a small nuclear RNA (snRNA), a small nucleolar RNA (snoRNA), a guide RNA (gRNA), an antisense RNA (asRNA), a small activating RNA (saRNA), a catalytic RNA, a riboswitch, an RNA aptamer.

6. The polynucleotide of claim 1, wherein the first or second inserted RNA is a mature miRNA.

7. The polynucleotide of claim 1, wherein the first and second inserted RNA comprise two or more mature miRNA independently selected from the group consisting of: let-7c, miR-298, miR-216, miR-34a, miR-124, miR-328, miR-144, miR-126, miR-16, miR-18, miR-125a, miR-195, miR-199a, miR-200, miR-224, miR-1291, miR-429, miR-148, miR-144, miR-1, miR-133, miR-888, miR-6775, miR-374, miR-92, miR-1180, miR-218, miR-7, miR-378, miR-17, miR-18a, miR-22, miR-122, miR-30b, miR-449, miR-506, miR-98, miR-4458, miR-206, miR-519, miR-93, miR-106, miR-373, and miR-520.

8. The polynucleotide of claim 1, wherein the first and second inserted RNA are mature miRNA independently selected from the group consisting of: miR-1291, miR-34, miR-124, miR-200, and miR-216.

9. The polynucleotide of claim 1, further wherein the tRNA and/or pre-miRNA are operably linked to one or more aptamers, small activating RNAs (saRNAs), or catalytic RNAs.

10. An expression cassette comprising the polynucleotide of claim 1.

11. A liposome or a nanoparticle comprising the polynucleotide of claim 1 or an expression cassette comprising the polynucleotide.

12. A viral vector comprising the polynucleotide of claim 1 or an expression cassette comprising the polynucleotide.

13. A host cell transfected or transformed with the polynucleotide of claim 1 or an expression cassette comprising the polynucleotide.

14. A method of treating non-small cell lung cancer (NSCLC) in a subject in need thereof, the method comprising administering to the subject a therapeutically effective amount of the polynucleotide of claim 1, wherein the tRNA is htRNA$^{Leu}$, and wherein the first and second inserted RNA molecules are: miR-34a and miR-124; or let-7c and miR-124.

15. The polynucleotide of claim 1, wherein the polynucleotide comprises a nucleotide sequence selected from the group consisting of SEQ ID NOS:183-192, or a nucleotide sequence having at least 90% sequence identity to a nucleotide sequence selected from the group consisting of SEQ ID NOS:183-192.

16. The polynucleotide of claim 1, wherein the first and second inserted RNA are independently selected from the group consisting of anti-miR-21-5p, miR-124, miR-124-3p, miR-34a, pre-miR-34a, miR-34a-5p, let-7c-5p, let-7c, miR-1241, and NRF2-siRNA.

* * * * *

UNITED STATES PATENT AND TRADEMARK OFFICE
CERTIFICATE OF CORRECTION

PATENT NO. : 11,946,049 B2  
APPLICATION NO. : 17/056203  
DATED : April 2, 2024  
INVENTOR(S) : Aiming Yu et al.

Page 1 of 5

It is certified that error appears in the above-identified patent and that said Letters Patent is hereby corrected as shown below:

In the Drawings

On Sheet 19 of 87, in figure 8D, Line 13, delete "Surival" and insert -- Survival --.

On Sheet 23 of 87, in figure 11A, Line 13, delete "innoculation" and insert -- inoculation --.

Figure 17:
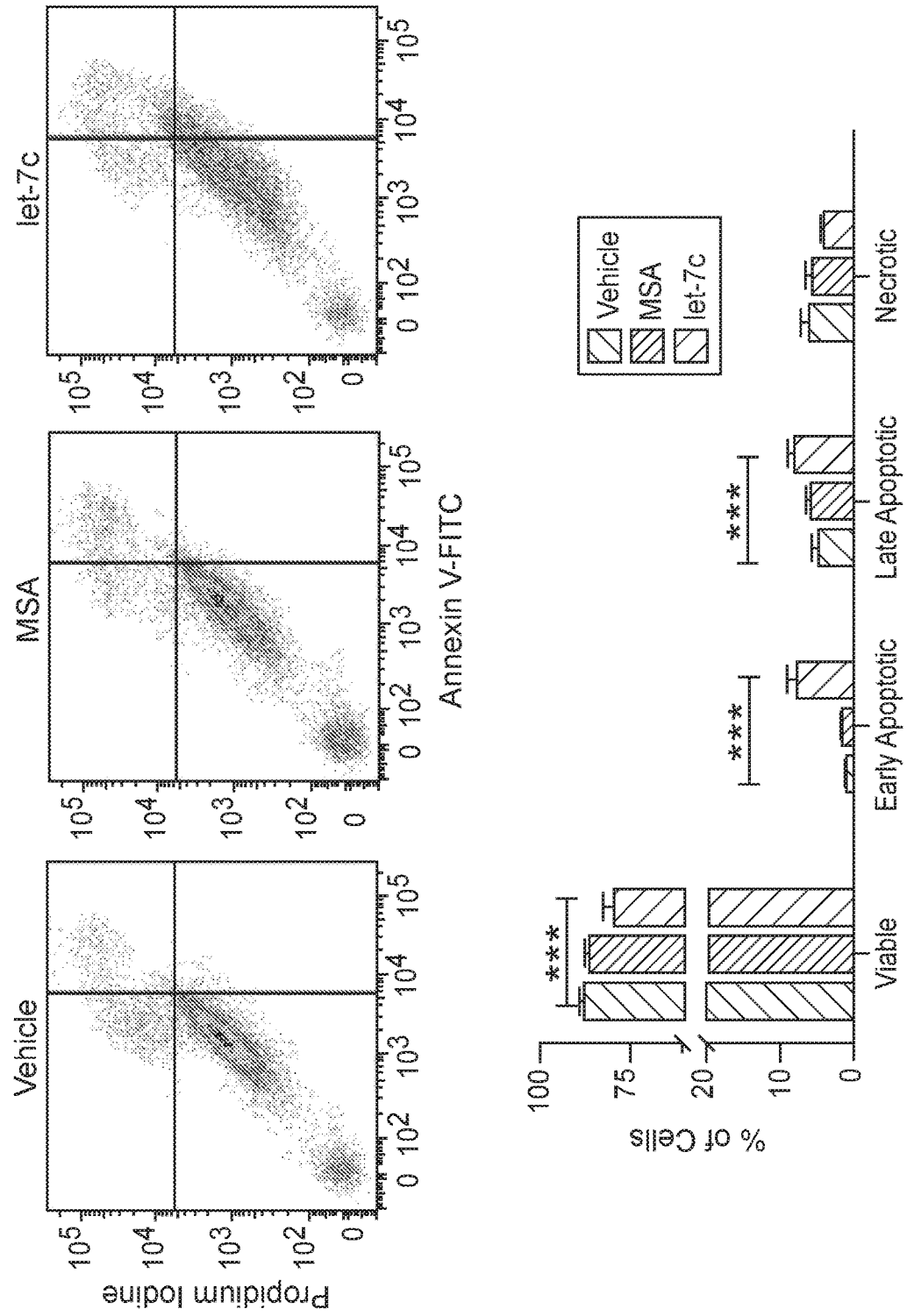
FIG. 17 illustrates apoptotic cell death is significantly induced by bioengineered let-7c. Sk-Hep-1 and Huh7 cells were transfected with 5 nM of MSA or let-7c for 48 h, stained with propidium iodide and Annexin V-FITC, and counted by a flow cytometer with a total cell gate of 10,000 events. A significant shift of the total population towards early and late apoptotic cells was observed, while total necrotic population showed no difference. Values are mean±SD (N=3 per group). *P<0.05, P<0.01, *P<0.001 (1-way ANOVA with Bonferroni's post-hoc test).
Figure 18A:
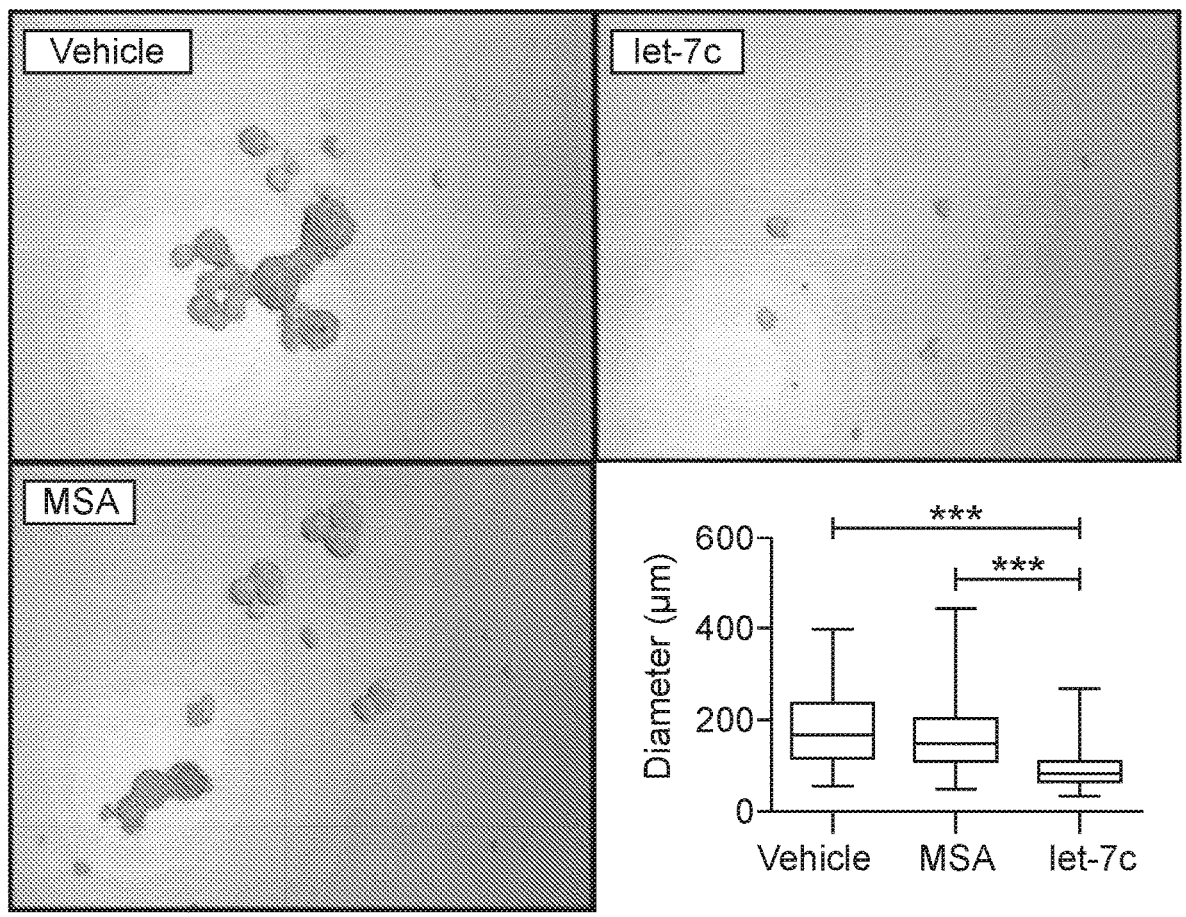
FIG. 18 illustrates bioengineered let-7c sharply reduces tumorsphere growth. Following transfection with MSA or let-7c in adherent conditions, an equal number of Huh7 cells were grown in serum-free/ultra-low attachment conditions for 7 days to yield primary tumorspheres. Primary tumorspheres were then digested to single-cell, transfected again, and grown for another 7 days in serum-free/ultra-low attachment conditions to yield secondary tumorspheres. let-7c treatment resulted in smaller primary and secondary tumorspheres. Values are mean±SD (N=3 per group). *P<0.05, P<0.01, *P<0.001 (1-way ANOVA with Bonferroni's post-hoc test).
Figure 18A:
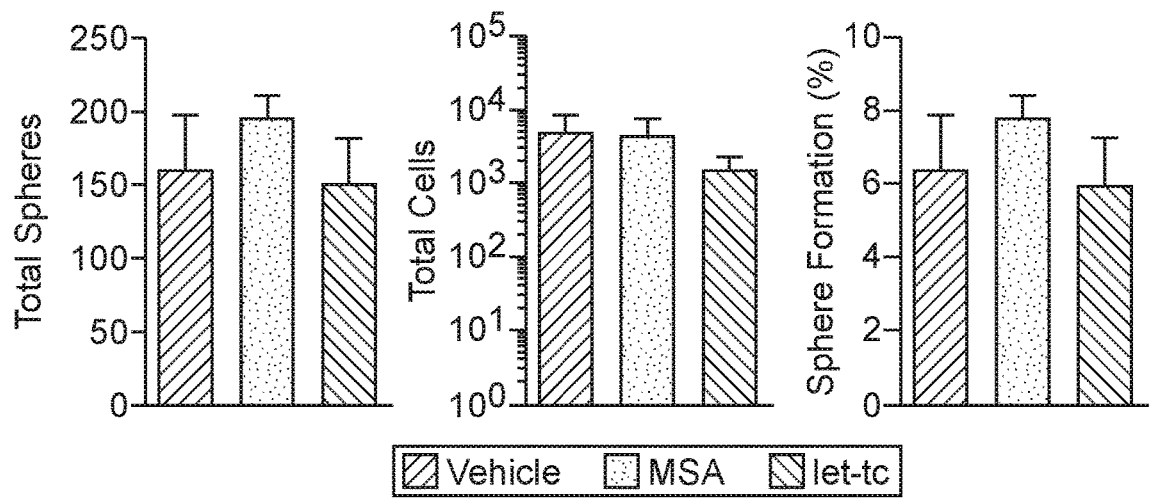
Figure 18B:
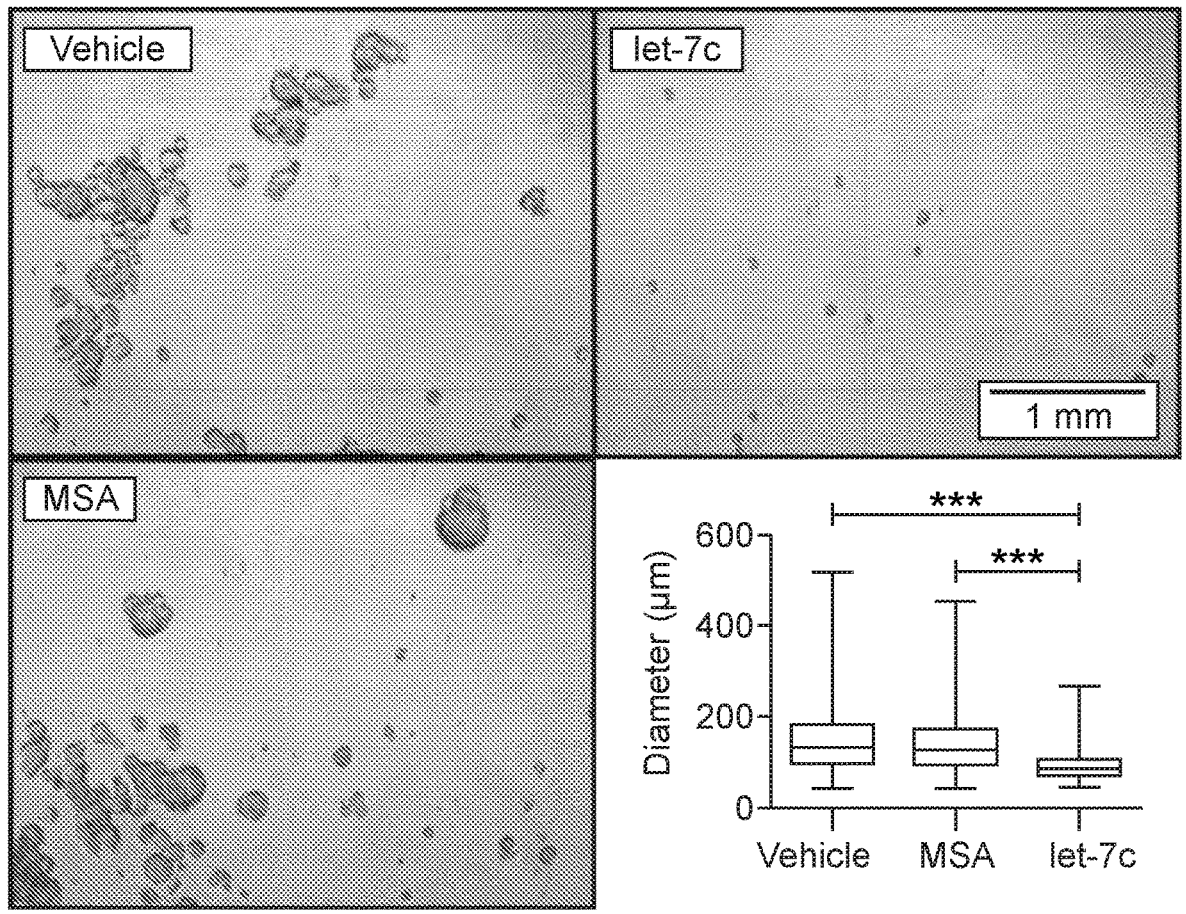
Figure 18B:
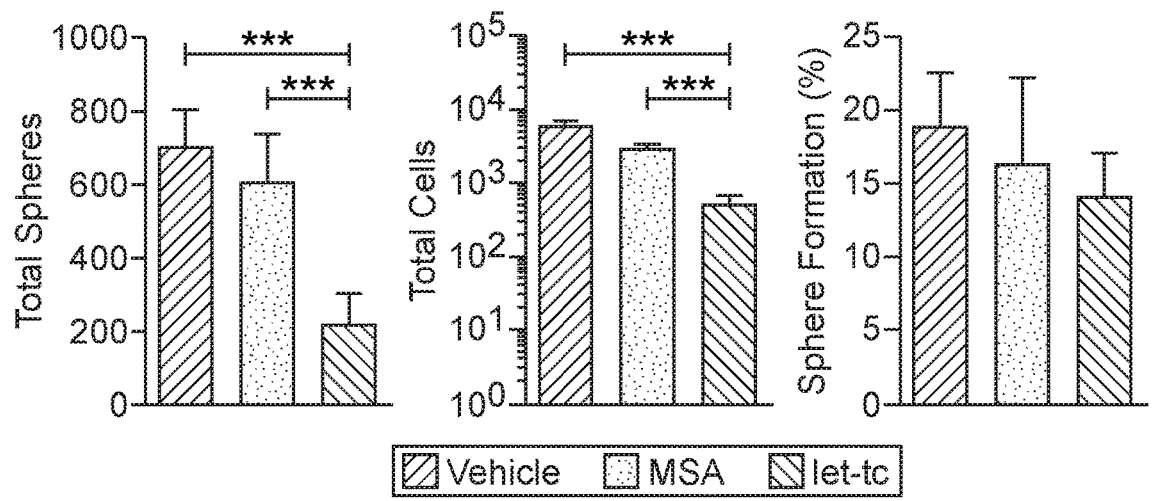

On Sheet 35 of 87, in figure 17, Line 4, delete "Iodine" and insert -- Iodide --.

On Sheet 36 of 87, in figure 17 (Cont.), Line 4, delete "Iodine" and insert -- Iodide --.

On Sheet 44 of 87, in figure 23A, Line 3, delete "Sacrafice" and insert -- Sacrifice --.

On Sheet 45 of 87, in figure 23B, Line 6, delete "(arbtrary" and insert -- (arbitrary --.

Figure 27B:
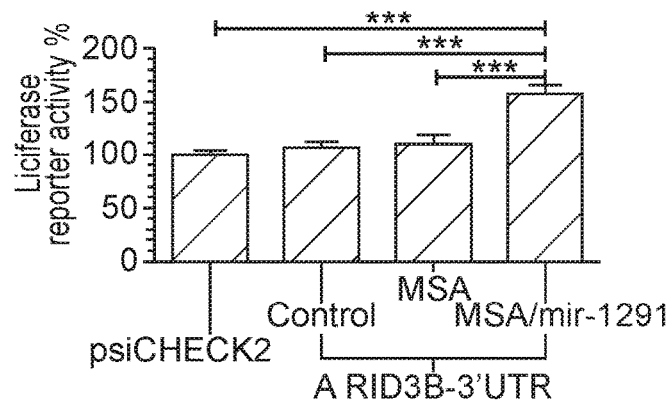
Figure 27C:
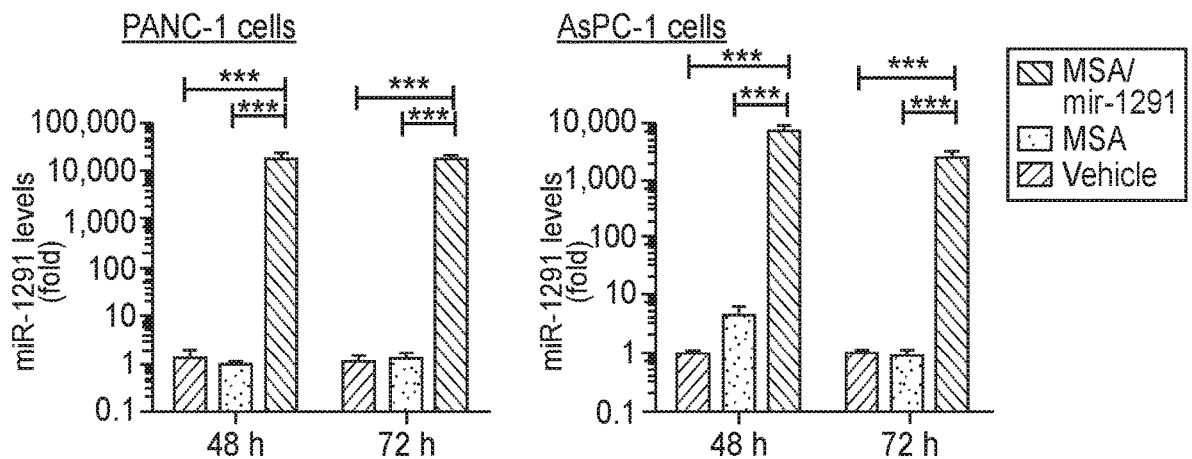
Figure 27D:
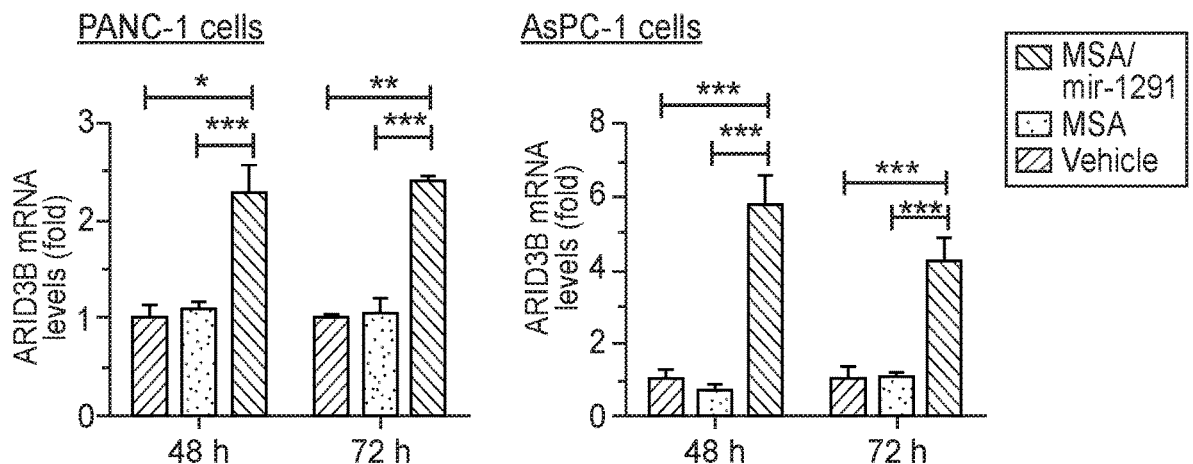
Figure 27E:
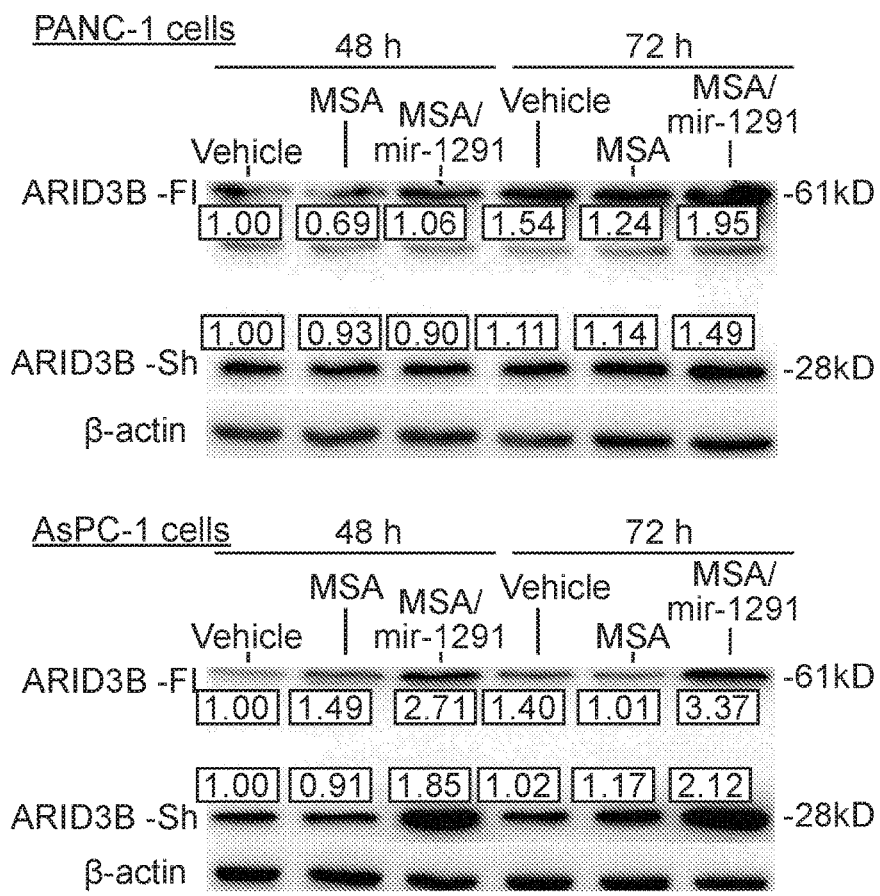
Figure 28A:
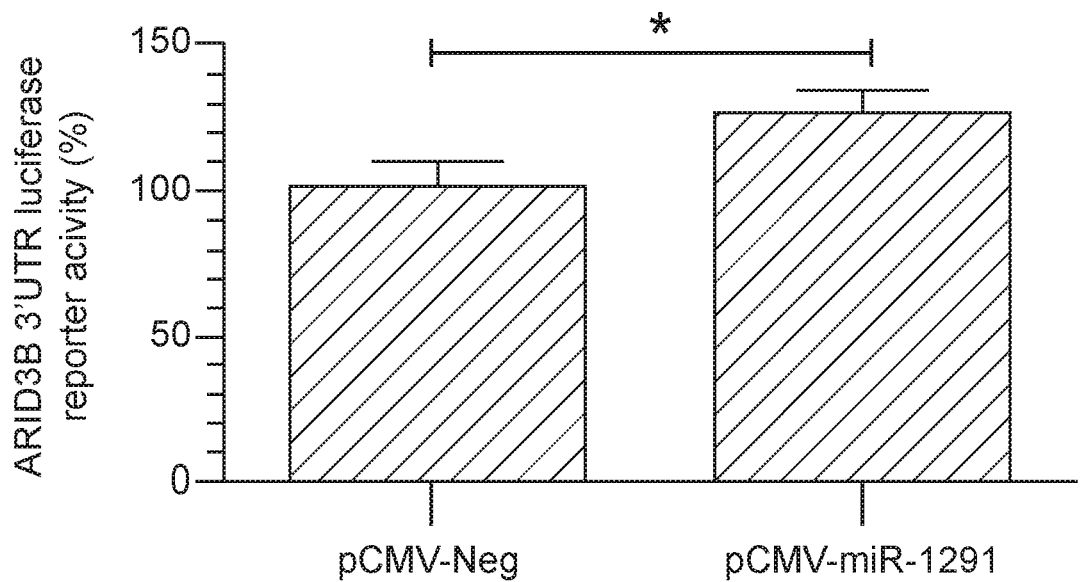
FIGS. 28A-B illustrate that luciferase report assays support the action of miR-1291 on ARID3B 3'UTR. ARID3B 3'UTR-luciferase activities were significantly increased in cells treated with miR-1291 expressing plasmid (A), whereas decreased by miR-1291 antagomir (B). PANC-1 cells were co-transfected with ARID3B-3'UTR luciferase reporter plasmid (psiCHEC2-ARID3B-3'UTR) and miR-1291 expression plasmid (pCMV-miR-1291), miR-1291 antagomir or their corresponding controls. Luciferase activities were determined at 48 h post-transfection. Values are mean±SD (N=3). *P<0.05, compared to the control (unpaired Student's t-test).
Figure 28B:
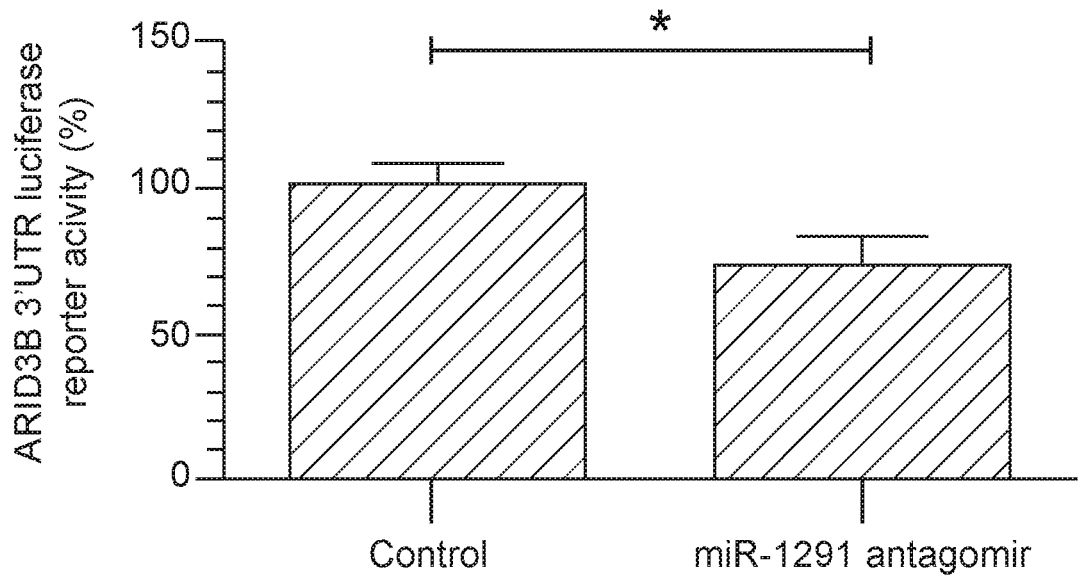

On Sheet 55 of 87, in figure 27B, Line 1, delete "Liciferase" and insert -- Luciferase --.

In the Specification

In Column 1, Line 24, delete "194,123" and insert -- 194, 123 --.

In Column 4, Line 4, delete "sephedex," and insert -- sephadex, --.

In Column 5, Line 23, delete "sephedex," and insert -- sephadex, --.

In Column 6, Line 56, delete "gemcitibine." and insert -- gemcitabine. --.

In Column 8, Line 3, delete "e.g," and insert -- e.g., --.

In Column 8, Line 16, delete "{i.e.," and insert -- (i.e., --.

Signed and Sealed this  
First Day of October, 2024

Katherine Kelly Vidal  
*Director of the United States Patent and Trademark Office*

CERTIFICATE OF CORRECTION (continued)
U.S. Pat. No. 11,946,049 B2

In Column 8, Line 53, delete "ncRNA," and insert -- IncRNA, --.

In Column 11, Line 17, delete "pegaptnib" and insert -- pegaptanib --.

In Column 11, Line 37, delete "Ipp" and insert -- lpp --.

In Column 14, Line 28, delete "let-7c" and insert -- Let-7c --.

In Column 16, Line 15, delete "(psiCHEC2-" and insert -- (psiCHECK2- --.

In Column 16, Line 48, delete "20 µm" and insert -- 20 µm. --.

In Column 18, Line 26, delete "I." and insert -- II. --.

In Column 18, Line 30, delete "B)" and insert -- b) --.

In Column 19, Line 59, delete "GCCC GUAAGGAAG" and insert -- GCCCGUAAGGAAG --.

In Column 20, Line 14, delete "GCCC GUAAGGAAG" and insert -- GCCCGUAAGGAAG --.

In Column 20, Line 37, delete "AGA AGUGCU" and insert -- AGAAGUGCU --.

In Column 21, Lines 6-7, delete "and or" and insert -- and/or --.

In Column 21, Line 26, delete "AGA AGUG" and insert -- AGAAGUG --.

In Column 21, Line 56, delete "CGGA GCCCU" and insert -- CGGAGCCCU --.

In Column 22, Line 17, delete "GGj" and insert -- GG --.

In Column 22, Line 59, delete "and or" and insert -- and/or --.

In Column 23, Line 12, delete "2-O-methyl" and insert -- 2'-O-methyl --.

In Column 23, Line 18, delete "(ddl)," and insert -- (ddI), --.

In Column 23, Line 28, delete "2'-O-methyoxyethyl" and insert -- 2'-O-methoxyethyl --.

In Column 29, Line 6, delete "(MI0003593." and insert -- (MI0003593), --.

In Column 32, Line 60, delete "(MI0014216;" and insert -- (MI0014216), --.

In Column 32, Line 62, delete "(MI0014215;" and insert -- (MI0014215), --.

In Column 43, Line 25, delete "Bl;" and insert -- B1; --.

CERTIFICATE OF CORRECTION (continued)
U.S. Pat. No. 11,946,049 B2

In Column 45, Line 9, delete "1660." and insert -- 1660). --.

In Column 45, Line 10, delete "picomavirus" and insert -- picornavirus --.

In Column 48, Line 57, delete "asialganglioside," and insert -- asialoganglioside, --.

In Column 51, Line 32, delete "15$^{st}$" and insert -- 15$^{th}$ --.

In Column 51, Line 53, delete "cancer" and insert -- cancer. --.

In Column 53, Line 59, delete "napthalenes." and insert -- naphthalenes. --.

In Column 55, Line 51, delete "doxorubincin," and insert -- doxorubicin, --.

In Column 58, Line 29, delete "e.g," and insert -- e.g., --.

In Columns 59-60, Line 26, delete "ERNA" and insert -- tRNA --.

In Columns 59-60, Line 34, delete "ERNA" and insert -- tRNA --.

In Columns 59-60, Line 42, delete "ERNA" and insert -- tRNA --.

In Columns 59-60, Line 54, delete "ERNA" and insert -- tRNA --.

In Columns 67-68, Line 24, delete "ERNA" and insert -- tRNA --.

In Columns 67-68, Line 40, delete "ERNA" and insert -- tRNA --.

In Columns 71-72, Line 12, delete "ERNA" and insert -- tRNA --.

In Columns 73-74, Line 47, delete "ERNA" and insert -- tRNA --.

In Columns 85-86, Line 30, delete "ERNA" and insert -- tRNA --.

In Columns 85-86, Line 35, delete "ERNA" and insert -- tRNA --.

In Columns 85-86, Line 40, delete "ERNA" and insert -- tRNA --.

In Columns 95-96, Line 12, delete "ERNA" and insert -- tRNA --.

In Columns 97-98, Line 44, delete "ERNA" and insert -- tRNA --.

In Columns 97-98, Line 57, delete "ERNA" and insert -- tRNA --.

In Columns 107-108, Line 13, delete "5′tRF_ miR-34a-5p" and insert -- 5′tRF_miR-34a-5p --.

CERTIFICATE OF CORRECTION (continued)
U.S. Pat. No. 11,946,049 B2

In Columns 107-108, Line 21, delete "3′tRF_ miR-34a-5p" and insert -- 3′tRF_miR-34a-5p --.

In Columns 109-110, Line 3, delete "arer eplaced" and insert -- are replaced --.

In Columns 111-112, Line 34, delete "RNA" and insert -- tRNA --.

In Columns 117-118, Line 35, delete "RNA" and insert -- tRNA --.

In Column 123, Line 25, delete "DH5u" and insert -- DH5α --.

In Column 124, Line 34, delete "DH5u" and insert -- DH5α --.

In Column 152, Line 29-30, delete "Rhodovolum" and insert -- Rhodovulum --.

In Column 154, Line 49, delete "equation equation:" and insert -- equation: --.

In Column 154, Line 61, delete "milk/I %" and insert -- milk/1 % --.

In Columns 155-156, Line 54, delete "5′-AACGCTTCACGA ATTTGCGT-3′" and insert -- 5′-AACGCTTCACGAATTTGCGT-3′ --.

In Column 157, Line 27, delete "lPEI/MSA," and insert -- IPEI/MSA, --.

In Column 157, Line 28, delete "1PEI/let-7c" and insert -- IPEI/let-7c --.

In Column 162, Line 55, delete "(RESORCE):" and insert -- (RESOURCE): --.

In Column 167, Line 24, delete "(GIBICO)," and insert -- (GIBCO), --.

In Column 167, Line 36, delete "((Log IC50–X)" and insert -- ((LogIC50–X) --.

In Column 168, Line 11, delete "p-actin" and insert -- β-actin --.

In Column 168, Line 31, delete "lmmunoReseach" and insert -- ImmunoResearch --.

In Column 168, Line 34, delete "Fluor ®" and insert -- Fluor® --.

In Column 168, Line 53, after "Observer.zl" insert -- . --.

In Column 179, Line 38, delete "DH5u" and insert -- DH5α --.

In Column 179, Line 65, delete "Ipswitch," and insert -- Ipswich, --.

In Column 180, Line 4, delete "DH5u" and insert -- DH5α --.

In Column 181, Line 6, delete "Cis" and insert -- $C_{18}$ --.

CERTIFICATE OF CORRECTION (continued)
U.S. Pat. No. 11,946,049 B2

In Columns 183-184, Line 17, delete "nEnrich" and insert -- Enrich --.

In Column 188, Line 51, delete "Rhodovolum" and insert -- Rhodovulum --.

In the Claims

In Column 423, Line 16, in Claim 1, before "of" insert -- 5′ --.

In Column 423, Line 24, in Claim 1, before "of" insert -- 5′ --.

SEQUENCE LISTING

<160> NUMBER OF SEQ ID NOS: 593

<210> SEQ ID NO 1
<211> LENGTH: 118
<212> TYPE: RNA
<213> ORGANISM: Artificial sequence
<220> FEATURE:
<223> OTHER INFORMATION: synthetic sequence

<400> SEQUENCE: 1
gcagcgaugg ccgagugguu aaggcguugg acuaguaauu uacgucgacg gugacgucga    60
ugguugcgga auccaauggg gucucccgc gcagguucga acccugcucg cugcgcca    118

<210> SEQ ID NO 2
<211> LENGTH: 101
<212> TYPE: RNA
<213> ORGANISM: Artificial sequence
<220> FEATURE:
<223> OTHER INFORMATION: synthetic sequence

<400> SEQUENCE: 2
gcagcgaugg ccgagugguu aaggcguugg acugcgacug guuacccggu cgaauccaau    60
ggggucuccc cgcgcagguu cgaacccugc ucgcugcgcc a    101

<210> SEQ ID NO 3
<211> LENGTH: 115
<212> TYPE: RNA
<213> ORGANISM: Artificial sequence
<220> FEATURE:
<223> OTHER INFORMATION: synthetic sequence

<400> SEQUENCE: 3
gcagcgaugg ccgagugguu aaggcguugg acuggcgaua ccagccgaaa ggcccuuggc    60
agcgucaauc caaugggguc uccccgcgca gguucgaacc cugcucgcug cgcca         115

<210> SEQ ID NO 4
<211> LENGTH: 118
<212> TYPE: RNA
<213> ORGANISM: Artificial sequence
<220> FEATURE:
<223> OTHER INFORMATION: synthetic sequence

<400> SEQUENCE: 4
gacgaggugg ccgagugguu aaggcgaugg acuaguaauu uacgucgacg gugacgucga    60
ugguugcgga auccauugug cucugcacgc guggguucga aucccacccu cgucgcca      118

<210> SEQ ID NO 5
<211> LENGTH: 101
<212> TYPE: RNA
<213> ORGANISM: Artificial sequence
<220> FEATURE:
<223> OTHER INFORMATION: synthetic sequence

<400> SEQUENCE: 5
gacgaggugg ccgagugguu aaggcgaugg acugcgacug guuacccggu cgaauccauu    60
gugcucugca cgcguggguu cgaaucccac ccucgucgcc a                       101

<210> SEQ ID NO 6
<211> LENGTH: 115
<212> TYPE: RNA
<213> ORGANISM: Artificial sequence
<220> FEATURE:
<223> OTHER INFORMATION: synthetic sequence

<400> SEQUENCE: 6
gacgaggugg ccgagugguu aaggcgaugg acuggcgaua ccagccgaaa ggcccuuggc    60
agcgucaauc cauugugcuc ugcacgcgug gguucgaauc cacccucgu cgcca          115

<210> SEQ ID NO 7
<211> LENGTH: 119
<212> TYPE: RNA
<213> ORGANISM: Artificial sequence
<220> FEATURE:
<223> OTHER INFORMATION: synthetic sequence

<400> SEQUENCE: 7
accaggaugg ccgagugguu aaggcguugg acuaguaauu uacgucgacg gugacgucga    60
ugguugcggg auccaaugga cauaugccg cgugggguucg aaccccacuc cugguacca     119

<210> SEQ ID NO 8
<211> LENGTH: 102
<212> TYPE: RNA
<213> ORGANISM: Artificial sequence
<220> FEATURE:
<223> OTHER INFORMATION: synthetic sequence

<400> SEQUENCE: 8
accaggaugg ccgagugguu aaggcguugg acugcgacug guuacccggu cggauccaau    60
ggacauaugu ccgcgugggu ucgaaccccca cuccugguac ca                     102

<210> SEQ ID NO 9
<211> LENGTH: 116
<212> TYPE: RNA
<213> ORGANISM: Artificial sequence

```
<220> FEATURE:
<223> OTHER INFORMATION: synthetic sequence

<400> SEQUENCE: 9
accaggaugg ccgagugguu aaggcguugg acuggcgaua ccagccgaaa ggcccuuggc    60
agcgucgauc caauggacau auguccgcgu ggguucgaac cccacuccug guacca       116

<210> SEQ ID NO 10
<211> LENGTH: 120
<212> TYPE: RNA
<213> ORGANISM: Artificial sequence
<220> FEATURE:
<223> OTHER INFORMATION: synthetic sequence

<400> SEQUENCE: 10
gucaggaugg ccgagugguc uaaggcgcca gacuaguaau uuacgucgac ggugacgucg    60
augguugcgg guucuggucu ccguauggag gcgugggüuc gaaucccacu ucugacacca   120

<210> SEQ ID NO 11
<211> LENGTH: 103
<212> TYPE: RNA
<213> ORGANISM: Artificial sequence
<220> FEATURE:
<223> OTHER INFORMATION: synthetic sequence

<400> SEQUENCE: 11
gucaggaugg ccgagugguc uaaggcgcca gacugcgacu gguuacccgg ucgguucugg    60
ucuccguaug gaggcguggg uucgaauccc acuucugaca cca                     103

<210> SEQ ID NO 12
<211> LENGTH: 117
<212> TYPE: RNA
<213> ORGANISM: Artificial sequence
<220> FEATURE:
<223> OTHER INFORMATION: synthetic sequence

<400> SEQUENCE: 12
gucaggaugg ccgagugguc uaaggcgcca gacuggcgau accagccgaa aggcccuugg    60
cagcgucguu cuggucuccg uauggaggcg ugggüucgaa ucccacuucu gacacca      117

<210> SEQ ID NO 13
<211> LENGTH: 107
<212> TYPE: RNA
<213> ORGANISM: Artificial sequence
<220> FEATURE:
<223> OTHER INFORMATION: synthetic sequence

<400> SEQUENCE: 13
gcaugggugg uucaguggua gaauucucgc cuaguaauuu acgucgacgg ugacgucgau    60
gguugcggac gcgggaggcc cgguucgauu cccggccca ugcacca                  107

<210> SEQ ID NO 14
<211> LENGTH: 90
<212> TYPE: RNA
<213> ORGANISM: Artificial sequence
<220> FEATURE:
<223> OTHER INFORMATION: synthetic sequence

<400> SEQUENCE: 14
gcaugggugg uucaguggua gaauucucgc cugcgacugg uuaccgguc gacgcgggag     60 gcccggguuc gauucccggc ccaugcacca                                    90
```

<210> SEQ ID NO 15
<211> LENGTH: 104
<212> TYPE: RNA
<213> ORGANISM: Artificial sequence
<220> FEATURE:
<223> OTHER INFORMATION: synthetic sequence

<400> SEQUENCE: 15
gcaugggugg uucagguggua gaauucucgc cuggcgauac cagccgaaag gcccuuggca    60
gcgucacgcg ggaggcccgg guucgauucc cggcccaugc acca    104

<210> SEQ ID NO 16
<211> LENGTH: 108
<212> TYPE: RNA
<213> ORGANISM: Artificial sequence
<220> FEATURE:
<223> OTHER INFORMATION: synthetic sequence

<400> SEQUENCE: 16
gcguuggugg uauagugguu agcauagcug ccuaguaauu acgucgacg gugacgucga    60 ugguugcgga agcaguugac ccggguucga uucccggcca acgcacca    108

<210> SEQ ID NO 17
<211> LENGTH: 91
<212> TYPE: RNA
<213> ORGANISM: Artificial sequence
<220> FEATURE:
<223> OTHER INFORMATION: synthetic sequence

<400> SEQUENCE: 17
gcguuggugg uauagugguu agcauagcug ccugcgacug guuacccggu cgaagcaguu    60 gacccgqguu cgauucccgg ccaacgcacc a    91

<210> SEQ ID NO 18
<211> LENGTH: 105
<212> TYPE: RNA
<213> ORGANISM: Artificial sequence
<220> FEATURE:
<223> OTHER INFORMATION: synthetic sequence

<400> SEQUENCE: 18
gcguuggugg uauagugguu agcauagcug ccuggcgaua ccagccgaaa ggcccuuggc    60
agcgucaagc aguugacccg gguucgauuc ccggccaacg cacca    105

<210> SEQ ID NO 19
<211> LENGTH: 108
<212> TYPE: RNA
<213> ORGANISM: Artificial sequence
<220> FEATURE:
<223> OTHER INFORMATION: synthetic sequence

<400> SEQUENCE: 19
ucccuggugg ucuagugguu aggauucggc gcuaguaauu acgucgacg gugacgucga    60 ugguugcgga ccgccgcggc ccggguucga uucccgguca gggaacca    108

<210> SEQ ID NO 20
<211> LENGTH: 91
<212> TYPE: RNA
<213> ORGANISM: Artificial sequence
<220> FEATURE:
<223> OTHER INFORMATION: synthetic sequence

<400> SEQUENCE: 20

```
ucccuggugg ucuagugguu aggauucggc gcugcgacug guuacccggu cgaccgccgc    60
ggcccggguu cgauucccgg ucagggaacc a                                  91

<210> SEQ ID NO 21
<211> LENGTH: 105
<212> TYPE: RNA
<213> ORGANISM: Artificial sequence
<220> FEATURE:
<223> OTHER INFORMATION: synthetic sequence

<400> SEQUENCE: 21
ucccuggugg ucuagugguu aggauucggc gcuggcgaua ccagccgaaa ggcccuuggc    60
agcgucaccg ccgcggcccg gguucgauuc ccggucaggg aacca                  105

<210> SEQ ID NO 22
<211> LENGTH: 108
<212> TYPE: RNA
<213> ORGANISM: Artificial sequence
<220> FEATURE:
<223> OTHER INFORMATION: synthetic sequence

<400> SEQUENCE: 22
uccucguuag uauaguggug aguaucccccg ccuaguaauu uacgucgacg gugacgucga    60
ugguugcgga cgcgggagac cgggguucga uuccccgacg gggagcca              108

<210> SEQ ID NO 23
<211> LENGTH: 91
<212> TYPE: RNA
<213> ORGANISM: Artificial sequence
<220> FEATURE:
<223> OTHER INFORMATION: synthetic sequence

<400> SEQUENCE: 23
uccucguuag uauaguggug aguaucccccg ccugcgacug guuacccggu cgacgcggga    60
gaccgggguu cgauuccccg acggggagcc a                                  91

<210> SEQ ID NO 24
<211> LENGTH: 105
<212> TYPE: RNA
<213> ORGANISM: Artificial sequence
<220> FEATURE:
<223> OTHER INFORMATION: synthetic sequence

<400> SEQUENCE: 24
uccucguuag uauaguggug aguaucccccg ccuggcgaua ccagccgaaa ggcccuuggc    60
agcgucacgc gggagaccgg gguucgauuc cccgacgggg agcca                  105

<210> SEQ ID NO 25
<211> LENGTH: 108
<212> TYPE: RNA
<213> ORGANISM: Artificial sequence
<220> FEATURE:
<223> OTHER INFORMATION: synthetic sequence

<400> SEQUENCE: 25
ggucccaugg uguaaugguu agcacucugg acuaguaauu uacgucgacg gugacgucga    60
ugguugcgga auccagcgau ccgaguucaa aucucggugg gaccucca              108

<210> SEQ ID NO 26
<211> LENGTH: 91
<212> TYPE: RNA
```

```
<213> ORGANISM: Artificial sequence
<220> FEATURE:
<223> OTHER INFORMATION: synthetic sequence

<400> SEQUENCE: 26 gucccaugg uguaaugguu agcacucugg acugcgacug guuacccggu cgaauccagc    60
gauccgaguu caaaucucgg ugggaccucc a                                  91

<210> SEQ ID NO 27
<211> LENGTH: 105
<212> TYPE: RNA
<213> ORGANISM: Artificial sequence
<220> FEATURE:
<223> OTHER INFORMATION: synthetic sequence

<400> SEQUENCE: 27
ggucccaugg uguaaugguu agcacucugg acugcgauua ccagccgaaa ggcccuuggc    60
agcgucaauc cagcgauccg aguucaaauc ucggugggac cucca                  105

<210> SEQ ID NO 28
<211> LENGTH: 108
<212> TYPE: RNA
<213> ORGANISM: Artificial sequence
<220> FEATURE:
<223> OTHER INFORMATION: synthetic sequence

<400> SEQUENCE: 28
gguuccaugg uguaaugguu agcacucugg acuaguaauu uacgucgacg gugacgucga    60
ugguugcgga auccagcgau ccgaguucaa aucucggugg aaccucca              108

<210> SEQ ID NO 29
<211> LENGTH: 91
<212> TYPE: RNA
<213> ORGANISM: Artificial sequence
<220> FEATURE:
<223> OTHER INFORMATION: synthetic sequence

<400> SEQUENCE: 29
gguuccaugg uguaaugguu agcacucugg acugcgacug guuacccggu cgaauccagc    60
gauccgaguu caaaucucgg uggaaccucc a                                  91

<210> SEQ ID NO 30
<211> LENGTH: 105
<212> TYPE: RNA
<213> ORGANISM: Artificial sequence
<220> FEATURE:
<223> OTHER INFORMATION: synthetic sequence

<400> SEQUENCE: 30
gguuccaugg uguaaugguu agcacucugg acuggcgaua ccagccgaaa ggcccuuggc    60
agcgucaauc cagcgauccg aguucaaauc ucgguggaac cucca                  105

<210> SEQ ID NO 31
<211> LENGTH: 109
<212> TYPE: RNA
<213> ORGANISM: Artificial sequence
<220> FEATURE:
<223> OTHER INFORMATION: synthetic sequence

<400> SEQUENCE: 31
gggccagugg cgcaauggau aacgcgucug acuaguaauu uacgucgacg gugacgucga    60
ugguugcggg aucagaagau uccagguucg acuccuggcu ggcucgcca              109
```

```
<210> SEQ ID NO 32
<211> LENGTH: 92
<212> TYPE: RNA
<213> ORGANISM: Artificial sequence
<220> FEATURE:
<223> OTHER INFORMATION: synthetic sequence

<400> SEQUENCE: 32
gggccagugg cgcaauggau aacgcgucug acugcgacug guuacccggu cggaucagaa      60
gauuccaggu ucgacuccug gcuggcucgc ca                                   92

<210> SEQ ID NO 33
<211> LENGTH: 106
<212> TYPE: RNA
<213> ORGANISM: Artificial sequence
<220> FEATURE:
<223> OTHER INFORMATION: synthetic sequence

<400> SEQUENCE: 33
gggccagugg cgcaauggau aacgcgucug acuggcgaua ccagccgaaa ggcccuuggc      60
agcgucgauc agaagauucc agguucgacu ccuggcuggc ucgcca                   106

<210> SEQ ID NO 34
<211> LENGTH: 109
<212> TYPE: RNA
<213> ORGANISM: Artificial sequence
<220> FEATURE:
<223> OTHER INFORMATION: synthetic sequence

<400> SEQUENCE: 34
ggcucugugg cgcaauggau agcgcauugg acuaguaauu uacgucgacg gugacgucga      60
ugguugcgga auucaaaggu uguggguucg aaucccacca gagucgcca               109

<210> SEQ ID NO 35
<211> LENGTH: 92
<212> TYPE: RNA
<213> ORGANISM: Artificial sequence
<220> FEATURE:
<223> OTHER INFORMATION: synthetic sequence

<400> SEQUENCE: 35
ggcucugugg cgcaauggau agcgcauugg acugcgacug guuacccggu cgaauucaaa      60
gguugugggu ucgaauccca ccagagucgc ca                                   92

<210> SEQ ID NO 36
<211> LENGTH: 106
<212> TYPE: RNA
<213> ORGANISM: Artificial sequence
<220> FEATURE:
<223> OTHER INFORMATION: synthetic sequence

<400> SEQUENCE: 36
ggcucugugg cgcaauggau agcgcauugg acuggcgaua ccagccgaaa ggcccuuggc      60
agcgucaauu caagguugu ggguucgaau cccaccagag ucgcca                    106

<210> SEQ ID NO 37
<211> LENGTH: 108
<212> TYPE: RNA
<213> ORGANISM: Artificial sequence
<220> FEATURE:
<223> OTHER INFORMATION: synthetic sequence
```

<400> SEQUENCE: 37
gggggcauag cucaguggua gagcauuuga cuaguaauuu acgucgacgg ugacgucgau    60
gguugcggga ucaagagguc ccugguucaa auccaggugc ccccucca    108

<210> SEQ ID NO 38
<211> LENGTH: 91
<212> TYPE: RNA
<213> ORGANISM: Artificial sequence
<220> FEATURE:
<223> OTHER INFORMATION: synthetic sequence

<400> SEQUENCE: 38
gggggcauag cucaguggua gagcauuuga cugcgacugg uuacccgguc ggaucaagag    60
gucccugguu caaauccagg ugcccccucc a    91

<210> SEQ ID NO 39
<211> LENGTH: 105
<212> TYPE: RNA
<213> ORGANISM: Artificial sequence
<220> FEATURE:
<223> OTHER INFORMATION: synthetic sequence

<400> SEQUENCE: 39
gggggcauag cucaguggua gagcauuuga cuggcgauac cagccgaaag gcccuuggca    60
gcgucgauca agaggucccu gguucaaauc caggugcccc cucca    105

<210> SEQ ID NO 40
<211> LENGTH: 109
<212> TYPE: RNA
<213> ORGANISM: Artificial sequence
<220> FEATURE:
<223> OTHER INFORMATION: synthetic sequence

<400> SEQUENCE: 40
gcccggcuag cucagucggu agagcauggg acuaguaauu uacgucgacg gugacgucga    60
ugguugcgga aucccagggu cguggguucg agccccacgu ugggcgcca    109

<210> SEQ ID NO 41
<211> LENGTH: 92
<212> TYPE: RNA
<213> ORGANISM: Artificial sequence
<220> FEATURE:
<223> OTHER INFORMATION: synthetic sequence

<400> SEQUENCE: 41
gcccggcuag cucagucggu agagcauggg acugcgacug guuacccggu cgaaucccag    60
ggucgugggu ucgagcccca cguugggcgc ca    92

<210> SEQ ID NO 42
<211> LENGTH: 106
<212> TYPE: RNA
<213> ORGANISM: Artificial sequence
<220> FEATURE:
<223> OTHER INFORMATION: synthetic sequence

<400> SEQUENCE: 42
gcccggcuag cucagucggu agagcauggg acuggcgaua ccagccgaaa ggcccuuggc    60
agcgucaauc ccaggguscgu ggguucgagc cccacguugg gcgcca    106

<210> SEQ ID NO 43
<211> LENGTH: 109

```
<212> TYPE: RNA
<213> ORGANISM: Artificial sequence
<220> FEATURE:
<223> OTHER INFORMATION: synthetic sequence

<400> SEQUENCE: 43
gccuggauag cucaguuggu agagcaucag acuaguaauu uacgucgacg gugacgucga    60
ugguugcgga aucugagggu ccaggguuca agucccuguu caggcacca             109

<210> SEQ ID NO 44
<211> LENGTH: 92
<212> TYPE: RNA
<213> ORGANISM: Artificial sequence
<220> FEATURE:
<223> OTHER INFORMATION: synthetic sequence

<400> SEQUENCE: 44
gccuggauag cucaguuggu agagcaucag acugcgacug guuacccggu cgaaucugag    60
gguccagggu ucaagucccu guucaggcac ca                                 92

<210> SEQ ID NO 45
<211> LENGTH: 106
<212> TYPE: RNA
<213> ORGANISM: Artificial sequence
<220> FEATURE:
<223> OTHER INFORMATION: synthetic sequence

<400> SEQUENCE: 45
gccuggauag cucaguuggu agagcaucag acuggcgaua ccagccgaaa ggcccuuggc    60
agcgucaauc ugagggucca ggguucaagu cccguucag gcacca                  106

<210> SEQ ID NO 46
<211> LENGTH: 109
<212> TYPE: RNA
<213> ORGANISM: Artificial sequence
<220> FEATURE:
<223> OTHER INFORMATION: synthetic sequence

<400> SEQUENCE: 46
gccucguuag cgcaguaggu agcgcgucag ucuaguaauu uacgucgacg gugacgucga    60
ugguugcgga aucugaaggu cgugaguucg auccucacac ggggcacca             109

<210> SEQ ID NO 47
<211> LENGTH: 92
<212> TYPE: RNA
<213> ORGANISM: Artificial sequence
<220> FEATURE:
<223> OTHER INFORMATION: synthetic sequence

<400> SEQUENCE: 47
gccucguuag cgcaguaggu agcgcgucag ucugcgacug guuacccggu cgaaucugaa    60
ggucgugagu ucgauccuca cacggggcac ca                                 92

<210> SEQ ID NO 48
<211> LENGTH: 106
<212> TYPE: RNA
<213> ORGANISM: Artificial sequence
<220> FEATURE:
<223> OTHER INFORMATION: synthetic sequence

<400> SEQUENCE: 48
gccucguuag cgcaguaggu agcgcgucag ucuggcgaua ccagccgaaa ggcccuuggc    60
```
agcgucaauc ugaaggucgu gaguucgauc cucacacggg gcacca    106

<210> SEQ ID NO 49
<211> LENGTH: 110
<212> TYPE: RNA
<213> ORGANISM: Artificial sequence
<220> FEATURE:
<223> OTHER INFORMATION: synthetic sequence

<400> SEQUENCE: 49
gucucugugg cgcaaucggu uagcgcguuc ggcuaguaau uuacgucgac ggugacgucg    60
augguugcgg aaccgaaagg uuggugguuc gaucccaccc agggacgcca    110

<210> SEQ ID NO 50
<211> LENGTH: 93
<212> TYPE: RNA
<213> ORGANISM: Artificial sequence
<220> FEATURE:
<223> OTHER INFORMATION: synthetic sequence

<400> SEQUENCE: 50
gucucugugg cgcaaucggu uagcgcguuc ggcugcgacu gguuacccgg ucgaaccgaa    60
agguuggugg uucgauccca cccagggacg cca    93

<210> SEQ ID NO 51
<211> LENGTH: 107
<212> TYPE: RNA
<213> ORGANISM: Artificial sequence
<220> FEATURE:
<223> OTHER INFORMATION: synthetic sequence

<400> SEQUENCE: 51
gucucugugg cgcaaucggu uagcgcguuc ggcuggcgau accagccgaa aggcccuugg    60
cagcgucaac cgaaagguug gugguucgau cccacccagg gacgcca    107

<210> SEQ ID NO 52
<211> LENGTH: 108
<212> TYPE: RNA
<213> ORGANISM: Artificial sequence
<220> FEATURE:
<223> OTHER INFORMATION: synthetic sequence

<400> SEQUENCE: 52 gggggguguag cucaguggua gagcgcgugc uuaguaauuu acgucgacgg ugacgucgau    60
gguugcggau gcacgaggcc ccggguucaa uccccggcac cuccacca    108

<210> SEQ ID NO 53
<211> LENGTH: 91
<212> TYPE: RNA
<213> ORGANISM: Artificial sequence
<220> FEATURE:
<223> OTHER INFORMATION: synthetic sequence

<400> SEQUENCE: 53 gggggguguag cucaguggua gagcgcgugc uugcgacugg uuacccgguc gaugcacgag    60
gccccggguu caauccccgg caccuccacc a    91

<210> SEQ ID NO 54
<211> LENGTH: 105
<212> TYPE: RNA
<213> ORGANISM: Artificial sequence
<220> FEATURE:
<223> OTHER INFORMATION: synthetic sequence

<400> SEQUENCE: 54
ggggguguag cucaguggua gagcgcgugc uuggcgauac cagccgaaag gcccuuggca    60
gcgucaugca cgaggccccg gguucaaucc ccggcaccuc cacca                  105

<210> SEQ ID NO 55
<211> LENGTH: 108
<212> TYPE: RNA
<213> ORGANISM: Artificial sequence
<220> FEATURE:
<223> OTHER INFORMATION: synthetic sequence

<400> SEQUENCE: 55
gccgugaucg uauagugguu aguacucugc guuaguaauu acgucgacg gugacgucga    60 ugguugcggg ccgcagcaac cucgguucga auccgaguca cggcacca              108

<210> SEQ ID NO 56
<211> LENGTH: 91
<212> TYPE: RNA
<213> ORGANISM: Artificial sequence
<220> FEATURE:
<223> OTHER INFORMATION: synthetic sequence

<400> SEQUENCE: 56
gccgugaucg uauagugguu aguacucugc guugcgacug guuacccggu cggccgcagc    60
aaccucgguu cgaauccgag ucacggcacc a                                  91

<210> SEQ ID NO 57
<211> LENGTH: 105
<212> TYPE: RNA
<213> ORGANISM: Artificial sequence
<220> FEATURE:
<223> OTHER INFORMATION: synthetic sequence

<400> SEQUENCE: 57
gccgugaucg uauagugguu aguacucugc guuggcgaua ccagccgaaa ggcccuuggc    60
agcgucgccg cagcaaccuc gguucgaauc cgagucacgg cacca                  105

<210> SEQ ID NO 58
<211> LENGTH: 110
<212> TYPE: RNA
<213> ORGANISM: Artificial sequence
<220> FEATURE:
<223> OTHER INFORMATION: synthetic sequence

<400> SEQUENCE: 58
ggccgguuag cucaguuggu uagagcgugg ugcuaguaau uuacgucgac ggugacgucg    60
augguugcgg aacgccaagg ucgcggguuc gauccccgua cuggccacca             110

<210> SEQ ID NO 59
<211> LENGTH: 93
<212> TYPE: RNA
<213> ORGANISM: Artificial sequence
<220> FEATURE:
<223> OTHER INFORMATION: synthetic sequence

<400> SEQUENCE: 59
ggccgguuag cucaguuggu uagagcgugg ugcugcgacu gguuacccgg ucgaacgcca    60
aggucgcggg uucgaucccc guacuggcca cca                                93

<210> SEQ ID NO 60

```
<211> LENGTH: 107
<212> TYPE: RNA
<213> ORGANISM: Artificial sequence
<220> FEATURE:
<223> OTHER INFORMATION: synthetic sequence

<400> SEQUENCE: 60
ggccgguuag cucaguuggu uagagcgugg ugcuggcgau accagccgaa aggcccuugg      60
cagcgucaac gccaaggucg cggguucgau ccccguacug gccacca                  107

<210> SEQ ID NO 61
<211> LENGTH: 110
<212> TYPE: RNA
<213> ORGANISM: Artificial sequence
<220> FEATURE:
<223> OTHER INFORMATION: synthetic sequence

<400> SEQUENCE: 61
gcuccagugg cgcaaucggu uagcgcgcgg uacuaguaau uuacgucgac ggugacgucg      60
augguugcgg aaugccgagg uugugaguuc gauccucacc uggagcacca              110

<210> SEQ ID NO 62
<211> LENGTH: 93
<212> TYPE: RNA
<213> ORGANISM: Artificial sequence
<220> FEATURE:
<223> OTHER INFORMATION: synthetic sequence

<400> SEQUENCE: 62
gcuccagugg cgcaaucggu uagcgcgcgg uacugcgacu gguuacccgg ucgaaugccg      60
agguugugag uucgauccuc accuggagca cca                                  93

<210> SEQ ID NO 63
<211> LENGTH: 107
<212> TYPE: RNA
<213> ORGANISM: Artificial sequence
<220> FEATURE:
<223> OTHER INFORMATION: synthetic sequence

<400> SEQUENCE: 63
gcuccagugg cgcaaucggu uagcgcgcgg uacuggcgau accagccgaa aggcccuugg      60
cagcgucaau gccgagguug ugaguucgau ccucaccugg agcacca                  107

<210> SEQ ID NO 64
<211> LENGTH: 109
<212> TYPE: RNA
<213> ORGANISM: Artificial sequence
<220> FEATURE:
<223> OTHER INFORMATION: synthetic sequence

<400> SEQUENCE: 64
gccgaaauag cucaguuggg agagcguuag acuaguaauu uacgucgacg gugacgucga      60
ugguugcggg aucuaaaggu cccugguucg auccoggguu ucggcacca               109

<210> SEQ ID NO 65
<211> LENGTH: 92
<212> TYPE: RNA
<213> ORGANISM: Artificial sequence
<220> FEATURE:
<223> OTHER INFORMATION: synthetic sequence

<400> SEQUENCE: 65
gccgaaauag cucaguuggg agagcguuag acugcgacug guuacccggu cggaucuaaa      60
```

```
ggucccuggu ucgaucccgg guuucggcac ca                                  92
```

<210> SEQ ID NO 66
<211> LENGTH: 106
<212> TYPE: RNA
<213> ORGANISM: Artificial sequence
<220> FEATURE:
<223> OTHER INFORMATION: synthetic sequence

<400> SEQUENCE: 66

```
gccgaaauag cucaguuggg agagcguuag acuggcgaua ccagccgaaa ggcccuuggc    60
agcgucgauc uaaaggcccc ugguucgauc ccggguuucg gcacca                 106
```

<210> SEQ ID NO 67
<211> LENGTH: 108
<212> TYPE: RNA
<213> ORGANISM: Artificial sequence
<220> FEATURE:
<223> OTHER INFORMATION: synthetic sequence

<400> SEQUENCE: 67

```
ggcucguugg ucuaggggua ugauucucgc uuaguaauuu acgucgacgg ugacgucgau    60
gguugcggau gcgagagguc ccggguucaa aucccggacg agccccca                108
```

<210> SEQ ID NO 68
<211> LENGTH: 91
<212> TYPE: RNA
<213> ORGANISM: Artificial sequence
<220> FEATURE:
<223> OTHER INFORMATION: synthetic sequence

<400> SEQUENCE: 68

```
ggcucguugg ucuaggggua ugauucucgc uugcgacugg uuacccgguc gaugcgagag    60
gucccggguu caaaucccgg acgagccccc a                                   91
```

<210> SEQ ID NO 69
<211> LENGTH: 105
<212> TYPE: RNA
<213> ORGANISM: Artificial sequence
<220> FEATURE:
<223> OTHER INFORMATION: synthetic sequence

<400> SEQUENCE: 69

```
ggcucguugg ucuaggggua ugauucucgc uuggcgauac cagccgaaag gcccuuggca    60
gcgucaugcg agaggucccg gguucaaauc ccggacgagc cccca                  105
```

<210> SEQ ID NO 70
<211> LENGTH: 108
<212> TYPE: RNA
<213> ORGANISM: Artificial sequence
<220> FEATURE:
<223> OTHER INFORMATION: synthetic sequence

<400> SEQUENCE: 70

```
gaccucgugg cgcaacggua gcgcgucuga cuaguaauuu acgucgacgg ugacgucgau    60
gguugcggga ucagaaggcu gcguguucga aucacgucgg ggucacca                108
```

<210> SEQ ID NO 71
<211> LENGTH: 91
<212> TYPE: RNA
<213> ORGANISM: Artificial sequence
<220> FEATURE:

<223> OTHER INFORMATION: synthetic sequence

<400> SEQUENCE: 71
gaccucgugg cgcaacggua gcgcgucuga cugcgacugg uuacccgguc ggaucagaag    60
gcugcguguu cgaaucacgu cggggucacc a    91

<210> SEQ ID NO 72
<211> LENGTH: 105
<212> TYPE: RNA
<213> ORGANISM: Artificial sequence
<220> FEATURE:
<223> OTHER INFORMATION: synthetic sequence

<400> SEQUENCE: 72
gaccucgugg cgcaacggua gcgcgucuga cuggcgauac cagccgaaag gcccuuggca    60
gcgucgauca gaaggcugcg uguucgaauc acgucgggu cacca    105

<210> SEQ ID NO 73
<211> LENGTH: 109
<212> TYPE: RNA
<213> ORGANISM: Artificial sequence
<220> FEATURE:
<223> OTHER INFORMATION: synthetic sequence

<400> SEQUENCE: 73
ccuucgauag cucaguuggu agagcggagg acuaguaauu uacgucgacg gugacgucga    60
ugguugcggg auccuuaggu cgcugguucg aauccggcuc gaaggacca    109

<210> SEQ ID NO 74
<211> LENGTH: 92
<212> TYPE: RNA
<213> ORGANISM: Artificial sequence
<220> FEATURE:
<223> OTHER INFORMATION: synthetic sequence

<400> SEQUENCE: 74
ccuucgauag cucaguuggu agagcggagg acugcgacug guuacccggu cggauccuua    60
ggucgcuggu ucgaauccgg cucgaaggac ca    92

<210> SEQ ID NO 75
<211> LENGTH: 106
<212> TYPE: RNA
<213> ORGANISM: Artificial sequence
<220> FEATURE:
<223> OTHER INFORMATION: synthetic sequence

<400> SEQUENCE: 75
ccuucgauag cucaguuggu agagcggagg acuggcgaua ccagccgaaa ggcccuuggc    60
agcgucgauc cuuaggucgc ugguucgaau ccggcucgaa ggacca    106

<210> SEQ ID NO 76
<211> LENGTH: 109
<212> TYPE: RNA
<213> ORGANISM: Artificial sequence
<220> FEATURE:
<223> OTHER INFORMATION: synthetic sequence

<400> SEQUENCE: 76
guuuccguag uguaguugguu aucacguucg ccuaguaauu uacgucgacg gugacgucga    60
ugguugcgga cgcgaaaggu ccccgguucg aaaccgggcg gaaacacca    109

```
<210> SEQ ID NO 77
<211> LENGTH: 92
<212> TYPE: RNA
<213> ORGANISM: Artificial sequence
<220> FEATURE:
<223> OTHER INFORMATION: synthetic sequence

<400> SEQUENCE: 77
guuuccguag uguagugguu aucacguucg ccugcgacug guuacccggu cgacgcgaaa    60 ggucccccggu ucgaaaccgg gcggaaacac ca                                 92

<210> SEQ ID NO 78
<211> LENGTH: 106
<212> TYPE: RNA
<213> ORGANISM: Artificial sequence
<220> FEATURE:
<223> OTHER INFORMATION: synthetic sequence

<400> SEQUENCE: 78
guuuccguag uguagugguu aucacguucg ccuggcgaua ccagccgaaa ggcccuuggc    60
agcgucacgc gaaaggcccc cgguucgaaa ccgggcggaa acacca                  106

<210> SEQ ID NO 79
<211> LENGTH: 110
<212> TYPE: RNA
<213> ORGANISM: Artificial sequence
<220> FEATURE:
<223> OTHER INFORMATION: synthetic sequence

<400> SEQUENCE: 79
ggcucuaugg cuuaguuggu uaaagcgccu gucuaguaau uuacgucgac ggugacgucg    60
augguugcgg aaacaggaga uccuggguuc gaaucccagu agagccucca              110

<210> SEQ ID NO 80
<211> LENGTH: 93
<212> TYPE: RNA
<213> ORGANISM: Artificial sequence
<220> FEATURE:
<223> OTHER INFORMATION: synthetic sequence

<400> SEQUENCE: 80
ggcucuaugg cuuaguuggu uaaagcgccu gucugcgacu gguuacccgg ucgaaacagg    60
agauccuggg uucgaauccc aguagagccu cca                                93

<210> SEQ ID NO 81
<211> LENGTH: 107
<212> TYPE: RNA
<213> ORGANISM: Artificial sequence
<220> FEATURE:
<223> OTHER INFORMATION: synthetic sequence

<400> SEQUENCE: 81
ggcucuaugg cuuaguuggu uaaagcgccu gucuggcgau accagccgaa aggcccuugg    60
cagcgucaaa caggagaucc uggguucgaa ucccaguaga gccucca                 107

<210> SEQ ID NO 82
<211> LENGTH: 110
<212> TYPE: RNA
<213> ORGANISM: Artificial sequence
<220> FEATURE:
<223> OTHER INFORMATION: synthetic sequence

<400> SEQUENCE: 82
```

```
ggcgccgugg cuuaguuggu aaagcgccu gucuaguaau uuacgucgac ggugacgucg    60
augguugcgg aaacaggaga uccuggguuc gaaucccagc ggugccucca             110
```

<210> SEQ ID NO 83
<211> LENGTH: 93
<212> TYPE: RNA
<213> ORGANISM: Artificial sequence
<220> FEATURE:
<223> OTHER INFORMATION: synthetic sequence

<400> SEQUENCE: 83

```
ggcgccgugg cuuaguuggu aaagcgccu gucugcgacu gguuacccgg ucgaaacagg    60
agauccuggg uucgaauccc agcggugccu cca                                93
```

<210> SEQ ID NO 84
<211> LENGTH: 107
<212> TYPE: RNA
<213> ORGANISM: Artificial sequence
<220> FEATURE:
<223> OTHER INFORMATION: synthetic sequence

<400> SEQUENCE: 84

```
ggcgccgugg cuuaguuggu aaagcgccu gucuggcgau accagccgaa aggcccuugg    60
cagcgucaaa caggagaucc uggguucgaa ucccagcggu gccucca                 107
```

<210> SEQ ID NO 85
<211> LENGTH: 182
<212> TYPE: RNA
<213> ORGANISM: Artificial sequence
<220> FEATURE:
<223> OTHER INFORMATION: synthetic sequence

<400> SEQUENCE: 85

```
gccuggauag cucaguuggu agagcaucag acuggccagc ugugagUguu ucuuuggcag   60
ugucuuagcu gguuguugug agcaauagua aggaagcaau cagcaaguau acugcccuag  120
aagugcugca cguguuggc ccaaucugag gguccagggu ucaagucccu guucaggcgc   180
ca                                                                  182
```

<210> SEQ ID NO 86
<211> LENGTH: 182
<212> TYPE: RNA
<213> ORGANISM: Artificial sequence
<220> FEATURE:
<223> OTHER INFORMATION: synthetic sequence

<400> SEQUENCE: 86

```
gcccggcuag cucagucggu agagcauggg acuggccagc ugugagUguu ucuuuggcag   60
ugucuuagcu gguuguugug agcaauagua aggaagcaau cagcaaguau acugcccuag  120
aagugcugca cguguuggc ccaucccag ggucgugggu ucgagcccca cguugggcgc    180
ca                                                                  182
```

<210> SEQ ID NO 87
<211> LENGTH: 181
<212> TYPE: RNA
<213> ORGANISM: Artificial sequence
<220> FEATURE:
<223> OTHER INFORMATION: synthetic sequence

<400> SEQUENCE: 87

```
ggucccaugg uguaaugguu agcacucugg acuggccagc ugugagUguu ucuuuggcag   60
```

-continued

```
ugucuuagcu gguuguugug agcaauagua aggaagcaau cagcaaguau acugcccuag    120
aagugcugca cguuguuggc ccaauccagc gauccgaguu caaaucucgg ugggaccucc    180
a                                                                     181
```

<210> SEQ ID NO 88
<211> LENGTH: 181
<212> TYPE: RNA
<213> ORGANISM: Artificial sequence
<220> FEATURE:
<223> OTHER INFORMATION: synthetic sequence

<400> SEQUENCE: 88

```
gguccaugg uguaaugguu agcacucugg acuggccagc ugugagueguu ucuuggcag     60 ugucuuagcu gguuguugug agcaauagua aggaagcaau cagcaaguau acugcccuag    120
aagugcugca cguuguuggc ccaauccagc gauccgaguu caaaucucgg uggaaccucc    180
a                                                                     181
```

<210> SEQ ID NO 89
<211> LENGTH: 181
<212> TYPE: RNA
<213> ORGANISM: Artificial sequence
<220> FEATURE:
<223> OTHER INFORMATION: synthetic sequence

<400> SEQUENCE: 89

```
gggggcauag cucaguggua gagcauuuga cuggccagcu gugagueguuu cuuggcagu    60 gucuuagcug guuguuguga gcaauaguaa ggaagcaauc agcaaguaua cugcccuaga    120
agugcugcac guuguuggcc cgaucaagag gucccugguu caaauccagg ugccccucc     180 a                                                                     181
```

<210> SEQ ID NO 90
<211> LENGTH: 182
<212> TYPE: RNA
<213> ORGANISM: Artificial sequence
<220> FEATURE:
<223> OTHER INFORMATION: synthetic sequence

<400> SEQUENCE: 90

```
ccuucgauag cucaguuggu agagcggagg acuggccagc ugugagueguu ucuuggcag     60 ugucuuagcu gguuguugug agcaauagua aggaagcaau cagcaaguau acugcccuag    120
aagugcugca cguuguuggc ccgauccuua ggucgcuggu ucgaauccgg cucgaaggac    180
ca                                                                    182
```

<210> SEQ ID NO 91
<211> LENGTH: 191
<212> TYPE: RNA
<213> ORGANISM: Artificial sequence
<220> FEATURE:
<223> OTHER INFORMATION: synthetic sequence

<400> SEQUENCE: 91

```
gcagcgaugg ccgagugguu aaggcguugg acuggccagc ugugagueguu ucuuggcag     60 ugucuuagcu gguuguugug agcaauagua aggaagcaau cagcaaguau acugcccuag    120
aagugcugca cguuguuggc ccaauccaau ggggucuccc cgcgcagguu cgaacccugc    180
ucgcugcgcc a                                                          191
```

<210> SEQ ID NO 92
<211> LENGTH: 191
<212> TYPE: RNA
<213> ORGANISM: Artificial sequence
<220> FEATURE:
<223> OTHER INFORMATION: synthetic sequence

<400> SEQUENCE: 92
gacgaggugg ccgagugguu aaggcgaugg acuggccagc ugugaguguu ucuuuggcag    60
ugucuuagcu gguuguugug agcaauagua aggaagcaau cagcaaguau acugcccuag   120
aagugcugca cguuguuggc ccaauccauu gugcucugca cgcgugggu cgaaucccac    180 ccucgucgcc a                                                        191

<210> SEQ ID NO 93
<211> LENGTH: 192
<212> TYPE: RNA
<213> ORGANISM: Artificial sequence
<220> FEATURE:
<223> OTHER INFORMATION: synthetic sequence

<400> SEQUENCE: 93
accaggaugg ccgagugguu aaggcguugg acuggccagc ugugaguguu ucuuuggcag    60
ugucuuagcu gguuguugug agcaauagua aggaagcaau cagcaaguau acugcccuag   120
aagugcugca cguuguuggc ccgauccaau ggacauaugu ccgcgugggu cgaaccccca   180
cuccugguac ca                                                       192

<210> SEQ ID NO 94
<211> LENGTH: 193
<212> TYPE: RNA
<213> ORGANISM: Artificial sequence
<220> FEATURE:
<223> OTHER INFORMATION: synthetic sequence

<400> SEQUENCE: 94
gucaggaugg ccgagugguc uaaggcgcca gacuggccag cugugagugu uucuuuggca    60
gugucuuagc ugguuguugu gagcaauagu aaggaagcaa ucagcaagua uacugcccua   120
gaagugcugc acguuguugg cccguucugg ucuccguaug gaggcguggg uucgaauccc   180
acuucugaca cca                                                      193

<210> SEQ ID NO 95
<211> LENGTH: 180
<212> TYPE: RNA
<213> ORGANISM: Artificial sequence
<220> FEATURE:
<223> OTHER INFORMATION: synthetic sequence

<400> SEQUENCE: 95
gcaugggugg uucaguggua gaauucucgc cuggccagcu gugaguguuu cuuggcagu     60 gucuuagcug guuguuguga gcaauaguaa ggaagcaauc agcaaguaua cugcccuaga   120
agugcugcac guuguuggcc cacgcgggag gcccgggguuc gauucccggc ccaugcacca  180

<210> SEQ ID NO 96
<211> LENGTH: 181
<212> TYPE: RNA
<213> ORGANISM: Artificial sequence
<220> FEATURE:
<223> OTHER INFORMATION: synthetic sequence

<400> SEQUENCE: 96

```
gcguuggugg uauagugguu agcauagcug ccuggccagc ugugaguguu ucuuuggcag    60
ugucuuagcu gguuguugug agcaauagua aggaagcaau cagcaaguau acugcccuag   120
aagugcugca cguuguuggc ccaagcaguu gacccggguu cgauucccgg ccaacgcacc   180
a                                                                  181

<210> SEQ ID NO 97
<211> LENGTH: 181
<212> TYPE: RNA
<213> ORGANISM: Artificial sequence
<220> FEATURE:
<223> OTHER INFORMATION: synthetic sequence

<400> SEQUENCE: 97
ucccuggugg ucuagugguu aggauucggc gcuggccagc ugugaguguu ucuuuggcag    60
ugucuuagcu gguuguugug agcaauagua aggaagcaau cagcaaguau acugcccuag   120
aagugcugca cguuguuggc ccaccgccgc ggcccggguu cgauucccgg ucagggaacc   180
a                                                                  181

<210> SEQ ID NO 98
<211> LENGTH: 181
<212> TYPE: RNA
<213> ORGANISM: Artificial sequence
<220> FEATURE:
<223> OTHER INFORMATION: synthetic sequence

<400> SEQUENCE: 98
uccucguuag uauaguggug aguauccccg ccuggccagc ugugaguguu ucuuuggcag    60
ugucuuagcu gguuguugug agcaauagua aggaagcaau cagcaaguau acugcccuag   120
aagugcugca cguuguuggc ccacgcggga daccggggguu cgauuccccg acggggagcc   180
a                                                                  181

<210> SEQ ID NO 99
<211> LENGTH: 182
<212> TYPE: RNA
<213> ORGANISM: Artificial sequence
<220> FEATURE:
<223> OTHER INFORMATION: synthetic sequence

<400> SEQUENCE: 99
gggccagugg cgcaauggau aacgcgucug acuggccagc ugugaguguu ucuuuggcag    60
ugucuuagcu gguuguugug agcaauagua aggaagcaau cagcaaguau acugcccuag   120
aagugcugca cguuguuggc ccgaucagaa gauuccaggu ucgacuccug gcuggucgc    180 ca                                                                 182

<210> SEQ ID NO 100
<211> LENGTH: 182
<212> TYPE: RNA
<213> ORGANISM: Artificial sequence
<220> FEATURE:
<223> OTHER INFORMATION: synthetic sequence

<400> SEQUENCE: 100
ggcucugugg cgcaauggau agcgcauugg acuggccagc ugugaguguu ucuuuggcag    60
ugucuuagcu gguuguugug agcaauagua aggaagcaau cagcaaguau acugcccuag   120
aagugcugca cguuguuggc ccaauucaaa gguugugggu ucgaauccca ccagagucgc   180
``` ca                                                                        182

<210> SEQ ID NO 101
<211> LENGTH: 182
<212> TYPE: RNA
<213> ORGANISM: Artificial sequence
<220> FEATURE:
<223> OTHER INFORMATION: synthetic sequence

<400> SEQUENCE: 101
gccucguuag cgcaguaggu agcgcgucag ucuggccagc ugugaguguu ucuuuggcag        60
ugucuuagcu gguuguugug agcaauagua aggaagcaau cagcaaguau acugcccuag       120
aagugcugca cguuguuggc ccaaucugaa ggucgugagu cgauccuca cacggggcac       180 ca                                                                        182

<210> SEQ ID NO 102
<211> LENGTH: 183
<212> TYPE: RNA
<213> ORGANISM: Artificial sequence
<220> FEATURE:
<223> OTHER INFORMATION: synthetic sequence

<400> SEQUENCE: 102
gucucugugg cgcaaucggu uagcgcguuc ggcuggccag cugugagugu uucuuuggca        60
gugucuuagc ugguuguugu gagcaauagu aaggaagcaa ucagcaagua uacugcccua       120
gaagugcugc acguuguugg cccaaccgaa agguuggugg uucgauccca cccagggacg       180
cca                                                                       183

<210> SEQ ID NO 103
<211> LENGTH: 181
<212> TYPE: RNA
<213> ORGANISM: Artificial sequence
<220> FEATURE:
<223> OTHER INFORMATION: synthetic sequence

<400> SEQUENCE: 103 gggggguguag cucaguggua gagcgcgugc uuggccagcu ugagaguuu cuuuggcagu        60 gucuuagcug guuguuguga gcaauaguaa ggaagcaauc agcaaguaua cugcccuaga       120
agugcugcac guuguuggcc caugcacgag gccccgggu caaucccggg caccuccacc       180
a                                                                         181

<210> SEQ ID NO 104
<211> LENGTH: 181
<212> TYPE: RNA
<213> ORGANISM: Artificial sequence
<220> FEATURE:
<223> OTHER INFORMATION: synthetic sequence

<400> SEQUENCE: 104
gccgugaucg uauaguggu aguacucugc guuggccagc ugugaguguu ucuuuggcag         60
ugucuuagcu gguuguugug agcaauagua aggaagcaau cagcaaguau acugcccuag       120
aagugcugca cguuguuggc ccgccgcagc aaccucgguu cgaauccgag ucacggcacc       180
a                                                                         181

<210> SEQ ID NO 105
<211> LENGTH: 183
<212> TYPE: RNA
<213> ORGANISM: Artificial sequence
<220> FEATURE:
<223> OTHER INFORMATION: synthetic sequence

<400> SEQUENCE: 105

```
ggccgguuag cucaguuggu uagagcgugg ugcuggccag cugugagugu uucuuuggca      60
gugucuuagc ugguuguugu gagcaauagu aaggaagcaa ucagcaagua uacugcccua     120
gaagugcugc acguuguugg cccaacgcca aggucgcggg uucgaucccc guacuggcca     180
cca                                                                  183
```

<210> SEQ ID NO 106
<211> LENGTH: 183
<212> TYPE: RNA
<213> ORGANISM: Artificial sequence
<220> FEATURE:
<223> OTHER INFORMATION: synthetic sequence

<400> SEQUENCE: 106

```
gcuccagugg cgcaaucggu uagcgcgcgg uacuggccag cugugagugu uucuuuggca      60
gugucuuagc ugguuguugu gagcaauagu aaggaagcaa ucagcaagua uacugcccua     120
gaagugcugc acguuguugg cccaaugccg agguugugag uucgauccuc accggagca     180
cca                                                                  183
```

<210> SEQ ID NO 107
<211> LENGTH: 182
<212> TYPE: RNA
<213> ORGANISM: Artificial sequence
<220> FEATURE:
<223> OTHER INFORMATION: synthetic sequence

<400> SEQUENCE: 107

```
gccgaaauag cucaguuggg agagcguuag acuggccagc ugugaguguu ucuuuggcag      60
ugucuuagcu ggguuguugu agcaauagua aggaagcaau cagcaaguau acugcccuag     120
aagugcugca cguuguuggc ccgaucuaaa ggucccuggu ucgaucccgg guuucggcac     180
ca                                                                   182
```

<210> SEQ ID NO 108
<211> LENGTH: 181
<212> TYPE: RNA
<213> ORGANISM: Artificial sequence
<220> FEATURE:
<223> OTHER INFORMATION: synthetic sequence

<400> SEQUENCE: 108

```
ggcucguugg ucuaggggua ugauucucgc uuggccagcu gugaguguuu cuuggcagu      60
gucuuagcug guuguguga gcaauaguaa ggaagcaauc agcaaguaua cugcccuaga     120
agugcugcac guuguuggcc caugcgagag gucccggguu caaucccgg acgagccccc     180
a                                                                    181
```

<210> SEQ ID NO 109
<211> LENGTH: 181
<212> TYPE: RNA
<213> ORGANISM: Artificial sequence
<220> FEATURE:
<223> OTHER INFORMATION: synthetic sequence

<400> SEQUENCE: 109

```
gaccucgugg cgcaacggua gcgcgucuga cuggccagcu gugaguguuu cuuggcagu      60
```

| | |
|---|---|
| gucuuagcug guuguuguga gcaauaguaa ggaagcaauc agcaaguaua cugcccuaga | 120 |
| agugcugcac guuguuggcc cgaucagaag gcugcguguu cgaaucacgu cggggucacc | 180 |
| a | 181 |

<210> SEQ ID NO 110
<211> LENGTH: 182
<212> TYPE: RNA
<213> ORGANISM: Artificial sequence
<220> FEATURE:
<223> OTHER INFORMATION: synthetic sequence

<400> SEQUENCE: 110

| | |
|---|---|
| guuuccguag uguagugguu aucacguucg ccuggccagc ugugagguguu ucuuuggcag | 60 |
| ugucuuagcu gguuguugug agcaauagua aggaagcaau cagcaaguau acugcccuag | 120 |
| aagugcugca cguuguuggc ccacgcgaaa gguccccggu cgaaaccgg gcggaaacac | 180 |
| ca | 182 |

<210> SEQ ID NO 111
<211> LENGTH: 183
<212> TYPE: RNA
<213> ORGANISM: Artificial sequence
<220> FEATURE:
<223> OTHER INFORMATION: synthetic sequence

<400> SEQUENCE: 111

| | |
|---|---|
| ggcucuaugg cuuaguuggu uaaagcgccu gucuggccag cugugagugu uucuuuggca | 60 |
| gugucuuagc gguuguugu gagcaauagu aaggaagcaa ucagcaagua uacugcccua | 120 |
| gaagugcugc acguuguugg cccaaacagg agauccuggg uucgaauccc aguagagccu | 180 |
| cca | 183 |

<210> SEQ ID NO 112
<211> LENGTH: 183
<212> TYPE: RNA
<213> ORGANISM: Artificial sequence
<220> FEATURE:
<223> OTHER INFORMATION: synthetic sequence

<400> SEQUENCE: 112

| | |
|---|---|
| ggcgccgugg cuuaguuggu uaaagcgccu gucuggccag cugugagugu uucuuuggca | 60 |
| gugucuuagc gguuguugu gagcaauagu aaggaagcaa ucagcaagua uacugcccua | 120 |
| gaagugcugc acguuguugg cccaaacagg agauccuggg uucgaauccc agcggugccu | 180 |
| cca | 183 |

<210> SEQ ID NO 113
<211> LENGTH: 192
<212> TYPE: RNA
<213> ORGANISM: Artificial sequence
<220> FEATURE:
<223> OTHER INFORMATION: synthetic sequence

<400> SEQUENCE: 113

| | |
|---|---|
| accaggaugg ccgaguggu aaggcguugg acuggccagc ugugagugu ucuuggucug | 60 |
| aaucuugcuc agcuugugug agcaauagua aggaacaagc ugagaaguau ucagacauag | 120 |
| aagugcugca cguuguuggc ccgauccaau ggacauaugu ccgcguggu ucgaacccca | 180 |
| cuccugguac ca | 192 |

```
<210> SEQ ID NO 114
<211> LENGTH: 192
<212> TYPE: RNA
<213> ORGANISM: Artificial sequence
<220> FEATURE:
<223> OTHER INFORMATION: synthetic sequence

<400> SEQUENCE: 114
accaggaugg ccgagugguu aaggcguugg acuggccagc ugugaguguu ucuucuggcc     60
cucucugccc uuccguugug agcaauagua aggaagcggg ggggagaugg gggccauuag    120
aagugcugca cguuguuggc ccgauccaau ggacauaugu ccgcgugggu cgaaccccca    180
cuccugguac ca                                                       192

<210> SEQ ID NO 115
<211> LENGTH: 192
<212> TYPE: RNA
<213> ORGANISM: Artificial sequence
<220> FEATURE:
<223> OTHER INFORMATION: synthetic sequence

<400> SEQUENCE: 115
accaggaugg ccgagugguu aaggcguugg acuggccagc ugugaguguu ucuuuaaggc     60
acgcggugaa ugccguugug agcaauagua aggaagcggu guucccgucg ugccuucuag    120
aagugcugca cguuguuggc ccgauccaau ggacauaugu ccgcgugggu cgaaccccca    180
cuccugguac ca                                                       192

<210> SEQ ID NO 116
<211> LENGTH: 193
<212> TYPE: RNA
<213> ORGANISM: Artificial sequence
<220> FEATURE:
<223> OTHER INFORMATION: synthetic sequence

<400> SEQUENCE: 116
accaggaugg ccgagugguu aaggcguugg acuggccagc ugugaguguu ucuugaggu      60 aguagguugu augguuugug agcaauagua aggaagaacu guacaccuua cuaccuuuca    120
gaagugcugc acguuguugg cccgauccaa uggacauaug ccgcguggg uucgaacccc     180 acuccuggua cca                                                      193

<210> SEQ ID NO 117
<211> LENGTH: 192
<212> TYPE: RNA
<213> ORGANISM: Artificial sequence
<220> FEATURE:
<223> OTHER INFORMATION: synthetic sequence

<400> SEQUENCE: 117
accaggaugg ccgagugguu aaggcguugg acuggccagc ugugaguguu ucuuuaauug     60
ucaacuacug ucaguuugug agcaauagua aggaaaacug acagauaug acaauucuag     120 aagugcugca cguuguuggc ccgauccaau ggacauaugu ccgcgugggu cgaaccccca    180
cuccugguac ca                                                       192

<210> SEQ ID NO 118
<211> LENGTH: 192
<212> TYPE: RNA
<213> ORGANISM: Artificial sequence
<220> FEATURE:
<223> OTHER INFORMATION: synthetic sequence
```

```
<400> SEQUENCE: 118
accaggaugg ccgaguggu aaggcguugg acuggccagc ugugaguguu ucuuaagcug      60
ccaguugaag aacuguugug agcaauagua aggaagcagu ucuuagcuug gcagcucuag    120
aagugcugca cguuguuggc ccgauccaau ggacauaugu ccgcgugggu ucgaacccca    180
cuccugguac ca                                                        192

<210> SEQ ID NO 119
<211> LENGTH: 192
<212> TYPE: RNA
<213> ORGANISM: Artificial sequence
<220> FEATURE:
<223> OTHER INFORMATION: synthetic sequence

<400> SEQUENCE: 119
accaggaugg ccgaguggu aaggcguugg acuggccagc ugugaguguu ucuuaauac      60 ugccugguaa ugaugaugug agcaauagua aggaaucauc auuauagugc aguauucuag    120
aagugcugca cguuguuggc ccgauccaau ggacauaugu ccgcgugggu ucgaacccca    180
cuccugguac ca                                                        192

<210> SEQ ID NO 120
<211> LENGTH: 192
<212> TYPE: RNA
<213> ORGANISM: Artificial sequence
<220> FEATURE:
<223> OTHER INFORMATION: synthetic sequence

<400> SEQUENCE: 120
accaggaugg ccgaguggu aaggcguugg acuggccagc ugugaguguu ucuucagug      60 cacuacagaa cuuuguugug agcaauagua aggaagcaaa guucguaugu gcacugcuag    120
aagugcugca cguuguuggc ccgauccaau ggacauaugu ccgcgugggu ucgaacccca    180
cuccugguac ca                                                        192

<210> SEQ ID NO 121
<211> LENGTH: 192
<212> TYPE: RNA
<213> ORGANISM: Artificial sequence
<220> FEATURE:
<223> OTHER INFORMATION: synthetic sequence

<400> SEQUENCE: 121
accaggaugg ccgaguggu aaggcguugg acuggccagc ugugaguguu ucuuaggccc      60
uguccucugc cccaguugug agcaauagua aggaagcugg ggcaaggcgc agggcccuag    120
aagugcugca cguuguuggc ccgauccaau ggacauaugu ccgcgugggu ucgaacccca    180
cuccugguac ca                                                        192

<210> SEQ ID NO 122
<211> LENGTH: 192
<212> TYPE: RNA
<213> ORGANISM: Artificial sequence
<220> FEATURE:
<223> OTHER INFORMATION: synthetic sequence

<400> SEQUENCE: 122
accaggaugg ccgaguggu aaggcguugg acuggccagc ugugaguguu ucuuuggaau      60
guaaagaagu auguauugug agcaauagua aggaaaauaca uacucuucua cauucccuag    120
aagugcugca cguuguuggc ccgauccaau ggacauaugu ccgcgugggu ucgaacccca    180
``` cuccuggua ca                                                          192

<210> SEQ ID NO 123
<211> LENGTH: 193
<212> TYPE: RNA
<213> ORGANISM: Artificial sequence
<220> FEATURE:
<223> OTHER INFORMATION: synthetic sequence

<400> SEQUENCE: 123
accaggaugg ccgagugguu aaggcguugg acuggccagc ugugaguguu ucuuuuggu      60 ccccuucaac cagcugugug agcaauagua aggaagcagc gguuaagug ggaccaacua     120 gaagugcugc acguuguugg cccgauccaa uggacauaug ccgcguggg uucgaaccccc    180 acuccuggua cca                                                        193

<210> SEQ ID NO 124
<211> LENGTH: 193
<212> TYPE: RNA
<213> ORGANISM: Artificial sequence
<220> FEATURE:
<223> OTHER INFORMATION: synthetic sequence

<400> SEQUENCE: 124
accaggaugg ccgagugguu aaggcguugg acuggccagc ugugaguguu ucuuuggagu     60
gugacaaugg uguuugugug agcaauagua aggaagcaaa cgccauguac acacucccua    120
gaagugcugc acguuguugg cccgauccaa uggacauaug ccgcguggg uucgaaccccc    180 acuccuggua cca                                                        193

<210> SEQ ID NO 125
<211> LENGTH: 192
<212> TYPE: RNA
<213> ORGANISM: Artificial sequence
<220> FEATURE:
<223> OTHER INFORMATION: synthetic sequence

<400> SEQUENCE: 125
accaggaugg ccgaguggu aaggcguugg acuggccagc ugugaguguu ucuucaaaca     60
ccauugucac acuccaugug agcaauagua aggaauggag ugugcaauug guguuuuuag    120
aagugcugca cguuguuggc ccgauccaau ggacauaugu ccgcggggu ucgaacccca    180 cuccugguac ca                                                         192

<210> SEQ ID NO 126
<211> LENGTH: 192
<212> TYPE: RNA
<213> ORGANISM: Artificial sequence
<220> FEATURE:
<223> OTHER INFORMATION: synthetic sequence

<400> SEQUENCE: 126
accaggaugg ccgaguggu aaggcguugg acuggccagc ugugaguguu ucuuuacuca     60
aaaagcuguc agucauugug agcaauagua aggaagugac ugacgcucuu uugagucuag    120
aagugcugca cguuguuggc ccgauccaau ggacauaugu ccgcggggu ucgaacccca    180 cuccugguac ca                                                         192

<210> SEQ ID NO 127
<211> LENGTH: 191
<212> TYPE: RNA

<213> ORGANISM: Artificial sequence
<220> FEATURE:
<223> OTHER INFORMATION: synthetic sequence

<400> SEQUENCE: 127

```
gcagcgaugg ccgaguggnu aaggcguugg acuggccagc ugugaguguu ucuucuggcc    60
cucucugccc uuccguugug agcaauagua aggaagcggg ggggagaugg gggccauuag   120
aagugcugca cguuguuggc ccaauccaau ggggucuccc cgcgcaggau cgaacccugc   180
ucgcugcgcc a                                                       191
```

<210> SEQ ID NO 128
<211> LENGTH: 191
<212> TYPE: RNA
<213> ORGANISM: Artificial sequence
<220> FEATURE:
<223> OTHER INFORMATION: synthetic sequence

<400> SEQUENCE: 128

```
gcagcgaugg ccgaguggnu aaggcguugg acuggccagc ugugaguguu ucuuuaaggc    60
acgcggugaa ugccguugug agcaauagua aggaagcggu guuccgucg ugccuucuag    120
aagugcugca cguuguuggc ccaauccaau ggggucuccc cgcgcaggau cgaacccugc   180
ucgcugcgcc a                                                       191
```

<210> SEQ ID NO 129
<211> LENGTH: 192
<212> TYPE: RNA
<213> ORGANISM: Artificial sequence
<220> FEATURE:
<223> OTHER INFORMATION: synthetic sequence

<400> SEQUENCE: 129

```
gcagcgaugg ccgaguggnu aaggcguugg acuggccagc ugugaguguu ucuuugaggu    60
aguagguugu augguuugug agcaauagua aggaagaacu guacaccuua cuaccuuuca   120
gaagugcugc acguuguugg cccaauccaa uggggucucc ccgcgcaggu cgaacccug    180
cucgcugcgc ca                                                      192
```

<210> SEQ ID NO 130
<211> LENGTH: 191
<212> TYPE: RNA
<213> ORGANISM: Artificial sequence
<220> FEATURE:
<223> OTHER INFORMATION: synthetic sequence

<400> SEQUENCE: 130

```
gcagcgaugg ccgaguggnu aaggcguugg acuggccagc ugugaguguu ucuuuaauug    60
ucaacuacug ucaguuugug agcaauagua aggaaaacug acagaguaug acaauucuag   120
aagugcugca cguuguuggc ccaauccaau ggggucuccc cgcgcaggau cgaacccugc   180
ucgcugcgcc a                                                       191
```

<210> SEQ ID NO 131
<211> LENGTH: 187
<212> TYPE: RNA
<213> ORGANISM: Artificial sequence
<220> FEATURE:
<223> OTHER INFORMATION: synthetic sequence

<400> SEQUENCE: 131

```
gcagcgaugg ccgaguggnu aaggcguugg acuggccagc ugugaguguu ucuucgagc     60
```

```
cauugaaaua agccugugag caauaguaag gaaggcuuau ucauauggcu cgcuagaagu        120
gcugcacguu guuggcccaa uccaauggg ucuccccgcg cagguucgaa cccugcucgc         180
ugcgcca                                                                  187

<210> SEQ ID NO 132
<211> LENGTH: 191
<212> TYPE: RNA
<213> ORGANISM: Artificial sequence
<220> FEATURE:
<223> OTHER INFORMATION: synthetic sequence

<400> SEQUENCE: 132
gcagcgaugg ccgaguggu aaggcguugg acuggccagc ugugaguguu ucuuucgagc         60
cauugaaaua agccguugug agcaauagua aggaagcggc uuauucauau ggcucgcuag        120
aagugcugca cguuguuggc ccaauccaau ggggucuccc cgcgcagguu cgaacccugc        180
ucgcugcgcc a                                                             191

<210> SEQ ID NO 133
<211> LENGTH: 191
<212> TYPE: RNA
<213> ORGANISM: Artificial sequence
<220> FEATURE:
<223> OTHER INFORMATION: synthetic sequence

<400> SEQUENCE: 133
gcagcgaugg ccgaguggu aaggcguugg acuggccagc ugugaguguu ucuuaagcug        60
ccaguugaag aacuguugug agcaauagua aggaagcagu ucuuagcuug gcagcucuag       120
aagugcugca cguuguuggc ccaauccaau ggggucuccc cgcgcagguu cgaacccugc       180
ucgcugcgcc a                                                             191

<210> SEQ ID NO 134
<211> LENGTH: 191
<212> TYPE: RNA
<213> ORGANISM: Artificial sequence
<220> FEATURE:
<223> OTHER INFORMATION: synthetic sequence

<400> SEQUENCE: 134
gcagcgaugg ccgaguggu aaggcguugg acuggccagc ugugaguguu ucuuaauac        60 ugccugguaa ugaugaugug agcaauagua aggaaucauc auuauagugc aguauucuag      120
aagugcugca cguuguuggc ccaauccaau ggggucuccc cgcgcagguu cgaacccugc      180
ucgcugcgcc a                                                             191

<210> SEQ ID NO 135
<211> LENGTH: 191
<212> TYPE: RNA
<213> ORGANISM: Artificial sequence
<220> FEATURE:
<223> OTHER INFORMATION: synthetic sequence

<400> SEQUENCE: 135
gcagcgaugg ccgaguggu aaggcguugg acuggccagc ugugaguguu ucuucagug        60 cacuacagaa cuuuguugug agcaauagua aggaagcaaa guucguaugu gcacugcuag      120
aagugcugca cguuguuggc ccaauccaau ggggucuccc cgcgcagguu cgaacccugc      180
ucgcugcgcc a                                                             191
```

<210> SEQ ID NO 136
<211> LENGTH: 191
<212> TYPE: RNA
<213> ORGANISM: Artificial sequence
<220> FEATURE:
<223> OTHER INFORMATION: synthetic sequence

<400> SEQUENCE: 136

```
gcagcgaugg ccgagugguu aaggcguugg acuggccagc ugugaguguu ucuuaggccc    60
uguccucugc cccaguugug agcaauagua aggaagcugg ggcaaggcgc agggcccuag   120
aagugcugca cguuguuggc ccaauccaau ggggucuccc cgcgcagguu cgaacccugc   180
ucgcugcgcc a                                                       191
```

<210> SEQ ID NO 137
<211> LENGTH: 193
<212> TYPE: RNA
<213> ORGANISM: Artificial sequence
<220> FEATURE:
<223> OTHER INFORMATION: synthetic sequence

<400> SEQUENCE: 137

```
gcagcgaugg ccgagugguu aaggcguugg acuggccagc ugugaguguu ucuucggccu    60
gauucacaac accagcuugu gagcaauagu aaggaaagcu gguguuugau aucaggccuu   120
agaagugcug cacguuguug gcccaaucca auggggucuc ccgcgcaggu ucgaacccu    180
gcucgcugcg cca                                                     193
```

<210> SEQ ID NO 138
<211> LENGTH: 191
<212> TYPE: RNA
<213> ORGANISM: Artificial sequence
<220> FEATURE:
<223> OTHER INFORMATION: synthetic sequence

<400> SEQUENCE: 138

```
gcagcgaugg ccgagugguu aaggcguugg acuggccagc ugugaguguu ucuuuggaau    60
guaaagaagu auguauugug agcaauagua aggaaauaca uacucuucua cauucccuag   120
aagugcugca cguuguuggc ccaauccaau ggggucuccc cgcgcagguu cgaacccugc   180
ucgcugcgcc a                                                       191
```

<210> SEQ ID NO 139
<211> LENGTH: 192
<212> TYPE: RNA
<213> ORGANISM: Artificial sequence
<220> FEATURE:
<223> OTHER INFORMATION: synthetic sequence

<400> SEQUENCE: 139

```
gcagcgaugg ccgagugguu aaggcguugg acuggccagc ugugaguguu ucuuuuggu     60
ccccuucaac cagcugugug agcaauagua aggaagcagc ugguuaagug ggaccaacua   120
gaagugcugc acguuguugg cccaauccaa uggggucucc ccgcgcaggu ucgaacccug   180
cucgcugcgc ca                                                      192
```

<210> SEQ ID NO 140
<211> LENGTH: 192
<212> TYPE: RNA
<213> ORGANISM: Artificial sequence
<220> FEATURE:
<223> OTHER INFORMATION: synthetic sequence

<400> SEQUENCE: 140

| gcagcgaugg ccgagugguu aaggcguugg acuggccagc ugugagyguu ucuuuggagu | 60 |
| gugacaaugg uguuugugug agcaauagua aggaagcaaa cgccauguac acacucccua | 120 |
| gaagugcugc acguuguugg cccaauccaa uggggucucc cgcgcaggu ucgaacccug | 180 |
| cucgcugcgc ca | 192 |

<210> SEQ ID NO 141
<211> LENGTH: 191
<212> TYPE: RNA
<213> ORGANISM: Artificial sequence
<220> FEATURE:
<223> OTHER INFORMATION: synthetic sequence

<400> SEQUENCE: 141

| gcagcgaugg ccgagugguu aaggcguugg acuggccagc ugugagyguu ucuucaaaca | 60 |
| ccauugucac acuccaugug agcaauagua aggaauggag ugugcaauug guguuuuuag | 120 |
| aagugcugca cguuguuggc ccaauccaau ggggucuccc cgcgcaggu cgaacccugc | 180 |
| ucgcugcgcc a | 191 |

<210> SEQ ID NO 142
<211> LENGTH: 191
<212> TYPE: RNA
<213> ORGANISM: Artificial sequence
<220> FEATURE:
<223> OTHER INFORMATION: synthetic sequence

<400> SEQUENCE: 142

| gcagcgaugg ccgagugguu aaggcguugg acuggccagc ugugagyguu ucuuuacuca | 60 |
| aaaagcuguc agucauugug agcaauagua aggaaugac ugacgcucuu uugagucuag | 120 |
| aagugcugca cguuguuggc ccaauccaau ggggucuccc cgcgcaggu cgaacccugc | 180 |
| ucgcugcgcc a | 191 |

<210> SEQ ID NO 143
<211> LENGTH: 169
<212> TYPE: RNA
<213> ORGANISM: Artificial sequence
<220> FEATURE:
<223> OTHER INFORMATION: synthetic sequence

<400> SEQUENCE: 143

| gcagcgaugg ccgagugguu aaggcguugg acugguagaa uuccagugc ccugacugaa | 60 |
| gaccagcagu uguacugugg cuguuggyuu caagcagagg ccuaaaggac ugucuuccug | 120 |
| aauccaaugg ggucuccccg cgcagguucg aacccugcuc gcugcgcca | 169 |

<210> SEQ ID NO 144
<211> LENGTH: 169
<212> TYPE: RNA
<213> ORGANISM: Artificial sequence
<220> FEATURE:
<223> OTHER INFORMATION: synthetic sequence

<400> SEQUENCE: 144

| gacgaggugg ccgagugguu aaggcgaugg acugguagaa uuccagugc ccugacugaa | 60 |
| gaccagcagu uguacugugg cuguuggyuu caagcagagg ccuaaaggac ugucuuccug | 120 |
| aauccauugu gcucugcacg cguggguucg aaucccaccc ucgucgcca | 169 |

<210> SEQ ID NO 145
<211> LENGTH: 170
<212> TYPE: RNA
<213> ORGANISM: Artificial sequence
<220> FEATURE:
<223> OTHER INFORMATION: synthetic sequence

<400> SEQUENCE: 145
accaggaugg ccgagugguu aaggcguugg acugguagaa uuccaguggc ccugacugaa        60
gaccagcagu uguacugugg cuguugguuu caagcagagg ccuaaaggac ugucuuccug       120
gauccaaugg acauaugucc gcgugggiuc gaaccccacu ccugguacca                  170

<210> SEQ ID NO 146
<211> LENGTH: 171
<212> TYPE: RNA
<213> ORGANISM: Artificial sequence
<220> FEATURE:
<223> OTHER INFORMATION: synthetic sequence

<400> SEQUENCE: 146
gucaggaugg ccgagugguc uaaggcgcca gacugguaga auuccaguga cccugacuga        60
agaccagcag uuguacugug gcuguugguu ucaagcagag gccuaaagga cugucuuccu       120
gguucugguc uccguaugga ggcguggguu cgaaucccac uucugacacc a                171

<210> SEQ ID NO 147
<211> LENGTH: 158
<212> TYPE: RNA
<213> ORGANISM: Artificial sequence
<220> FEATURE:
<223> OTHER INFORMATION: synthetic sequence

<400> SEQUENCE: 147
gcaugggugg uucaguggua gaauucucgc cugguagaau uccaguggcc cugacugaag        60
accagcaguu guacuguggc uguugguuuc aagcagaggc cuaaaggacu gucuuccuga       120
cgcgggaggc ccggguucga uucccggccc augcacca                               158

<210> SEQ ID NO 148
<211> LENGTH: 159
<212> TYPE: RNA
<213> ORGANISM: Artificial sequence
<220> FEATURE:
<223> OTHER INFORMATION: synthetic sequence

<400> SEQUENCE: 148
gcguuggugg uauagugguu agcauagcug ccgguagaa uuccaguggc ccugacugaa         60
gaccagcagu uguacugugg cuguugguuu caagcagagg ccuaaaggac ugucuuccug       120
aagcaguuga cccgggiucg auucccggcc aacgcacca                              159

<210> SEQ ID NO 149
<211> LENGTH: 159
<212> TYPE: RNA
<213> ORGANISM: Artificial sequence
<220> FEATURE:
<223> OTHER INFORMATION: synthetic sequence

<400> SEQUENCE: 149
ucccuggugg ucuagugguu aggauucggc gcugguagaa uuccaguggc ccugacugaa        60
gaccagcagu uguacugugg cuguugguuu caagcagagg ccuaaaggac ugucuuccug       120
accgccgcgg cccgggiucg auucccgguc agggaacca                              159

<210> SEQ ID NO 150
<211> LENGTH: 159
<212> TYPE: RNA
<213> ORGANISM: Artificial sequence
<220> FEATURE:
<223> OTHER INFORMATION: synthetic sequence

<400> SEQUENCE: 150
uccucguuag uauaguggug aguauccccg ccugguagaa uuccagugge ccugacugaa     60 gaccagcagu uguacugugg cuguuggu uu caagcagagg ccuaaaggac ugucuuccug   120
acgcgggaga ccggg guucg auuccccgac ggggagcca                          159

<210> SEQ ID NO 151
<211> LENGTH: 159
<212> TYPE: RNA
<213> ORGANISM: Artificial sequence
<220> FEATURE:
<223> OTHER INFORMATION: synthetic sequence

<400> SEQUENCE: 151
ggucccaugg uguaauggu u agcacucugg acugguagaa uuccagugge ccugacugaa    60 gaccagcagu uguacugugg cuguugguuu caagcagagg ccuaaaggac ugucuuccug   120
aauccagcga uccgaguuca aaucucggug ggaccucca                          159

<210> SEQ ID NO 152
<211> LENGTH: 159
<212> TYPE: RNA
<213> ORGANISM: Artificial sequence
<220> FEATURE:
<223> OTHER INFORMATION: synthetic sequence

<400> SEQUENCE: 152 gguccaugg uguaauggu u agcacucugg acugguagaa uuccagugge ccugacugaa     60 gaccagcagu uguacugugg cuguugguuu caagcagagg ccuaaaggac ugucuuccug   120
aauccagcga uccgaguuca aaucucggug gaaccucca                          159

<210> SEQ ID NO 153
<211> LENGTH: 160
<212> TYPE: RNA
<213> ORGANISM: Artificial sequence
<220> FEATURE:
<223> OTHER INFORMATION: synthetic sequence

<400> SEQUENCE: 153
gggccagugg cgcaauggau aacgcgucug acugguagaa uuccagugge ccugacugaa     60 gaccagcagu uguacugugg cuguugguuu caagcagagg ccuaaaggac ugucuuccug   120
gaucagaaga uuccagguuc gacuccuggc uggcucgcca                          160

<210> SEQ ID NO 154
<211> LENGTH: 160
<212> TYPE: RNA
<213> ORGANISM: Artificial sequence
<220> FEATURE:
<223> OTHER INFORMATION: synthetic sequence

<400> SEQUENCE: 154
ggcucugugg cgcaauggau agcgcauugg acugguagaa uuccagugge ccugacugaa     60 gaccagcagu uguacugugg cuguugguuu caagcagagg ccuaaaggac ugucuuccug   120
aauucaaagg uuguggguuc gaaucccacc agagucgcca            160

<210> SEQ ID NO 155
<211> LENGTH: 159
<212> TYPE: RNA
<213> ORGANISM: Artificial sequence
<220> FEATURE:
<223> OTHER INFORMATION: synthetic sequence

<400> SEQUENCE: 155
gggggcauag cucaguggua gagcauuuga cugguagaau uccagugggcc cugacugaag            60 accagcaguu guacugugge uguugguuuc aagcagaggc cuaaaggacu gucuuccugg            120
aucaagaggu cccugguuca aauccaggug cccccucca            159

<210> SEQ ID NO 156
<211> LENGTH: 160
<212> TYPE: RNA
<213> ORGANISM: Artificial sequence
<220> FEATURE:
<223> OTHER INFORMATION: synthetic sequence

<400> SEQUENCE: 156
gcccggcuag cucagucggu agagcauggg acugguagaa uuccaguggc ccugacugaa            60
gaccagcagu uguacugugg cuguugguuu caagcagagg ccuaaaggac ugucuuccug            120
aaucccaggg ucgugggguuc gagccccacg uugggcgcca            160

<210> SEQ ID NO 157
<211> LENGTH: 160
<212> TYPE: RNA
<213> ORGANISM: Artificial sequence
<220> FEATURE:
<223> OTHER INFORMATION: synthetic sequence

<400> SEQUENCE: 157
gccuggauag cucaguuggu agagcaucag acugguagaa uuccaguggc ccugacugaa            60
gaccagcagu uguacugugg cuguugguuu caagcagagg ccuaaaggac ugucuuccug            120
aaucugaggg uccagggguuc aagucccugu ucaggcacca            160

<210> SEQ ID NO 158
<211> LENGTH: 160
<212> TYPE: RNA
<213> ORGANISM: Artificial sequence
<220> FEATURE:
<223> OTHER INFORMATION: synthetic sequence

<400> SEQUENCE: 158
gccucguuag cgcaguaggu agcgcgucag ucugguagaa uuccaguggc ccugacugaa            60
gaccagcagu uguacugugg cuguugguuu caagcagagg ccuaaaggac ugucuuccug            120
aaucugaagg ucgugaguuc gauccucaca cggggcacca            160

<210> SEQ ID NO 159
<211> LENGTH: 161
<212> TYPE: RNA
<213> ORGANISM: Artificial sequence
<220> FEATURE:
<223> OTHER INFORMATION: synthetic sequence

<400> SEQUENCE: 159
gucucugugg cgcaaucggu uagcgcguuc ggcugguaga auuccagugg cccugacuga            60
agaccagcag uuguacugug gcuguugguu ucaagcagag gccuaaagga cugucuuccu            120

```
gaaccgaaag guuggugguu cgaucccacc cagggacgcc a                161
```

<210> SEQ ID NO 160
<211> LENGTH: 159
<212> TYPE: RNA
<213> ORGANISM: Artificial sequence
<220> FEATURE:
<223> OTHER INFORMATION: synthetic sequence

<400> SEQUENCE: 160

```
gggggguguag cucaguggua gagcgcgugc uugguagaau uccaguggcc cugacugaag   60
accagcaguu guacugugg cguugguuuc aagcagaggc cuaaaggacu gucuuccuga   120
ugcacgaggc cccggguuca auccccggca ccuccacca                          159
```

<210> SEQ ID NO 161
<211> LENGTH: 159
<212> TYPE: RNA
<213> ORGANISM: Artificial sequence
<220> FEATURE:
<223> OTHER INFORMATION: synthetic sequence

<400> SEQUENCE: 161

```
gccgugaucg uauagugguu aguacucugc guuggguagaa uuccaguggc ccugacugaa   60
gaccagcagu uguacugugg cuguugguuu caagcagagg ccuaaaggac ugucuuccug   120
gccgcagcaa ccucgguucg aauccgaguc acggcacca                          159
```

<210> SEQ ID NO 162
<211> LENGTH: 161
<212> TYPE: RNA
<213> ORGANISM: Artificial sequence
<220> FEATURE:
<223> OTHER INFORMATION: synthetic sequence

<400> SEQUENCE: 162

```
ggccgguuag cucaguuggu uagagcgugg ugcugguaga auccagugg cccugacuga    60
agaccagcag uuguacugug gcuguugguu ucaagcagag gccuaaagga cugucuuccu  120
gaacgccaag gucgcgdgguu cgauccccgu acuggccacc a                     161
```

<210> SEQ ID NO 163
<211> LENGTH: 161
<212> TYPE: RNA
<213> ORGANISM: Artificial sequence
<220> FEATURE:
<223> OTHER INFORMATION: synthetic sequence

<400> SEQUENCE: 163

```
gcuccagugg cgcaaucggu uagcgcgcgg uacugguaga auccagugg cccugacuga    60
agaccagcag uuguacugug gcuguugguu ucaagcagag gccuaaagga cugucuuccu  120
gaaugccgag guugugaguu cgauccucac cuggagcacc a                      161
```

<210> SEQ ID NO 164
<211> LENGTH: 160
<212> TYPE: RNA
<213> ORGANISM: Artificial sequence
<220> FEATURE:
<223> OTHER INFORMATION: synthetic sequence

<400> SEQUENCE: 164

```
gccgaaauag cucaguuggg agagcguuag acugguagaa uuccaguggc ccugacugaa   60
```

```
gaccagcagu uguacugugg cguuggutu caagcagagg ccuaaaggac ugucuuccug    120
gaucuaaagg ucccugguuc gaucccgggu uucggcacca                         160

<210> SEQ ID NO 165
<211> LENGTH: 159
<212> TYPE: RNA
<213> ORGANISM: Artificial sequence
<220> FEATURE:
<223> OTHER INFORMATION: synthetic sequence

<400> SEQUENCE: 165
ggcucguugg ucuaggggua ugauucucgc uugguagaau uccaguggcc cugacugaag    60
accagcaguu guacugugge uguugguuuc aagcagagge cuaaaggacu gucuuccuga   120
ugcgagaggu cccgguuca aaucccggac gagccccca                            159

<210> SEQ ID NO 166
<211> LENGTH: 159
<212> TYPE: RNA
<213> ORGANISM: Artificial sequence
<220> FEATURE:
<223> OTHER INFORMATION: synthetic sequence

<400> SEQUENCE: 166
gaccucgugg cgcaacggua gcgcgucuga cugguagaau uccaguggcc cugacugaag    60
accagcaguu guacugugge uguugguuuc aagcagagge cuaaaggacu gucuuccugg   120
aucagaaggc ugcguguucg aaucacgucg gggucacca                           159

<210> SEQ ID NO 167
<211> LENGTH: 160
<212> TYPE: RNA
<213> ORGANISM: Artificial sequence
<220> FEATURE:
<223> OTHER INFORMATION: synthetic sequence

<400> SEQUENCE: 167
ccuucgauag cucaguuggu agagcggagg acugguagaa uuccaguggc ccugacugaa    60
gaccagcagu uguacugugg cguuggutu caagcagagg ccuaaaggac ugucuuccug    120
gauccuuagg ucgcugguuc gaauccggcu cgaaggacca                          160

<210> SEQ ID NO 168
<211> LENGTH: 160
<212> TYPE: RNA
<213> ORGANISM: Artificial sequence
<220> FEATURE:
<223> OTHER INFORMATION: synthetic sequence

<400> SEQUENCE: 168
guuuccguag uguaguggut aucacguucg ccugguagaa uuccaguggc ccugacugaa    60
gaccagcagu uguacugugg cguuggutu caagcagagg ccuaaaggac ugucuuccug    120
acgcgaaagg uccccgguuc gaaaccgggc ggaaacacca                          160

<210> SEQ ID NO 169
<211> LENGTH: 161
<212> TYPE: RNA
<213> ORGANISM: Artificial sequence
<220> FEATURE:
<223> OTHER INFORMATION: synthetic sequence

<400> SEQUENCE: 169
ggcucuaugg cuuaguuggu uaaagcgccu gucuggduaga auuccagugg cccugacuga    60
```

```
agaccagcag uuguacugug gcuguugguu ucaagcagag gccuaaagga cugucuuccu    120
gaaacaggag auccuggguu cgaaucccag uagagccucc a                        161

<210> SEQ ID NO 170
<211> LENGTH: 161
<212> TYPE: RNA
<213> ORGANISM: Artificial sequence
<220> FEATURE:
<223> OTHER INFORMATION: synthetic sequence

<400> SEQUENCE: 170
ggcgccgugg cuuaguuggu uaaagcgccu gucugguaga auccagugg cccugacuga     60 agaccagcag uuguacugug gcuguugguu ucaagcagag gccuaaagga cugucuuccu    120
gaaacaggag auccuggguu cgaaucccag cggugccucc a                        161

<210> SEQ ID NO 171
<211> LENGTH: 178
<212> TYPE: RNA
<213> ORGANISM: Artificial sequence
<220> FEATURE:
<223> OTHER INFORMATION: synthetic sequence

<400> SEQUENCE: 171
accaggaugg ccgagugguu aaggcguugg acuccagcuc gggcagccgu ggccaucuua    60
cugggcagca uuggauggag ucaggucucu aauacugccu gguaaugaug acggcggagc   120
ccugcacgga uccaauggac auauguccgc guggguucga accccacucc gguacca      178

<210> SEQ ID NO 172
<211> LENGTH: 171
<212> TYPE: RNA
<213> ORGANISM: Artificial sequence
<220> FEATURE:
<223> OTHER INFORMATION: synthetic sequence

<400> SEQUENCE: 172
accaggaugg ccgagugguu aaggcguugg acuacaaugc uuugcuagag cugguaaaau    60
ggaaccaaau cgccucuuca auggauuugg uccccuucaa ccagcuguag cuaugcauug   120
agauccaaug gacauauguc cgcguggguu cgaaccccac uccgguacc a              171

<210> SEQ ID NO 173
<211> LENGTH: 168
<212> TYPE: RNA
<213> ORGANISM: Artificial sequence
<220> FEATURE:
<223> OTHER INFORMATION: synthetic sequence

<400> SEQUENCE: 173
gcagcgaugg ccgagugguu aaggcguugg acuugccagu cucuaggucc cugagacccu    60
uuaaccugug aggacaucca ggucacagg ugagguucuu gggagccugg cgucuggcca    120
auccaauggg gucuccccgc gcagguucga acccugcucg cugcgcca                168

<210> SEQ ID NO 174
<211> LENGTH: 166
<212> TYPE: RNA
<213> ORGANISM: Artificial sequence
<220> FEATURE:
<223> OTHER INFORMATION: synthetic sequence

<400> SEQUENCE: 174
```

```
gcagcgaugg ccgagugguu aaggcguugg acuugccagu cucuaggugg cagugucuua    60
gcugguugug gacauccagg guccaaucag caaguauacu gcccuuggcg ucuggccaau   120
ccaauggggu cuccccgcgc agguucgaac ccugcucgcu gcgcca                 166
```

<210> SEQ ID NO 175
<211> LENGTH: 166
<212> TYPE: RNA
<213> ORGANISM: Artificial sequence
<220> FEATURE:
<223> OTHER INFORMATION: synthetic sequence

<400> SEQUENCE: 175

```
gcagcgaugg ccgagugguu aaggcguugg acugcauccg gguugaggua guagguugua    60
ugguuuagag uuacacccug ggaguuaacu guacaaccuu cuagcuuucc uuggagcaau   120
ccaauggggu cuccccgcgc agguucgaac ccugcucgcu gcgcca                 166
```

<210> SEQ ID NO 176
<211> LENGTH: 167
<212> TYPE: RNA
<213> ORGANISM: Artificial sequence
<220> FEATURE:
<223> OTHER INFORMATION: synthetic sequence

<400> SEQUENCE: 176

```
gcagcgaugg ccgagugguu aaggcguugg acuaggccuc ucucuccgug uucacagcgg    60
accuugauuu aaauguccau acaauuaagg cacgcgguga augccaagaa uggggcugaa   120 uccaauggggg ucuccccgcg cagguucgaa cccugcucgc ugcgcca                167
```

<210> SEQ ID NO 177
<211> LENGTH: 93
<212> TYPE: RNA
<213> ORGANISM: Artificial sequence
<220> FEATURE:
<223> OTHER INFORMATION: synthetic sequence

<400> SEQUENCE: 177

```
uggcaguguc uuagcugguu gucuaaucgc cgaguaauuu acgcccgggu gguugcggcg    60
cggcccgggu ucgauucccg gcacugacaa cca                                93
```

<210> SEQ ID NO 178
<211> LENGTH: 93
<212> TYPE: RNA
<213> ORGANISM: Artificial sequence
<220> FEATURE:
<223> OTHER INFORMATION: synthetic sequence

<400> SEQUENCE: 178

```
uggcaguguc uuagcugguu guccagacgc cgaguaauuu acgcccgggu gguugcggcg    60
ugacccgggu ucgauucccg gcacugccaa cca                                93
```

<210> SEQ ID NO 179
<211> LENGTH: 103
<212> TYPE: RNA
<213> ORGANISM: Artificial sequence
<220> FEATURE:
<223> OTHER INFORMATION: synthetic sequence

<400> SEQUENCE: 179

```
uggcaguguc uuagcugguu guaauaaccg ccgaguaauu uacgcccggg gguugcggc    60 gucucuucgg gggcgugggu ucaaaucccca ccacugccaa cca                  103
```

```
<210> SEQ ID NO 180
<211> LENGTH: 103
<212> TYPE: RNA
<213> ORGANISM: Artificial sequence
<220> FEATURE:
<223> OTHER INFORMATION: synthetic sequence

<400> SEQUENCE: 180
uggcaguguc uuagcugguu guauaaccgc cgaguaauuu acgcccgggu gguugcggcg      60
ugugcucugc acgcguggu ucgaauccca ucacugccaa cca                       103

<210> SEQ ID NO 181
<211> LENGTH: 191
<212> TYPE: RNA
<213> ORGANISM: Artificial sequence
<220> FEATURE:
<223> OTHER INFORMATION: synthetic sequence

<400> SEQUENCE: 181
accaggaugg acucaacauc agucugauaa gcggccagcu gugaguguuu cuuggcagu      60 gucuuagcug guuguuguga gcaauaguaa ggaagcaauc agcaaguaua cugcccuaga    120
agugcugcac guuguuggcc cgauuaucag gacauauguc cgcgugggu cgaaccccac    180 uccugguacc a                                                         191

<210> SEQ ID NO 182
<211> LENGTH: 191
<212> TYPE: RNA
<213> ORGANISM: Artificial sequence
<220> FEATURE:
<223> OTHER INFORMATION: synthetic sequence

<400> SEQUENCE: 182
ucagacuugg ccgagugguu aaggcguugg acuggccagc ugugaguguu ucuuuggcag      60
ugucuuagcu gguuguugug agcaauagua aggaagcaau cagcaaguau acugcccuag    120
aagugcugca cguuguuggc ccgauccaau ggacauaugu ccgcgaugac cgucaacauc    180
agucugauaa g                                                         191

<210> SEQ ID NO 183
<211> LENGTH: 297
<212> TYPE: RNA
<213> ORGANISM: Artificial sequence
<220> FEATURE:
<223> OTHER INFORMATION: synthetic sequence

<400> SEQUENCE: 183
accaggaugg ccgagugguu aaggcguugg acuggccagc ugugaguguu ucuuucaaca      60
ucagucugau aagcuaugug agcggccagc ugugaguguu ucuuggcag ugucuuagcu    120 gguuguugug agcaauagua aggaagcaau cagcaaguau acugcccuag aagugcugca    180
cguuguuggc ccguaaggaa guagcuuaua agaaugaugu ugcagaagug cugcacguug    240
uuggcccgau ccaauggaca uaugccgcg ugggucgaa ccccacuccu gguacca         297

<210> SEQ ID NO 184
<211> LENGTH: 297
<212> TYPE: RNA
<213> ORGANISM: Artificial sequence
<220> FEATURE:
<223> OTHER INFORMATION: synthetic sequence
```

<400> SEQUENCE: 184
accaggaugg ccgagugguu aaggcguugg acuggccagc ugugaguguu ucuuuggcag     60
ugucuuagcu gguuguugug agcggccagc ugugaguguu ucuuuaaggc acgcggugaa    120
ugccguugug agcaauagua aggaagcggu guucccgucg ugccuucuag aagugcugca    180
cguuguuggc ccguaaggaa gcaaucagca aguauacugc ccugaagug cugcacguug    240 uuggcccgau ccaauggaca uauguccgcg ugggucgaa ccccacuccu gguacca       297

<210> SEQ ID NO 185
<211> LENGTH: 298
<212> TYPE: RNA
<213> ORGANISM: Artificial sequence
<220> FEATURE:
<223> OTHER INFORMATION: synthetic sequence

<400> SEQUENCE: 185
accaggaugg ccgagugguu aaggcguugg acuggccagc ugugaguguu ucuuugaggu     60
aguagguugu augguuugug agcggccagc ugugaguguu ucuuuaaggc acgcggugaa    120
ugccguugug agcaauagua aggaagcggu guucccgucg ugccuucuag aagugcugca    180
cguuguuggc ccguaaggaa gaacuguaca ccuuacuacc uuucagaagu gcugcacguu    240
guuggcccga uccaauggac auauguccgc gugggucga accccacuccc gguacca      298

<210> SEQ ID NO 186
<211> LENGTH: 297
<212> TYPE: RNA
<213> ORGANISM: Artificial sequence
<220> FEATURE:
<223> OTHER INFORMATION: synthetic sequence

<400> SEQUENCE: 186
accaggaugg ccgagugguu aaggcguugg acuggccagc ugugaguguu ucuuuaaggc     60
acgcggugaa ugccguugug agcggccagc ugugaguguu ucuuuggcag ugucuuagcu    120
gguuguugug agcaauagua aggaagcaau cagcaaguau acugcccuag aagugcugca    180
cguuguuggc ccguaaggaa gcgguguucc cgucgugccu ucuagaagug cugcacguug    240
uuggcccgau ccaauggaca uauguccgcg ugggucgaa ccccacuccu gguacca       297

<210> SEQ ID NO 187
<211> LENGTH: 296
<212> TYPE: RNA
<213> ORGANISM: Artificial sequence
<220> FEATURE:
<223> OTHER INFORMATION: synthetic sequence

<400> SEQUENCE: 187
gcagcgaugg ccgagugguu aaggcguugg acuggccagc ugugaguguu ucuuuaauug     60
ucaacuacug ucaguuugug agcggccagc ugugaguguu ucuuuggcag ugucuuagcu    120
gguuguugug agcaauagua aggaagcaau cagcaaguau acugcccuag aagugcugca    180
cguuguuggc ccguaaggaa aacugacaga guaugacaau ucuagaagug cugcacguug    240
uuggcccaau ccaauggggu cuccccgcgc agguucgaac ccugcucgcu gcgcca        296

<210> SEQ ID NO 188
<211> LENGTH: 298
<212> TYPE: RNA
<213> ORGANISM: Artificial sequence
<220> FEATURE:
<223> OTHER INFORMATION: synthetic sequence

<400> SEQUENCE: 188

```
accaggaugg ccgagugguu aaggcguugg acuggccagc ugugaguguu ucuuugaggu    60
aguagguugu augguuugug agcggccagc ugugaguguu ucuuggcag ugucuuagcu    120 gguuguugug agcaauagua aggaagcaau cagcaaguau acugcccuag aagugcugca    180
cguuguuggc ccguaaggaa gaacuguaca ccuuacuacc uuucagaagu gcugcacguu    240
guuggcccga uccaauggac auauguccgc gugggugcga accccacucc gguacca     298
```

<210> SEQ ID NO 189
<211> LENGTH: 296
<212> TYPE: RNA
<213> ORGANISM: Artificial sequence
<220> FEATURE:
<223> OTHER INFORMATION: synthetic sequence

<400> SEQUENCE: 189

```
gcagcgaugg ccgagugguu aaggcguugg acuggccagc ugugaguguu ucuuuaaggc    60
acgcggugaa ugccguugug agcggccagc ugugaguguu ucuuggcag ugucuuagcu    120 gguuguugug agcaauagua aggaagcaau cagcaaguau acugcccuag aagugcugca    180
cguuguuggc ccguaaggaa gcgguguucc cgucugugccu ucuagaagug cugcacguug    240
uuggcccaau ccaauggggu cuccccgcgc agguucgaac ccugcucgcu gcgcca        296
```

<210> SEQ ID NO 190
<211> LENGTH: 297
<212> TYPE: RNA
<213> ORGANISM: Artificial sequence
<220> FEATURE:
<223> OTHER INFORMATION: synthetic sequence

<400> SEQUENCE: 190

```
gcagcgaugg ccgagugguu aaggcguugg acuggccagc ugugaguguu ucuuugaggu    60
aguagguugu augguuugug agcggccagc ugugaguguu ucuuuaaggc acgcggugaa    120
ugccguugug agcaauagua aggaagcggu guccccgucg ugccuucuag aagugcugca    180
cguuguuggc ccguaaggaa gaacuguaca ccuuacuacc uuucagaagu gcugcacguu    240
guuggcccaa ccaauggggu cuccccgcgc agguucgaa cccugcucgc ugcgcca       297
```

<210> SEQ ID NO 191
<211> LENGTH: 297
<212> TYPE: RNA
<213> ORGANISM: Artificial sequence
<220> FEATURE:
<223> OTHER INFORMATION: synthetic sequence

<400> SEQUENCE: 191

```
gcagcgaugg ccgagugguu aaggcguugg acuggccagc ugugaguguu ucuuugaggu    60
aguagguugu augguuugug agcggccagc ugugaguguu ucuuggcag ugucuuagcu    120 gguuguugug agcaauagua aggaagcaau cagcaaguau acugcccuag aagugcugca    180
cguuguuggc ccguaaggaa gaacuguaca ccuuacuacc uuucagaagu gcugcacguu    240
guuggcccaa ccaauggggu cuccccgcgc agguucgaa cccugcucgc ugcgcca       297
```

<210> SEQ ID NO 192
<211> LENGTH: 297
<212> TYPE: RNA
<213> ORGANISM: Artificial sequence
<220> FEATURE:

<223> OTHER INFORMATION: synthetic sequence

<400> SEQUENCE: 192

| accaggaugg ccgagugguu aaggcguugg acuggccagc ugugaguguu ucuuuaauug | 60 |
| ucaacuacug ucaguuugug agcggccagc ugugagguguu ucuuggcag ugucuuagcu | 120 |
| gguuguugug agcaauagua aggaagcaau cagcaaguau acugcccuag aagugcugca | 180 |
| cguuguggc ccguaaggaa aacugacaga guaugacaau ucuagaagug cugcacguug | 240 |
| uuggcccgau ccaauggaca uauguccgcg ugggucgaa ccccacuccu gguacca | 297 |

<210> SEQ ID NO 193
<211> LENGTH: 331
<212> TYPE: RNA
<213> ORGANISM: Artificial sequence
<220> FEATURE:
<223> OTHER INFORMATION: synthetic sequence

<400> SEQUENCE: 193

| accaggaugg ccgagugguu aaggcguugg acuggcgaua ccagccgaaa ggcccuuggc | 60 |
| agcgucggcc agcugugagu guuucuuuga gguaguaggu uguaugguuu gugagcggcc | 120 |
| agcugugagu guuucuuuaa ggcacgcggu gaaugccguu gugagcaaua guaaggaagc | 180 |
| gguguccccg ucgugccuuc uagaagugcu gcacguuguu ggcccguaag gaagaacugu | 240 |
| acaccuuacu accuuucaga gugcugcac guuguuggcc cgauccaaug gacauauguc | 300 |
| cgcgugggguu cgaaccccac uccugguacc a | 331 |

<210> SEQ ID NO 194
<211> LENGTH: 330
<212> TYPE: RNA
<213> ORGANISM: Artificial sequence
<220> FEATURE:
<223> OTHER INFORMATION: synthetic sequence

<400> SEQUENCE: 194

| accaggaugg ccgagugguu aaggcguugg acuggcgaua ccagccgaaa ggcccuuggc | 60 |
| agcgucggcc agcugugagu guuucuuuaa ggcacgcggu gaaugccguu gugagcggcc | 120 |
| agcugugagu guuucuuugg cagugucuua gcugguuguu gugagcaaua guaaggaagc | 180 |
| aaucagcaag uauacugccc uagaagugcu gcacguuguu ggcccguaag gaagcggugu | 240 |
| ucccgucgug ccuucuagaa gugcugcacg uuguuggccc gauccaaugg acauaugucc | 300 |
| gcgugggguuc gaaccccacu ccugguacca | 330 |

<210> SEQ ID NO 195
<211> LENGTH: 330
<212> TYPE: RNA
<213> ORGANISM: Artificial sequence
<220> FEATURE:
<223> OTHER INFORMATION: synthetic sequence

<400> SEQUENCE: 195

| accaggaugg ccgagugguu aaggcguugg acuggcgaua ccagccgaaa ggcccuuggc | 60 |
| agcgucggcc agcugugagu guuucuuugg cagugucuua gcugguuguu gugagcggcc | 120 |
| agcugugagu guuucuuuaa ggcacgcggu gaaugccguu gugagcaaua guaaggaagc | 180 |
| gguguccccg ucgugccuuc uagaagugcu gcacguuguu ggcccguaag gaagcaauca | 240 |
| gcaaguauac ugcccuagaa gugcugcacg uuguuggccc gauccaaugg acauaugucc | 300 |
| gcgugggguuc gaaccccacu ccugguacca | 330 |

<210> SEQ ID NO 196
<211> LENGTH: 331
<212> TYPE: RNA
<213> ORGANISM: Artificial sequence
<220> FEATURE:
<223> OTHER INFORMATION: synthetic sequence

<400> SEQUENCE: 196
accaggaugg ccgagugguu aaggcguugg acuggccagc ugugaguguu ucuugaggu      60 aguagguugu augguuugug agcggccagc ugugaguguu ucuuuaaggc acgcggugaa    120
ugccguugug agcaauagua aggaagcggu guucccgucg ugccuucuag aagugcugca    180
cguuguuggc ccguaaggaa gaacuguaca ccuuacuacc uuucagaagu gcugcacguu    240
guuggcccgg cgauaccagc cgaaaggccc uuggcagcgu cgauccaaug gacauauguc    300
cgcguggguu cgaaccccac uccugguacc a                                  331

<210> SEQ ID NO 197
<211> LENGTH: 330
<212> TYPE: RNA
<213> ORGANISM: Artificial sequence
<220> FEATURE:
<223> OTHER INFORMATION: synthetic sequence

<400> SEQUENCE: 197
accaggaugg ccgaguggu aaggcguugg acuggccagc ugugaguguu ucuuuaaggc      60
acgcggugaa ugccguugug agcggccagc ugugaguguu ucuuggcag ugucuuagcu    120 gguuguugug agcaauagua aggaagcaau cagcaaguau acugcccuag aagugcugca    180
cguuguuggc ccguaaggaa gcgguguucc cgucgugccu ucuagaagug cugcacguug    240
uuggcccggc gauaccagcc gaaaggcccu uggcagcguc gauccaaugg acauaugucc    300
gcguggguuc gaaccccacu ccugguacca                                    330

<210> SEQ ID NO 198
<211> LENGTH: 330
<212> TYPE: RNA
<213> ORGANISM: Artificial sequence
<220> FEATURE:
<223> OTHER INFORMATION: synthetic sequence

<400> SEQUENCE: 198
accaggaugg ccgaguggu aaggcguugg acuggccagc ugugaguguu ucuuggcag      60 ugucuuagcu gguuguugug agcggccagc ugugaguguu ucuuuaaggc acgcggugaa    120
ugccguugug agcaauagua aggaagcggu guucccgucg ugccuucuag aagugcugca    180
cguuguuggc ccguaaggaa gcaaucagca aguauacugc cuagaagug cugcacguug    240 uuggcccggc gauaccagcc gaaaggcccu uggcagcguc gauccaaugg acauaugucc    300
gcguggguuc gaaccccacu ccugguacca                                    330

<210> SEQ ID NO 199
<211> LENGTH: 364
<212> TYPE: RNA
<213> ORGANISM: Artificial sequence
<220> FEATURE:
<223> OTHER INFORMATION: synthetic sequence

<400> SEQUENCE: 199
accaggaugg ccgaguggu aaggcguugg acuggcgaua ccagccgaaa ggcccuuggc      60

| | |
|---|---|
| agcgucggcc agcugugagu guuucuuuga gguaguaggu uguaugguuu gugagcggcc | 120 |
| agcugugagu guuucuuuaa ggcacgcggu gaaugccguu gugagcaaua guaaggaagc | 180 |
| gguguucccg ucgugccuuc uagaagugcu gcacguuguu ggcccguaag gaagaacugu | 240 |
| acaccuuacu accuuucaga agugcugcac guuguuggcc cggcgauacc agccgaaagg | 300 |
| cccuuggcag cgucgaucca auggacauau guccgcgugg guucgaaccc cacuccuggu | 360 |
| acca | 364 |

<210> SEQ ID NO 200
<211> LENGTH: 363
<212> TYPE: RNA
<213> ORGANISM: Artificial sequence
<220> FEATURE:
<223> OTHER INFORMATION: synthetic sequence

<400> SEQUENCE: 200

| | |
|---|---|
| accaggaugg ccgagugguu aaggcguugg acuggcgaua ccagccgaaa ggcccuuggc | 60 |
| agcgucggcc agcugugagu guuucuuaa ggcacgcggu gaaugccguu gugagcggcc | 120 |
| agcugugagu guuucuuugg cagugucuua gcugguuguu gugagcaaua guaaggaagc | 180 |
| aaucagcaag uauacugccc uagaagugcu gcacguuguu ggcccguaag gaagcggugu | 240 |
| ucccgucgug ccuucuagaa gugcugcacg uuguuggccc ggcgauacca gccgaaaggc | 300 |
| ccuuggcagc gucgauccaa uggacauaug uccgcguggg uucgaaccccc acuccgguac | 360 |
| cca | 363 |

<210> SEQ ID NO 201
<211> LENGTH: 363
<212> TYPE: RNA
<213> ORGANISM: Artificial sequence
<220> FEATURE:
<223> OTHER INFORMATION: synthetic sequence

<400> SEQUENCE: 201

| | |
|---|---|
| accaggaugg ccgagugguu aaggcguugg acuggcgaua ccagccgaaa ggcccuuggc | 60 |
| agcgucggcc agcugugagu guuucuuugg cagugucuua gcugguuguu gugagcggcc | 120 |
| agcugugagu guuucuuuaa ggcacgcggu gaaugccguu gugagcaaua guaaggaagc | 180 |
| gguguucccg ucgugccuuc uagaagugcu gcacguuguu ggcccguaag gaagcaauca | 240 |
| gcaaguauac ugcccuagaa gugcugcacg uuguuggccc ggcgauacca gccgaaaggc | 300 |
| ccuuggcagc gucgauccaa uggacauaug uccgcguggg uucgaaccccc acuccgguac | 360 |
| cca | 363 |

<210> SEQ ID NO 202
<211> LENGTH: 331
<212> TYPE: RNA
<213> ORGANISM: Artificial sequence
<220> FEATURE:
<223> OTHER INFORMATION: synthetic sequence

<400> SEQUENCE: 202

| | |
|---|---|
| accaggaugg ccgagugguu aaggcguugg acuggccagc ugugaguguu ucuuugaggu | 60 |
| aguagguugu augguuugug agcggcgaua ccagccgaaa ggcccuuggc agcgucggcc | 120 |
| agcugugagu guuucuuuaa ggcacgcggu gaaugccguu gugagcaaua guaaggaagc | 180 |
| gguguucccg ucgugccuuc uagaagugcu gcacguuguu ggcccguaag gaagaacugu | 240 |
| acaccuuacu accuuucaga agugcugcac guuguuggcc cgauccaaug gacauauguc | 300 | cgcguggguu cgaaccccac uccugguacc a              331

<210> SEQ ID NO 203
<211> LENGTH: 330
<212> TYPE: RNA
<213> ORGANISM: Artificial sequence
<220> FEATURE:
<223> OTHER INFORMATION: synthetic sequence

<400> SEQUENCE: 203
accaggaugg ccgagugguu aaggcguugg acuggccagc ugugaguguu ucuuuaaggc    60
acgcggugaa ugccguugug agcggcgaua ccagccgaaa ggcccuuggc agcgucggcc   120
agcugugagu guuucuuugg cagugucuua gcugguuguu gugagcaaua guaaggaagc   180
aaucagcaag uauacugccc uagaagugcu gcacgugugu ggcccguaag gaagcggugu   240
ucccgucgug ccuucuagaa gugcugcacg uuguuggccc gauccaaugg acauaugucc   300
gcgugggguuc gaaccccacu ccugguacca                                   330

<210> SEQ ID NO 204
<211> LENGTH: 330
<212> TYPE: RNA
<213> ORGANISM: Artificial sequence
<220> FEATURE:
<223> OTHER INFORMATION: synthetic sequence

<400> SEQUENCE: 204
accaggaugg ccgagugguu aaggcguugg acuggccagc ugugaguguu ucuuuggcag    60
ugucuuagcu gguuguugug agcggcgaua ccagccgaaa ggcccuuggc agcgucggcc   120
agcugugagu guuucuuuaa ggcacgcggu gaaugccguu gugagcaaua guaaggaagc   180
gguguucccg ucgugccuuc uagaagugcu gcacguugu ggcccguaag gaagcaauca    240
gcaaguauac ugcccuagaa gugcugcacg uuguuggccc gauccaaugg acauaugucc   300
gcgugggguuc gaaccccacu ccugguacca                                   330

<210> SEQ ID NO 205
<211> LENGTH: 331
<212> TYPE: RNA
<213> ORGANISM: Artificial sequence
<220> FEATURE:
<223> OTHER INFORMATION: synthetic sequence

<400> SEQUENCE: 205
accaggaugg ccgagugguu aaggcguugg acuggccagc ugugaguguu ucuugaggu    60
aguagguugu augguuugug agcggccagc ugugaguguu ucuuuaaggc acgcggugaa   120
ugccguugug agcaauagua aggaagcggu guucccgucg ugccuucuag aagugcugca   180
cguuguuggc ccggcgauac cagccgaaag gcccuuggca gcgucguaag gaagaacugu   240
acaccuuacu accuuucaga agugcugcac guuguuggcc cgauccaaug gacauauguc   300
cgcgugggguu cgaaccccac uccugguacc a                                 331

<210> SEQ ID NO 206
<211> LENGTH: 330
<212> TYPE: RNA
<213> ORGANISM: Artificial sequence
<220> FEATURE:
<223> OTHER INFORMATION: synthetic sequence

<400> SEQUENCE: 206

| | |
|---|---|
| accaggaugg ccgagugguu aaggcguugg acuggccagc ugugaguguu ucuuuaaggc | 60 |
| acgcggugaa ugccguugug agcggccagc ugugaguguu ucuuggcag ugucuuagcu | 120 |
| gguuguugug agcaauagua aggaagcaau cagcaaguau acugcccuag aagugcugca | 180 |
| cguuguggc ccggcgauac cagccgaaag gcccuuggca gcgucguaag gaagcggugu | 240 |
| ucccgucgug ccuucuagaa gugcugcacg uuguuggccc gauccaaugg acauaugucc | 300 |
| gcguggguuc gaaccccacu ccugguacca | 330 |

<210> SEQ ID NO 207
<211> LENGTH: 330
<212> TYPE: RNA
<213> ORGANISM: Artificial sequence
<220> FEATURE:
<223> OTHER INFORMATION: synthetic sequence

<400> SEQUENCE: 207

| | |
|---|---|
| accaggaugg ccgagugguu aaggcguugg acuggccagc ugugaguguu ucuuuggcag | 60 |
| ugucuuagcu gguuguugug agcggccagc ugugaguguu ucuuuaaggc acgcggugaa | 120 |
| ugccguugug agcaauagua aggaagcggu guucccgucg ugccuucuag aagugcugca | 180 |
| cguuguggc ccggcgauac cagccgaaag gcccuuggca gcgucguaag gaagcaauca | 240 |
| gcaaguauac ugcccuagaa gugcugcacg uuguuggccc gauccaaugg acauaugucc | 300 |
| gcguggguuc gaaccccacu ccugguacca | 330 |

<210> SEQ ID NO 208
<211> LENGTH: 364
<212> TYPE: RNA
<213> ORGANISM: Artificial sequence
<220> FEATURE:
<223> OTHER INFORMATION: synthetic sequence

<400> SEQUENCE: 208

| | |
|---|---|
| accaggaugg ccgagugguu aaggcguugg acuggccagc ugugaguguu ucuugaggu | 60 |
| aguagguugu auugguuugu agcggcgaua ccagccgaaa ggcccuuggc agcgucggcc | 120 |
| agcugugagu guucuuuaa ggcacgcggu gaaugccguu gugagcaaua guaaggaagc | 180 |
| gguguccccg ucgugccuuc uagaagugcu gcacguuguu ggcccggcga uaccagccga | 240 |
| aaggcccuug gcagcgucgu aaggaagaac uguacaccuu acuaccuuuc agaagugcug | 300 |
| cacguuguug gcccgauccaa auggacauau guccgcgugg guucgaaccc cacuccuggu | 360 |
| acca | 364 |

<210> SEQ ID NO 209
<211> LENGTH: 363
<212> TYPE: RNA
<213> ORGANISM: Artificial sequence
<220> FEATURE:
<223> OTHER INFORMATION: synthetic sequence

<400> SEQUENCE: 209

| | |
|---|---|
| accaggaugg ccgagugguu aaggcguugg acuggccagc ugugaguguu ucuuuaaggc | 60 |
| acgcggugaa ugccguugug agcggcgaua ccagccgaaa ggcccuuggc agcgucggcc | 120 |
| agcugugagu guucuuugg cagugucuua gcugguuguu gugagcaaua guaaggaagc | 180 |
| aaucagcaag uauacugccc uagaagugcu gcacguuguu ggcccggcga uaccagccga | 240 |
| aaggcccuug gcagcgucgu aaggaagcgg uguccccguc gugccuucua gaagugcugc | 300 |
| acguuguugg cccgauccaa uggacauaug uccgcguggg uucgaacccc acuccuggua | 360 |

```
cca                                                                        363

<210> SEQ ID NO 210
<211> LENGTH: 363
<212> TYPE: RNA
<213> ORGANISM: Artificial sequence
<220> FEATURE:
<223> OTHER INFORMATION: synthetic sequence

<400> SEQUENCE: 210
accaggaugg ccgagugguu aaggcguugg acuggccagc ugugagucuu ucuuuggcag          60
ugucuuagcu gguuguugug agcggcgaua ccagccgaaa ggcccuuggc agcgucggcc         120
agcugugagu guucuuuaa ggcacgcggu gaaugccguu gugagcaaua guaaggaagc          180
gguguccccg ucgugccuuc uagaagugcu gcacguuguu ggcccggcga uaccagccga         240
aaggcccuug gcagcgucgu aaggaagcaa ucagcaagua uacugcccua gaagugcugc         300
acguuguugg cccgauccaa uggacauaug uccgcguggg uucgaacccc acuccgguaa         360
cca                                                                        363

<210> SEQ ID NO 211
<211> LENGTH: 180
<212> TYPE: RNA
<213> ORGANISM: Artificial sequence
<220> FEATURE:
<223> OTHER INFORMATION: synthetic sequence

<400> SEQUENCE: 211
ggcuacguag cucaguuggu uagagcagcg gccgggccag cugugagugu uucuuuggca          60
gugucuuagc ugguuguugu gagcaauagu aaggaagcaa ucagcaagua uacugcccua         120
gaagugcugc acguuguugg cccccgcggg ucacagguuc gaaucccguc guagccacca         180

<210> SEQ ID NO 212
<211> LENGTH: 192
<212> TYPE: RNA
<213> ORGANISM: Artificial sequence
<220> FEATURE:
<223> OTHER INFORMATION: synthetic sequence

<400> SEQUENCE: 212
accaggaugg ccgagugguu aaggcguugg acuggccagc ugugagucuu ucuuuggcag          60
ugucuuagcu gguuguugug agcaauagua aggaagcaau cagcaaguau acugcccuag         120
aagugcugca cguuguuggc ccgauccaau ggacauaugu ccgcguggu ucgaacccca          180 cuccugguac ca                                                             192

<210> SEQ ID NO 213
<211> LENGTH: 191
<212> TYPE: RNA
<213> ORGANISM: Artificial sequence
<220> FEATURE:
<223> OTHER INFORMATION: synthetic sequence

<400> SEQUENCE: 213
gcagcgaugg ccgagugguu aaggcguugg acuggccagc ugugagucuu ucuuuggcag          60
ugucuuagcu gguuguugug agcaauagua aggaagcaau cagcaaguau acugcccuag         120
aagugcugca cguuguuggc ccaauccaau ggggucuccc cgcgcagguu cgaacccugc         180
ucgcugcgcc a                                                              191
```

<210> SEQ ID NO 214
<211> LENGTH: 182
<212> TYPE: RNA
<213> ORGANISM: Artificial sequence
<220> FEATURE:
<223> OTHER INFORMATION: synthetic sequence

<400> SEQUENCE: 214

| | | | | | |
|---|---|---|---|---|---|
| gccuggauag | cucaguuggu | agagcaucag | acuggccagc | ugugagucuu | ucuuuggcag | 60 |
| ugucuuagcu | gguuguugug | agcaauagua | aggaagcaau | cagcaaguau | acugcccuag | 120 |
| aagugcugca | cguuguuggc | ccaaucugag | gguccagggu | ucaagucccu | guucaggcgc | 180 |
| ca | | | | | | 182 |

<210> SEQ ID NO 215
<211> LENGTH: 181
<212> TYPE: RNA
<213> ORGANISM: Artificial sequence
<220> FEATURE:
<223> OTHER INFORMATION: synthetic sequence

<400> SEQUENCE: 215

| | | | | | |
|---|---|---|---|---|---|
| ggucccaugg | uguaaugguu | agcacucugg | acuggccagc | ugugagucuu | ucuuuggcag | 60 |
| ugucuuagcu | gguuguugug | agcaauagua | aggaagcaau | cagcaaguau | acugcccuag | 120 |
| aagugcugca | cguuguuggc | ccaauccagc | gauccgaguu | caaaucucgg | ugggaccucc | 180 |
| a | | | | | | 181 |

<210> SEQ ID NO 216
<211> LENGTH: 181
<212> TYPE: RNA
<213> ORGANISM: Artificial sequence
<220> FEATURE:
<223> OTHER INFORMATION: synthetic sequence

<400> SEQUENCE: 216

| | | | | | |
|---|---|---|---|---|---|
| gggggcauag | cucaguggua | gagcauuuga | cuggccagcu | gugaguguuu | cuuggcagu | 60 |
| gucuuagcug | guuguuguga | gcaauaguaa | ggaagcaauc | agcaaguaua | cugcccuaga | 120 |
| agugcugcac | guuguuggcc | cgaucaagag | guccugguu | caaauccagg | ugcccccucc | 180 |
| a | | | | | | 181 |

<210> SEQ ID NO 217
<211> LENGTH: 167
<212> TYPE: RNA
<213> ORGANISM: Artificial sequence
<220> FEATURE:
<223> OTHER INFORMATION: synthetic sequence

<400> SEQUENCE: 217

| | | | | | |
|---|---|---|---|---|---|
| accaggaugg | ccgaguggu | aaggcguugg | acaggccucu | cucuccgugu | ucacagcgga | 60 |
| ccuugauuua | aauguccaua | caauuaaggc | acgcggugaa | ugccaagaau | ggggcuggau | 120 |
| ccaauggaca | uauguccgcg | ugggucgaa | ccccacuccu | gguacca | | 167 |

<210> SEQ ID NO 218
<211> LENGTH: 167
<212> TYPE: RNA
<213> ORGANISM: Artificial sequence
<220> FEATURE:
<223> OTHER INFORMATION: synthetic sequence

<400> SEQUENCE: 218

```
gcagcgaugg ccgaguggu  aaggcguugg acuaggccuc ucucuccgug uucacagcgg      60
accuugauuu aaauguccau acaauuaagg cacgcgguga augccaagaa ugggggcugaa    120 uccaaugggg ucucccgcg cagguucgaa cccugcucgc ugcgcca                   167
```

```
<210> SEQ ID NO 219
<211> LENGTH: 158
<212> TYPE: RNA
<213> ORGANISM: Artificial sequence
<220> FEATURE:
<223> OTHER INFORMATION: synthetic sequence

<400> SEQUENCE: 219
gccuggauag cucaguuggu agagcaucag acuaggccuc ucucuccgug uucacagcgg     60
accuugauuu aaauguccau acaauuaagg cacgcgguga augccaagaa ugggggcugaa   120 ucugaggguc cagguucaa gucccuguuc aggcgcca                             158
```

```
<210> SEQ ID NO 220
<211> LENGTH: 157
<212> TYPE: RNA
<213> ORGANISM: Artificial sequence
<220> FEATURE:
<223> OTHER INFORMATION: synthetic sequence

<400> SEQUENCE: 220
ggucccaugg uguaauggu  agcacucugg acuaggccuc ucucuccgug uucacagcgg      60
accuugauuu aaauguccau acaauuaagg cacgcgguga augccaagaa ugggggcugaa   120 uccagcgauc cgaguucaaa ucucgguggg accucca                            157
```

```
<210> SEQ ID NO 221
<211> LENGTH: 157
<212> TYPE: RNA
<213> ORGANISM: Artificial sequence
<220> FEATURE:
<223> OTHER INFORMATION: synthetic sequence

<400> SEQUENCE: 221 ggggggcauag cucaguggua gagcauuuga cuaggccucu cucuccgugu ucacagcgga    60
ccuugauuua aauguccaua caauuaaggc acgcggugaa ugccaagaau ggggcuggau   120
caagaggucc cugguucaaa uccaggugcc cccucca                             157
```

```
<210> SEQ ID NO 222
<211> LENGTH: 181
<212> TYPE: RNA
<213> ORGANISM: Artificial sequence
<220> FEATURE:
<223> OTHER INFORMATION: synthetic sequence

<400> SEQUENCE: 222
ggcuacguag cucaguuggu uagagcagcg gccgggccag cugugagugu uucuuugagg     60
uaguagguug uaugguuugu gagcaauagu aaggaagaac uguacaccuu acuaccuuuc   120
agaagugcug cacguuguug gccccgcgcg gucacagguu cgaaucccgu cguagccacc   180
a                                                                   181
```

```
<210> SEQ ID NO 223
<211> LENGTH: 193
<212> TYPE: RNA
<213> ORGANISM: Artificial sequence
<220> FEATURE:
```

<223> OTHER INFORMATION: synthetic sequence

<400> SEQUENCE: 223

| accaggaugg ccgaguggut aaggcguugg acuggccagc ugugaguguu ucuuugaggu | 60 |
| aguagguugu augguuugug agcaauagua aggaagaacu guacaccuua cuaccuuuca | 120 |
| gaagugcugc acguuguugg cccgauccaa uggacauaug uccgcguggg uucgaaccc | 180 |
| acuccuggua cca | 193 |

<210> SEQ ID NO 224
<211> LENGTH: 192
<212> TYPE: RNA
<213> ORGANISM: Artificial sequence
<220> FEATURE:
<223> OTHER INFORMATION: synthetic sequence

<400> SEQUENCE: 224

| gcagcgaugg ccgaguggut aaggcguugg acuggccagc ugugaguguu ucuuugaggu | 60 |
| aguagguugu augguuugug agcaauagua aggaagaacu guacaccuua cuaccuuuca | 120 |
| gaagugcugc acguuguugg cccaauccaa uggggucucc ccgcgcaggu ucgaacccug | 180 |
| cucgcugcgc ca | 192 |

<210> SEQ ID NO 225
<211> LENGTH: 183
<212> TYPE: RNA
<213> ORGANISM: Artificial sequence
<220> FEATURE:
<223> OTHER INFORMATION: synthetic sequence

<400> SEQUENCE: 225

| gccuggauag cucaguuggu agagcaucag acuggccagc ugugaguguu ucuuugaggu | 60 |
| aguagguugu augguuugug agcaauagua aggaagaacu guacaccuua cuaccuuuca | 120 |
| gaagugcugc acguuguugg cccaaucuga ggguccaggg uucaagucc uguucaggcg | 180 |
| cca | 183 |

<210> SEQ ID NO 226
<211> LENGTH: 182
<212> TYPE: RNA
<213> ORGANISM: Artificial sequence
<220> FEATURE:
<223> OTHER INFORMATION: synthetic sequence

<400> SEQUENCE: 226

| ggucccaugg uguaaugguu agcacucugg acuggccagc ugugaguguu ucuuugaggu | 60 |
| aguagguugu augguuugug agcaauagua aggaagaacu guacaccuua cuaccuuuca | 120 |
| gaagugcugc acguuguugg cccaaccag cgauccgagu ucaaaucucg gugggaccuc | 180 |
| ca | 182 |

<210> SEQ ID NO 227
<211> LENGTH: 182
<212> TYPE: RNA
<213> ORGANISM: Artificial sequence
<220> FEATURE:
<223> OTHER INFORMATION: synthetic sequence

<400> SEQUENCE: 227

| gggggcauag cucaguggua gagcauuuga cuggccagcu ugagaguuu cuugaggua | 60 |
| guagguugua ugguuuguga gcaauaguaa ggaagaacug uacaccuuac uaccuuucag | 120 |

```
aagugcugca cguuguuggc ccgaucaaga ggucccuggu ucaaauccag gugcccccuc      180
ca                                                                    182

<210> SEQ ID NO 228
<211> LENGTH: 166
<212> TYPE: RNA
<213> ORGANISM: Artificial sequence
<220> FEATURE:
<223> OTHER INFORMATION: synthetic sequence

<400> SEQUENCE: 228
gcagcgaugg ccgagugguu aaggcguugg acugcauccg gguugaggua guagguugua      60
ugguuuagag uuacacccug ggaguuaacu guacaaccuu cuagcuuucc uuggagcaau     120
ccaauggggu cucccgcgc agguucgaac ccugcucgcu cgcca                     166

<210> SEQ ID NO 229
<211> LENGTH: 168
<212> TYPE: RNA
<213> ORGANISM: Artificial sequence
<220> FEATURE:
<223> OTHER INFORMATION: synthetic sequence

<400> SEQUENCE: 229
accaggaugg ccgagugguu aaggcguugg acugcauccg gguugaggua guagguugua      60
ugguuuagag uuacacccug ggaguuaacu guacaaccuu cuagcuuucc uuggagcaga     120
uccaauggac auauguccgc guggguucga accccacucc ugguacca                 168

<210> SEQ ID NO 230
<211> LENGTH: 152
<212> TYPE: RNA
<213> ORGANISM: Artificial sequence
<220> FEATURE:
<223> OTHER INFORMATION: synthetic sequence

<400> SEQUENCE: 230
gccuggauag cucaguuggu agagcaugca uccggguuga gguaguaggu uguauggunu      60
agaguuacac ccugggaguu aacuguacaa ccuucuagcu uccuuggag caaaucugag     120 gguccagggu ucaagucccu guucaggcgc ca                                  152

<210> SEQ ID NO 231
<211> LENGTH: 157
<212> TYPE: RNA
<213> ORGANISM: Artificial sequence
<220> FEATURE:
<223> OTHER INFORMATION: synthetic sequence

<400> SEQUENCE: 231
gggggcauag cucaguggua gagcauuuga cugcauccgg guugagguag uagguuguau      60
gguuuagagu uacacccugg gaguuaacug uacaaccuuc uagcuuuccu uggagcagau     120
caagaggucc cugguucaaa uccaggugcc cccucca                              157

<210> SEQ ID NO 232
<211> LENGTH: 157
<212> TYPE: RNA
<213> ORGANISM: Artificial sequence
<220> FEATURE:
<223> OTHER INFORMATION: synthetic sequence

<400> SEQUENCE: 232
```

```
ggucccaugg uguaaugguu agcacucugg acugcauccg gguugaggua guagguugua      60
ugguuuagag uuacacccug ggaguuaacu guacaaccuu cuagcuuucc uuggagcaaa     120
uccagcgauc cgaguucaaa ucucgguggg accucca                             157
```

```
<210> SEQ ID NO 233
<211> LENGTH: 180
<212> TYPE: RNA
<213> ORGANISM: Artificial sequence
<220> FEATURE:
<223> OTHER INFORMATION: synthetic sequence

<400> SEQUENCE: 233
ggcuacguag cucaguuggu uagagcagcg gccgggccag cugugagugu uucuucuggc     60
ccucucugcc cuuccguugu gagcaauagu aaggaagcgg gggggagaug ggggccauua    120
gaagugcugc acguuguugg cccccgcggg ucacagguuc gaaucccguc guagccacca    180
```

```
<210> SEQ ID NO 234
<211> LENGTH: 192
<212> TYPE: RNA
<213> ORGANISM: Artificial sequence
<220> FEATURE:
<223> OTHER INFORMATION: synthetic sequence

<400> SEQUENCE: 234
accaggaugg ccgagugguu aaggcguugg acuggccagc ugugagaguu ucuucuggcc     60
cucucugccc uuccguugug agcaauagua aggaagcggg ggggagaugg gggccauuag    120
aagugcugca cguuguuggc ccgauccaau ggacauaugu ccgcggggu ucgaacccca    180 cuccugguac ca                                                       192
```

```
<210> SEQ ID NO 235
<211> LENGTH: 191
<212> TYPE: RNA
<213> ORGANISM: Artificial sequence
<220> FEATURE:
<223> OTHER INFORMATION: synthetic sequence

<400> SEQUENCE: 235
gcagcgaugg ccgagugguu aaggcguugg acuggccagc ugugagaguu ucuucuggcc     60
cucucugccc uuccguugug agcaauagua aggaagcggg ggggagaugg gggccauuag    120
aagugcugca cguuguuggc ccaauccaau ggggucuccc cgcgcagguu cgaacccugc    180
ucgcugcgcc a                                                        191
```

```
<210> SEQ ID NO 236
<211> LENGTH: 182
<212> TYPE: RNA
<213> ORGANISM: Artificial sequence
<220> FEATURE:
<223> OTHER INFORMATION: synthetic sequence

<400> SEQUENCE: 236
gccuggauag cucaguuggu agagcaucag acuggccagc ugugagaguu ucuucuggcc     60
cucucugccc uuccguugug agcaauagua aggaagcggg ggggagaugg gggccauuag    120
aagugcugca cguuguuggc ccaaucugag gguccagggu ucaagucccu guucaggcgc    180
ca                                                                   182
```

```
<210> SEQ ID NO 237
<211> LENGTH: 181
```

```
<212> TYPE: RNA
<213> ORGANISM: Artificial sequence
<220> FEATURE:
<223> OTHER INFORMATION: synthetic sequence

<400> SEQUENCE: 237
ggucccaugg uguaaugguu agcacucugg acuggccagc ugugaguguu ucuucuggcc    60
cucucugccc uuccguugug agcaauagua aggaagcggg ggggagaugg gggccauuag   120
aagugcugca cguuguuggc ccaauccagc gauccgaguu caaaucucgg ugggaccucc   180
a                                                                  181

<210> SEQ ID NO 238
<211> LENGTH: 181
<212> TYPE: RNA
<213> ORGANISM: Artificial sequence
<220> FEATURE:
<223> OTHER INFORMATION: synthetic sequence

<400> SEQUENCE: 238
gggggcauag cucagugagua gagcauuuga cuggccagcu gugaguguuu cuucuggccc    60
ucucugcccu uccguuguga gcaauaguaa ggaagcgggg gggagauggg ggccauuaga   120
agugcugcac guuguuggcc cgaucaagag gucccugguu caaauccagg ugccccucc    180 a                                                                  181

<210> SEQ ID NO 239
<211> LENGTH: 180
<212> TYPE: RNA
<213> ORGANISM: Artificial sequence
<220> FEATURE:
<223> OTHER INFORMATION: synthetic sequence

<400> SEQUENCE: 239
ggcuacguag cucaguuggu uagagcagcg gccgggccag cugugagugu uucuuuaagg    60
cacgcgguga augccguugu gagcaauagu aaggaagcgg uguccccguc gugccuucua   120
gaagugcugc acguuguugg cccccgcggg ucacagguuc gaaucccguc guagccacca   180

<210> SEQ ID NO 240
<211> LENGTH: 192
<212> TYPE: RNA
<213> ORGANISM: Artificial sequence
<220> FEATURE:
<223> OTHER INFORMATION: synthetic sequence

<400> SEQUENCE: 240
accaggaugg ccgagugguu aaggcguugg acuggccagc ugugaguguu ucuuuaaggc    60
acgcggugaa ugccguugug agcaauagua aggaagcggu guucccgucg ugccuucuag   120
aagugcugca cguuguuggc ccgauccaau ggacauaugu ccgcguggu ucgaaccccca    180 cuccugguac ca                                                      192

<210> SEQ ID NO 241
<211> LENGTH: 191
<212> TYPE: RNA
<213> ORGANISM: Artificial sequence
<220> FEATURE:
<223> OTHER INFORMATION: synthetic sequence

<400> SEQUENCE: 241
gcagcgaugg ccgagugguu aaggcguugg acuggccagc ugugaguguu ucuuuaaggc    60
```

```
acgcggugaa ugccguugug agcaauagua aggaagcggu guucccgucg ugccuucuag    120
aagugcugca cguuguuggc ccaauccaau ggggucuccc cgcgcagguu cgaacccugc    180
ucgcugcgcc a                                                         191
```

<210> SEQ ID NO 242
<211> LENGTH: 182
<212> TYPE: RNA
<213> ORGANISM: Artificial sequence
<220> FEATURE:
<223> OTHER INFORMATION: synthetic sequence

<400> SEQUENCE: 242

```
gccuggauag cucaguuggu agagcaucag acuggccagc ugugagUguu ucuuuaaggc    60
acgcggugaa ugccguugug agcaauagua aggaagcggu guucccgucg ugccuucuag    120
aagugcugca cguuguuggc ccaaucugag gguccagggu caaguccccu guucaggcgc    180
ca                                                                   182
```

<210> SEQ ID NO 243
<211> LENGTH: 181
<212> TYPE: RNA
<213> ORGANISM: Artificial sequence
<220> FEATURE:
<223> OTHER INFORMATION: synthetic sequence

<400> SEQUENCE: 243

```
ggucccaugg uguaauggu agcacucugg acuggccagc ugugaguguu ucuuuaaggc     60
acgcggugaa ugccguugug agcaauagua aggaagcggu guucccgucg ugccuucuag    120
aagugcugca cguuguuggc ccaaccagc gauccgaguu caaaucucgg ugggaccucc     180
a                                                                    181
```

<210> SEQ ID NO 244
<211> LENGTH: 181
<212> TYPE: RNA
<213> ORGANISM: Artificial sequence
<220> FEATURE:
<223> OTHER INFORMATION: synthetic sequence

<400> SEQUENCE: 244

```
gggggcauag cucaguggua gagcauuuga cuggccagcu gugaguguuu cuuuaaggca    60
cgcggugaau gccguuguga gcaauaguaa ggaagcggug uucccgucgu gccuucuaga    120
agugcugcac guuguuggcc cgaucaagag gucccugguu caaaccaggu gccccuccc    180 a                                                                    181
```

<210> SEQ ID NO 245
<211> LENGTH: 180
<212> TYPE: RNA
<213> ORGANISM: Artificial sequence
<220> FEATURE:
<223> OTHER INFORMATION: synthetic sequence

<400> SEQUENCE: 245

```
ggcuacguag cucaguuggu uagagcagcg gccgggccag cugugagugu uucuuucgua    60
ccgugaguaa uaaugcgugu gagcaauagu aaggaagugc auuauucucu augguacgca    120
gaagugcugc acguuguugg ccccgcgggg ucacagguuc gaaucccguc guagccacca    180
```

<210> SEQ ID NO 246
<211> LENGTH: 192

```
<212> TYPE: RNA
<213> ORGANISM: Artificial sequence
<220> FEATURE:
<223> OTHER INFORMATION: synthetic sequence

<400> SEQUENCE: 246
accaggaugg ccgagugguu aaggcguugg acuggccagc ugugaguguu ucuuucguac    60
cgugaguaau aaugcgugug agcaauagua aggaaggugc auuauucucu augguacgag   120
aagugcugca cguuguuggc ccgauccaau ggacauaugu ccgcggggu ucgaacccca    180 cuccugguac ca                                                       192

<210> SEQ ID NO 247
<211> LENGTH: 191
<212> TYPE: RNA
<213> ORGANISM: Artificial sequence
<220> FEATURE:
<223> OTHER INFORMATION: synthetic sequence

<400> SEQUENCE: 247
gcagcgaugg ccgagugguu aaggcguugg acuggccagc ugugaguguu ucuucguac     60 cgugaguaau aaugcgugug agcaauagua aggaaggugc auuauucucu augguacgag   120
aagugcugca cguuguuggc ccaauccaau ggggucuccc cgcgcaggu cgacccugc    180 ucgcugcgcc a                                                        191

<210> SEQ ID NO 248
<211> LENGTH: 182
<212> TYPE: RNA
<213> ORGANISM: Artificial sequence
<220> FEATURE:
<223> OTHER INFORMATION: synthetic sequence

<400> SEQUENCE: 248
gccuggauag cucaguuggu agagcaucag acuggccagc ugugaguguu ucuucguac     60 cgugaguaau aaugcgugug agcaauagua aggaaggugc auuauucucu augguacgag   120
aagugcugca cguuguuggc ccaaucugag ggccagggu ucaaguccu guucaggcgc    180 ca                                                                  182

<210> SEQ ID NO 249
<211> LENGTH: 181
<212> TYPE: RNA
<213> ORGANISM: Artificial sequence
<220> FEATURE:
<223> OTHER INFORMATION: synthetic sequence

<400> SEQUENCE: 249
ggucccaugg uguaauggu agcacucugg acuggccagc ugugaguguu ucuucguac     60 cgugaguaau aaugcgugug agcaauagua aggaaggugc auuauucucu augguacgag   120
aagugcugca cguuguuggc ccaauccagc gauccgaguu caaaucucgg ugggaccucc   180
a                                                                   181

<210> SEQ ID NO 250
<211> LENGTH: 181
<212> TYPE: RNA
<213> ORGANISM: Artificial sequence
<220> FEATURE:
<223> OTHER INFORMATION: synthetic sequence

<400> SEQUENCE: 250
```

| | |
|---|---:|
| gggggcauag cucaguggua gagcauuuga cuggccagcu gugaguguuu cuuucguacc | 60 |
| gugaguaaua augcguguga gcaauaguaa ggaaggugca uuauucucua ugguacgaga | 120 |
| agugcugcac guuguuggcc cgaucaagag gucccugguu caaauccagg ugcccccucc | 180 |
| a | 181 |

<210> SEQ ID NO 251
<211> LENGTH: 180
<212> TYPE: RNA
<213> ORGANISM: Artificial sequence
<220> FEATURE:
<223> OTHER INFORMATION: synthetic sequence

<400> SEQUENCE: 251

| | |
|---|---:|
| ggcuacguag cucaguuggu uagagcagcg gccgggccag cugugagugu uucuuagcag | 60 |
| aagcagggag guucucccau gagcaauagu aaggagggga gaaccccccau gcuuuugaca | 120 |
| gaagugcugc acguuguugg cccccgcggg ucacagguuc gaaucccguc guagccacca | 180 |

<210> SEQ ID NO 252
<211> LENGTH: 194
<212> TYPE: RNA
<213> ORGANISM: Artificial sequence
<220> FEATURE:
<223> OTHER INFORMATION: synthetic sequence

<400> SEQUENCE: 252

| | |
|---|---:|
| accaggaugg ccgagugguu aaggcguugg acuggccagc ugugaguguu ucuuagcaga | 60 |
| agcagggagg uucucccaug ugagcaauag uaaggaaggg agaaccccca ugcuuuugac | 120 |
| agaagugcug cacguuguug gcccgaucca auggacauau guccgcgugg guucgaaccc | 180 |
| cacuccuggu acca | 194 |

<210> SEQ ID NO 253
<211> LENGTH: 193
<212> TYPE: RNA
<213> ORGANISM: Artificial sequence
<220> FEATURE:
<223> OTHER INFORMATION: synthetic sequence

<400> SEQUENCE: 253

| | |
|---|---:|
| gcagcgaugg ccgaguggu aaggcguugg acuggccagc ugugaguguu ucuuagcaga | 60 |
| agcagggagg uucucccaug ugagcaauag uaaggaaggg agaaccccca ugcuuuugac | 120 |
| agaagugcug cacguuguug gcccaaucca auggggucuc cccgcgcagg uucgaacccu | 180 |
| gcucgcugcg cca | 193 |

<210> SEQ ID NO 254
<211> LENGTH: 184
<212> TYPE: RNA
<213> ORGANISM: Artificial sequence
<220> FEATURE:
<223> OTHER INFORMATION: synthetic sequence

<400> SEQUENCE: 254

| | |
|---|---:|
| gccuggauag cucaguuggu agagcaucag acuggccagc ugugaguguu ucuuagcaga | 60 |
| agcagggagg uucucccaug ugagcaauag uaaggaaggg agaaccccca ugcuuuugac | 120 |
| agaagugcug cacguuguug gcccaaucug agggccagg guucaagucc cuguucaggc | 180 |
| gcca | 184 |

```
<210> SEQ ID NO 255
<211> LENGTH: 183
<212> TYPE: RNA
<213> ORGANISM: Artificial sequence
<220> FEATURE:
<223> OTHER INFORMATION: synthetic sequence

<400> SEQUENCE: 255
ggucccaugg uguaaugguu agcacucugg acuggccagc ugugagyguu ucuuagcaga      60
agcagggagg uucucccaug ugagcaauag uaaggaaggg agaaccccca ugcuuugac     120 agaagugcug cacguuguug gcccaaucca gcgauccgag uucaaaucuc gguggaccu     180 cca                                                                  183

<210> SEQ ID NO 256
<211> LENGTH: 183
<212> TYPE: RNA
<213> ORGANISM: Artificial sequence
<220> FEATURE:
<223> OTHER INFORMATION: synthetic sequence

<400> SEQUENCE: 256
gggggcauag cucagugguga gagcauuuga cuggccagcu gugaguguuu cuuagcagaa     60
gcagggaggu ucucccaugu gagcaauagu aaggaaggga gaaccccccau gcuuugaca    120 gaagugcugc acguuguggg cccgaucaag aggucccugg uucaaauccagguugcccccu    180 cca                                                                   183

<210> SEQ ID NO 257
<211> LENGTH: 180
<212> TYPE: RNA
<213> ORGANISM: Artificial sequence
<220> FEATURE:
<223> OTHER INFORMATION: synthetic sequence

<400> SEQUENCE: 257
ggcuacguag cucaguuggu uagagcagcg gccgggccag cugugagugu uucuuuggca     60
gugucuuagc ugguuguguu gagcaauagu aaggaagcaa ucagcaagua uacugcccua    120
gaagugcugc acguuguggg ccccccgcggg ucacagguuc gaaucccguc guagccacca   180

<210> SEQ ID NO 258
<211> LENGTH: 180
<212> TYPE: RNA
<213> ORGANISM: Artificial sequence
<220> FEATURE:
<223> OTHER INFORMATION: synthetic sequence

<400> SEQUENCE: 258
ggcuacguag cucaguuggu uagagcagcg gccgggccag cugugagugu uucuuuaagg     60
cacgcgguga augccguugu gagcaauagu aaggaagcgg uguucccguc gugccuucua    120
gaagugcugc acguuguggg ccccccgcggg ucacagguuc gaaucccguc guagccacca   180

<210> SEQ ID NO 259
<211> LENGTH: 181
<212> TYPE: RNA
<213> ORGANISM: Artificial sequence
<220> FEATURE:
<223> OTHER INFORMATION: synthetic sequence

<400> SEQUENCE: 259
ggcuacguag cucaguuggu uagagcagcg gccgggccag cugugagugu uucuuugagg     60
```
uaguagguug uauggpuugu gagcaauagu aaggaagaac uguacaccuu acuaccuuuc    120
agaagugcug cacguuguug gcccccgcgg gucacagguu cgaaucccgu cguagccacc    180
a                                                                   181

<210> SEQ ID NO 260
<211> LENGTH: 180
<212> TYPE: RNA
<213> ORGANISM: Artificial sequence
<220> FEATURE:
<223> OTHER INFORMATION: synthetic sequence

<400> SEQUENCE: 260
ggcuacguaa gacucaacau cagucugaua agcgggccag cugugagugu uucuuuggca    60
gugucuuagc ugguuguugu gagcaauagu aaggaagcaa ucagcaagua uacugcccua    120
gaagugcugc acguuguugg cccuuauggg ucacagguuc gaaucccguc guagccacca    180

<210> SEQ ID NO 261
<211> LENGTH: 180
<212> TYPE: RNA
<213> ORGANISM: Artificial sequence
<220> FEATURE:
<223> OTHER INFORMATION: synthetic sequence

<400> SEQUENCE: 261
ucagacuuag cucaguuggu uagagcagcg gccgggccag cugugagugu uucuuuggca    60
gugucuuagc ugguuguugu gagcaauagu aaggaagcaa ucagcaagua uacugcccua    120
gaagugcugc acguuguugg cccccgcugu acacagguuc gucaacauca gucugaucca    180

<210> SEQ ID NO 262
<211> LENGTH: 180
<212> TYPE: RNA
<213> ORGANISM: Artificial sequence
<220> FEATURE:
<223> OTHER INFORMATION: synthetic sequence

<400> SEQUENCE: 262
ggcuacguau aaguggcagu gucuuagcug guugggccag cugugagugu uucuuucaac    60
aucagucuga uaagcuaugu gagcaauagu aaggaaguag cuuauaagaa ugauguugca    120
gaagugcugc acguuguugg cccccagggg ucacagguuc gaaucccguc guagccacca    180

<210> SEQ ID NO 263
<211> LENGTH: 180
<212> TYPE: RNA
<213> ORGANISM: Artificial sequence
<220> FEATURE:
<223> OTHER INFORMATION: synthetic sequence

<400> SEQUENCE: 263
gcuaagauag cucaguuggu uagagcagcg gccgggccag cugugagugu uucuuucaac    60
aucagucuga uaagcuaugu gagcaauagu aaggaaguag cuuauaagaa ugauguugca    120
gaagugcugc acguuguugg cccccgccug acacagguuc guggcagugu cuuagcucca    180

<210> SEQ ID NO 264
<211> LENGTH: 227
<212> TYPE: RNA
<213> ORGANISM: Artificial sequence
<220> FEATURE:
<223> OTHER INFORMATION: synthetic sequence

<400> SEQUENCE: 264

```
ggcuacguag cucaguuggu uagagcagcg gccgaguaau uuacgucgac gaguucuguc    60
cgugagccuu ggguagaauu ccaguggccc ugacugaaga ccagcaguug uacuguggcu   120
guugguuuca agcagaggcc uaaaggacug ucuuccugug gucuguuggc ugugacgucg   180
augguugcgg ccgcggguca cagguucgaa ucccgucgua gccacca                 227
```

<210> SEQ ID NO 265
<211> LENGTH: 285
<212> TYPE: RNA
<213> ORGANISM: Artificial sequence
<220> FEATURE:
<223> OTHER INFORMATION: synthetic sequence

<400> SEQUENCE: 265

```
ggcuacguag cucaguuggu uagagcagcg gccgggccag cugugagugu uucuucaac    60 aucagucuga uaagcuaugu gagcggccag cugugagugu uucuuuggca gugucuuagc   120
ugguuguugu gagcaauagu aaggaagcaa ucagcaagua uacugcccua gaagugcugc   180
acguuguugg cccguaagga aguagcuuau aagaaugaug uugcagaagu gcugcacguu   240
guuggccccc gcggucaca gguucgaauc ccgucguagc cacca                   285
```

<210> SEQ ID NO 266
<211> LENGTH: 285
<212> TYPE: RNA
<213> ORGANISM: Artificial sequence
<220> FEATURE:
<223> OTHER INFORMATION: synthetic sequence

<400> SEQUENCE: 266

```
ggcuacguag cucaguuggu uagagcagcg gccgggccag cugugagugu uucuuuggca    60
gugucuuagc ugguuguugu gagcggccag cugugagugu uucuuaagg cacgcgguga   120 augccguugu gagcaauagu aaggaagcgg uguccccguc gugccuucua gaagugcugc   180
acguuguugg cccguaagga agcaaucagc aaguauacug cccuagaagu gcugcacguu   240
guuggccccc gcggucaca gguucgaauc ccgucguagc cacca                   285
```

<210> SEQ ID NO 267
<211> LENGTH: 286
<212> TYPE: RNA
<213> ORGANISM: Artificial sequence
<220> FEATURE:
<223> OTHER INFORMATION: synthetic sequence

<400> SEQUENCE: 267

```
ggcuacguag cucaguuggu uagagcagcg gccgggccag cugugagugu uucuuugagg    60
uaguagguug uaugguuugu gagcggccag cugugagugu uucuuuaagg cacgcgguga   120
augccguugu gagcaauagu aaggaagcgg uguccccguc gugccuucua gaagugcugc   180
acguuguugg cccguaagga agaacuguac accuuacuac cuuucagaag ugcugcacgu   240
uguuggcccc cgcgggucac agguucgaau cccgucguag ccacca                 286
```

<210> SEQ ID NO 268
<211> LENGTH: 285
<212> TYPE: RNA
<213> ORGANISM: Artificial sequence
<220> FEATURE:
<223> OTHER INFORMATION: synthetic sequence

<400> SEQUENCE: 268

```
ggcuacguag cucaguuggu uagagcagcg gccgggccag cugugagugu uucuuuaagg    60
cacgcgguga augccguugu gagcggccag cugugagugu uucuuuggca gugucuuagc   120
ugguuguugu gagcaauagu aaggaagcaa ucagcaagua uacugcccua gaagugcugc   180
acguuguugg cccguaagga agcgguguuc ccgucgugcc uucuagaagu gcugcacguu   240
guuggccccc gcgggucaca gguucgaauc ccgucguagc cacca                   285
```

<210> SEQ ID NO 269
<211> LENGTH: 286
<212> TYPE: RNA
<213> ORGANISM: Artificial sequence
<220> FEATURE:
<223> OTHER INFORMATION: synthetic sequence

<400> SEQUENCE: 269

```
ggcuacguag cucaguuggu uagagcagcg gccgggccag cugugagugu uucuuugagg    60
uaguagguug uaugguuugu gagcggccag cugugagugu uucuuuggca gugucuuagc   120
ugguuguugu gagcaauagu aaggaagcaa ucagcaagua uacugcccua gaagugcugc   180
acguuguugg cccguaagga agaacuguac accuuacuac cuuucagaag ugcugcacgu   240
uguuggcccc cgcgggucac agguucgaau cccgucguag ccacca                  286
```

<210> SEQ ID NO 270
<211> LENGTH: 285
<212> TYPE: RNA
<213> ORGANISM: Artificial sequence
<220> FEATURE:
<223> OTHER INFORMATION: synthetic sequence

<400> SEQUENCE: 270

```
ggcuacguag cucaguuggu uagagcagcg gccgggccag cugugagugu uucuuuaauu    60
gucaacuacu gucaguuugu gagcggccag cugugagugu uucuuuggca gugucuuagc   120
ugguuguugu gagcaauagu aaggaagcaa ucagcaagua uacugcccua gaagugcugc   180
acguuguugg cccguaagga aaacugacag aguaugacaa uucuagaagu gcugcacguu   240
guuggccccc gcgggucaca gguucgaauc ccgucguagc cacca                   285
```

<210> SEQ ID NO 271
<211> LENGTH: 319
<212> TYPE: RNA
<213> ORGANISM: Artificial sequence
<220> FEATURE:
<223> OTHER INFORMATION: synthetic sequence

<400> SEQUENCE: 271

```
ggcuacguag cucaguuggu uagagcagcg gccgggcgau accagccgaa aggcccuugg    60
cagcgucggc cagcugugag uguuucuuug agguaguagg uuguaugguu ugugagcggc   120
cagcugugag uguuucuuua aggcacgcgg ugaaugccgu ugugagcaau aguaaggaag   180
cgguguuccc gucgugccuu cuagaagugc ugcacguugu ggcccguaa ggaagaacug    240 uacaccuuac uaccuuucag aagugcugca cguuguuggc cccgcgggu cacagguucg    300 aaucccgucg uagccacca                                                319
```

<210> SEQ ID NO 272
<211> LENGTH: 318
<212> TYPE: RNA
<213> ORGANISM: Artificial sequence
<220> FEATURE:
<223> OTHER INFORMATION: synthetic sequence

<400> SEQUENCE: 272

| ggcuacguag cucaguuggu uagagcagcg gccgggcgau accagccgaa aggcccuugg | 60 |
| cagcgucggc cagcugugag uguuucuuua aggcacgcgg ugaaugccgu ugugagcggc | 120 |
| cagcugugag uguuucuuug gcagugucuu agcgguugu ugugagcaau aguaaggaag | 180 |
| caaucagcaa guauacugcc cuagaagugc ugcacguugu uggcccguaa ggaagcggug | 240 |
| uucccgucgu gccuucuaga agugcugcac guuguuggcc cccgcgggguc acagguucga | 300 |
| aucccgucgu agccacca | 318 |

<210> SEQ ID NO 273
<211> LENGTH: 318
<212> TYPE: RNA
<213> ORGANISM: Artificial sequence
<220> FEATURE:
<223> OTHER INFORMATION: synthetic sequence

<400> SEQUENCE: 273

| ggcuacguag cucaguuggu uagagcagcg gccgggcgau accagccgaa aggcccuugg | 60 |
| cagcgucggc cagcugugag uguuucuuug gcagugucuu agcgguugu ugugagcggc | 120 |
| cagcugugag uguuucuuua aggcacgcgg ugaaugccgu ugugagcaau aguaaggaag | 180 |
| cgguguccc gucgugccuu cuagaagugc ugcacguugu uggcccguaa ggaagcaauc | 240 |
| agcaaguaua cugcccuaga agugcugcac guuguuggcc cccgcgggguc acagguucga | 300 |
| aucccgucgu agccacca | 318 |

<210> SEQ ID NO 274
<211> LENGTH: 319
<212> TYPE: RNA
<213> ORGANISM: Artificial sequence
<220> FEATURE:
<223> OTHER INFORMATION: synthetic sequence

<400> SEQUENCE: 274

| ggcuacguag cucaguuggu uagagcagcg gccgggccag cugugagugu uucuuugagg | 60 |
| uaguagguug uaugguuugu gagcggccag cugugagugu uucuuuaagg cacgcgguga | 120 |
| augccguugu gagcaauagu aaggaagcgg uguccccguc gugccuucua gaagugcugc | 180 |
| acguuguugg cccguaagga agaacuguac accuuacuac cuucagaag ugcugcacgu | 240 |
| uguuggcccg gcgauaccag ccgaaaggcc cuuggcagcg ucccgcgggu cacagguucg | 300 |
| aaucccgucg uagccacca | 319 |

<210> SEQ ID NO 275
<211> LENGTH: 318
<212> TYPE: RNA
<213> ORGANISM: Artificial sequence
<220> FEATURE:
<223> OTHER INFORMATION: synthetic sequence

<400> SEQUENCE: 275

| ggcuacguag cucaguuggu uagagcagcg gccgggccag cugugagugu uucuuuaagg | 60 |
| cacgcgguga augccguugu gagcggccag cugugagugu uucuuggca gugucuuagc | 120 |
| ugguuguugu gagcaauagu aaggaagcaa ucagcaagua cugcccua gaagugcugc | 180 |
| acguuguugg cccguaagga agcgguguuc ccgucgugcc uucuagaagu gcugcacguu | 240 |
| guuggcccgg cgauaccagc cgaaaggccc uuggcagcgu cccgcgggguc acagguucga | 300 |

```
aucccgucgu agccacca                                          318

<210> SEQ ID NO 276
<211> LENGTH: 318
<212> TYPE: RNA
<213> ORGANISM: Artificial sequence
<220> FEATURE:
<223> OTHER INFORMATION: synthetic sequence

<400> SEQUENCE: 276
ggcuacguag cucaguuggu uagagcagcg gccgggccag cugugagugu uucuuuggca    60
gugucuuagc ugguuguugu gagcggccag cugugagugu uucuuuaagg cacgcgguga   120
augccguugu gagcaauagu aaggaagcgg uguucccguc gugccuucua gaagugcugc   180
acguuguugg cccguaagga agcaaucagc aaguauacug cccuagaagu gcugcacguu   240
guuggcccgg cgauaccagc cgaaaggccc uuggcagcgu cccgcgdguc acagguucga   300
aucccgucgu agccacca                                          318

<210> SEQ ID NO 277
<211> LENGTH: 352
<212> TYPE: RNA
<213> ORGANISM: Artificial sequence
<220> FEATURE:
<223> OTHER INFORMATION: synthetic sequence

<400> SEQUENCE: 277
ggcuacguag cucaguuggu uagagcagcg gccgggcgau accagccgaa aggcccuugg    60
cagcgucggc cagcugugag uguuucuuug agguaguagg uuguauggudu ugugagcggc   120 cagcugugag uguuucuuua aggcacgcgg ugaaugccgu gugagcaau aguaaggaag    180 cgguuccc gucgugccuu cuagaagugc ugcacguugu uggcccguaa ggaagaacug     240
uacaccuuac uaccuuucag aagugcugca cguuguuggc ccggcgauac cagccgaaag   300
gcccuuggca gcucccgcg ggucacaggu ucgaaucccg ucguagccac ca            352

<210> SEQ ID NO 278
<211> LENGTH: 351
<212> TYPE: RNA
<213> ORGANISM: Artificial sequence
<220> FEATURE:
<223> OTHER INFORMATION: synthetic sequence

<400> SEQUENCE: 278
ggcuacguag cucaguuggu uagagcagcg gccgggcgau accagccgaa aggcccuugg    60
cagcgucggc cagcugugag uguuucuuua aggcacgcgg ugaaugccgu gugagcggc    120 cagcugugag uguuucuuug gcagugucuu agcugguugu ugugagcaau aguaaggaag   180
caaucagcaa guauacugcc cuagaagugc ugcacguugu uggcccguaa ggaagcgdgug   240 uucccgucgu gccuucuaga agugcugcac guuguuggcc cggcgauacc agccgaaagg   300
cccuuggcag cucccgcgg gucacagguu cgaaucccgu cguagccacc a             351

<210> SEQ ID NO 279
<211> LENGTH: 351
<212> TYPE: RNA
<213> ORGANISM: Artificial sequence
<220> FEATURE:
<223> OTHER INFORMATION: synthetic sequence

<400> SEQUENCE: 279
ggcuacguag cucaguuggu uagagcagcg gccgggcgau accagccgaa aggcccuugg    60
```

```
cagcgucggc cagcugugag uguuucuuug gcagugucuu agcugguugu ugugagcggc    120
cagcugugag uguuucuuua aggcacgcgg ugaaugccgu ugugagcaau aguaaggaag    180
cgguguuccc gucgugccuu cuagaagugc ugcacguugu uggcccguaa ggaagcaauc    240
agcaaguaua cugcccuaga agugcugcac guuguuggcc cggcgauacc agccgaaagg    300
cccuuggcag cgucccgcgg gucacagguu cgaaucccgu cguagccacc a             351
```

<210> SEQ ID NO 280
<211> LENGTH: 319
<212> TYPE: RNA
<213> ORGANISM: Artificial sequence
<220> FEATURE:
<223> OTHER INFORMATION: synthetic sequence

<400> SEQUENCE: 280

```
ggcuacguag cucaguuggu uagagcagcg gccgggccag cugugagugu uucuuugagg     60
uaguagguug uauggúuugu gagcggcgau accagccgaa aggcccuugg cagcgucggc    120
cagcugugag uguuucuuua aggcacgcgg ugaaugccgu ugugagcaau aguaaggaag    180
cgguguuccc gucgugccuu cuagaagugc ugcacguugu uggcccguaa ggaagaacug    240
uacaccuuac uaccuuucag aagugcugca cguuguuggc ccccgcgggu cacagguucg    300
aaucccgucg uagccacca                                                 319
```

<210> SEQ ID NO 281
<211> LENGTH: 318
<212> TYPE: RNA
<213> ORGANISM: Artificial sequence
<220> FEATURE:
<223> OTHER INFORMATION: synthetic sequence

<400> SEQUENCE: 281

```
ggcuacguag cucaguuggu uagagcagcg gccgggccag cugugagugu uucuuuaagg     60
cacgcgguga augccguugu gagcggcgau accagccgaa aggcccuugg cagcgucggc    120
cagcugugag uguuucuuug gcagugucuu agcugguugu ugugagcaau aguaaggaag    180
caaucagcaa guauacugcc cuagaagugc ugcacguugu uggcccguaa ggaagcggug    240
uucccgucgu gccuucuaga augcugcac guuguuggcc cccgcgggucacagguucga    300 aucccgucgu agccacca                                                  318
```

<210> SEQ ID NO 282
<211> LENGTH: 318
<212> TYPE: RNA
<213> ORGANISM: Artificial sequence
<220> FEATURE:
<223> OTHER INFORMATION: synthetic sequence

<400> SEQUENCE: 282

```
ggcuacguag cucaguuggu uagagcagcg gccgggccag cugugagugu uucuuuggca     60
gugucuuagc ugguuguugu gagcggcgau accagccgaa aggcccuugg cagcgucggc    120
cagcugugag uguuucuuua aggcacgcgg ugaaugccgu ugugagcaau aguaaggaag    180
cgguguuccc gucgugccuu cuagaagugc ugcacguugu uggcccguaa ggaagcaauc    240
agcaaguaua cugcccuaga agugcugcac guuguuggcc cccgcgggucacagguucga    300 aucccgucgu agccacca                                                  318
```

<210> SEQ ID NO 283

```
<211> LENGTH: 319
<212> TYPE: RNA
<213> ORGANISM: Artificial sequence
<220> FEATURE:
<223> OTHER INFORMATION: synthetic sequence

<400> SEQUENCE: 283
ggcuacguag cucaguuggu uagagcagcg gccgggccag cugugagugu uucuuugagg      60
uaguagguug uaugguuugu gagcggccag cugugagugu uucuuuaagg cacgcgguga    120
augccguugu gagcaauagu aaggaagcgg uguucccguc gugccuucua gaagugcugc    180
acguuguugg cccggcgaua ccagccgaaa ggcccuuggc agcgucguaa ggaagaacug    240
uacaccuuac uaccuuucag aagugcugca cguuguuggc ccccgcgggu cacagguucg    300
aaucccgucg uagccacca                                                 319

<210> SEQ ID NO 284
<211> LENGTH: 318
<212> TYPE: RNA
<213> ORGANISM: Artificial sequence
<220> FEATURE:
<223> OTHER INFORMATION: synthetic sequence

<400> SEQUENCE: 284
ggcuacguag cucaguuggu uagagcagcg gccgggccag cugugagugu uucuuuaagg      60
cacgcgguga augccguugu gagcggccag cugugagugu uucuuggca gugucuuagc    120 ugguuguugu gagcaauagu aaggaagcaa ucagcaagua acugcccua gaagugcugc    180 acguuguugg cccggcgaua ccagccgaaa ggcccuuggc agcgucguaa ggaagcggug    240
uucccgucgu gccuucuaga agugcugcac guuguuggcc cccgcgggu cacagguucga   300 aucccgucgu agccacca                                                 318

<210> SEQ ID NO 285
<211> LENGTH: 318
<212> TYPE: RNA
<213> ORGANISM: Artificial sequence
<220> FEATURE:
<223> OTHER INFORMATION: synthetic sequence

<400> SEQUENCE: 285
ggcuacguag cucaguuggu uagagcagcg gccgggccag cugugagugu uucuuuggca     60
gugucuuagc ugguuguugu gagcggccag cugugagugu uucuuuaagg cacgcgguga   120
augccguugu gagcaauagu aaggaagcgg uguucccguc gugccuucua gaagugcugc   180
acguuguugg cccggcgaua ccagccgaaa ggcccuuggc agcgucguaa ggaagcaauc   240
agcaaguaua cugcccuaga agugcugcac guuguuggcc cccgcgggu cacagguucga   300 aucccgucgu agccacca                                                 318

<210> SEQ ID NO 286
<211> LENGTH: 352
<212> TYPE: RNA
<213> ORGANISM: Artificial sequence
<220> FEATURE:
<223> OTHER INFORMATION: synthetic sequence

<400> SEQUENCE: 286
ggcuacguag cucaguuggu uagagcagcg gccgggccag cugugagugu uucuuugagg     60
uaguagguug uaugguuugu gagcggcgau accagccgaa aggcccuugg cagcgucggc   120
cagcugugag uguucuuua aggcacgcgg ugaaugccgu gugagcaau aguaaggaag    180
```

```
cgguguuccc gucgugccuu cuagaagugc ugcacguugu uggcccggcg auaccagccg    240
aaaggcccuu ggcagcgucg uaaggaagaa cuguacaccu uacuaccuuu cagaagugcu    300
gcacguuguu ggccccgcg ggucacaggu ucgaaucccg ucguagccac ca             352
```

<210> SEQ ID NO 287
<211> LENGTH: 351
<212> TYPE: RNA
<213> ORGANISM: Artificial sequence
<220> FEATURE:
<223> OTHER INFORMATION: synthetic sequence

<400> SEQUENCE: 287

```
ggcuacguag cucaguuggu uagagcagcg gccgggccag cugugagugu uucuuuaagg    60
cacgcgguga augccguugu gagcggcgau accagccgaa aggcccuugg cagcgucggc    120
cagcugugag uguucuuug gcagugucuu agcugguugu ugugagcaau aguaaggaag     180
caaucagcaa guauacugcc cuagaagugc ugcacguugu uggcccggcg auaccagccg    240
aaaggcccuu ggcagcgucg uaaggaagcg guguccccgu cgugccuucu agaagugcug    300
cacguuguug gccccgcgg gucacagguu cgaaucccgu cguagccacc a              351
```

<210> SEQ ID NO 288
<211> LENGTH: 351
<212> TYPE: RNA
<213> ORGANISM: Artificial sequence
<220> FEATURE:
<223> OTHER INFORMATION: synthetic sequence

<400> SEQUENCE: 288

```
ggcuacguag cucaguuggu uagagcagcg gccgggccag cugugagugu uucuuuggca    60
gugucuuagc ugguuguugu gagcggcgau accagccgaa aggcccuugg cagcgucggc    120
cagcugugag uguucuuua aggcacgcgu ugaaugccgu ugugagcaau aguaaggaag     180
cgguguuccc gucgugccuu cuagaagugc ugcacguugu uggcccggcg auaccagccg    240
aaaggcccuu ggcagcgucg uaaggaagca aucagcaagu auacugcccu agaagugcug    300
cacguuguug gccccgcgg gucacagguu cgaaucccgu cguagccacc a              351
```

<210> SEQ ID NO 289
<211> LENGTH: 65
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide at position 1 is attached to an
      optional aptamer, small activating (saRNA) or catalytic RNA
<220> FEATURE:
<221> NAME/KEY: misc_feature
<222> LOCATION: (21)..(22)
<223> OTHER INFORMATION: [N1 18-200] is present between the nucleotides
      at positions 21 and 22.
<220> FEATURE:
<221> NAME/KEY: misc_feature
<222> LOCATION: (41)..(42)
<223> OTHER INFORMATION: [N2 18-200] is present between the nucleotides
      at positions 41 and 42
<220> FEATURE:
<221> NAME/KEY: misc_feature
<222> LOCATION: (65)..(65)
<223> OTHER INFORMATION: The nucleotide at position 65 is attached to an
      opional aptamer, small activating RNA (saRNA) or catalytic RNA -continued

<400> SEQUENCE: 289
ggccagcugu gaguguuucu uugugagcaa uaguaaggaa gagaagugcu gcacguuguu    60
ggccc                                                                65

<210> SEQ ID NO 290
<211> LENGTH: 39
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide at position 1 is attached to an
      optional aptamer, small activating RNA (saRNA) or catalytic RNA
<220> FEATURE:
<221> NAME/KEY: misc_feature
<222> LOCATION: (13)..(14)
<223> OTHER INFORMATION: [N1 18-200] is present between the nucleotides
      at positions 13 and 14.
<220> FEATURE:
<221> NAME/KEY: misc_feature
<222> LOCATION: (22)..(23)
<223> OTHER INFORMATION: [N2 18-200] is present between the nucleotides
      at positions 22 and 23.
<220> FEATURE:
<221> NAME/KEY: misc_feature
<222> LOCATION: (39)..(39)
<223> OTHER INFORMATION: The nucleotide at position 39 is attached to an
      optional aptamer, small activating RNA (saRNA) or catalytic RNA

<400> SEQUENCE: 290
gguagaauuc caguguacug ugaaaggacu gucuuccug                           39

<210> SEQ ID NO 291
<211> LENGTH: 54
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide at position 1 is attached to an
      optional aptamer, small activating RNA (saRNA) or catalytic RNA
<220> FEATURE:
<221> NAME/KEY: misc_feature
<222> LOCATION: (20)..(21)
<223> OTHER INFORMATION: [N1 18-200] is present between the nucleotides
      at positions 20 and 21.
<220> FEATURE:
<221> NAME/KEY: misc_feature
<222> LOCATION: (34)..(35)
<223> OTHER INFORMATION: [N2 18-200] is present between the nucleotides
      at positions 34 and 35.
<220> FEATURE:
<221> NAME/KEY: misc_feature
<222> LOCATION: (54)..(54)
<223> OTHER INFORMATION: The nucleotide at position 54 is attached to an
      optional aptamer, small activating RNA (saRNA) or catalytic RNA

<400> SEQUENCE: 291
ccagcucggg cagccguggc uggagucagg ucucugacgg cggagcccug cacg           54

<210> SEQ ID NO 292
<211> LENGTH: 44
<212> TYPE: RNA
<213> ORGANISM: Artificial sequence
<220> FEATURE:
<223> OTHER INFORMATION: synthetic sequence
<220> FEATURE:
<221> NAME/KEY: misc_feature

```
<222> LOCATION: (1)..(1)
<223> OTHER INFORMATION: The nucleotide at position 1 is attached to an
      optional aptamer, small ativating RNA (saRNA) or catalytic RNA
<220> FEATURE:
<221> NAME/KEY: misc_feature
<222> LOCATION: (15)..(16)
<223> OTHER INFORMATION: [N1 18-200] is present between the nucleotides
      at positions 15 and 16.
<220> FEATURE:
<221> NAME/KEY: misc_feature
<222> LOCATION: (30)..(31)
<223> OTHER INFORMATION: [N2 18-200] is present between the nucleotides
      at positions 30 and 31.
<220> FEATURE:
<221> NAME/KEY: misc_feature
<222> LOCATION: (44)..(44)
<223> OTHER INFORMATION: The nucleotide at position 44 is attached to an
      optional aptamer, small activating RNA (saRNA) or catalytic RNA

<400> SEQUENCE: 292
acaaugcuuu gcuagcgccu cuucaaugga uagcuaugca uuga                           44

<210> SEQ ID NO 293
<211> LENGTH: 40
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide at position 1 is attached to an
      optional aptamer, small activating RNA (saRNA) or catalytic RNA
<220> FEATURE:
<221> NAME/KEY: misc_feature
<222> LOCATION: (14)..(15)
<223> OTHER INFORMATION: [N1 18-200] is present between the nucleotides
      at positions 14 and 15.
<220> FEATURE:
<221> NAME/KEY: misc_feature
<222> LOCATION: (28)..(29)
<223> OTHER INFORMATION: [N2 18-200] is present between the nucleotides
      at positions 28 and 29.
<220> FEATURE:
<221> NAME/KEY: misc_feature
<222> LOCATION: (40)..(40)
<223> OTHER INFORMATION: The nucleotide at position 40 is attached to an
      optional aptamer, small activating RNA (saRNA) or catalytic RNA

<400> SEQUENCE: 293
ugccagucuc uaggggacau ccagggucug gcgucuggcc                                40

<210> SEQ ID NO 294
<211> LENGTH: 40
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide at position 1 is attached to an
      optional aptamer, small activating RNA (saRNA) or catalytic RNA
<220> FEATURE:
<221> NAME/KEY: misc_feature
<222> LOCATION: (10)..(11)
<223> OTHER INFORMATION: [N1 18-200] is present between the nucleotides
      at positions 10 and 11.
<220> FEATURE:
<221> NAME/KEY: misc_feature
<222> LOCATION: (33)..(34)
<223> OTHER INFORMATION: [N2 18-200] is present between the nucleotides
      at positions 33 and 34.
<220> FEATURE:
<221> NAME/KEY: misc_feature
```

```
<222> LOCATION: (40)..(40)
<223> OTHER INFORMATION: The nucleotide at position 40 is attached to an
      optional aptamer, small activating RNA (saRNA) or catalytic RNA

<400> SEQUENCE: 294
gcauccgggu uagaguuaca cccugggagu uaauuggagc                              40

<210> SEQ ID NO 295
<211> LENGTH: 43
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide at position 1 is attached to an
      optional aptamer, small activating RNA (saRNA) or catalytic RNA
<220> FEATURE:
<221> NAME/KEY: misc_feature
<222> LOCATION: (13)..(14)
<223> OTHER INFORMATION: [N1 18-200] is present between the nucleotides
      at positions 13 and 14.
<220> FEATURE:
<221> NAME/KEY: misc_feature
<222> LOCATION: (30)..(31)
<223> OTHER INFORMATION: [N2 18-200] is present between the nucleotides
      at positions 30 and 31.
<220> FEATURE:
<221> NAME/KEY: misc_feature
<222> LOCATION: (43)..(43)
<223> OTHER INFORMATION: The nucleotide at position 43 is attached to an
      optional aptamer, small activating RNA (saRNA) or catalytic RNA

<400> SEQUENCE: 295
aggccucucu cucuuaaaug uccauacaau aagaaugggg cug                          43

<210> SEQ ID NO 296
<211> LENGTH: 126
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (21)..(22)
<223> OTHER INFORMATION: [N1 18-200] is present between the nucleotides
      at positions 21 and 22.
<220> FEATURE:
<221> NAME/KEY: misc_feature
<222> LOCATION: (49)..(50)
<223> OTHER INFORMATION: [N3 18-200] is present between the nucleotides
      at positions 49 and 50.
<220> FEATURE:
<221> NAME/KEY: misc_feature
<222> LOCATION: (69)..(70)
<223> OTHER INFORMATION: [N4 18-200] is present between the nucleotides
      at positions 69 and 70.
<220> FEATURE:
<221> NAME/KEY: misc_feature
<222> LOCATION: (102)..(103)
<223> OTHER INFORMATION: [N2 18-200] is present between the nucleotides
      at positions 102 and 103.

<400> SEQUENCE: 296
ggccagcugu gaguguuucu uugugagcgg ccagcuguga guguuucuuu gugagcaaua        60
guaaggaaga gaagugcugc acguuguugg cccguaagga agagaagugc ugcacguugu       120
uggccc                                                                 126

<210> SEQ ID NO 297
<211> LENGTH: 126
```

```
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: The nucleotide at position 1 is attached to an
      optional aptamer, small activating RNA (saRNA) or catalytic RNA
<220> FEATURE:
<221> NAME/KEY: misc_feature
<222> LOCATION: (21)..(22)
<223> OTHER INFORMATION: [N1 18-200] is present between the nucleotides
      at positions 21 and 22.
<220> FEATURE:
<221> NAME/KEY: misc_feature
<222> LOCATION: (49)..(50)
<223> OTHER INFORMATION: [N3 18-200] is present between the nucleotides
      at positions 49 and 50.
<220> FEATURE:
<221> NAME/KEY: misc_feature
<222> LOCATION: (69)..(70)
<223> OTHER INFORMATION: [N4 18-200] is present between the nucleotides
      at positions 69 and 70.
<220> FEATURE:
<221> NAME/KEY: misc_feature
<222> LOCATION: (103)..(104)
<223> OTHER INFORMATION: [N2 18-200] is present between the nucleotides
      at positions 103 and 104
<220> FEATURE:
<221> NAME/KEY: misc_feature
<222> LOCATION: (126)..(126)
<223> OTHER INFORMATION: The nucleotide at position 126 is attached to
      an optional aptamer, small activating RNA (saRNA) or catalytic RNA

<400> SEQUENCE: 297
ggccagcugu gaguguuucu uugugagcgg ccagcuguga guguuucuuu gugagcaaua      60
guaaggaaga gaagugcugc acguuguugg cccguaagga agagaagugc ugcacguugu     120
uggccc                                                               126

<210> SEQ ID NO 298
<211> LENGTH: 126
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (21)..(22)
<223> OTHER INFORMATION: [N1 18-200] is present between the nucleotides
      at positions 21 and 22
<220> FEATURE:
<221> NAME/KEY: misc_feature
<222> LOCATION: (28)..(29)
<223> OTHER INFORMATION: An optional aptamer, small activating RNA
      (saRNA) or catalytic RNA is present between the nucleotides at
      positions 28 and 29
<220> FEATURE:
<221> NAME/KEY: misc_feature
<222> LOCATION: (49)..(50)
<223> OTHER INFORMATION: [N3 18-200] is present between the nucleotides
      at positions 49 and 50.
<220> FEATURE:
<221> NAME/KEY: misc_feature
<222> LOCATION: (69)..(70)
<223> OTHER INFORMATION: [N4 18-200] is present between the nucleotides
      at positiosn 69 and 70
<220> FEATURE:
<221> NAME/KEY: misc_feature
<222> LOCATION: (93)..(94)
<223> OTHER INFORMATION: An optional aptamer, small activating RNA
      (saRNA) or catalytic RNA is present between the nucleotides at
      positions 93 and 94
<220> FEATURE:
<221> NAME/KEY: misc_feature
```

<222> LOCATION: (102)..(103)
<223> OTHER INFORMATION: [N2 18-200] is present between the nucleotides
      at positions 102 and 103.

<400> SEQUENCE: 298
ggccagcugu gaguguuucu uugugagcgg ccagcuguga guguuucuuu gugagcaaua    60
guaaggaaga gaagugcugc acguuguugg cccguaagga agagaagugc ugcacguugu   120
uggccc                                                              126

<210> SEQ ID NO 299
<211> LENGTH: 14
<212> TYPE: RNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (1)..(14)
<223> OTHER INFORMATION: n is a, c, g, or u

<400> SEQUENCE: 299
nnnnnnnnnn nnnn                                                      14

<210> SEQ ID NO 300
<211> LENGTH: 33
<212> TYPE: RNA
<213> ORGANISM: Artificial sequence
<220> FEATURE:
<223> OTHER INFORMATION: synthetic sequence

<400> SEQUENCE: 300
gcagcgaugg ccgagugguu aaggcguugg acu                                 33

<210> SEQ ID NO 301
<211> LENGTH: 49
<212> TYPE: RNA
<213> ORGANISM: Artificial sequence
<220> FEATURE:
<223> OTHER INFORMATION: synthetic sequence

<400> SEQUENCE: 301
aauccaaugg ggucuccccg cgcagguucg aacccugcuc gcugcgcca               49

<210> SEQ ID NO 302
<211> LENGTH: 33
<212> TYPE: RNA
<213> ORGANISM: Artificial sequence
<220> FEATURE:
<223> OTHER INFORMATION: synthetic sequence

<400> SEQUENCE: 302
gacgaggugg ccgagugguu aaggcgaugg acu                                 33

<210> SEQ ID NO 303
<211> LENGTH: 49
<212> TYPE: RNA
<213> ORGANISM: Artificial sequence
<220> FEATURE:
<223> OTHER INFORMATION: synthetic sequence

<400> SEQUENCE: 303
aauccauugu gcucugcacg cguggguucg aaucccaccc ucgucgcca                49

<210> SEQ ID NO 304
<211> LENGTH: 33

```
<212> TYPE: RNA
<213> ORGANISM: Artificial sequence
<220> FEATURE:
<223> OTHER INFORMATION: synthetic sequence

<400> SEQUENCE: 304
accaggaugg ccgagugguu aaggcguugg acu                              33

<210> SEQ ID NO 305
<211> LENGTH: 50
<212> TYPE: RNA
<213> ORGANISM: Artificial sequence
<220> FEATURE:
<223> OTHER INFORMATION: synthetic sequence

<400> SEQUENCE: 305
gauccaaugg acauaugucc gcguggguuc gaaccccacu ccugguacca            50

<210> SEQ ID NO 306
<211> LENGTH: 34
<212> TYPE: RNA
<213> ORGANISM: Artificial sequence
<220> FEATURE:
<223> OTHER INFORMATION: synthetic sequence

<400> SEQUENCE: 306
gucaggaugg ccgagugguc uaaggcgcca gacu                             34

<210> SEQ ID NO 307
<211> LENGTH: 50
<212> TYPE: RNA
<213> ORGANISM: Artificial sequence
<220> FEATURE:
<223> OTHER INFORMATION: synthetic sequence

<400> SEQUENCE: 307
guucuggucu ccguauggag gcguggguuc gaaucccacu ucugacacca            50

<210> SEQ ID NO 308
<211> LENGTH: 32
<212> TYPE: RNA
<213> ORGANISM: Artificial sequence
<220> FEATURE:
<223> OTHER INFORMATION: synthetic sequence

<400> SEQUENCE: 308 gcauggugg uucaguggua gaauucucgc cu                                32

<210> SEQ ID NO 309
<211> LENGTH: 39
<212> TYPE: RNA
<213> ORGANISM: Artificial sequence
<220> FEATURE:
<223> OTHER INFORMATION: synthetic sequence

<400> SEQUENCE: 309
acgcgggagg cccggguucg auucccggcc caugcacca                        39

<210> SEQ ID NO 310
<211> LENGTH: 33
<212> TYPE: RNA
<213> ORGANISM: Artificial sequence
<220> FEATURE:
<223> OTHER INFORMATION: synthetic sequence

<400> SEQUENCE: 310
```
gcguuggugg uauagugguu agcauagcug ccu          33

<210> SEQ ID NO 311
<211> LENGTH: 39
<212> TYPE: RNA
<213> ORGANISM: Artificial sequence
<220> FEATURE:
<223> OTHER INFORMATION: synthetic sequence

<400> SEQUENCE: 311
aagcaguuga cccggguucg auucccggcc aacgcacca          39

<210> SEQ ID NO 312
<211> LENGTH: 33
<212> TYPE: RNA
<213> ORGANISM: Artificial sequence
<220> FEATURE:
<223> OTHER INFORMATION: synthetic sequence

<400> SEQUENCE: 312 ucccugguggg ucuagugguu aggauucggc gcu          33

<210> SEQ ID NO 313
<211> LENGTH: 39
<212> TYPE: RNA
<213> ORGANISM: Artificial sequence
<220> FEATURE:
<223> OTHER INFORMATION: synthetic sequence

<400> SEQUENCE: 313
accgccgcgg cccgggu ucg auucccgguc agggaacca          39

<210> SEQ ID NO 314
<211> LENGTH: 33
<212> TYPE: RNA
<213> ORGANISM: Artificial sequence
<220> FEATURE:
<223> OTHER INFORMATION: synthetic sequence

<400> SEQUENCE: 314
uccucguuag uauaguggug aguauccccg ccu          33

<210> SEQ ID NO 315
<211> LENGTH: 39
<212> TYPE: RNA
<213> ORGANISM: Artificial sequence
<220> FEATURE:
<223> OTHER INFORMATION: synthetic sequence

<400> SEQUENCE: 315
acgcgggaga ccggguucg auuccccgac ggggagcca          39

<210> SEQ ID NO 316
<211> LENGTH: 33
<212> TYPE: RNA
<213> ORGANISM: Artificial sequence
<220> FEATURE:
<223> OTHER INFORMATION: synthetic sequence

<400> SEQUENCE: 316
ggucccaugg uguaaugguu agcacucugg acu          33

<210> SEQ ID NO 317
<211> LENGTH: 39
<212> TYPE: RNA
<213> ORGANISM: Artificial sequence

```
<220> FEATURE:
<223> OTHER INFORMATION: synthetic sequence

<400> SEQUENCE: 317
aauccagcga uccgaguuca aaucucggug ggaccucca                39

<210> SEQ ID NO 318
<211> LENGTH: 33
<212> TYPE: RNA
<213> ORGANISM: Artificial sequence
<220> FEATURE:
<223> OTHER INFORMATION: synthetic sequence

<400> SEQUENCE: 318 gguccaugg uguaaugguu agcacucugg acu                       33

<210> SEQ ID NO 319
<211> LENGTH: 39
<212> TYPE: RNA
<213> ORGANISM: Artificial sequence
<220> FEATURE:
<223> OTHER INFORMATION: synthetic sequence

<400> SEQUENCE: 319
aauccagcga uccgaguuca aaucucggug gaaccucca                39

<210> SEQ ID NO 320
<211> LENGTH: 33
<212> TYPE: RNA
<213> ORGANISM: Artificial sequence
<220> FEATURE:
<223> OTHER INFORMATION: synthetic sequence

<400> SEQUENCE: 320
gggccagugg cgcaauggau aacgcgucug acu                      33

<210> SEQ ID NO 321
<211> LENGTH: 40
<212> TYPE: RNA
<213> ORGANISM: Artificial sequence
<220> FEATURE:
<223> OTHER INFORMATION: synthetic sequence

<400> SEQUENCE: 321
gaucagaaga uuccagguuc gacuccuggc uggcucgcca               40

<210> SEQ ID NO 322
<211> LENGTH: 33
<212> TYPE: RNA
<213> ORGANISM: Artificial sequence
<220> FEATURE:
<223> OTHER INFORMATION: synthetic sequence

<400> SEQUENCE: 322
ggcucugugg cgcaauggau agcgcauugg acu                      33

<210> SEQ ID NO 323
<211> LENGTH: 40
<212> TYPE: RNA
<213> ORGANISM: Artificial sequence
<220> FEATURE:
<223> OTHER INFORMATION: synthetic sequence

<400> SEQUENCE: 323
aauucaaagg uuguggguuc gaaucccacc agagucgcca               40
```

<210> SEQ ID NO 324
<211> LENGTH: 32
<212> TYPE: RNA
<213> ORGANISM: Artificial sequence
<220> FEATURE:
<223> OTHER INFORMATION: synthetic sequence

<400> SEQUENCE: 324
gggggcauag cucaguggua gagcauuuga cu                                      32

<210> SEQ ID NO 325
<211> LENGTH: 40
<212> TYPE: RNA
<213> ORGANISM: Artificial sequence
<220> FEATURE:
<223> OTHER INFORMATION: synthetic sequence

<400> SEQUENCE: 325
gaucaagagg ucccugguuc aaauccaggu gcccccucca                              40

<210> SEQ ID NO 326
<211> LENGTH: 33
<212> TYPE: RNA
<213> ORGANISM: Artificial sequence
<220> FEATURE:
<223> OTHER INFORMATION: synthetic sequence

<400> SEQUENCE: 326
gcccggcuag cucagucggu agagcauggg acu                                     33

<210> SEQ ID NO 327
<211> LENGTH: 40
<212> TYPE: RNA
<213> ORGANISM: Artificial sequence
<220> FEATURE:
<223> OTHER INFORMATION: synthetic sequence

<400> SEQUENCE: 327
aaucccaggg ucgugggpuc gagccccacg uugggcgcca                              40

<210> SEQ ID NO 328
<211> LENGTH: 33
<212> TYPE: RNA
<213> ORGANISM: Artificial sequence
<220> FEATURE:
<223> OTHER INFORMATION: synthetic sequence

<400> SEQUENCE: 328
gccuggauag cucaguuggu agagcaucag acu                                     33

<210> SEQ ID NO 329
<211> LENGTH: 40
<212> TYPE: RNA
<213> ORGANISM: Artificial sequence
<220> FEATURE:
<223> OTHER INFORMATION: synthetic sequence

<400> SEQUENCE: 329
aaucugaggg uccagggpuc aagucccugu ucaggcacca                              40

<210> SEQ ID NO 330
<211> LENGTH: 33
<212> TYPE: RNA
<213> ORGANISM: Artificial sequence
<220> FEATURE:
<223> OTHER INFORMATION: synthetic sequence -continued

```
<400> SEQUENCE: 330
gccucguuag cgcaguaggu agcgcgucag ucu                                    33

<210> SEQ ID NO 331
<211> LENGTH: 40
<212> TYPE: RNA
<213> ORGANISM: Artificial sequence
<220> FEATURE:
<223> OTHER INFORMATION: synthetic sequence

<400> SEQUENCE: 331
aaucugaagg ucgugaguuc gauccucaca cggggcacca                             40

<210> SEQ ID NO 332
<211> LENGTH: 34
<212> TYPE: RNA
<213> ORGANISM: Artificial sequence
<220> FEATURE:
<223> OTHER INFORMATION: synthetic sequence

<400> SEQUENCE: 332
gucucugugg cgcaaucggu uagcgcguuc ggcu                                   34

<210> SEQ ID NO 333
<211> LENGTH: 40
<212> TYPE: RNA
<213> ORGANISM: Artificial sequence
<220> FEATURE:
<223> OTHER INFORMATION: synthetic sequence

<400> SEQUENCE: 333
aaccgaaagg uuggugguuc gaucccaccc agggacgcca                             40

<210> SEQ ID NO 334
<211> LENGTH: 32
<212> TYPE: RNA
<213> ORGANISM: Artificial sequence
<220> FEATURE:
<223> OTHER INFORMATION: synthetic sequence

<400> SEQUENCE: 334 gggggguguag cucaguggua gagcgcgugc uu                                    32

<210> SEQ ID NO 335
<211> LENGTH: 40
<212> TYPE: RNA
<213> ORGANISM: Artificial sequence
<220> FEATURE:
<223> OTHER INFORMATION: synthetic sequence

<400> SEQUENCE: 335
augcacgagg ccccggguuc aauccccggc accuccacca                             40

<210> SEQ ID NO 336
<211> LENGTH: 33
<212> TYPE: RNA
<213> ORGANISM: Artificial sequence
<220> FEATURE:
<223> OTHER INFORMATION: synthetic sequence

<400> SEQUENCE: 336
gccgugaucg uauagugguu aguacucugc guu                                    33

<210> SEQ ID NO 337
```

<211> LENGTH: 39
<212> TYPE: RNA
<213> ORGANISM: Artificial sequence
<220> FEATURE:
<223> OTHER INFORMATION: synthetic sequence

<400> SEQUENCE: 337
gccgcagcaa ccucgguucg aauccgaguc acggcacca                                39

<210> SEQ ID NO 338
<211> LENGTH: 34
<212> TYPE: RNA
<213> ORGANISM: Artificial sequence
<220> FEATURE:
<223> OTHER INFORMATION: synthetic sequence

<400> SEQUENCE: 338
ggccgguuag cucaguuggu uagagcgugg ugcu                                     34

<210> SEQ ID NO 339
<211> LENGTH: 40
<212> TYPE: RNA
<213> ORGANISM: Artificial sequence
<220> FEATURE:
<223> OTHER INFORMATION: synthetic sequence

<400> SEQUENCE: 339
aacgccaagg ucgcggguuc gaucccgua cuggccacca                                40

<210> SEQ ID NO 340
<211> LENGTH: 34
<212> TYPE: RNA
<213> ORGANISM: Artificial sequence
<220> FEATURE:
<223> OTHER INFORMATION: synthetic sequence

<400> SEQUENCE: 340
gcuccagugg cgcaaucggu uagcgcgcgg uacu                                     34

<210> SEQ ID NO 341
<211> LENGTH: 40
<212> TYPE: RNA
<213> ORGANISM: Artificial sequence
<220> FEATURE:
<223> OTHER INFORMATION: synthetic sequence

<400> SEQUENCE: 341
aaugccgagg uugugaguuc gauccucacc uggagcacca                               40

<210> SEQ ID NO 342
<211> LENGTH: 33
<212> TYPE: RNA
<213> ORGANISM: Artificial sequence
<220> FEATURE:
<223> OTHER INFORMATION: synthetic sequence

<400> SEQUENCE: 342
gccgaaauag cucaguuggg agagcguuag acu                                      33

<210> SEQ ID NO 343
<211> LENGTH: 40
<212> TYPE: RNA
<213> ORGANISM: Artificial sequence
<220> FEATURE:
<223> OTHER INFORMATION: synthetic sequence

<400> SEQUENCE: 343

```
gaucuaaagg ucccuggunc gaucccgggu uucggcacca                              40

<210> SEQ ID NO 344
<211> LENGTH: 32
<212> TYPE: RNA
<213> ORGANISM: Artificial sequence
<220> FEATURE:
<223> OTHER INFORMATION: synthetic sequence

<400> SEQUENCE: 344
ggcucguugg ucuaggggua ugauucucgc uu                                     32

<210> SEQ ID NO 345
<211> LENGTH: 40
<212> TYPE: RNA
<213> ORGANISM: Artificial sequence
<220> FEATURE:
<223> OTHER INFORMATION: synthetic sequence

<400> SEQUENCE: 345
augcgagagg ucccggguuc aaaucccgga cgagccccca                             40

<210> SEQ ID NO 346
<211> LENGTH: 32
<212> TYPE: RNA
<213> ORGANISM: Artificial sequence
<220> FEATURE:
<223> OTHER INFORMATION: synthetic sequence

<400> SEQUENCE: 346
gaccucgugg cgcaacggua gcgcgucuga cu                                     32

<210> SEQ ID NO 347
<211> LENGTH: 40
<212> TYPE: RNA
<213> ORGANISM: Artificial sequence
<220> FEATURE:
<223> OTHER INFORMATION: synthetic sequence

<400> SEQUENCE: 347
gaucagaagg cugcguguuc gaaucacguc ggggucacca                             40

<210> SEQ ID NO 348
<211> LENGTH: 33
<212> TYPE: RNA
<213> ORGANISM: Artificial sequence
<220> FEATURE:
<223> OTHER INFORMATION: synthetic sequence

<400> SEQUENCE: 348
ccuucgauag cucaguuggu agagcggagg acu                                    33

<210> SEQ ID NO 349
<211> LENGTH: 40
<212> TYPE: RNA
<213> ORGANISM: Artificial sequence
<220> FEATURE:
<223> OTHER INFORMATION: synthetic sequence

<400> SEQUENCE: 349
gauccuuagg ucgcugguuc gaauccggcu cgaaggacca                             40

<210> SEQ ID NO 350
<211> LENGTH: 33
<212> TYPE: RNA
```

<213> ORGANISM: Artificial sequence
<220> FEATURE:
<223> OTHER INFORMATION: synthetic sequence

<400> SEQUENCE: 350
guuuccguag uguagugguu aucacguucg ccu                33

<210> SEQ ID NO 351
<211> LENGTH: 40
<212> TYPE: RNA
<213> ORGANISM: Artificial sequence
<220> FEATURE:
<223> OTHER INFORMATION: synthetic sequence

<400> SEQUENCE: 351
acgcgaaagg uccccgguuc gaaaccgggc ggaaacacca                40

<210> SEQ ID NO 352
<211> LENGTH: 34
<212> TYPE: RNA
<213> ORGANISM: Artificial sequence
<220> FEATURE:
<223> OTHER INFORMATION: synthetic sequence

<400> SEQUENCE: 352
ggcucuaugg cuuaguuggu uaaagcgccu gucu                34

<210> SEQ ID NO 353
<211> LENGTH: 40
<212> TYPE: RNA
<213> ORGANISM: Artificial sequence
<220> FEATURE:
<223> OTHER INFORMATION: synthetic sequence

<400> SEQUENCE: 353
aaacaggaga uccuggguuc gaauccagu agagccucca                40

<210> SEQ ID NO 354
<211> LENGTH: 34
<212> TYPE: RNA
<213> ORGANISM: Artificial sequence
<220> FEATURE:
<223> OTHER INFORMATION: synthetic sequence

<400> SEQUENCE: 354
ggcgccgugg cuuaguuggu uaaagcgccu gucu                34

<210> SEQ ID NO 355
<211> LENGTH: 40
<212> TYPE: RNA
<213> ORGANISM: Artificial sequence
<220> FEATURE:
<223> OTHER INFORMATION: synthetic sequence

<400> SEQUENCE: 355
aaacaggaga uccuggguuc gaauccagc ggugccucca                40

<210> SEQ ID NO 356
<211> LENGTH: 36
<212> TYPE: RNA
<213> ORGANISM: Artificial sequence
<220> FEATURE:
<223> OTHER INFORMATION: synthetic sequence

<400> SEQUENCE: 356
aguaauuuac gucgacggug acgucgaugg uugcgg                36

<210> SEQ ID NO 357
<211> LENGTH: 33
<212> TYPE: RNA
<213> ORGANISM: Artificial sequence
<220> FEATURE:
<223> OTHER INFORMATION: synthetic sequence

<400> SEQUENCE: 357
ggcgauacca gccgaaaggc ccuuggcagc guc                          33

<210> SEQ ID NO 358
<211> LENGTH: 27
<212> TYPE: RNA
<213> ORGANISM: Artificial sequence
<220> FEATURE:
<223> OTHER INFORMATION: synthetic sequence

<400> SEQUENCE: 358
cggaaucagu gaaugcuuau acauccg                                 27

<210> SEQ ID NO 359
<211> LENGTH: 19
<212> TYPE: RNA
<213> ORGANISM: Artificial sequence
<220> FEATURE:
<223> OTHER INFORMATION: synthetic sequence

<400> SEQUENCE: 359
gcgacugguu acccggucg                                          19

<210> SEQ ID NO 360
<211> LENGTH: 20
<212> TYPE: RNA
<213> ORGANISM: Artificial sequence
<220> FEATURE:
<223> OTHER INFORMATION: synthetic sequence

<400> SEQUENCE: 360
gccucagucu gcuucgcacc                                         20

<210> SEQ ID NO 361
<211> LENGTH: 20
<212> TYPE: RNA
<213> ORGANISM: Artificial sequence
<220> FEATURE:
<223> OTHER INFORMATION: synthetic sequence

<400> SEQUENCE: 361
gcccaagcug gcauccguca                                         20

<210> SEQ ID NO 362
<211> LENGTH: 19
<212> TYPE: RNA
<213> ORGANISM: Artificial sequence
<220> FEATURE:
<223> OTHER INFORMATION: synthetic sequence

<400> SEQUENCE: 362
uaauugucaa cuucuguca                                          19

<210> SEQ ID NO 363
<211> LENGTH: 19
<212> TYPE: RNA
<213> ORGANISM: Artificial sequence
<220> FEATURE:

```
<223> OTHER INFORMATION: synthetic sequence

<400> SEQUENCE: 363
guaguuguaa guaucauga                                                19

<210> SEQ ID NO 364
<211> LENGTH: 22
<212> TYPE: RNA
<213> ORGANISM: Artificial sequence
<220> FEATURE:
<223> OTHER INFORMATION: synthetic sequence

<400> SEQUENCE: 364
aguuguacuc cagcuugugc cc                                            22

<210> SEQ ID NO 365
<211> LENGTH: 22
<212> TYPE: RNA
<213> ORGANISM: Artificial sequence
<220> FEATURE:
<223> OTHER INFORMATION: synthetic sequence

<400> SEQUENCE: 365
guguaacacg ucuauacgcc ca                                            22

<210> SEQ ID NO 366
<211> LENGTH: 22
<212> TYPE: RNA
<213> ORGANISM: Artificial sequence
<220> FEATURE:
<223> OTHER INFORMATION: synthetic sequence

<400> SEQUENCE: 366
guucgucugu agacgguugu ug                                            22

<210> SEQ ID NO 367
<211> LENGTH: 21
<212> TYPE: RNA
<213> ORGANISM: Artificial sequence
<220> FEATURE:
<223> OTHER INFORMATION: synthetic sequence

<400> SEQUENCE: 367
uucuccgaag cugucacguu u                                             21

<210> SEQ ID NO 368
<211> LENGTH: 22
<212> TYPE: RNA
<213> ORGANISM: Artificial sequence
<220> FEATURE:
<223> OTHER INFORMATION: synthetic sequence

<400> SEQUENCE: 368
aagcgcgcuu uguaggauuc gu                                            22

<210> SEQ ID NO 369
<211> LENGTH: 22
<212> TYPE: RNA
<213> ORGANISM: Artificial sequence
<220> FEATURE:
<223> OTHER INFORMATION: synthetic sequence

<400> SEQUENCE: 369
ggugucguuu cucggugag ua                                             22
```

```
<210> SEQ ID NO 370
<211> LENGTH: 20
<212> TYPE: RNA
<213> ORGANISM: Artificial sequence
<220> FEATURE:
<223> OTHER INFORMATION: synthetic sequence

<400> SEQUENCE: 370
gccucagucu gcuucgcacc                                              20

<210> SEQ ID NO 371
<211> LENGTH: 20
<212> TYPE: RNA
<213> ORGANISM: Artificial sequence
<220> FEATURE:
<223> OTHER INFORMATION: synthetic sequence

<400> SEQUENCE: 371
gcccaagcug gcauccguca                                              20

<210> SEQ ID NO 372
<211> LENGTH: 19
<212> TYPE: RNA
<213> ORGANISM: Artificial sequence
<220> FEATURE:
<223> OTHER INFORMATION: synthetic sequence

<400> SEQUENCE: 372
uaauugucaa cuucuguca                                               19

<210> SEQ ID NO 373
<211> LENGTH: 19
<212> TYPE: RNA
<213> ORGANISM: Artificial sequence
<220> FEATURE:
<223> OTHER INFORMATION: synthetic sequence

<400> SEQUENCE: 373
guaguuguaa guaucauga                                               19

<210> SEQ ID NO 374
<211> LENGTH: 22
<212> TYPE: RNA
<213> ORGANISM: Artificial sequence
<220> FEATURE:
<223> OTHER INFORMATION: synthetic sequence

<400> SEQUENCE: 374
aguuguacuc cagcuugugc cc                                           22

<210> SEQ ID NO 375
<211> LENGTH: 33
<212> TYPE: RNA
<213> ORGANISM: Artificial sequence
<220> FEATURE:
<223> OTHER INFORMATION: synthetic sequence

<400> SEQUENCE: 375
ggcgauacca gccgaaaggc ccuuggcagc guc                               33

<210> SEQ ID NO 376
<211> LENGTH: 27
<212> TYPE: RNA
<213> ORGANISM: Artificial sequence
<220> FEATURE:
<223> OTHER INFORMATION: synthetic sequence
```

<400> SEQUENCE: 376
cggaaucagu gaaugcuuau acauccg                                    27

<210> SEQ ID NO 377
<211> LENGTH: 19
<212> TYPE: RNA
<213> ORGANISM: Artificial sequence
<220> FEATURE:
<223> OTHER INFORMATION: synthetic sequence

<400> SEQUENCE: 377
gcgacugguu acccggucg                                             19

<210> SEQ ID NO 378
<211> LENGTH: 22
<212> TYPE: RNA
<213> ORGANISM: Artificial sequence
<220> FEATURE:
<223> OTHER INFORMATION: synthetic sequence

<400> SEQUENCE: 378
guguaacacg ucuauacgcc ca                                         22

<210> SEQ ID NO 379
<211> LENGTH: 22
<212> TYPE: RNA
<213> ORGANISM: Artificial sequence
<220> FEATURE:
<223> OTHER INFORMATION: synthetic sequence

<400> SEQUENCE: 379
guucgucugu agacgguugu ug                                         22

<210> SEQ ID NO 380
<211> LENGTH: 21
<212> TYPE: RNA
<213> ORGANISM: Artificial sequence
<220> FEATURE:
<223> OTHER INFORMATION: synthetic sequence

<400> SEQUENCE: 380
uucuccgaag cugucacguu u                                          21

<210> SEQ ID NO 381
<211> LENGTH: 22
<212> TYPE: RNA
<213> ORGANISM: Artificial sequence
<220> FEATURE:
<223> OTHER INFORMATION: synthetic sequence

<400> SEQUENCE: 381
aagcgcgcuu uguaggauuc gu                                         22

<210> SEQ ID NO 382
<211> LENGTH: 22
<212> TYPE: RNA
<213> ORGANISM: Artificial sequence
<220> FEATURE:
<223> OTHER INFORMATION: synthetic sequence

<400> SEQUENCE: 382
ggugucguuu cucuggugag ua                                         22

<210> SEQ ID NO 383
<211> LENGTH: 233

```
<212> TYPE: RNA
<213> ORGANISM: Artificial sequence
<220> FEATURE:
<223> OTHER INFORMATION: synthetic sequence

<400> SEQUENCE: 383
ggcuacguag cucaguuggu uagagcagcg gccgaguaau uuacgucgac guggaccggc    60
cagcugugag uguuucuuug gcagugucuu agcugguugu ugugagcaau aguaaggaag   120
caaucagcaa guauacugcc cuagaagugc ugcacguugu ggggcccaag agggaagaug   180
acgucgaugg uugcggccgc gggucacagg uucgaauccc gucguagcca cca          233

<210> SEQ ID NO 384
<211> LENGTH: 180
<212> TYPE: RNA
<213> ORGANISM: Artificial sequence
<220> FEATURE:
<223> OTHER INFORMATION: synthetic sequence

<400> SEQUENCE: 384
ggcuacguag cucaguuggu uagagcagcg gccgggccag cugugagugu uucuuggca     60 gugucuuagc ugguuguugu gagcaauagu aaggaagcaa ucagcaagua uacugcccua   120
gaagugcugc acguugugggg gccccgcggg ucacagguuc gaaucccguc guagccacca   180

<210> SEQ ID NO 385
<211> LENGTH: 181
<212> TYPE: RNA
<213> ORGANISM: Artificial sequence
<220> FEATURE:
<223> OTHER INFORMATION: synthetic sequence

<400> SEQUENCE: 385
ggcuacguag cucaguuggu uagagcagcg gccgggccag cugugagugu uucuuggca     60 gugucuuagc ugguuguugu gagcaauagu aaggaagcaa ucagcaagua uacugcccua   120
gaagugcugc acguugugggg gccccgcgg gucacagguu cgaaucccgu cguagccacc   180
a                                                                    181

<210> SEQ ID NO 386
<211> LENGTH: 181
<212> TYPE: RNA
<213> ORGANISM: Artificial sequence
<220> FEATURE:
<223> OTHER INFORMATION: synthetic sequence

<400> SEQUENCE: 386
ggcuacguag cucaguuggu uagagcagcg gccgggccag cugugagugu uucuuggca     60 gugucuuagc ugguuguugu gagcaauagu aaggaagcaa ucagcaagua uacugcccua   120
gaagugcugc acguuguugg cccccgcggg ucacagguuc gaaucccguc guagccacca   180 r                                                                    181

<210> SEQ ID NO 387
<211> LENGTH: 40
<212> TYPE: DNA
<213> ORGANISM: Artificial sequence
<220> FEATURE:
<223> OTHER INFORMATION: synthetic sequence

<400> SEQUENCE: 387
agtaatttac gtcgacgtgg accggccagc tgtgagtgtt                          40
```

```
<210> SEQ ID NO 388
<211> LENGTH: 45
<212> TYPE: DNA
<213> ORGANISM: Artificial sequence
<220> FEATURE:
<223> OTHER INFORMATION: synthetic sequence

<400> SEQUENCE: 388
cggccgcaac catcgacgtc atcttccctc ttgggcccca caacg          45

<210> SEQ ID NO 389
<211> LENGTH: 39
<212> TYPE: DNA
<213> ORGANISM: Artificial sequence
<220> FEATURE:
<223> OTHER INFORMATION: synthetic sequence

<400> SEQUENCE: 389
gttagagcag cggccgggcc agctgtgagt gtttctttg               39

<210> SEQ ID NO 390
<211> LENGTH: 36
<212> TYPE: DNA
<213> ORGANISM: Artificial sequence
<220> FEATURE:
<223> OTHER INFORMATION: synthetic sequence

<400> SEQUENCE: 390
tcgaacctgt gacccgcggg gccccacaac gtgcag                 36

<210> SEQ ID NO 391
<211> LENGTH: 39
<212> TYPE: DNA
<213> ORGANISM: Artificial sequence
<220> FEATURE:
<223> OTHER INFORMATION: synthetic sequence

<400> SEQUENCE: 391
gttagagcag cggccgggcc agctgtgagt gtttctttg               39

<210> SEQ ID NO 392
<211> LENGTH: 37
<212> TYPE: DNA
<213> ORGANISM: Artificial sequence
<220> FEATURE:
<223> OTHER INFORMATION: synthetic sequence

<400> SEQUENCE: 392
tcgaacctgt gacccgcggg ggccccacaa cgtgcag                37

<210> SEQ ID NO 393
<211> LENGTH: 39
<212> TYPE: DNA
<213> ORGANISM: Artificial sequence
<220> FEATURE:
<223> OTHER INFORMATION: synthetic sequence

<400> SEQUENCE: 393
gttagagcag cggccgggcc agctgtgagt gtttctttg               39

<210> SEQ ID NO 394
<211> LENGTH: 37
<212> TYPE: DNA
<213> ORGANISM: Artificial sequence
<220> FEATURE:
<223> OTHER INFORMATION: synthetic sequence
```

<400> SEQUENCE: 394
tcgaacctgt gacccgcggg ggccaacaac gtgcagc        37

<210> SEQ ID NO 395
<211> LENGTH: 36
<212> TYPE: DNA
<213> ORGANISM: Artificial sequence
<220> FEATURE:
<223> OTHER INFORMATION: synthetic sequence

<400> SEQUENCE: 395
gttagagcag cggccgggcc ccgctgtgag tgtttc         36

<210> SEQ ID NO 396
<211> LENGTH: 37
<212> TYPE: DNA
<213> ORGANISM: Artificial sequence
<220> FEATURE:
<223> OTHER INFORMATION: synthetic sequence

<400> SEQUENCE: 396
tcgaacctgt gacccgcggg ggccccacaa cgtgcag        37

<210> SEQ ID NO 397
<211> LENGTH: 181
<212> TYPE: RNA
<213> ORGANISM: Artificial sequence
<220> FEATURE:
<223> OTHER INFORMATION: synthetic sequence

<400> SEQUENCE: 397
ggcuacguag cucaguuggu uagagcagcg gccgggccag cugugagugu uucuuuucac        60
aguggcuaag uuccgcuugu gagcaauagu aaggaaggca gggcuuagcu gcuugugacu       120
agaagugcug cacguuguug gccccgcggg ucacagguu cgaaucccgu cguagccacc       180
a                                                                     181

<210> SEQ ID NO 398
<211> LENGTH: 180
<212> TYPE: RNA
<213> ORGANISM: Artificial sequence
<220> FEATURE:
<223> OTHER INFORMATION: synthetic sequence

<400> SEQUENCE: 398
ggcuacguag cucaguuggu uagagcagcg gccgggccag cugugagugu uucuuuucac        60
aguggcuaag uucugcuugu gagcaauagu aaggaaggca gagcuagcuc auugugacca       120
gaagugcugc acguuguugg ccccgcgggu cacagguuc gaaucccguc guagccacca       180

<210> SEQ ID NO 399
<211> LENGTH: 180
<212> TYPE: RNA
<213> ORGANISM: Artificial sequence
<220> FEATURE:
<223> OTHER INFORMATION: synthetic sequence

<400> SEQUENCE: 399
ggcuacguag cucaguuggu uagagcagcg gccgggccag cugugagugu uucuucacug        60
gcuccuuucu ggguagaugu gagcaauagu aaggaaucua cucagaagug agccaguuua       120
gaagugcugc acguuguugg ccccgcgggu cacagguuc gaaucccguc guagccacca       180

```
<210> SEQ ID NO 400
<211> LENGTH: 180
<212> TYPE: RNA
<213> ORGANISM: Artificial sequence
<220> FEATURE:
<223> OTHER INFORMATION: synthetic sequence

<400> SEQUENCE: 400
ggcuacguag cucaguuggu uagagcagcg gccgggccag cugugagugu uucuuaaacc    60
guuaccauua cugaguuugu gagcaauagu aaggaagacu aguaugguu aauguucua    120 gaagugcugc acguuguugg cccccgcggg ucacagguuc gaaucccguc guagccacca   180

<210> SEQ ID NO 401
<211> LENGTH: 180
<212> TYPE: RNA
<213> ORGANISM: Artificial sequence
<220> FEATURE:
<223> OTHER INFORMATION: synthetic sequence

<400> SEQUENCE: 401
ggcuacguag cucaguuggu uagagcagcg gccgggccag cugugagugu uucuuugccu    60
cagucugcuu cgcaccuugu gagcaauagu aaggaagggu gcgaacagua cugaggccua   120
gaagugcugc acguuguugg cccccgcggg ucacagguuc gaaucccguc guagccacca   180

<210> SEQ ID NO 402
<211> LENGTH: 180
<212> TYPE: RNA
<213> ORGANISM: Artificial sequence
<220> FEATURE:
<223> OTHER INFORMATION: synthetic sequence

<400> SEQUENCE: 402
ggcuacguag cucaguuggu uagagcagcg gccgggccag cugugagugu uucuuaccac    60
cagaacaugc aaugcaaugu gagcaauagu aaggaauugc auugcguauu cuggugggua   120
gaagugcugc acguuguugg cccccgcggg ucacagguuc gaaucccguc guagccacca   180

<210> SEQ ID NO 403
<211> LENGTH: 180
<212> TYPE: RNA
<213> ORGANISM: Artificial sequence
<220> FEATURE:
<223> OTHER INFORMATION: synthetic sequence

<400> SEQUENCE: 403
ggcuacguag cucaguuggu uagagcagcg gccgggccag cugugagugu uucuuagcau    60
ggcacucauu auuacgcugu gagcaauagu aaggaagcgu aauaagaguu gccaugccua   120
gaagugcugc acguuguugg cccccgcggg ucacagguuc gaaucccguc guagccacca   180

<210> SEQ ID NO 404
<211> LENGTH: 180
<212> TYPE: RNA
<213> ORGANISM: Artificial sequence
<220> FEATURE:
<223> OTHER INFORMATION: synthetic sequence

<400> SEQUENCE: 404
ggcuacguag cucaguuggu uagagcagcg gccgggccag cugugagugu uucuuugccc    60
aagcuggcau ccgucauugu gagcaauagu aaggaaguga cggauccaug cuugggccua   120
gaagugcugc acguuguugg cccccgcggg ucacagguuc gaaucccguc guagccacca   180
```

```
<210> SEQ ID NO 405
<211> LENGTH: 180
<212> TYPE: RNA
<213> ORGANISM: Artificial sequence
<220> FEATURE:
<223> OTHER INFORMATION: synthetic sequence

<400> SEQUENCE: 405
ggcuacguag cucaguuggu uagagcagcg gccgggccag cugugagugu uucuuagcag      60
aagcagggag guucucccau gagcaauagu aaggagggga gaaccccccau gcuuugaca     120 gaagugcugc acguuguugg cccccgcggg ucacagguuc gaaucccguc guagccacca    180

<210> SEQ ID NO 406
<211> LENGTH: 180
<212> TYPE: RNA
<213> ORGANISM: Artificial sequence
<220> FEATURE:
<223> OTHER INFORMATION: synthetic sequence

<400> SEQUENCE: 406
ggcuacguag cucaguuggu uagagcagcg gccgggccag cugugagugu uucuucucua      60
gagggaagcg cuuucugugu gagcaauagu aaggaacaga aagugcaucu uuuuagauua    120
gaagugcugc acguuguugg cccccgcggg ucacagguuc gaaucccguc guagccacca    180

<210> SEQ ID NO 407
<211> LENGTH: 180
<212> TYPE: RNA
<213> ORGANISM: Artificial sequence
<220> FEATURE:
<223> OTHER INFORMATION: synthetic sequence

<400> SEQUENCE: 407
ggcuacguag cucaguuggu uagagcagcg gccgggccag cugugagugu uucuuuggag      60
ugugacaaug guguuugugu gagcaauagu aaggaacaaa cgccauguac acacucccua    120
gaagugcugc acguuguugg cccccgcggg ucacagguuc gaaucccguc guagccacca    180

<210> SEQ ID NO 408
<211> LENGTH: 180
<212> TYPE: RNA
<213> ORGANISM: Artificial sequence
<220> FEATURE:
<223> OTHER INFORMATION: synthetic sequence

<400> SEQUENCE: 408
ggcuacguag cucaguuggu uagagcagcg gccgggccag cugugagugu uucuuuaauu      60
gucaacuacu gucaguuugu gagcaauagu aaggaaaacu gacagaguau gacaauucua    120
gaagugcugc acguuguugg cccccgcggg ucacagguuc gaaucccguc guagccacca    180

<210> SEQ ID NO 409
<211> LENGTH: 181
<212> TYPE: RNA
<213> ORGANISM: Artificial sequence
<220> FEATURE:
<223> OTHER INFORMATION: synthetic sequence

<400> SEQUENCE: 409
ggcuacguag cucaguuggu uagagcagcg gccgggccag cugugagugu uucuuucaag      60
agcaauaacg aaaaauguug ugagcaauag uaaggaaccg uuuuucauua ugcucuugcu    120
```

```
agaagugcug cacguuguug gccccgcgg gucacagguu cgaaucccgu cguagccacc    180
a                                                                   181

<210> SEQ ID NO 410
<211> LENGTH: 180
<212> TYPE: RNA
<213> ORGANISM: Artificial sequence
<220> FEATURE:
<223> OTHER INFORMATION: synthetic sequence

<400> SEQUENCE: 410
ggcuacguag cucaguuggu uagagcagcg gccgggccag cugugagugu uucuuucgua    60
ccgugaguaa uaaugcgugu gagcaauagu aaggaagugc auuauucucu augguacgca    120
gaagugcugc acguuguugg ccccgcggg ucacagguuc gaaucccguc guagccacca     180

<210> SEQ ID NO 411
<211> LENGTH: 180
<212> TYPE: RNA
<213> ORGANISM: Artificial sequence
<220> FEATURE:
<223> OTHER INFORMATION: synthetic sequence

<400> SEQUENCE: 411
ggcuacguag cucaguuggu uagagcagcg gccgggccag cugugagugu uucuuggaua    60
ucaucauaua cuguaagugu gagcaauagu aaggaauuua caguaaugua ugauaucaua    120
gaagugcugc acguuguugg ccccgcggg ucacagguuc gaaucccguc guagccacca     180

<210> SEQ ID NO 412
<211> LENGTH: 180
<212> TYPE: RNA
<213> ORGANISM: Artificial sequence
<220> FEATURE:
<223> OTHER INFORMATION: synthetic sequence

<400> SEQUENCE: 412
ggcuacguag cucaguuggu uagagcagcg gccgggccag cugugagugu uucuuguagu    60
uguaaguauc augauguugu gagcaauagu aaggaagcau caugaacuau acaacuaaua    120
gaagugcugc acguuguugg ccccgcggg ucacagguuc gaaucccguc guagccacca     180

<210> SEQ ID NO 413
<211> LENGTH: 180
<212> TYPE: RNA
<213> ORGANISM: Artificial sequence
<220> FEATURE:
<223> OTHER INFORMATION: synthetic sequence

<400> SEQUENCE: 413
ggcuacguag cucaguuggu uagagcagcg gccgggccag cugugagugu uucuucgucu    60
uacccagcag uguuuggugu gagcaauagu aaggaaucaa acacucugug guaagaccua    120
gaagugcugc acguuguugg ccccgcggg ucacagguuc gaaucccguc guagccacca     180

<210> SEQ ID NO 414
<211> LENGTH: 180
<212> TYPE: RNA
<213> ORGANISM: Artificial sequence
<220> FEATURE:
<223> OTHER INFORMATION: synthetic sequence

<400> SEQUENCE: 414
ggcuacguag cucaguuggu uagagcagcg gccgggccag cugugagugu uucuuaguug    60
```
uacuccagcu ugugcccugu gagcaauagu aaggaagggc acaaguggua guacaaccua    120
gaagugcugc acguuguugg cccccgcggg ucacagguuc gaaucccguc guagccacca    180

<210> SEQ ID NO 415
<211> LENGTH: 181
<212> TYPE: RNA
<213> ORGANISM: Artificial sequence
<220> FEATURE:
<223> OTHER INFORMATION: synthetic sequence

<400> SEQUENCE: 415
ggcuacguag cucaguuggu uagagcagcg gccgggccag cugugagugu uucuuugagg    60
uaguagguug uaugguuugu gagcaauagu aaggaagaac uguacaccuu acuaccuuuc    120
agaagugcug cacguuguug gccccgcggg ucacagguu cgaaucccgu cguagccacc     180
a                                                                   181

<210> SEQ ID NO 416
<211> LENGTH: 185
<212> TYPE: RNA
<213> ORGANISM: Artificial sequence
<220> FEATURE:
<223> OTHER INFORMATION: synthetic sequence

<400> SEQUENCE: 416
ggcuacguag cucaguuggu uagagcagcg gccgggccag cugugagugu uucuaucgga    60
uccgucugag cuuggcuugu gagcaauagu aaggaaagcc ugcugaagcu cagagggcuc    120
ugauagaagu gcugcacguu guuggccccc gcgggucaca gguucgaauc ccgucguagc    180
cacca                                                               185

<210> SEQ ID NO 417
<211> LENGTH: 180
<212> TYPE: RNA
<213> ORGANISM: Artificial sequence
<220> FEATURE:
<223> OTHER INFORMATION: synthetic sequence

<400> SEQUENCE: 417
ggcuacguag cucaguuggu uagagcagcg gccgggccag cugugagugu uucuuuggca    60
gugucuuagc ugguuguugu gagcaauagu aaggaagcaa ucagcaagua uacugcccua    120
gaagugcugc acguuguugg cccccgcggg ucacagguuc gaaucccguc guagccacca    180

<210> SEQ ID NO 418
<211> LENGTH: 180
<212> TYPE: RNA
<213> ORGANISM: Artificial sequence
<220> FEATURE:
<223> OTHER INFORMATION: synthetic sequence

<400> SEQUENCE: 418
ggcuacguag cucaguuggu uagagcagcg gccgggccag cugugagugu uucuuuaagg    60
cacgcgguga augccguugu gagcaauagu aaggaagcgg uguucccguc ugccuucua     120 gaagugcugc acguuguugg cccccgcggg ucacagguuc gaaucccguc guagccacca    180

<210> SEQ ID NO 419
<211> LENGTH: 180
<212> TYPE: RNA
<213> ORGANISM: Artificial sequence
<220> FEATURE:

<223> OTHER INFORMATION: synthetic sequence

<400> SEQUENCE: 419
ggcuacguag cucaguuggu uagagcagcg gccgggccag cugugagugu uucuucuggc    60
ccucucugcc cuuccguugu gagcaauagu aaggaagcgg gggggagaug ggggccauua   120
gaagugcugc acguuguugg cccccgcggg ucacagguuc gaaucccguc guagccacca   180

<210> SEQ ID NO 420
<211> LENGTH: 180
<212> TYPE: RNA
<213> ORGANISM: Artificial sequence
<220> FEATURE:
<223> OTHER INFORMATION: synthetic sequence

<400> SEQUENCE: 420
ggcuacguag cucaguuggu uagagcagcg gccgggccag cugugagugu uucuccguu     60 ccuuuggcaa ugguaauugu gagcaauagu aaggaaauua ccauuccaua aggaacguua   120
gaagugcugc acguuguugg cccccgcggg ucacagguuc gaaucccguc guagccacca   180

<210> SEQ ID NO 421
<211> LENGTH: 75
<212> TYPE: RNA
<213> ORGANISM: Artificial sequence
<220> FEATURE:
<223> OTHER INFORMATION: synthetic sequence

<400> SEQUENCE: 421
ggcuacguag cucaguuggu uagagcagcg gccgauaucc gcgggucaca gguucgaauc    60
ccgucguagc cacca                                                    75

<210> SEQ ID NO 422
<211> LENGTH: 148
<212> TYPE: RNA
<213> ORGANISM: Artificial sequence
<220> FEATURE:
<223> OTHER INFORMATION: synthetic sequence

<400> SEQUENCE: 422
ggcuacguag cucaguuggu uagagcagcg gccgaguaau uuacgucgac ggugacgucg    60
augguugcgg ccgcggguca cagguucgaa ucccgucgua gccaccacug cagauccuua   120
gcgaaagcua aggauuuuuu uuaagcuu                                     148

<210> SEQ ID NO 423
<211> LENGTH: 180
<212> TYPE: RNA
<213> ORGANISM: Artificial sequence
<220> FEATURE:
<223> OTHER INFORMATION: synthetic sequence

<400> SEQUENCE: 423
ggcuacguag cucaguuggu uagagcagcg gccgggccag cugugagugu uucuuuggaa    60
uguaaggaag uguguggugu gagcaauagu aaggaaccac augcuucuuu auaucccaa   120 gaagugcugc acguuguugg cccccgcggg ucacagguuc gaaucccguc guagccacca   180

<210> SEQ ID NO 424
<211> LENGTH: 180
<212> TYPE: RNA
<213> ORGANISM: Artificial sequence
<220> FEATURE:
<223> OTHER INFORMATION: synthetic sequence

<400> SEQUENCE: 424
ggcuacguag cucaguuggu uagagcagcg gccgggccag cugugagugu uucuugacug    60
guguugccau gagauuuugu gagcaauagu aaggaagaau cucaugcaua caccaguaua   120
gaagugcugc acguuguugg cccccgcggg ucacagguuc gaaucccguc guagccacca   180

<210> SEQ ID NO 425
<211> LENGTH: 180
<212> TYPE: RNA
<213> ORGANISM: Artificial sequence
<220> FEATURE:
<223> OTHER INFORMATION: synthetic sequence

<400> SEQUENCE: 425
ggcuacguag cucaguuggu uagagcagcg gccgggccag cugugagugu uucuugugca    60
uuguaguugc auugcauugu gagcaauagu aaggaaggug caaugaaacg acaaugcaaa   120
gaagugcugc acguuguugg cccccgcggg ucacagguuc gaaucccguc guagccacca   180

<210> SEQ ID NO 426
<211> LENGTH: 180
<212> TYPE: RNA
<213> ORGANISM: Artificial sequence
<220> FEATURE:
<223> OTHER INFORMATION: synthetic sequence

<400> SEQUENCE: 426
ggcuacguag cucaguuggu uagagcagcg gccgggccag cugugagugu uucuucagug    60
caaugaugaa agggcauugu gagcaauagu aaggaagugc ucuuuccccg uugcacuaua   120
gaagugcugc acguuguugg cccccgcggg ucacagguuc gaaucccguc guagccacca   180

<210> SEQ ID NO 427
<211> LENGTH: 180
<212> TYPE: RNA
<213> ORGANISM: Artificial sequence
<220> FEATURE:
<223> OTHER INFORMATION: synthetic sequence

<400> SEQUENCE: 427
ggcuacguag cucaguuggu uagagcagcg gccgggccag cugugagugu uucuugauuc    60
aacagucaac aucagucugu gagcaauagu aaggaagacu gaugugacuu guugaauaua   120
gaagugcugc acguuguugg cccccgcggg ucacagguuc gaaucccguc guagccacca   180

<210> SEQ ID NO 428
<211> LENGTH: 180
<212> TYPE: RNA
<213> ORGANISM: Artificial sequence
<220> FEATURE:
<223> OTHER INFORMATION: synthetic sequence

<400> SEQUENCE: 428
ggcuacguag cucaguuggu uagagcagcg gccgggccag cugugagugu uucuuuuacc    60
acaaacacag auuugauugu gagcaauagu aaggaaauca aaucuugucu ugugguacua   120
gaagugcugc acguuguugg cccccgcggg ucacagguuc gaaucccguc guagccacca   180

<210> SEQ ID NO 429
<211> LENGTH: 180
<212> TYPE: RNA
<213> ORGANISM: Artificial sequence
<220> FEATURE:

<223> OTHER INFORMATION: synthetic sequence

<400> SEQUENCE: 429
ggcuacguag cucaguuggu uagagcagcg gccgggccag cugugagugu uucuuggugu    60
cguuucucug gugaguaugu gagcaauagu aaggaaguac ucaccauaga acgacacaa    120 gaagugcugc acguuguugg cccccgcggg ucacagguuc gaaucccguc guagccacca   180

<210> SEQ ID NO 430
<211> LENGTH: 180
<212> TYPE: RNA
<213> ORGANISM: Artificial sequence
<220> FEATURE:
<223> OTHER INFORMATION: synthetic sequence

<400> SEQUENCE: 430
ggcuacguag cucaguuggu uagagcagcg gccgggccag cugugagugu uucuuaagcg    60
cgcuuuguag gauucguugu gagcaauagu aaggaagcga auccucaaua gcgcgcugua   120
gaagugcugc acguuguugg cccccgcggg ucacagguuc gaaucccguc guagccacca   180

<210> SEQ ID NO 431
<211> LENGTH: 180
<212> TYPE: RNA
<213> ORGANISM: Artificial sequence
<220> FEATURE:
<223> OTHER INFORMATION: synthetic sequence

<400> SEQUENCE: 431
ggcuacguag cucaguuggu uagagcagcg gccgggccag cugugagugu uucuuguucg    60
ucuguagacg guuguugugu gagcaauagu aaggaagcaa caaccuucuc cagacgaaaa   120
gaagugcugc acguuguugg cccccgcggg ucacagguuc gaaucccguc guagccacca   180

<210> SEQ ID NO 432
<211> LENGTH: 180
<212> TYPE: RNA
<213> ORGANISM: Artificial sequence
<220> FEATURE:
<223> OTHER INFORMATION: synthetic sequence

<400> SEQUENCE: 432
ggcuacguag cucaguuggu uagagcagcg gccgggccag cugugagugu uucuuuucuc    60
cgaagcuguc acguuuuugu gagcaauagu aaggaagaau cguguagcuu ucggagacua   120
gaagugcugc acguuguugg cccccgcggg ucacagguuc gaaucccguc guagccacca   180

<210> SEQ ID NO 433
<211> LENGTH: 180
<212> TYPE: RNA
<213> ORGANISM: Artificial sequence
<220> FEATURE:
<223> OTHER INFORMATION: synthetic sequence

<400> SEQUENCE: 433
ggcuacguag cucaguuggu uagagcagcg gccgggccag cugugagugu uucuugugua    60
acacgucuau acgcccaugu gagcaauagu aaggaagugg gcuacagaa guguuacaaa    120 gaagugcugc acguuguugg cccccgcggg ucacagguuc gaaucccguc guagccacca   180

<210> SEQ ID NO 434
<211> LENGTH: 180
<212> TYPE: RNA
<213> ORGANISM: Artificial sequence

```
<220> FEATURE:
<223> OTHER INFORMATION: synthetic sequence

<400> SEQUENCE: 434
ggcuacguag cucaguuggu uagagcagcg gccgggccag cugugagugu uucuuuagcu      60
uaucagacug auguugaugu gagcaauagu aaggaaguca acauccgucg augggcugua     120
gaagugcugc acguuguugg cccccgcggg ucacagguuc gaaucccguc guagccacca     180

<210> SEQ ID NO 435
<211> LENGTH: 180
<212> TYPE: RNA
<213> ORGANISM: Artificial sequence
<220> FEATURE:
<223> OTHER INFORMATION: synthetic sequence

<400> SEQUENCE: 435
ggcuacguag cucaguuggu uagagcagcg gccgggccag cugugagugu uucuuucaac      60
aucagucuga uaagcuaugu gagcaauagu aaggaaguag cuuauaagaa ugauguugca     120
gaagugcugc acguuguugg cccccgcggg ucacagguuc gaaucccguc guagccacca     180

<210> SEQ ID NO 436
<211> LENGTH: 213
<212> TYPE: RNA
<213> ORGANISM: Artificial sequence
<220> FEATURE:
<223> OTHER INFORMATION: synthetic sequence

<400> SEQUENCE: 436
ggcuacguag cucaguuggu uagagcagcg gccgggccag cugugagugu uucuuuggca      60
gugucuuagc ugguuguugu gagcaauagu aaggaagcaa ucagcaagua uacugcccua     120
gaagugcugc acguuguugg cccggcgaua ccagccgaaa ggcccuuggc agcgucccgc     180
gggucacagg uucgaauccc gucguagcca cca                                  213

<210> SEQ ID NO 437
<211> LENGTH: 246
<212> TYPE: RNA
<213> ORGANISM: Artificial sequence
<220> FEATURE:
<223> OTHER INFORMATION: synthetic sequence

<400> SEQUENCE: 437
ggcuacguag cucaguuggu uagagcagcg gccgggcgau accagccgaa aggcccuugg      60
cagcgucggc cagcgugag uguuucuuug gcagugucuu agcugguugu ugugagcaau     120
aguaaggaag caaucagcaa guauacugcc cuagaagugc ugcacguugu uggcccggcg     180
auaccagccg aaaggcccuu ggcagcgucc cgcgggucac agguucgaau cccgucguag     240
ccacca                                                                246

<210> SEQ ID NO 438
<211> LENGTH: 207
<212> TYPE: RNA
<213> ORGANISM: Artificial sequence
<220> FEATURE:
<223> OTHER INFORMATION: synthetic sequence

<400> SEQUENCE: 438
ggcuacguag cucaguuggu uagagcagcg gccgggccag cugugagugu uucuuuacuc      60
aaaaagcugu cagucauugu gagcaauagu aaggaaguga cugacgcuuu uuugggucua     120
```

-continued

| | |
|---|---|
| gaagugcugc acguuguugg ccccggaauc agugaaugcu uauacauccg ccgcgggguca | 180 |
| cagguucgaa ucccgucgua gccacca | 207 |

<210> SEQ ID NO 439
<211> LENGTH: 207
<212> TYPE: RNA
<213> ORGANISM: Artificial sequence
<220> FEATURE:
<223> OTHER INFORMATION: synthetic sequence

<400> SEQUENCE: 439

| | |
|---|---|
| ggcuacguag cucaguuggu uagagcagcg gccgcggaau cagugaaugc uuauacaucc | 60 |
| gggccagcug ugaguguuuc uuuggcagug ucuuagcugg uuguugugag caauaguaag | 120 |
| gaagcaauca gcaaguauac ugcccuagaa gugcugcacg uguuggccc ccgcgggguca | 180 |
| cagguucgaa ucccgucgua gccacca | 207 |

<210> SEQ ID NO 440
<211> LENGTH: 199
<212> TYPE: RNA
<213> ORGANISM: Artificial sequence
<220> FEATURE:
<223> OTHER INFORMATION: synthetic sequence

<400> SEQUENCE: 440

| | |
|---|---|
| ggcuacguag cucaguuggu uagagcagcg gccgggccag cugugagugu uucuuuggca | 60 |
| gugucuuagc ugguuguugu gagcaauagu aaggaagcaa ucagcaagua uacugcccua | 120 |
| gaagugcugc acguuguugg cccgcgacug guuacccggu cgccgcgggu cacagguucg | 180 |
| aaucccgucg uagccacca | 199 |

<210> SEQ ID NO 441
<211> LENGTH: 74
<212> TYPE: DNA
<213> ORGANISM: Artificial sequence
<220> FEATURE:
<223> OTHER INFORMATION: synthetic sequence

<400> SEQUENCE: 441

| | |
|---|---|
| gttagagcag cggccgggcc agctgtgagt gtttcttttc acagtggcta agttccgctt | 60 |
| gtgagcaata gtaa | 74 |

<210> SEQ ID NO 442
<211> LENGTH: 81
<212> TYPE: DNA
<213> ORGANISM: Artificial sequence
<220> FEATURE:
<223> OTHER INFORMATION: synthetic sequence

<400> SEQUENCE: 442

| | |
|---|---|
| tcgaacctgt gacccgcggg ggccaacaac gtgcagcact tctagtcaca agcagctaag | 60 |
| ccctgccttc cttactattg c | 81 |

<210> SEQ ID NO 443
<211> LENGTH: 74
<212> TYPE: DNA
<213> ORGANISM: Artificial sequence
<220> FEATURE:
<223> OTHER INFORMATION: synthetic sequence

<400> SEQUENCE: 443

| | |
|---|---|
| gttagagcag cggccgggcc agctgtgagt gtttcttttc acagtggcta agttctgctt | 60 |

```
<210> SEQ ID NO 444
<211> LENGTH: 80
<212> TYPE: DNA
<213> ORGANISM: Artificial sequence
<220> FEATURE:
<223> OTHER INFORMATION: synthetic sequence

<400> SEQUENCE: 444
tcgaacctgt gacccgcggg ggccaacaac gtgcagcact tctggtcaca gtgagctagc    60
tctgccttcc ttactattgc                                                80

<210> SEQ ID NO 445
<211> LENGTH: 74
<212> TYPE: DNA
<213> ORGANISM: Artificial sequence
<220> FEATURE:
<223> OTHER INFORMATION: synthetic sequence

<400> SEQUENCE: 445
gttagagcag cggccgggcc agctgtgagt gtttcttcac tggctccttt ctgggtagat    60
gtgagcaata gtaa                                                      74

<210> SEQ ID NO 446
<211> LENGTH: 80
<212> TYPE: DNA
<213> ORGANISM: Artificial sequence
<220> FEATURE:
<223> OTHER INFORMATION: synthetic sequence

<400> SEQUENCE: 446
tcgaacctgt gacccgcggg ggccaacaac gtgcagcact tctaaactgg ctcacttctg    60
agtagattcc ttactattgc                                                80

<210> SEQ ID NO 447
<211> LENGTH: 74
<212> TYPE: DNA
<213> ORGANISM: Artificial sequence
<220> FEATURE:
<223> OTHER INFORMATION: synthetic sequence

<400> SEQUENCE: 447
gttagagcag cggccgggcc agctgtgagt gtttcttaaa ccgttaccat tactgagttt    60
gtgagcaata gtaa                                                      74

<210> SEQ ID NO 448
<211> LENGTH: 80
<212> TYPE: DNA
<213> ORGANISM: Artificial sequence
<220> FEATURE:
<223> OTHER INFORMATION: synthetic sequence

<400> SEQUENCE: 448
tcgaacctgt gacccgcggg ggccaacaac gtgcagcact tctagaacca ttaaccatac    60
taagtcttcc ttactattgc                                                80

<210> SEQ ID NO 449
<211> LENGTH: 74
<212> TYPE: DNA
<213> ORGANISM: Artificial sequence
<220> FEATURE:
```

<223> OTHER INFORMATION: synthetic sequence

<400> SEQUENCE: 449

```
gttagagcag cggccgggcc agctgtgagt gtttctttgc ctcagtctgc ttcgcacctt    60
gtgagcaata gtaa                                                     74
```

<210> SEQ ID NO 450
<211> LENGTH: 80
<212> TYPE: DNA
<213> ORGANISM: Artificial sequence
<220> FEATURE:
<223> OTHER INFORMATION: synthetic sequence

<400> SEQUENCE: 450

```
tcgaacctgt gacccgcggg ggccaacaac gtgcagcact tctaggcctc agtactgttc    60
gcacccttcc ttactattgc                                                80
```

<210> SEQ ID NO 451
<211> LENGTH: 69
<212> TYPE: DNA
<213> ORGANISM: Artificial sequence
<220> FEATURE:
<223> OTHER INFORMATION: synthetic sequence

<400> SEQUENCE: 451

```
gttagagcag cggccgggcc agctgtgagt gtttcttacc accagaacat gcaatgcaat    60
gtgagcaat                                                            69
```

<210> SEQ ID NO 452
<211> LENGTH: 73
<212> TYPE: DNA
<213> ORGANISM: Artificial sequence
<220> FEATURE:
<223> OTHER INFORMATION: synthetic sequence

<400> SEQUENCE: 452

```
tcgaacctgt gacccgcggg ggccaacaac gtgcagcact tctacccacc agaatacgca    60
atgcaattcc tta                                                       73
```

<210> SEQ ID NO 453
<211> LENGTH: 74
<212> TYPE: DNA
<213> ORGANISM: Artificial sequence
<220> FEATURE:
<223> OTHER INFORMATION: synthetic sequence

<400> SEQUENCE: 453

```
gttagagcag cggccgggcc agctgtgagt gtttcttagc atggcactca ttattacgct    60
gtgagcaata gtaa                                                     74
```

<210> SEQ ID NO 454
<211> LENGTH: 80
<212> TYPE: DNA
<213> ORGANISM: Artificial sequence
<220> FEATURE:
<223> OTHER INFORMATION: synthetic sequence

<400> SEQUENCE: 454

```
tcgaacctgt gacccgcggg ggccaacaac gtgcagcact tctaggcatg gcaactctta    60
ttacgcttcc ttactattgc                                                80
```

```
<210> SEQ ID NO 455
<211> LENGTH: 74
<212> TYPE: DNA
<213> ORGANISM: Artificial sequence
<220> FEATURE:
<223> OTHER INFORMATION: synthetic sequence

<400> SEQUENCE: 455
gttagagcag cggccgggcc agctgtgagt gtttctttgc ccaagctggc atccgtcatt    60
gtgagcaata gtaa                                                      74

<210> SEQ ID NO 456
<211> LENGTH: 80
<212> TYPE: DNA
<213> ORGANISM: Artificial sequence
<220> FEATURE:
<223> OTHER INFORMATION: synthetic sequence

<400> SEQUENCE: 456
tcgaacctgt gacccgcggg ggccaacaac gtgcagcact tctaggccca agcatggatc    60
cgtcacttcc ttactattgc                                                80

<210> SEQ ID NO 457
<211> LENGTH: 74
<212> TYPE: DNA
<213> ORGANISM: Artificial sequence
<220> FEATURE:
<223> OTHER INFORMATION: synthetic sequence

<400> SEQUENCE: 457
gttagagcag cggccgggcc agctgtgagt gtttcttagc agaagcaggg aggttctccc    60
atgagcaata gtaa                                                      74

<210> SEQ ID NO 458
<211> LENGTH: 80
<212> TYPE: DNA
<213> ORGANISM: Artificial sequence
<220> FEATURE:
<223> OTHER INFORMATION: synthetic sequence

<400> SEQUENCE: 458
tcgaacctgt gacccgcggg ggccaacaac gtgcagcact tctgtcaaaa gcatgggggt    60
tctcccctcc ttactattgc                                                80

<210> SEQ ID NO 459
<211> LENGTH: 74
<212> TYPE: DNA
<213> ORGANISM: Artificial sequence
<220> FEATURE:
<223> OTHER INFORMATION: synthetic sequence

<400> SEQUENCE: 459
gttagagcag cggccgggcc agctgtgagt gtttcttctc tagagggaag cgctttctgt    60
gtgagcaata gtaa                                                      74

<210> SEQ ID NO 460
<211> LENGTH: 80
<212> TYPE: DNA
<213> ORGANISM: Artificial sequence
<220> FEATURE:
<223> OTHER INFORMATION: synthetic sequence

<400> SEQUENCE: 460
```

```
tcgaacctgt gacccgcggg ggccaacaac gtgcagcact tctaatctaa aaagatgcac    60
tttctgttcc ttactattgc                                                80
```

<210> SEQ ID NO 461
<211> LENGTH: 74
<212> TYPE: DNA
<213> ORGANISM: Artificial sequence
<220> FEATURE:
<223> OTHER INFORMATION: synthetic sequence

<400> SEQUENCE: 461

```
gttagagcag cggccgggcc agctgtgagt gtttctttgg agtgtgacaa tggtgtttgt    60
gtgagcaata gtaa                                                      74
```

<210> SEQ ID NO 462
<211> LENGTH: 78
<212> TYPE: DNA
<213> ORGANISM: Artificial sequence
<220> FEATURE:
<223> OTHER INFORMATION: synthetic sequence

<400> SEQUENCE: 462

```
tcgaacctgt gacccgcggg ggccaacaac gtgcagcact tctagggagt gtgtacatgg    60
cgtttgttcc ttactatt                                                  78
```

<210> SEQ ID NO 463
<211> LENGTH: 73
<212> TYPE: DNA
<213> ORGANISM: Artificial sequence
<220> FEATURE:
<223> OTHER INFORMATION: synthetic sequence

<400> SEQUENCE: 463

```
gttagagcag cggccgggcc agctgtgagt gtttctttaa ttgtcaacta ctgtcagttt    60
gtgagcaata gta                                                       73
```

<210> SEQ ID NO 464
<211> LENGTH: 77
<212> TYPE: DNA
<213> ORGANISM: Artificial sequence
<220> FEATURE:
<223> OTHER INFORMATION: synthetic sequence

<400> SEQUENCE: 464

```
tcgaacctgt gacccgcggg ggccaacaac gtgcagcact tctagaattg tcatactctg    60
tcagttttcc ttactat                                                   77
```

<210> SEQ ID NO 465
<211> LENGTH: 69
<212> TYPE: DNA
<213> ORGANISM: Artificial sequence
<220> FEATURE:
<223> OTHER INFORMATION: synthetic sequence

<400> SEQUENCE: 465

```
gttagagcag cggccgggcc agctgtgagt gtttctttca agagcaataa cgaaaaatgt    60
tgtgagcaa                                                            69
```

<210> SEQ ID NO 466
<211> LENGTH: 74
<212> TYPE: DNA
<213> ORGANISM: Artificial sequence
<220> FEATURE:
<223> OTHER INFORMATION: synthetic sequence

<400> SEQUENCE: 466
tcgaacctgt gacccgcggg ggccaacaac gtgcagcact tctagcaaga gcataatgaa    60
aaacggttcc ttac                                                      74

<210> SEQ ID NO 467
<211> LENGTH: 68
<212> TYPE: DNA
<213> ORGANISM: Artificial sequence
<220> FEATURE:
<223> OTHER INFORMATION: synthetic sequence

<400> SEQUENCE: 467
gttagagcag cggccgggcc agctgtgagt gtttctttcg taccgtgagt aataatgcgt    60
gtgagcaa                                                             68

<210> SEQ ID NO 468
<211> LENGTH: 75
<212> TYPE: DNA
<213> ORGANISM: Artificial sequence
<220> FEATURE:
<223> OTHER INFORMATION: synthetic sequence

<400> SEQUENCE: 468
tcgaacctgt gacccgcggg ggccaacaac gtgcagcact tctgcgtacc atagagaata    60
atgcacttcc ttact                                                     75

<210> SEQ ID NO 469
<211> LENGTH: 73
<212> TYPE: DNA
<213> ORGANISM: Artificial sequence
<220> FEATURE:
<223> OTHER INFORMATION: synthetic sequence

<400> SEQUENCE: 469
gttagagcag cggccgggcc agctgtgagt gtttcttgga tatcatcata tactgtaagt    60
gtgagcaata gta                                                       73

<210> SEQ ID NO 470
<211> LENGTH: 79
<212> TYPE: DNA
<213> ORGANISM: Artificial sequence
<220> FEATURE:
<223> OTHER INFORMATION: synthetic sequence

<400> SEQUENCE: 470
tcgaacctgt gacccgcggg ggccaacaac gtgcagcact tctatgatat catacattac    60
tgtaaattcc ttactattg                                                 79

<210> SEQ ID NO 471
<211> LENGTH: 74
<212> TYPE: DNA
<213> ORGANISM: Artificial sequence
<220> FEATURE:
<223> OTHER INFORMATION: synthetic sequence

<400> SEQUENCE: 471
gttagagcag cggccgggcc agctgtgagt gtttcttgta gttgtaagta tcatgatgtt    60
gtgagcaata gtaa                                                      74

<210> SEQ ID NO 472
<211> LENGTH: 80
<212> TYPE: DNA
<213> ORGANISM: Artificial sequence
<220> FEATURE:
<223> OTHER INFORMATION: synthetic sequence

<400> SEQUENCE: 472
tcgaacctgt gacccgcggg ggccaacaac gtgcagcact tctattagtt gtatagttca    60
tgatgcttcc ttactattgc                                                80

<210> SEQ ID NO 473
<211> LENGTH: 74
<212> TYPE: DNA
<213> ORGANISM: Artificial sequence
<220> FEATURE:
<223> OTHER INFORMATION: synthetic sequence

<400> SEQUENCE: 473
gttagagcag cggccgggcc agctgtgagt gtttcttcgt cttacccagc agtgtttggt    60
gtgagcaata gtaa                                                      74

<210> SEQ ID NO 474
<211> LENGTH: 79
<212> TYPE: DNA
<213> ORGANISM: Artificial sequence
<220> FEATURE:
<223> OTHER INFORMATION: synthetic sequence

<400> SEQUENCE: 474
tcgaacctgt gacccgcggg ggccaacaac gtgcagcact tctaggtctt accacagagt    60
gtttgattcc ttactattg                                                 79

<210> SEQ ID NO 475
<211> LENGTH: 74
<212> TYPE: DNA
<213> ORGANISM: Artificial sequence
<220> FEATURE:
<223> OTHER INFORMATION: synthetic sequence

<400> SEQUENCE: 475
gttagagcag cggccgggcc agctgtgagt gtttcttagt tgtactccag cttgtgccct    60
gtgagcaata gtaa                                                      74

<210> SEQ ID NO 476
<211> LENGTH: 80
<212> TYPE: DNA
<213> ORGANISM: Artificial sequence
<220> FEATURE:
<223> OTHER INFORMATION: synthetic sequence

<400> SEQUENCE: 476
tcgaacctgt gacccgcggg ggccaacaac gtgcagcact tctaggttgt actaccactt    60
gtgcccttcc ttactattgc                                                80

<210> SEQ ID NO 477
<211> LENGTH: 68
<212> TYPE: DNA
<213> ORGANISM: Artificial sequence
<220> FEATURE:
<223> OTHER INFORMATION: synthetic sequence

<400> SEQUENCE: 477

```
gttagagcag cggccgggcc agctgtgagt gtttctttga ggtagtaggt tgtatggttt    60
gtgagcaa                                                             68
```

<210> SEQ ID NO 478
<211> LENGTH: 76
<212> TYPE: DNA
<213> ORGANISM: Artificial sequence
<220> FEATURE:
<223> OTHER INFORMATION: synthetic sequence

<400> SEQUENCE: 478

```
tcgaacctgt gacccgcggg ggccaacaac gtgcagcact tctgaaaggt agtaaggtgt    60
acagttcttc cttact                                                    76
```

<210> SEQ ID NO 479
<211> LENGTH: 69
<212> TYPE: DNA
<213> ORGANISM: Artificial sequence
<220> FEATURE:
<223> OTHER INFORMATION: synthetic sequence

<400> SEQUENCE: 479

```
gttagagcag cggccgggcc agctgtgagt gtttctatcg gatccgtctg agcttggctt    60
gtgagcaat                                                            69
```

<210> SEQ ID NO 480
<211> LENGTH: 78
<212> TYPE: DNA
<213> ORGANISM: Artificial sequence
<220> FEATURE:
<223> OTHER INFORMATION: synthetic sequence

<400> SEQUENCE: 480

```
tcgaacctgt gacccgcggg ggccaacaac gtgcagcact tctatcagag ccctctgagc    60
ttcagcaggc tttcctta                                                  78
```

<210> SEQ ID NO 481
<211> LENGTH: 39
<212> TYPE: DNA
<213> ORGANISM: Artificial sequence
<220> FEATURE:
<223> OTHER INFORMATION: synthetic sequence

<400> SEQUENCE: 481

```
gttagagcag cggccgggcc agctgtgagt gtttctttg                           39
```

<210> SEQ ID NO 482
<211> LENGTH: 37
<212> TYPE: DNA
<213> ORGANISM: Artificial sequence
<220> FEATURE:
<223> OTHER INFORMATION: synthetic sequence

<400> SEQUENCE: 482

```
tcgaacctgt gacccgcggg ggccaacaac gtgcagc                             37
```

<210> SEQ ID NO 483
<211> LENGTH: 68
<212> TYPE: DNA
<213> ORGANISM: Artificial sequence
<220> FEATURE:
<223> OTHER INFORMATION: synthetic sequence

<400> SEQUENCE: 483
gttagagcag cggccgggcc agctgtgagt gtttctttaa ggcacgcggt gaatgccgtt        60
gtgagcaa        68

<210> SEQ ID NO 484
<211> LENGTH: 77
<212> TYPE: DNA
<213> ORGANISM: Artificial sequence
<220> FEATURE:
<223> OTHER INFORMATION: synthetic sequence

<400> SEQUENCE: 484
tcgaacctgt gacccgcggg ggccaacaac gtgcagcact tctagaaggc acgacgggaa        60
caccgcttcc ttactat        77

<210> SEQ ID NO 485
<211> LENGTH: 74
<212> TYPE: DNA
<213> ORGANISM: Artificial sequence
<220> FEATURE:
<223> OTHER INFORMATION: synthetic sequence

<400> SEQUENCE: 485
gttagagcag cggccgggcc agctgtgagt gtttcttctg gccctctctg cccttccgtt        60
gtgagcaata gtaa        74

<210> SEQ ID NO 486
<211> LENGTH: 80
<212> TYPE: DNA
<213> ORGANISM: Artificial sequence
<220> FEATURE:
<223> OTHER INFORMATION: synthetic sequence

<400> SEQUENCE: 486
tcgaacctgt gacccgcggg ggccaacaac gtgcagcact tctaatggcc cccatctccc        60
ccccgcttcc ttactattgc        80

<210> SEQ ID NO 487
<211> LENGTH: 73
<212> TYPE: DNA
<213> ORGANISM: Artificial sequence
<220> FEATURE:
<223> OTHER INFORMATION: synthetic sequence

<400> SEQUENCE: 487
gttagagcag cggccgggcc agctgtgagt gtttcttccg ttcctttggc aatggtaatt        60
gtgagcaata gta        73

<210> SEQ ID NO 488
<211> LENGTH: 76
<212> TYPE: DNA
<213> ORGANISM: Artificial sequence
<220> FEATURE:
<223> OTHER INFORMATION: synthetic sequence

<400> SEQUENCE: 488
tcgaacctgt gacccgcggg ggccaacaac gtgcagcact tctaacgttc cttatggaat        60
ggtaatttcc ttacta        76

<210> SEQ ID NO 489
<211> LENGTH: 69

```
<212> TYPE: DNA
<213> ORGANISM: Artificial sequence
<220> FEATURE:
<223> OTHER INFORMATION: synthetic sequence

<400> SEQUENCE: 489
ttgtaacgct gaattcggct acgtagctca gttggttaga gcagcggccg atatccgcgg    60
gtcacaggt                                                            69

<210> SEQ ID NO 490
<211> LENGTH: 61
<212> TYPE: DNA
<213> ORGANISM: Artificial sequence
<220> FEATURE:
<223> OTHER INFORMATION: synthetic sequence

<400> SEQUENCE: 490
ctttcgctaa ggatctgcag tggtggctac gacgggattc gaacctgtga cccgcggata    60
t                                                                    61

<210> SEQ ID NO 491
<211> LENGTH: 68
<212> TYPE: DNA
<213> ORGANISM: Artificial sequence
<220> FEATURE:
<223> OTHER INFORMATION: synthetic sequence

<400> SEQUENCE: 491
gttagagcag cggccgggcc agctgtgagt gtttctttgg aatgtaagga agtgtgtggt    60
gtgagcaa                                                             68

<210> SEQ ID NO 492
<211> LENGTH: 76
<212> TYPE: DNA
<213> ORGANISM: Artificial sequence
<220> FEATURE:
<223> OTHER INFORMATION: synthetic sequence

<400> SEQUENCE: 492
tcgaacctgt gacccgcggg ggccaacaac gtgcagcact tcttgggat ataaagaagc     60 atgtggttcc ttacta                                                    76

<210> SEQ ID NO 493
<211> LENGTH: 70
<212> TYPE: DNA
<213> ORGANISM: Artificial sequence
<220> FEATURE:
<223> OTHER INFORMATION: synthetic sequence

<400> SEQUENCE: 493
gttagagcag cggccgggcc agctgtgagt gtttcttgac tggtgttgcc atgagatttt    60
gtgagcaata                                                           70

<210> SEQ ID NO 494
<211> LENGTH: 74
<212> TYPE: DNA
<213> ORGANISM: Artificial sequence
<220> FEATURE:
<223> OTHER INFORMATION: synthetic sequence

<400> SEQUENCE: 494
tcgaacctgt gacccgcggg ggccaacaac gtgcagcact tctatactgg tgtatgcatg    60
```

-continued agattcttcc ttac 74

<210> SEQ ID NO 495
<211> LENGTH: 69
<212> TYPE: DNA
<213> ORGANISM: Artificial sequence
<220> FEATURE:
<223> OTHER INFORMATION: synthetic sequence

<400> SEQUENCE: 495
gttagagcag cggccgggcc agctgtgagt gtttcttgtg cattgtagtt gcattgcatt 60
gtgagcaat 69

<210> SEQ ID NO 496
<211> LENGTH: 75
<212> TYPE: DNA
<213> ORGANISM: Artificial sequence
<220> FEATURE:
<223> OTHER INFORMATION: synthetic sequence

<400> SEQUENCE: 496
tcgaacctgt gacccgcggg ggccaacaac gtgcagcact tctttgcatt gtcgtttcat 60
tgcaccttcc ttact 75

<210> SEQ ID NO 497
<211> LENGTH: 74
<212> TYPE: DNA
<213> ORGANISM: Artificial sequence
<220> FEATURE:
<223> OTHER INFORMATION: synthetic sequence

<400> SEQUENCE: 497
gttagagcag cggccgggcc agctgtgagt gtttcttcag tgcaatgatg aaagggcatt 60
gtgagcaata gtaa 74

<210> SEQ ID NO 498
<211> LENGTH: 80
<212> TYPE: DNA
<213> ORGANISM: Artificial sequence
<220> FEATURE:
<223> OTHER INFORMATION: synthetic sequence

<400> SEQUENCE: 498
tcgaacctgt gacccgcggg ggccaacaac gtgcagcact tctatagtgc aacagggaaa 60
gagcacttcc ttactattgc 80

<210> SEQ ID NO 499
<211> LENGTH: 72
<212> TYPE: DNA
<213> ORGANISM: Artificial sequence
<220> FEATURE:
<223> OTHER INFORMATION: synthetic sequence

<400> SEQUENCE: 499
gttagagcag cggccgggcc agctgtgagt gtttcttgat tcaacagtca acatcagtct 60
gtgagcaata gt 72

<210> SEQ ID NO 500
<211> LENGTH: 74
<212> TYPE: DNA
<213> ORGANISM: Artificial sequence
<220> FEATURE:
<223> OTHER INFORMATION: synthetic sequence -continued

<400> SEQUENCE: 500
tcgaacctgt gacccgcggg ggccaacaac gtgcagcact tctatattca acaagtcaca    60
tcagtcttcc ttac    74

<210> SEQ ID NO 501
<211> LENGTH: 73
<212> TYPE: DNA
<213> ORGANISM: Artificial sequence
<220> FEATURE:
<223> OTHER INFORMATION: synthetic sequence

<400> SEQUENCE: 501
gttagagcag cggccgggcc agctgtgagt gtttctttta ccacaaacac agatttgatt    60
gtgagcaata gta    73

<210> SEQ ID NO 502
<211> LENGTH: 76
<212> TYPE: DNA
<213> ORGANISM: Artificial sequence
<220> FEATURE:
<223> OTHER INFORMATION: synthetic sequence

<400> SEQUENCE: 502
tcgaacctgt gacccgcggg ggccaacaac gtgcagcact tctagtacca caagacaaga    60
tttgatttcc ttacta    76

<210> SEQ ID NO 503
<211> LENGTH: 69
<212> TYPE: DNA
<213> ORGANISM: Artificial sequence
<220> FEATURE:
<223> OTHER INFORMATION: synthetic sequence

<400> SEQUENCE: 503
gttagagcag cggccgggcc agctgtgagt gtttcttggt gtcgtttctc tggtgagtat    60
gtgagcaat    69

<210> SEQ ID NO 504
<211> LENGTH: 76
<212> TYPE: DNA
<213> ORGANISM: Artificial sequence
<220> FEATURE:
<223> OTHER INFORMATION: synthetic sequence

<400> SEQUENCE: 504
tcgaacctgt gacccgcggg ggccaacaac gtgcagcact tcttgtgtcg tttctatggt    60
gagtacttcc ttacta    76

<210> SEQ ID NO 505
<211> LENGTH: 68
<212> TYPE: DNA
<213> ORGANISM: Artificial sequence
<220> FEATURE:
<223> OTHER INFORMATION: synthetic sequence

<400> SEQUENCE: 505
gttagagcag cggccgggcc agctgtgagt gtttcttaag cgcgctttgt aggattcgtt    60
gtgagcaa    68

<210> SEQ ID NO 506

```
<211> LENGTH: 77
<212> TYPE: DNA
<213> ORGANISM: Artificial sequence
<220> FEATURE:
<223> OTHER INFORMATION: synthetic sequence

<400> SEQUENCE: 506
tcgaacctgt gacccgcggg ggccaacaac gtgcagcact tctacagcgc gctattgagg    60
attcgcttcc ttactat                                                   77

<210> SEQ ID NO 507
<211> LENGTH: 69
<212> TYPE: DNA
<213> ORGANISM: Artificial sequence
<220> FEATURE:
<223> OTHER INFORMATION: synthetic sequence

<400> SEQUENCE: 507
gttagagcag cggccgggcc agctgtgagt gtttcttgtt cgtctgtaga cggttgttgt    60
gtgagcaat                                                            69

<210> SEQ ID NO 508
<211> LENGTH: 76
<212> TYPE: DNA
<213> ORGANISM: Artificial sequence
<220> FEATURE:
<223> OTHER INFORMATION: synthetic sequence

<400> SEQUENCE: 508
tcgaacctgt gacccgcggg ggccaacaac gtgcagcact tcttttcgtc tggagaaggt    60
tgttgcttcc ttacta                                                    76

<210> SEQ ID NO 509
<211> LENGTH: 69
<212> TYPE: DNA
<213> ORGANISM: Artificial sequence
<220> FEATURE:
<223> OTHER INFORMATION: synthetic sequence

<400> SEQUENCE: 509
gttagagcag cggccgggcc agctgtgagt gtttcttttc tccgaagctg tcacgttttt    60
gtgagcaat                                                            69

<210> SEQ ID NO 510
<211> LENGTH: 77
<212> TYPE: DNA
<213> ORGANISM: Artificial sequence
<220> FEATURE:
<223> OTHER INFORMATION: synthetic sequence

<400> SEQUENCE: 510
tcgaacctgt gacccgcggg ggccaacaac gtgcagcact tctagtctcc gaaagctaca    60
cgattcttcc ttactat                                                   77

<210> SEQ ID NO 511
<211> LENGTH: 68
<212> TYPE: DNA
<213> ORGANISM: Artificial sequence
<220> FEATURE:
<223> OTHER INFORMATION: synthetic sequence

<400> SEQUENCE: 511
gttagagcag cggccgggcc agctgtgagt gtttcttgtg taacacgtct atacgcccat    60
``` gtgagcaa 68

<210> SEQ ID NO 512
<211> LENGTH: 79
<212> TYPE: DNA
<213> ORGANISM: Artificial sequence
<220> FEATURE:
<223> OTHER INFORMATION: synthetic sequence

<400> SEQUENCE: 512
tcgaacctgt gacccgcggg ggccaacaac gtgcagcact tctttgtaac acttctgtac    60
gcccacttcc ttactattg                                                 79

<210> SEQ ID NO 513
<211> LENGTH: 69
<212> TYPE: DNA
<213> ORGANISM: Artificial sequence
<220> FEATURE:
<223> OTHER INFORMATION: synthetic sequence

<400> SEQUENCE: 513
gttagagcag cggccgggcc agctgtgagt gtttctttag cttatcagac tgatgttgat    60
gtgagcaat                                                            69

<210> SEQ ID NO 514
<211> LENGTH: 76
<212> TYPE: DNA
<213> ORGANISM: Artificial sequence
<220> FEATURE:
<223> OTHER INFORMATION: synthetic sequence

<400> SEQUENCE: 514
tcgaacctgt gacccgcggg ggccaacaac gtgcagcact tctacagccc atcgacggat    60
gttgacttcc ttacta                                                    76

<210> SEQ ID NO 515
<211> LENGTH: 68
<212> TYPE: DNA
<213> ORGANISM: Artificial sequence
<220> FEATURE:
<223> OTHER INFORMATION: synthetic sequence

<400> SEQUENCE: 515
gttagagcag cggccgggcc agctgtgagt gtttctttca acatcagtct gataagctat    60
gtgagcaa                                                             68

<210> SEQ ID NO 516
<211> LENGTH: 76
<212> TYPE: DNA
<213> ORGANISM: Artificial sequence
<220> FEATURE:
<223> OTHER INFORMATION: synthetic sequence

<400> SEQUENCE: 516
tcgaacctgt gacccgcggg ggccaacaac gtgcagcact tctgcaacat cattcttata    60
agctacttcc ttacta                                                    76

<210> SEQ ID NO 517
<211> LENGTH: 36
<212> TYPE: DNA
<213> ORGANISM: Artificial sequence
<220> FEATURE:

<223> OTHER INFORMATION: synthetic sequence

<400> SEQUENCE: 517
gttagagcag cggccgggcc agctgtgagt gtttct                                36

<210> SEQ ID NO 518
<211> LENGTH: 70
<212> TYPE: DNA
<213> ORGANISM: Artificial sequence
<220> FEATURE:
<223> OTHER INFORMATION: synthetic sequence

<400> SEQUENCE: 518
tcgaacctgt gacccgcggg acgctgccaa gggcctttcg gctggtatcg ccgggccaac      60
aacgtgcagc                                                            70

<210> SEQ ID NO 519
<211> LENGTH: 67
<212> TYPE: DNA
<213> ORGANISM: Artificial sequence
<220> FEATURE:
<223> OTHER INFORMATION: synthetic sequence

<400> SEQUENCE: 519
gttagagcag cggccgggcg ataccagccg aaaggccctt ggcagcgtcg gccagctgtg      60
agtgttt                                                               67

<210> SEQ ID NO 520
<211> LENGTH: 70
<212> TYPE: DNA
<213> ORGANISM: Artificial sequence
<220> FEATURE:
<223> OTHER INFORMATION: synthetic sequence

<400> SEQUENCE: 520
tcgaacctgt gacccgcggg acgctgccaa gggcctttcg gctggtatcg ccgggccaac      60
aacgtgcagc                                                            70

<210> SEQ ID NO 521
<211> LENGTH: 74
<212> TYPE: DNA
<213> ORGANISM: Artificial sequence
<220> FEATURE:
<223> OTHER INFORMATION: synthetic sequence

<400> SEQUENCE: 521
gttagagcag cggccgggcc agctgtgagt gtttctttac tcaaaaagct gtcagtcatt      60
gtgagcaata gtaa                                                       74

<210> SEQ ID NO 522
<211> LENGTH: 107
<212> TYPE: DNA
<213> ORGANISM: Artificial sequence
<220> FEATURE:
<223> OTHER INFORMATION: synthetic sequence

<400> SEQUENCE: 522
tcgaacctgt gacccgcggc ggatgtataa gcattcactg attccggggc caacaacgtg      60
cagcacttct agacccaaaa aagcgtcagt cacttcctta ctattgc                   107

<210> SEQ ID NO 523
<211> LENGTH: 101

```
<212> TYPE: DNA
<213> ORGANISM: Artificial sequence
<220> FEATURE:
<223> OTHER INFORMATION: synthetic sequence

<400> SEQUENCE: 523
gttagagcag cggccgcgga atcagtgaat gcttatacat ccgggccagc tgtgagtgtt      60
tctttggcag tgtcttagct ggttgttgtg agcaatagta a                         101

<210> SEQ ID NO 524
<211> LENGTH: 80
<212> TYPE: DNA
<213> ORGANISM: Artificial sequence
<220> FEATURE:
<223> OTHER INFORMATION: synthetic sequence

<400> SEQUENCE: 524
gcattcactg attccgcggg ggccaacaac gtgcagcact tctagggcag tatacttgct      60
gattgcttcc ttactattgc                                                  80

<210> SEQ ID NO 525
<211> LENGTH: 36
<212> TYPE: DNA
<213> ORGANISM: Artificial sequence
<220> FEATURE:
<223> OTHER INFORMATION: synthetic sequence

<400> SEQUENCE: 525
gttagagcag cggccgggcc agctgtgagt gtttct                                36

<210> SEQ ID NO 526
<211> LENGTH: 58
<212> TYPE: DNA
<213> ORGANISM: Artificial sequence
<220> FEATURE:
<223> OTHER INFORMATION: synthetic sequence

<400> SEQUENCE: 526
tcgaacctgt gacccgcggc gaccgggtaa ccagtcgcgg gccaacaacg tgcagcac        58

<210> SEQ ID NO 527
<211> LENGTH: 17
<212> TYPE: DNA
<213> ORGANISM: Artificial sequence
<220> FEATURE:
<223> OTHER INFORMATION: synthetic sequence

<400> SEQUENCE: 527
ctcgcttcgg cagcaca                                                     17

<210> SEQ ID NO 528
<211> LENGTH: 20
<212> TYPE: DNA
<213> ORGANISM: Artificial sequence
<220> FEATURE:
<223> OTHER INFORMATION: synthetic sequence

<400> SEQUENCE: 528
aacgcttcac gaatttgcgt                                                  20

<210> SEQ ID NO 529
<211> LENGTH: 50
<212> TYPE: DNA
<213> ORGANISM: Artificial sequence
<220> FEATURE:
```

<223> OTHER INFORMATION: synthetic sequence

<400> SEQUENCE: 529
gtcgtatcca gtgcagggtc cgaggtattc gcactggata cgacacaacc        50

<210> SEQ ID NO 530
<211> LENGTH: 21
<212> TYPE: DNA
<213> ORGANISM: Artificial sequence
<220> FEATURE:
<223> OTHER INFORMATION: synthetic sequence

<400> SEQUENCE: 530
cgcgctggca gtgtcttagc t        21

<210> SEQ ID NO 531
<211> LENGTH: 16
<212> TYPE: DNA
<213> ORGANISM: Artificial sequence
<220> FEATURE:
<223> OTHER INFORMATION: synthetic sequence

<400> SEQUENCE: 531
gtgcagggtc cgaggt        16

<210> SEQ ID NO 532
<211> LENGTH: 50
<212> TYPE: DNA
<213> ORGANISM: Artificial sequence
<220> FEATURE:
<223> OTHER INFORMATION: synthetic sequence

<400> SEQUENCE: 532
gtcgtatcca gtgcagggtc cgaggtattc gcactggata cgacggcatt        50

<210> SEQ ID NO 533
<211> LENGTH: 18
<212> TYPE: DNA
<213> ORGANISM: Artificial sequence
<220> FEATURE:
<223> OTHER INFORMATION: synthetic sequence

<400> SEQUENCE: 533
gcgctaaggc acgcggtg        18

<210> SEQ ID NO 534
<211> LENGTH: 16
<212> TYPE: DNA
<213> ORGANISM: Artificial sequence
<220> FEATURE:
<223> OTHER INFORMATION: synthetic sequence

<400> SEQUENCE: 534
gtgcagggtc cgaggt        16

<210> SEQ ID NO 535
<211> LENGTH: 20
<212> TYPE: DNA
<213> ORGANISM: Artificial sequence
<220> FEATURE:
<223> OTHER INFORMATION: synthetic sequence

<400> SEQUENCE: 535
gtaacccgtt gaaccccatt        20

```
<210> SEQ ID NO 536
<211> LENGTH: 20
<212> TYPE: DNA
<213> ORGANISM: Artificial sequence
<220> FEATURE:
<223> OTHER INFORMATION: synthetic sequence

<400> SEQUENCE: 536
ccatccaatc ggtagtagcg                                           20

<210> SEQ ID NO 537
<211> LENGTH: 36
<212> TYPE: DNA
<213> ORGANISM: Artificial sequence
<220> FEATURE:
<223> OTHER INFORMATION: synthetic sequence

<400> SEQUENCE: 537
gcgaattcgg agacccaaaa ggatgaagct gctcag                         36

<210> SEQ ID NO 538
<211> LENGTH: 30
<212> TYPE: DNA
<213> ORGANISM: Artificial sequence
<220> FEATURE:
<223> OTHER INFORMATION: synthetic sequence

<400> SEQUENCE: 538
ccttgctctt ccggtgacgg cggatactgc                                30

<210> SEQ ID NO 539
<211> LENGTH: 22
<212> TYPE: DNA
<213> ORGANISM: Artificial sequence
<220> FEATURE:
<223> OTHER INFORMATION: synthetic sequence

<400> SEQUENCE: 539
agccacatta ggcgctcggt ct                                        22

<210> SEQ ID NO 540
<211> LENGTH: 24
<212> TYPE: DNA
<213> ORGANISM: Artificial sequence
<220> FEATURE:
<223> OTHER INFORMATION: synthetic sequence

<400> SEQUENCE: 540
agttagaggt tcgcgagcca cacg                                      24

<210> SEQ ID NO 541
<211> LENGTH: 21
<212> TYPE: DNA
<213> ORGANISM: Artificial sequence
<220> FEATURE:
<223> OTHER INFORMATION: synthetic sequence

<400> SEQUENCE: 541
gctttgtaca ggtggcacat c                                         21

<210> SEQ ID NO 542
<211> LENGTH: 20
<212> TYPE: DNA
<213> ORGANISM: Artificial sequence
<220> FEATURE:
<223> OTHER INFORMATION: synthetic sequence
```

```
<400> SEQUENCE: 542
gaacgtggct cttgagggtc                                              20

<210> SEQ ID NO 543
<211> LENGTH: 18
<212> TYPE: DNA
<213> ORGANISM: Artificial sequence
<220> FEATURE:
<223> OTHER INFORMATION: synthetic sequence

<400> SEQUENCE: 543
ggtagcgggc acggtaca                                                18

<210> SEQ ID NO 544
<211> LENGTH: 19
<212> TYPE: DNA
<213> ORGANISM: Artificial sequence
<220> FEATURE:
<223> OTHER INFORMATION: synthetic sequence

<400> SEQUENCE: 544
gcattgagca ccccaacac                                               19

<210> SEQ ID NO 545
<211> LENGTH: 20
<212> TYPE: DNA
<213> ORGANISM: Artificial sequence
<220> FEATURE:
<223> OTHER INFORMATION: synthetic sequence

<400> SEQUENCE: 545
ctggggtttg ttaccagttg                                              20

<210> SEQ ID NO 546
<211> LENGTH: 20
<212> TYPE: DNA
<213> ORGANISM: Artificial sequence
<220> FEATURE:
<223> OTHER INFORMATION: synthetic sequence

<400> SEQUENCE: 546
gggggaaagg tgtaatatgg                                              20

<210> SEQ ID NO 547
<211> LENGTH: 19
<212> TYPE: DNA
<213> ORGANISM: Artificial sequence
<220> FEATURE:
<223> OTHER INFORMATION: synthetic sequence

<400> SEQUENCE: 547
gaaagcccag gaaatccag                                               19

<210> SEQ ID NO 548
<211> LENGTH: 20
<212> TYPE: DNA
<213> ORGANISM: Artificial sequence
<220> FEATURE:
<223> OTHER INFORMATION: synthetic sequence

<400> SEQUENCE: 548
tccatacaag ccaacatcag                                              20

<210> SEQ ID NO 549
<211> LENGTH: 22
```

```
<212> TYPE: DNA
<213> ORGANISM: Artificial sequence
<220> FEATURE:
<223> OTHER INFORMATION: synthetic sequence

<400> SEQUENCE: 549
gctcgggcta catcaccatc gg                                          22

<210> SEQ ID NO 550
<211> LENGTH: 20
<212> TYPE: DNA
<213> ORGANISM: Artificial sequence
<220> FEATURE:
<223> OTHER INFORMATION: synthetic sequence

<400> SEQUENCE: 550
gggtcccggc tttcgttcag                                             20

<210> SEQ ID NO 551
<211> LENGTH: 19
<212> TYPE: DNA
<213> ORGANISM: Artificial sequence
<220> FEATURE:
<223> OTHER INFORMATION: synthetic sequence

<400> SEQUENCE: 551
accaacccca tcggtacac                                              19

<210> SEQ ID NO 552
<211> LENGTH: 20
<212> TYPE: DNA
<213> ORGANISM: Artificial sequence
<220> FEATURE:
<223> OTHER INFORMATION: synthetic sequence

<400> SEQUENCE: 552
ggggtgtagg ggaattctgt                                             20

<210> SEQ ID NO 553
<211> LENGTH: 20
<212> TYPE: DNA
<213> ORGANISM: Artificial sequence
<220> FEATURE:
<223> OTHER INFORMATION: synthetic sequence

<400> SEQUENCE: 553
cggggatgac ttcgtctctc                                             20

<210> SEQ ID NO 554
<211> LENGTH: 19
<212> TYPE: DNA
<213> ORGANISM: Artificial sequence
<220> FEATURE:
<223> OTHER INFORMATION: synthetic sequence

<400> SEQUENCE: 554
gtggtgacgt agactgcgt                                              19

<210> SEQ ID NO 555
<211> LENGTH: 25
<212> TYPE: DNA
<213> ORGANISM: Artificial sequence
<220> FEATURE:
<223> OTHER INFORMATION: synthetic sequence

<400> SEQUENCE: 555
```
cctctacagg gagcagatta agcga                                          25

<210> SEQ ID NO 556
<211> LENGTH: 23
<212> TYPE: DNA
<213> ORGANISM: Artificial sequence
<220> FEATURE:
<223> OTHER INFORMATION: synthetic sequence

<400> SEQUENCE: 556
ccctgtctgg tcttggctga ggt                                            23

<210> SEQ ID NO 557
<211> LENGTH: 20
<212> TYPE: DNA
<213> ORGANISM: Artificial sequence
<220> FEATURE:
<223> OTHER INFORMATION: synthetic sequence

<400> SEQUENCE: 557
tggttgcttc aaggacacat                                                20

<210> SEQ ID NO 558
<211> LENGTH: 20
<212> TYPE: DNA
<213> ORGANISM: Artificial sequence
<220> FEATURE:
<223> OTHER INFORMATION: synthetic sequence

<400> SEQUENCE: 558
gcagatgagc cctcagattt                                                20

<210> SEQ ID NO 559
<211> LENGTH: 22
<212> TYPE: DNA
<213> ORGANISM: Artificial sequence
<220> FEATURE:
<223> OTHER INFORMATION: synthetic sequence

<400> SEQUENCE: 559
acactggatg cctggattgg gc                                             22

<210> SEQ ID NO 560
<211> LENGTH: 22
<212> TYPE: DNA
<213> ORGANISM: Artificial sequence
<220> FEATURE:
<223> OTHER INFORMATION: synthetic sequence

<400> SEQUENCE: 560
aagccgagga gcagagacag ca                                             22

<210> SEQ ID NO 561
<211> LENGTH: 20
<212> TYPE: DNA
<213> ORGANISM: Artificial sequence
<220> FEATURE:
<223> OTHER INFORMATION: synthetic sequence

<400> SEQUENCE: 561
gcagccaagt tgaagaggaa                                                20

<210> SEQ ID NO 562
<211> LENGTH: 20
<212> TYPE: DNA
<213> ORGANISM: Artificial sequence

```
<220> FEATURE:
<223> OTHER INFORMATION: synthetic sequence

<400> SEQUENCE: 562
cagttttgag ttccgctggt                                              20

<210> SEQ ID NO 563
<211> LENGTH: 20
<212> TYPE: DNA
<213> ORGANISM: Artificial sequence
<220> FEATURE:
<223> OTHER INFORMATION: synthetic sequence

<400> SEQUENCE: 563
gagaactttg ccgttgaagc                                              20

<210> SEQ ID NO 564
<211> LENGTH: 20
<212> TYPE: DNA
<213> ORGANISM: Artificial sequence
<220> FEATURE:
<223> OTHER INFORMATION: synthetic sequence

<400> SEQUENCE: 564
tccagcagct tcctgtaggt                                              20

<210> SEQ ID NO 565
<211> LENGTH: 50
<212> TYPE: DNA
<213> ORGANISM: Artificial sequence
<220> FEATURE:
<223> OTHER INFORMATION: synthetic sequence

<400> SEQUENCE: 565
gtcgtatcca gtgcagggtc ccaggtattc gcactggata cgacaaccat             50

<210> SEQ ID NO 566
<211> LENGTH: 18
<212> TYPE: DNA
<213> ORGANISM: Artificial sequence
<220> FEATURE:
<223> OTHER INFORMATION: synthetic sequence

<400> SEQUENCE: 566
gcgctaaggc acgcggtg                                                18

<210> SEQ ID NO 567
<211> LENGTH: 21
<212> TYPE: DNA
<213> ORGANISM: Artificial sequence
<220> FEATURE:
<223> OTHER INFORMATION: synthetic sequence

<400> SEQUENCE: 567
cgcgctgagg tagtaggttg t                                            21

<210> SEQ ID NO 568
<211> LENGTH: 20
<212> TYPE: DNA
<213> ORGANISM: Artificial sequence
<220> FEATURE:
<223> OTHER INFORMATION: synthetic sequence

<400> SEQUENCE: 568
acgtaaacgg ccacaagttc                                              20
```

<210> SEQ ID NO 569
<211> LENGTH: 20
<212> TYPE: DNA
<213> ORGANISM: Artificial sequence
<220> FEATURE:
<223> OTHER INFORMATION: synthetic sequence

<400> SEQUENCE: 569
aagtcgtgct gcttcatgtg                                            20

<210> SEQ ID NO 570
<211> LENGTH: 20
<212> TYPE: DNA
<213> ORGANISM: Artificial sequence
<220> FEATURE:
<223> OTHER INFORMATION: synthetic sequence

<400> SEQUENCE: 570
gtaacccgtt gaaccccatt                                            20

<210> SEQ ID NO 571
<211> LENGTH: 20
<212> TYPE: DNA
<213> ORGANISM: Artificial sequence
<220> FEATURE:
<223> OTHER INFORMATION: synthetic sequence

<400> SEQUENCE: 571
ccatccaatc ggtagtagcg                                            20

<210> SEQ ID NO 572
<211> LENGTH: 17
<212> TYPE: DNA
<213> ORGANISM: Artificial sequence
<220> FEATURE:
<223> OTHER INFORMATION: synthetic sequence

<400> SEQUENCE: 572
ctcgcttcgg cagcaca                                               17

<210> SEQ ID NO 573
<211> LENGTH: 20
<212> TYPE: DNA
<213> ORGANISM: Artificial sequence
<220> FEATURE:
<223> OTHER INFORMATION: synthetic sequence

<400> SEQUENCE: 573
aacgcttcac gaatttgcgt                                            20

<210> SEQ ID NO 574
<211> LENGTH: 43
<212> TYPE: DNA
<213> ORGANISM: Artificial sequence
<220> FEATURE:
<223> OTHER INFORMATION: synthetic sequence

<400> SEQUENCE: 574
ccgctcgagg tccgtctgtc caggctccat tcaggtcctg ctg                  43

<210> SEQ ID NO 575
<211> LENGTH: 43
<212> TYPE: DNA
<213> ORGANISM: Artificial sequence
<220> FEATURE:
<223> OTHER INFORMATION: synthetic sequence

```
<400> SEQUENCE: 575
ttgcggccgc ggggccgggt tacccaatca cttgcttggc ttt           43

<210> SEQ ID NO 576
<211> LENGTH: 17
<212> TYPE: DNA
<213> ORGANISM: Artificial sequence
<220> FEATURE:
<223> OTHER INFORMATION: synthetic sequence

<400> SEQUENCE: 576
ctcgcttcgg cagcaca                                        17

<210> SEQ ID NO 577
<211> LENGTH: 20
<212> TYPE: DNA
<213> ORGANISM: Artificial sequence
<220> FEATURE:
<223> OTHER INFORMATION: synthetic sequence

<400> SEQUENCE: 577
aacgcttcac gaatttgcgt                                     20

<210> SEQ ID NO 578
<211> LENGTH: 21
<212> TYPE: DNA
<213> ORGANISM: Artificial sequence
<220> FEATURE:
<223> OTHER INFORMATION: synthetic sequence

<400> SEQUENCE: 578
gtggcaccca tgtccaatct a                                   21

<210> SEQ ID NO 579
<211> LENGTH: 21
<212> TYPE: DNA
<213> ORGANISM: Artificial sequence
<220> FEATURE:
<223> OTHER INFORMATION: synthetic sequence

<400> SEQUENCE: 579
aggatcaccg tccagttcat a                                   21

<210> SEQ ID NO 580
<211> LENGTH: 21
<212> TYPE: DNA
<213> ORGANISM: Artificial sequence
<220> FEATURE:
<223> OTHER INFORMATION: synthetic sequence

<400> SEQUENCE: 580
atcaccatct tccaggagcg a                                   21

<210> SEQ ID NO 581
<211> LENGTH: 21
<212> TYPE: DNA
<213> ORGANISM: Artificial sequence
<220> FEATURE:
<223> OTHER INFORMATION: synthetic sequence

<400> SEQUENCE: 581
gcttcaccac cttcttgatg t                                   21

<210> SEQ ID NO 582
```

```
<211> LENGTH: 22
<212> TYPE: DNA
<213> ORGANISM: Artificial Sequence
<220> FEATURE:
<223> OTHER INFORMATION: synthetic sequence

<400> SEQUENCE: 582
tggagtgtga caatggtgtt tg                                              22

<210> SEQ ID NO 583
<211> LENGTH: 21
<212> TYPE: DNA
<213> ORGANISM: Artificial Sequence
<220> FEATURE:
<223> OTHER INFORMATION: synthetic sequence

<400> SEQUENCE: 583
tccctcacac atgtaccgca a                                               21

<210> SEQ ID NO 584
<211> LENGTH: 22
<212> TYPE: DNA
<213> ORGANISM: Artificial Sequence
<220> FEATURE:
<223> OTHER INFORMATION: synthetic sequence

<400> SEQUENCE: 584
taattgtcaa ctactgtcag tt                                              22

<210> SEQ ID NO 585
<211> LENGTH: 23
<212> TYPE: DNA
<213> ORGANISM: Artificial Sequence
<220> FEATURE:
<223> OTHER INFORMATION: synthetic sequence

<400> SEQUENCE: 585
tcttaacagt atgagacagt caa                                             23

<210> SEQ ID NO 586
<211> LENGTH: 22
<212> TYPE: DNA
<213> ORGANISM: Artificial Sequence
<220> FEATURE:
<223> OTHER INFORMATION: synthetic sequence

<400> SEQUENCE: 586
tgaggtagta ggttgtatgg tt                                              22

<210> SEQ ID NO 587
<211> LENGTH: 23
<212> TYPE: DNA
<213> ORGANISM: Artificial Sequence
<220> FEATURE:
<223> OTHER INFORMATION: synthetic sequence

<400> SEQUENCE: 587
ctttccatca ttccacatgt caa                                             23

<210> SEQ ID NO 588
<211> LENGTH: 180
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
```

```
<222> LOCATION: (56)..(77)
<223> OTHER INFORMATION: n is a, c, g, or t
<220> FEATURE:
<221> NAME/KEY: misc_feature
<222> LOCATION: (98)..(119)
<223> OTHER INFORMATION: n is a, c, g, or t

<400> SEQUENCE: 588
ggctacgtag ctcagttggt tagagcagcg gccgggccag ctgtgagtgt ttcttnnnnn    60
nnnnnnnnnn nnnnnnntgt gagcaatagt aaggaagnnn nnnnnnnnnn nnnnnnnna   120 gaagtgctgc acgttgttgg cccccgcggg tcacaggttc gaatcccgtc gtagccacca  180

<210> SEQ ID NO 589
<211> LENGTH: 23
<212> TYPE: RNA
<213> ORGANISM: Artificial Sequence
<220> FEATURE:
<223> OTHER INFORMATION: synthetic sequence

<400> SEQUENCE: 589
cuucugccau gaccccaggg cca                                           23

<210> SEQ ID NO 590
<211> LENGTH: 24
<212> TYPE: RNA
<213> ORGANISM: Artificial Sequence
<220> FEATURE:
<223> OTHER INFORMATION: synthetic sequence

<400> SEQUENCE: 590
ugacgaccag aagucagucc cggu                                          24

<210> SEQ ID NO 591
<211> LENGTH: 23
<212> TYPE: RNA
<213> ORGANISM: Artificial Sequence
<220> FEATURE:
<223> OTHER INFORMATION: synthetic sequence

<400> SEQUENCE: 591
ucuugaauca guccucaggg ccc                                           23

<210> SEQ ID NO 592
<211> LENGTH: 23
<212> TYPE: RNA
<213> ORGANISM: Artificial Sequence
<220> FEATURE:
<223> OTHER INFORMATION: synthetic sequence

<400> SEQUENCE: 592
gcugugaggg caguucaggg cca                                           23

<210> SEQ ID NO 593
<211> LENGTH: 23
<212> TYPE: RNA
<213> ORGANISM: Artificial Sequence
<220> FEATURE:
<223> OTHER INFORMATION: synthetic sequence

<400> SEQUENCE: 593
agggcaguuc agggccaggg ccc                                           23
```